United States Patent
Chiu et al.

(10) Patent No.: US 11,697,713 B2
(45) Date of Patent: *Jul. 11, 2023

(54) CHROMOPHORIC POLYMER DOTS WITH NARROW-BAND EMISSION

(71) Applicant: University of Washington through its Center for Commercialization, Seattle, WA (US)

(72) Inventors: Daniel T. Chiu, Seattle, WA (US); Changfeng Wu, Changchun (CN); Yu Rong, Seattle, WA (US); Yong Zhang, Seattle, WA (US); Yi-Che Wu, Seattle, WA (US); Yang-Hsiang Chan, Seattle, WA (US); Xuanjun Zhang, Linkoping (SE); Jiangbo Yu, Seattle, WA (US); Wei Sun, Seattle, WA (US)

(73) Assignee: University of Washington through its Center for Commercialization, Seattle, WA (US)

( * ) Notice: Subject to any disclaimer, the term of this patent is extended or adjusted under 35 U.S.C. 154(b) by 239 days.

This patent is subject to a terminal disclaimer.

(21) Appl. No.: 16/138,732

(22) Filed: Sep. 21, 2018

(65) Prior Publication Data

US 2019/0106542 A1  Apr. 11, 2019

Related U.S. Application Data

(63) Continuation of application No. 14/366,863, filed as application No. PCT/US2012/071767 on Dec. 27, 2012, now Pat. No. 10,150,841.

(Continued)

(51) Int. Cl.
*A61K 47/32*    (2006.01)
*C08G 77/00*    (2006.01)
(Continued)

(52) U.S. Cl.
CPC .......... *C08G 75/32* (2013.01); *A61K 49/0019* (2013.01); *A61K 49/0067* (2013.01);
(Continued)

(58) Field of Classification Search
CPC ..... C08G 79/00; C08G 75/32; H01L 51/0036; H01L 51/0034; H01L 51/0043;
(Continued)

(56) References Cited

U.S. PATENT DOCUMENTS 4,774,339 A   9/1988  Haugland et al.
4,946,778 A   8/1990  Ladner et al.
(Continued)

FOREIGN PATENT DOCUMENTS

CN    1541136 A    10/2004
CN    101302353 A   11/2008
(Continued)

OTHER PUBLICATIONS

Wu et al. Novel poly(fluorene-alt-squaraine) derivatives having large coverage with solar spectrum. e-Polymers, 2007, No. 077, pp. 1-10. (Year: 2007).*

(Continued)

*Primary Examiner* — Shafiqul Haq
(74) *Attorney, Agent, or Firm* — Christensen O'Connor Johnson Kindness PLLC

(57) ABSTRACT

Polymers, monomers, chromophoric polymer dots and related methods are provided. Highly fluorescent chromophoric polymer dots with narrow-band emissions are provided. Methods for synthesizing the chromophoric polymers, preparation methods for forming the chromophoric polymer dots, and biological applications using the unique properties of narrow-band emissions are also provided.

26 Claims, 124 Drawing Sheets

Related U.S. Application Data

(60) Provisional application No. 61/607,455, filed on Mar. 6, 2012, provisional application No. 61/582,181, filed on Dec. 30, 2011.

(51) Int. Cl.

| | | |
|---|---|---|
| *C08G 77/398* | (2006.01) | |
| *C08G 75/32* | (2006.01) | |
| *G01N 33/58* | (2006.01) | |
| *A61K 49/00* | (2006.01) | |
| *C09B 69/10* | (2006.01) | |
| *H10K 85/10* | (2023.01) | |
| *C08G 79/00* | (2006.01) | |
| *B82Y 40/00* | (2011.01) | |
| *B82Y 30/00* | (2011.01) | |
| *G01N 21/64* | (2006.01) | |
| *H10K 50/11* | (2023.01) | |

(52) U.S. Cl.
CPC ............ *C08G 79/00* (2013.01); *C09B 69/105* (2013.01); *G01N 33/582* (2013.01); *G01N 33/587* (2013.01); *H10K 85/10* (2023.02); *H10K 85/113* (2023.02); *H10K 85/115* (2023.02); *H10K 85/151* (2023.02); *B82Y 30/00* (2013.01); *B82Y 40/00* (2013.01); *G01N 2021/6439* (2013.01); *H10K 50/11* (2023.02)

(58) Field of Classification Search
CPC ............ H01L 51/0039; H01L 51/5012; C09B 69/105; A61K 49/0067; A61K 49/0019; G01N 33/582; G01N 33/587; G01N 2021/6439; B82Y 40/00; B82Y 30/00
See application file for complete search history.

(56) References Cited

U.S. PATENT DOCUMENTS

| | | | |
|---|---|---|---|
| 5,723,218 | A | 3/1998 | Haugland et al. |
| 6,417,402 | B1 | 7/2002 | Das et al. |
| 7,432,298 | B2 | 10/2008 | Lam et al. |
| 7,462,325 | B2 | 12/2008 | Hancock et al. |
| 7,521,232 | B2 | 4/2009 | Moon |
| 7,985,426 | B1 | 7/2011 | Sung et al. |
| 8,367,042 | B2 | 2/2013 | Kim et al. |
| 9,382,473 | B2 | 7/2016 | Chiu et al. |
| 9,797,840 | B2 | 10/2017 | Chiu et al. |
| 9,810,693 | B2 | 11/2017 | Chiu et al. |
| 9,849,197 | B2 | 12/2017 | Saji et al. |
| 10,067,139 | B2 | 9/2018 | Chiu et al. |
| 10,150,841 | B2 | 12/2018 | Chiu et al. |
| 10,191,060 | B2 | 1/2019 | Chiu et al. |
| 2002/0045045 | A1 | 4/2002 | Adams et al. |
| 2004/0018379 | A1 | 1/2004 | Kinlen |
| 2004/0101822 | A1 | 5/2004 | Wiesner et al. |
| 2004/0131886 | A1 | 7/2004 | Marrocco et al. |
| 2005/0019265 | A1 | 1/2005 | Hammer et al. |
| 2005/0171289 | A1 | 8/2005 | Kataoka et al. |
| 2005/0255044 | A1 | 11/2005 | Lomnes et al. |
| 2006/0029978 | A1 | 2/2006 | O'Neill et al. |
| 2006/0127929 | A1 | 6/2006 | Swager et al. |
| 2007/0031490 | A1 | 2/2007 | Loebenberg et al. |
| 2007/0224345 | A1 | 9/2007 | Metz et al. |
| 2008/0081192 | A1 | 4/2008 | Goh et al. |
| 2008/0085566 | A1 | 4/2008 | Swager et al. |
| 2008/0178763 | A1 | 7/2008 | Schwartz et al. |
| 2008/0199700 | A1 | 8/2008 | Anderson et al. |
| 2008/0242806 | A1 | 10/2008 | Chen et al. |
| 2009/0075295 | A1 | 3/2009 | Lindsey |
| 2009/0130665 | A1 | 5/2009 | Sleiman et al. |
| 2009/0220434 | A1 | 9/2009 | Sharma |
| 2009/0294691 | A1 | 12/2009 | Trinquet et al. |
| 2010/0016472 | A1 | 1/2010 | Wang et al. |
| 2010/0098902 | A1 | 4/2010 | Kotov et al. |
| 2010/0290999 | A1 | 11/2010 | Kim et al. |
| 2011/0159605 | A1 | 6/2011 | Whitten et al. |
| 2011/0278503 | A1 | 11/2011 | Janczewski et al. |
| 2011/0278536 | A1 | 11/2011 | Walker et al. |
| 2012/0015190 | A1 | 1/2012 | Goh et al. |
| 2012/0175571 | A1 | 7/2012 | Sarkar |
| 2012/0282632 | A1 | 11/2012 | Chiu et al. |
| 2013/0234067 | A1 | 9/2013 | Chiu et al. |
| 2013/0234068 | A1 | 9/2013 | Chiu et al. |
| 2013/0266957 | A1 | 10/2013 | Chiu et al. |
| 2014/0302516 | A1 | 10/2014 | Chiu et al. |
| 2014/0350183 | A1 | 11/2014 | Chiu et al. |
| 2015/0037259 | A1 | 2/2015 | Chiu et al. |
| 2016/0018395 | A1 | 1/2016 | Chiu et al. |
| 2016/0161475 | A1 | 6/2016 | Chiu et al. |
| 2016/0341737 | A1 | 11/2016 | Chiu et al. |
| 2019/0004056 | A1 | 1/2019 | Chiu et al. |

FOREIGN PATENT DOCUMENTS

| | | |
|---|---|---|
| CN | 101302353 A | 11/2008 |
| CN | 102791827 A | 11/2012 |
| EP | 2251043 A2 | 11/2010 |
| JP | 2006525527 A | 11/2006 |
| JP | 2007-530051 A | 11/2007 |
| JP | 2008-504517 A | 2/2008 |
| JP | 2008-506970 A | 3/2008 |
| JP | 2013168424 A | 8/2013 |
| JP | 2013168424 A | 8/2013 |
| WO | 2005/094532 A2 | 10/2005 |
| WO | WO-2007027159 A1 | 3/2007 |
| WO | WO-2007095506 A1 | 8/2007 |
| WO | WO-2008063378 A2 | 5/2008 |
| WO | WO-2009051560 A1 | 4/2009 |
| WO | WO-2009107859 A2 | 9/2009 |
| WO | WO-2010006753 A2 | 1/2010 |
| WO | 2010075512 A1 | 7/2010 |
| WO | 2010075514 A1 | 7/2010 |
| WO | WO-2010075512 A1 | 7/2010 |
| WO | WO-2010075514 A1 | 7/2010 |
| WO | WO-2010099273 A1 | 9/2010 |
| WO | WO-2011057295 A2 | 5/2011 |
| WO | WO-2012054525 A2 | 4/2012 |
| WO | WO-2012118136 A1 | 9/2012 |
| WO | WO-2013101902 A2 | 7/2013 |
| WO | WO-2013116614 A1 | 8/2013 |
| WO | WO-2014153051 A1 | 9/2014 |

OTHER PUBLICATIONS

Wu et al. Bioconjugation of ultrabright semiconducting polymer dots for specific cellular targeting. J. Am. Chem. Soc. 2010, vol. 132, pp. 15410-15417. (Year: 2010).*
CN201080060982.3 Office Action dated Jan. 14, 2014.
CN201080060982.3 Office Action dated Dec. 1, 2014.
CN201080060982.3 Office Action dated Jan. 5, 2016.
CN201080060982.3 Office Action dated Jul. 31, 2015.
CN201610969596.5 Office Action dated Aug. 23, 2018.
Australian Examination Report dated Jun. 13, 2018 for AU Application No. AU2017204805.
CA2814790 Office Action dated May 28, 2018.
CN 201280070923.3 Fourth Office Action dated Apr. 23, 2018 (w/ English translation).
CN 201480028351.1 Third Office Action dated Mar. 28, 2018 (w/ English translation).
Co-pending U.S. Appl. No. 16/041,569, filed Jul. 20, 2018.
Co-pending U.S. Appl. No. 16/209,729, filed Dec. 4, 2018.
European search report with written opinion dated Oct. 24, 2018 for EP Application No. 18193806.
Green, et al. Simple conjugated polymer nanoparticles as biological labels. Proc. R. Soc. A. 2009. 465. 2751-2759; DOI: 10.1098/rspa.2009.0181. Published Jul. 27, 2009.
JP 2016-235598 Office Action dated Mar. 28, 2018 (w/ English translation).

(56) References Cited

OTHER PUBLICATIONS

JP 2016-235598 Office Action dated Oct. 3, 2018 (w/ English translation).
Notice of allowance dated Aug. 8, 2018 for U.S. Appl. No. 14/373,835.
Notice of allowance dated Sep. 6, 2018 for U.S. Appl. No. 13/508,981.
Notice of allowance dated Dec. 26, 2018 for U.S. Appl. No. 13/508,981.
Office action dated Jun. 29, 2018 for U.S. Appl. No. 14/774,971.
Office action dated Dec. 4, 2018 for U.S. Appl. No. 16/041,569.
U.S. Appl. No. 14/373,835 Notice of Allowance dated Apr. 24, 2018.
"AU 2017200592 Office Action dated Mar. 29, 2018".
Australian examination report dated Apr. 8, 2016 for AU Application 2015204342.
Australian Examination Report dated Oct. 25, 2018 for AU Application No. AU2017200592.
"EP 14770843.2 Office Action dated Apr. 13, 2018".
European office action dated Mar. 2, 2016 for EP Application No. 11835019.8.
Office action dated Nov. 6, 2018 for EP Application No. 14770843.
Zhu et al., Efficient Tuning Nonlinear Optical Properties: Synthesis and Characterization of a Series of Novel Poly (aryleneethynylene)s Co-Containing BODIPY, Journal of Polymer Science: Part A: Polymer Chemistry, vol. 46, pp. 7401-7410 (2008).
Thivierge et al., Brilliant BODIPY—Fluorene Copolymers with Dispersed Absorption and Emission Maxima, ACS Publications, 2011 American Chemical Society, Macromolecules 2011, 44, pp. 4012-4015.
Rong et al., Multicolor Fluorescent Semiconducting Polymer Dots with Narrow Emissions and High Brightness, Article, Published online Jan. 2, 2013, vol. 7, No. 1, pp. 376-384.
Riddle et al., Signal-Amplifying Resonance Energy Transfer: A Dynamic Multichromophore Array for Allosteric Switching, Article, 2007, pp. 7019-7022.
Nagai, A. and Chujo, Y., "Organoboron Conjugated Polymers," in "Conjugated Polymer Synthesis: Methods and Reactions," ed. Y. Chujo, Wiley-VCH Verlag GmbH & Co KGaA, Weinheim, pp. 195-214, 2010.
Nagai et al., Highly Luminescent BODIPY-Based Organoboron Polymer Exhibiting Supramolecular Self-Assemble Structure, Article, Department of Polymer Chemistry, Graduate School of Engineering, 2008 American Chemical Society, pp. 15276-15278.
Benstead et al., Addressing fluorescence and liquid crystal behaviour in multi-mesogenic BODIPY materials, Article, Published Apr. 13, 2011, 35, pp. 1410-1417.
European Extended Search Report, completed on Jun. 8, 2020, issued in correspondence to European Application No. 20166712.8, 17 pages.
Abbel, et al. Multicolour self-assembled particles of fluorene-based bolaamphiphiles. Chem Commun (Camb). Apr. 7, 2009;(13):1697-9. doi: 10.1039/b822943k. Epub Feb. 17, 2009.
Abdelwahed, et al. Freeze-drying of nanoparticles: formulation, process and storage considerations. Adv Drug Deliv Rev. Dec. 30, 2006;58(15):1688-713.
Achari, et al. 1.67-A X-ray structure of the B2 immunoglobulin-binding domain of Streptococcal protein G and comparison to the NMR structure of the B1 domain. Biochemistry. Nov. 3, 1992;31(43):10449-57.
Agard, et al. A comparative study of bioorthogonal reactions with azides. ACS Chem Biol. Nov. 21, 2006;1(10):644-8.
Akerstrom, et al. A physicochemical study of protein G, a molecule with unique immunoglobulin G-binding properties. J Biol Chem. Aug. 5, 1986;261(22):10240-7.
Alivistatos, et al. Quantum dots as cellular probes. Annu Rev Biomed Eng. 2005;7:55-76.
Ausborn, et al. The protective effect of free and membrane-bound cryoprotectants during freezing and freeze-drying of liposomes. Journal of Controlled Release. 1994; 30:105-116.

Baier, et al. Fluorescent conjugated polymer nanoparticles by polymerization in miniemulsion. J Am Chem Soc. Oct. 14, 2009;131(40):14267-73. doi: 10.1021/ja905077c.
Benstead, et al. Addressing fluorescence and liquid crystal behaviour in multi-mesogenic BODIPY materials. New Journal of Chemistry. 2011; 35(7):1410-1417.
Berlier, et al. Quantitative comparison of long-wavelength Alexa Fluor dyes to Cy dyes: fluorescence of the dyes and their bioconjugates. J Histochem Cytochem. Dec. 2003;51(12):1699-712.
Bernardin, et al. Copper-free click chemistry for highly luminescent quantum dot conjugates: application to in vivo metabolic imaging. Bioconjug Chem. Apr. 21, 2010;21(4):583-8. doi: 10.1021/bc900564w.
Best. Click chemistry and bioorthogonal reactions: unprecedented selectivity in the labeling of biological molecules. Biochemistry. Jul. 21, 2009;48(28):6571-84. doi: 10.1021/bi9007726.
Bird, et al. Single-chain antigen-binding proteins. Science. Oct. 21, 1988;242(4877):423-6.
Boyere, et al. Elaboration of drug nanocarriers based on a glucosamine labeled amphiphilic polymer. Polymer Chemistry. 2014; 5:3030-3037.
Breidenbach, et al. Targeted metabolic labeling of yeast N-glycans with unnatural sugars. Proc Natl Acad Sci U S A. Mar. 2, 2010;107(9):3988-93. doi: 10.1073/pnas.0911247107. Epub Feb. 8, 2010.
Bruchez, et al. Semiconductor nanocrystals as fluorescent biological labels. Science. Sep. 25, 1998;281(5385):2013-6.
Caruso. Nanoengineering of Particle Surfaces. Adv. Mater. 2001; 13:11-22.
Chalfie, et al. Green fluorescent protein as a marker for gene expression. Science. Feb. 11, 1994;263(5148):802-5.
Chan, et al. Copper(II) and iron(II) ion sensing with semiconducting polymer dots. Chem Commun (Camb). Mar. 14, 2011;47(10):2820-2. doi: 10.1039/c0cc04929h. Epub Jan. 14, 2011.
Chan, et al. Development of ultrabright semiconducting polymer dots for ratiometric pH sensing. Anal Chem. Feb. 15, 2011;83(4):1448-55. doi: 10.1021/ac103140x. Epub Jan. 18, 2011.
Chan, et al. Hybrid semiconducting polymer dot-quantum dot with narrow-band emission, near-infrared fluorescence, and high brightness. J Am Chem Soc. May 2, 2012;134(17):7309-12. doi: 10.1021/ja3022973. Epub Apr. 23, 2012.
Chan, et al. Quantum dot bioconjugates for ultrasensitive nonisotopic detection. Science. Sep. 25, 1998;281(5385):2016-8.
Chan, et al. Ultrasensitive copper(II) detection using plasmon-enhanced and photo-brightened luminescence of CdSe quantum dots. Anal Chem. May 1, 2010;82(9):3671-8. doi: 10.1021/ac902985p.
Chen, et al. Highly sensitive biological and chemical sensors based on reversible fluorescence quenching in a conjugated polymer. Proc Natl Acad Sci U S A. Oct. 26, 1999;96(22):12287-92.
Choi, et al. Design considerations for tumour-targeted nanoparticles. Nat Nanotechnol. Jan. 2010;5(1):42-7. doi: 10.1038/nnano.2009.314. Epub Nov. 1, 2009.
Choi, et al. Renal clearance of quantum dots. Nat Biotechnol. Oct. 2007;25(10):1165-70. Epub Sep. 23, 2007.
Clafton, et al. Chemical defects in the highly fluorescent conjugated polymer dots. Langmuir. Dec. 7, 2010;26(23):17785-9. doi: 10.1021/la103063p. Epub Nov. 11, 2010.
"CN 201610969596.5 First Office Action dated Jan. 22, 2018".
Collini, et al. Coherent intrachain energy migration in a conjugated polymer at room temperature. Science. Jan. 16, 2009;323(5912):369-73. doi: 10.1126/science.1164016.
"Corrected Notice of Allowability dated Dec. 1, 2017 for U.S. Appl. No. 13/508,981".
Derfus, et al. Probing the Cytotoxicity of Semiconductor Quantum Dots. Nano Letters. 2004; 4(1):11-18.
Dieterich, et al. Selective identification of newly synthesized proteins in mammalian cells using bioorthogonal noncanonical amino acid tagging (BONCAT). Proc Natl Acad Sci U S A. Jun. 20, 2006;103(25):9482-7. Epub Jun. 12, 2006.
Dube, et al. Probing mucin-type O-linked glycosylation in living animals. Proc Natl Acad Sci U S A. Mar. 28, 2006;103(13):4819-24. Epub Mar. 20, 2006.

(56) References Cited

OTHER PUBLICATIONS

European search report and opinion dated Mar. 19, 2014 for EP Application No. 11835019.8.
European search report and opinion dated May 31, 2016 for EP Application No. 12861954.
European search report and opinion dated Aug. 12, 2015 for EP Application No. 15175146.8.
European search report and opinion dated Sep. 8, 2016 for EP Application No. 14770843.2.
European search report and opinion dated Sep. 18, 2013 for EP Application No. 10829306.9.
European search report and opinion dated Oct. 8, 2015 for EP Application No. 13743132.6.
Fan, et al. Beyond superquenching: hyper-efficient energy transfer from conjugated polymers to gold nanoparticles. Proc Natl Acad Sci U S A. May 27, 2003;100(11):6297-301. Epub May 15, 2003.
Fernandez-Suarez, et al. Fluorescent probes for super-resolution imaging in living cells. Nat Rev Mol Cell Biol. Dec. 2008;9(12):929-43. doi: 10.1038/nrm2531. Epub Nov. 12, 2008.
Fernando, et al. Mechanism of cellular uptake of highly fluorescent conjugated polymer nanoparticles. Biomacromolecules. Oct. 11, 2010;11(10):2675-82. doi: 10.1021/bm1007103.
Friend, et al. Electroluminescence in conjugated polymers. Nature. 1999; 397:121-128.
Giepmans, et al. The fluorescent toolbox for assessing protein location and function. Science. Apr. 14, 2006;312(5771):217-24.
Green. Avidin and streptavidin. Methods Enzymol. Wilchek and Bayer. New York, Academic Press, Inc. 1990;184:51-67.
Greenham et al., Efficient light-emitting diodes based on polymers with high electron affinities, Nature, vol. 365:628-630, published Oct. 14, 1993, print retrieved on Oct. 10, 2016.
"Greenham, et al., Measurement of Absolute Photoluminescence Quantum Efficiencies in Conjugated Polymers, Chemical Physics Letters, Jul. 14, 1995, 241(1995) 89-96".
Gunes, et al. Conjugated polymer-based organic solar cells. Chem Rev. Apr. 2007;107(4):1324-38.
Han, et al. Development of a bioorthogonal and highly efficient conjugation method for quantum dots using tetrazine-norbornene cycloaddition. J Am Chem Soc. Jun. 16, 2010;132(23):7838-9. doi: 10.1021/ja101677r.
Hashim, et al. Luminescent quantum-dot-sized conjugated polymer nanoparticles—nanoparticle formation in miniemulsion system. Journal of Materials Chemistry. 2011; 21: 1797-1803.
Hermanson. Bioconjugate techniques, Academic Press, San Diego, 1996; Ch 13, 570-591.
Hou, et al. Novel red-emitting fluorene-based copolymers. Journal of Materials Chemistry. 2002; 12:2887-2892.
Hou, et al. Synthesis and electroluminescent properties of high-efficiency saturated red emitter based on copolymers from fluorene and 4,7-di(4-hexylthien-2-yl)-2,1,3-benzothiadiazole, Macromolecules. 2004; 37:6299-6305.
Howarth, et al. Monovalent, reduced-size quantum dots for imaging receptors on living cells. Nat Methods. May 2008;5(5):397-9. doi: 10.1038/nmeth.1206. Epub Apr. 20, 2008.
Howes, et al. Colloidal and optical stability of PEG-capped and phospholipid-encapsulated semiconducting polymer nanospheres in different aqueous media. Photochem Photobiol Sci. Aug. 2010;9(8):1159-66. doi: 10.1039/c0pp00106f. Epub Jun. 29, 2010.
Howes, et al. Magnetic conjugated polymer nanoparticles as bimodal imaging agents. J Am Chem Soc. Jul. 21, 2010;132(28):9833-42. doi: 10.1021/ja1031634.
Howes, et al. Phospholipid encapsulated semiconducting polymer nanoparticles: their use in cell imaging and protein attachment. J Am Chem Soc. Mar. 24, 2010;132(11):3989-96. doi: 10.1021/ja1002179.
Howes, et al. Synthesis, characterisation and intracellular imaging of PEG capped BEHP-PPV nanospheres. Chem Commun (Camb). May 14, 2009;(18):2490-2. doi: 10.1039/b903405f. Epub Apr. 2, 2009.
Huyal, et al., White emitting polyfluorene functionalized with azide hybridized on near-UV light emitting diode for high color rendering index, Optics Express , Jan. 21, 2008, 16(2):1115-24.
International preliminary report on patentability dated Apr. 23, 2013 for PCT/US2011/056768.
International search report and written opinion dated Mar. 27, 2013 for PCT/US2012/071767.
International search report and written opinion dated Apr. 9, 2013 for PCT/US2013/024300.
International search report and written opinion dated Jun. 26, 2012 for PCT/US2011/056768.
International search report and written opinion dated Jul. 28, 2011 for PCT/US2010/056079.
International search report and written opinion dated Aug. 22, 2014 for PCT/US2014/028846.
Jin, et al., Generation of functionalized and robust semiconducting polymer dots with polyelectrolytes, Chem Commun (Camb). Mar. 28, 2012;48(26): doi: 10.1039/c2cc17703j.
Jin, et al. Near-infrared fluorescent dye-doped semiconducting polymer dots. ACS Nano. Feb. 22, 2011;5(2):1468-75. doi: 10.1021/nn103304m. Epub Jan. 31, 2011.
Jin, et al. Silica Nanoparticles with Continuously Tunable Sizes: Synthesis and Size Effects on Cellular Imaging. Chem. Mater. 2008, 20:4411-4419.
Johnston, et al. Layer-by-layer engineered capsules and their applications. Curr. Opin. Colloid Interface Sci. 2006; 11:203-209.
JP 2016-502922 Office Action dated Feb. 6, 2018.
Kaeser, et al. Fluorescent nanoparticles based on self-assembled pi-conjugated systems. Adv Mater. Jul. 27, 2010;22(28):2985-97. doi: 10.1002/adma.201000427.
Kietzke, et al. Novel approaches to polymer blends based on polymer nanoparticles. Nat Mater. Jun. 2003;2(6):408-12.
Kim, et al. Conjugated polymer nanoparticles for biomedical in vivo imaging. Chem Commun (Camb). Mar. 14, 2010;46(10):1617-9. doi: 10.1039/b923309a. Epub Jan. 12, 2010.
Kolb, et al. Click Chemistry: Diverse Chemical Function from a Few Good Reactions, w Chem Int Ed Engl. Jun. 1, 2001;40(11):2004-2021.
Kolb, et al. The growing impact of click chemistry on drug discovery. Drug Discov Today. Dec. 15, 2003;8(24):1128-37.
Kumar, et al. Photon antibunching from oriented semiconducting polymer nanostructures. J Am Chem Soc. Mar. 24, 2004;126(11):3376-7.
Laughlin, et al. Imaging the glycome. Proc Natl Acad Sci U S A. Jan. 6, 2009;106(1):12-7. doi: 10.1073/pnas.0811481106. Epub Dec. 22, 2008.
Lee, et al. Recent advances in fluorescent and colorimetric conjugated polymer-based biosensors. Analyst. Sep. 2010;135(9):2179-89. doi: 10.1039/c0an00239a. Epub Jun. 11, 2010.
Li, et al. Polymer encapsulated conjugated polymer nanoparticles for fluorescence bioimaging. Journal of Materials Chemistry 2012; 22:1257-1264.
Mccafferty, et al. Phage antibodies: filamentous phage displaying antibody variable domains. Nature. Dec. 6, 1990;348(6301):552-4.
Meng, et al. Color tuning of polyfluorene emission with BODIPY monomers, Macromolecules 2009,42:1995-2001.
Michalet, et al. Quantum dots for live cells, in vivo imaging, and diagnostics. Science. Jan. 28, 2005;307(5709):538-44.
Moon, et al. Conjugated polymer nanoparticles for small interfering RNA delivery. Chem Commun (Camb). Aug. 7, 2011;47(29):8370-2. doi: 10.1039/c1cc10991j. Epub Jun. 22, 2011.
Moon, et al. Live-cell-permeable poly(p-phenylene ethynylene). Angew Chem Int Ed Engl. 2007;46(43):8223-5.
Moses, et al. The growing applications of click chemistry. Chem Soc Rev. Aug. 2007;36(8):1249-62. Epub May 3, 2007.
Murcia, et al., Biofunctionalization of Fluorescent Nanoparticles, Nanotechnologies for the Life Sciences, 2005, vol. 1, 40 pages.
Nagai, et al. Highly luminescent BODIPY-based organoboron polymer exhibiting supramolecular self-assemble structure. J Am Chem Soc. Nov. 19, 2008;130(46):15276-8. doi: 10.1021/ja806939w.
Nagai, et al. Organoboron conjugated polymers. In Conjugated Polymer Synthesis: Methods and reactions. Ed. Yoshiki Chujo. Wiley-VCH Verlag GmbH & Co KGaA, Weinheim. 2010. 195-214.

(56) References Cited

OTHER PUBLICATIONS

Nirmal, et al. Fluorescence intermittency in single cadmium selenide nanocrystals. Nature. 1996; 383:802-804. doi:10.1038/383802a0.
Notice of allowance dated Jun. 16, 2017 for U.S. Appl. No. 13/687,813.
Notice of allowance dated Jun. 23, 2017 for U.S. Appl. No. 13/865,942.
Notice of allowance dated Jun. 27, 2018 for U.S. Appl. No. 14/366,863.
Notice of allowance dated Jul. 23, 2018 for U.S. Appl. No. 14/366,863.
Notice of allowance dated Aug. 29, 2017 for U.S. Appl. No. 13/508,981.
Notice of Allowance dated Oct. 19, 2017 for U.S. Appl. No. 13/508,981.
Office action dated Jan. 29, 2016 for AU Application 2012362466.
Office action dated Feb. 2, 2016 for CN Application No. 201180068242.
Office action dated Feb. 4, 2015 for CN Application No. 201180068242.
Office action dated Feb. 19, 2016 for CN Application 2012800709233.
Office action dated Mar. 8, 2017 for AU Application No. 2015204342.
Office action dated Mar. 15, 2017 for JP Application No. 2013-535014.
Office action dated Mar. 29, 2016 for JP Application No. 2012-538915.
Office action dated Mar. 30, 2017 for U.S. Appl. No. 14/373,835.
Office action dated Apr. 5, 2017 for EP Application No. 15175146.8.
Office action dated Apr. 28, 2014 for AU Application No. 2011317142.
Office action dated Apr. 28, 2017 for U.S. Appl. No. 13/865,942.
Office action dated May 16, 2016 for U.S. Appl. No. 14/373,835.
Office action dated May 20, 2016 for EP Application No. 10829306.9.
Office action dated May 29, 2017 for CA Application No. 2,814,790.
Office action dated May 30, 2014 for CN Application No. 201180068242.
Office action dated Jun. 6, 2017 for JP Application No. 2016-151438.
Office action dated Jun. 15, 2017 for CN Application No. 201180060824.2.
Office action dated Jun. 23, 2017 for CN Application No. 201480028351.1.
Office action dated Jul. 26, 2017 for CN Application No. 201280070923.3.
Office action dated Jul. 28, 2017 for EP Application No. 14770843.
Office action dated Aug. 4, 2015 for CN Application No. 201180068242.
Office action dated Sep. 21, 2017 for EP Application No. 15175146.8.
Office action dated Sep. 22, 2017 for EP Application No. 11835019.8.
Office action dated Sep. 26, 2016 for CN Application No. 201480028351.1.
Office action dated Sep. 27, 2016 for EP Application No. 11835019.8.
Office action dated Sep. 27, 2016 for JP Application 2014-550455.
Office action dated Sep. 29, 2016 for CN Application No. 201180060824.2.
Office Action dated Oct. 10, 2017 for U.S. Appl. No. 14/366,863.
Office action dated Oct. 20, 2016 for U.S. Appl. No. 13/687,813.
Office action dated Nov. 4, 2016 for CN Application No. 201280070923.3.
Office Action dated Nov. 24, 2017 for CN Patent Application No. 201180060824.2.
Office Action dated Nov. 30, 2017 for U.S. Appl. No. 14/373,835.
Office action dated Dec. 3, 2015 for JP Application No. 2013-535014.
Office action dated Dec. 29, 2016 for U.S. Appl. No. 13/865,942.
Office Action dated Jan. 26, 2018 for EP Application No. 12861954.1.
Office action dated Jan. 30, 2017 for AU Application No. 2012362466.
Office action dated Feb. 22, 2017 for U.S. Appl. No. 13/508,981.
Office action dated Mar. 1, 2017 for U.S. Appl. No. 14/366,863.
Office action dated Sep. 13, 2016 for U.S. Appl. No. 14/373,835.
Palacios, et al. Charging and discharging of single conjugated-polymer nanoparticles. Nat Mater. Sep. 2007;6(9):680-5. Epub Jul. 22, 2007.
Park, et al., White-Emitting Conjugated Polymer Nanoparticles with Cross-Linked Shell for Mechanical Stability and Controllable photometric Properties in Color-Conversion LED Applications, ACS Nano, 2011, 5(4):2483-92.
Pecher, et al. Nanoparticles of conjugated polymers. Chem Rev. Oct. 13, 2010;110(10):6260-79. doi: 10.1021/cr100132y.
Pepperkok, et al. High-throughput fluorescence microscopy for systems biology. Nat Rev Mol Cell Biol. Sep. 2006;7(9):690-6. Epub Jul. 19, 2006.
Poon, et al. Controlling in vivo stability and biodistribution in electrostatically assembled nanoparticles for systemic delivery. Nano Lett. May 11, 2011;11(5):2096-103. doi: 10.1021/nl200636r. Epub Apr. 27, 2011.
Poon, et al. Layer-by-layer nanoparticles with a pH-sheddable layer for in vivo targeting of tumor hypoxia. ACS Nano. Jun. 28, 2011;5(6):4284-92. doi: 10.1021/nn200876f. Epub Apr. 29, 2011.
Pras, et al. Photoluminescence of 2,7-poly(9,9-dialkylfluorene-co-fluorenone) nanoparticles: effect of particle size and inert polymer addition. Langmuir. Sep. 21, 2010;26(18):14437-42. doi: 10.1021/la1011742.
Prescher, et al. Chemical remodelling of cell surfaces in living animals. Nature. Aug. 19, 2004;430(7002):873-7.
Prescher, et al. Chemistry in living systems. Nat Chem Biol. Jun. 2005;1(1):13-21.
Pu, et al. Fluorescent conjugated polyelectroltyes for bioimaging. Advanced Functional Materials. 2011; 21:3408-3423.
Pu, et al. Fluorescent single-molecular core-shell nanospheres of hyperbranched conjugated polyelectrolyte for live-cell imaging. Chem. Mater. 2009;21:3816-3822.
Que, et al. Metals in neurobiology: probing their chemistry and biology with molecular imaging. Chem Rev. May 2008;108(5):1517-49. doi: 10.1021/cr078203u. Epub Apr. 22, 2008.
Rahim, et al. Conjugated Polymer Nanoparticles for Two-Photon Imaging of Endothelial Cells in a Tissue Model. Adv. Mater. 2009; 21(34):3492-3496.
Resch-Genger, et al. Quantum dots versus organic dyes as fluorescent labels. Nat Methods. Sep. 2008;5(9):763-75. doi: 10.1038/nmeth.1248.
Riddle, et al. Signal-Amplifying Resonance Energy Transfer: A Dynamic Multichromophore Array for Allosteric Switching. Angewandte Chemie International Edition. 2007; 46(37:)7019-7022.
Rong, et al. Multicolor fluorescent semiconducting polymer dots with narrow emissions and high brightness. Acs Nano. 2013; 7(1)L376-384.
Sadtler, et al. Selective facet reactivity during cation exchange in cadmium sulfide nanorods. J Am Chem Soc. Apr. 15, 2009;131(14):5285-93. doi: 10.1021/ja809854q.
Sigma Aldrich. Product Information Triton X-1 00. Apr. 21, 1999. Retrieved at http://www.sigmaaldrich.com/content!dam/sigmaaldrich/docs/Sigma/Product_Information-Sheet/1/t8532pis.pdf on Mar. 14, 2014.
Sletten, et al. Bioorthogonal chemistry: fishing for selectivity in a sea of functionality. Angew Chem Int Ed Engl. 2009;48(38):6974-98. doi: 10.1002/anie.200900942.
Smith, et al. Investigating lyophilization of lipid nanocapsules with fluorescence correlation spectroscopy. Investigating lyophilization of lipid nanocapsules with fluorescence correlation spectroscopy.
Speers, et al. Activity-based protein profiling in vivo using a copper(i)-catalyzed azide-alkyne [3+2] cycloaddition. J Am Chem Soc. Apr. 23, 2003;125(16):4686-7.
Sun, et al. Lyophilization of semiconducting polymer dot bioconjugates. Anal Chem. May 7, 2013;85(9):4316-20. doi: 10.1021/ac4007123. Epub Apr. 19, 2013.

(56) References Cited

OTHER PUBLICATIONS

Szymanski, et al. Single molecule nanoparticles of the conjugated polymer MEH-PPV, preparation and characterization by near-field scanning optical microscopy. J Phys Chem B. May 12, 2005;109(18):8543-6.

Thivierge, et al. Brilliant BODIPY-fluorene Copolymers With Dispersed Absorption and Emission Maxima. Macromolecules. May 24, 2011;44(10):4012-4015.

Thomas, et al. Chemical sensors based on amplifying fluorescent conjugated polymers. Chem Rev. Apr. 2007;107(4):1339-86. Epub Mar. 27, 2007.

Tian, et al. Amplified energy transfer in conjugated polymer nanoparticle tags and sensors. Nanoscale. Oct. 2010;2(10):1999-2011. doi: 10.1039/c0nr00322k. Epub Aug. 10, 2010.

Tsien. The green fluorescent protein. Annu Rev Biochem. 1998;67:509-44.

Tuncel, et al. Conjugated polymer nanoparticles. Nanoscale. Apr. 2010;2(4):484-94. doi: 10.1039/b9nr00374f. Epub Mar. 6, 2010.

U.S. Appl. No. 13/508,981 Office Action dated Mar. 28, 2018.

U.S. Appl. No. 14/774,971 Office Action dated Feb. 16, 2018.

Veiseh, et al. Specific targeting of brain tumors with an optical/magnetic resonance imaging nanoprobe across the blood-brain barrier. Cancer Res. Aug. 1, 2009;69(15):6200-7. doi: 10.1158/0008-5472.CAN-09-1157. Epub Jul. 28, 2009.

Wang, et al. Bioconjugation by copper(I)-catalyzed azide-alkyne [3+2] cycloaddition. J Am Chem Soc. Mar. 19, 2003;125(11):3192-3.

Wang, et al. Non-blinking semiconductor nanocrystals. Nature. Jun. 4, 2009;459(7247):686-9. doi: 10.1038/nature08072.

Wang, et al. Watching silica nanoparticles glow in the biological world. Anal. Chem. 2006;78(3):646-654.

Wu, et al. Bioconjugation of ultrabright semiconducting polymer dots for specific cellular targeting. J Am Chem Soc. Nov. 3, 2010;132(43):15410-7. doi: 10.1021/ja107196s.

Wu, et al. Conjugated polymer dots for multiphoton fluorescence imaging. J Am Chem Soc. Oct. 31, 2007;129(43):12904-5. Epub Oct. 6, 2007.

Wu, et al. Corrigendum: Immunofluorescent labeling of cancer marker Her2 and other cellular targets with semiconductor quantum dots. Nat Biotechnol. Jan. 2003;21(1):41-6. Epub Dec. 2, 2002.

Wu, et al. Design of highly emissive polymer dot bioconjugates for in vivo tumor targeting. Angew Chem Int Ed Engl. Apr. 4, 2011;50(15):3430-4. doi: 10.1002/anie.201007461. Epub Mar. 4, 2011.

Wu, et al. Energy Transfer in a Nanoscale Multichromophoric System: Fluorescent Dye-Doped Conjugated Polymer Nanoparticles. Phys Chem C Nanomater Interfaces. Feb. 14, 2008;112(6):1772-1781.

Wu, et al. Energy transfer mediated fluorescence from blended conjugated polymer nanoparticles. J Phys Chem B. Jul. 27, 2006;110(29):14148-54.

Wu, et al. Highly fluorescent semiconducting polymer dots for biology and medicine. Angew Chem Int Ed Engl. Mar. 11, 2013;52(11):3086-109. doi: 10.1002/anie.201205133. Epub Jan. 10, 2013.

Wu, et al. Immunofluorescent labeling of cancer marker Her2 and other cellular targets with semiconductor quantum dots. Nat Biotechnol. Jan. 2003;21(1):41-6. Epub Dec. 2, 2002.

Wu, et al. Multicolor conjugated polymer dots for biological fluorescence imaging. ACS Nano. Nov. 25, 2008;2(11):2415-23. doi: 10.1021/nn800590n.

Wu, et al. Preparation and encapsulation of highly fluorescent conjugated polymer nanoparticles. Langmuir. Mar. 28, 2006;22(7):2956-60.

Wu, et al. Ratiometric single-nanoparticle oxygen sensors for biological imaging. Angew Chem Int Ed Engl. 2009;48(15):2741-5. doi: 10.1002/anie.200805894.

Wu, et al. Swelling-controlled polymer phase and fluorescence properties of polyfluorene nanoparticles. Langmuir. Jun. 3, 2008;24(11):5855-61. doi: 10.1021/la8000762. Epub May 7, 2008.

Wu, et al. Ultrabright and bioorthogonal labeling of cellular targets using semiconducting polymer dots and click cAngew Chem Int Ed Engl. Dec. 3, 2010;49(49):9436-40. doi: 10.1002/anie.201004260. hemistry.

Wu. Fluorescent conjugated polymer dots for single molecule imaging and sensing application A Dissertation presented to the Graduate School of Clemson University. Dec. 1, 2008. pp. 1-182. http://etd.lib.clemson.edu/documents/1239895063/Wu_clemson_005D_10023.pdf.

Xie, et al. Luminescent CdSe—ZnSe quantum dots as selective Cu2+ probe. Spectrochimica Acta Part A. 2004; 60:2527-2530.

Xing, et al. Bioconjugated quantum dots for multiplexed and quantitative immunohistochemistry. Nat Protoc. 2007;2(5):1152-65.

Yang, et al. Deep-red electroluminescent polymers: Synthesis and characterization of new low-band-gap conjugated copolymers for light-emitting diodes and photovoltaic devices. Macromolecules 2005; 38:244-253.

Yao, et al. Blinking and nonradiant dark fraction of water-soluble quantum dots in aqueous solution. Proc Natl Acad Sci U S A. Oct. 4, 2005;102(40):14284-9. Epub Sep. 16, 2005.

Yao, et al., Fluorescent Nanoparticles Comprising Amphiphilic Rod-Coil Graft Copolymers, Macromolecules, 2008, 41:1438-43.

Ye, et al. A compact and highly fluorescent orange-emitting polymer dot for specific subcellular imaging. Chem Commun (Camb). Feb. 7, 2012;48(12):1778-80. doi: 10.1039/c2cc16486h. Epub Jan. 4, 2012.

Ye, et al. Ratiometric temperature sensing with semiconducting polymer dots. J Am Chem Soc. Jun. 1, 2011;133(21):8146-9. doi: 10.1021/ja202945g. Epub May 11, 2011.

Yu, et al. Nanoscale 3D tracking with conjugated polymer nanoparticles. J Am Chem Soc. Dec. 30, 2009;131(51):18410-4. doi: 10.1021/ja907228q.

Yu, et al. Stable functionalization of small semiconducting polymer dots via covalent cross-linking and their application for specific cellular imaging. Adv Mater. Jul. 10, 2012;24(26):3498-504. doi: 10.1002/adma.201201245. Epub Jun. 11, 2012.

Zhang, et al. Importance of having low-density functional groups for generating high-performance semiconducting polymer dots. ACS Nano. Jun. 26, 2012;6(6):5429-39. doi: 10.1021/nn301308w. Epub May 24, 2012.

Zhang, et al., Synthesis and characterization of a novel water-soluble block copolymer with a rod-coil structure, Materials Letters 60, (2006), pp. 679-684.

Zheng. Detection of the cancer marker CD146 expression in melanoma cells with semiconductor quantum dot label (Abstract). J Biomed Nanotechnol. Aug. 2010;6(4):303-11.

Zhu, et al. Efficient tuning nonlinear optical properties: Synthesis and characterization of a series of novel poly (aryleneethynylene) s co-containing BODIPY. Journal of Polymer Science Part A: Polymer Chemistry. 2008; 46(22):7401-7410.

Japanese office action dated Jan. 8, 2019 for JP Application No. 2017092547.

Office action dated Mar. 1, 2019 for U.S. Appl. No. 14/774,971.

Notice of Final Rejection dated Apr. 26, 2019, issued in corresponding Japanese application No. 2017-92547, filed Dec. 27, 2012, 16 pages.

Oki, Michinori et al., (Dictionary of Chemistry), Tokyo Kagaku Dojin, 1994, 160-161, 3 pages.

Japanese Penultimate Office Action dated Aug. 5, 2021, in Japanese Patent Application No. 2019-153611, with English translation.

European Patent Office Communication pursuant to Article 94(3) EPC, dated Mar. 30, 2022, issued in corresponding European Application No. 20166712.8, 17 pages.

Decision on Rejection dated Nov. 22, 2022, issued in corresponding Chinese Application No. 201910130972.5, filed on Dec. 27, 2012, and its English translation thereof, 14 pages.

Chen, D. et al., "Semiconducting polymer dots with bright narrow-band emission at 800 nm for biological applications," Chemical Science, 2017, 8, pp. 3390-3398.

Final Official Action dated Jun. 1, 2022, issued in corresponding Japanese Patent Application No. 2019-153611, filed Dec. 27, 2012, 2 pages.

(56) References Cited

OTHER PUBLICATIONS

Denial of Entry of Amendment dated Jun. 1, 2022, issued in corresponding Japanese Patent Application No. 2019-153611, filed Dec. 27, 2012, 5 pages.

* cited by examiner

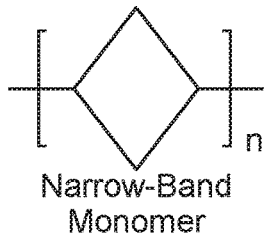
FIG. 1A
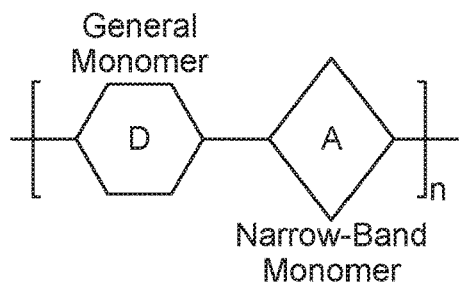
FIG. 1B
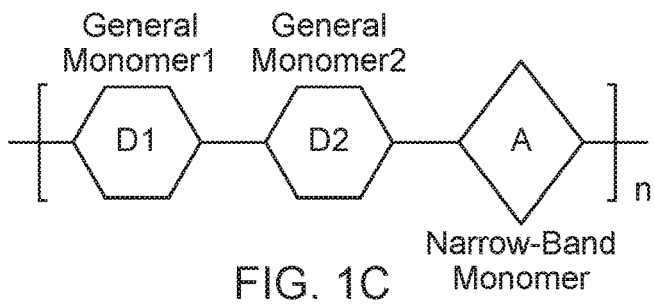
FIG. 1C
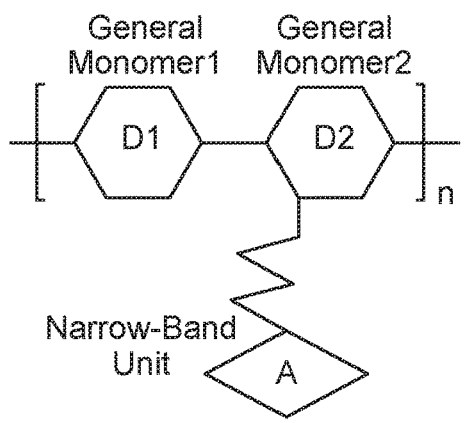
FIG. 1D
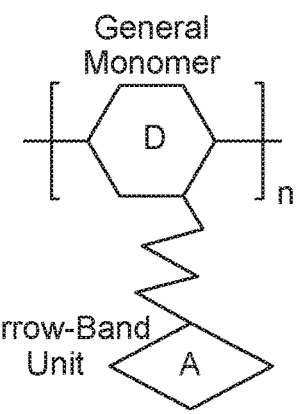
FIG. 1E
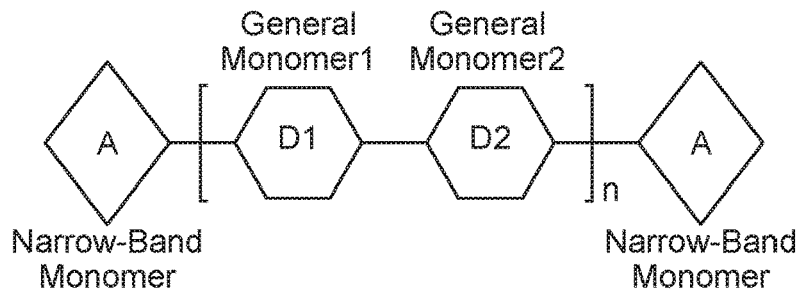
FIG. 1F
D: Energy Donor    A: Energy Acceptor
FIG. 1

G: General monomer        Ln: Lanthanide Complex $L_1$ = anion ligand: β-diketone; pyrazolone; isoxazolone; carboxylic acid; phthalocyanine; 8-hydroxyquinoline; pyrazol borate; porphyrin; and other macrocyclic ligands 4-(4,6-di(1H-pyrazol-1-yl)-1,3,5-triazin-2-yl)
-N,N-dimethylbenzenamine $L_2$ = netural ligands:

I: N-contained ligand: pyridine-, bipyridine-, tripyridine-, and 1,10-phenanthroline based diravitives containing N atom which can coordinate with lanthanide metal ions;

II: N-contained ligand:phosphine oxide

Ln= Ce(III), Pr(III), Nd(III), Sm(III), Eu(III), Tb(III),
Dy(III), Ho(III), Er(III), Tm(III), Yb(III).

Ln(TTA)₃Phen-NH₂     Ln(DPA)₂DPA-NH₂

Ln: Eu, Tb, Gd, La, Ce, Pr, Nd, Pm, Sm, Dy, Ho, Er, Tm, Yb

X/(X+Y)= 2: 100
X/(X+Y)= 5: 100
X/(X+Y)= 10:100
X/(X+Y)= 25: 100
X/(X+Y)= 50: 100

Polymer510

Polymer590

Polymer680

| | Abs | Em (405 nm) | Em (675 nm) | QY (405 nm) | QY (675 nm) | Particle size (nm) |
|---|---|---|---|---|---|---|
| 4%(2%)* | 675 nm | 693 nm | 693 nm | 24 | 23 | ~40 |
| 19%(25%)* | 675 nm | 702 nm | 702 nm | 0.3 | 0.7 | ~50 |

PFS Pdots

| Ratio (%)[a] | Abs (nm) | Em (nm) | QY (%)[b] | Particle Size (nm) |
|---|---|---|---|---|
| 1.5 | 675 | 693 | 30 | 19 |
| 3 | 675 | 696 | 7.9 | 18 |
| 7 | 675 | 700 | 2.1 | 21 |
| 9.4 | 675 | 701 | 1.8 | 13 |
| 19 | 675 | 702 | 0.4 | 16 |

PFS 5.5 Pdots

| Ratio (%)[a] | Abs (nm) | Em (nm) | QY (%)[b] | Particle Size (nm) |
|---|---|---|---|---|
| 1.5 | 695 | 711 | 17 | 19 |
| 5 | 695 | 715 | 3.4 | 12 |
| 10 | 695 | 722 | 1 | 16 |

FIG. 25E

|  | UV peak (nm) | PL peak (nm) | QY (%) ex@488 | DLS (nm) |
|---|---|---|---|---|
| PSPEG Pdot | 492 | 599 | 10 | 17 |
| PSMA Pdot | 493 | 596 | 15 | 19 |

FIG. 44C

2. Europium complex: EuDNM

CHROMOPHORIC POLYMER DOTS WITH NARROW-BAND EMISSION

CROSS REFERENCES TO RELATED APPLICATIONS

The present application is a continuation application of U.S. application Ser. No. 14/366,863, filed Jun. 19, 2014, now U.S. Pat. No. 10,150,841, issued Dec. 13, 2018, which is a U.S. National Phase Application under 35 U.S.C. § 371 of International Application No. PCT/US2012/071767, filed Dec. 27, 2012, which claims priority to U.S. Provisional Application No. 61/582,181, filed Dec. 30, 2011, and U.S. Provisional Application Na 61/607,455, filed on Mar. 6, 2012, the entirety of each of which is incorporated by reference herein.

STATEMENT AS TO RIGHTS TO INVENTIONS MADE UNDER FEDERALLY SPONSORED RESEARCH OR DEVELOPMENT

This invention was made with government support under grant number CA147831 awarded by the National Institutes of Health. The government has certain rights in the invention.

BACKGROUND OF THE INVENTION

Recent developments in fluorescence detection coupled with bioconjugation techniques are leading to a rapid proliferation of advanced fluorescence-based techniques in chemistry and the life sciences, such as fluorescence microscopy, flow cytometry, versatile biological assays, and biosensors. These fluorescence techniques make extensive use of organic dye molecules as probes. However, intrinsic limitations of the conventional dyes, such as low absorptivity and poor photostability, have posed difficulties in further developments of high-sensitivity imaging techniques and high-throughput assays. A number of strategies for developing brighter fluorescent probes have been pursued. For example, luminescent nanoparticles such as inorganic semiconductor quantum dots (Qdots) are under active development and now commercially available from Life Technologies (Invitrogen). (Bruchez, M.; Moronne, M.; Gin, P.; Weiss, S.; Alivisatos, A. P, Science 1998, 281, 2013-2016. Michalet, X.; Pinaud, F. F.; Bentolila, L. A.; Tsay, J. M.; Doose, S.; Li, J. J.; Sundaresan, G.; Wu, A. M.; Gambhir, S. S.; Weiss, S. Science 2005, 307, 538-544.) An alternative fluorescent nanoparticle is dye doped latex spheres, which exhibit improved brightness and photostability as compared to single fluorescent molecules because of multiple dye molecules per particle and the protective latex matrix. (Wang, L.; Wang, K. M.; Santra, S.; Zhao, X. J.; Hilliard, L. R.; Smith, J. E.; Wu, J. R.; Tan, W. H. Anal. Chem. 2006, 78, 646-654).

The limitations of current luminescent particles provide a need for exploring alternative strategies for the design of more highly fluorescent nanoparticles. Recently, fluorescence semiconducting polymer dots (Pdots) have attracted interest because of their fluorescence brightness and photostability as compared to Qdots and dye-loaded latex beads. The use of fluorescent polymer dots as fluorescent probes also can confer other useful aspects. Recently, surface functionalization has been achieved by a co-condensation scheme where amphiphilic polymer molecules bearing functional groups were blended with semiconducting polymers to form Pdots with surface reactive groups. Bioconjugation has been demonstrated by reacting the functional groups with biomolecules, and the Pdot-bioconjugates can specifically and effectively label biomolecules for cellular imaging, bioorthogonal labeling, and in vivo tumor targeting.

However, there can be drawbacks when the current Pdots are used as fluorescent probes in practical applications. Many biological applications can include detecting multiple targets simultaneously; thus, there is a need for probes that possess narrow-band emission peaks for spectral multiplexing. However, currently available Pdots can exhibit very broad emission spectra, which limit their usefulness in practical applications. The spectral width of a fluorescent probe can be characterized by the full width at half maximum (FWHM) of its emission peak. In general, currently available Pdots exhibit broad emission spectra with large FWHMs. Such broad emission spectra are a drawback for multi-target detection in biology. Therefore, there is a need to design and develop new type of Pdots with narrow-band emissions.

BRIEF SUMMARY OF THE INVENTION

The present invention provides chromophoric polymers that can form, for example, highly fluorescent chromophoric polymer dots with narrow-band emissions. The present invention also provides design considerations in synthesizing these chromophoric polymers, preparation methods for forming the relative polymer dots, and biological applications using the unique properties of narrow-band emissions. Chromophoric polymer dots with narrow-band emissions bring forward unique properties of highly fluorescent nanoparticle bioconjugates for a wide range of fluorescence-based applications.

In one aspect, the present invention provides chromophoric polymer dots with narrow-band emissions. The emission wavelength of the polymer dots can vary from ultraviolet to near infrared region. The full width at half maximum (FWHM) of the emission band is less than 70 nm. In some embodiments, the FWHM is less than about 65 nm. In some embodiments, the FWHM is less than about 60 nm. In some embodiments, the FWHM is less than about 55 nm. In some embodiments, the FWHM is less than about 50 nm. In some embodiments, the FWHM is less than about 45 nm. In some embodiments, the FWHM is less than about 40 nm. In some embodiments, the FWHM is less than about 35 nm. In some embodiments, the FWHM is less than about 30 nm. In some embodiments, the FWHM is less than about 25 nm. In some embodiments, the FWHM is less than about 20 nm. In some embodiments, the FWHM is less than about 10 nm. In some embodiments, the FWHM of the polymer dots described herein can range between about 5 nm to about 70 nm, from about 10 nm to about 60 nm, from about 20 nm to about 50 nm, or from about 30 nm to about 45 nm.

In some embodiments, the narrow-band emissive Pdots include at least one chromophoric polymer. The narrow-band emissive Pdots can also include a narrow-band emissive unit covalently attached to the chromophroic polymer, where the narrow-band emissive unit gives narrow-band emissions. The narrow-band emissive unit can be incorporated into the polymer backbone. The narrow-band emissive unit can also be covalently attached to the side chain, or terminal unit of the polymer. The narrow-band emissive Pdots can also include chromophoric polymer dots doped with inorganic materials, where the inorganic materials give narrow-band emissions. The narrow-band emissive Pdots can include only chromophoric polymers, where the chromophoric polymers give narrow-band emissions. The emission FWHM of the above Pdots is less than 70 nm. In certain embodiments, the FWHM is less than 60 nm, less than 50 nm, less than 40 nm, less than 30 nm, or less than 20 nm.

In some embodiments, the narrow-band emissive Pdots include chromophoric polymer dots chemically cross-linked with other narrow-band species such as dyes (e.g., polymer or small molecule dyes). The narrow-band emissive Pdots can include only chromophoric polymers that give narrow-band emissions. The emission FWHM of the above Pdots is less than 70 nm. In certain embodiments, the FWHM is less than 60 nm, less than 50 nm, less than 40 nm, less than 30 nm, or less than 20 nm.

In some embodiments, the narrow-band emissive polymer dots include at least one narrow-band emissive chromophoric polymers. The narrow-band emissive polymers in good solvents may exhibit broad emissions or narrow emissions. However, their nanoparticle form gives narrow-band emissions. The emission FWHM of the above Pdots is less than 70 nm. In certain embodiments, the FWHM is less than 60 nm, less than 50 nm, less than 40 nm, less than 30 nm, or less than 20 nm.

In some embodiments, the narrow-band emissive polymers for making Pdots can include narrow-band monomers. The narrow-band emissive polymer dots can also include any other monomers. The narrow-band monomers can be energy acceptors so that the final Pdots can exhibit narrow-band emissions. The narrow-band emissive chromophoric polymers in good solvents may exhibit broad emissions or narrow emissions. However, their nanoparticle form gives narrow-band emissions. The emission FWHM of the above Pdots is less than 70 nm. In certain embodiments, the FWHM is less than 60 nm, less than 50 nm, less than 40 nm, less than 30 nm, or less than 20 nm.

In some embodiments, the narrow-band emissive polymers for making Pdots include boron-dipyrromethene (4,4-difluoro-4-bora-3a,4a-diaza-s-indacene, BODIPY) based monomers and their derivatives as narrow-band monomers. BODIPY monomers and their derivatives include but are not limited to their alkyl derivatives, aryl derivatives, alkyne derivatives, aromatic derivatives, alkoxide derivatives, aza derivatives, BODIPY extended systems and BODIPY analogues. The narrow-band emissive polymers can also include any other monomers. The BODIPY based-monomers can be energy acceptors so that the final Pdots can exhibit narrow-band emissions. The narrow-band emissive chromophoric polymers in good solvents may exhibit broad emissions or narrow emissions. However, their nanoparticle form gives narrow-band emissions. The emission FWHM of the above Pdots is less than 70 nm. In certain embodiments, the FWHM is less than 60 nm, less than 50 nm, less than 40 nm, less than 30 nm, or less than 20 nm.

In some embodiments, the narrow-band emissive polymers for making Pdots include squaraine and their derivatives as narrow-band monomers. Squaraine derivatives include but are not limited to their alkyl derivatives, aryl derivatives, alkyne derivatives, aromatic derivatives, alkoxide derivatives, aza derivatives, their extended systems and analogues. The narrow-band emissive polymers can also include any other monomers. The squaraine and their derivatives can be energy acceptors so that the final Pdots can exhibit narrow-band emissions. The narrow-band emissive chromophoric polymers in good solvents may exhibit broad emissions or narrow emissions. However, their nanoparticle form gives narrow-band emissions. The emission FWHM of the above Pdots is less than 70 nm. In certain embodiments, the FWHM is less than 60 nm, less than 50 nm, less than 40 nm, less than 30 nm, or less than 20 nm.

In some embodiments, the narrow-band emissive polymers for making Pdots include metal complexes and their derivatives as narrow-band monomers. Metal complexes and their derivatives include but are not limited to their alkyl derivatives, aryl derivatives, alkyne derivatives, aromatic derivatives, alkoxide derivatives, aza derivatives, their extended systems and analogues. The narrow-band emissive polymers can also include any other monomers. The metals can be any metal such as Na, Li, Zn, Mg, Fe, Mn, Co, Ni, Cu, In, Si, Ga, Al, Pt, Pd, Ru, Rh, Re, Os, Ir, Ag, Au and so on. The metal complexes can be energy acceptors so that the final Pdots can exhibit narrow-band emissions. The narrow-band emissive chromophoric polymers in good solvents may exhibit broad emissions or narrow emissions. However, their nanoparticle form gives narrow-band emissions. The emission FWHM of the above Pdots is less than 70 nm. In certain embodiments, the FWHM is less than 60 nm, less than 50 nm, less than 40 nm, less than 30 nm, or less than 20 nm.

In some embodiments, the narrow-band emissive polymers for making Pdots include porphyrin, metalloporphyrin, and their derivatives as narrow-band monomers. Porphyrin, metalloporphyrin, and their derivatives include but are not limited to their alkyl derivatives, aryl derivatives, alkyne derivatives, aromatic derivatives, alkoxide derivatives, aza derivatives, their extended systems and analogues. The metals in the metalloporphyrins can be any metal such as Na, Li, Zn, Mg, Fe, Mn, Co, Ni, Cu, In, Si, Ga, Al, Pt, Pd, Ru, Rh, Re, Os, Ir, Ag, Au and so on. The narrow-band emissive polymers can also include any other monomers. The porphyrin, metalloporphyrin and their derivatives can be energy acceptors so that the final Pdots can exhibit narrow-band emissions. The narrow-band emissive chromophoric polymers in good solvents may exhibit broad emissions or narrow emissions. However, their nanoparticle form gives narrow-band emissions. The emission FWHM of the above Pdots is less than 70 nm. In certain embodiments, the FWHM is less than 60 nm, less than 50 nm, less than 40 nm, less than 30 nm, or less than 20 nm.

In some embodiments, the narrow-band emissive polymers for making Pdots include phthalocyanine and its derivatives as narrow-band monomers. Phthalocyanine derivatives include but are not limited to their alkyl derivatives, aryl derivatives, alkyne derivatives, aromatic derivatives, alkoxide derivatives, aza derivatives, their extended systems and analogues. The metals in the phthalocyanine derivatives can be any metal such as Na, Li, Zn, Mg, Fe, Mn, Co, Ni, Cu, In, Si, Ga, Al, Pt, Pd, Ru, Rh, Re, Os, Ir, Ag, Au and so on. The narrow-band emissive polymers can also include any other monomers. The phthalocyanine derivatives can be energy acceptors so that the final Pdots can exhibit narrow-band emissions. The narrow-band emissive chromophoric polymers in good solvents may exhibit broad emissions or narrow emissions. However, their nanoparticle form gives narrow-band emissions. The emission FWHM of the above Pdots is less than 70 nm. In certain embodiments, the FWHM is less than 60 nm, less than 50 nm, less than 40 nm, less than 30 nm, or less than 20 nm.

In some embodiments, the narrow-band emissive polymers for making Pdots include Lanthanide complexes and their derivatives as narrow-band monomers. Lanthanide complexes and their derivatives include but are not limited to their alkyl derivatives, aryl derivatives, alkyne derivatives, aromatic derivatives, alkoxide derivatives, aza derivatives, their extended systems and analogues. The narrow-band emissive polymers can also include any other monomers. The Lanthanide complexes and their derivatives can be energy acceptors so that the final Pdots can exhibit narrow-band emissions. The narrow-band emissive chromophoric polymers in good solvents may exhibit broad emissions or narrow emissions. However, their nanoparticle form gives narrow-band emissions. The emission FWHM of the above Pdots is less than 70 nm. In certain embodiments, the FWHM is less than 60 nm, less than 50 nm, less than 40 nm, less than 30 nm, or less than 20 nm.

In some embodiments, the narrow-band emissive polymers for making Pdots include perylene and its derivatives as narrow-band monomers. Perylene derivatives include but are not limited to their alkyl derivatives, aryl derivatives, alkyne derivatives, aromatic derivatives, alkoxide derivatives, aza derivatives, their extended systems and analogues. The narrow-band emissive polymers can also include any other monomers. The perylene derivatives can be energy acceptors so that the final Pdots can exhibit narrow-band emissions. The narrow-band emissive chromophoric polymers in good solvents may exhibit broad emissions or narrow emissions. However, their nanoparticle form gives narrow-band emissions. The emission FWHM of the above Pdots is less than 70 nm. In certain embodiments, the FWHM is less than 60 nm, less than 50 nm, less than 40 nm, less than 30 nm, or less than 20 nm.

In some embodiments, the narrow-band emissive polymers for making Pdots include cyanine and its derivatives as narrow-band monomers. Cyanine derivatives include but are not limited to their alkyl derivatives, aryl derivatives, alkyne derivatives, aromatic derivatives, alkoxide derivatives, aza derivatives, their extended systems and analogues. The narrow-band emissive polymers can also include any other monomers. The cyanine derivatives can be energy acceptors so that the final Pdots can exhibit narrow-band emissions. The narrow-band emissive chromophoric polymers in good solvents may exhibit broad emissions or narrow emissions. However, their nanoparticle form gives narrow-band emissions. The emission FWHM of the above Pdots is less than 70 nm. In certain embodiments, the FWHM is less than 60 nm, less than 50 nm, less than 40 nm, less than 30 nm, or less than 20 nm.

In some embodiments, the narrow-band emissive polymers for making Pdots include rhodamine and its derivatives as narrow-band monomers. Rhodamine derivatives include but are not limited to their alkyl derivatives, aryl derivatives, alkyne derivatives, aromatic derivatives, alkoxide derivatives, aza derivatives, their extended systems and analogues. The narrow-band emissive polymers can also include any other monomers. The rhodamine derivatives can be energy acceptors so that the final Pdots can exhibit narrow-band emissions. The narrow-band emissive chromophoric polymers in good solvents may exhibit broad emissions or narrow emissions. However, their nanoparticle form gives narrow-band emissions. The emission FWHM of the above Pdots is less than 70 nm. In certain embodiments, the FWHM is less than 60 nm, less than 50 nm, less than 40 nm, less than 30 nm, or less than 20 nm.

In some embodiments, the narrow-band emissive polymers for making Pdots include coumarin and its derivatives as narrow-band monomers. Coumarin derivatives include but are not limited to their alkyl derivatives, aryl derivatives, alkyne derivatives, aromatic derivatives, alkoxide derivatives, aza derivatives, their extended systems and analogues. The narrow-band emissive polymers can also include any other monomers. The coumarin derivatives can be energy acceptors so that the final Pdots can exhibit narrow-band emissions. The narrow-band emissive chromophoric polymers in good solvents may exhibit broad emissions or narrow emissions. However, their nanoparticle form gives narrow-band emissions. The emission FWHM of the above Pdots is less than 70 nm. In certain embodiments, the FWHM is less than 60 nm, less than 50 nm, less than 40 nm, less than 30 nm, or less than 20 nm.

In some embodiments, the narrow-band emissive polymers for making Pdots include xanthene and its derivatives as narrow-band monomers. Xanthene derivatives include but are not limited to their alkyl derivatives, aryl derivatives, alkyne derivatives, aromatic derivatives, alkoxide derivatives, aza derivatives, their extended systems and analogues. The narrow-band emissive polymers can also include any other monomers. The xanthene derivatives can be energy acceptors so that the final Pdots can exhibit narrow-band emissions. The narrow-band emissive chromophoric polymers in good solvents may exhibit broad emissions or narrow emissions. However, their nanoparticle form gives narrow-band emissions. The emission FWHM of the above Pdots is less than 70 nm. In certain embodiments, the FWHM is less than 60 nm, less than 50 nm, less than 40 nm, less than 30 nm, or less than 20 nm.

In another aspect, the present invention provides functionalized chromophoric polymer dot. The functionalized Pdot include a narrow-band emissive Pdot and a functional group that is physically or chemically attached to the Pdot.

In yet another aspect, the present invention discloses a bioconjugate of the polymer dots with narrow-band emissions. The bioconjugate is formed by the attachment of a biomolecule to one or more functional groups of the narrow-band emissive chromophoric polymer dot. The attachment may be direct or indirect.

In yet another aspect, methods of preparing narrow-band emissive chromophoric polymer dots are disclosed. In some embodiments, these chromophoric polymer dots can be formed using nanoprecipitation. The nanoprecipitation method involves the introduction of a solution of a polymer in a good solvent into a poor solvent, where the solubility collapse the polymer into a nanoparticle form. In certain embodiments, the chromophoric polymer with narrow-band emissions can be prepared using the mini-emulsion method.

BRIEF DESCRIPTION OF THE DRAWINGS

FIG. 1A shows the structure of a homopolymer that comprises only one narrow-band monomer. FIG. 1B shows the structure of a two-unit copolymer that includes one narrow-band monomer and one general monomer. The narrow-band monomer can be an energy-acceptor and the general monomer can be an energy-donor. Energy-transfer inside Pdots can result in narrow-band emissions. FIG. 1C shows the structure of a three-unit copolymer that includes one narrow-band monomer and two general monomers such as general monomer 1 (D1) and general monomer 2 (D2). The narrow-band monomer can be an energy-acceptor, general monomer 1 can be an energy-donor, general monomer 2 can also be a donor to the narrow-band monomer. In some embodiments, general monomer 2 can be simultaneously an energy-acceptor from monomer 1 and an energy-donor to the narrow-band monomer. Multi-step energy-transfer inside Pdots can result in narrow-band emissions. FIG. 1D shows the structure of a two-unit copolymer that includes the narrow-band unit cross-linked with the side-chains. The copolymer backbone can be an energy-donor, and the narrow-band unit can be an energy-acceptor. Energy-transfer inside Pdots can result in narrow-band emissions. FIG. 1E shows the structure of a homopolymer that includes the narrow-band unit crosslinked with the side-chains. The homopolymer backbone can be an energy-donor, and the narrow-band unit can be an energy-acceptor. Energy-transfer inside Pdots can result in narrow-band emissions. FIG. 1F shows a structure of a polymer that includes a narrow-band unit attached to a terminus of the polymer. The polymer backbone can be an energy-donor, and the narrow-band unit can be an energy-acceptor. Energy-transfer inside Pdots can result in narrow-band emissions. FIG. 1G-1L show example schematic structures of narrow-band emissive polymers that inclue a general monomer, a narrow-band monomer, and a functional monomer (or a functional group). The functional monomer can, e.g., provide reactive chemical group for chemical reactions or bioconjugation reactions.

FIG. 2A shows a non-limiting list of examples of the general monomers. FIGS. 2B-2N shows a non-limiting list of examples of the narrow-band emissive copolymer including one general monomer chosen from FIG. 2A and different BODIPY derivatives or other boron-containing units as narrow-band monomers. FIGS. 2M and 2N show some specific examples of the narrow-band emissive copolymers based on the chemical structures in FIGS. 2B-2L.

FIG. 3A shows example D1 monomers. FIGS. 3B, 3C, 3D and 3E show example D2 monomers and example derivatives of D2 monomers. The derivatives of D2 monomers are marked as D2' monomers in the figures. The general D1 type monomers can, e.g., be copolymerized with the D2 type (or D2' type) and the narrow-band monomer to obtain narrow-band emissive polymer. Any, e.g., of the D1 type monomers, D2 type, or D2' type monomers can also be separately used to copolymerize with one narrow-band monomer to obtain the narrow-band emissive polymers as in FIG. 1. Rather than copolymerization, a narrow band emissive unit can, e.g., be attached to the side chains or termini of a polymer formed from any of the D1 type monomers, D2 type, or D2' type monomers.

FIG. 10A shows example schematic structures of narrow-band emissive polymers that include lanthanide complexes as narrow-band emissive units. FIG. 10B shows example structures of europium (Eu) and terbium (Tb) complexes as narrow-band monomers in the listed polymers. The D type monomers can be energy donors that transfer energy to lanthanide complex. FIG. 10C shows example chemical structures of general polymers as donors that can transfer energy to lanthanide complexes in narrow-band emissive Pdots. FIG. 10D shows example chemical structures of anionic ligand (L1) to form lanthanide complexes. FIG. 10E shows example chemical structures of the substituted groups in the ligands (L1 and L2) of lanthanide complexes. FIG. 10F shows example chemical structures of neutral ligands (L2) to form lanthanide complexes. FIG. 10G shows a schematic illustration of forming narrow-band emissive polymers that include general polymer as donors and the lanthanide complex as narrow-band emissive units. Both the general polymer and lanthanide complexes include amino groups which can be, e.g., covalently cross-linked with an amine-reactive polymer to form the lanthanide-complex grafted polymers for preparing narrow-band emissive Pdots. FIG. 10H shows schematic illustration of forming narrow-band emissive polymers that include only the lanthanide complex as narrow-band emissive units. The lanthanide complexes include amino groups which can be, e.g., covalently cross-linked with an amine-reactive polymer to form the lanthanide-complex grafted polymers for preparing narrow-band emissive Pdots.

FIG. 18A shows the side scattering (SSC) versus forward scattering (FSC). FIG. 18B shows the fluorescence intensity distributions of the MCF-7 cells labeled with Polymer590 Pdots. Blue curve is the negative control, and orange curve is the positive labeling. FIG. 18C shows the fluorescence intensity distributions of the MCF-7 cells labeled with Polymer680 Pdots. Green curve is the negative control, and red curve is the positive labeling.

FIG. 25E shows photophysical data and particle size of the narrow-band emissive PFS Pdots and PFS 5.5 Pdots with varying squaraine ratio.

FIG. 29E shows fluorescence spectra of chromophoric polymer dots of polymer 2b (single polymer) (I in FIG. 29D). FIG. 29F shows fluorescence spectra of blended chromophoric polymer dots formed from II in FIG. 29D (10% mol BODIPY polymer:PFBT=1:10). FIG. 29G shows fluorescence spectra of chromophoric polymer dots of polymer 3b (single polymer) (III in FIG. 29D). FIG. 29H shows fluorescence spectra of blended chromophoric polymer dots formed from IV in FIG. 29D (10% mol deep red BODIPY polymer:PFTBT:PFBT=10:30:60).

FIG. 44C shows the optical performance of PFVBT-BODIPY2 Pdots functionalized with PSPEG and PSMA polymers.

DETAILED DESCRIPTION OF THE INVENTION

Figure 1:
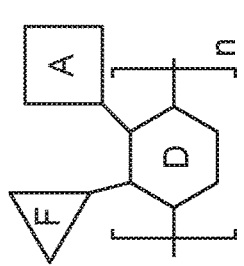
FIG. 1 shows example schematic structures of narrow-band emissive polymers.
Figure 1:
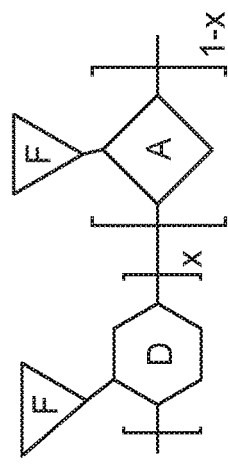
Figure 1:
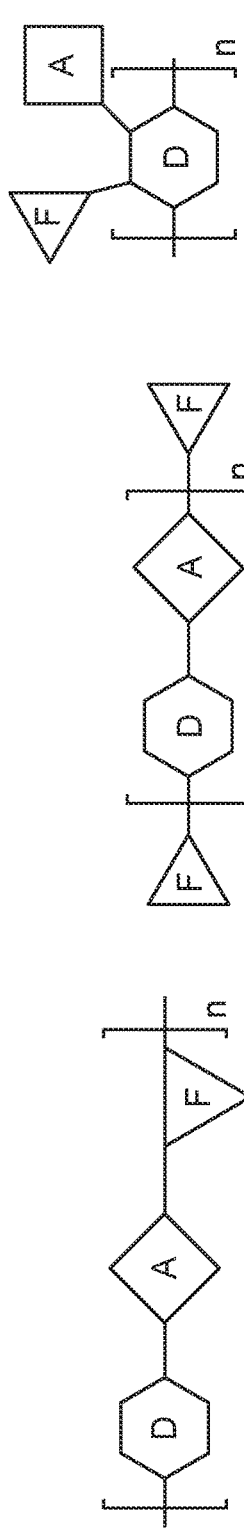
Figure 1:
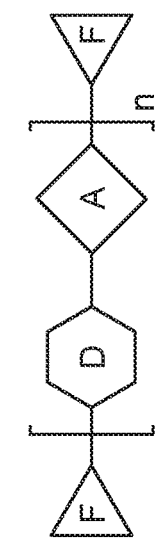
Figure 1:
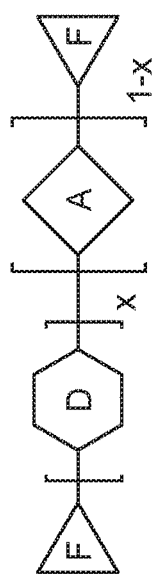
Figure 1:
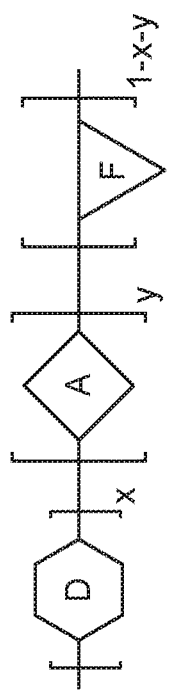

Embodiments of the present invention relate to a novel class of fluorescent probe, referred to as narrow-band emissive chromophoric polymer dots, and their biomolecular conjugates for a variety of applications, including but not limited to flow cytometry, fluorescence activated sorting, immunofluorescence, immunohistochemistry, fluorescence multiplexing, single molecule imaging, single particle tracking, protein folding, protein rotational dynamics, DNA and gene analysis, protein analysis, metabolite analysis, lipid analysis, FRET based sensors, high throughput screening, cell detection, bacteria detection, virus detection, biomarker detection, cellular imaging, in vivo imaging, bioorthogonal labeling, click reactions, fluorescence-based biological assays such as immunoassays and enzyme-based assays, and a variety of fluorescence techniques in biological assays and measurements.

While not limited to any particular theory or concept, the present invention is based at least in-part on the fact that fluorescent Pdots based on semiconducting polymers typically possess broad emission spectra with FWHM larger than 70 nm. Such a broad-band emission can be a significant drawback for fluorescence techniques in biology. To overcome this challenge with the current Pdots, the present invention provides compositions and methods to obtain next-generation Pdots with narrow-band emissions. Furthermore, the present invention provides compositions and methods that allow bioconjugation to polymer dots while also maintaining their narrow-band emissions.

In some aspects, the properties of the narrow-band emissive polymers and polymer dots can be dependent on the polymer structures. Therefore, the polymer backbone (main chain), side chains, terminal units, and substituted groups can be varied to obtain specific properties. In some embodiments, the optical properties of the narrow-band polymer and polymer dots can be tuned by varying the structures of the polymer backbone (main chain). For example, the absorption and fluorescence emission can be red-shifted by increasing the conjugation length of the polymer backbone, or the absorption and fluorescence emission can be blue-shifted by decreasing the conjugation length of the polymer backbone. As another example, the inclusion of BT monomer can increase the photostability of the resulting polymer dot compared with polymers that do not have BT in their polymer backbone.

In some embodiments, the optical properties of the narrow-band emissive polymer and polymer dots can be modified by varying the side chains, terminal units, and substituent groups. For example, the fluorescence emission wavelength can be tuned by attaching chromophoric units to the side-chains and/or termini. The emission bandwidth, fluorescence quantum yield, fluorescence lifetime, photostability, and other properties can also be modified by varying the polymer side-chain and/or terminal units in addition to the polymer backbone. For example, fluorescence quantum yield can be increased in some polymer dots by attaching bulky side-chain groups to minimize inter-chain interactions in polymer dots. In another example, the attachment and presence of anti-fade agents, such as derivatives of butylated hydroxytoluene, trolox, carotenoids, ascorbate, reduced glutathione, propyl gallate, propionic acid stearyl ester, hydroxyquinone, p-phenylenediamine, triphenylamine, beta mercaptoethanol, trans-stilbene, imidazole, Mowiol, or combinations thereof, or any other combinations of anti-fade agents known in the art, to the polymer via side chains, terminal units, backbone, and/or substituent groups, can increase quantum yield, photostability, or both. These anti-fade agents generally act as anti-oxidants to reduce oxygen, and/or act as scavengers of reactive oxygen species, and/or act to suppress photogenerated hole polarons within the polymer dot. In a preferred embodiment, the anti-fade agent is hydrophobic in nature so as not to adversely affect the packing and/or colloidal stability of the polymer dot. In some embodiments, the absorption, emission peak, emission bandwidth, fluorescence quantum yield, fluorescence lifetime, photostability, and other properties of the narrow-band emissive polymer and polymer dots can also be modified by substituent groups on the polymers. For example, the degree of electron-donating or electron-withdrawing capability of the substituent groups can be used to tune the optical properties. For example, the two-photon absorption cross sections can be increased by modular structures such as donor-pi-donor or donor-acceptor-donor units.

In some embodiments, the colloidal properties of the polymer dots can be improved by varying the polymer backbone (main chain), side chains, terminal units, and substitutent groups. In some embodiments, the polymer dots can include hydrophobic functional groups in the side-chains, terminal units, and/or substitutent groups. In other embodiments, the polymer dots can include hydrophilic functional groups in the side-chains, terminal units, and/or substitutent groups. The length, size, and nature of the hydrophobic/hydrophilic side chains can modify the chain-chain interactions, and control the packing of the polymers, and affect the colloidal stability and size of the polymer dots. The length, size, and nature of the hydrophobic/hydrophilic side chains can also affect the absorption, emission peak, emission bandwidth, fluorescence quantum yield, fluorescence lifetime, photostability, and other properties of the narrow-band emissive polymer and polymer dots. For example, a large number of very hydrophilic functional groups can reduced the brightness of the polymer dots, and/or broaden the emission spectrum, and/or also adversely affect their colloidal stability and nonspecific binding properties.

Definitions

As used herein, the term "chromophoric polymer nanoparticle" or "chromophoric polymer dot" refers to a structure comprising one or more polymers (e.g., chromophoric polymers) that have been formed into a stable sub-micron sized particle. The chromophoric polymer nanoparticles or chromophoric polymer dots of the present invention can, e.g., include a single polymer or a plurality of polymers that can be, e.g., chemically crosslinked and/or physically blended. "Polymer dot" and "Pdot" can be used interchangeably to represent "chromophoric nanoparticle" or "chromophoric polymer dot". The chromophoric polymer dots provided herein may be formed by any method known in the art, including without limitation, methods relying on precipitation, methods relying on the formation of emulsions (e.g. mini or micro emulsion), and methods relying on condensation. Pdots described herein are different and distinct from nanoparticles formed from an aggregate of polyelectrolytes.

As used herein, "polymer" is a molecule composed of at least 2 repeating structural units typically connected by covalent chemical bonds. The repeating structural unit may be one type of monomer, and the resulting polymer is a homopolymer. In some embodiments, the polymers can include two different types of monomers, or three different types of monomers, or more types of monomers. One of ordinary skill in the art will appreciate that the different types of monomers can be distributed along a polymer chain in a variety of ways. For example, three different types of monomers can be randomly distributed along the polymer. It will similarly be appreciated that the distribution of monomers along the polymer can be represented in different ways. The number of repeating structural units (e.g., monomers) along the length of a polymer can be represented by "n." In some embodiments, n can range, e.g., from at least 2, from at least 100, from at least 500, from at least 1000, from at least 5000, or from at least 10,000, or from at least 100,000, or higher. In certain embodiments, n can range from 2 to 10000, from 20 to 10000, from 20 to 500, from 50 to 300, from 100 to 1000, or from 500 to 10,000.

Polymers generally have extended molecular structures comprising backbones that optionally contain pendant side groups. The polymers provided herein can include, but are not limited to, linear polymers and branched polymers such as star polymers, comb polymers, brush polymers, ladders, and dendrimers. As described further herein, the polymers can include semiconducting polymers generally well known in the art.

As used herein, the term "chromophoric polymer" is a polymer in which at least a portion of the polymer includes chromophoric units. The term "chromophore" is given its ordinary meaning in the art. A chromophore absorbs certain wavelength of light from UV to near infrared region, and may be or may not be emissive. The chromophoric polymer can, e.g., be a "conjugated polymer". The term "conjugated polymer" is recognized in the art. Electrons, holes, or electronic energy, can be conducted along the conjugated structure. In some embodiments, a large portion of the polymer backbone can be conjugated. In some embodiments, the entire polymer backbone can be conjugated. In some embodiments, the polymer can include conjugated structures in their side chains or termini. In some embodiments, the conjugated polymer can have conducting properties, e.g. the polymer can conduct electricity. In some embodiments, the conjugated polymer can have semiconducting properties, e.g. the polymers can exhibit a direct band gap, leading to an efficient absorption or emission at the band edge.

A "chromophoric unit" in this invention includes, but is not limited to, a unit of structures with delocalized pi-electrons, a unit of small organic dye molecules, and/or a unit of metal complexes. Examples of chromophoric polymers can include polymers comprising units of structures with delocalized pi-electrons such as semiconducting polymers, polymers comprising units of small organic dye molecules, polymers comprising units of metal complexes, and polymers comprising units of any combinations thereof. The chromophoric unit can be incorporated into the polymer backbone. The chromophoric unit can also be covalently attached to the side chain, or the terminal unit of the polymer.

An "emission spectrum" of a polymer dot is defined as the spectrum of wavelengths (or frequencies) of electromagnetic radiation emitted by the polymer dot when it is excited to a higher energy state and then returned to a lower energy state. The width of the emission spectrum can be characterized by its full width at half maximum (FWHM). The FWHM of an emission spectrum is defined as the distance between points on the emission curve at which the emission intensity reaches half its maximum value. The emission properties of a polymer dot can also be characterized by fluorescence quantum yield and fluorescence lifetime. The fluorescence quantum yield gives the efficiency of the fluorescence process. It is defined as the ratio of the number of photons emitted to the number of photons absorbed by the Pdots. The fluorescence lifetime is defined as the average time the polymer dot stays in its excited state before emitting a photon. All the above defined parameters, such as emission spectrum, FWHM, fluorescence quantum yield, and fluorescence lifetime can be experimentally measured. In this invention, these parameters can be specifically used to characterize the narrow-band emissive Pdots.

As used herein, the term "alkyl" refers to a straight or branched, saturated, aliphatic radical having the number of carbon atoms indicated. For example, $C_1$-$C_6$ alkyl includes, but is not limited to, methyl, ethyl, propyl, isopropyl, butyl, isobutyl, sec-butyl, tert-butyl, pentyl, isopentyl, hexyl, etc. Other alkyl groups include, but are not limited to heptyl, octyl, nonyl, decyl, etc. Alkyl can include any number of carbons, such as 1-2, 1-3, 1-4, 1-5, 1-6, 1-7, 1-8, 1-9, 1-10, 2-3, 2-4, 2-5, 2-6, 3-4, 3-5, 3-6, 4-5, 4-6 and 5-6. The alkyl group is typically monovalent, but can be divalent, such as when the alkyl group links two moieties together. As used herein, the term "heteroalkyl" refers to a straight or branched, saturated, aliphatic radical of carbon atoms, where at least one of the carbon atoms is replaced with a heteroatom, such as N, O or S. Additional heteroatoms can also be useful, including, but not limited to, B, Al, Si and P.

The term "lower" referred to above and hereinafter in connection with organic radicals or compounds respectively defines a compound or radical which can be branched or unbranched with up to and including 7, preferably up to and including 4 and (as unbranched) one or two carbon atoms.

As used herein, the term "alkylene" refers to an alkyl group, as defined above, linking at least two other groups, i.e., a divalent hydrocarbon radical. The two moieties linked to the alkylene can be linked to the same atom or different atoms of the alkylene. For instance, a straight chain alkylene can be the bivalent radical of —$(CH_2)_n$—, where n is 1, 2, 3, 4, 5 or 6. Alkylene groups include, but are not limited to, methylene, ethylene, propylene, isopropylene, butylene, isobutylene, sec-butylene, pentylene and hexylene.

The groups described herein can be substituted or unsubstituted. Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be a variety of groups, such as alkyl, aryl, cyano (CN), amino, sulfide, aldehyde, ester, ether, acid, hydroxyl or halide. Substituents can be a reactive group, such as but not limited to chloro, bromo, iodo, hydroxyl, or amino. Suitable substituents can be selected from: —OR', =O, =NR', =N—OR', —NR'R", —SR', -halogen, —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NH—C(NH$_2$)=NH, —NR'C(NH$_2$)=NH, —NH—C(NH$_2$)=NR', —S(O)R', —S(O)$_2$R', —S(O)$_2$NR'R", —CN and —NO$_2$ in a number ranging from zero to (2m'+1), where m' is the total number of carbon atoms in such radical. R', R" and R''' each independently refer to hydrogen, unsubstituted ($C_1$-$C_8$)alkyl and heteroalkyl, unsubstituted aryl, alkoxy or thioalkoxy groups, or aryl-($C_1$-$C_4$)alkyl groups. When R' and R" are attached to the same nitrogen atom, they can be combined with the nitrogen atom to form a 5-, 6-, or 7-membered ring. For example, —NR'R" is meant to include 1-pyrrolidinyl and 4-morpholinyl. From the above discussion of substituents, one of skill in the art will understand that the term "alkyl" is meant to include groups such as haloalkyl (e.g., —$CF_3$ and —$CH_2CF_3$) and acyl (e.g., —$C(O)CH_3$, —$C(O)CF_3$, —$C(O)CH_2OCH_3$, and the like).

As used herein, the term "alkoxy" refers to an alkyl group having an oxygen atom that either connects the alkoxy group to the point of attachment or is linked to two carbons of the alkoxy group. Alkoxy groups include, for example, methoxy, ethoxy, propoxy, iso-propoxy, butoxy, 2-butoxy, iso-butoxy, sec-butoxy, tert-butoxy, pentoxy, hexoxy, etc. The alkoxy groups can be further substituted with a variety of substituents described within. For example, the alkoxy groups can be substituted with halogens to form a "haloalkoxy" group.

As used herein, the term "alkenyl" refers to either a straight chain or branched hydrocarbon of 2 to 6 carbon atoms, having at least one double bond. Examples of alkenyl groups include, but are not limited to, vinyl, propenyl, isopropenyl, 1-butenyl, 2-butenyl, isobutenyl, butadienyl, 1-pentenyl, 2-pentenyl, isopentenyl, 1,3-pentadienyl, 1,4-pentadienyl, 1-hexenyl, 2-hexenyl, 3-hexenyl, 1,3-hexadienyl, 1,4-hexadienyl, 1,5-hexadienyl, 2,4-hexadienyl, or 1,3,5-hexatrienyl.

As used herein, the term "alkenylene" refers to an alkenyl group, as defined above, linking at least two other groups, i.e., a divalent hydrocarbon radical. The two moieties linked to the alkenylene can be linked to the same atom or different atoms of the alkenylene. Alkenylene groups include, but are not limited to, ethenylene, propenylene, isopropenylene, butenylene, isobutenylene, sec-butenylene, pentenylene and hexenylene.

As used herein, the term "alkynyl" refers to either a straight chain or branched hydrocarbon of 2 to 6 carbon atoms, having at least one triple bond. Examples of alkynyl groups include, but are not limited to, acetylenyl, propynyl, 1-butynyl, 2-butynyl, isobutynyl, sec-butynyl, butadiynyl, 1-pentynyl, 2-pentynyl, isopentynyl, 1,3-pentadiynyl, 1,4-pentadiynyl, 1-hexynyl, 2-hexynyl, 3-hexynyl, 1,3-hexadiynyl, 1,4-hexadiynyl, 1,5-hexadiynyl, 2,4-hexadiynyl, or 1,3,5-hexatriynyl.

As used herein, the term "alkynylene" refers to an alkynyl group, as defined above, linking at least two other groups, i.e., a divalent hydrocarbon radical. The two moieties linked to the alkynylene can be linked to the same atom or different atoms of the alkynylene. Alkynylene groups include, but are not limited to, ethynylene, propynylene, isopropynylene, butynylene, sec-butynylene, pentynylene and hexynylene.

As used herein, the term "alkyl amine" refers to an alkyl groups as defined within, having one or more amino groups. The amino groups can be primary, secondary or tertiary. The alkyl amine can be further substituted with a hydroxy group. Alkyl amines can include, but are not limited to, ethyl amine, propyl amine, isopropyl amine, ethylene diamine and ethanolamine. The amino group can link the alkyl amine to the point of attachment with the rest of the compound, be at the omega position of the alkyl group, or link together at least two carbon atoms of the alkyl group.

As used herein, the term "halogen" or "halide" refers to fluorine, chlorine, bromine and iodine. As used herein, the term "haloalkyl" refers to alkyl as defined above where some or all of the hydrogen atoms are substituted with halogen atoms. Halogen (halo) preferably represents chloro or fluoro, but may also be bromo or iodo. As used herein, the term "halo-alkoxy" refers to an alkoxy group having at least one halogen. Halo-alkoxy is as defined for alkoxy where some or all of the hydrogen atoms are substituted with halogen atoms. The alkoxy groups can be substituted with 1, 2, 3, or more halogens. When all the hydrogens are replaced with a halogen, for example by fluorine, the compounds are per-substituted, for example, perfluorinated. Halo-alkoxy includes, but is not limited to, trifluoromethoxy, 2,2,2,-trifluoroethoxy, perfluoroethoxy, etc.

As used herein, the term "cycloalkyl" refers to a saturated or partially unsaturated, monocyclic, fused bicyclic or bridged polycyclic ring assembly containing from 3 to 12 ring atoms, or the number of atoms indicated. Monocyclic rings include, for example, cyclopropyl, cyclobutyl, cyclopentyl, cyclohexyl, and cyclooctyl. Bicyclic and polycyclic rings include, for example, norbornane, decahydronaphthalene and adamantane. For example, $C_{3-8}$cycloalkyl includes cyclopropyl, cyclobutyl, cyclopentyl, cyclohexyl, cyclooctyl, and norbornane.

As used herein, the term "cycloalkylene" refers to a cycloalkyl group, as defined above, linking at least two other groups, i.e., a divalent hydrocarbon radical. The two moieties linked to the cycloalkylene can be linked to the same atom or different atoms of the cycloalkylene. Cycloalkylene groups include, but are not limited to, cyclopropylene, cyclobutylene, cyclopentylene, cyclohexylene, and cyclooctylene.

As used herein, the term "heterocycloalkyl" refers to a ring system having from 3 ring members to about 20 ring members and from 1 to about 5 heteroatoms such as N, O and S. Additional heteroatoms can also be useful, including, but not limited to, B, Al, Si and P. The heteroatoms can also be oxidized, such as, but not limited to, —S(O)— and —S(O)$_2$—.

As used herein, the term "heterocycloalkylene" refers to a heterocycloalkyl group, as defined above, linking at least two other groups. The two moieties linked to the heterocycloalkylene can be linked to the same atom or different atoms of the heterocycloalkylene.

As used herein, the term "aryl" refers to a monocyclic or fused bicyclic, tricyclic or greater, aromatic ring assembly containing 6 to 16 ring carbon atoms. For example, aryl may be phenyl, benzyl, azulenyl or naphthyl. "Arylene" means a divalent radical derived from an aryl group. Aryl groups can be mono-, di- or tri-substituted by one, two or three radicals selected from alkyl, alkoxy, aryl, hydroxy, halogen, cyano, amino, amino-alkyl, trifluoromethyl, alkylenedioxy and oxy-$C_2$-$C_3$-alkylene; all of which are optionally further substituted, for instance as hereinbefore defined; or 1- or 2-naphthyl; or 1- or 2-phenanthrenyl. Alkylenedioxy is a divalent substitute attached to two adjacent carbon atoms of phenyl, e.g. methylenedioxy or ethylenedioxy. Oxy-$C_2$-$C_3$-alkylene is also a divalent substituent attached to two adjacent carbon atoms of phenyl, e.g. oxyethylene or oxypropylene. An example for oxy-$C_2$-$C_3$-alkylene-phenyl is 2,3-dihydrobenzofuran-5-yl.

Aryl groups can include, but are not limited to, naphthyl, phenyl or phenyl mono- or disubstituted by alkoxy, phenyl, halogen, alkyl or trifluoromethyl, phenyl or phenyl-mono- or disubstituted by alkoxy, halogen or trifluoromethyl, and in particular phenyl.

As used herein, the term "arylene" refers to an aryl group, as defined above, linking at least two other groups. The two moieties linked to the arylene are linked to different atoms of the arylene. Arylene groups include, but are not limited to, phenylene.

As used herein, the terms "alkoxy-aryl" or "aryloxy" refers to an aryl group, as defined above, where one of the moieties linked to the aryl is linked through an oxygen atom. Alkoxy-aryl groups include, but are not limited to, phenoxy ($C_6H_5O$—). The present invention also includes alkoxy-heteroaryl or heteroaryloxy groups.

As used herein, the term "heteroaryl" refers to a monocyclic or fused bicyclic or tricyclic aromatic ring assembly containing 5 to 16 ring atoms, where from 1 to 4 of the ring atoms are a heteroatom each N, O or S. For example, heteroaryl includes pyridyl, indolyl, indazolyl, quinoxalinyl, quinolinyl, isoquinolinyl, benzothienyl, benzofuranyl, furanyl, pyrrolyl, thiazolyl, benzothiazolyl, oxazolyl, isoxazolyl, triazolyl, tetrazolyl, pyrazolyl, imidazolyl, thienyl, or any other radicals substituted, especially mono- or di-substituted, by e.g. alkyl, nitro or halogen. Suitable groups for the present invention can also include heteroarylene and heterarylene-oxy groups similar to the description above for arylene and arylene-oxy groups.

Similarly, aryl and heteroaryl groups described herein can be substituted or unsubstituted. Substituents for the aryl and heteroaryl groups are varied, such as alkyl, aryl, CN, amino, sulfide, aldehyde, ester, ether, acid, hydroxyl or halide. Substituents can be a reactive group, such as but not limited to chloro, bromo, iodo, hydroxyl, or amino. Substituents can be selected from: -halogen, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R', —NR'—C(O)NR"R'", —NH—C(NH$_2$)=NH, —NR'C(NH$_2$)=NH, —NH—C(NH$_2$)=NR', —S(O)R', —S(O)$_2$R', —S(O)$_2$NR'R", —N$_3$, —CH(Ph)$_2$, in a number ranging from zero to the total number of open valences on the aromatic ring system; and where R', R" and R'" are independently selected from hydrogen, ($C_1$-$C_5$)alkyl and heteroalkyl, unsubstituted aryl and heteroaryl, (unsubstituted aryl)-($C_1$-$C_4$)alkyl, and (unsubstituted aryl)oxy-($C_1$-$C_4$)alkyl.

As used herein, the term "alkyl-aryl" refers to a radical having an alkyl component and an aryl component, where the alkyl component links the aryl component to the point of attachment. The alkyl component is as defined above, except that the alkyl component is at least divalent in order to link to the aryl component and to the point of attachment. In some instances, the alkyl component can be absent. The aryl component is as defined above. Examples of alkyl-aryl groups include, but are not limited to, benzyl. The present invention also includes alkyl-heteroaryl groups.

As used herein, the term "alkenyl-aryl" refers to a radical having both an alkenyl component and an aryl component, where the alkenyl component links the aryl component to the point of attachment. The alkenyl component is as defined above, except that the alkenyl component is at least divalent in order to link to the aryl component and to the point of attachment. The aryl component is as defined above. Examples of alkenyl-aryl include ethenyl-phenyl, among others. The present invention also includes alkenyl-heteroaryl groups.

As used herein, the term "alkynyl-aryl" refers to a radical having both an alkynyl component and a aryl component, where the alkynyl component links the aryl component to the point of attachment. The alkynyl component is as defined above, except that the alkynyl component is at least divalent in order to link to the aryl component and to the point of attachment. The aryl component is as defined above. Examples of alkynyl-aryl include ethynyl-phenyl, among others. The present invention also includes alkynyl-heteroaryl groups.

As will be appreciated by one of ordinary skill in the art, the various chemical terms defined herein can be used for describing chemical structures of the polymers and monomers of the present invention. For example, a variety of the monomer derivatives (e.g., BODIPY derivatives) can include a variety of the chemical substituents and groups described herein. For example, in some embodiments, derivatives of the various monomers can be substituted with hydrogen, deuterium, alkyl, aralkyl, aryl, alkoxy-aryl, N-dialkyl-4-phenyl, N-diphenyl-4-phenyl, N-dialkoxyphenyl-4-phenyl, amino, sulfide, aldehyde, ester, ether, acid, and/or hydroxyl.

Optical Properties of Narrow-Band Emissive Chromophoric Polymer Dots

The present invention provides, in one embodiment, chromophoric polymer dots with narrow-band emissions. The emission wavelength of the polymer dots can vary from ultraviolet to the near infrared region. The chromophoric polymer dot includes at least one chromophoric polymer. As provided herein, the chemical composition and structure of the chromophoric polymer can be tuned to obtain small bandwidth (FWHM) of the Pdot emission. Other species such as narrow-band emissive units, metal complexes or inorganic materials can be blended or chemically cross linked within the chromophric polymer dots to obtain small bandwidth (FWHM) of the Pdot emission. In some embodiments, the FWHM is less than about 70 nm. In some embodiments, the FWHM is less than about 65 nm. In some embodiments, the FWHM is less than about 60 nm. In some embodiments, the FWHM is less than about 55 nm. In some embodiments, the FWHM is less than about 50 nm. In some embodiments, the FWHM is less than about 45 nm. In some embodiments, the FWHM is less than about 40 nm. In some embodiments, the FWHM is less than about 35 nm. In some embodiments, the FWHM is less than about 30 nm. In some embodiments, the FWHM is less than about 25 nm. In certain embodiments, the FWHM is less than about 24 nm, 23 nm, 22 nm, 21 nm, 20 nm, 19 nm, 18 nm, 17 nm, 16 nm, 15 nm, 14 nm, 13 nm, 12 nm, 11 nm, 10 nm, or less. In some embodiments, the FWHM of the polymer dots described herein can range between about 5 nm to about 70 nm, from about 10 nm to about 60 nm, from about 20 nm to about 50 nm, or from about 30 nm to about 45 nm.

In some embodiments, the chemical composition and structure of the chromophoric polymer in the polymer dots can affect the absorption spectrum of the narrow-band emissive Pdots. The absorption peak can shift from ultraviolet region to near infrared region. In some embodiments, the absorption peak of the narrow-band emissive polymer dots can be tuned to a certain laser wavelength. In some embodiments, for example, the absorption peak can be tuned to around 266 nm. In some embodiments the absorption peak can be tuned to around 355 nm. In some embodiments, the absorption peak can be tuned to around 405 nm. In some embodiments, the absorption peak can be tuned to around 450 nm. In some embodiments, the absorption peak can be tuned to around 488 nm. In some embodiments, the absorption peak can be tuned to around 532 nm. In some embodiments, the absorption peak can be tuned to around 560 nm. In some embodiments, the absorption peak can be tuned to around 635 nm. In some embodiments, the absorption peak can be tuned to around 655 nm. In some embodiments, the absorption peak can be tuned to around 700 nm. In some embodiments, the absorption peak can be tuned to around 750 nm. In some embodiments, the absorption peak can be tuned to around 800 nm. In some embodiments, the absorption peak can be tuned to around 900 nm. In some embodiments, the absorption peak can be tuned to around 980 nm. In some embodiments, the absorption peak can be tuned to around 1064 nm.

In certain embodiments, the chemical composition and structure of the chromophoric polymer in the polymer dots can affect the fluorescence quantum yield of the narrow-band emissive Pdots. The fluorescence quantum yield, for example, can vary from 100% to 0.1%. In some embodiments, the quantum yield can be greater than about 90%. In some embodiments, the quantum yield can be greater than about 80%. In some embodiments, the quantum yield can be greater than about 70%. In some embodiments, the quantum yield can be greater than about 60%. In some embodiments, the quantum yield can be greater than about 50%. In some embodiments, the quantum yield can be greater than about 40%. In some embodiments, the quantum yield can be greater than about 30%. In some embodiments, the quantum yield can be greater than about 20%. In some embodiments, the quantum yield can be greater than about 10%. In some embodiments, the quantum yield can be greater than about 5%. In some embodiments, the quantum yield can be greater than about 1%.

In some embodiments, the narrow-band emissive Pdots have both narrow emission FWHM and high fluorescence quantum yield. For example, the narrow-band Pdots can have an emission FWHM less than 70 nm and fluorescence quantum yield larger than 10%. The narrow-band Pdots can have an emission FWHM less than 60 nm and fluorescence quantum yield larger than 10%. The narrow-band Pdots can have an emission FWHM less than 50 nm and fluorescence quantum yield larger than 10%. The narrow-band Pdots can have an emission FWHM less than 40 nm and fluorescence quantum yield larger than 10%. The narrow-band Pdots can have an emission FWHM less than 30 nm and fluorescence quantum yield larger than 10%. The narrow-band Pdots can have an emission FWHM less than 20 nm and fluorescence quantum yield larger than 10%. In certain embodiments, the quantum yield is greater than 20%, greater than 30%, greater than 40%, greater than 50%, greater than 60%, greater than 70%, greater than 80%, or greater than 90%.

In some embodiments, the narrow-band emissive Pdots may have a secondary emission peak. For example, when the narrow-band monomers as energy acceptors are copolymerized with other monomer donors to produce narrow-band emissive Pdots, the final Pdots may have secondary peak because of incomplete fluorescence quenching. In some embodiments, the narrow-band emissive Pdots may also have a secondary peak in the composite Pdot chemically cross-linked with fluorescent dyes (e.g., fluorescent polymers and/or fluorescent small molecules), metal complexes, lanthanide complexes, inorganic quantum dots etc. Besides the narrow emission with FWHM less than 70 nm for the main peak, the secondary peak in the Pdots is less than 30% of the maximum intensity of the main narrow-band emission. In some embodiments, the secondary peak in the Pdots is less than 25% of the maximum intensity of the main narrow-band emission. In some embodiments, the secondary peak in the Pdots is less than 20% of the maximum intensity of the main narrow-band emission. In some embodiments, the secondary peak in the Pdots is less than 10% of the maximum intensity of the main narrow-band emission. In some embodiments, the secondary peak in the Pdots is less than 5% of the maximum intensity of the main narrow-band emission. In some embodiments, the secondary peak in the Pdots is less than 1% of the maximum intensity of the main narrow-band emission, or less. Also, in certain embodiments, the quantum yield is greater than 10%, greater than 20%, greater than 30%, greater than 40%, greater than 50%, greater than 60%, greater than 70%, greater than 80%, or greater than 90%.

In certain embodiments, the chemical composition and structure of the chromophoric polymer in the polymer dots can affect the fluorescence lifetime of the narrow-band emissive Pdots. The fluorescence lifetime can vary from 10 ps to 1 ms. In some embodiments, the fluorescence lifetime varies from 10 ps to 100 ps. In some embodiments, the fluorescence lifetime varies from 100 ps to 1 ns. In some embodiments, the fluorescence lifetime varies from 1 ns to 10 ns. In some embodiments, the fluorescence lifetime varies from 10 ns to 100 ns. In some embodiments, the fluorescence lifetime varies from 100 ns to 1 μs. In some embodiments, the fluorescence lifetime varies from 1 μs to 10 μs. In some embodiments, the fluorescence lifetime varies from 10 μs to 100 μs. In some embodiments, the fluorescence lifetime varies from 100 μs to 1 ms.

In certain embodiments, the narrow-band emissive Pdots can be characterized by their stability. The optical properties (e.g. emission spectrum, emission band width, fluorescence quantum yield, fluorescence lifetime, side peaks, brightness at the particular wavelength or emission intensity at a particular wavelength) can be stable for over 1 day, or 1 week, or 2 weeks, or 1 month, or 2 months, or 3 months, or 6 months, or 1 year, or longer. The stable fluorescence quantum yield means that the fluorescence quantum yield of the narrow-band emission does not change by more than 5%, or 10%, or 20%, or 50%, or higher. The stable emission spectrum means that intensity ratio of the secondary peak relative to the main peak doesn't change by more than 5%, or 10%, or 20%, or 50%, or higher.

In some embodiments, the narrow-band emissive Pdots can possess all of the following characteristics: (1) Narrow band emission that has a FWHM of less than 70 nm, preferably less than 60 nm, less than 50 nm, less than 40 nm, less than 30 nm, or less than 20 nm; (2) High quantum yield that is greater than 5%, preferably greater than 10%, preferably greater than 20%, greater than 30%, greater than 40%, greater than 50%, greater than 60%, greater than 70%, greater than 80%, or greater than 90%; (3) With a secondary emission peak that is less than 30% of the main peak, preferably less than 20%, less than 10%, less than 5%, or less than 1%; (4) Have high stability over at least 2 weeks, preferably 1 month, 2 month, 3 month, 6 months, 1 year, or longer.

Compositions of Narrow-Band Emissive Chromophoric Polymer Dots

The present invention can include polymer dots, e.g., narrow-band emissive chromophoric polymer dots. As described further herein, the present invention includes a wide variety of polymer dots that exhibit narrow band emission properties (e.g., a FWHM less than 70 nm). As described further herein, the variety of polymer dots of the present invention can include polymers that have a narrow band emissive unit (e.g., a narrow band monomer and/or a narrow band unit). For example, the present invention can include a homopolymer or heteropolymer including a narrow band monomer, such as BODIPY and/or BODIPY derivative monomer, a squaraine and/or squaraine derivative, a metal complex and/or metal complex derivative monomer, a porphyrin and/or porphyrin derivative monomer, a phthalocyanine and/or phthalocynanine derivative monomer, a lanthanide complex and/or lanthanide complex derivative monomer, a perylene and/or perylene derivative monomer, a cyanine and/or cyanine derivative monomer, a rhodamine and/or rhodamine derivative monomer, a coumarin and/or coumarin derivative monomer, and/or a xanthene and/or xanthene derivative monomer. A narrow band unit can be, e.g., a narrow band monomer or a fluorescent nanoparticle embedded in or attached to the polymer dot. The fluorescent nanoparticle can be, e.g., a quantum dot. A narrow band unit can also include a polymer or fluorescent dye molecule that gives a narrow emission in a polymer dot of the present invention.

The narrow band monomers can be integrated into a heteropolymer with other general monomers that can, e.g., act as energy donors. For example, the general monomers can include an emission spectrum that is tuned to substantially overlap the absorption spectrum of a narrow band monomer, thereby acting as an energy donor for the narrow band monomer. The energy transfer, e.g., can occur along the backbone of a polymer (e.g., intrachain) or between multiple polymer backbones (e.g., interchain). In some embodiments, the narrow band units (e.g., narrow band monomers) can be attached (e.g., covalently attached) to a polymer backbone or sidechain of the polymer. For example, the narrow band unit (e.g., a narrow band monomer) can be attached to a general monomer that can include an emission spectrum that is tuned to substantially overlap the absorption spectrum of a narrow band unit, thereby acting as an energy donor for the narrow band unit. The general monomers can include a wide variety of structures that are further described herein (e.g., D1, D2, D2', monomers of P1-P10, and/or M1-M10). In some embodiments, the general monomers can include, e.g., fluorene, a fluorene derivative, a phenyl vinylene, a phenyl vinylene derivative, a phenylene, a phenylene derivative, a benzothiazole, a benzothiazole derivative, a thiophene, a thiophene derivative, a carbazole fluorene, and/or a carbazole fluorene derivative. As also described herein, the various polymers used in the polymer dots can be combined in a variety of ways. For example, the polymers of the present invention can be chemically cross-linked and/or physically blended in the polymer dots. The polymers described herein can further include at least one functional group for, e.g., conjugation reactions, such as for bioconjugation reactions to antibodies or other biomolecules further described herein. The present invention further includes compositions including the polymer dots described herein. The compositions of the present invention can include, e.g., polymer dots described herein suspended in a solvent (e.g., an aqueous solution).

In some embodiments, the narrow-band emissive chromophoric polymer dots include at least one narrow-band emissive polymer. The narrow-band emissive polymer can be a homopolymer or a heteropolymer (e.g., a copolymer). The narrow-band emissive polymers may have broad-band emissions in good solvents. However, the final Pdots made from the narrow-band polymers have narrow-band emissions. In certain embodiments, the chromophoric polymer dots can include luminescent semiconducting polymer with delocalized pi-electrons. The term "semiconducting polymer" is recognized in the art. Conventional luminescent semiconducting polymers include, but are not limited to fluorene polymers, phenylene vinylene polymers, phenylene polymers, benzothiadiazole polymers, thiophene polymers, carbazole polymers and related copolymers. While those conventional semiconducting polymers typically have broad-band emissions, narrow-band emissive polymers in this invention include chemical units such as narrow-band monomers so that the final Pdots give narrow-band emissions. The emission FWHM of the final Pdots is less than 70 nm. In certain embodiments, the FWHM is less than 60 nm, less than 50 nm, less than 40 nm, less than 30 nm, or less than 20 nm. The narrow-band monomers include but are not limited to BODIPY, squaraine, porphyrin, metallophyrin, metal complexes, lanthanide complexes, phthalocyanine, perylene, rhodamine, coumarin, xanthene, cyanine, and their derivatives. A non-limiting list of the narrow-band emissive monomers (or chemical units) and a non-limiting list of the narrow-band emissive polymer can be, for example, found in the attached figures.

In some embodiments, the narrow-band emissive polymers for making Pdots include narrow-band monomers. The narrow-band emissive polymer dots can also include other monomers that are broad-band emissive. The narrow-band monomers can be energy acceptors and other monomers can be energy donors. For example, polymer dots of the present invention can include condensed polymer nanoparticles that have intrachain energy transfer between, e.g., a narrow-band monomer and one or more general monomers on the same polymer chain. The polymer dots can also have interchain energy transfer in which a condensed polymer nanoparticle can include two or more polymer chains physically blended and/or chemically crosslinked together. For interchain energy transfer, one of the chains may include a narrow-band monomer and another chain may include one or more general monomers that can act as an energy donor to the narrow band monomer, which is an energy acceptor. Some of the polymer dots can include both intrachain and interchain energy transfer. In some instances, the combination of intrachain and interchain energy transfer can increase the quantum yield of the polymer dots. In certain embodiments, the final Pdots can exhibit narrow-band emissions because of energy transfer to the narrow-band monomers. The narrow-band emissive chromophoric polymers in good solvents may exhibit broad emissions or narrow emissions. However, their nanoparticle form gives narrow-band emissions. The emission FWHM of the above Pdots is less than 70 nm. In certain embodiments, the FWHM is less than 60 nm, less than 50 nm, less than 40 nm, less than 30 nm, or less than 20 nm. In some embodiments, the FWHM of the polymer dots described herein can range between about 5 nm to about 70 nm, from about 10 nm to about 60 nm, from about 20 nm to about 50 nm, or from about 30 nm to about 45 nm. In some embodiments, the narrow-band emissive Pdots are narrow band emission without relying on the formation of any defined secondary structures, such as beta phase.

In some embodiments, the narrow-band emissive polymer is a homopolymer that includes only narrow-band emissive monomer (FIG. 1A). As described further herein, example narrow band monomers can include BODIPY and/or a BODIPY derivative monomer, a squaraine and/or squaraine derivative, a metal complex and/or metal complex derivative monomer, a porphyrin and/or porphyrin derivative monomer, a phthalocyanine and/or phthalocynanine derivative monomer, a lanthanide complex and/or lanthanide complex derivative monomer, a perylene and/or perylene derivative monomer, a cyanine and/or cyanine derivative monomer, a rhodamine and/or rhodamine derivative monomer, a coumarin and/or coumarin derivative monomer, and/or a xanthene and/or xanthene derivative monomer. In some embodiments, the narrow-band emissive polymer is a two-unit copolymer that includes one narrow-band monomer and one general monomer (e.g., D, D1, D2, and/or D2') (FIG. 1B). In some embodiments, the general monomers can be broad-band emissive. The general monomer can be an energy donor and the narrow-band monomer can be an energy-acceptor. Energy-transfer inside Pdots can result in narrow-band emissions. In some embodiments, the narrow-band emissive polymer is a three-unit copolymer that includes one narrow-band monomer and two general monomers such as general monomer 1 and general monomer 2 (e.g., selected from D, D1, D2, and/or D2') (FIG. 1C). The narrow-band monomer can be an energy-acceptor, general monomer 1 can be an energy-donor, general monomer 2 can also be a donor to the narrow-band monomer. In some embodiments, general monomer 2 can be an energy-acceptor from general monomer 1 and simultaneously an energy-donor to the narrow-band monomer. Both general monomer 1 and general monomer 2 can be broad-band emissive. However, multi-step energy-transfer inside Pdots can result in narrow-band emissions. In certain embodiments, the narrow-band emissive polymer can be a heteropolymer, such as a multi-unit (>3) copolymer, that includes at least one type of narrow-band emissive monomer so that the final Pdots give narrow-band emissions.

In some embodiments, the narrow-band emissive polymer is copolymer that includes the narrow-band unit cross-linked with the side-chains (FIG. 1D). The copolymer can include 2 types of general monomers, or 3 types of general monomers, or more than 3 types of general monomers (e.g., selected from D, D1, D2, and/or D2'). However, the narrow-band emissive polymer can include at least one type of narrow-band emissive unit in the side-chains. The copolymer backbone can be an energy-donor, and the narrow-band emissive unit can be an energy-acceptor. Energy-transfer inside Pdots results in narrow-band emissions. In some embodiments, the narrow-band emissive polymer is a homopolymer that includes the narrow-band unit cross-linked with the side-chains (FIG. 1E). The homopolymer backbone can be an energy-donor, and the narrow-band unit can be an energy-acceptor. Energy-transfer inside Pdots can result in narrow-band emissions.

In some embodiments, the narrow-band emissive polymer can be a polymer that includes a narrow-band monomer attached to one terminus or both termini of the linear polymer (FIG. 1F) or all termini in case of a branched polymer. The polymer can, e.g., include one type of a general monomer (e.g., any one of D, D1, D2, or D2'), or two types of general monomers (e.g., any one of D, D1, D2 or D2'), or three types of general monomers, or more than three types of general monomers. In some embodiments, the narrow-band emissive polymer can include at least one type of narrow-band emissive unit in one terminus or both termini of the linear polymer (e.g., FIG. 1F) or all termini in case of a branched polymer. The polymer backbone can be an energy-donor, and the narrow-band emissive unit can be an energy-acceptor. Energy-transfer inside Pdots results in narrow-band emissions. In some embodiments, the narrow-band emissive polymer can be a homopolymer or heteropolymer that includes the narrow-band unit attached to the terminus of the polymer. The homopolymer or heteropolymer backbone can be an energy-donor, and the narrow-band unit can be an energy-acceptor. Energy-transfer inside Pdots can result in narrow-band emissions.

FIGS. 1G-L show other examples of schematic structures for the narrow-band emissive polymers that can include, e.g., general monomers as donors (D) and narrow band monomers as acceptors (A). In some aspects, the donors can absorb energy and transfer the energy, either directly or indirectly (e.g. by cascade energy transfer), to the narrow-band monomers. Besides the general monomer and narrow band monomer, these polymers can also include functional monomers (F) that provide reactive functional groups for, e.g., chemical reactions and bioconjugation reactions. The functional monomers can be copolymerized with the general monomers and narrow band monomers (e.g., FIG. 1G), or cross-linked with these two kinds of monomers. The functional monomers can be used as a terminus (or for both termini) of the polymers (e.g., FIG. 1H and FIG. 1K). Functional groups can be included either in the general monomer or the narrow band monomers (e.g., FIG. 1I). In some embodiments, the narrow band monomers can also be copolymerized with any of the general polymers to synthesize a narrow-band emissive copolymer or heteropolymer that contains more than two types of monomers (e.g., FIG. 1J). The narrow band monomer can be covalently attached to the side-chains of the polymer (e.g, FIG. 1I). In some embodiments, the narrow band emissive units can be covalently attached to the terminus of the polymer. In some embodiments, the narrow band emissive units can be physically mixed or blended with conventional semiconducting polymers to form narrow-band emissive polymer dots. In one embodiment, the narrow band emissive units can be covalently cross-linked with conventional semiconducting polymers to form narrow-band emissive polymer dots. The conventional semiconducting polymers can absorb energy and transfer the energy, either directly or indirectly (e.g. by cascade energy transfer) to the narrow band monomer.

Figure 31A:
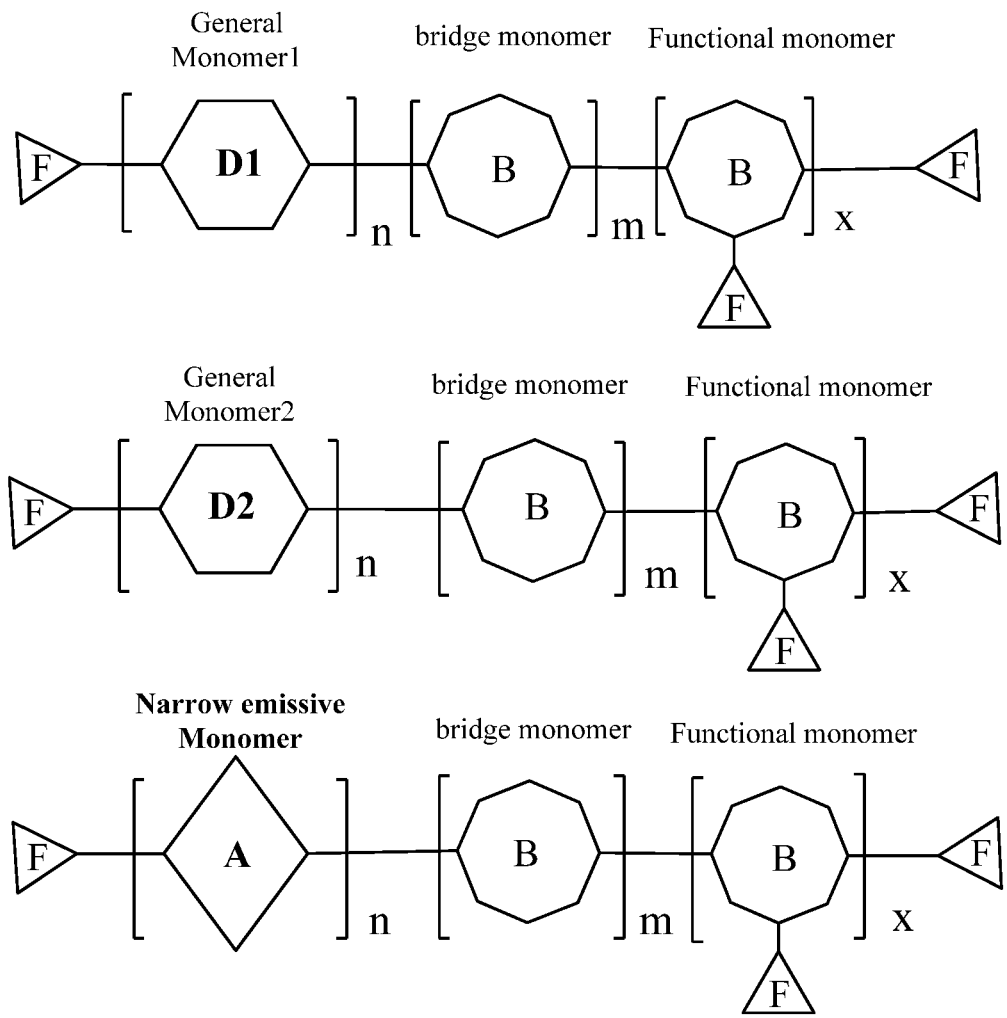
FIG. 31A shows the schematic structures of narrow-band emissive polymers chemically cross-linked with two or more broad-band polymers.

All the narrow-band emissive polymers described above in FIGS. 1A-L can, e.g., be physically blended or chemically cross-linked with one or more general broad-band polymers. In some aspects, the broad-band polymers can be energy donors and the narrow-band emissive polymer can be energy acceptors. Multi-step energy transfer can occur from the broad-band polymer to the narrow-band emissive polymer so that the polymer dots give narrow-band emissions. One example of chemical crosslinking is shown in FIG. 31A. The chemical cross-linking between polymers can use the functional reactive groups such as haloformyl, hydroxyl, aldehyde, alkenyl, alkynyl, anhydride, carboxamide, amines, azo compound, carbonate, carboxylate, carboxyl, cyanates, ester, haloalkane, imine, isocyanates, nitrile, nitro, phosphino, phosphate, phosphate, pyridyl, sulfonyl, sulfonic acid, sulfoxide, thiol groups. These functional groups can be attached to the side chains and/or the terminus of each polymer chain.

Figure 2A:
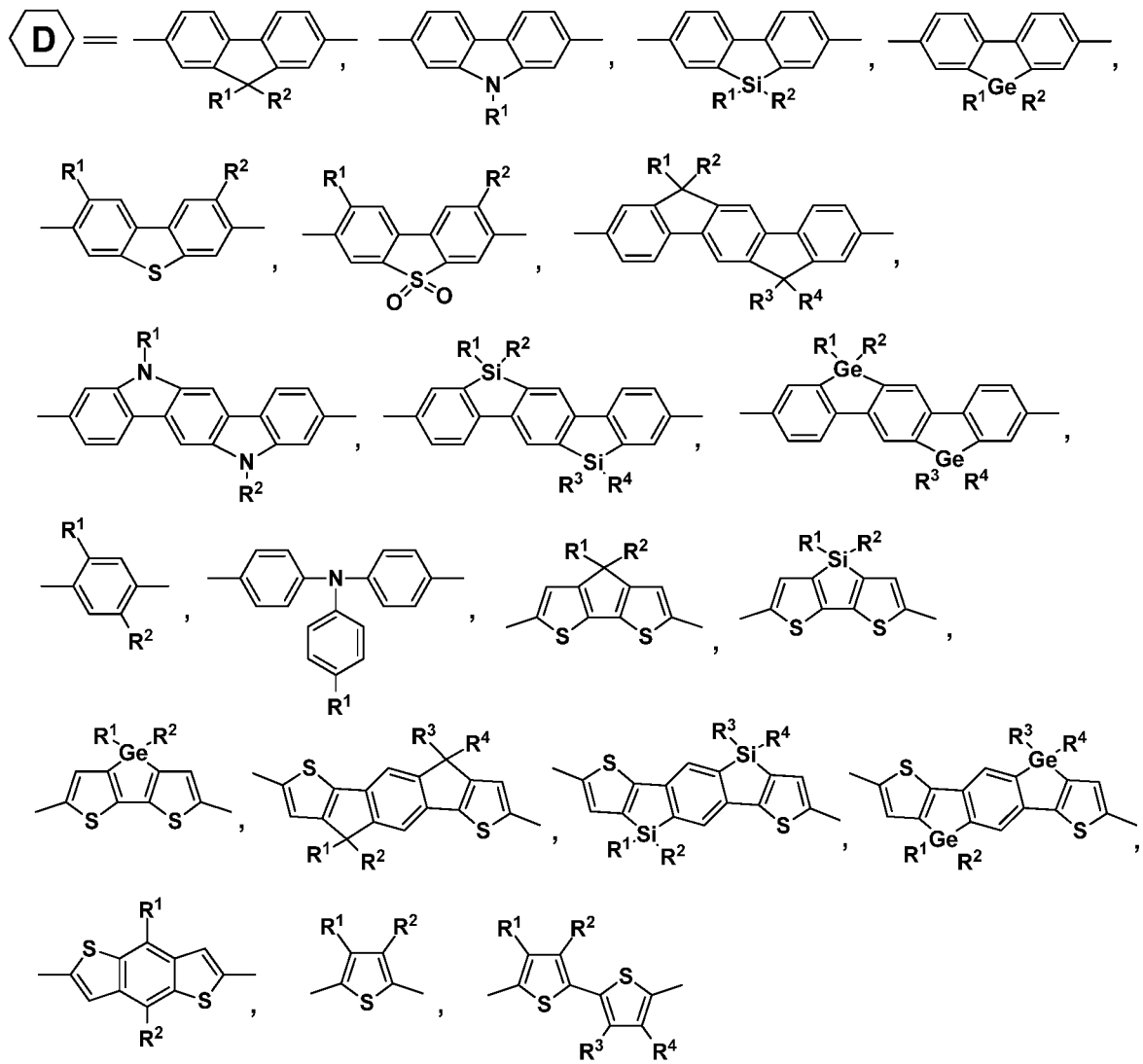
FIGS. 2A-2N show non-limiting examples of the chemical structures of narrow-band emissive copolymers. The copolymer can include one general monomer as an energy donor and one narrow-band monomer as an acceptor.

As described herein, the present invention can include general monomers that can be polymerized with the narrow band monomers disclosed herein. FIG. 2A provides a non-limited list of example general monomers (D). In some embodiments, the general monomer can act as an energy donor for a narrow band monomer in the polymer. A variety of derivatized monomeric units can be used. For example, for the structures shown in FIG. 2A, each of $R^1$, $R^2$, $R^3$ and $R^4$ can be independently selected from, but are not limited to, alkyl, phenyl, alkyl-substituted phenyl, alkyl-substituted fluorenyl and alkyl-substituted carbazolyl. Alkyl substituted phenyl can include 2-alkylphenyl, 3-alkylphenyl, 4-alkylphenyl, 2,4-dialkylphenyl, 3,5-dialkylphenyl, and 3,4-dialkylphenyl. Alkyl-substituted fluorenyl can include 9,9-dialkyl-substituted fluorenyl, 7-alkyl-9,9-dialkyl-substituted fluorenyl, 7-triphenylaminyl-9,9-dialkyl-substitute fluorenyl and 7-diphenylaminyl-9,9-dialkyl-substitute fluorenyl. The alkyl substituents can include $C_nH_{2n+1}$ or $C_nF_{2n+1}$ or —$CH_2CH_2[OCH_2CH_2]_n$—$OCH_3$ wherein n is 1 to 20. In some embodiments, n can be between 1 to 50 or higher. The general monomers can also be substituted with other substituents as defined herein.

Figure 3A:
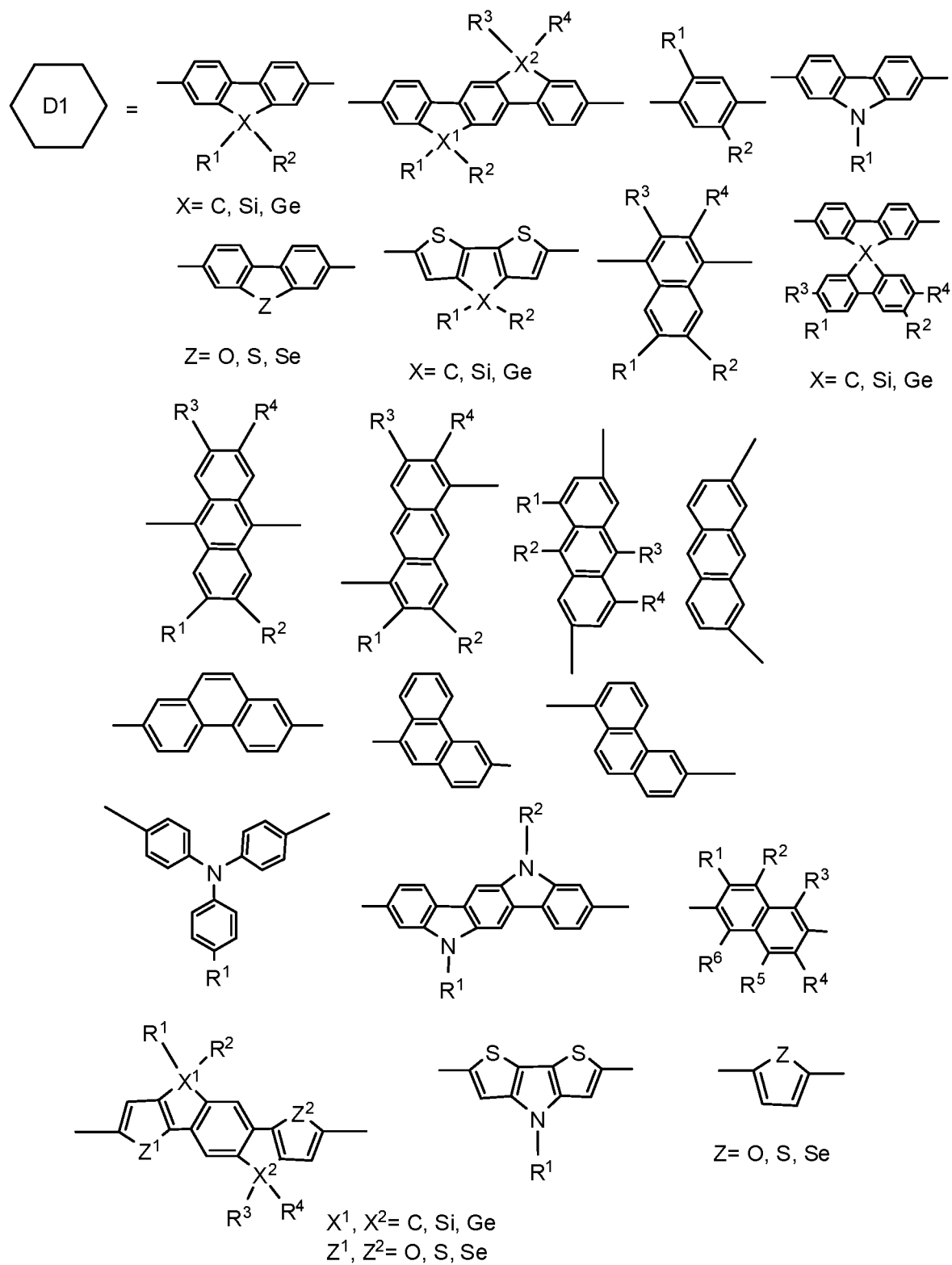
FIGS. 3A-E show a non-limiting list of examples of the chemical structures of general D1 type monomers and D2 type monomers used for synthesizing narrow-band emissive polymers, e.g., as in FIG. 1 and FIG. 31A.

In certain embodiments, a polymer can include one or more types of general monomers. As shown in FIGS. 3A-E, three example types of general monomers are shown, D1, D2 and D2'. Each of the general D1 type monomers can be copolymerized with each of the D2 and D2' type monomers and one narrow-band monomer to obtain narrow-band emissive polymer. Any of the D1 type monomers or D2 type monomers can also be separately used to copolymerize with one narrow-band monomer to obtain the narrow-band emissive polymers as, e.g., in FIGS. 1B and 1E. For the structures shown in FIG. 3A, a variety of substituents can be attached to the base structures. For example, each of $R^1$, $R^2$, $R^3$, $R^3$, $R^4$, $R^5$, and $R^6$ can be independently selected from the group consisting of, but not limited to, hydrogen (H), deuterium (D), halogen, direct or branched alkyl, heteroalkyl, heterocycloalkyl, heterocycloalkylene, alkoxy, aryl, hydroxyl, cyano, nitro, ether and its derivatives, ester and its derivatives, alkyl ketone, alkylester, arylester, alkynyl, alkyl amine, fluoroalkyl, fluoroaryl, and polyalkalene (e.g, mehtoxyethoxyethoxy, ethoxyethoxy, and —$(OCH_2CH_2)_n$OH, n=1-50), phenyl, alkyl-(alkoxy-, aryl-, fluoroalkyl-, fluoroaryl-)substituted phenyl, pyridyl, alkyl-(alkoxy-, aryl-, fluoroalkyl-, fluoroaryl-)substituted pyridyl, bipyridyl, alkyl-(alkoxy-, aryl-, fluoroalkyl-, fluoroaryl-)substituted bipyridyl tripyridyl, alkyl-(alkoxy-, aryl-, fluoroalkyl-, fluoroaryl-)substituted tripyridyl, furyl, alkyl-(alkoxy-, aryl-, fluoroalkyl-, fluoroaryl-)substituted furyl, thienyl, alkyl-(alkoxy-, aryl-, fluoroalkyl-, fluoroaryl-)substituted thienyl, pyrrolyl, alkyl-(alkoxy-, aryl-, fluoroalkyl-, fluoroaryl-)substituted pyrrolyl, pyrazolyl, alkyl-(alkoxy-, aryl-, fluoroalkyl-, fluoroaryl-)substituted pyrazolyl, oxazolyl, alkyl-(alkoxy-, aryl-, fluoroalkyl-, fluoroaryl-)substituted oxazolyl, thiazolyl, alkyl-(alkoxy-, aryl-, fluoroalkyl-, fluoroaryl-)substituted thiazolyl, imidazolyl, alkyl-(alkoxy-, aryl-, fluoroalkyl-, fluoroaryl-)substituted imidazolyl, pyrazinyl, alkyl-(alkoxy-, aryl-, fluoroalkyl-, fluoroaryl-)substituted pyrazinyl, benzooxadizolyl, alkyl-(alkoxy-, aryl-, fluoroalkyl-, fluoroaryl-)substituted benzooxadizolyl, benzothiadizolyl, alkyl-(alkoxy-, aryl-, fluoroalkyl-, fluoroaryl-)substituted benzothiadizolyl, fluorenyl, alkyl-(alkoxy-, aryl-, fluoroalkyl-, fluoroaryl-)substituted fluorenyl, triphenylaminyl-substituted fluorenyl, diphenylaminyl-substituted fluorenyl, alkyl-substituted carbazolyl, alkyl-substituted triphenylaminyl and alkyl-substituted thiophenyl. As exemplary embodiments, alkyl substituted phenyl can include 2-alkylphenyl, 3-alkylphenyl, 4-alkylphenyl, 2,4-dialkylphenyl, 3,5-dialkylphenyl, 3,4-dialkylphenyl; alkyl-substituted fluorenyl can include 9,9-dialkyl-substituted fluorenyl, 7-alkyl-9,9-dialkyl-substituted fluorenyl, 6-alkyl-9,9-dialkyl-substituted fluorenyl, 7-triphenylaminyl-9,9-dialkyl-substituted fluorenyl and 7-diphenylaminyl-9,9-dialkyl-substituted fluorenyl; alkyl-substituted carbazolyl can include N-alkyl-substituted carbazolyl, 6-alkyl-substituted carbazolyl and 7-alkyl-substituted carbazolyl; alkyl-substituted triphenylaminyl can include 4'-alkyl-substituted triphenylaminyl, 3'-alkyl-substituted triphenylaminyl, 3',4'-dialkyl-substituted triphenylaminyl and 4',4"-alkyl-substituted triphenylaminyl; alkyl-substituted thiophenyl can include 2-alkylthiophenyl, 3-alkylthiophenyl, 4-alkylthiophenyl, N-dialkyl-4-phenyl, N-diphenyl-4-phenyl, and N-dialkoxyphenyl-4-phenyl. The alkyl substituents can include $C_nH_{2n+1}$, or $C_nF_{2n+1}$ or —$CH_2CH_2[OCH_2CH_2]_n$—$OCH_3$ wherein n is 1 to 20. In some embodiments, n can be between 1 to 50 or higher. The general monomers can also be substituted with other substituents as defined herein. As shown in FIG. 3A, each of X, $X^1$, and $X^2$ can be independently selected from the group consisting of carbon (C), silicon (Si), and germanium (Ge). Z, $Z^1$, $Z^2$ can be selected from the group consisting of oxygen (O), sulfur (S), and selenium (Se).

Figure 3B:
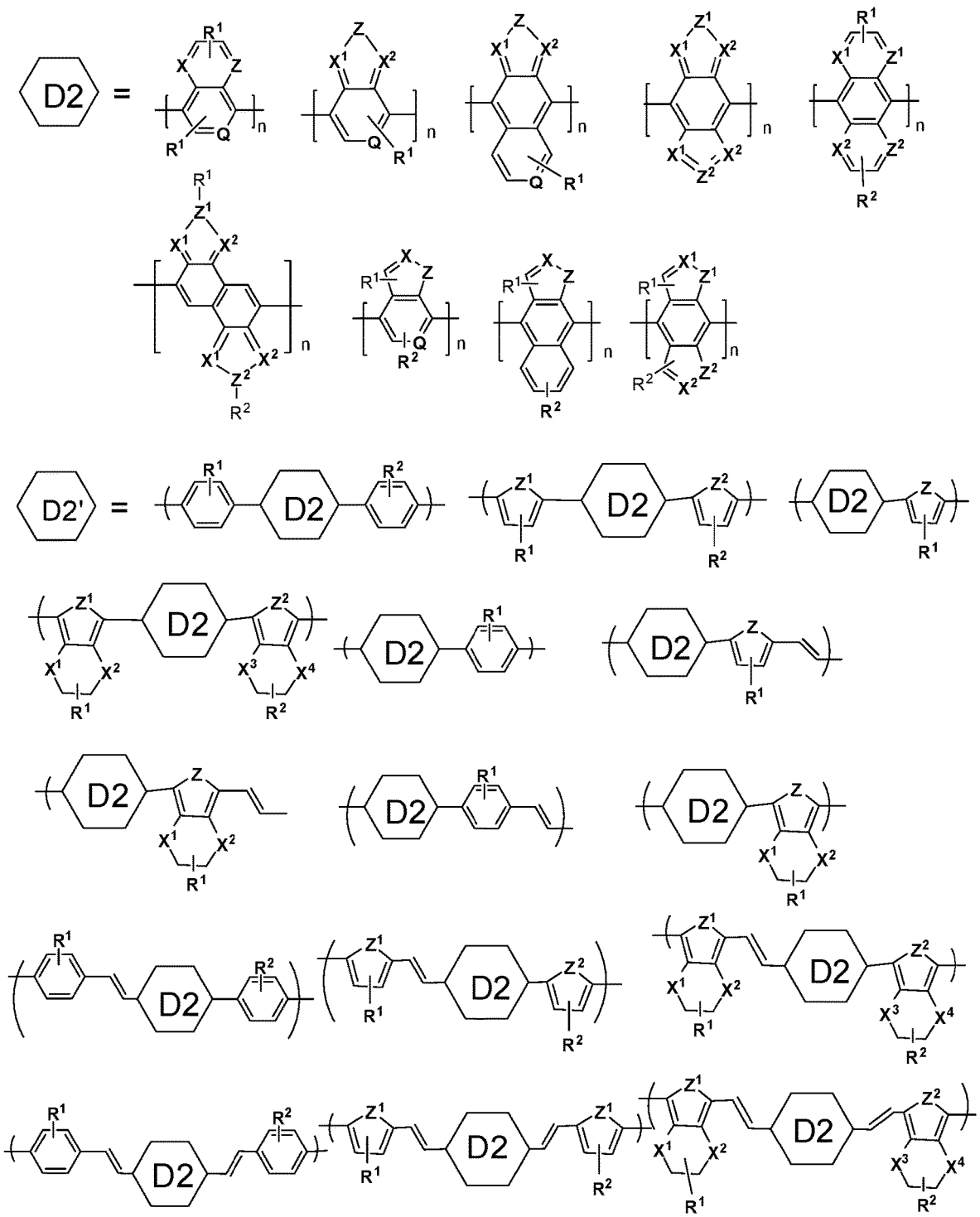

FIG. 3B shows a non-limiting list of general donors in the narrow-band emissive polymers. As shown in the chemical structures of donors in FIG. 3B, each of X, $X^1$, $X^2$, $X^3$, $X^4$, Q, Z, $Z^1$, and $Z^2$ can be heteroatoms, e.g., and can be independently selected from the group consisting of, O, S, Se, Te, N and so on. Each of $R^1$ and $R^2$ is independently selected from non-limiting examples of hydrogen (H), deuterium (D), halogen, direct or branched alkyl, heteroalkyl, heterocycloalkyl, heterocycloalkylene, alkoxy, aryl, hydroxyl, cyano, nitro, ether and its derivatives, ester and its derivatives, alkyl ketone, alkylester, arylester, alkynyl, alkyl amine, fluoroalkyl, fluoroaryl, and polyalkalene (e.g, mehtoxyethoxyethoxy, ethoxyethoxy, and —$(OCH_2CH_2)_n$OH, n=1-50), phenyl, alkyl-(alkoxy-, aryl-, fluoroalkyl-, fluoroaryl-)substituted phenyl, pyridyl, alkyl-(alkoxy-, aryl-, fluoroalkyl-, fluoroaryl-)substituted pyridyl, bipyridyl, alkyl-(alkoxy-, aryl-, fluoroalkyl-, fluoroaryl-)substituted bipyridyl tripyridyl, alkyl-(alkoxy-, aryl-, fluoroalkyl-, fluoroaryl-)substituted tripyridyl, furyl, alkyl-(alkoxy-, aryl-, fluoroalkyl-, fluoroaryl-)substituted furyl, thienyl, alkyl-(alkoxy-, aryl-, fluoroalkyl-, fluoroaryl-)substituted thienyl, pyrrolyl, alkyl-(alkoxy-, aryl-, fluoroalkyl-, fluoroaryl-)substituted pyrrolyl, pyrazolyl, alkyl-(alkoxy-, aryl-, fluoroalkyl-, fluoroaryl-)substituted pyrazolyl, oxazolyl, alkyl-(alkoxy-, aryl-, fluoroalkyl-, fluoroaryl-)substituted oxazolyl, thiazolyl, alkyl-(alkoxy-, aryl-, fluoroalkyl-, fluoroaryl-)substituted thiazolyl, imidazolyl, alkyl-(alkoxy-, aryl-, fluoroalkyl-, fluoroaryl-)substituted imidazolyl, pyrazinyl, alkyl-(alkoxy-, aryl-, fluoroalkyl-, fluoroaryl-)substituted pyrazinyl, benzooxadizolyl, alkyl-(alkoxy-, aryl-, fluoroalkyl-, fluoroaryl-)substituted benzooxadizolyl, benzothiadizolyl, alkyl-(alkoxy-, aryl-, fluoroalkyl-, fluoroaryl-)substituted benzothiadizolyl, fluorenyl, alkyl-(alkoxy-, aryl-, fluoroalkyl-, fluoroaryl-)substituted fluorenyl, triphenylaminyl-substituted fluorenyl, diphenylaminyl-substituted fluorenyl, alkyl-substituted carbazolyl, alkyl-substituted triphenylaminyl and alkyl-substituted thiophenyl. As exemplary embodiments, alkyl substituted phenyl can include 2-alkylphenyl, 3-alkylphenyl, 4-alkylphenyl, 2,4-dialkylphenyl, 3,5-dialkylphenyl, 3,4-dialkylphenyl; alkyl-substituted fluorenyl can include 9, 9-dialkyl-substituted fluorenyl, 7-alkyl-9,9-dialkyl-substituted fluorenyl, 6-alkyl-9,9-dialkyl-substituted fluorenyl, 7-triphenylaminyl-9,9-dialkyl-substituted fluorenyl and 7-diphenylaminyl-9,9-dialkyl-substituted fluorenyl; alkyl-substituted carbazolyl can include N-alkyl-substituted carbazolyl, 6-alkyl-substituted carbazolyl and 7-alkyl-substituted carbazolyl; alkyl-substituted triphenylaminyl can include 4'-alkyl-substituted triphenylaminyl, 3'-alkyl-substituted triphenylaminyl, 3',4'-dialkyl-substituted triphenylaminyl and 4',4"-alkyl-substituted triphenylaminyl; alkyl-substituted thiophenyl can include 2-alkylthiophenyl, 3-alkylthiophenyl, and 4-alkylthiophenyl, N-dialkyl-4-phenyl, N-diphenyl-4-phenyl, and N-dialkoxyphenyl-4-phenyl.

Figure 3C:
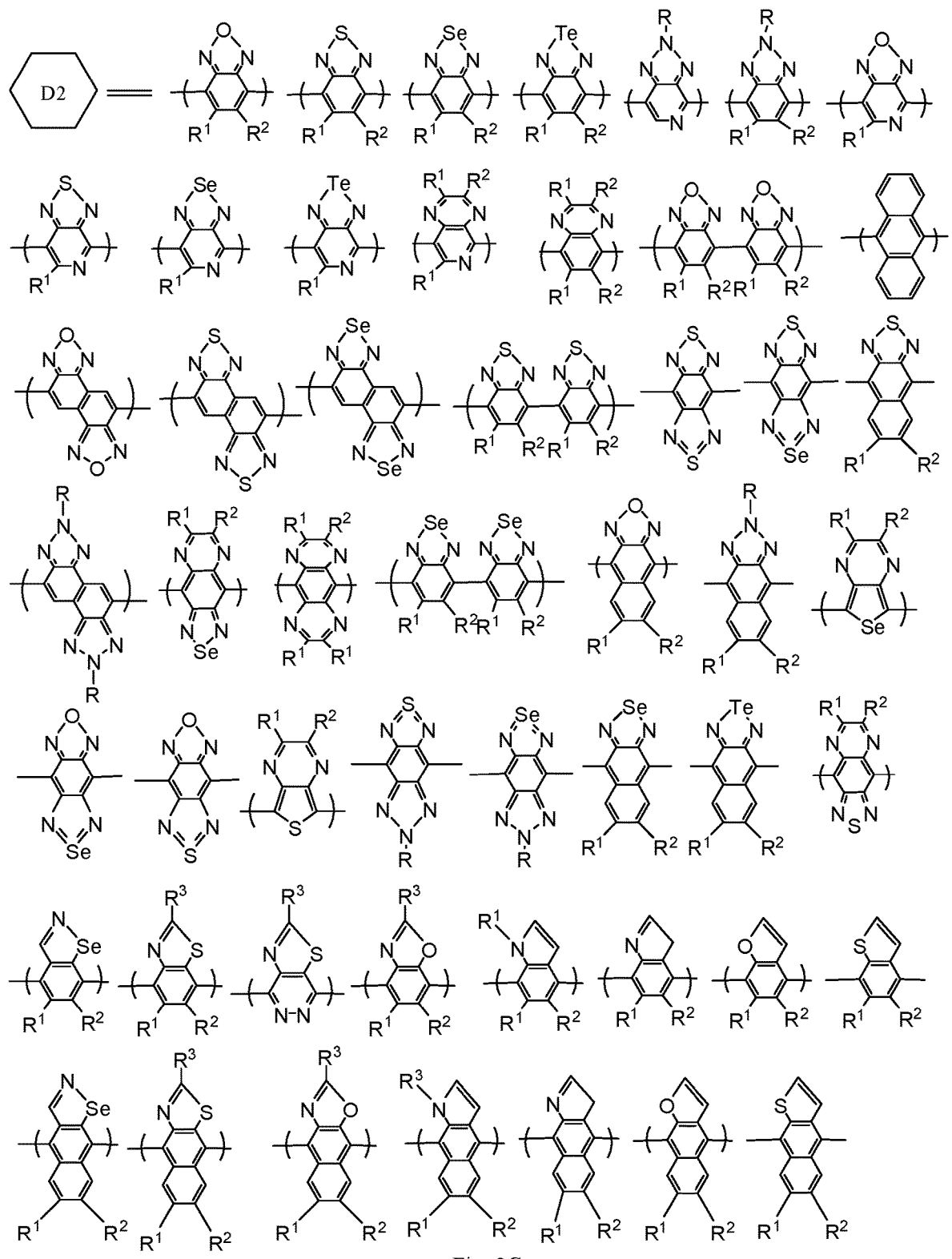
Figure 3D:
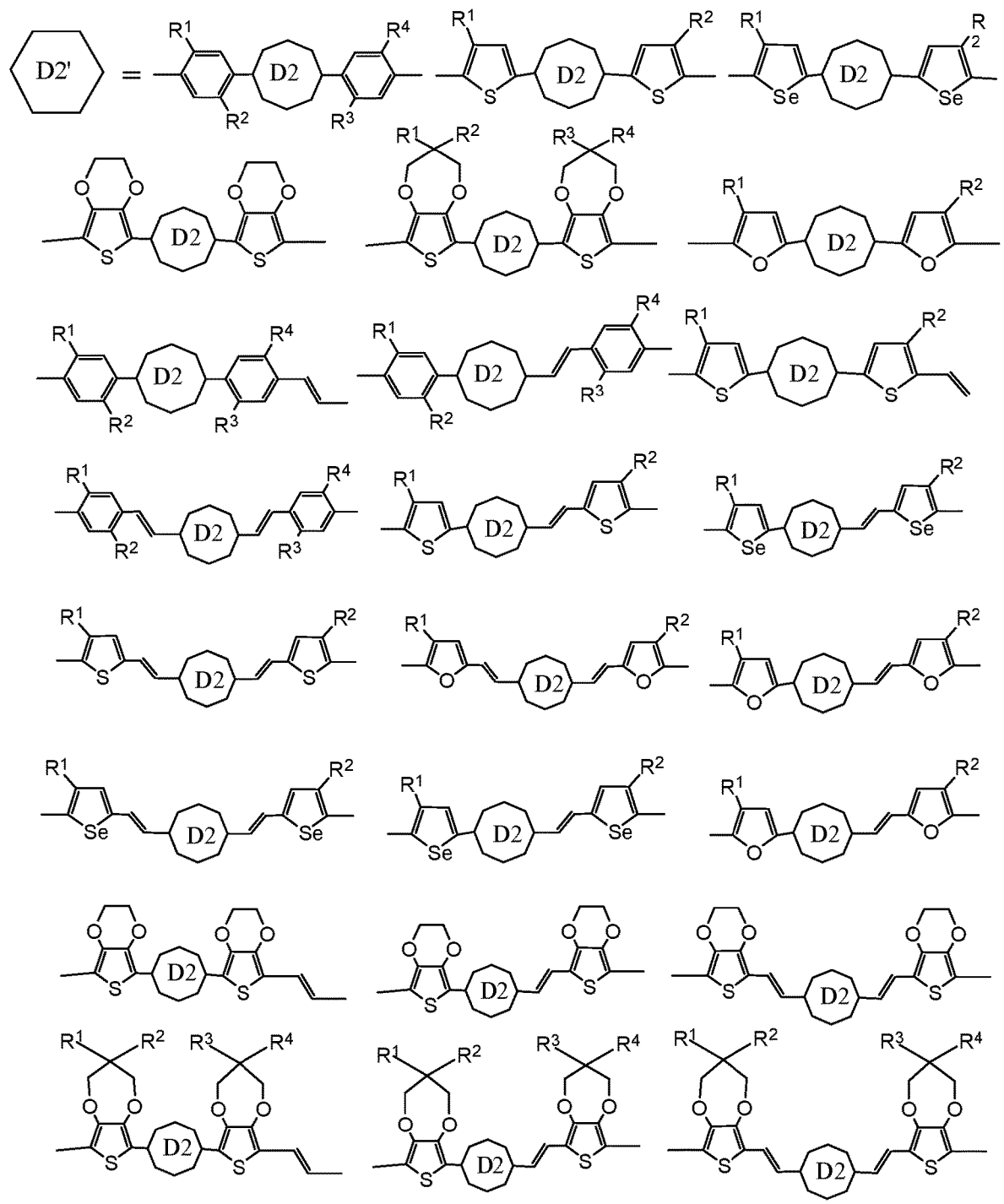
Figure 3E:
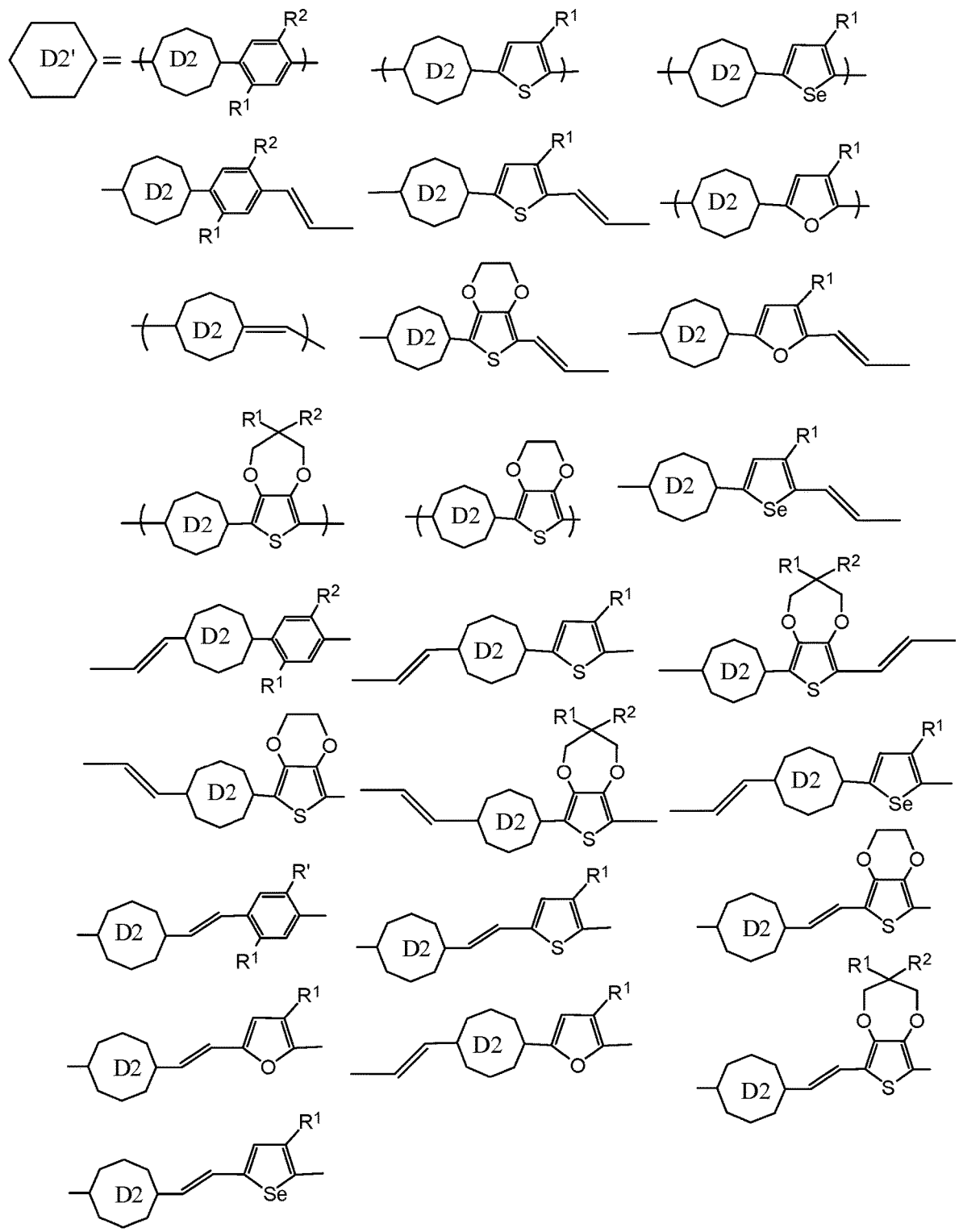

In some embodiments, the general donors can be selected (but not limited to) from the group shown in FIGS. 3C, 3D and 3E. As shown in the various D2 and D2' structures in FIGS. 3C, 3D, and 3E, each of $R^1$, $R^2$, $R^3$, and $R^4$ can be independently selected from non-limiting examples of hydrogen (H), deuterium (D), halogen, direct or branched alkyl, heteroalkyl, heterocycloalkyl, heterocycloalkylene, alkoxy, aryl, hydroxyl, cyano, nitro, ether and its derivatives, ester and its derivatives, alkyl ketone, alkylester, arylester, alkynyl, alkyl amine, fluoroalkyl, fluoroaryl, and polyalkalene (e.g, mehtoxyethoxyethoxy, ethoxyethoxy, and —$(OCH_2CH_2)_nOH$, n=1-50), phenyl, alkyl-(alkoxy-, aryl-, fluoroalkyl-, fluoroaryl-)substituted phenyl, pyridyl, alkyl-(alkoxy-, aryl-, fluoroalkyl-, fluoroaryl-)substituted pyridyl, bipyridyl, alkyl-(alkoxy-, aryl-, fluoroalkyl-, fluoroaryl-)substituted bipyridyl tripyridyl, alkyl-(alkoxy-, aryl-, fluoroalkyl-, fluoroaryl-)substituted tripyridyl, furyl, alkyl-(alkoxy-, aryl-, fluoroalkyl-, fluoroaryl-)substituted furyl, thienyl, alkyl-(alkoxy-, aryl-, fluoroalkyl-, fluoroaryl-)substituted thienyl, pyrrolyl, alkyl-(alkoxy-, aryl-, fluoroalkyl-, fluoroaryl-)substituted pyrrolyl, pyrazolyl, alkyl-(alkoxy-, aryl-, fluoroalkyl-, fluoroaryl-)substituted pyrazolyl, oxazolyl, alkyl-(alkoxy-, aryl-, fluoroalkyl-, fluoroaryl-)substituted oxazolyl, thiazolyl, alkyl-(alkoxy-, aryl-, fluoroalkyl-, fluoroaryl-)substituted thiazolyl, imidazolyl, alkyl-(alkoxy-, aryl-, fluoroalkyl-, fluoroaryl-)substituted imidazolyl, pyrazinyl, alkyl-(alkoxy-, aryl-, fluoroalkyl-, fluoroaryl-)substituted pyrazinyl, benzooxadizolyl, alkyl-(alkoxy-, aryl-, fluoroalkyl-, fluoroaryl-)substituted benzooxadizolyl, benzothiadizolyl, alkyl-(alkoxy-, aryl-, fluoroalkyl-, fluoroaryl-)substituted benzothiadizolyl, fluorenyl, alkyl-(alkoxy-, aryl-, fluoroalkyl-, fluoroaryl-)substituted fluorenyl, triphenylaminyl-substituted fluorenyl, diphenylaminyl-substituted fluorenyl, alkyl-substituted carbazolyl, alkyl-substituted triphenylaminyl and alkyl-substituted thiophenyl. As exemplary embodiments, alkyl substituted phenyl can include 2-alkylphenyl, 3-alkylphenyl, 4-alkylphenyl, 2,4-dialkylphenyl, 3,5-dialkylphenyl, 3,4-dialkylphenyl; alkyl-substituted fluorenyl can include 9, 9-dialkyl-substituted fluorenyl, 7-alkyl-9,9-dialkyl-substituted fluorenyl, 6-alkyl-9,9-dialkyl-substituted fluorenyl, 7-triphenylaminyl-9,9-dialkyl-substituted fluorenyl and 7-diphenylaminyl-9,9-dialkyl-substituted fluorenyl; alkyl-substituted carbazolyl can include N-alkyl-substituted carbazolyl, 6-alkyl-substituted carbazolyl and 7-alkyl-substituted carbazolyl; alkyl-substituted triphenylaminyl can include 4'-alkyl-substituted triphenylaminyl, 3'-alkyl-substituted triphenylaminyl, 3',4'-dialkyl-substituted triphenylaminyl and 4',4"-alkyl-substituted triphenylaminyl; alkyl-substituted thiophenyl can include 2-alkylthiophenyl, 3-alkylthiophenyl, and 4-alkylthiophenyl, N-dialkyl-4-phenyl, N-diphenyl-4-phenyl, and N-dialkoxyphenyl-4-phenyl.

In some embodiments, the narrow-band emissive polymers for making Pdots include boron-dipyrromethene (4,4-difluoro-4-bora-3a,4a-diaza-s-indacene, BODIPY) and their derivatives as narrow-band monomers. BODIPY monomers and their derivatives include but are not limited to their alkyl derivatives, aryl derivatives, alkyne derivatives, aromatic derivatives, alkoxide derivatives, aza derivatives, BODIPY extended systems and other BODIPY derivatives. The narrow-band emissive polymers can also include any other monomers. The BODIPY based-monomers can be energy acceptors and other monomers can be energy donors so that the final Pdots can exhibit narrow-band emissions. The narrow-band emissive chromophoric polymers in good solvents may exhibit broad emissions or narrow emissions. However, their nanoparticle form gives narrow-band emissions. The emission FWHM of the above Pdots is less than 70 nm. In certain embodiments, the FWHM is less than 60 nm, less than 50 nm, less than 40 nm, less than 30 nm, or less than 20 nm.

Figure 2B:
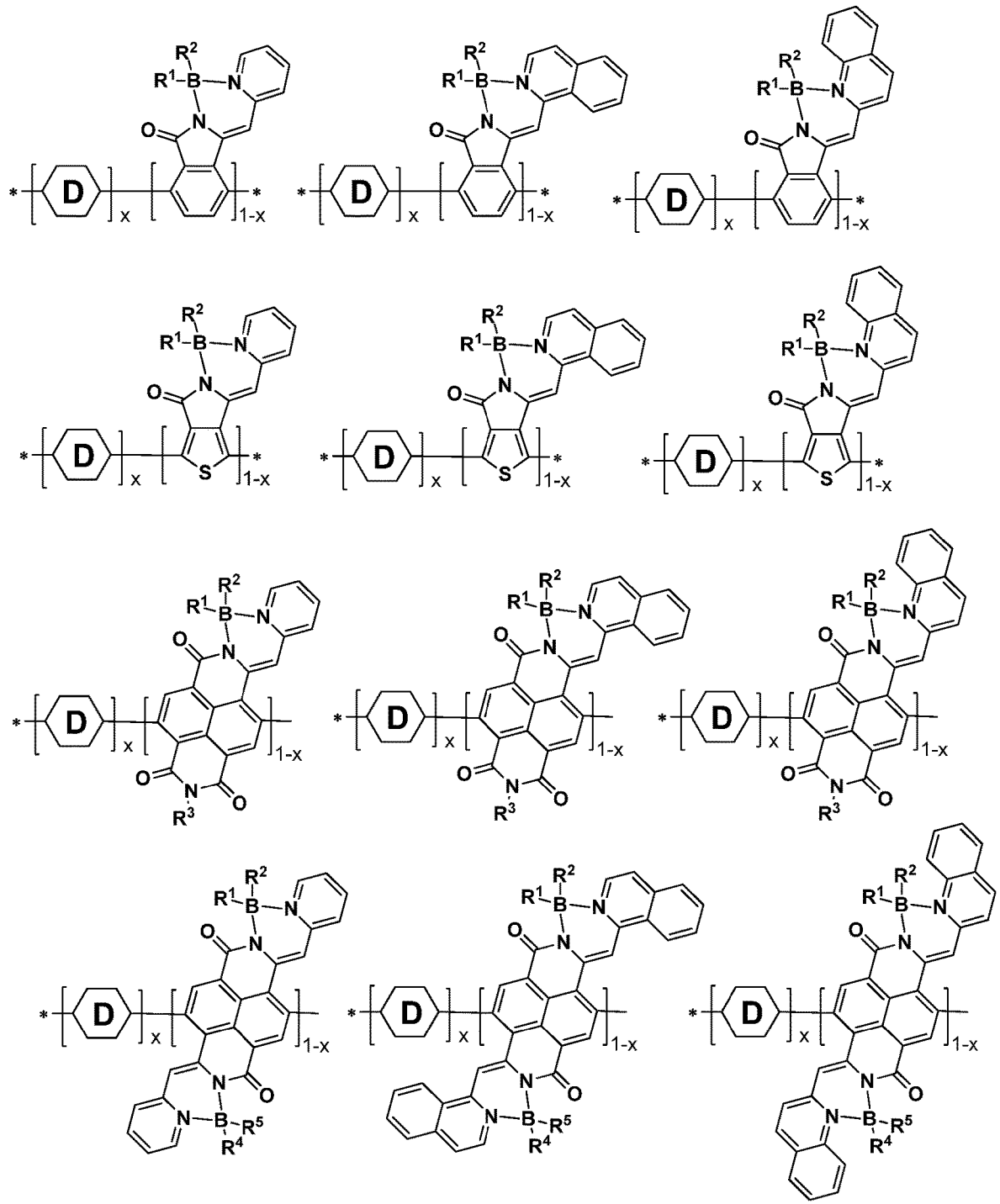
Figure 2C:
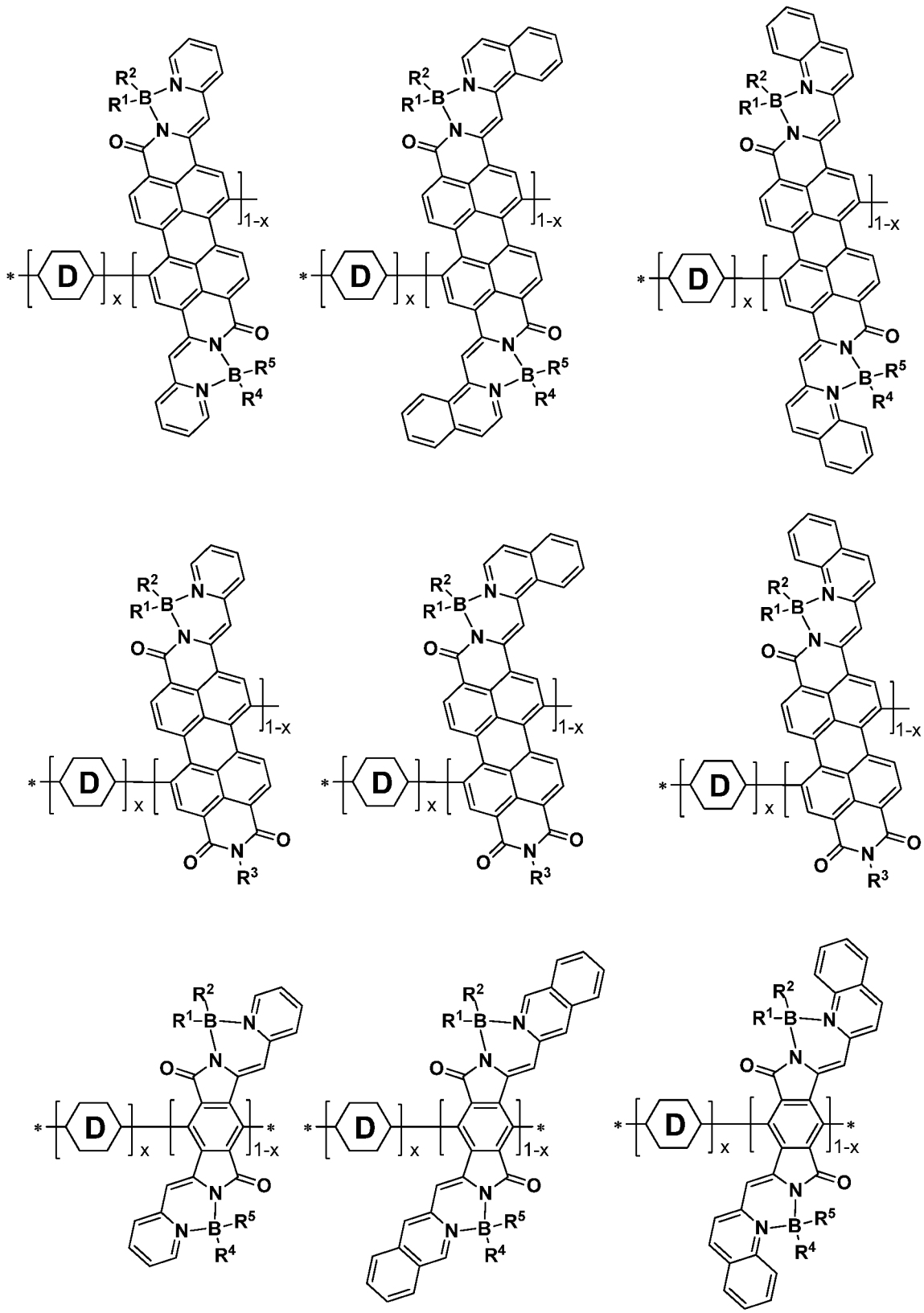
Figure 2D:
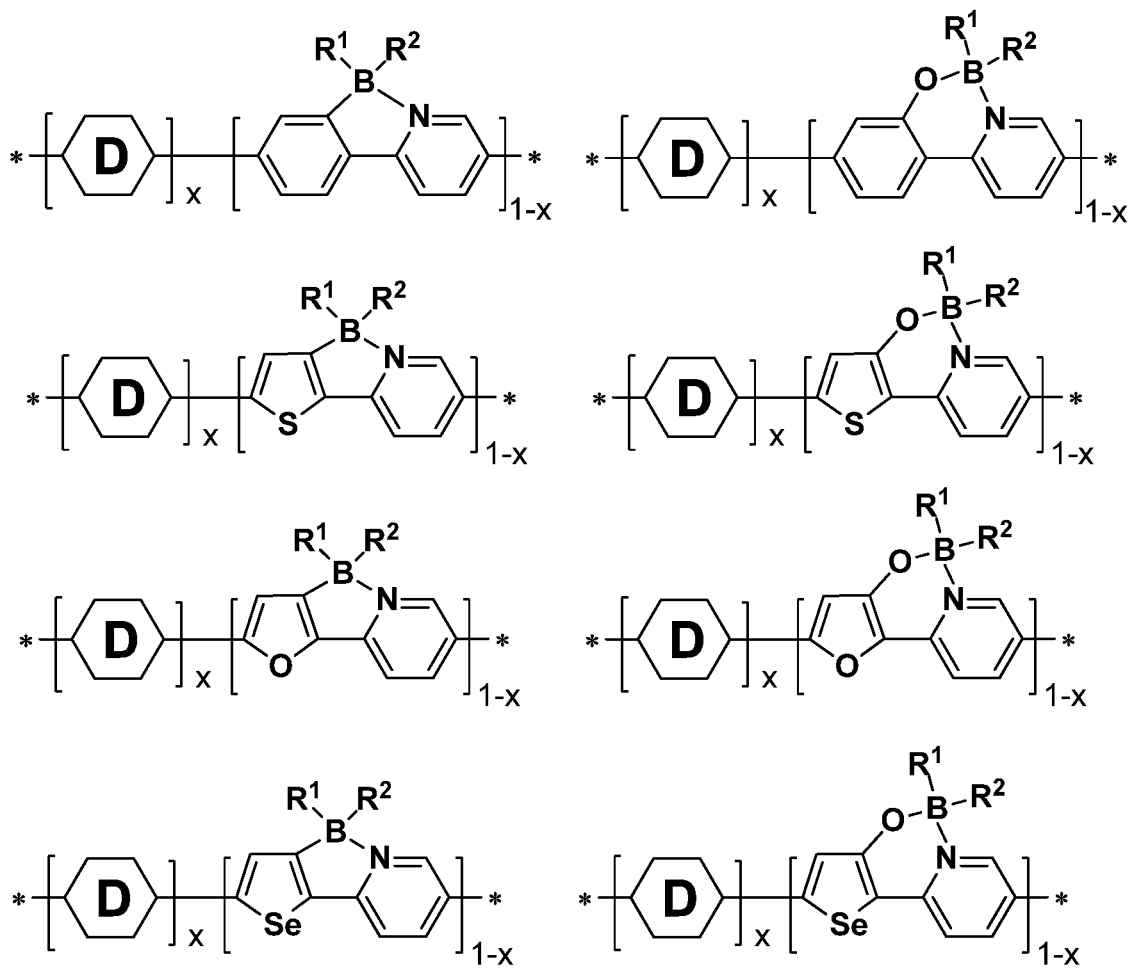
Figure 2E:
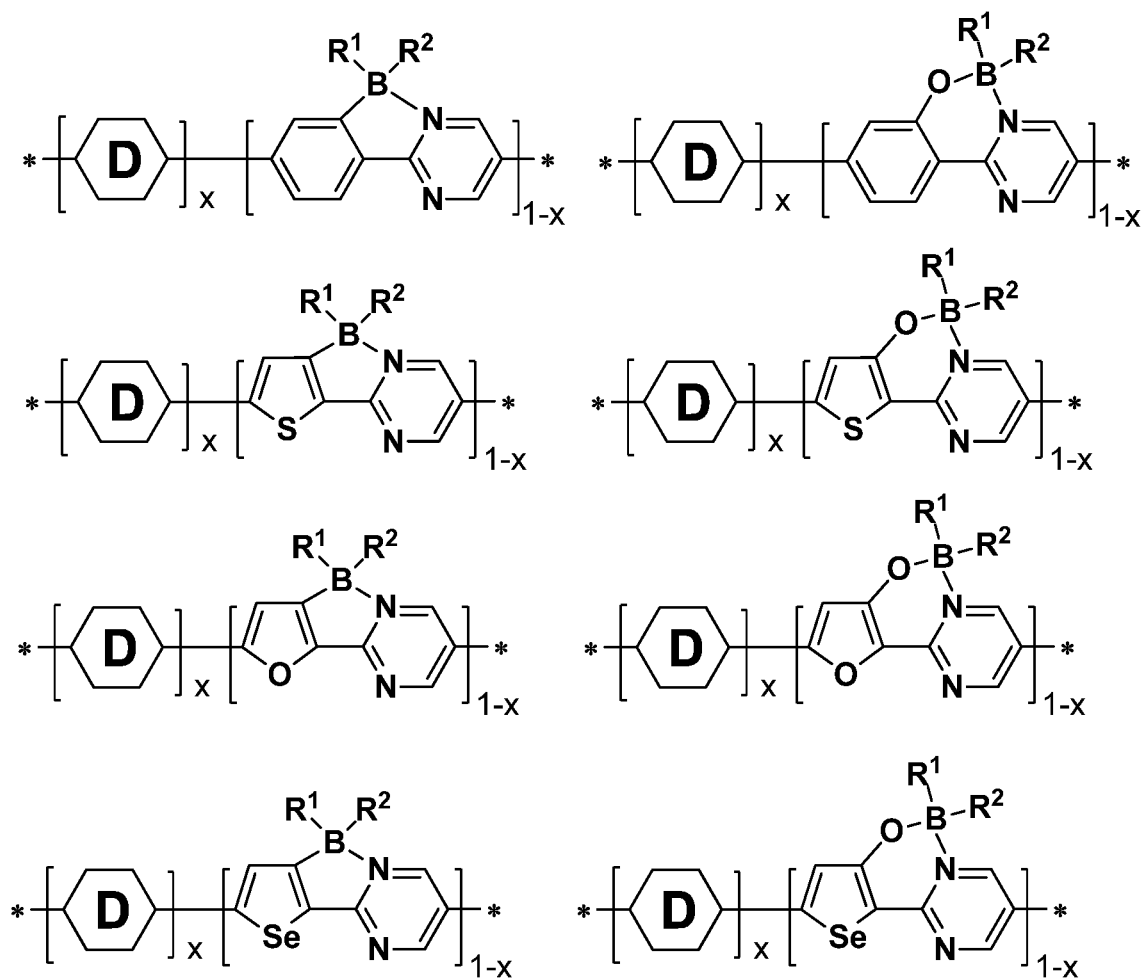
Figure 2F:
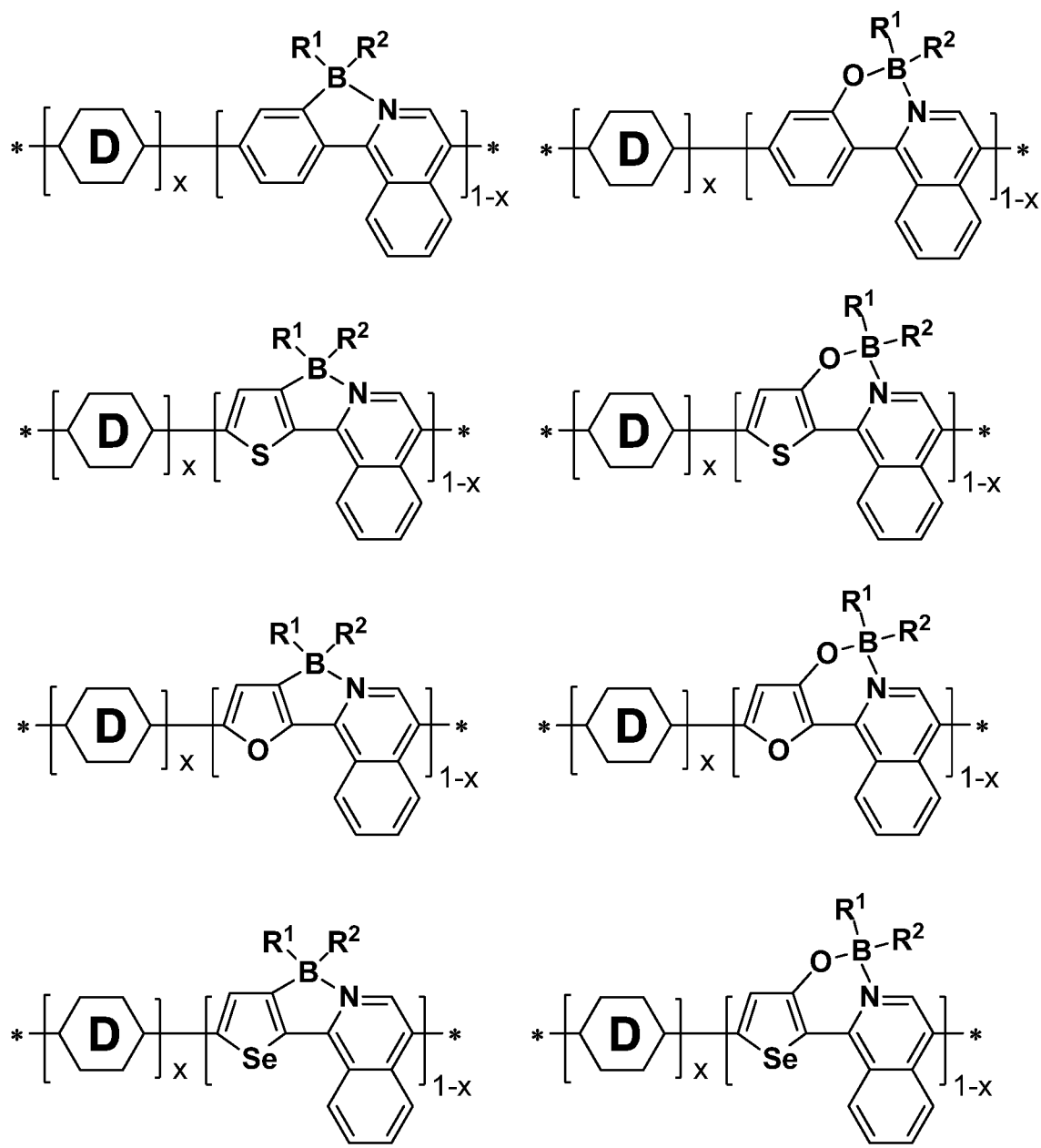
Figure 2G:
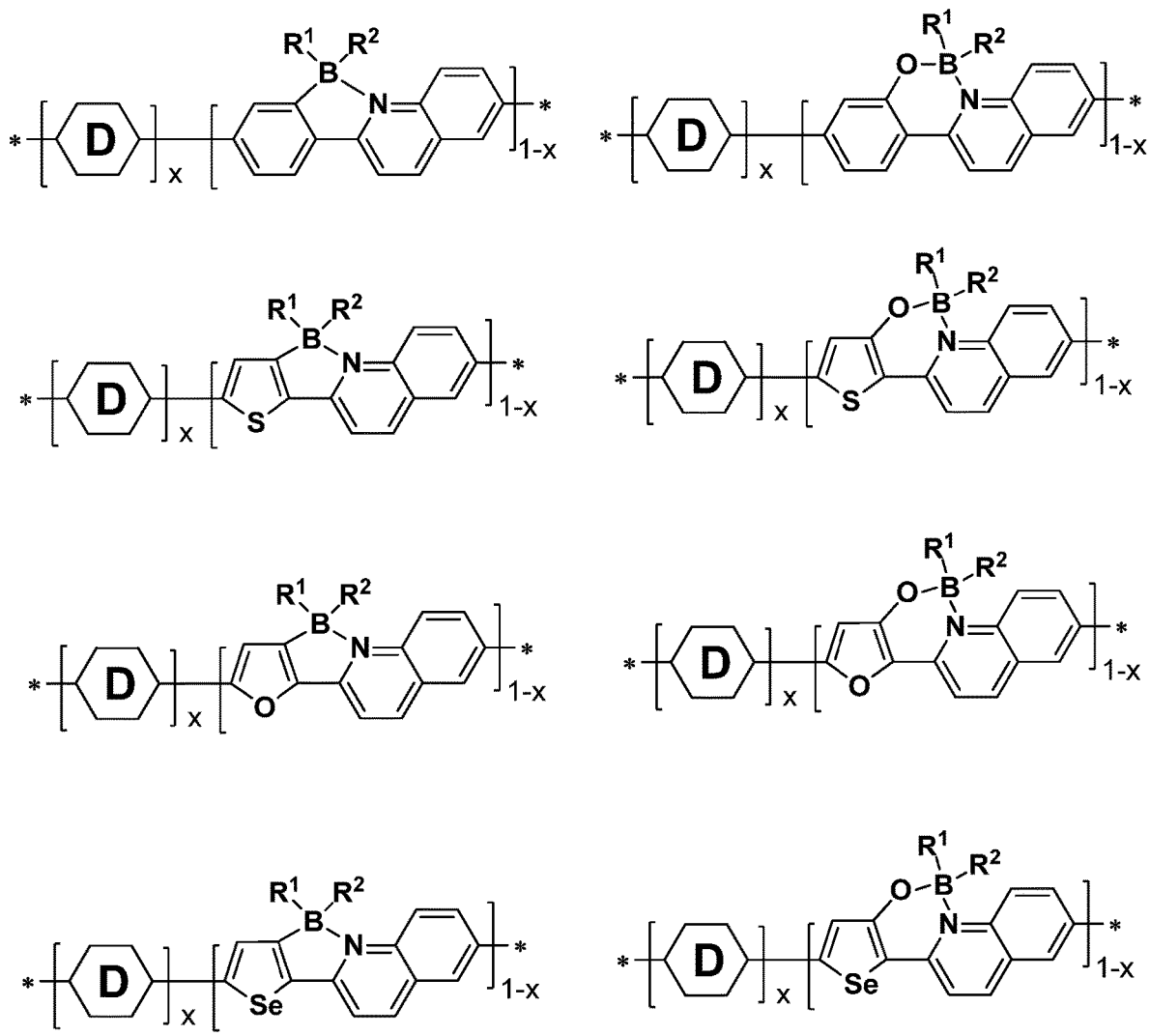

Suitable narrow band monomers of the present invention can include BODIPY derivatives and other boron-containing monomers. FIGS. 2B-2N shows a non-limiting list of examples of the narrow-band emissive copolymer including one general monomer chosen from FIG. 2A and different BODIPY derivatives or other boron-containing units as narrow-band monomers. The narrow band monomers in FIGS. 2B-2L can include a variety of substituents defined herein. For example, for the structures shown in FIGS. 2B and 2C, each of $R^1$, $R^2$, $R^4$ and $R^5$ can be independently selected from the group consisting of fluorine (F), phenyl, naphthyl, alkyl-substituted phenyl, alkyl-substituted naphthyl and alkyl-substituted thiophenyl. Alkyl substituted phenyl can include 2-alkylphenyl, 3-alkylphenyl, 4-alkylphenyl, 2,4-dialkylphenyl, 3,5-dialkylphenyl, and 3,4-dialkylphenyl. Alkyl-substituted naphthyl can include 3-alkyl-substituted naphthyl, 4-alkyl-substituted naphthyl, 6-alkyl-substituted naphthyl and 7-alkyl-substituted naphthyl. Alkyl-substituted thiophenyl can include 2-alkylthiophenyl, 3-alkylthiophenyl, 4-alkylthiophenyl. The alkyl substituents can include $C_nH_{2n+1}$ or $C_nF_{2n+1}$ or —$CH_2CH_2[OCH_2CH_2]_n$—$OCH_3$ wherein n is 1 to 20. In some embodiments, n can be between 1 to 50 or higher. $R^3$ can be selected from the group consisting of phenyl, alkyl-substituted phenyl, and alkyl-substituted thiophenyl, and in some cases, from cyano (CN), fluorine (F), and trifluoro ($CF_3$). Additional narrow-band monomers are shown in FIGS. 2D-2G in which each of $R^1$ and $R^2$ are independently selected from the group consisting of, but not limited to, fluorine, alkyl, phenyl, alkyl-substituted phenyl, alkyl-substituted fluorenyl and alkyl-substituted carbazolyl. Alkyl substituted phenyl can include 2-alkylphenyl, 3-alkylphenyl, 4-alkylphenyl, 2,4-dialkylphenyl, 3,5-dialkylphenyl, and 3,4-dialkylphenyl. Alkyl-substituted fluorenyl can include 9,9-dialkyl-substituted fluorenyl, 7-alkyl-9,9-dialkyl-substituted fluorenyl, 7-triphenylaminyl-9,9-dialkyl-substituted fluorenyl and 7-diphenylaminyl-9,9-dialkyl-substituted fluorenyl. The alkyl substituents can include $C_nH_{2n+1}$ or $C_nF_{2n+1}$ or —$CH_2CH_2[OCH_2CH_2]_n$—$OCH_3$ wherein n is 1 to 20. In some embodiments, n can be between 1 to 50 or higher.

Figure 2H:
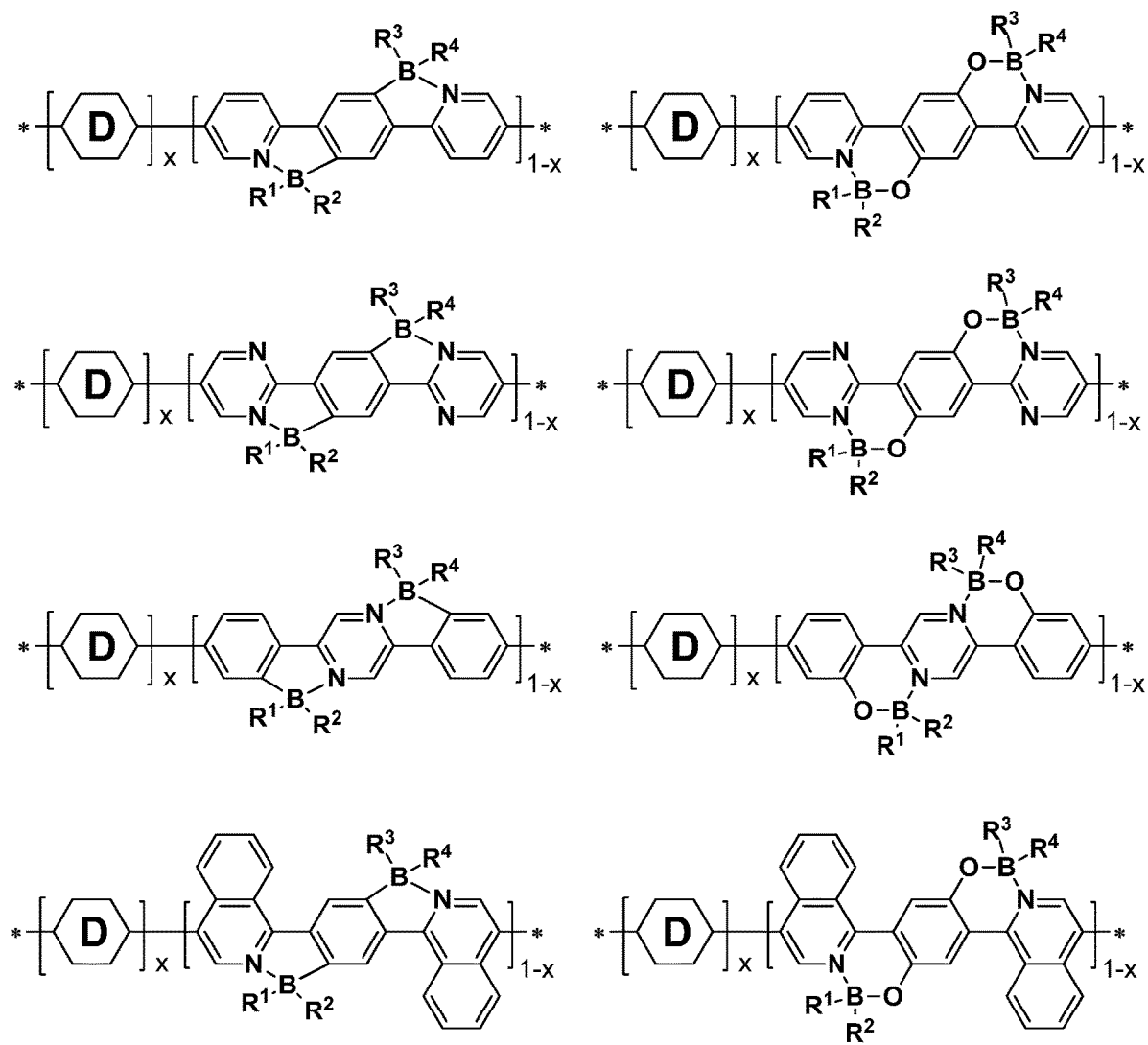
Figure 2I:
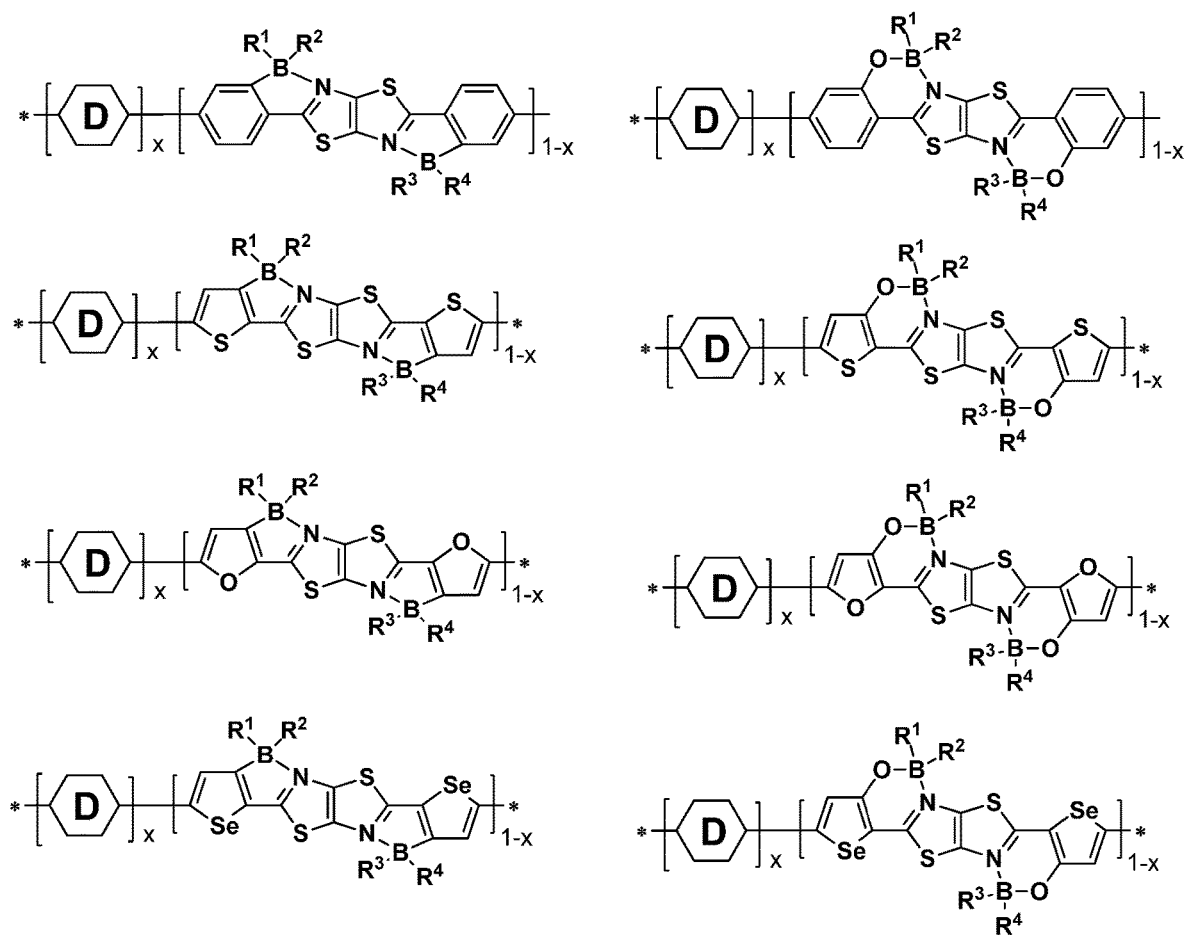

FIGS. 2H and 2I show additional example monomers in which each of $R^1$, $R^2$, $R^3$ and $R^4$ are independently selected from the group consisting of, but not limited to, fluorine, alkyl, phenyl, alkyl-substituted phenyl, alkyl-substituted fluorenyl, alkyl-substituted carbazolyl and alkyl-substituted thiophenyl. Alkyl substituted phenyl can include 2-alkylphenyl, 3-alkylphenyl, 4-alkylphenyl, 2,4-dialkylphenyl, 3,5-dialkylphenyl, and 3,4-dialkylphenyl. Alkyl-substituted fluorenyl can include 9,9-dialkyl-substituted fluorenyl, 7-alkyl-9,9-dialkyl-substituted fluorenyl, 7-triphenylaminyl-9,9-dialkyl-substituted fluorenyl and 7-diphenylaminyl-9,9-dialkyl-substituted fluorenyl. Alkyl-substituted thiophenyl can include 3-alkyl-substituted thiophenyl, 4-alkyl-substituted thiophenyl, 5-alkyl-substituted thiophenyl, 3,4-dialkyl-substituted thiophenyl, 3,5-dialkyl-substituted thiophenyl and 4,5-dialkyl-substituted thiophenyl. The alkyl substituents can include $C_nH_{2n+1}$, or $C_nF_{2n+1}$ or —$CH_2CH_2[OCH_2CH_2]_n$—$OCH_3$ wherein n is 1 to 20. In some embodiments, n can be between 1 to 50 or higher.

Figure 2J:
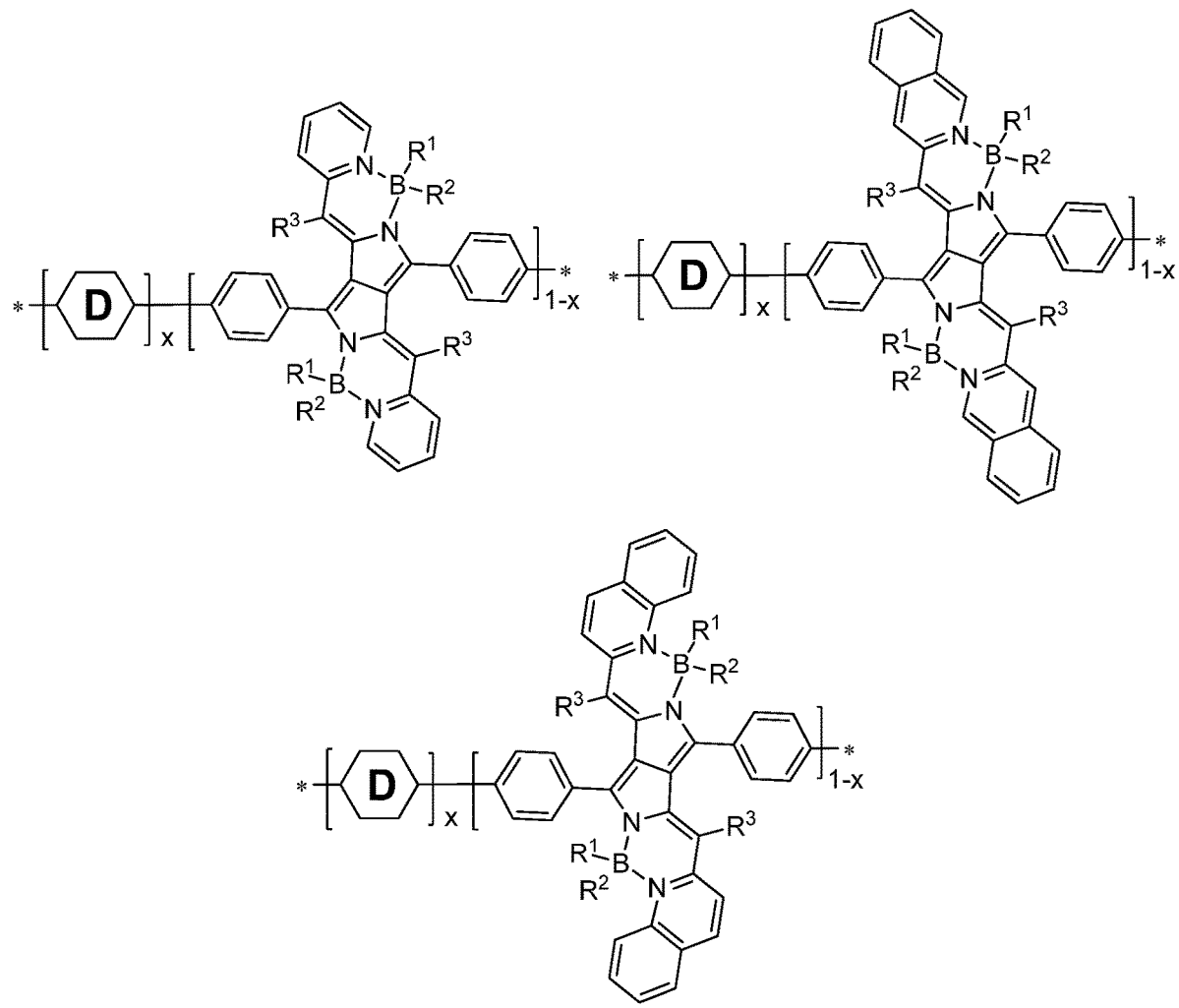
Figure 2K:
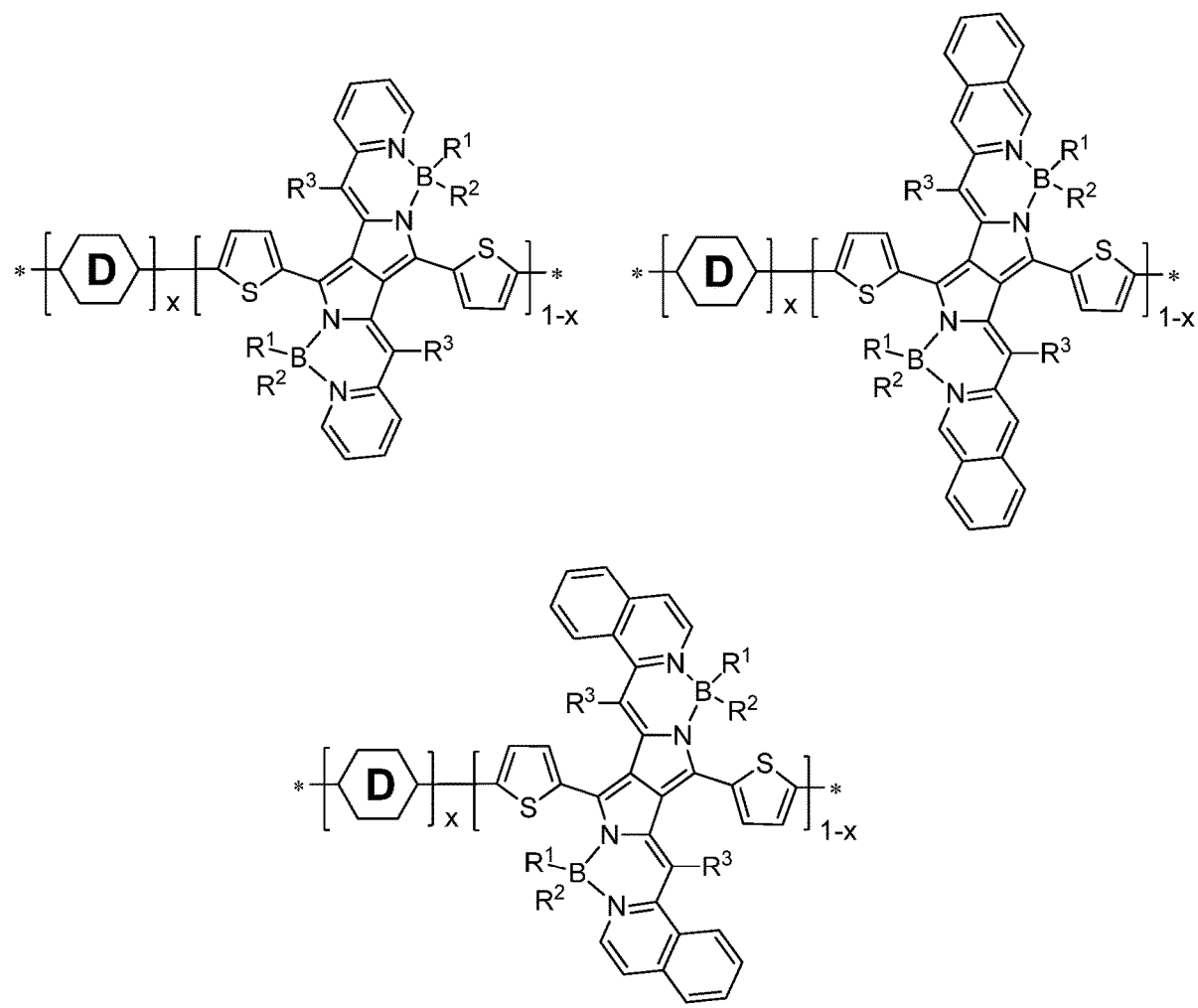
Figure 2L:
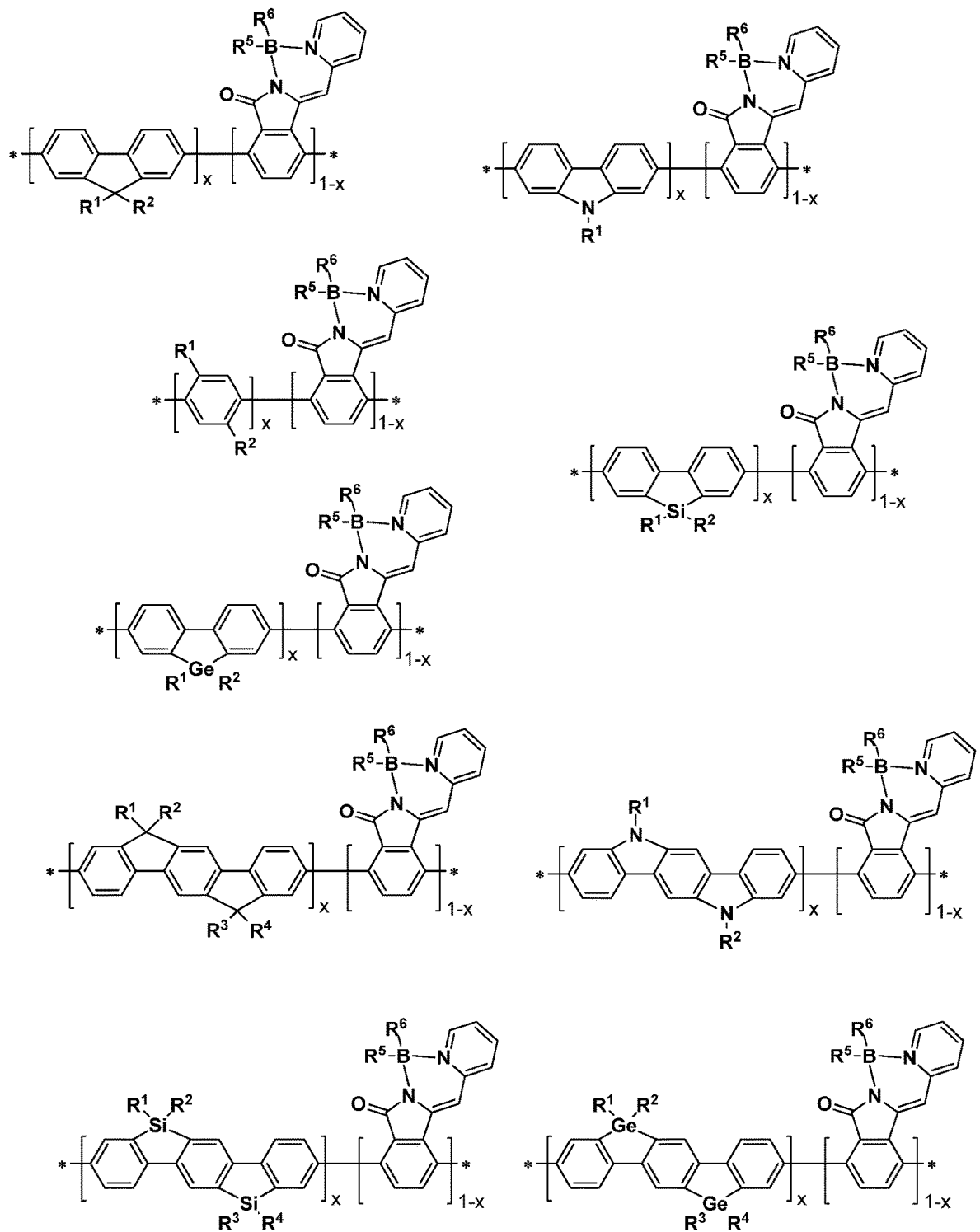
Figure 2M:
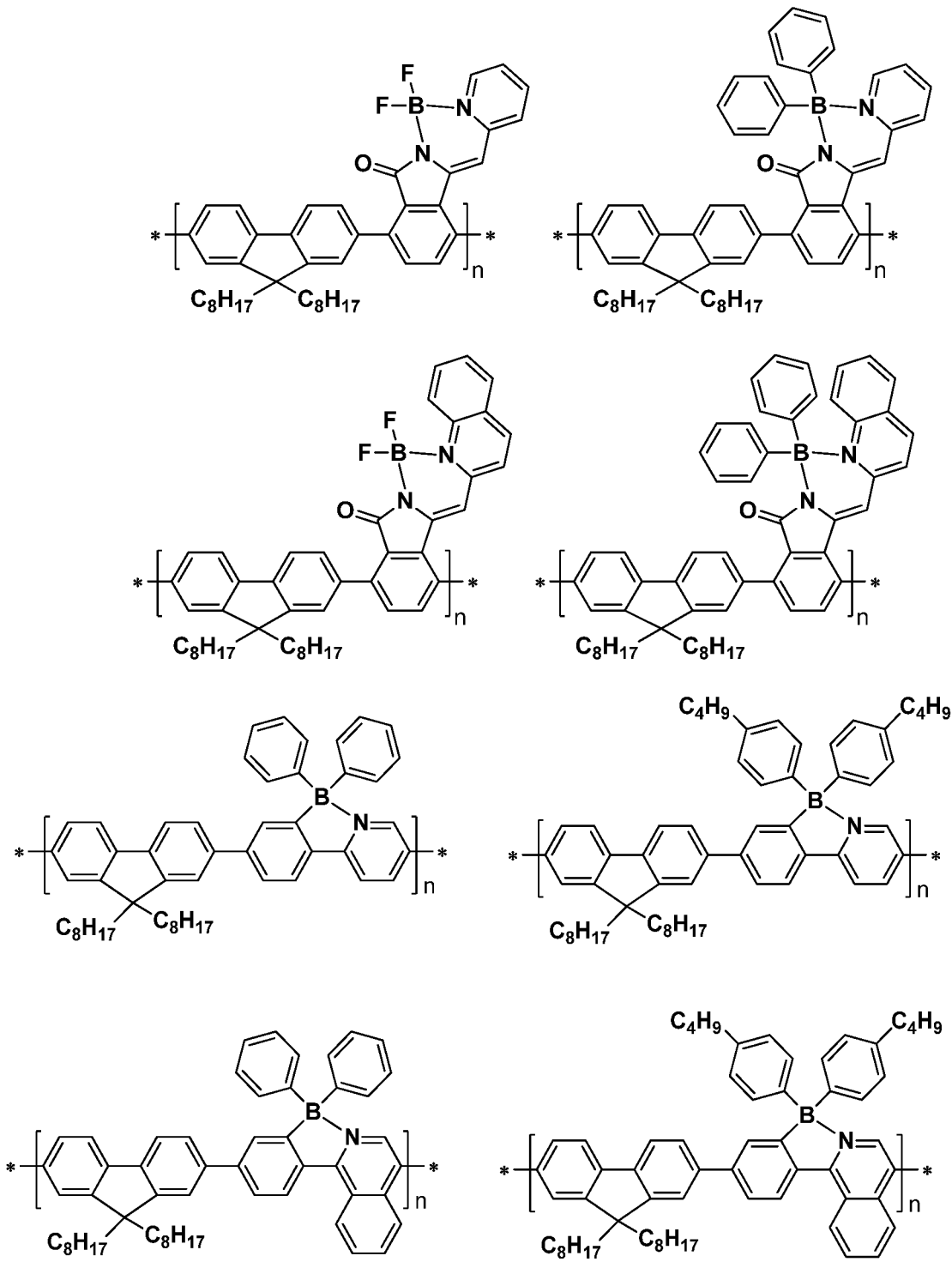
Figure 2N:
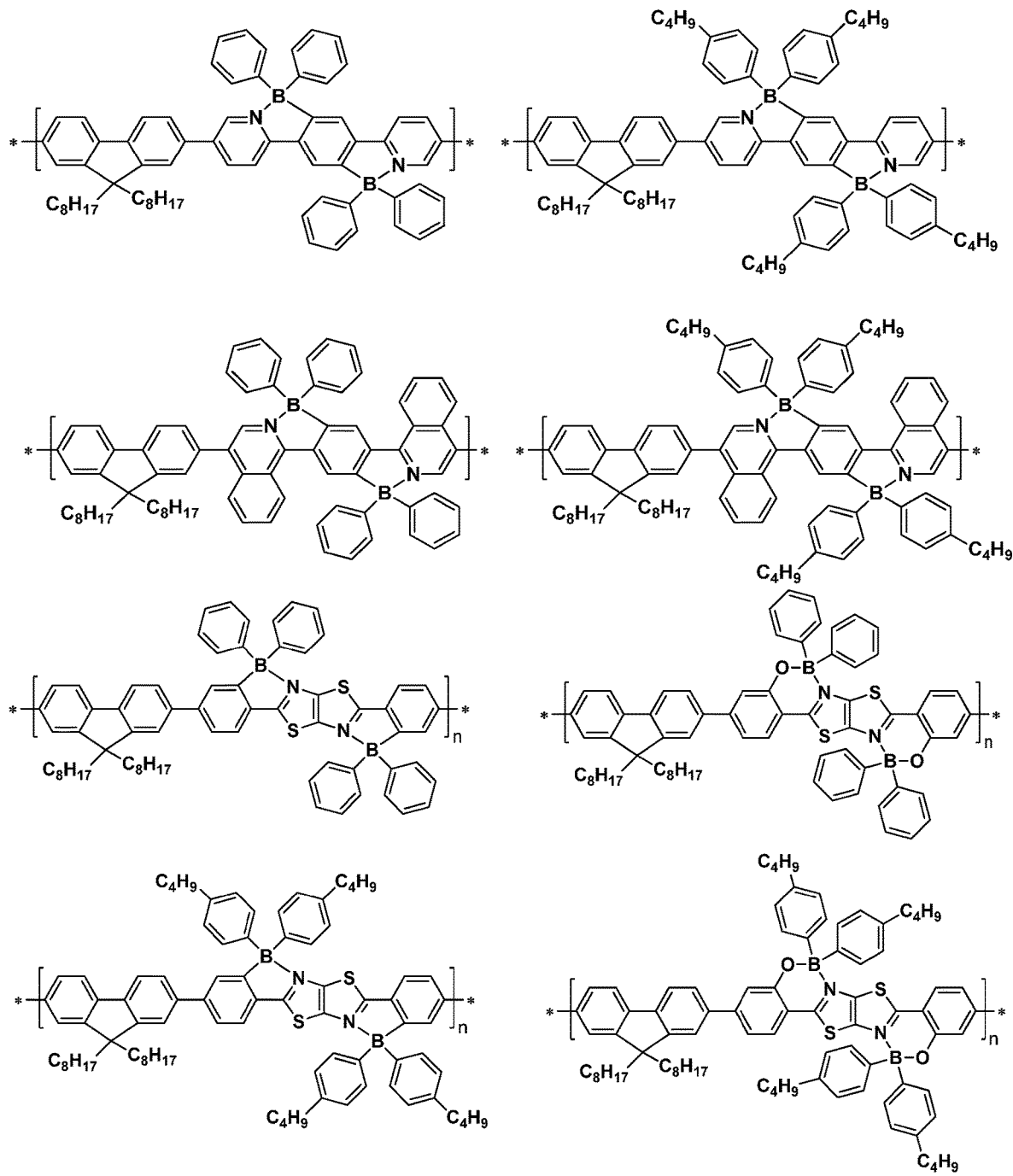

FIGS. 2J and 2K show additional monomers in which $R^1$ and $R^2$ are independently selected from the group consisting of, but not limited to, fluorine, alkyl, phenyl, alkyl-substituted phenyl, alkyl-substituted fluorenyl, alkyl-substituted carbazolyl and alkyl-substituted thiophenyl. Alkyl substituted phenyl can include 2-alkylphenyl, 3-alkylphenyl, 4-alkylphenyl, 2,4-dialkylphenyl, 3,5-dialkylphenyl, and 3,4-dialkylphenyl. Alkyl-substituted fluorenyl can include 9,9-dialkyl-substituted fluorenyl, 7-alkyl-9,9-dialkyl-substituted fluorenyl, 7-triphenylaminyl-9,9-dialkyl-substituted fluorenyl and 7-diphenylaminyl-9,9-dialkyl-substituted fluorenyl. Alkyl-substituted thiophenyl can include 3-alkyl-substituted thiophenyl, 4-alkyl-substituted thiophenyl, 5-alkyl-substituted thiophenyl, 3,4-dialkyl-substituted thiophenyl, 3,5-dialkyl-substituted thiophenyl and 4,5-dialkyl-substituted thiophenyl. The alkyl substituents can include $C_nH_{2n+1}$, or $C_nF_{2n+1}$ or —$CH_2CH_2[OCH_2CH_2]_n$—$OCH_3$ wherein n is 1 to 20. In some embodiments, n can be between 1 to 50 or higher. $R^3$ can be hydrogen, fluorine, trifluoro or —CN. FIG. 2L further shows generic structures for both general monomers and narrow-band monomers present in a copolymer provided by the present invention. In FIG. 2L, each of $R^1$, $R^2$, $R^3$ and $R^4$ can be independently selected from the group consisting of, but not limited to, fluorine, alkyl, phenyl, alkyl-substituted phenyl, alkyl-substituted fluorenyl, alkyl-substituted carbazolyl and alkyl-substituted thiophenyl. Alkyl substituted phenyl can include 2-alkylphenyl, 3-alkylphenyl, 4-alkylphenyl, 2,4-dialkylphenyl, 3,5-dialkylphenyl, and 3,4-dialkylphenyl. Alkyl-substituted fluorenyl can include 9,9-dialkyl-substituted fluorenyl, 7-alkyl-9,9-dialkyl-substituted fluorenyl, 7-triphenylaminyl-9,9-dialkyl-substituted fluorenyl and 7-diphenylaminyl-9,9-dialkyl-substituted fluorenyl. Alkyl-substituted thiophenyl can include 3-alkyl-substituted thiophenyl, 4-alkyl-substituted thiophenyl, 5-alkyl-substituted thiophenyl, 3,4-dialkyl-substituted thiophenyl, 3,5-dialkyl-substituted thiophenyl and 4,5-dialkyl-substituted thiophenyl. The alkyl substituents include $C_nH_{2n+1}$, or $C_nF_{2n+1}$ or —$CH_2CH_2[OCH_2CH_2]_n$—$OCH_3$, wherein n is 1 to 20. In some embodiments, n can be between 1 to 50 or higher. Each of $R^5$ and $R^6$ are independently selected from the group consisting of, but not limited to, fluorine, alkyl, phenyl, alkyl-substituted phenyl, alkyl-substituted fluorenyl and alkyl-substituted carbazolyl. Alkyl substituted phenyl can include 2-alkylphenyl, 3-alkylpheny, 4-alkylphenyl, 2,4-dialkylphenyl, 3,5-dialkylphenyl, and 3,4-dialkylphenyl. Alkyl-substituted fluorenyl can include 9,9-dialkyl-substituted fluorenyl, 7-alkyl-9,9-dialkyl-substituted fluorenyl, 7-triphenylaminyl-9,9-dialkyl-substituted fluorenyl and 7-diphenylaminyl-9,9-dialkyl-substituted fluorenyl. The alkyl substituents include $C_nH_{2n+1}$ or $C_nF_{2n+1}$ or —$CH_2CH_2[OCH_2CH_2]_n$—$OCH_3$, wherein n is 1 to 20. In some embodiments, n can be between 1 to 50 or higher.

Figure 4A:
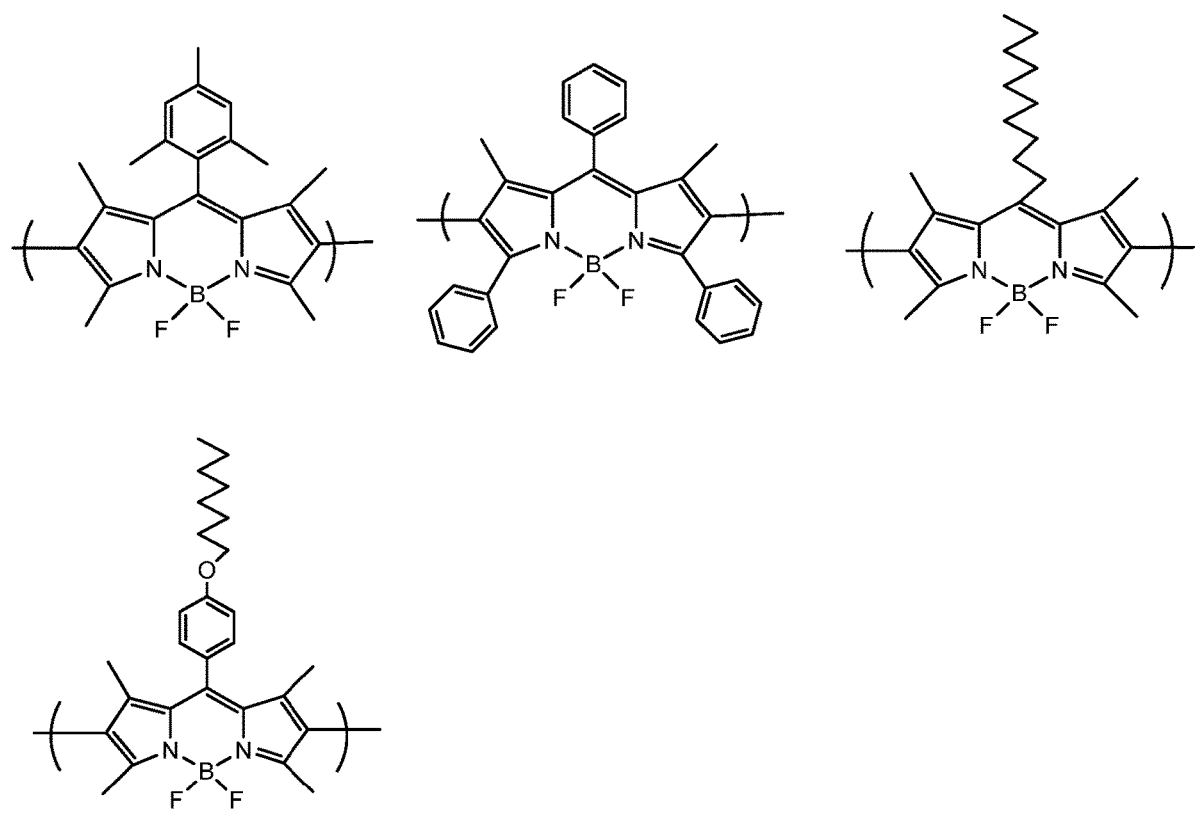
FIGS. 4A-4H show a non-limiting list of different BODIPY derivatives as some specific examples as a narrow-band monomer. Each of the BODIPY derivatives can be used to synthesize a narrow-band emissive homopolymer. Each of the BODIPY derivatives can also be copolymerized with any of the general polymers to synthesize a narrow-band emissive copolymer. Each of the BODIPY derivatives can be used as a narrow-band emissive unit to cross-link with the side-chains of conventional semiconducting polymers to form narrow-band emissive polymers.

A variety of other BODIPY derivatives can be used for the present invention. BODIPY and BODIPY derivatives can be polymerized to form polymers (e.g., homopolymers or heteropolymers) and/or can be attached (e.g., covalently attached) to a polymer backbone, sidechain and/or terminus. In some embodiments, the chromophoric polymer dots of the present invention can include a polymer that includes a narrow-band monomer having the formula:

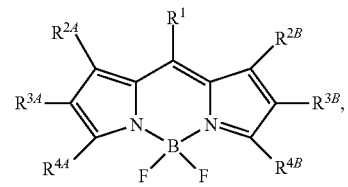

wherein each of $R^1$, $R^{2A}$, $R^{2B}$, $R^{3A}$, $R^{3B}$, $R^{4A}$ and $R^{4B}$ is independently selected from the group consisting of, but not limited to, hydrogen (H), deuterium (D), halogen, direct or branched alkyl, heteroalkyl, heterocycloalkyl, heterocycloalkylene, alkoxy, aryl, hydroxyl, cyano, nitro, ether and its derivatives, ester and its derivatives, alkyl ketone, alkylester, arylester, alkynyl, alkyl amine, fluoroalkyl, fluoroaryl, and polyalkalene (e.g, mehtoxyethoxyethoxy, ethoxyethoxy, and —$(OCH_2CH_2)_nOH$, n=1-50), phenyl, alkyl-(alkoxy-, aryl-, fluoroalkyl-, fluoroaryl-)substituted phenyl, pyridyl, alkyl-(alkoxy-, aryl-, fluoroalkyl-, fluoroaryl-)substituted pyridyl, bipyridyl, alkyl-(alkoxy-, aryl-, fluoroalkyl-, fluoroaryl-)substituted bipyridyl tripyridyl, alkyl-(alkoxy-, aryl-, fluoroalkyl-, fluoroaryl-)substituted tripyridyl, furyl, alkyl-(alkoxy-, aryl-, fluoroalkyl-, fluoroaryl-)substituted furyl, thienyl, alkyl-(alkoxy-, aryl-, fluoroalkyl-, fluoroaryl-)substituted thienyl, pyrrolyl, alkyl-(alkoxy-, aryl-, fluoroalkyl-, fluoroaryl-)substituted pyrrolyl, pyrazolyl, alkyl-(alkoxy-, aryl-, fluoroalkyl-, fluoroaryl-)substituted pyrazolyl, oxazolyl, alkyl-(alkoxy-, aryl-, fluoroalkyl-, fluoroaryl-)substituted oxazolyl, thiazolyl, alkyl-(alkoxy-, aryl-, fluoroalkyl-, fluoroaryl-)substituted thiazolyl, imidazolyl, alkyl-(alkoxy-, aryl-, fluoroalkyl-, fluoroaryl-)substituted imidazolyl, pyrazinyl, alkyl-(alkoxy-, aryl-, fluoroalkyl-, fluoroaryl-) substituted pyrazinyl, benzooxadizolyl, alkyl-(alkoxy-, aryl-, fluoroalkyl-, fluoroaryl-)substituted benzooxadizolyl, benzothiadizolyl, alkyl-(alkoxy-, aryl-, fluoroalkyl-, fluoroaryl-)substituted benzothiadizolyl, fluorenyl, alkyl-(alkoxy-, aryl-, fluoroalkyl-, fluoroaryl-)substituted fluorenyl, triphenylaminyl-substituted fluorenyl, diphenylaminyl-substituted fluorenyl, alkyl-substituted carbazolyl, alkyl-substituted triphenylaminyl and alkyl-substituted thiophenyl. As exemplary embodiments, alkyl substituted phenyl can include 2-alkylphenyl, 3-alkylphenyl, 4-alkylphenyl, 2,4-dialkylphenyl, 3,5-dialkylphenyl, 3,4-dialkylphenyl; alkyl-substituted fluorenyl can include 9, 9-dialkyl-substituted fluorenyl, 7-alkyl-9,9-dialkyl-substituted fluorenyl, 6-alkyl-9,9-dialkyl-substituted fluorenyl, 7-triphenylaminyl-9,9-dialkyl-substituted fluorenyl and 7-diphenylaminyl-9,9-dialkyl-substituted fluorenyl; alkyl-substituted carbazolyl can include N-alkyl-substituted carbazolyl, 6-alkyl-substituted carbazolyl and 7-alkyl-substituted carbazolyl; alkyl-substituted triphenylaminyl can include 4'-alkyl-substituted triphenylaminyl, 3'-alkyl-substituted triphenylaminyl, 3',4'-dialkyl-substituted triphenylaminyl and 4',4"-alkyl-substituted triphenylaminyl; alkyl-substituted thiophenyl can include 2-alkylthiophenyl, 3-alkylthiophenyl, and 4-alkylthiophenyl, N-dialkyl-4-phenyl, N-diphenyl-4-phenyl, and N-dialkoxyphenyl-4-phenyl. The narrow-band monomer can be integrated into a backbone of the polymer (e.g., polymerized in the polymer) and/or covalently attached to the backbone, a terminus, or a sidechain of the polymer through at least one attachment to $R^1$, $R^{2A}$, $R^{2B}$, $R^{3A}$, $R^{3B}$, $R^{4A}$, $R^{4B}$, or a combination thereof. FIG. 4A shows examples of monomers that, e.g., can be integrated with the polymer by attachment to $R^{3A}$ and $R^{3B}$ groups.

Figure 4B:
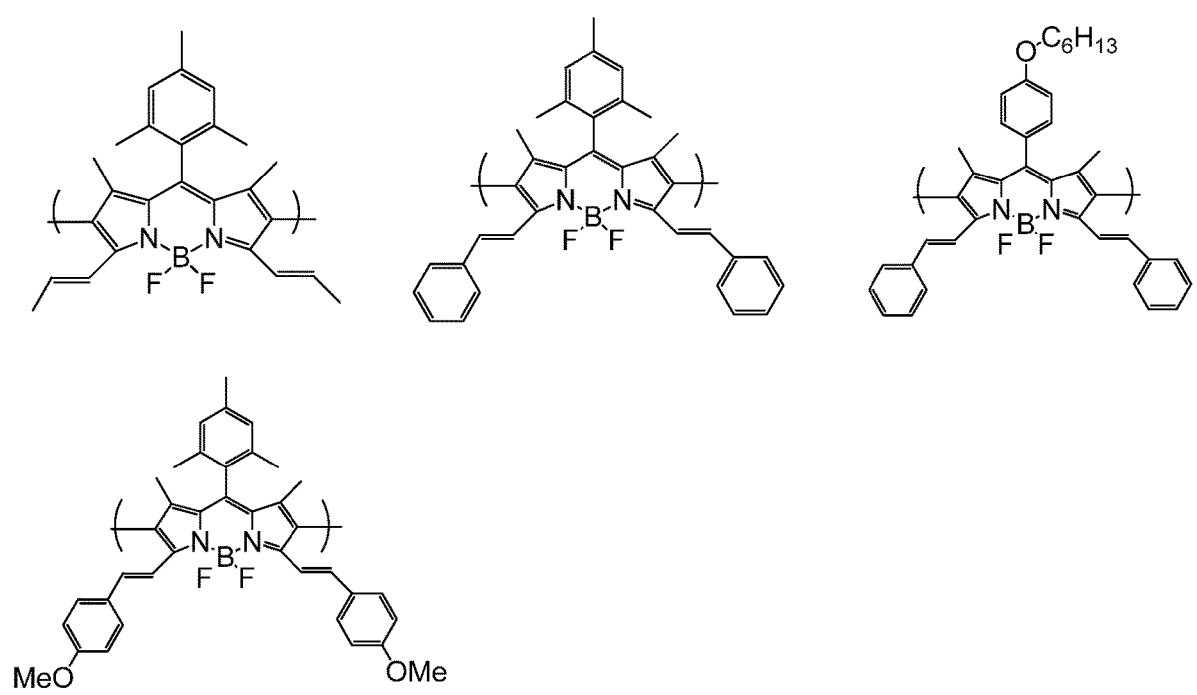

In some embodiments, the chromophoric polymer dots of the present invention can include a polymer that includes a narrow-band monomer having the formula:

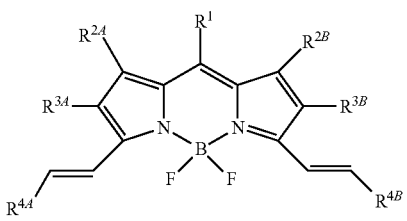

wherein each of $R^1$, $R^{2A}$, $R^{2B}$, $R^{3A}$, $R^{3B}$, $R^{4A}$ and $R^{4B}$ is independently selected from the group consisting of, but not limited to, hydrogen (H), deuterium (D), halogen, direct or branched alkyl, heteroalkyl, heterocycloalkyl, heterocycloalkylene, alkoxy, aryl, hydroxyl, cyano, nitro, ether and its derivatives, ester and its derivatives, alkyl ketone, alkylester, arylester, alkynyl, alkyl amine, fluoroalkyl, fluoroaryl, and polyalkalene (e.g, mehtoxyethoxyethoxy, ethoxyethoxy, and —$(OCH_2CH_2)_nOH$, n=1-50), phenyl, alkyl-(alkoxy-, aryl-, fluoroalkyl-, fluoroaryl-)substituted phenyl, pyridyl, alkyl-(alkoxy-, aryl-, fluoroalkyl-, fluoroaryl-)substituted pyridyl, bipyridyl, alkyl-(alkoxy-, aryl-, fluoroalkyl-, fluoroaryl-)substituted bipyridyl tripyridyl, alkyl-(alkoxy-, aryl-, fluoroalkyl-, fluoroaryl-)substituted tripyridyl, furyl, alkyl-(alkoxy-, aryl-, fluoroalkyl-, fluoroaryl-)substituted furyl, thienyl, alkyl-(alkoxy-, aryl-, fluoroalkyl-, fluoroaryl-)substituted thienyl, pyrrolyl, alkyl-(alkoxy-, aryl-, fluoroalkyl-, fluoroaryl-)substituted pyrrolyl, pyrazolyl, alkyl-(alkoxy-, aryl-, fluoroalkyl-, fluoroaryl-)substituted pyrazolyl, oxazolyl, alkyl-(alkoxy-, aryl-, fluoroalkyl-, fluoroaryl-)substituted oxazolyl, thiazolyl, alkyl-(alkoxy-, aryl-, fluoroalkyl-, fluoroaryl-)substituted thiazolyl, imidazolyl, alkyl-(alkoxy-, aryl-, fluoroalkyl-, fluoroaryl-)substituted imidazolyl, pyrazinyl, alkyl-(alkoxy-, aryl-, fluoroalkyl-, fluoroaryl-)substituted pyrazinyl, benzooxadizolyl, alkyl-(alkoxy-, aryl-, fluoroalkyl-, fluoroaryl-)substituted benzooxadizolyl, benzothiadizolyl, alkyl-(alkoxy-, aryl-, fluoroalkyl-, fluoroaryl-)substituted benzothiadizolyl, fluorenyl, alkyl-(alkoxy-, aryl-, fluoroalkyl-, fluoroaryl-)substituted fluorenyl, triphenylaminyl-substituted fluorenyl, diphenylaminyl-substituted fluorenyl, alkyl-substituted carbazolyl, alkyl-substituted triphenylaminyl and alkyl-substituted thiophenyl. As exemplary embodiments, alkyl substituted phenyl can include 2-alkylphenyl, 3-alkylphenyl, 4-alkylphenyl, 2,4-dialkylphenyl, 3,5-dialkylphenyl, 3,4-dialkylphenyl; alkyl-substituted fluorenyl can include 9, 9-dialkyl-substituted fluorenyl, 7-alkyl-9,9-dialkyl-substituted fluorenyl, 6-alkyl-9,9-dialkyl-substituted fluorenyl, 7-triphenylaminyl-9,9-dialkyl-substituted fluorenyl and 7-diphenylaminyl-9,9-dialkyl-substituted fluorenyl; alkyl-substituted carbazolyl can include N-alkyl-substituted carbazolyl, 6-alkyl-substituted carbazolyl and 7-alkyl-substituted carbazolyl; alkyl-substituted triphenylaminyl can include 4'-alkyl-substituted triphenylaminyl, 3'-alkyl-substituted triphenylaminyl, 3',4'-dialkyl-substituted triphenylaminyl and 4',4"-alkyl-substituted triphenylaminyl; alkyl-substituted thiophenyl can include 2-alkylthiophenyl, 3-alkylthiophenyl, and 4-alkylthiophenyl, N-dialkyl-4-phenyl, N-diphenyl-4-phenyl, and N-dialkoxyphenyl-4-phenyl. The narrow-band monomer can be integrated into a backbone of the polymer (e.g., polymerized in the polymer) and/or covalently attached to the backbone, a terminus, or a sidechain of the polymer through at least one attachment to $R^1$, $R^{2A}$, $R^{2B}$, $R^{3A}$, $R^{3B}$, $R^{4A}$, $R^{4B}$, or a combination thereof. The monomer can, for example, integrate with the backbone of the polymer by attachment to the $R^{3A}$ and $R^{3B}$ groups. FIG. 4B shows examples of monomers that, e.g., can be integrated with the polymer by attachment to $R^{3A}$ and $R^{3B}$ groups.

Figure 4C:
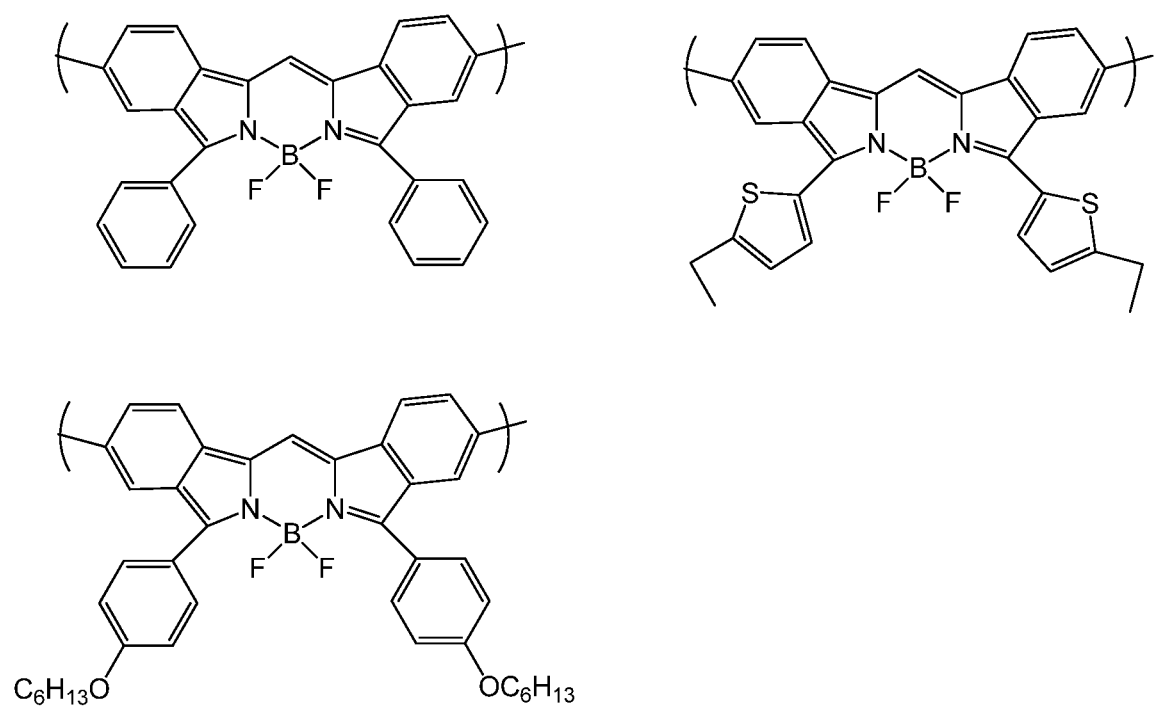

In some embodiments, the chromophoric polymer dots of the present invention can include a polymer that includes a narrow-band monomer having the formula:

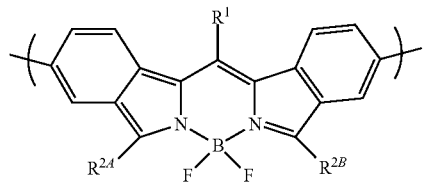

wherein each of $R^1$, $R^{2A}$ and $R^{2B}$ is independently selected from the group consisting of, but not limited to, hydrogen (H), deuterium (D), halogen, direct or branched alkyl, heteroalkyl, heterocycloalkyl, heterocycloalkylene, alkoxy, aryl, hydroxyl, cyano, nitro, ether and its derivatives, ester and its derivatives, alkyl ketone, alkylester, arylester, alkynyl, alkyl amine, fluoroalkyl, fluoroaryl, and polyalkalene (e.g, mehtoxyethoxyethoxy, ethoxyethoxy, and —$(OCH_2CH_2)_nOH$, n=1-50), phenyl, alkyl-(alkoxy-, aryl-, fluoroalkyl-, fluoroaryl-)substituted phenyl, pyridyl, alkyl-(alkoxy-, aryl-, fluoroalkyl-, fluoroaryl-)substituted pyridyl, bipyridyl, alkyl-(alkoxy-, aryl-, fluoroalkyl-, fluoroaryl-) substituted bipyridyl tripyridyl, alkyl-(alkoxy-, aryl-, fluoroalkyl-, fluoroaryl-)substituted tripyridyl, furyl, alkyl-(alkoxy-, aryl-, fluoroalkyl-, fluoroaryl-)substituted furyl, thienyl, alkyl-(alkoxy-, aryl-, fluoroalkyl-, fluoroaryl-)substituted thienyl, pyrrolyl, alkyl-(alkoxy-, aryl-, fluoroalkyl-, fluoroaryl-)substituted pyrrolyl, pyrazolyl, alkyl-(alkoxy-, aryl-, fluoroalkyl-, fluoroaryl-)substituted pyrazolyl, oxazolyl, alkyl-(alkoxy-, aryl-, fluoroalkyl-, fluoroaryl-)substituted oxazolyl, thiazolyl, alkyl-(alkoxy-, aryl-, fluoroalkyl-, fluoroaryl-)substituted thiazolyl, imidazolyl, alkyl-(alkoxy-, aryl-, fluoroalkyl-, fluoroaryl-)substituted imidazolyl, pyrazinyl, alkyl-(alkoxy-, aryl-, fluoroalkyl-, fluoroaryl-)substituted pyrazinyl, benzooxadizolyl, alkyl-(alkoxy-, aryl-, fluoroalkyl-, fluoroaryl-)substituted benzooxadizolyl, benzothiadizolyl, alkyl-(alkoxy-, aryl-, fluoroalkyl-, fluoroaryl-)substituted benzothiadizolyl, fluorenyl, alkyl-(alkoxy-, aryl-, fluoroalkyl-, fluoroaryl-)substituted fluorenyl, triphenylaminyl-substituted fluorenyl, diphenylaminyl-substituted fluorenyl, alkyl-substituted carbazolyl, alkyl-substituted triphenylaminyl and alkyl-substituted thiophenyl. As exemplary embodiments, alkyl substituted phenyl can include 2-alkylphenyl, 3-alkylphenyl, 4-alkylphenyl, 2,4-dialkylphenyl, 3,5-dialkylphenyl, 3,4-dialkylphenyl; alkyl-substituted fluorenyl can include 9, 9-dialkyl-substituted fluorenyl, 7-alkyl-9,9-dialkyl-substituted fluorenyl, 6-alkyl-9,9-dialkyl-substituted fluorenyl, 7-triphenylaminyl-9,9-dialkyl-substituted fluorenyl and 7-diphenylaminyl-9,9-dialkyl-substituted fluorenyl; alkyl-substituted carbazolyl can include N-alkyl-substituted carbazolyl, 6-alkyl-substituted carbazolyl and 7-alkyl-substituted carbazolyl; alkyl-substituted triphenylaminyl can include 4'-alkyl-substituted triphenylaminyl, 3'-alkyl-substituted triphenylaminyl, 3',4'-dialkyl-substituted triphenylaminyl and 4',4"-alkyl-substituted triphenylaminyl; alkyl-substituted thiophenyl can include 2-alkylthiophenyl, 3-alkylthiophenyl, and 4-alkylthiophenyl, N-dialkyl-4-phenyl, N-diphenyl-4-phenyl, and N-dialkoxyphenyl-4-phenyl. The narrow-band monomer can be integrated into a backbone of the polymer (e.g., polymerized in the polymer) and/or covalently attached to the backbone, a terminus, or a sidechain of the polymer through at least one attachment, e.g., to $R^1$, $R^{2A}$, $R^{2B}$, or a combination thereof. The parentheses indicate points of attachment of the monomer to the backbone of the polymer. FIG. 4C shows examples of monomers that, e.g., can be integrated with the polymer (e.g., copolymerized in the polymer).

Figure 4D:
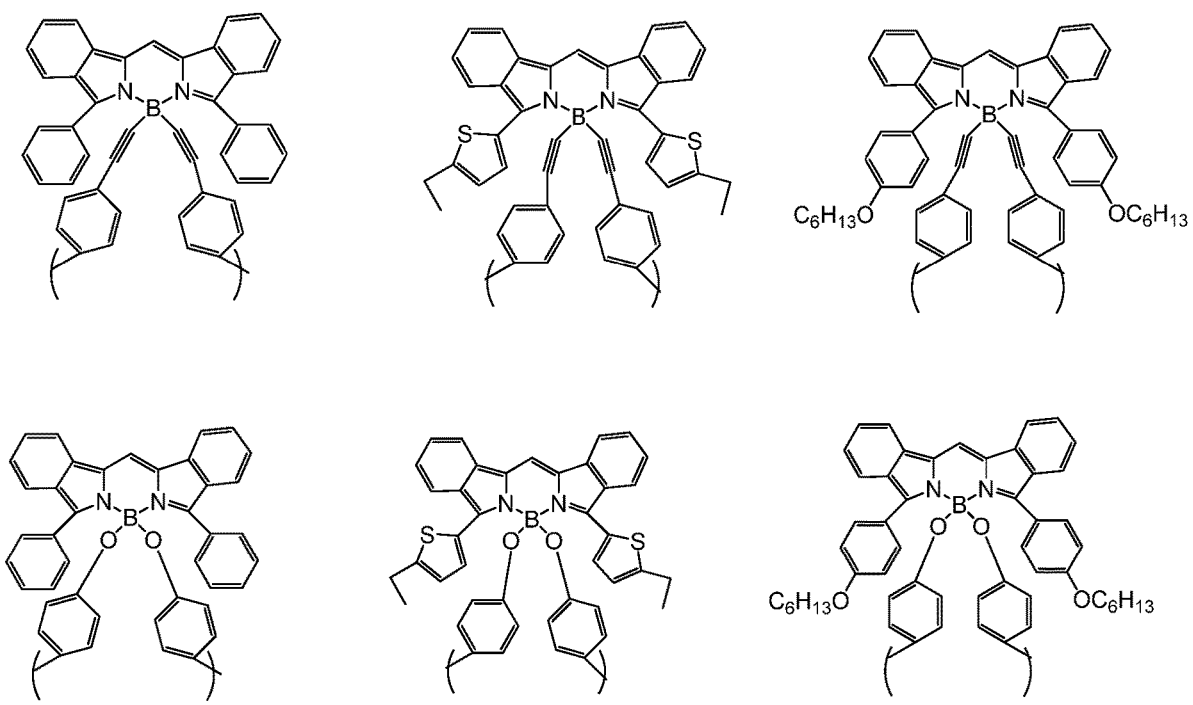

In some embodiments, the chromophoric polymer dots of the present invention can include a polymer that includes a narrow-band monomer having the formula:

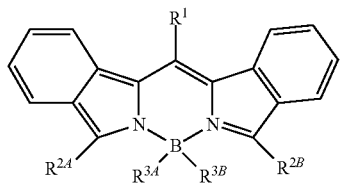

wherein each of $R^1$, $R^{2A}$, $R^{2B}$, $R^{3A}$, and $R^{3B}$ is independently selected from the group consisting of, but not limited to, hydrogen (H), deuterium (D), halogen, direct or branched alkyl, heteroalkyl, heterocycloalkyl, heterocycloalkylene, alkoxy, aryl, hydroxyl, cyano, nitro, ether and its derivatives, ester and its derivatives, alkyl ketone, alkylester, arylester, alkynyl, alkyl amine, fluoroalkyl, fluoroaryl, and polyalkalene (e.g, mehtoxyethoxyethoxy, ethoxyethoxy, and —$(OCH_2CH_2)_nOH$, n=1-50), phenyl, alkyl-(alkoxy-, aryl-, fluoroalkyl-, fluoroaryl-)substituted phenyl, pyridyl, alkyl-(alkoxy-, aryl-, fluoroalkyl-, fluoroaryl-)substituted pyridyl, bipyridyl, alkyl-(alkoxy-, aryl-, fluoroalkyl-, fluoroaryl-)substituted bipyridyl tripyridyl, alkyl-(alkoxy-, aryl-, fluoroalkyl-, fluoroaryl-)substituted tripyridyl, furyl, alkyl-(alkoxy-, aryl-, fluoroalkyl-, fluoroaryl-)substituted furyl, thienyl, alkyl-(alkoxy-, aryl-, fluoroalkyl-, fluoroaryl-)substituted thienyl, pyrrolyl, alkyl-(alkoxy-, aryl-, fluoroalkyl-, fluoroaryl-)substituted pyrrolyl, pyrazolyl, alkyl-(alkoxy-, aryl-, fluoroalkyl-, fluoroaryl-)substituted pyrazolyl, oxazolyl, alkyl-(alkoxy-, aryl-, fluoroalkyl-, fluoroaryl-)substituted oxazolyl, thiazolyl, alkyl-(alkoxy-, aryl-, fluoroalkyl-, fluoroaryl-)substituted thiazolyl, imidazolyl, alkyl-(alkoxy-, aryl-, fluoroalkyl-, fluoroaryl-)substituted imidazolyl, pyrazinyl, alkyl-(alkoxy-, aryl-, fluoroalkyl-, fluoroaryl-)substituted pyrazinyl, benzooxadizolyl, alkyl-(alkoxy-, aryl-, fluoroalkyl-, fluoroaryl-)substituted benzooxadizolyl, benzothiadizolyl, alkyl-(alkoxy-, aryl-, fluoroalkyl-, fluoroaryl-)substituted benzothiadizolyl, fluorenyl, alkyl-(alkoxy-, aryl-, fluoroalkyl-, fluoroaryl-)substituted fluorenyl, triphenylaminyl-substituted fluorenyl, diphenylaminyl-substituted fluorenyl, alkyl-substituted carbazolyl, alkyl-substituted triphenylaminyl and alkyl-substituted thiophenyl. As exemplary embodiments, alkyl substituted phenyl can include 2-alkylphenyl, 3-alkylphenyl, 4-alkylphenyl, 2,4-dialkylphenyl, 3,5-dialkylphenyl, 3,4-dialkylphenyl; alkyl-substituted fluorenyl can include 9, 9-dialkyl-substituted fluorenyl, 7-alkyl-9,9-dialkyl-substituted fluorenyl, 6-alkyl-9,9-dialkyl-substituted fluorenyl, 7-triphenylaminyl-9,9-dialkyl-substituted fluorenyl and 7-diphenylaminyl-9,9-dialkyl-substituted fluorenyl; alkyl-substituted carbazolyl can include N-alkyl-substituted carbazolyl, 6-alkyl-substituted carbazolyl and 7-alkyl-substituted carbazolyl; alkyl-substituted triphenylaminyl can include 4'-alkyl-substituted triphenylaminyl, 3'-alkyl-substituted triphenylaminyl, 3',4'-dialkyl-substituted triphenylaminyl and 4',4"-alkyl-substituted triphenylaminyl; alkyl-substituted thiophenyl can include 2-alkylthiophenyl, 3-alkylthiophenyl, and 4-alkylthiophenyl, N-dialkyl-4-phenyl, N-diphenyl-4-phenyl, and N-dialkoxyphenyl-4-phenyl. The narrow-band monomer can be integrated into a backbone of the polymer (e.g., polymerized in the polymer) and/or covalently attached to the backbone, a terminus, or a sidechain of the polymer. through at least one attachment to $R^1$, $R^{2A}$, $R^{2B}$, $R^{3A}$, and $R^{3B}$ or a combination thereof. FIG. 4D shows examples of monomers that, e.g., can be integrated with the polymer by attachment to $R^{3A}$ and $R^{3B}$ groups.

Figure 4E:
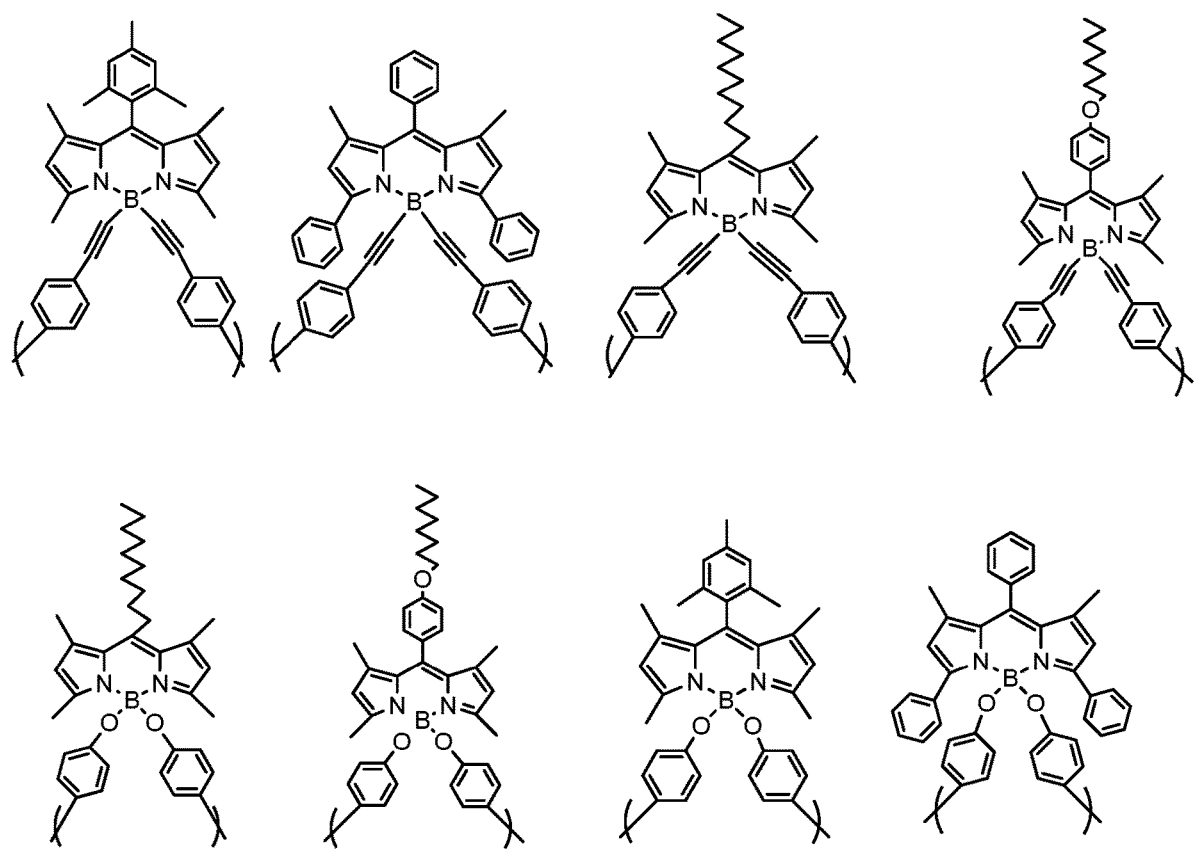

In some embodiments, the chromophoric polymer dots of the present invention can include a polymer that includes a narrow-band monomer having the formula:

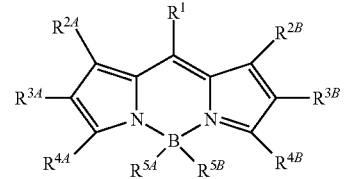

wherein each of $R^1$, $R^{2A}$, $R^{2B}$, $R^{3A}$, $R^{3B}$, $R^{4A}$, $R^{4B}$, $R^{5A}$, and $R^{5B}$ is independently selected from the group consisting of, but not limited to, hydrogen (H), deuterium (D), halogen, direct or branched alkyl, heteroalkyl, heterocycloalkyl, heterocycloalkylene, alkoxy, aryl, hydroxyl, cyano, nitro, ether and its derivatives, ester and its derivatives, alkyl ketone, alkylester, arylester, alkynyl, alkyl amine, fluoroalkyl, fluoroaryl, and polyalkalene (e.g, mehtoxyethoxyethoxy, ethoxyethoxy, and —$(OCH_2CH_2)_nOH$, n=1-50), phenyl, alkyl-(alkoxy-, aryl-, fluoroalkyl-, fluoroaryl-)substituted phenyl, pyridyl, alkyl-(alkoxy-, aryl-, fluoroalkyl-, fluoroaryl-)substituted pyridyl, bipyridyl, alkyl-(alkoxy-, aryl-, fluoroalkyl-, fluoroaryl-)substituted bipyridyl tripyridyl, alkyl-(alkoxy-, aryl-, fluoroalkyl-, fluoroaryl-)substituted tripyridyl, furyl, alkyl-(alkoxy-, aryl-, fluoroalkyl-, fluoroaryl-)substituted furyl, thienyl, alkyl-(alkoxy-, aryl-, fluoroalkyl-, fluoroaryl-)substituted thienyl, pyrrolyl, alkyl-(alkoxy-, aryl-, fluoroalkyl-, fluoroaryl-)substituted pyrrolyl, pyrazolyl, alkyl-(alkoxy-, aryl-, fluoroalkyl-, fluoroaryl-)substituted pyrazolyl, oxazolyl, alkyl-(alkoxy-, aryl-, fluoroalkyl-, fluoroaryl-)substituted oxazolyl, thiazolyl, alkyl-(alkoxy-, aryl-, fluoroalkyl-, fluoroaryl-)substituted thiazolyl, imidazolyl, alkyl-(alkoxy-, aryl-, fluoroalkyl-, fluoroaryl-)substituted imidazolyl, pyrazinyl, alkyl-(alkoxy-, aryl-, fluoroalkyl-, fluoroaryl-)substituted pyrazinyl, benzooxadizolyl, alkyl-(alkoxy-, aryl-, fluoroalkyl-, fluoroaryl-)substituted benzooxadizolyl, benzothiadizolyl, alkyl-(alkoxy-, aryl-, fluoroalkyl-, fluoroaryl-)substituted benzothiadizolyl, fluorenyl, alkyl-(alkoxy-, aryl-, fluoroalkyl-, fluoroaryl-)substituted fluorenyl, triphenylaminyl-substituted fluorenyl, diphenylaminyl-substituted fluorenyl, alkyl-substituted carbazolyl, alkyl-substituted triphenylaminyl and alkyl-substituted thiophenyl. As exemplary embodiments, alkyl substituted phenyl can include 2-alkylphenyl, 3-alkylphenyl, 4-alkylphenyl, 2,4-dialkylphenyl, 3,5-dialkylphenyl, 3,4-dialkylphenyl; alkyl-substituted fluorenyl can include 9, 9-dialkyl-substituted fluorenyl, 7-alkyl-9,9-dialkyl-substituted fluorenyl, 6-alkyl-9,9-dialkyl-substituted fluorenyl, 7-triphenylaminyl-9,9-dialkyl-substituted fluorenyl and 7-diphenylaminyl-9,9-dialkyl-substituted fluorenyl; alkyl-substituted carbazolyl can include N-alkyl-substituted carbazolyl, 6-alkyl-substituted carbazolyl and 7-alkyl-substituted carbazolyl; alkyl-substituted triphenylaminyl can include 4'-alkyl-substituted triphenylaminyl, 3'-alkyl-substituted triphenylaminyl, 3',4'-dialkyl-substituted triphenylaminyl and 4',4''-alkyl-substituted triphenylaminyl; alkyl-substituted thiophenyl can include 2-alkylthiophenyl, 3-alkylthiophenyl, and 4-alkylthiophenyl, N-dialkyl-4-phenyl, N-diphenyl-4-phenyl, and N-dialkoxyphenyl-4-phenyl. The narrow-band monomer can be integrated into a backbone of the polymer (e.g., copolymerized in the polymer) and/or covalently attached to the backbone, a terminus, or a sidechain of the polymer through at least one attachment to $R^1$, $R^{2A}$, $R^{2B}$, $R^{3A}$, $R^{3B}$, $R^{4A}$, $R^{4B}$, $R^{5A}$, $R^{5B}$, or a combination thereof. In certain embodiments, the narrow-band monomers can be integrated into the backbone by attachment to the $R^{5A}$ and $R^{5B}$ groups. FIG. 4E shows examples of monomers that, e.g., can be integrated with the polymer by attachment to $R^{5A}$ and $R^{5B}$ groups.

Figure 4F:
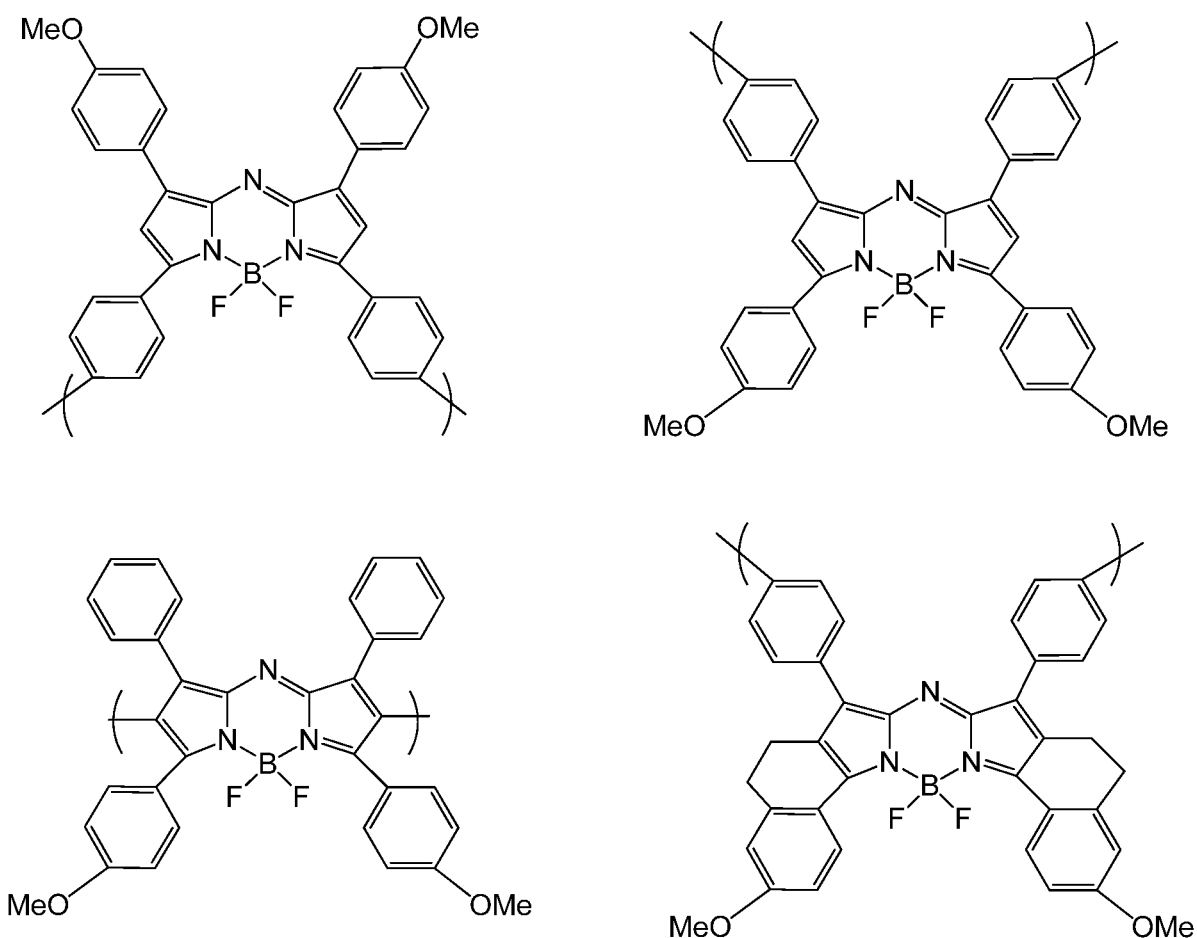

In some embodiments, the chromophoric polymer dots of the present invention can include a polymer that includes a narrow-band monomer having the formula:

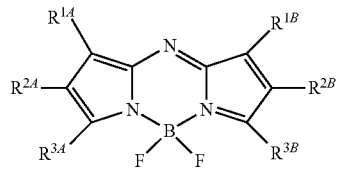

wherein each of $R^{1A}$, $R^{1B}$, $R^{2A}$, $R^{2B}$, $R^{3A}$ and $R^{3B}$ is independently selected from the group consisting of, but not limited to, hydrogen (H), deuterium (D), halogen, direct or branched alkyl, heteroalkyl, heterocycloalkyl, heterocycloalkylene, alkoxy, aryl, hydroxyl, cyano, nitro, ether and its derivatives, ester and its derivatives, alkyl ketone, alkylester, arylester, alkynyl, alkyl amine, fluoroalkyl, fluoroaryl, and polyalkalene (e.g, mehtoxyethoxyethoxy, ethoxyethoxy, and —$(OCH_2CH_2)_nOH$, n=1-50), phenyl, alkyl-(alkoxy-, aryl-, fluoroalkyl-, fluoroaryl-)substituted phenyl, pyridyl, alkyl-(alkoxy-, aryl-, fluoroalkyl-, fluoroaryl-)substituted pyridyl, bipyridyl, alkyl-(alkoxy-, aryl-, fluoroalkyl-, fluoroaryl-)substituted bipyridyl tripyridyl, alkyl-(alkoxy-, aryl-, fluoroalkyl-, fluoroaryl-)substituted tripyridyl, furyl, alkyl-(alkoxy-, aryl-, fluoroalkyl-, fluoroaryl-)substituted furyl, thienyl, alkyl-(alkoxy-, aryl-, fluoroalkyl-, fluoroaryl-)substituted thienyl, pyrrolyl, alkyl-(alkoxy-, aryl-, fluoroalkyl-, fluoroaryl-)substituted pyrrolyl, pyrazolyl, alkyl-(alkoxy-, aryl-, fluoroalkyl-, fluoroaryl-)substituted pyrazolyl, oxazolyl, alkyl-(alkoxy-, aryl-, fluoroalkyl-, fluoroaryl-)substituted oxazolyl, thiazolyl, alkyl-(alkoxy-, aryl-, fluoroalkyl-, fluoroaryl-)substituted thiazolyl, imidazolyl, alkyl-(alkoxy-, aryl-, fluoroalkyl-, fluoroaryl-)substituted imidazolyl, pyrazinyl, alkyl-(alkoxy-, aryl-, fluoroalkyl-, fluoroaryl-)substituted pyrazinyl, benzooxadizolyl, alkyl-(alkoxy-, aryl-, fluoroalkyl-, fluoroaryl-)substituted benzooxadizolyl, benzothiadizolyl, alkyl-(alkoxy-, aryl-, fluoroalkyl-, fluoroaryl-)substituted benzothiadizolyl, fluorenyl, alkyl-(alkoxy-, aryl-, fluoroalkyl-, fluoroaryl-)substituted fluorenyl, triphenylaminyl-substituted fluorenyl, diphenylaminyl-substituted fluorenyl, alkyl-substituted carbazolyl, alkyl-substituted triphenylaminyl and alkyl-substituted thiophenyl. As exemplary embodiments, alkyl substituted phenyl can include 2-alkylphenyl, 3-alkylphenyl, 4-alkylphenyl, 2,4-dialkylphenyl, 3,5-dialkylphenyl, 3,4-dialkylphenyl; alkyl-substituted fluorenyl can include 9, 9-dialkyl-substituted fluorenyl, 7-alkyl-9,9-dialkyl-substituted fluorenyl, 6-alkyl-9,9-dialkyl-substituted fluorenyl, 7-triphenylaminyl-9,9-dialkyl-substituted fluorenyl and 7-diphenylaminyl-9,9-dialkyl-substituted fluorenyl; alkyl-substituted carbazolyl can include N-alkyl-substituted carbazolyl, 6-alkyl-substituted carbazolyl and 7-alkyl-substituted carbazolyl; alkyl-substituted triphenylaminyl can include 4'-alkyl-substituted triphenylaminyl, 3'-alkyl-substituted triphenylaminyl, 3',4'-dialkyl-substituted triphenylaminyl and 4',4''-alkyl-substituted triphenylaminyl; alkyl-substituted thiophenyl can include 2-alkylthiophenyl, 3-alkylthiophenyl, and 4-alkylthiophenyl, N-dialkyl-4-phenyl, N-diphenyl-4-phenyl, and N-dialkoxyphenyl-4-phenyl. The narrow-band monomer can be integrated into a backbone of the polymer (e.g., polymerized in the polymer) and/or covalently attached to the backbone, a terminus, or a sidechain of the polymer through at least one attachment to $R^{1A}$, $R^{1B}$, $R^{2A}$, $R^{2B}$, $R^{3A}$, $R^{3B}$, or a combination thereof. FIG. 4F shows examples of monomers that, e.g., can be integrated with the polymer by attachment to $R^{1A}$, $R^{1B}$, $R^{2A}$, $R^{2B}$, $R^{3A}$ or $R^{3B}$ groups.

Figure 4G:
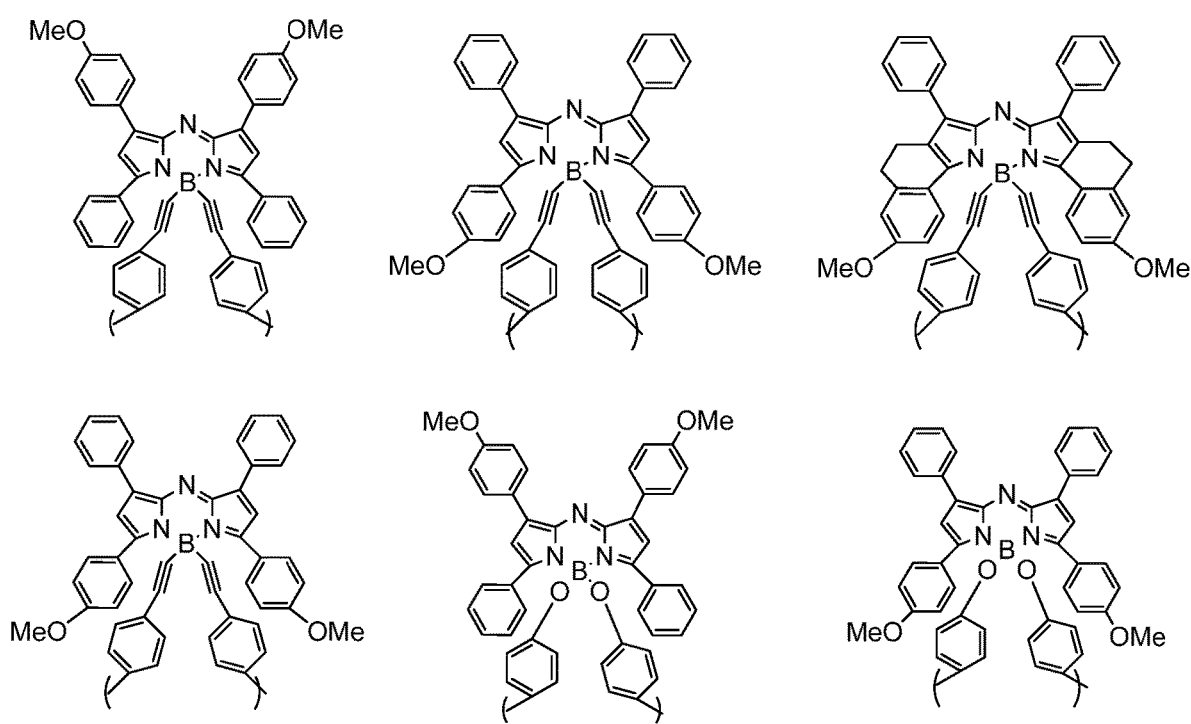

In some embodiments, the chromophoric polymer dots of the present invention can include a polymer that includes a narrow-band monomer having the formula:

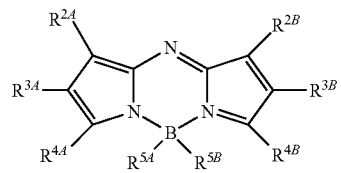

wherein each of $R^{2A}$, $R^{2B}$, $R^{3A}$, $R^{3B}$, $R^{4A}$, $R^{4B}$, $R^{5A}$ and $R^{5B}$ is independently selected from the group consisting of, but not limited to, hydrogen (H), deuterium (D), halogen, direct or branched alkyl, heteroalkyl, heterocycloalkyl, heterocycloalkylene, alkoxy, aryl, hydroxyl, cyano, nitro, ether and its derivatives, ester and its derivatives, alkyl ketone, alkylester, arylester, alkynyl, alkyl amine, fluoroalkyl, fluoroaryl, and polyalkalene (e.g, mehtoxyethoxyethoxy, ethoxyethoxy, and —$(OCH_2CH_2)_nOH$, n=1-50), phenyl, alkyl-(alkoxy-, aryl-, fluoroalkyl-, fluoroaryl-)substituted phenyl, pyridyl, alkyl-(alkoxy-, aryl-, fluoroalkyl-, fluoroaryl-)substituted pyridyl, bipyridyl, alkyl-(alkoxy-, aryl-, fluoroalkyl-, fluoroaryl-)substituted bipyridyl tripyridyl, alkyl-(alkoxy-, aryl-, fluoroalkyl-, fluoroaryl-)substituted tripyridyl, furyl, alkyl-(alkoxy-, aryl-, fluoroalkyl-, fluoroaryl-)substituted furyl, thienyl, alkyl-(alkoxy-, aryl-, fluoroalkyl-, fluoroaryl-)substituted thienyl, pyrrolyl, alkyl-(alkoxy-, aryl-, fluoroalkyl-, fluoroaryl-)substituted pyrrolyl, pyrazolyl, alkyl-(alkoxy-, aryl-, fluoroalkyl-, fluoroaryl-)substituted pyrazolyl, oxazolyl, alkyl-(alkoxy-, aryl-, fluoroalkyl-, fluoroaryl-)substituted oxazolyl, thiazolyl, alkyl-(alkoxy-, aryl-, fluoroalkyl-, fluoroaryl-)substituted thiazolyl, imidazolyl, alkyl-(alkoxy-, aryl-, fluoroalkyl-, fluoroaryl-)substituted imidazolyl, pyrazinyl, alkyl-(alkoxy-, aryl-, fluoroalkyl-, fluoroaryl-) substituted pyrazinyl, benzooxadizolyl, alkyl-(alkoxy-, aryl-, fluoroalkyl-, fluoroaryl-)substituted benzooxadizolyl, benzothiadizolyl, alkyl-(alkoxy-, aryl-, fluoroalkyl-, fluoroaryl-)substituted benzothiadizolyl, fluorenyl, alkyl-(alkoxy-, aryl-, fluoroalkyl-, fluoroaryl-)substituted fluorenyl, triphenylaminyl-substituted fluorenyl, diphenylaminyl-substituted fluorenyl, alkyl-substituted carbazolyl, alkyl-substituted triphenylaminyl and alkyl-substituted thiophenyl. As exemplary embodiments, alkyl substituted phenyl can include 2-alkylphenyl, 3-alkylphenyl, 4-alkylphenyl, 2,4-dialkylphenyl, 3,5-dialkylphenyl, 3,4-dialkylphenyl; alkyl-substituted fluorenyl can include 9, 9-dialkyl-substituted fluorenyl, 7-alkyl-9,9-dialkyl-substituted fluorenyl, 6-alkyl-9,9-dialkyl-substituted fluorenyl, 7-triphenylaminyl-9,9-dialkyl-substituted fluorenyl and 7-diphenylaminyl-9,9-dialkyl-substituted fluorenyl; alkyl-substituted carbazolyl can include N-alkyl-substituted carbazolyl, 6-alkyl-substituted carbazolyl and 7-alkyl-substituted carbazolyl; alkyl-substituted triphenylaminyl can include 4'-alkyl-substituted triphenylaminyl, 3'-alkyl-substituted triphenylaminyl, 3',4'-dialkyl-substituted triphenylaminyl and 4',4"-alkyl-substituted triphenylaminyl; alkyl-substituted thiophenyl can include 2-alkylthiophenyl, 3-alkylthiophenyl, and 4-alkylthiophenyl, N-dialkyl-4-phenyl, N-diphenyl-4-phenyl, and N-dialkoxyphenyl-4-phenyl The narrow-band monomer can be integrated into a backbone of the polymer (e.g., polymerized in the polymer) and/or covalently attached to the backbone, a terminus, or a sidechain of the polymer) through at least one attachment to $R^{2A}$, $R^{2B}$, $R^{3A}$, $R^{3B}$, $R^{4A}$, $R^{4B}$, $R^{5A}$, $R^{5B}$, or a combination thereof. FIG. 4G shows examples of monomers that, e.g., can be integrated with the polymer by attachment to $R^{5A}$ and $R^{5B}$ groups.

Figure 4H:
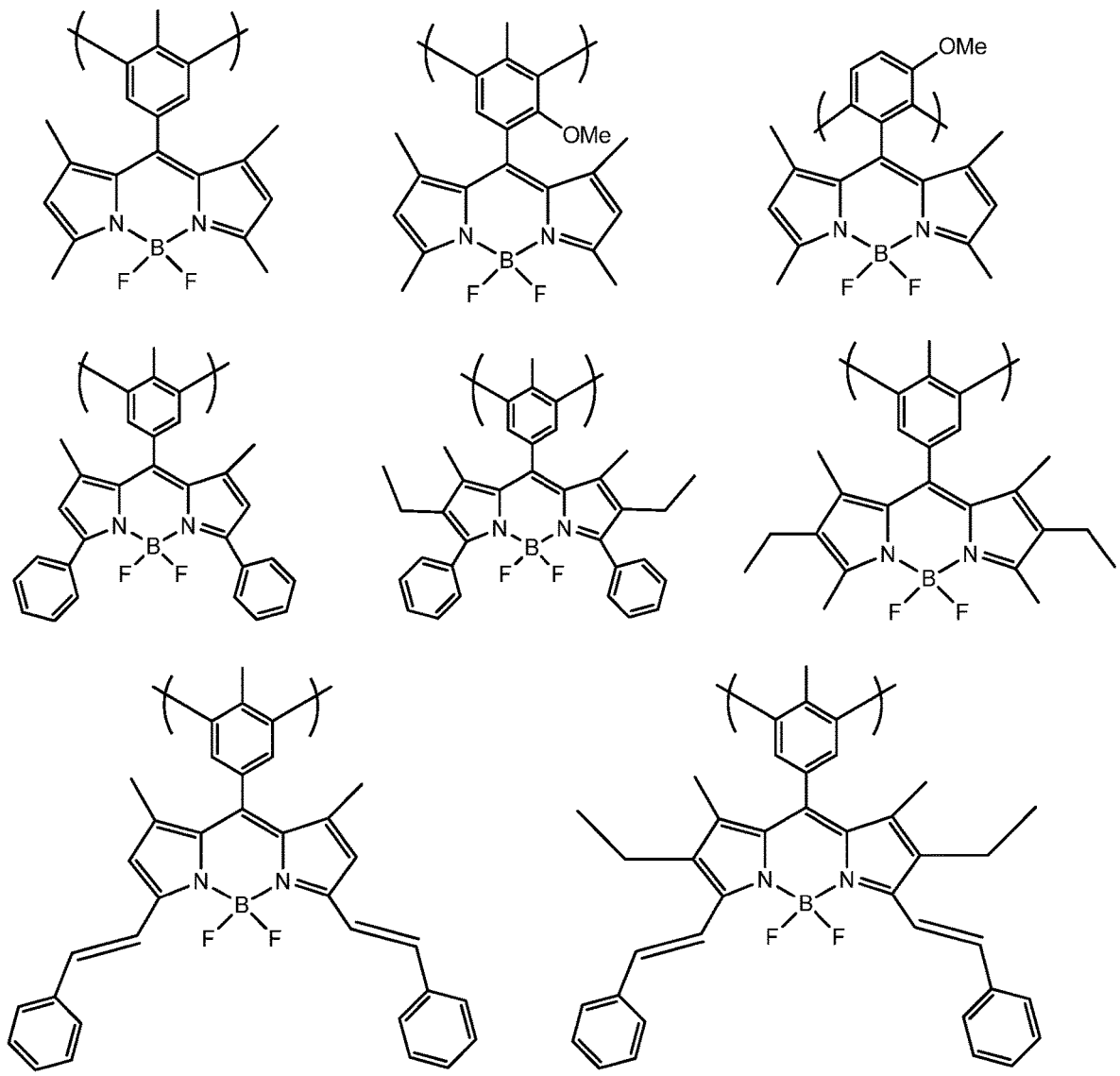

In some embodiments, the chromophoric polymer dots of the present invention can include a polymer that includes a narrow-band monomer having the formula:

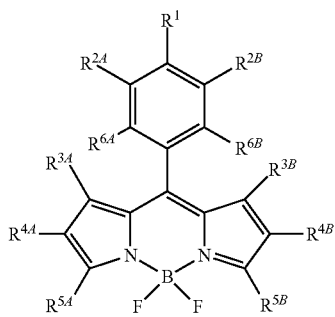

wherein each of $R^{1A}$, $R^{1B}$, $R^{2A}$, $R^{2B}$, $R^{3A}$, $R^{3B}$, $R^{4A}$ and $R^{4B}$, is independently selected from the group consisting of, but not limited to, hydrogen (H), deuterium (D), halogen, direct or branched alkyl, heteroalkyl, heterocycloalkyl, heterocycloalkylene, alkoxy, aryl, hydroxyl, cyano, nitro, ether and its derivatives, ester and its derivatives, alkyl ketone, alkylester, arylester, alkynyl, alkyl amine, fluoroalkyl, fluoroaryl, and polyalkalene (e.g, mehtoxyethoxyethoxy, ethoxyethoxy, and —$(OCH_2CH_2)_nOH$, n=1-50), phenyl, alkyl-(alkoxy-, aryl-, fluoroalkyl-, fluoroaryl-)substituted phenyl, pyridyl, alkyl-(alkoxy-, aryl-, fluoroalkyl-, fluoroaryl-)substituted pyridyl, bipyridyl, alkyl-(alkoxy-, aryl-, fluoroalkyl-, fluoroaryl-)substituted bipyridyl tripyridyl, alkyl-(alkoxy-, aryl-, fluoroalkyl-, fluoroaryl-)substituted tripyridyl, furyl, alkyl-(alkoxy-, aryl-, fluoroalkyl-, fluoroaryl-)substituted furyl, thienyl, alkyl-(alkoxy-, aryl-, fluoroalkyl-, fluoroaryl-)substituted thienyl, pyrrolyl, alkyl-(alkoxy-, aryl-, fluoroalkyl-, fluoroaryl-)substituted pyrrolyl, pyrazolyl, alkyl-(alkoxy-, aryl-, fluoroalkyl-, fluoroaryl-)substituted pyrazolyl, oxazolyl, alkyl-(alkoxy-, aryl-, fluoroalkyl-, fluoroaryl-)substituted oxazolyl, thiazolyl, alkyl-(alkoxy-, aryl-, fluoroalkyl-, fluoroaryl-)substituted thiazolyl, imidazolyl, alkyl-(alkoxy-, aryl-, fluoroalkyl-, fluoroaryl-)substituted imidazolyl, pyrazinyl, alkyl-(alkoxy-, aryl-, fluoroalkyl-, fluoroaryl-) substituted pyrazinyl, benzooxadizolyl, alkyl-(alkoxy-, aryl-, fluoroalkyl-, fluoroaryl-)substituted benzooxadizolyl, benzothiadizolyl, alkyl-(alkoxy-, aryl-, fluoroalkyl-, fluoroaryl-)substituted benzothiadizolyl, fluorenyl, alkyl-(alkoxy-, aryl-, fluoroalkyl-, fluoroaryl-)substituted fluorenyl, triphenylaminyl-substituted fluorenyl, diphenylaminyl-substituted fluorenyl, alkyl-substituted carbazolyl, alkyl-substituted triphenylaminyl and alkyl-substituted thiophenyl. As exemplary embodiments, alkyl substituted phenyl can include 2-alkylphenyl, 3-alkylphenyl, 4-alkylphenyl, 2,4-dialkylphenyl, 3,5-dialkylphenyl, 3,4-dialkylphenyl; alkyl-substituted fluorenyl can include 9, 9-dialkyl-substituted fluorenyl, 7-alkyl-9,9-dialkyl-substituted fluorenyl, 6-alkyl-9,9-dialkyl-substituted fluorenyl, 7-triphenylaminyl-9,9-dialkyl-substituted fluorenyl and 7-diphenylaminyl-9,9-dialkyl-substituted fluorenyl; alkyl-substituted carbazolyl can include N-alkyl-substituted carbazolyl, 6-alkyl-substituted carbazolyl and 7-alkyl-substituted carbazolyl; alkyl-substituted triphenylaminyl can include 4'-alkyl-substituted triphenylaminyl, 3'-alkyl-substituted triphenylaminyl, 3',4'-dialkyl-substituted triphenylaminyl and 4',4"-alkyl-substituted triphenylaminyl; alkyl-substituted thiophenyl can include 2-alkylthiophenyl, 3-alkylthiophenyl, and 4-alkylthiophenyl, N-dialkyl-4-phenyl, N-diphenyl-4-phenyl, and N-dialkoxyphenyl-4-phenyl, and wherein each of $R^{5A}$, $R^{5B}$, $R^{6A}$ and $R^{6B}$ are independently selected from the group consisting of, but not limited to, hydrogen (H), deuterium (D), halogen, direct or branched alkyl, heteroalkyl, heterocycloalkyl, heterocycloalkylene, alkoxy, aryl, hydroxyl, cyano, nitro, ether and its derivatives, ester and its derivatives, alkyl ketone, alkylester, arylester, alkynyl, alkyl amine, fluoroalkyl, fluoroaryl, and polyalkalene (e.g, mehtoxyethoxyethoxy, ethoxyethoxy, and —$(OCH_2CH_2)_nOH$, n=1-50), phenyl, alkyl-(alkoxy-, aryl-, fluoroalkyl-, fluoroaryl-)substituted phenyl, pyridyl, alkyl-(alkoxy-, aryl-, fluoroalkyl-, fluoroaryl-)substituted pyridyl, bipyridyl, alkyl-(alkoxy-, aryl-, fluoroalkyl-, fluoroaryl-)substituted bipyridyl tripyridyl, alkyl-(alkoxy-, aryl-, fluoroalkyl-, fluoroaryl-) substituted tripyridyl, furyl, alkyl-(alkoxy-, aryl-, fluoroalkyl-, fluoroaryl-)substituted furyl, thienyl, alkyl-(alkoxy-, aryl-, fluoroalkyl-, fluoroaryl-)substituted thienyl, pyrrolyl, alkyl-(alkoxy-, aryl-, fluoroalkyl-, fluoroaryl-)substituted pyrrolyl, pyrazolyl, alkyl-(alkoxy-, aryl-, fluoroalkyl-, fluoroaryl-)substituted pyrazolyl, oxazolyl, alkyl-(alkoxy-, aryl-, fluoroalkyl-, fluoroaryl-)substituted oxazolyl, thiazolyl, alkyl-(alkoxy-, aryl-, fluoroalkyl-, fluoroaryl-)substituted thiazolyl, imidazolyl, alkyl-(alkoxy-, aryl-, fluoroalkyl-, fluoroaryl-)substituted imidazolyl, pyrazinyl, alkyl-(alkoxy-, aryl-, fluoroalkyl-, fluoroaryl-)substituted pyrazinyl, benzooxadizolyl, alkyl-(alkoxy-, aryl-, fluoroalkyl-, fluoroaryl-)substituted benzooxadizolyl, benzothiadizolyl, alkyl-(alkoxy-, aryl-, fluoroalkyl-, fluoroaryl-)substituted benzothiadizolyl, fluorenyl, alkyl-(alkoxy-, aryl-, fluoroalkyl-, fluoroaryl-)substituted fluorenyl, triphenylaminyl-substituted fluorenyl, diphenylaminyl-substituted fluorenyl, alkyl-substituted carbazolyl, alkyl-substituted triphenylaminyl and alkyl-substituted thiophenyl. As exemplary embodiments, alkyl substituted phenyl can include 2-alkylphenyl, 3-alkylphenyl, 4-alkylphenyl, 2,4-dialkylphenyl, 3,5-dialkylphenyl, 3,4-dialkylphenyl; alkyl-substituted fluorenyl can include 9, 9-dialkyl-substituted fluorenyl, 7-alkyl-9,9-dialkyl-substituted fluorenyl, 6-alkyl-9,9-dialkyl-substituted fluorenyl, 7-triphenylaminyl-9,9-dialkyl-substituted fluorenyl and 7-diphenylaminyl-9,9-dialkyl-substituted fluorenyl; alkyl-substituted carbazolyl can include N-alkyl-substituted carbazolyl, 6-alkyl-substituted carbazolyl and 7-alkyl-substituted carbazolyl; alkyl-substituted triphenylaminyl can include 4'-alkyl-substituted triphenylaminyl, 3'-alkyl-substituted triphenylaminyl, 3',4'-dialkyl-substituted triphenylaminyl and 4',4''-alkyl-substituted triphenylaminyl; alkyl-substituted thiophenyl can include 2-alkylthiophenyl, 3-alkylthiophenyl, and 4-alkylthiophenyl, N-dialkyl-4-phenyl, N-diphenyl-4-phenyl, and N-dialkoxyphenyl-4-phenyl. The narrow-band monomer can be integrated into a backbone of the polymer (e.g., copolymerized in the polymer) and/or covalently attached to the backbone, a terminus, or a sidechain of the polymer) through at least one attachment to $R^{1A}$, $R^{1B}$, $R^{2A}$, $R^{2B}$, $R^{3A}$, $R^{3B}$, $R^{4A}$, $R^{4B}$, $R^{5A}$, $R^{5B}$, $R^{6A}$, $R^{6B}$ or a combination thereof. FIG. 4H shows examples of monomers that, e.g., can be integrated with the polymer by attachment to $R^{2A}$, $R^{2B}$, $R^{6A}$ or $R^{6B}$ groups.

In some embodiments, the chromophoric polymer dots of the present invention can include a polymer that includes a narrow-band monomer having the formula:

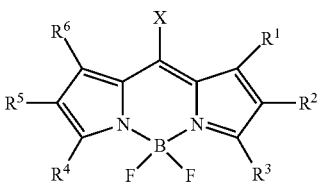

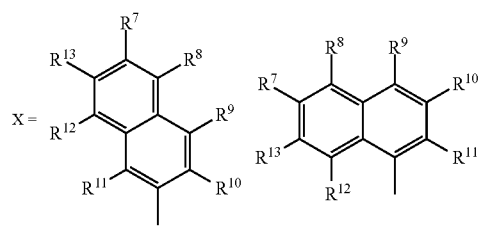

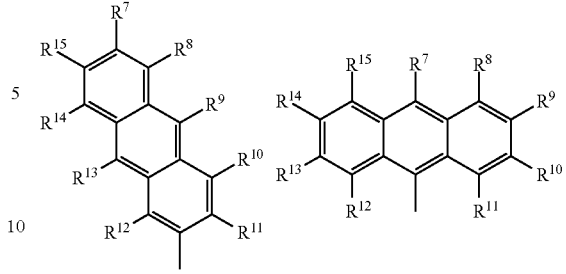

wherein X represents aryl group and its derivatives, each of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$ and $R^{15}$ is independently selected from the group consisting of, but not limited to, hydrogen (H), deuterium (D), halogen, direct or branched alkyl, heteroalkyl, heterocycloalkyl, heterocycloalkylene, alkoxy, aryl, hydroxyl, cyano, nitro, ether and its derivatives, ester and its derivatives, alkyl ketone, alkylester, arylester, alkynyl, alkyl amine, fluoroalkyl, fluoroaryl, and polyalkalene (e.g, mehtoxyethoxyethoxy, ethoxyethoxy, and —$(OCH_2CH_2)_nOH$, n=1-50), phenyl, alkyl-(alkoxy-, aryl-, fluoroalkyl-, fluoroaryl-)substituted phenyl, pyridyl, alkyl-(alkoxy-, aryl-, fluoroalkyl-, fluoroaryl-)substituted pyridyl, bipyridyl, alkyl-(alkoxy-, aryl-, fluoroalkyl-, fluoroaryl-)substituted bipyridyl tripyridyl, alkyl-(alkoxy-, aryl-, fluoroalkyl-, fluoroaryl-)substituted tripyridyl, furyl, alkyl-(alkoxy-, aryl-, fluoroalkyl-, fluoroaryl-)substituted furyl, thienyl, alkyl-(alkoxy-, aryl-, fluoroalkyl-, fluoroaryl-)substituted thienyl, pyrrolyl, alkyl-(alkoxy-, aryl-, fluoroalkyl-, fluoroaryl-)substituted pyrrolyl, pyrazolyl, alkyl-(alkoxy-, aryl-, fluoroalkyl-, fluoroaryl-)substituted pyrazolyl, oxazolyl, alkyl-(alkoxy-, aryl-, fluoroalkyl-, fluoroaryl-)substituted oxazolyl, thiazolyl, alkyl-(alkoxy-, aryl-, fluoroalkyl-, fluoroaryl-)substituted thiazolyl, imidazolyl, alkyl-(alkoxy-, aryl-, fluoroalkyl-, fluoroaryl-)substituted imidazolyl, pyrazinyl, alkyl-(alkoxy-, aryl-, fluoroalkyl-, fluoroaryl-)substituted pyrazinyl, benzooxadizolyl, alkyl-(alkoxy-, aryl-, fluoroalkyl-, fluoroaryl-)substituted benzooxadizolyl, benzothiadizolyl, alkyl-(alkoxy-, aryl-, fluoroalkyl-, fluoroaryl-)substituted benzothiadizolyl, fluorenyl, alkyl-(alkoxy-, aryl-, fluoroalkyl-, fluoroaryl-)substituted fluorenyl, triphenylaminyl-substituted fluorenyl, diphenylaminyl-substituted fluorenyl, alkyl-substituted carbazolyl, alkyl-substituted triphenylaminyl and alkyl-substituted thiophenyl. As exemplary embodiments, alkyl substituted phenyl can include 2-alkylphenyl, 3-alkylphenyl, 4-alkylphenyl, 2,4-dialkylphenyl, 3,5-dialkylphenyl, 3,4-dialkylphenyl; alkyl-substituted fluorenyl can include 9, 9-dialkyl-substituted fluorenyl, 7-alkyl-9,9-dialkyl substituted fluorenyl, 6-alkyl-9,9-dialkyl-substituted fluorenyl, 7-triphenylaminyl-9,9-dialkyl-substituted fluorenyl and 7-diphenylaminyl-9,9-dialkyl-substituted fluorenyl; alkyl-substituted carbazolyl can include N-alkyl-substituted carbazolyl, 6-alkyl-substituted carbazolyl and 7-alkyl-substituted carbazolyl; alkyl-substituted triphenylaminyl can include 4'-alkyl-substituted triphenylaminyl, 3'-alkyl-substituted triphenylaminyl, 3',4'-dialkyl-substituted triphenylaminyl and 4',4''-alkyl-substituted triphenylaminyl; alkyl-substituted thiophenyl can include 2-alkylthiophenyl, 3-alkylthiophenyl, and 4-alkylthiophenyl, N-dialkyl-4-phenyl, N-diphenyl-4-phenyl, and N-dialkoxyphenyl-4-phenyl. When X represents naphthalene and its derivatives, the narrow-band monomer can be integrated into a backbone (e.g., polymerized in the polymer) and/or covalently attached to the backbone, a terminus, or a sidechain of the polymer) of the polymer through at least one attachment to $R^7$, $R^8$, $R^9$, $R^{10}$, $R^{11}$, $R^{12}$ or a combination thereof. When X represents anthracene and its derivatives, the narrow-band monomer can be integrated into a backbone of the polymer and/or covalently attached to the backbone, a terminus, or a sidechain of the polymer through at least one attachment to $R^7$, $R^8$, $R^9$, $R^{10}$, $R^{11}$, $R^{12}$, $R^{13}$, $R^{14}$, $R^{15}$ or a combination thereof.

Narrow band monomers of the present invention can further include dipyrrin derivatives. Dipyrrin and dipyrrin derivatives can be polymerized to form polymers (e.g., homopolymers or heteropolymers) and/or can be attached (e.g., covalently attached) to a polymer backbone, sidechain and/or terminus. For example, the chromophoric polymer dots of the present invention can include a polymer that includes a narrow-band monomer having the formula:

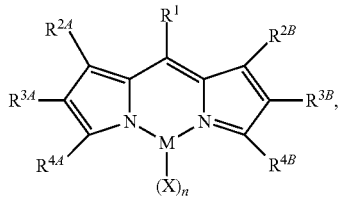

wherein M is a metal. Examples of M can be, but not limited to, Na, Li, Zn, Co, or Si. X can include substituents such as, but not limited to, halogen, alkyl, phenyl, alkylphenyl, thiophenyl, alkylthiophenyl, alkoxyl, alkoxylphenyl, alkyl-thiophenyl, ester, or hydroxyl. The number of X groups (n) can be 1 or more than 1, and n can be 0, 1, 2, 3, 4. Each of $R^1$, $R^{2A}$, $R^{2B}$, $R^{3A}$, $R^{3B}R^{4A}$, $R^{4B}$, $R^{5A}$, and $R^{5B}$ can be independently selected from the group consisting of, but not limited to, hydrogen (H), deuterium (D), halogen, direct or branched alkyl, heteroalkyl, heterocycloalkyl, heterocycloalkylene, alkoxy, aryl, hydroxyl, cyano, nitro, ether and its derivatives, ester and its derivatives, alkyl ketone, alkylester, arylester, alkynyl, alkyl amine, fluoroalkyl, fluoroaryl, and polyalkalene (e.g, mehtoxyethoxyethoxy, ethoxyethoxy, and —(OCH$_2$CH$_2$)$_n$OH, n=1-50), phenyl, alkyl-(alkoxy-, aryl-, fluoroalkyl-, fluoroaryl-)substituted phenyl, pyridyl, alkyl-(alkoxy-, aryl-, fluoroalkyl-, fluoroaryl-)substituted pyridyl, bipyridyl, alkyl-(alkoxy-, aryl-, fluoroalkyl-, fluoroaryl-)substituted bipyridyl tripyridyl, alkyl-(alkoxy-, aryl-, fluoroalkyl-, fluoroaryl-)substituted tripyridyl, furyl, alkyl-(alkoxy-, aryl-, fluoroalkyl-, fluoroaryl-)substituted furyl, thienyl, alkyl-(alkoxy-, aryl-, fluoroalkyl-, fluoroaryl-)substituted thienyl, pyrrolyl, alkyl-(alkoxy-, aryl-, fluoroalkyl-, fluoroaryl-)substituted pyrrolyl, pyrazolyl, alkyl-(alkoxy-, aryl-, fluoroalkyl-, fluoroaryl-)substituted pyrazolyl, oxazolyl, alkyl-(alkoxy-, aryl-, fluoroalkyl-, fluoroaryl-)substituted oxazolyl, thiazolyl, alkyl-(alkoxy-, aryl-, fluoroalkyl-, fluoroaryl-)substituted thiazolyl, imidazolyl, alkyl-(alkoxy-, aryl-, fluoroalkyl-, fluoroaryl-)substituted imidazolyl, pyrazinyl, alkyl-(alkoxy-, aryl-, fluoroalkyl-, fluoroaryl-) substituted pyrazinyl, benzooxadizolyl, alkyl-(alkoxy-, aryl-, fluoroalkyl-, fluoroaryl-)substituted benzooxadizolyl, benzothiadizolyl, alkyl-(alkoxy-, aryl-, fluoroalkyl-, fluoroaryl-)substituted benzothiadizolyl, fluorenyl, alkyl-(alkoxy-, aryl-, fluoroalkyl-, fluoroaryl-)substituted fluorenyl, triphenylaminyl-substituted fluorenyl, diphenylaminyl-substituted fluorenyl, alkyl-substituted carbazolyl, alkyl-substituted triphenylaminyl and alkyl-substituted thiophenyl. As exemplary embodiments, alkyl substituted phenyl can include 2-alkylphenyl, 3-alkylphenyl, 4-alkylphenyl, 2,4-dialkylphenyl, 3,5-dialkylphenyl, 3,4-dialkylphenyl; alkyl-substituted fluorenyl can include 9, 9-dialkyl-substituted fluorenyl, 7-alkyl-9,9-dialkyl-substituted fluorenyl, 6-alkyl-9,9-dialkyl-substituted fluorenyl, 7-triphenylaminyl-9,9-dialkyl-substituted fluorenyl and 7-diphenylaminyl-9,9-dialkyl-substituted fluorenyl; alkyl-substituted carbazolyl can include N-alkyl-substituted carbazolyl, 6-alkyl-substituted carbazolyl and 7-alkyl-substituted carbazolyl; alkyl-substituted triphenylaminyl can include 4'-alkyl-substituted triphenylaminyl, 3'-alkyl-substituted triphenylaminyl, 3',4'-dialkyl-substituted triphenylaminyl and 4',4"-alkyl-substituted triphenylaminyl; alkyl-substituted thiophenyl can include 2-alkylthiophenyl, 3-alkylthiophenyl, and 4-alkylthiophenyl, N-dialkyl-4-phenyl, N-diphenyl-4-phenyl, and N-dialkoxyphenyl-4-phenyl. The narrow-band monomer can be integrated into a backbone of the polymer (e.g., polymerized in the polymer) and/or covalently attached to the backbone, a terminus, or a sidechain of the polymer) through at least one attachment to $R^1$, $R^{2A}$, $R^{2B}$, $R^{3A}$, $R^{3B}$, $R^{4A}$, $R^{4B}R^{5A}$, $R^{5B}$, or a combination thereof.

Figure 5:
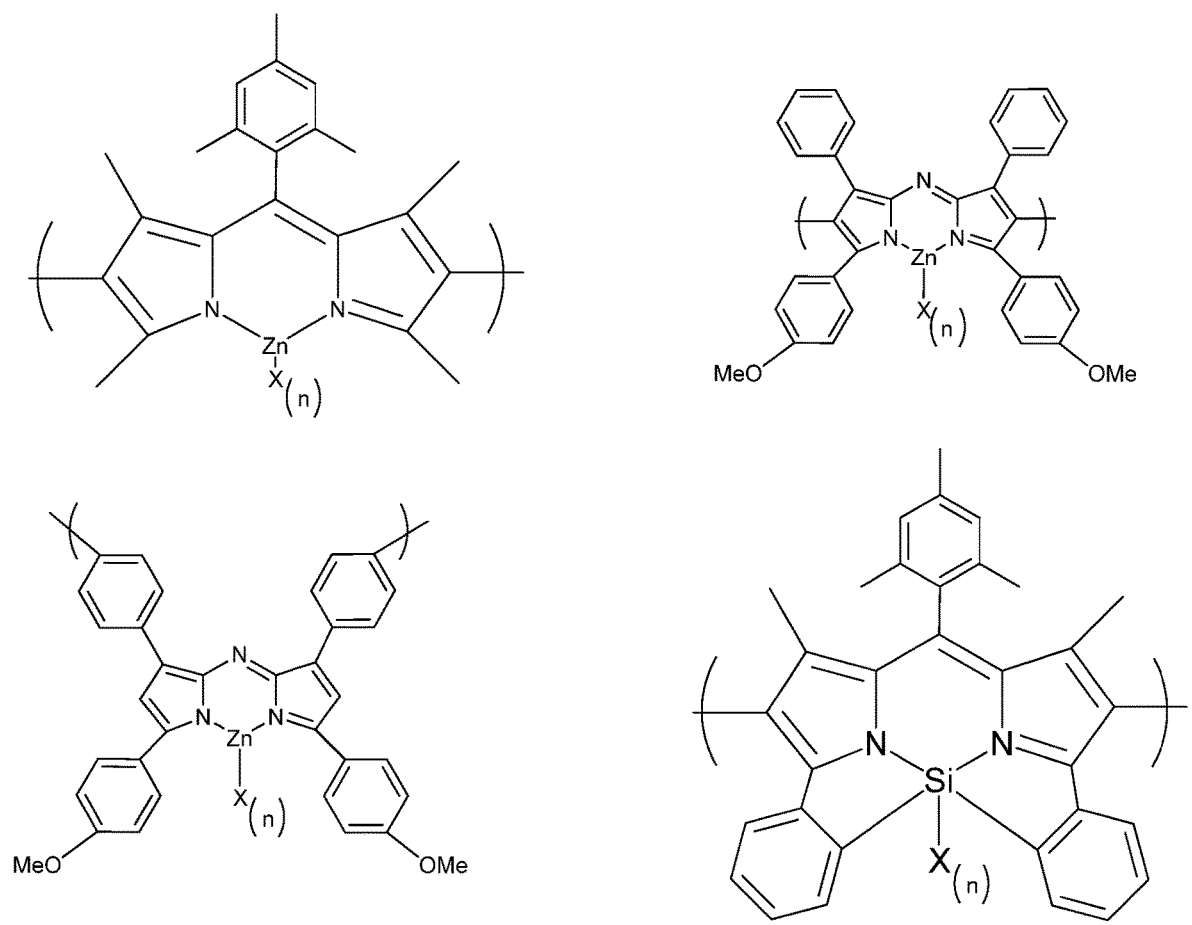
FIG. 5 shows a non-limiting list of dipyrrin-metal derivatives and some specific examples as narrow-band monomer. Each of the dipyrrin-metal derivatives can be used to synthesize a narrow-band emissive homopolymer. Each of the dipyrrin-metal derivatives can also be copolymerized with any of the general polymers to synthesize a narrow-band emissive copolymer. Each of the dipyrrin-metal derivatives can be used as a narrow-band emissive unit to cross-link with the side-chains of conventional semiconducting polymers to form narrow-band emissive polymers.

Additional examples of dipyrrin derivatives are shown in FIG. 5, wherein X can include substituents such as, but not limited to, halogen, alkyl, phenyl, alkylphenyl, thiophenyl, alkylthiophenyl, alkoxyl, ester, or hydroxyl. The number of X groups (n) can be 1 or more than 1, and n can be 0, 1, 2, 3, 4.

In some embodiments, the narrow-band emissive polymers for making Pdots include squaraine and squaraine derivatives as narrow-band monomers. Squaraine derivatives include but are not limited to their alkyl derivatives, aryl derivatives, alkyne derivatives, aromatic derivatives, alkoxide derivatives, aza derivatives, their extended systems and analogues. The narrow-band emissive polymers can also include any other monomers. The squaraine and their derivatives can be energy acceptors and other monomers can be energy donors so that the final Pdots can exhibit narrow-band emissions. The narrow-band emissive chromophoric polymers in good solvents may exhibit broad emissions or narrow emissions. However, their nanoparticle form gives narrow-band emissions. The emission FWHM of the above Pdots is less than 70 nm. In certain embodiments, the FWHM is less than 60 nm, less than 50 nm, less than 40 nm, less than 30 nm, or less than 20 nm.

Suitable squaraine derivatives for use in the present invention can include the following structures described below. Squaraine and squaraine derivatives can be polymerized to form polymers (e.g., homopolymers or heteropolymers) and/or can be attached (e.g., covalently attached) to a polymer backbone, sidechain and/or terminus. Chromophoric polymer dots of the present invention can include a polymer that includes a narrow-band monomer having the formula:

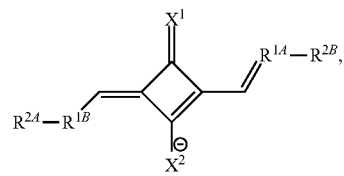

wherein each of $X^1$ and $X^2$ is independently selected from the group consisting of oxygen, sulfur and nitrogen; each of $R^{1A}$ and $R^{1B}$ is independently selected from the group consisting of, but not limited, alkylene, alkenylene, arylene, heteroarylene, phenylene, azulene, cycloalkylene, and heterocycloalkylene; and each of $R^{2A}$ and $R^{2B}$ is a reactive group independently selected from the group consisting of, but not limited to, a halide, hydroxyl, and amino. Other reactive groups can be used. In some embodiments, the halide is a chloro, a bromo, or an iodo group. The reactive group can be used to integrate the monomer into a polymer, e.g. along the backbone of the polymer (e.g., by polymerizing in the polymer) and/or to attach the monomer by covalent attachment to the backbone, a terminus, or a sidechain of the polymer.

The present invention can include oxygen-containing squaraine derivatives. Chromophoric polymer dots of the present invention can include a polymer that includes a narrow-band monomer having the formula:

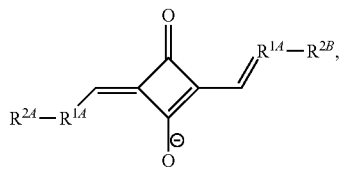

wherein each of $R^{1A}$ and $R^{1B}$ is independently selected from the group consisting of, but not limited to, alkylene, alkenylene, arylene, heteroarylene, phenylene, azulene, cycloalkylene, and heterocycloalkylene; and each of $R^{2A}$ and $R^{2B}$ is a reactive group independently selected from the group consisting of, but not limited to, a halide, hydroxyl, and amino. Other reactive groups can be used. In some embodiments, the halide is a chloro, a bromo, or an iodo group. The reactive group can be used to integrate the monomer into a polymer (e.g. along the backbone of the polymer by polymerizing in the polymer) and/or to attach the monomer by covalent attachment to the backbone, a terminus, or a sidechain of the polymer.

Figure 6A:
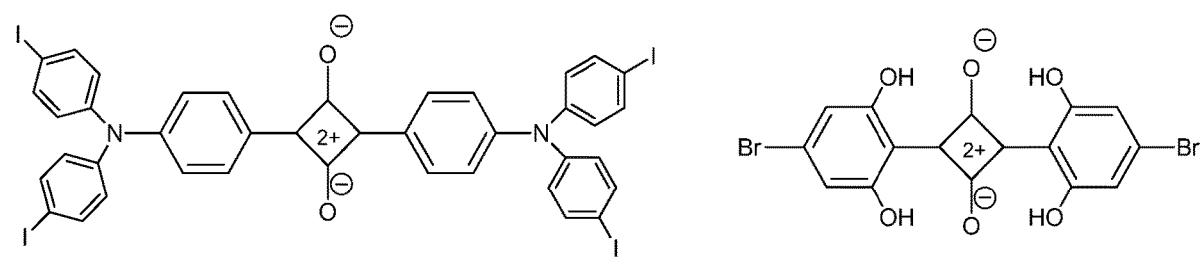
FIGS. 6A-6E show a non-limiting list of examples of squaraine derivatives as narrow-band monomer. Each of the squaraine derivatives can be used to synthesize a narrow-band emissive homopolymer. Each of the squaraine derivatives can also be copolymerized with any of the general polymers to synthesize a narrow-band emissive copolymer. Each of the squaraine derivatives can be used as a narrow-band emissive unit to cross-link with the side-chains of conventional semiconducting polymers to form narrow-band emissive polymers.

Chromophoric polymer dots of the present invention can include a polymer that includes a narrow-band monomer having the formula:

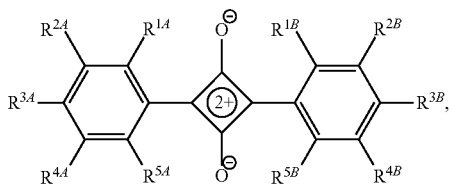

wherein each of $R^{1A}$ and $R^{1B}$ is independently selected from the group consisting of, but not limited to, hydrogen, methyl, alkyl, phenyl, araalkyl, and alkoxy-phenyl; each of $R^{2A}$ and $R^{2B}$ is independently selected from the group consisting of, but not limited to, hydrogen, methyl, alkyl, phenyl, araalkyl, and alkoxy-phenyl; each of $R^{3A}$ and $R^{3B}$ is a reactive group independently selected from the group consisting of, but not limited to, chloro, bromo, iodo, and hydroxyl; each of $R^{4A}$ and $R^{4B}$ is independently is selected from a group consisting of, but not limited to, hydroxyl, hydrogen, alkyl, phenyl, araalkyl, and alkoxy-phenyl; and each of $R^{5A}$ and $R^{5B}$ is independently selected from the group consisting of, but not limited to, hydrogen, methyl, alkyl, phenyl, araalkyl, and alkoxy-phenyl. Other reactive groups can be used. The reactive group can be used to integrate the monomer into a polymer (e.g. along the backbone of the polymer by polymerizing in the polymer) and/or to attach the monomer by covalent attachment to the backbone, a terminus, or a sidechain of the polymer. FIG. 6A shows some examples of narrow band monomers that can be integrated into the polymer by reaction with the reactive groups, e.g., I or Br.

Figure 6B:
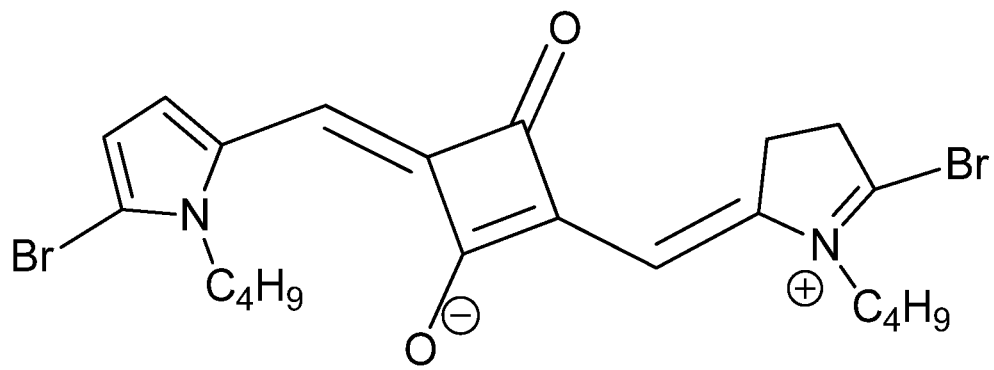
Figure 6B:
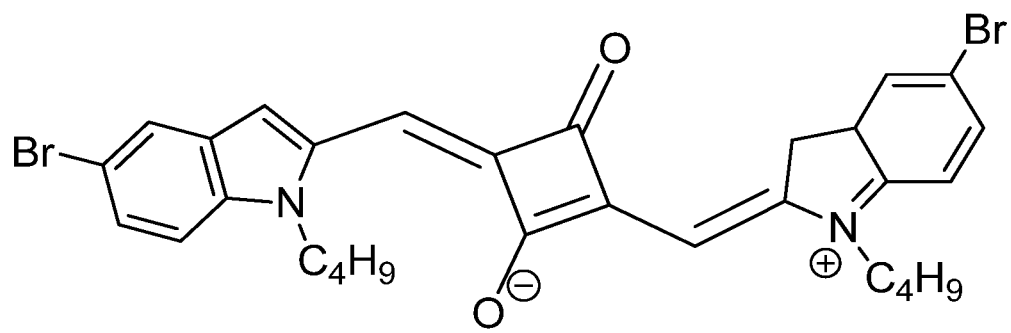
Figure 6B:
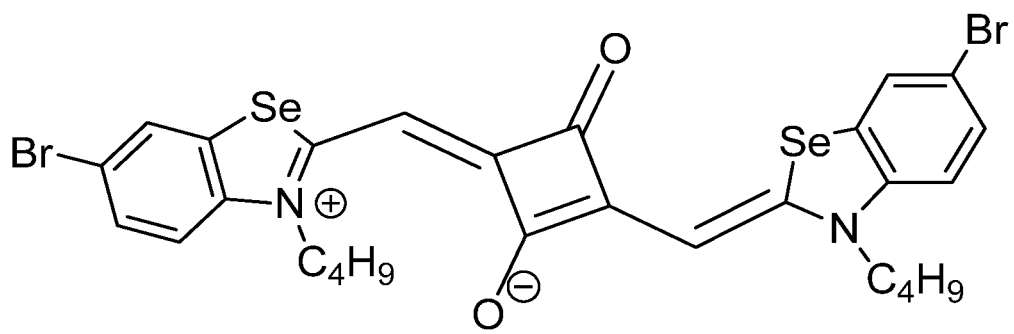
Figure 6B:
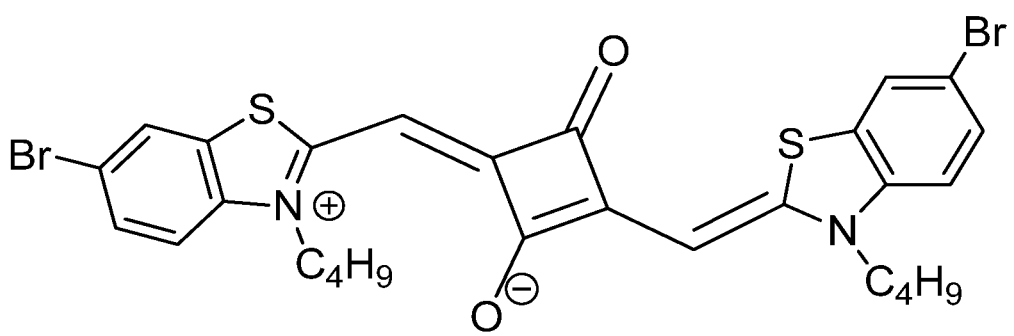

Chromophoric polymer dots of the present invention can include a polymer that includes a narrow-band monomer having the formula:

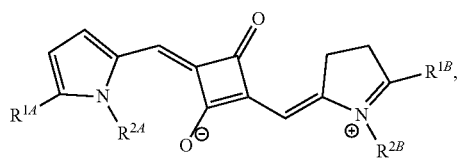

wherein each of $R^{1A}$ and $R^{1B}$ is a reactive group independently selected from the group consisting of, but not limited to, chloro, bromo, iodo, and hydroxyl; and each of $R^{2A}$ and $R^{2B}$ is selected from the group consisting of, but not limited to, hydrogen, methyl, alkyl, phenyl, araalkyl, and alkoxy-phenyl. Other reactive groups can be used. The reactive group can be used to integrate the monomer into a polymer (e.g. along the backbone of the polymer by polymerizing in the polymer) and/or attach the monomer by covalent attachment to the backbone, a terminus, or a sidechain of the polymer. FIG. 6B shows an example monomer that can be integrated into the polymer by reaction with the reactive groups, e.g., Br.

Chromophoric polymer dots of the present invention can include a polymer that includes a narrow-band monomer having the formula:

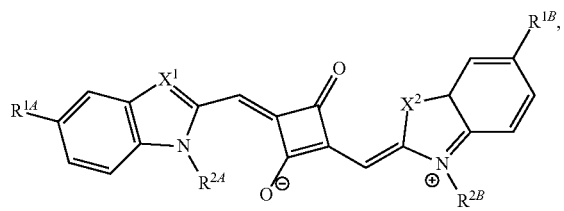

wherein each of $X^1$ and $X^2$ is independently selected from the group consisting of carbon, sulphur, and selenium; each of $R^{1A}$ and $R^{1B}$ is a reactive group independently selected from the group consisting of, but not limited to, chloro, bromo, iodo, and hydroxyl; and each of $R^{2A}$ and $R^{2B}$ is independently selected from the group consisting of, but not limited to, hydrogen, methyl, alkyl, phenyl, araalkyl, alkoxy-phenyl, N-dialkyl-4-phenyl, N-diphenyl-4-phenyl, and N-dialkoxyphenyl-4-phenyl. Other reactive groups can be used. The reactive group can be used to integrate the monomer into a polymer (e.g. along the backbone of the polymer by polymerizing in the polymer) and/or attach the monomer by covalent attachment to the backbone, a terminus, or a sidechain of the polymer. FIG. 6B shows example monomers that can be integrated into the polymer by reaction with the reactive groups, e.g., Br.

Chromophoric polymer dots of the present invention can include a polymer that includes a narrow-band monomer having the formula:

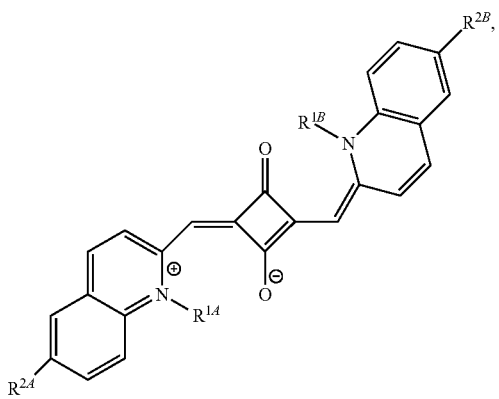

wherein each of $R^{2A}$ and $R^{2B}$ is a reactive group independently selected from the group consisting of, but not limited to, chloro, bromo, iodo, and hydroxyl; and each of $R^{1A}$ and $R^{1B}$ is selected from the group consisting of, but not limited to, hydrogen, methyl, alkyl, phenyl, araalkyl, alkoxy-phenyl, N-dialkyl-4-phenyl, N-diphenyl-4-phenyl, and N-dialkoxylphenyl-4-phenyl. Other reactive groups can be used. The reactive group can be used to integrate the monomer into a polymer (e.g. along the backbone of the polymer by polymerizing in the polymer) and/or attach the monomer by covalent attachment to the backbone, a terminus, or a sidechain of the polymer.

The present invention can include sulphur-containing squaraine derivatives. Chromophoric polymer dots of the present invention can include a polymer that includes a narrow-band monomer having the formula:

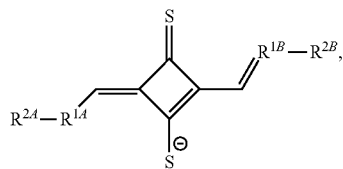

wherein each of $R^{1A}$ and $R^{1B}$ is independently selected from the group consisting of, but not limited to, alkylene, alkenylene, arylene, heteroarylene, phenylene, azulene, cycloalkylene, and heterocycloalkylene; and each of $R^{2A}$ and $R^{2B}$ is a reactive group independently selected from the group consisting of, but not limited to, a halide, hydroxyl, and amino. In some embodiments, the halide is a chloro, a bromo, or an iodo group. Other reactive groups can be used. The reactive group can be used to integrate the monomer into a polymer (e.g. along the backbone of the polymer by polymerizing in the polymer) and/or attach the monomer by covalent attachment to the backbone, a terminus, or a sidechain of the polymer.

Figure 6C:
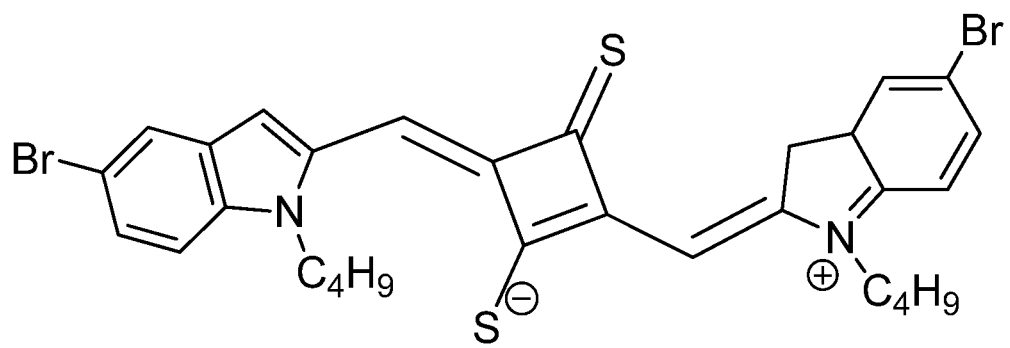
Figure 6C:
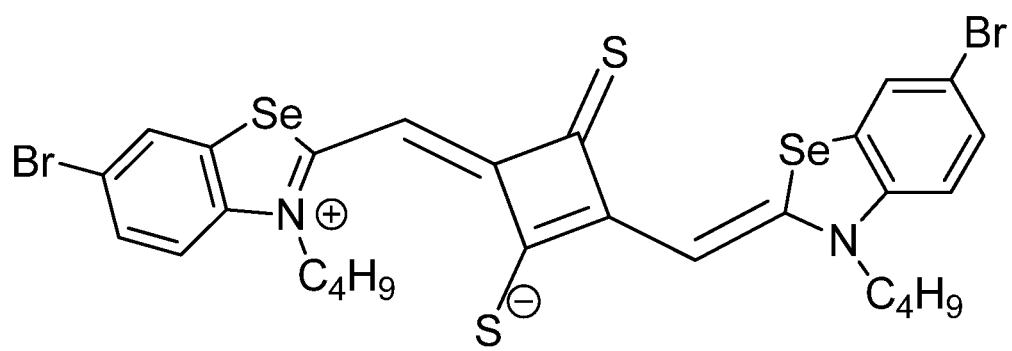
Figure 6C:
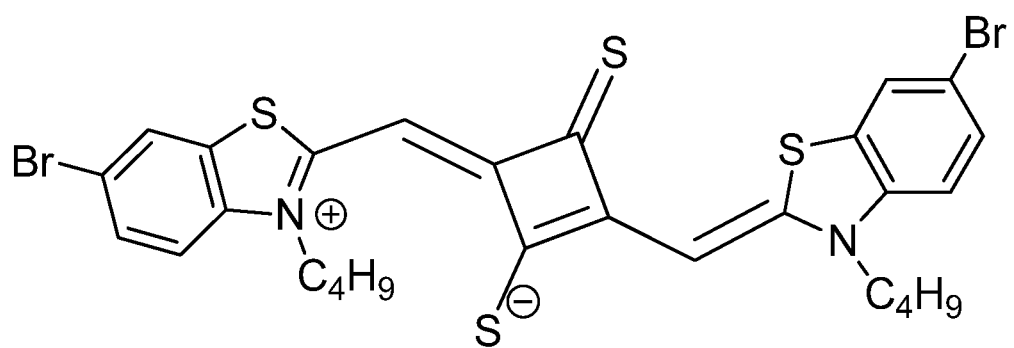

Chromophoric polymer dots of the present invention can include a polymer that includes a narrow-band monomer having the formula:

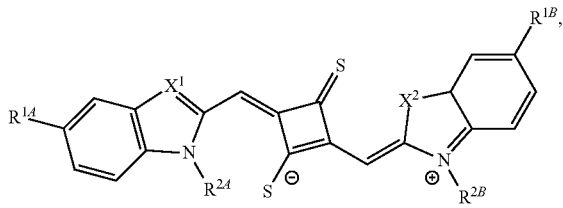

wherein each of $X^1$ and $X^2$ is independently selected from the group consisting of carbon, sulphur, and selenium; each of $R^{1A}$ and $R^{1B}$ is a reactive group independently selected from the group consisting of, but not limited to, chloro, bromo, iodo, and hydroxyl; and each of $R^{2A}$ and $R^{2B}$ is independently selected from the group consisting of, but not limited to, hydrogen, methyl, alkyl, phenyl, araalkyl, alkoxy-phenyl, N-dialkyl-4-phenyl, N-diphenyl-4-phenyl, and N-dialkoxylphenyl-4-phenyl. Other reactive groups can be used. FIG. 6C shows example monomers that can be integrated into the polymer by reaction with the reactive groups, e.g., Br (e.g. along the backbone of the polymer by polymerizing in the polymer) and/or attached by covalent attachment to the backbone, a terminus, or a sidechain of the polymer).

Figure 6D:
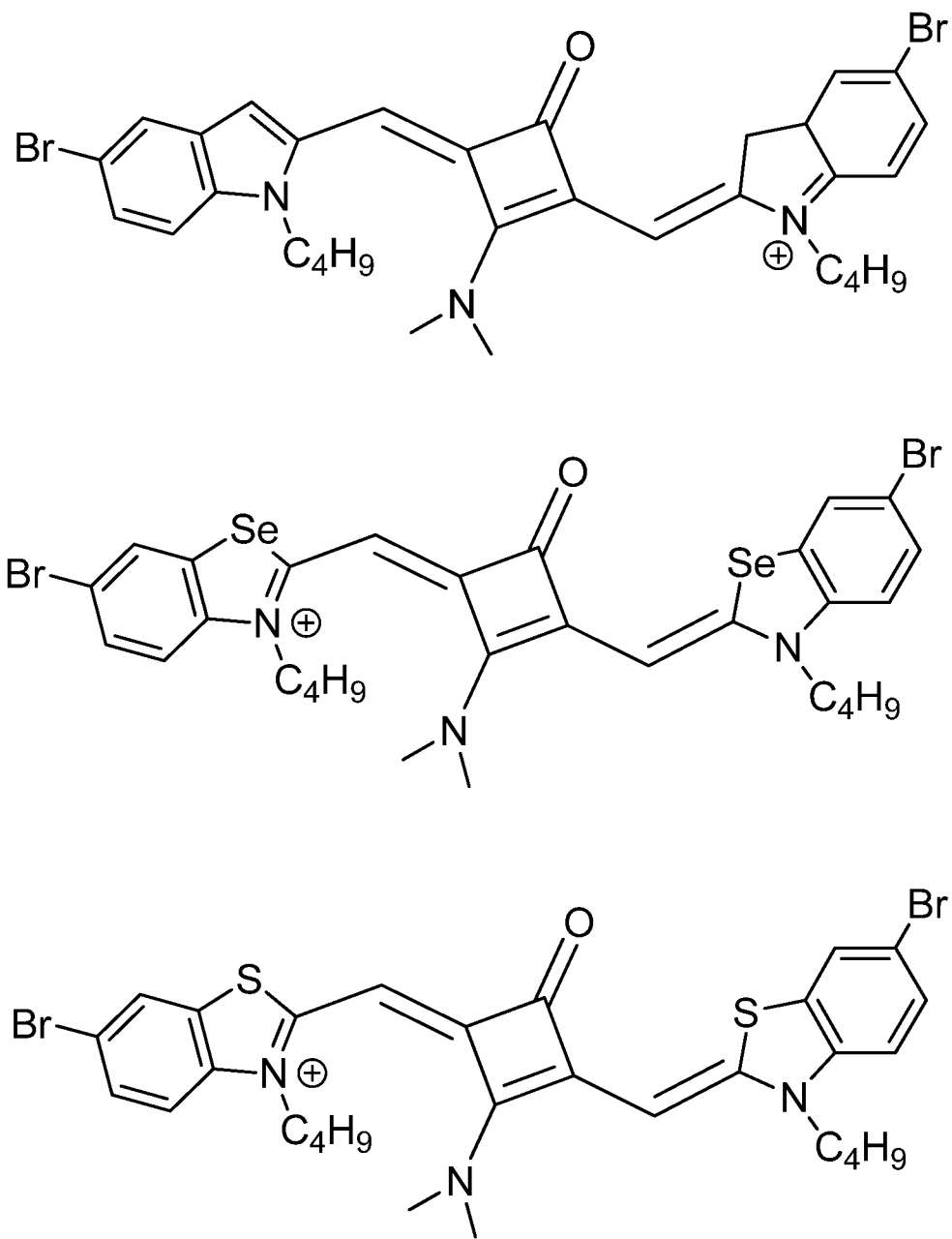

The present invention can include nitrogen-containing squaraine derivatives. Chromophoric polymer dots of the present invention can include a polymer that includes a narrow-band monomer having the formula:

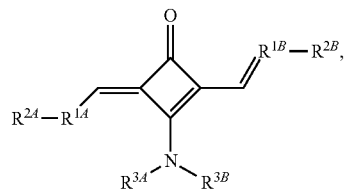

wherein each of $R^{1A}$ and $R^{1B}$ is independently selected from the group consisting of, but not limited to, alkylene, alkenylene, arylene, heteroarylene, phenylene, azulene, cycloalkylene, and heterocycloalkylene; each of $R^{2A}$ and $R^{2B}$ is a reactive group independently selected from the group consisting of, but not limited to, a halide, hydroxyl, and amino; and each of $R^{3A}$ and $R^{3B}$ is independently selected from the group consisting of hydrogen, methyl, alkyl, phenyl, aralkyl, and alkoxy-phenyl. Other reactive groups can be used. In some embodiments, the halide is a chloro, a bromo, or an iodo group. The reactive group can be used to integrate the monomer along into a polymer (e.g. along the backbone of the polymer by polymerizing in the polymer) and/or attach the monomer by covalent attachment to the backbone, a terminus, or a sidechain of the polymer. FIG. 6D shows example monomers that can be integrated into the polymer by reaction with the reactive groups, e.g., Br.

Chromophoric polymer dots of the present invention can include a polymer that includes a narrow-band monomer having the formula:

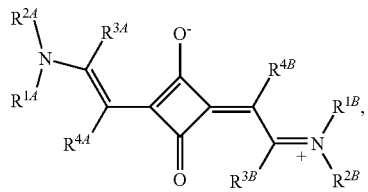

wherein each of $R^{1A}$, $R^{1B}$, $R^{2A}$ and $R^{2B}$ are independently selected from the group consisting of, but not limited to, hydrogen, deuterium, alkyl, aryl, acetyl, and hydroxyl; and each of $R^{3A}$, $R^{3B}$, $R^{4A}$ and $R^{4B}$ are independently selected from the group consisting of, but not limited to, hydrogen, deuterium, alkyl, aryl, amino, sulfide, aldehyde, ester, ether, acid, hydroxyl, and halide. The narrow-band monomer can be integrated into a backbone of the polymer (e.g. along the backbone of the polymer by polymerizing in the polymer) and/or attached by covalent attachment to the backbone, a terminus, or a sidechain of the polymer through at least one attachment to $R^{1A}$, $R^{1B}$, $R^{2A}$, $R^{2B}$, $R^{3A}$, $R^{3B}$, $R^{4A}$, $R^{4B}$ or a combination thereof.

Chromophoric polymer dots of the present invention can include a polymer that includes a narrow-band monomer having the formula:

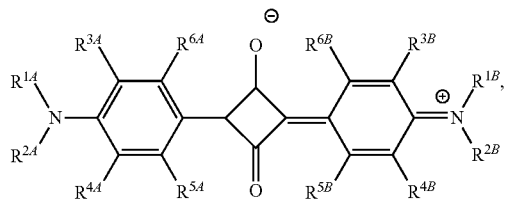

wherein each of $R^{1A}$, $R^{1B}$, $R^{2A}$ and $R^{2B}$ are independently selected from the group consisting of, but not limited to, hydrogen, deuterium, alkyl, aryl, acetyl, and hydroxyl; and each of $R^{3A}$, $R^{3B}$, $R^{4A}$, $R^{4B}$, $R^{5A}$, $R^{5B}$, $R^{6A}$ and $R^{6B}$ are independently selected from the group consisting of, but not limited to, hydrogen, deuterium, alkyl, aryl, amino, sulfide, aldehyde, ester, ether, acid, hydroxyl, and halide. The narrow-band monomer can be integrated into a backbone of the polymer (e.g. along the backbone of the polymer by polymerizing in the polymer) and/or attached by covalent attachment to the backbone, a terminus, or a sidechain of the polymer through at least one attachment to $R^{1A}$, $R^{1B}$, $R^{2A}$, $R^{2B}$, $R^{3A}$, $R^{3B}$, $R^{4A}$, $R^{4B}$, $R^{5A}$, $R^{5B}$, $R^{6A}$, $R^{6B}$ or a combination thereof.

Chromophoric polymer dots of the present invention can include a polymer that includes a narrow-band monomer having the formula:

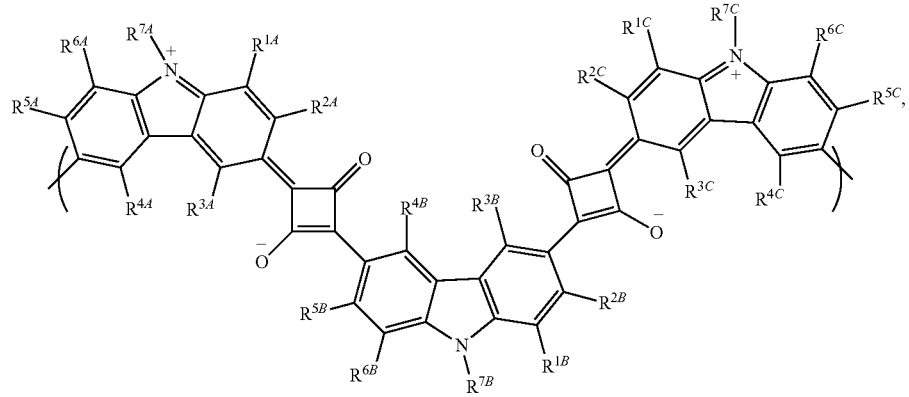

wherein each of $R^{1A}$, $R^{1B}$, $R^{1C}$, $R^{2A}$, $R^{2B}$, $R^{2C}$, $R^{3A}$, $R^{3B}$, $R^{3C}$, $R^{4A}$, $R^{4B}$, $R^{4C}$, $R^{5A}$, $R^{5B}$, $R^{5C}$, $R^{6A}$ $R^{6B}$, and $R^{6C}$ are independently selected from the group consisting of, but not limited to, hydrogen, deuterium, alkyl, aryl, amino, sulfide, aldehyde, ester, ether, acid, hydroxyl, and halide, and each of $R^{7A}$, $R^{7B}$, and $R^{7C}$ is independently selected from the group consisting of, but not limited to, hydrogen, deuterium, alkyl, aryl and acetyl. The narrow-band monomer can be integrated into a backbone of the polymer (e.g. along the backbone of the polymer by polymerizing in the polymer) and/or attached by covalent attachment to the backbone, a terminus, or a sidechain of the polymer through at least one attachment to $R^{1A}$, $R^{1B}$, $R^{1C}$, $R^{2A}R^{2B}$, $R^{2C}$, $R^{3A}$, $R^{3B}$, $R^{3C}$, $R^{4A}$, $R^{4B}$, $R^{4C}$, $R^{5A}$, $R^{5B}$, $R^{5C}$, $R^{6A}$, $R^{6B}$, $R^{6C}$, $R^{7A}$, $R^{7B}$ or a combination thereof. Alternatively, as shown here, the monomer described herein can be integrated with the polymer by attachment as shown by the parentheses.

Chromophoric polymer dots of the present invention can include a polymer that includes a narrow-band monomer having the formula:

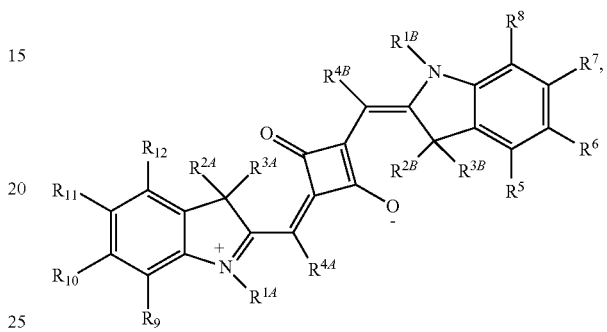

wherein each of $R^{1A}$ and $R^{1B}$ is independently selected from the group consisting of, but not limited to, hydrogen, deuterium, alkyl and aryl; and each of $R^{2A}$, $R^{2B}$, $R^{3A}$, $R^{3B}$, $R^{4A}$, $R^{4B}$, R, $R^6$, $R^7$, $R^8$, $R^9$, $R^{10}$, $R^{11}$ and $R^{12}$ are independently selected from the group consisting of, but not limited to, hydrogen, deuterium, alkyl, aryl, cyano, amino, sulfide, aldehyde, ester, ether, acid, hydroxyl, and halide. The narrow-band monomer can be integrated into a backbone of the polymer (e.g. along the backbone of the polymer by polymerizing in the polymer) and/or attached by covalent attachment to the backbone, a terminus, or a sidechain of the polymer through at least one attachment to $R^{1A}$, $R^{1B}$, $R^{2A}$, $R^{2B}$, $R^{3A}$, $R^{3B}$, $R^{4A}$, $R^{4B}$, $R^5$, $R^6$, $R^7$, $R^8$, $R^9$, $R^{10}$, $R^{11}$, $R^{12}$ or a combination thereof.

Figure 6E:
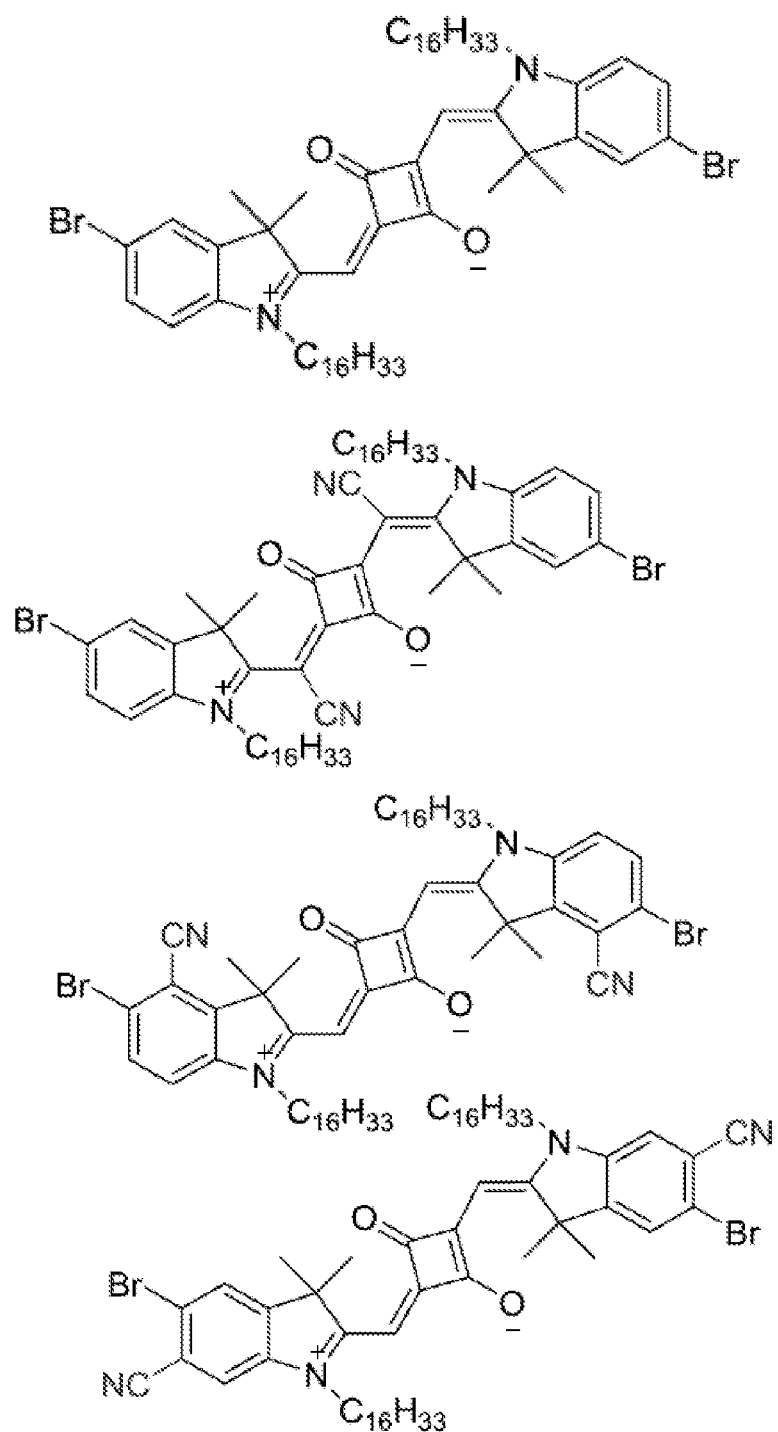

Chromophoric polymer dots of the present invention can include a polymer that includes a narrow-band monomer having the formula:

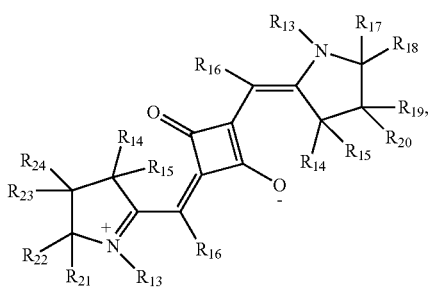

wherein each of $R^{13}$ is independently selected from the group consisting of, but not limited to, hydrogen, deuterium, alkyl and aryl; and $R^{14}$, $R^{15}$, $R^{16}$, $R^{17}$, $R^{18}$, $R^{19}$, $R^{20}$, $R^{21}$, $R^{22}$, $R^{23}$ and $R^{24}$ are independently selected from the group consisting of, but not limited to, hydrogen, deuterium, alkyl, aryl, cyano, amino, sulfide, aldehyde, ester, ether, acid, hydroxyl, and halide. The narrow-band monomer can be integrated into a backbone of the polymer (e.g. along the backbone of the polymer by polymerizing in the polymer) and/or attached by covalent attachment to the backbone, a terminus, or a sidechain of the polymer through at least one attachment to $R^{13}$, $R^{14}$, $R^{15}$, $R^{16}$, $R^{17}$, $R^{18}$, $R^{19}$, $R^{20}$, $R^{21}$, $R^{22}$, $R^{23}$ and $R^{24}$ or a combination thereof. FIG. 6E shows example monomers that can be integrated into the polymer by reaction with the reactive groups, e.g., Br.

In some embodiments, the narrow-band emissive polymers for making Pdots include metal complexes and their derivatives as narrow-band monomers. Metal complexes and their derivatives include but are not limited to their alkyl derivatives, aryl derivatives, alkyne derivatives, aromatic derivatives, alkoxide derivatives, aza derivatives, their extended systems and analogues. The narrow-band emissive polymers can also include any other monomers. The metals can be any metal such as Na, Li, Zn, Mg, Fe, Mn, Co, Ni, Cu, In, Si, Ga, Al, Pt, Pd, Ru, Rh, Re, Os, Ir, Ag, Au and so on. The metal complexes can be energy acceptors and other monomers can be energy donors so that the final Pdots can exhibit narrow-band emissions. The narrow-band emissive chromophoric polymers in good solvents may exhibit broad emissions or narrow emissions. However, their nanoparticle form gives narrow-band emissions. The emission FWHM of the above Pdots is less than 70 nm. In certain embodiments, the FWHM is less than 60 nm, less than 50 nm, less than 40 nm, less than 30 nm, or less than 20 nm.

Figure 7A:
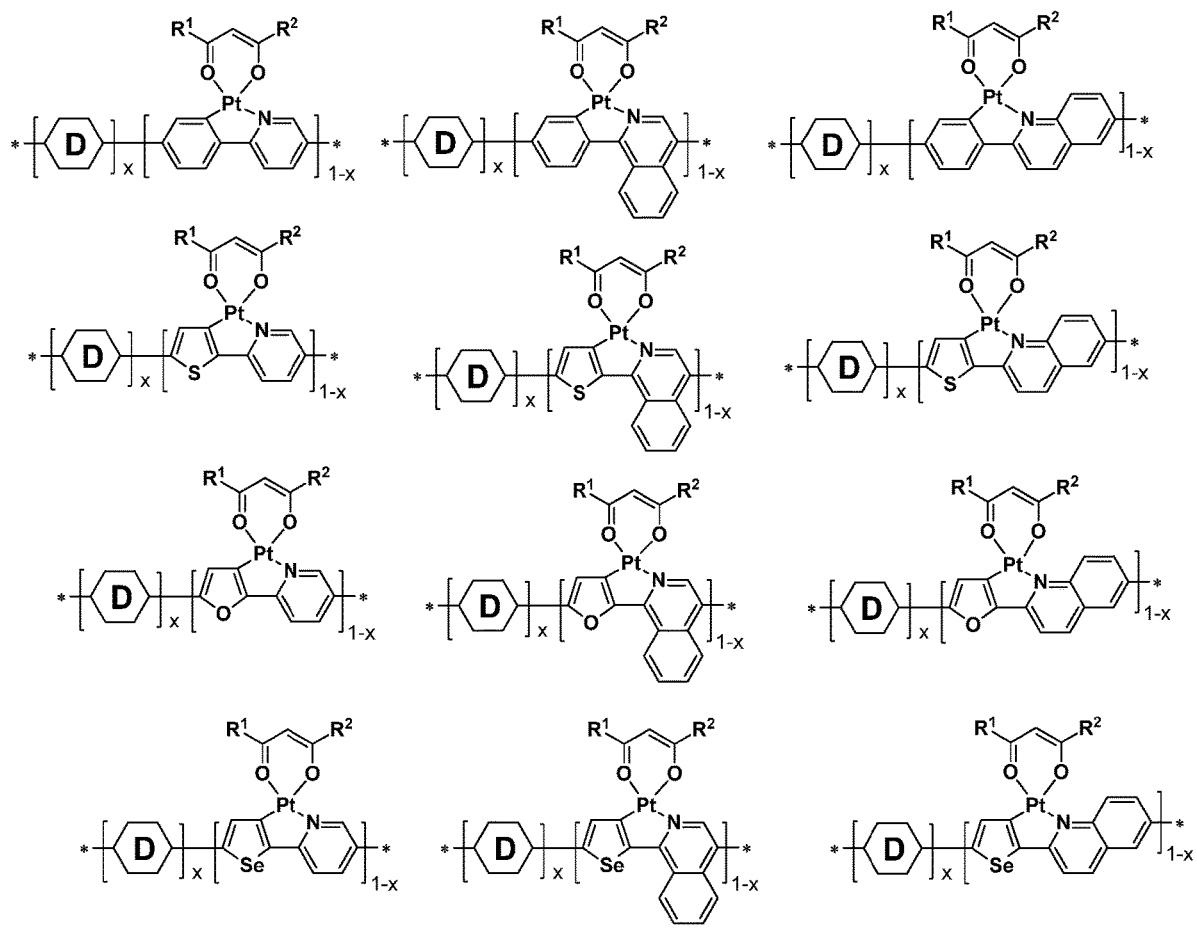
FIGS. 7A-7C show a non-limiting list of narrow-band emissive polymer including metal complexes and their derivatives as narrow-band monomer. Different Pt complexes were used as narrow-band monomers in the listed polymers, and other metal complexes can also be used. Each of the metal complexes can be used to synthesize a narrow-band emissive homopolymer. Each of the metal complexes can also be copolymerized with any of the general polymers to synthesize a narrow-band emissive copolymer. Each of the metal complexes can be used as a narrow-band emissive unit to cross-link with the side-chains of conventional semiconducting polymers to form narrow-band emissive polymers.
Figure 7B:
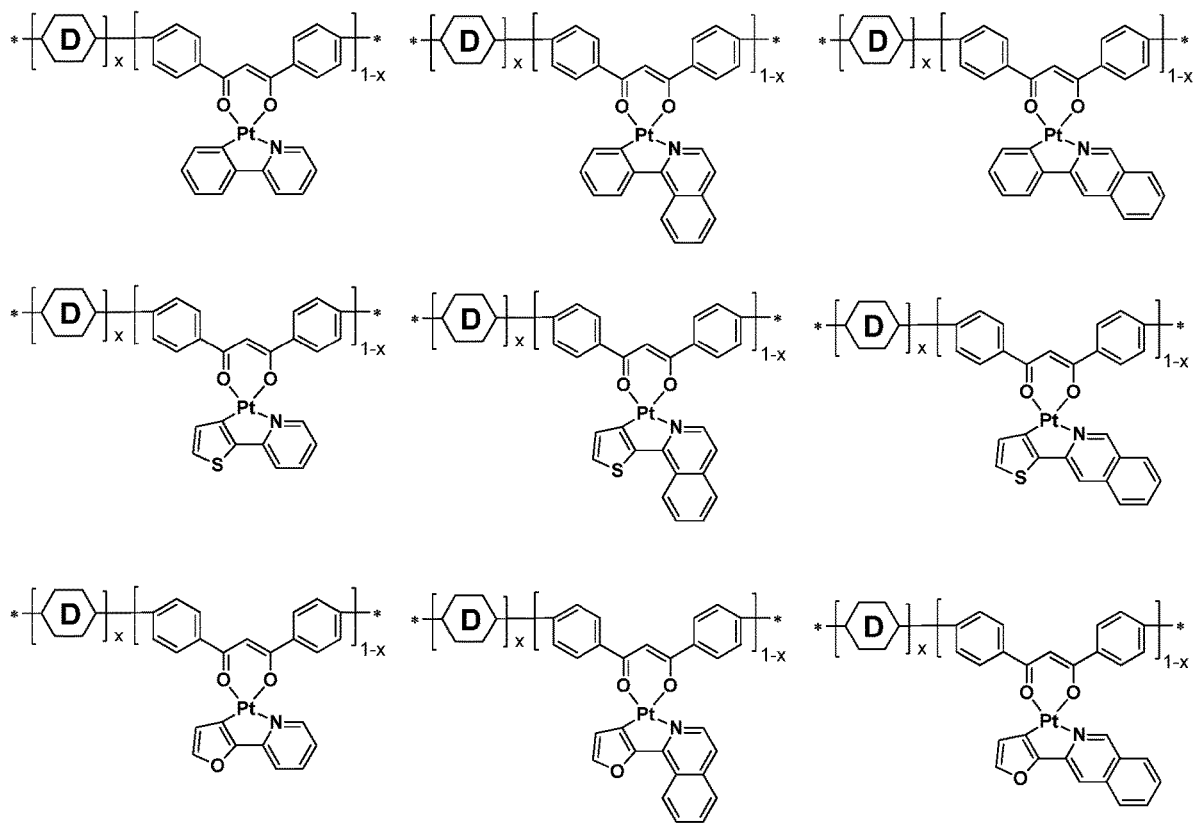
Figure 7C:
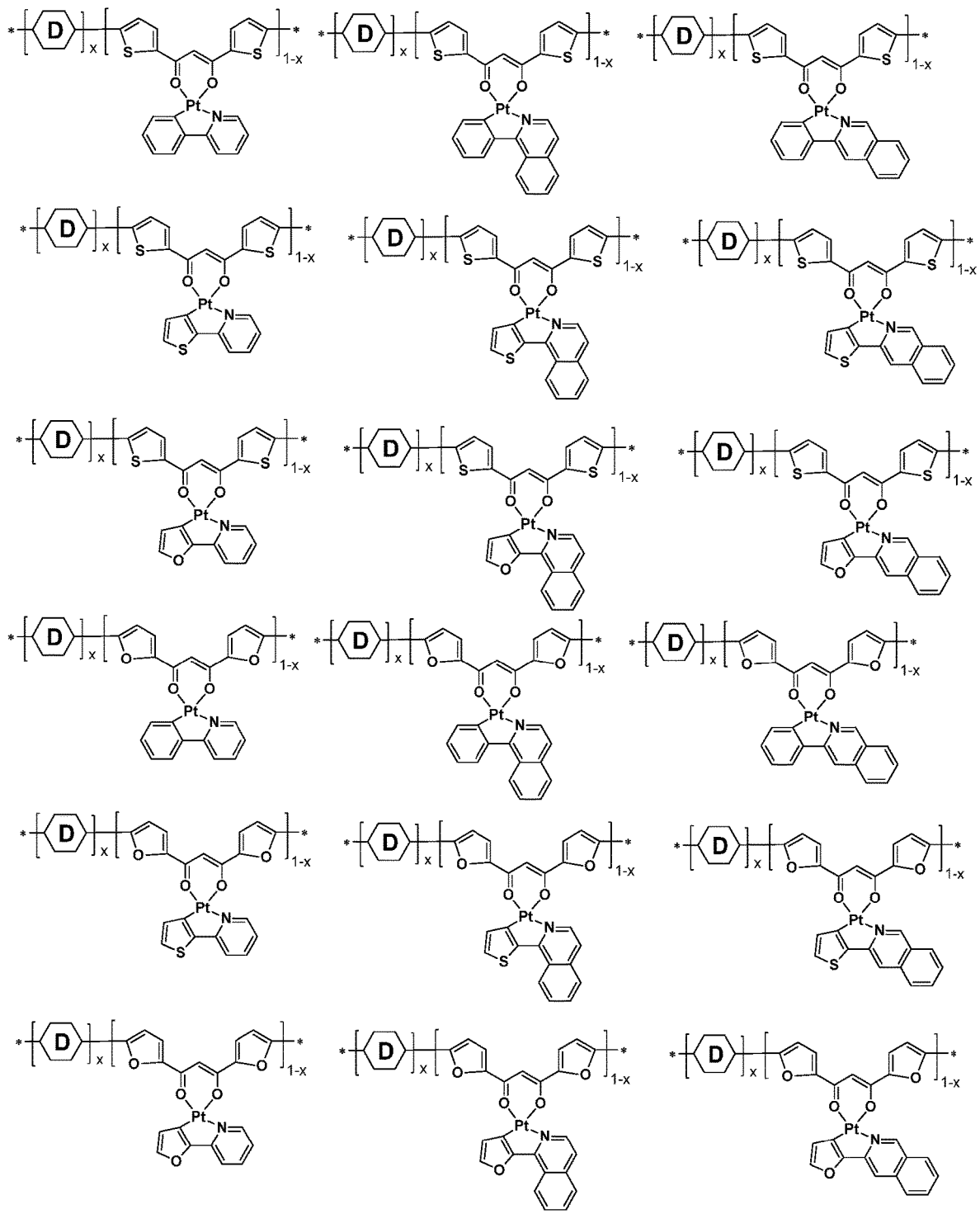

Examples of metal complexes and metal complex derivatives are shown in FIGS. 7A-7C. Metal complexes and metal complex derivatives can be polymerized to form polymers (e.g., homopolymers or heteropolymers) and/or can be attached (e.g., covalently attached) to a polymer backbone, sidechain and/or terminus. As shown in FIG. 7A, the metal complexes of the present invention include derivatives of the metal complexes. The metal complex monomers shown in FIG. 7A can include the compounds as shown, wherein $R^1$ and $R^2$ are independently selected from the group consisting of, but not limited to, phenyl, alkyl-substituted phenyl, alkyl-substituted fluorenyl, diphenyl-substituted fluorenyl, triphenylaminyl-substituted fluorenyl, diphenylaminyl-substituted fluorenyl, alkyl-substituted carbazolyl, alkyl-substituted triphenylaminyl and alkyl-substituted thiophenyl. Alkyl substituted phenyl can include 2-alkylphenyl, 3-alkylphenyl, 4-alkylphenyl, 2,4-dialkylphenyl, 3,5-dialkylphenyl, and 3,4-dialkylphenyl. Alkyl-substituted fluorenyl can include 9,9-dialkyl-substituted fluorenyl, 7-alkyl-9,9-dialkyl-substituted fluorenyl, 6-alkyl-9,9-dialkyl-substituted fluorenyl, 7-triphenylaminyl-9,9-dialkyl-substituted fluorenyl and 7-diphenylaminyl-9,9-dialkyl-substituted fluorenyl. Alkyl-substituted carbazolyl can include N-alkyl-substituted carbazolyl, 6-alkyl-substituted carbazolyl and 7-alkyl-substituted carbazolyl. Alkyl-substituted triphenylaminyl can include 4'-alkyl-substituted triphenylaminyl, 3'-alkyl-substituted triphenylaminyl, 3',4'-dialkyl-substituted triphenylaminyl and 4',4''-dialkyl-substituted triphenylaminyl. Alkyl-substituted thiophenyl can include 2-alkylthiophenyl, 3-alkylthiophenyl, and 4-alkylthiophenyl. The alkyl substituents can include $C_nH_{2n+1}$ or $C_nF_{2n+1}$ or $-CH_2CH_2[OCH_2CH_2]_n-OCH_3$, wherein n is 1 to 20. In some embodiments, n can be between 1 to 50 or higher. As will be further understood by one of ordinary skill in the art, the general monomer (D) and the narrow band metal complex monomers are present in the polymer at a ratio where D is present as x and the narrow band monomer is present as 1−x. For example, D may be present at 90% or x=0.9 and the narrow band monomer is present at 10% or 1−x=0.1. FIGS. 7B and 7C show additional example monomers for use in the present invention.

In some embodiments, the narrow-band emissive polymers for making Pdots include porphyrin, metalloporphyrin, and their derivatives as narrow-band monomers. Porphyrin, metalloporphyrin, and their derivatives can be polymerized to form polymers (e.g., homopolymers or heteropolymers) and/or can be attached (e.g., covalently attached) to a polymer backbone, sidechain and/or terminus. Porphyrin, metalloporphyrin, and their derivatives include but are not limited to their alkyl derivatives, aryl derivatives, alkyne derivatives, aromatic derivatives, alkoxide derivatives, aza derivatives, their extended systems and analogues. The metals in the metalloporphyrins can be any metal such as Na, Li, Zn, Mg, Fe, Mn, Co, Ni, Cu, In, Si, Ga, Al, Pt, Pd, Ru, Rh, Re, Os, Ir, Ag, Au and so on. The narrow-band emissive polymers can also include any other monomers. The porphyrin, metalloporphyrin and their derivatives can be energy acceptors and other monomers can be energy donors so that the final Pdots can exhibit narrow-band emissions. The narrow-band emissive chromophoric polymers in good solvents may exhibit broad emissions or narrow emissions. However, their nanoparticle form gives narrow-band emissions. The emission FWHM of the above Pdots is less than 70 nm. In certain embodiments, the FWHM is less than 60 nm, less than 50 nm, less than 40 nm, less than 30 nm, or less than 20 nm.

Figure 8:
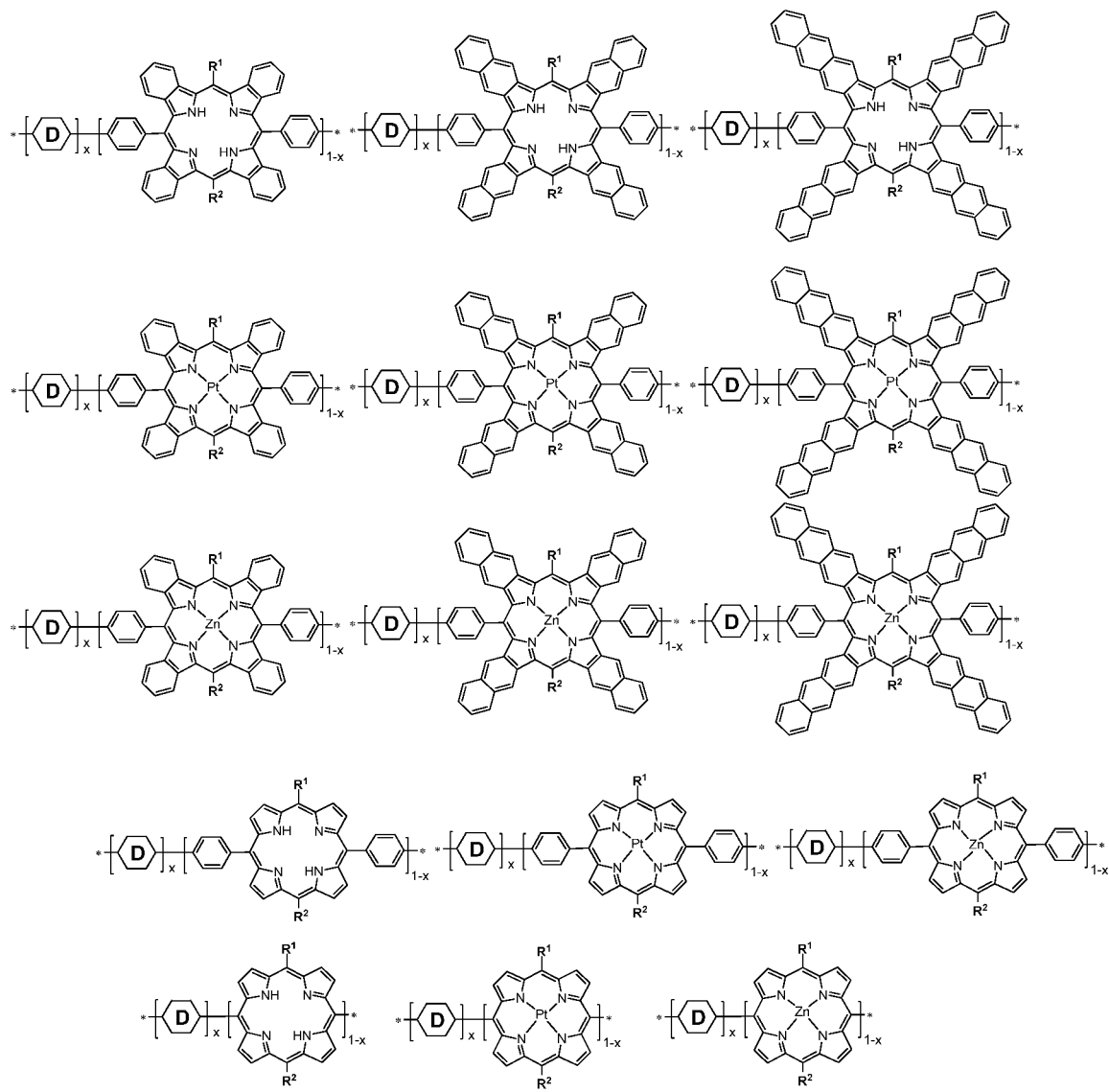
FIG. 8 shows a non-limiting list of narrow-band emissive polymer including porphyrin, metalloporphyrin and their derivatives as narrow-band monomer. Each of the porphyrin derivatives can be used to synthesize a narrow-band emissive homopolymer. Each of the porphyrin derivatives can also be copolymerized with any of the general polymers to synthesize a narrow-band emissive copolymer. Each of the porphyrin derivatives can be used as a narrow-band emissive unit to cross-link with the side-chains of conventional semiconducting polymers to form narrow-band emissive polymers.

FIG. 8 shows example porphyrin and porphyrin derivatives for use in the present invention. As shown in FIG. 8, the porphyrin derivatives can complex, e.g., with Pt and Zn. Also, $R^1$ and $R^2$ can be independently selected from the group consisting of, but not limited to, phenyl, alkyl-substituted phenyl, alkyl-substituted fluorenyl, alkyl-substituted carbazolyl, alkyl-substituted triphenylaminyl, alkyl-substituted thiophenyl, fluorine (F), cyano (CN) and trifluoro ($CF_3$). Alkyl substituted phenyl can include 2-alkylphenyl, 3-alkylphenyl, 4-alkylphenyl, 2,4-dialkylphenyl, 3,5-dialkylphenyl, and 3,4-dialkylphenyl. Alkyl-substituted fluorenyl can include 9,9-dialkyl-substituted fluorenyl, 7-alkyl-9,9-dialkyl-substituted fluorenyl and 6-alkyl-9,9-dialkyl-substituted fluorenyl. Alkyl-substituted carbazolyl can include N-alkyl-substituted carbazolyl, 6-alkyl-substituted carbazolyl and 7-alkyl-substituted carbazolyl. Alkyl-substituted thiophenyl can include 2-alkylthiophenyl, 3-alkylthiophenyl, and 4-alkylthiophenyl. The alkyl substituents can include $C_nH_{2n+1}$ or $C_nF_{2n+1}$ or $-CH_2CH_2[OCH_2CH_2]_n-OCH_3$, wherein n is 1 to 20. In some embodiments, n can be between 1 to 50 or higher. The narrow-band monomer can be integrated into a backbone of the polymer (e.g., by copolymerizing in the polymer) and/or attached by covalent attachment to the backbone, a terminus, or a sidechain of the polymer. through at least one attachment to $R^1$, $R^2$, or a combination thereof. Alternatively, as shown in FIG. 8, the monomers described herein can be integrated with the polymer by attachment as shown by brackets. As described herein, the general monomer (D) and the narrow band metal complex monomers are present in the polymer at a ratio where D is present as x and the narrow band monomer is present as 1-x.

In some embodiments, the narrow-band emissive polymers for making Pdots include phthalocyanine and its derivatives as monomers. Phthalocyanine and its derivatives as monomers can be polymerized to form polymers (e.g., homopolymers or heteropolymers) and/or can be attached (e.g., covalently attached) to a polymer backbone, sidechain and/or terminus. Phthalocyanine derivatives include but are not limited to their alkyl derivatives, aryl derivatives, alkyne derivatives, aromatic derivatives, alkoxide derivatives, aza derivatives, their extended systems and analogues. The metals in the phthalocyanine derivatives can be any metal such as Na, Li, Zn, Mg, Fe, Mn, Co, Ni, Cu, In, Si, Ga, Al, Pt, Ru, Rh, Re, Os, Ir, Ag, Au or Pd. The narrow-band emissive polymers can also include any other monomers. The phthalocyanine derivatives can be energy acceptors so that the final Pdots can exhibit narrow-band emissions. The narrow-band emissive chromophoric polymers in good solvents may exhibit broad emissions or narrow emissions. However, their nanoparticle form gives narrow-band emissions. The emission FWHM of the above Pdots is less than 70 nm. In certain embodiments, the FWHM is less than 60 nm, less than 50 nm, less than 40 nm, less than 30 nm, or less than 20 nm.

Figure 9:
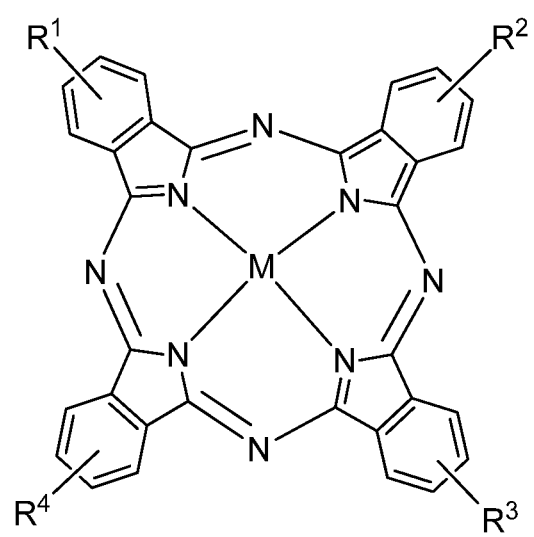
FIG. 9 shows a non-limiting list of phthalocyanine and its derivatives as narrow-band monomers. Each of the phthalocyanine derivatives can be used to synthesize a narrow-band emissive homopolymer. Each of the phthalocyanine derivatives can also be copolymerized with any of the general polymers to synthesize a narrow-band emissive copolymer. Each of the phthalocyanine derivatives can be used as a narrow-band emissive unit to cross-link with the side-chains of conventional semiconducting polymers to form narrow-band emissive polymers.

FIG. 9 shows an example phthalocyanine structure that can be used as a narrow band monomer in the present invention. As shown, M can be, but is not limited to, Cu, Zn, Mn, Fe, Si, Pt, Co, Ca, Ni, Na, Mg Ru, Rh, Re, Os, Ir, Ag, Au, Pd or Al. $R^1$, $R^2$, $R^3$, and $R^4$ can be a substituent attached to any suitable position in the isoindole portions of the monomer. The narrow-band monomer can be integrated into a backbone of the polymer (e.g., by copolymerizing in the polymer) and/or attached by covalent attachment to the backbone, a terminus, or a sidechain of the polymer through at least one attachment to $R^1$, $R^2$, $R^3$, $R^4$, or a combination thereof. In certain embodiments, each of $R^1$, $R^2$, $R^3$, and $R^4$ can be independently selected from the group consisting of, but not limited to, phenyl, alkyl-substituted phenyl, alkyl-substituted fluorenyl, alkyl-substituted carbazolyl, alkyl-substituted triphenylaminyl, alkyl-substituted thiophenyl, hydrogen, fluorine (F), cyano (CN) and trifluoro ($CF_3$). Alkyl substituted phenyl can include 2-alkylphenyl, 3-alkylphenyl, 4-alkylphenyl, 2,4-dialkylphenyl, 3,5-dialkylphenyl, 3,4-dialkylphenyl. Alkyl-substituted fluorenyl can include 9,9-dialkyl-substituted fluorenyl, 7-alkyl-9,9-dialkyl-substituted fluorenyl and 6-alkyl-9,9-dialkyl-substituted fluorenyl. Alkyl-substituted carbazolyl can include N-alkyl-substituted carbazolyl, 6-alkyl-substituted carbazolyl and 7-alkyl-substituted carbazolyl. Alkyl-substituted thiophenyl can include 2-alkylthiophenyl, 3-alkylthiophenyl, and 4-alkylthiophenyl. The alkyl substituents can include $C_nH_{2n+1}$, or $C_nF_{2n+1}$ or —$CH_2CH_2[OCH_2CH_2]_n$—$OCH_3$, wherein n is 1 to 20. In some embodiments, n can be between 1 to 50 or higher.

In some embodiments, the narrow-band emissive polymers for making Pdots include Lanthanide complexes and their derivatives as narrow-band monomers. Lanthanide complexes and lanthanide complex derivatives as monomers can be polymerized to form polymers (e.g., homopolymers or heteropolymers) and/or can be attached (e.g., covalently attached) to a polymer backbone, sidechain and/or terminus. Lanthanide complexes and their derivatives include but are not limited to their alkyl derivatives, aryl derivatives, alkyne derivatives, aromatic derivatives, alkoxide derivatives, aza derivatives, their extended systems and analogues. The narrow-band emissive polymers can also include any other monomers. The Lanthanide complexes and their derivatives can be energy acceptors and other monomers can be donors so that the final Pdots can exhibit narrow-band emissions. The narrow-band emissive chromophoric polymers in good solvents may exhibit broad emissions or narrow emissions. However, their nanoparticle form gives narrow-band emissions. The emission FWHM of the above Pdots is less than 70 nm. In certain embodiments, the FWHM is less than 60 nm, less than 50 nm, less than 40 nm, less than 30 nm, less than 20 nm, or less than 10 nm.

The lanthanide complexes described herein can have different narrow emission properties and mechanisms as compared to transition metal complexes. For example, a fluorescence mechanism of lanthanide (III) complexes (such as Ce (III), Pr(III), Nd(III), Sm(III), Eu(III), Tb(III), Dy(III), Ho(III), Er(III), Tm(III), or Yb(III)), whose 4f excited states are not empty and not fully filled by the electron, can be that energy absorbed by the organic ligand is first transferred from the singlet state to the triplet state (intersystem crossing) of the ligand, and then transferred (or is directly transferred from the singlet state of the organic ligand) to the 4f excited states of the lanthanide ions by the resonant energy transfer process. Here, the emission comes from the 4f-4f transitions of the Ln(III) ions. Due to the inner shell f orbital electrons being shielded from the environment by the filled $5S^25p^6$ sub-shells, they don't vary much with the environment. Consequently, the inner-shell 4f-4f transitions are sharp and result in narrow emission. For some divalent lanthanide ions, such as Sm(II), Eu (II), and YB (II), the emission is from the 5d-4f transitions. These properties of Lanthanide containing Pdots surprisingly can provide additional features as compared to other non-Lanthanide metal based Pdots, such as Pdots containing transition metal complexes.

In some embodiments, lanthanide complexes that can be used with the present invention can be described with the following formula:

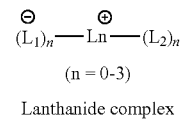

(n = 0-3)

Lanthanide complex

For example, the lanthanide complexes can be used as the narrow-band emissive monomers. The lanthanide complexes can, e.g., be repeating units of the polymer backbone. The lanthanide complexes can, e.g., be attached to the side-chains of the polymer. The lanthanide complexes can, e.g., be attached to the terminus of the polymer. Ln is lanthanide metal ion which has an unfilled inner shell and can accept energy from the organic ligands or general polymers to give narrow-band emission. There are several lanthanides that can be used, which can be the same or different, and can be selected from, e.g., Ce(III), Pr(III), Nd(III), Sm(III), Sm(II) Eu(III), Eu(II), Tb(III), Dy(III), Ho(III), Er(III), Tm(III), Yb(III), Yb(II). As shown in the formula above, $L_1$ and $L_2$ can be organic ligands. The ligands can be the same or different. There can be a plurality of ligands $L_1$. $L_1$ that can be anionic ligands coordinated with Ln. The total valences of $L_1$ and Ln can be equal to finally form a neutral lanthanide complex. In addition to acting as anionic ligands, $L_1$ can include additional groups to act as neutral ligands to be coordinated with Ln. $L_1$ can be monodentate, bidentate or polydentate and there can be one or more ligands $L_1$ in the lanthanide complex. In some embodiments, $L_1$ can be a bridged ligand and be coordinated with Ln to form binuclear, trinuclear and polynuclear lanthanide complexes. Some of bridged $L_1$ can form cryptands and can be coordinated to Ln to synthesize lanthanide cryptate. $L_2$ can be a neutral ligand. There can be a plurality of ligands $L_2$. $L_2$ can be the same or different. $L_2$ can be monodentate, bidentate or polydentate and there can be one or more ligands $L_2$ in the lanthanide complex. In some embodiments, $L_2$ can be a bridged ligand and be coordinated with Ln to form binuclear, trinuclear and polynuclear lanthanide complexes. Some of bridged $L_2$ can form cryptands and can be coordinated to Ln to synthesize lanthanide cryptate.

FIGS. 10A-10H shows example derivatives of lanthanide complexes that can be used as narrow band emissive units for the present invention. In some embodiments, the general monomers described herein can be designed to act as energy donors that transfer energy to selected lanthanide complexes. For example, the emission profile of a general monomer can overlap with the absorption profile of a lanthanide complex. Through energy transfer, the lanthanide complex can be excited and then emit light with a narrow band emission (e.g., of less than 70 nm FWHM). The energy transfer can be accomplished through a variety of ways. In some embodiments, homopolymers (e.g. P1-P10) or heteropolymers including general monomers (e.g., D1, D2, and/or monomers of homopolymer in P1-P10, and/or M1-M10) can be chemically bonded with lanthanide complexes and condensed into polymer dots. In certain embodiments, homopolymers (e.g. P1-P10) or heteropolymers including general monomers (e.g., D1, D2, and/or monomers of homopolymer in P1-P10, and/or M1-M10) can be chemically crosslinked with homo- or hetero-polymers including lanthanide complexes and condensed into polymer dots. In some embodiments, the general monomers (e.g., D1, D2, and/or monomers of homopolymer in P1-P10, and/or M1-M10) can be copolymerized in any combination with the lanthanide complexes. Due at least in part to packing of the polymers and the lanthanide complexes, energy transfer can be achieved between the general monomers and the lanthanide complexes.

Figure 10A:
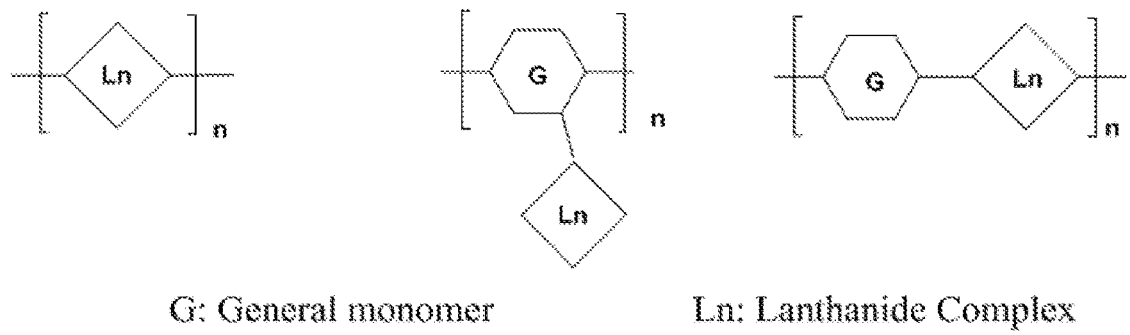
FIG. 10A-10H shows a non-limiting list of narrow-band emissive polymer comprising lanthanide complexes and their derivatives as e.g., narrow-band monomer.

The lanthanide complexes can be added to polymers in a variety of ways. For example, FIG. 10A shows schematic structures of narrow-band emissive polymers that can include lanthanide complexes. Lanthanide complexes can be used to produce a narrow-band emissive homopolymer. Lanthanide complexes can also be copolymerized with any of the general polymers to synthesize a narrow-band emissive copolymer or multi-component heteropolymer. Lanthanide complexes can be used as a narrow-band emissive unit to cross-link with the side-chains of conventional semiconducting polymers to form narrow-band emissive polymers. In some embodiments, the present invention can include lanthanide complexes as monomers in a homopolymer or heteropolymer. In certain embodiments, the lanthanide complexes can be linked (e.g., covalently bonded) to a side-chain of a homopolymer or heteropolymer having general monomers that, e.g., can act as energy donors to the lanthanide complexes (e.g., D1 and/or D2 and/or D2' monomers and/or monomers of homopolymer in P1-P10, and/or M1-M10 described herein can be the general monomers). The lanthanide complexes can also be copolymerized with a general monomer to form a heteropolymer. In each embodiment, the general monomer can be luminescent or non-luminescent. In some embodiments, the general monomer may absorb energy and transfer the energy, either directly or indirectly (e.g. via cascade energy transfer as described elsewhere in this application), to the lanthanide complexes. The length of the polymers as denoted, e.g., by n, in FIG. 10A can be designed to have any suitable length to result in any suitable polymer molecular weight (Mw). Mw, for example, can range between 500 and 1,000,000.

Figure 10B:
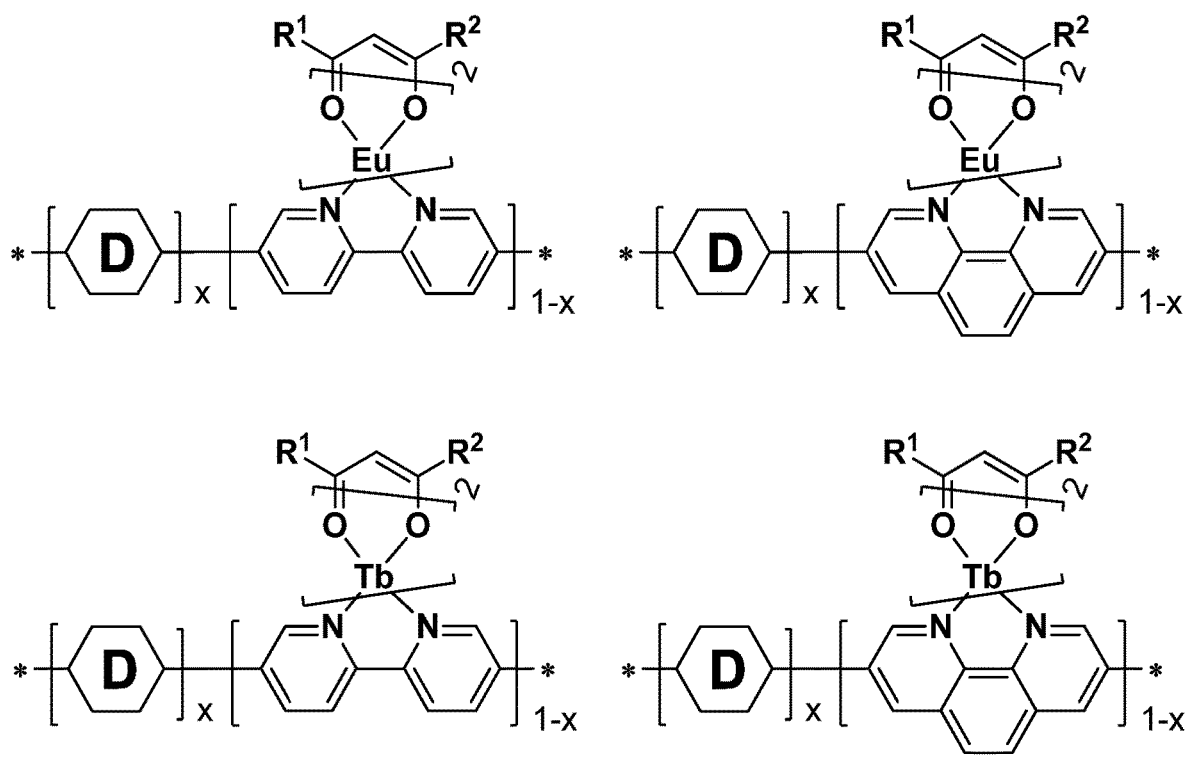

FIG. 10B shows example derivatives of lanthanide complexes that can be used as narrow band monomers for the present invention. A variety of elements in the Lanthanide series can be used, such as Europium (Eu) and Terbium (Tb). The lanthanide complex monomers shown in FIG. 10B can include the monomers as shown, wherein $R^1$ and $R^2$ are independently selected from the group consisting of, but not limited to, phenyl, alkyl-substituted phenyl, alkyl-substituted fluorenyl, diphenyl-substituted fluorenyl, triphenylaminyl-substituted fluorenyl, diphenylaminyl-substituted fluorenyl, alkyl-substituted carbazolyl, alkyl-substituted triphenylaminyl and alkyl-substituted thiophenyl. Alkyl substituted phenyl can include 2-alkylphenyl, 3-alkylphenyl, 4-alkylphenyl, 2,4-dialkylphenyl, 3,5-dialkylphenyl, 3,4-dialkylphenyl. Alkyl-substituted fluorenyl can include 9,9-dialkyl-substituted fluorenyl, 7-alkyl-9,9-dialkyl-substituted fluorenyl, 6-alkyl-9,9-dialkyl-substituted fluorenyl, 7-triphenylaminyl-9,9-dialkyl-substituted fluorenyl and 7-diphenylaminyl-9,9-dialkyl-substituted fluorenyl. Alkyl-substituted carbazolyl can include N-alkyl-substituted carbazolyl, 6-alkyl-substituted carbazolyl and 7-alkyl-substituted carbazolyl. Alkyl-substituted triphenylaminyl can include 4'-alkyl-substituted triphenylaminyl, 3'-alkyl-substituted triphenylaminyl, 3',4'-dialkyl-substituted triphenylaminyl and 4',4"-alkyl-substituted triphenylaminyl. Alkyl-substituted thiophenyl can include 2-alkylthiophenyl, 3-alkylthiophenyl, and 4-alkylthiophenyl. The alkyl substituents can include $C_nH_{2n+1}$ or $C_nF_{2n+1}$ or $-CH_2CH_2[OCH_2CH_2]_n-OCH_3$, wherein n is 1 to 20. In some embodiments, n can be between 1 to 50 or higher. As will be further understood by one of ordinary skill in the art, the general monomer (D) and the narrow band metal complex monomers are present in the polymer at a ratio where D is present as x and the narrow band monomer is present as 1−x. For example, D may be present at 90% or x=0.9 and the narrow band monomer is present at 10% or 1−x=0.1.

Figure 10C:
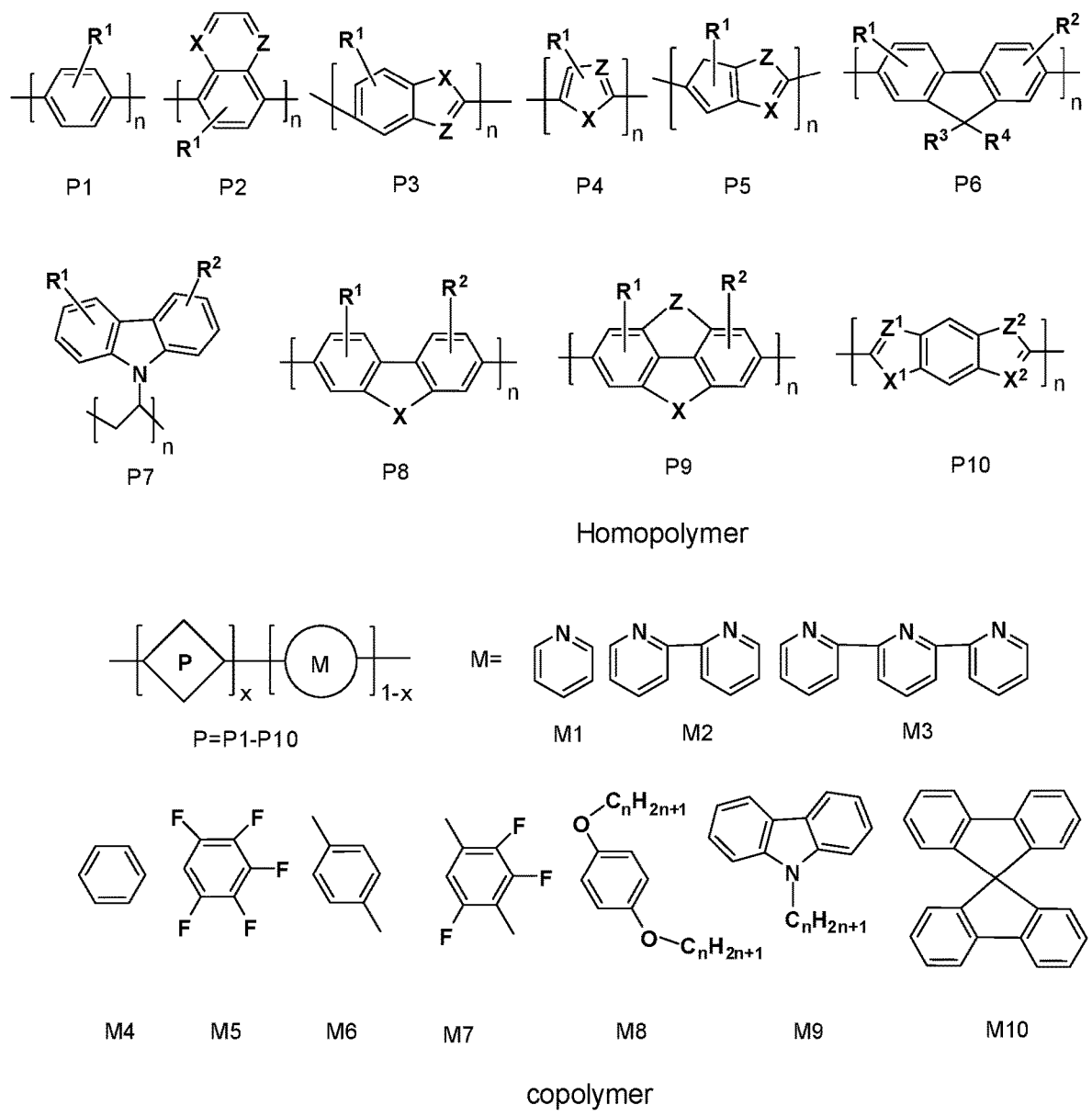

In some embodiments, the lanthanide complexes can be used as a narrow-band emissive unit to chemically crosslink with conventional semiconducting polymers to form narrow-band emissive polymer dots. The general semiconducting polymers can absorb energy and transfer the energy to the lanthanide complexes. FIG. 10C shows non-limiting examples of general homopolymers (e.g., P1-P10) and examples of general heterpolymers including one type of monomers of homopolymer P1-P10 and other types of monomers (e.g., M1-M10). The general polymers can be designed to act as energy donors to selected lanthanide complexes. In some embodiments, homo- or heteropolymers including general monomers (e.g., monomers of homopolymers P1-P10, and/or monomers of M1-M10) can be chemically bonded with lanthanide complexes and condensed into polymer dots. In certain embodiments, homo- or heteropolymers including general monomers (e.g., monomers of homopolymers P1-P10, and/or monomers of M1-M10) can be physically blended or chemically crosslinked with homo- or hetero-polymers with attached lanthanide complexes and condensed into polymer dots. In some embodiments, the general monomers (e.g monomers of homopolymers P1-P10, and/or monomers of M1-M10) can be copolymerized in any combination with the lanthanide complexes. Due at least in part to packing of the polymers and the lanthanide complexes, energy transfer can be achieved between the general polymers and the lanthanide complexes.

Some example general polymers that can transfer energy to lanthanide complexes are shown in FIG. 10C. For example, P1-P10 are homopolymers of the various monomers having a defined length, n. With respect to homopolymers of P1-P10 in FIG. 10C, each of $R^1$, $R^2$, $R^3$ and $R^4$ can be independently selected from, but not limited to, the group consisting of H, D, F, Cl, Br, I, alkoxy, aryloxy, alkyl, aryl, alkylketone, arylketone, alkylester, arylester, amide, carboxylic acid, fluoroalkyl, fluoroaryl, and polyalkaleneoxy. In some embodiments, two of the R groups (e.g., $R^1$, $R^2$, $R^3$ and $R^4$) may be bridging (e.g., covalently linked together to form a cyclic group, such as a cycloalkyl, hetercycloalkyl, aryl, or heteraryl group). Each of X and Z can be independently selected from the group consisting of —O—, —S—, —N—, —$NR^5$—, —$PR^5$— and —$CR^5R^6$—, —$CR^5R^6CR^7CR^8$—, —N=$CR^5$—, —$CR^5$=$CR^6$—, —N=N—, and —(CO)—, wherein each of $R^5$, $R^6$, $R^7$ and $R^8$ can be independently selected from, but not limited to, the group consisting of H, D, F, Cl, Br, I, alkoxy, aryloxy, alkyl, aryl, alkyleneoxy, polyalkaleneoxy, alkoxy, aryloxy, fluoroalkyl and fluoroaryl. Any two of $R^5$, $R^6$, $R^7$ and $R^8$ may be bridging. In certain embodiments, the polymers include general monomers that can be aromatic and have appropriate conjugation lengths leading to high extinction coefficient in typical wavelength in the region of ultraviolet (UV) to near infrared (NIR), i.e., 200-1800 nm, leading to typical fluorescence in the region of 200-1800 nm. The polymers can be good donors for transferring energy, either directly or indirectly (e.g. by cascade energy transfer), to lanthanide complexes. The general monomers can be included in polymers that are homopolymers, or copolymers, or heteropolymers that contain more than two types of monomers. These polymers may be linear, branched, hyperbranched, dendritic, crosslinked, random, block, graft, or any structural type. As also shown in FIG. 10C, some example general polymers include other types of monomers (M1-M10). The copolymer of P (a general monomer) and M (another general monomer) can be mixed in a suitable ratio, and as characterized by x and 1–x. As also shown, M8 and M9 can be substituted with a range of alkyl groups defined by the formula $C_nH_{2n+1}$ and 0<n<20.

Figure 10D:
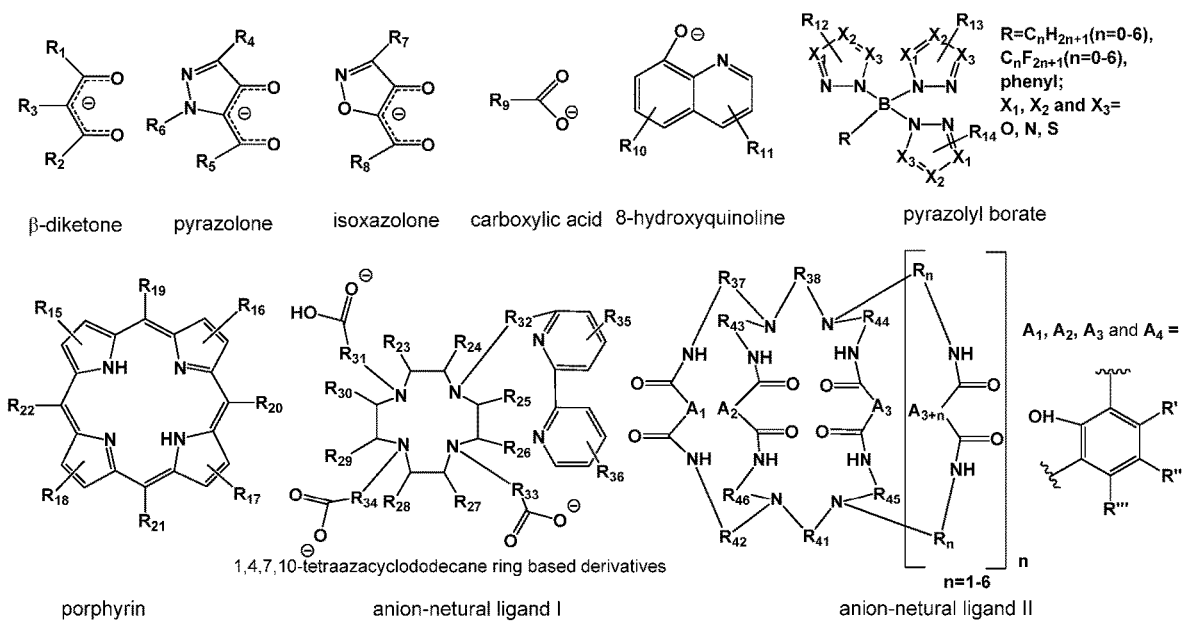
Figure 10D:
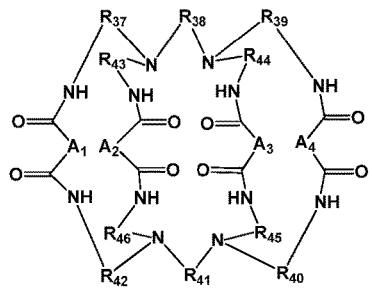
Figure 10D:
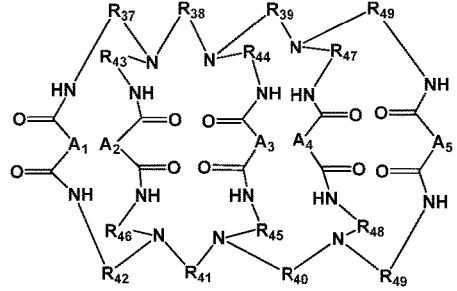

A variety of ligands can be used for the lanthanide complexes. Additional examples are shown, e.g., in FIG. 10D. FIG. 10D shows non-limiting examples of anionic ligands $L_1$ that can include β-diketone, pyrazolone, isoxazolone, carboxylic acid, phthalocyanine, 8-hydroxyquinoline, pyrazol borate, porphyrin, salicylaldehyde, phenylsalicylaldehyde, adenine, purine, 2-(2-hydroxyphenyl) benzothiadiazole, 2-(2-hydroxyphenyl)quinolone, 1-naphthol-2-carboxaldehyde, hydroxybenzophenone, 1,2-dihydroxybenzene, dihydroxynaphthalene, droxylfluorenone, 7-hydroxyinden-1-one, 7-hydroxy-3-phenylinden-1-one, 2-hydroxy-dimethylbenzene-1,3-diamide, 1,8-bis(4-methyl-2-hydroxy-benzamido)-3,6-dioxaoctane, 2-hydroxy-N-methylbenzamide, bis (2-hydroxy-N-methylbenzamide), and tri(2-hydroxy-N-methylbenzamide), 8-hydroxyquinazoline, 8-hydroxyquinoxaoline, hydroxybenzoxazole, hydroxy-2-phenyl benzoxazole, hypoxanthine, and the like. In some embodiments, $L_1$ has at least one aromatic ring. In some embodiments, $L_1$ has a direct chemical bond between two of the aryls groups to form a biaryl group, or has two rings in a fused ring system. The ligand can also have a multi-aryl group or a fused multi-ring group. The functional aryl groups can be bridged by alkyl, aryl, amine and other groups to form (semi-)macrocyclic ligands. In some embodiments, some of the bridged $L_1$ ligands can form cryptands and can be coordinated to Ln to synthesize lanthanide cryptate. In some embodiments, the ligand can include aromatic ring member groups (the anionic-neutral ligand II in FIG. 10F). As shown, $A_1$-$A_4$ can be ring members and independently selected from substituted or unsubstituted aryl and heteroaryl (e.g., azulene) moieties. In some embodiments, each R', R" and R'" groups can be independently selected from H, substituted or unsubstituted alkyl, substituted or unsubstituted heteroalkyl, substituted or unsubstituted heteroaryl, halogen, cyano (CN), substituted or unsubstituted aryl, substituted or unsubstituted fluoroalkyl, substituted or unsubstituted fluoroaryl, substituted or unsubstituted alkoxy, substituted or unsubstituted heteroaryl and acyl.

Figure 10E:
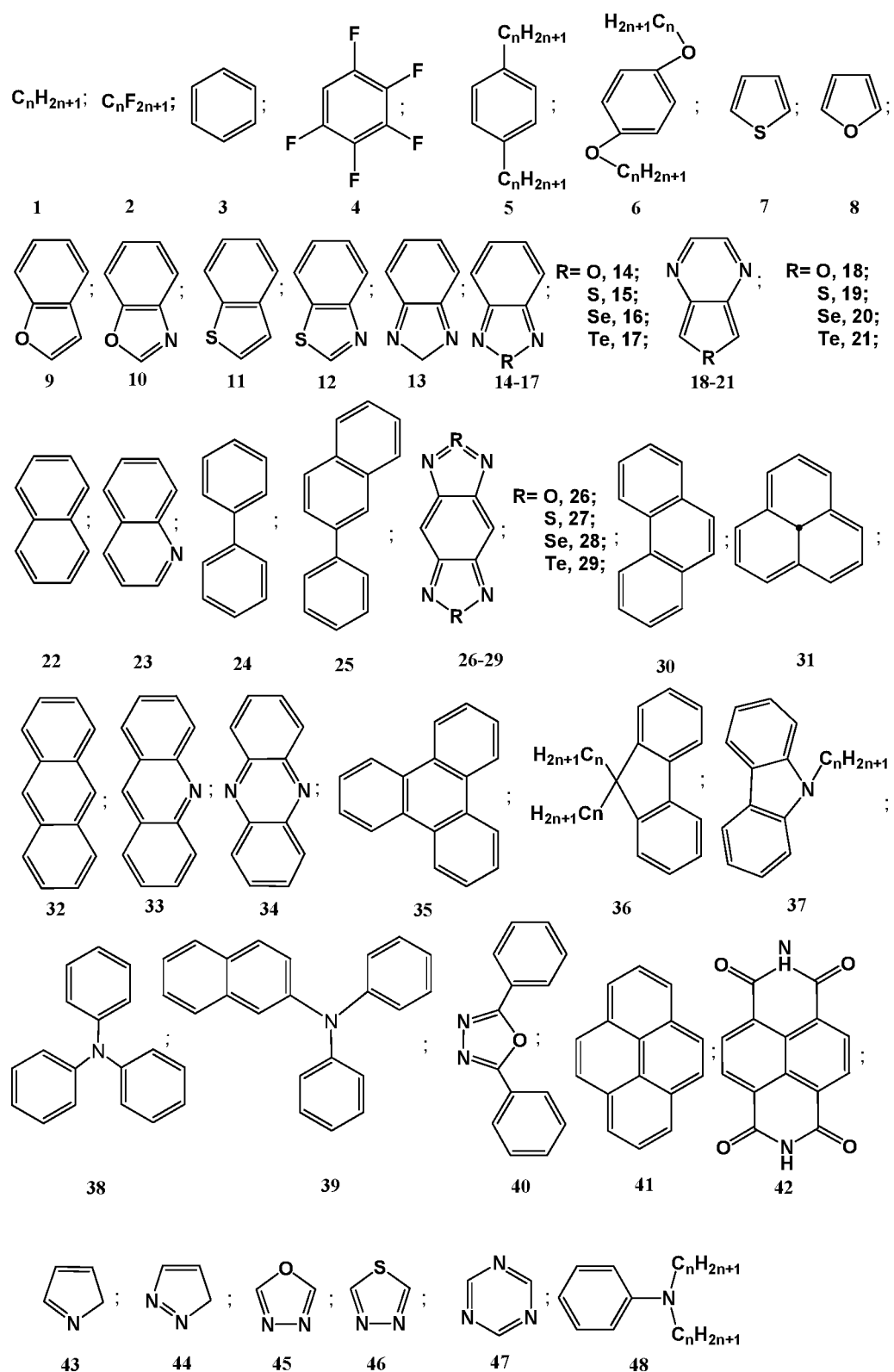

FIG. 10E shows non-limiting examples of some substituted groups in the anionic ligands $L_1$. In some embodiments, $R_1$-$R_{40+n}$ can be independently selected from, but not limited to, H, D, halogen, direct or branched alkyl, alkoxy, aryl, alkyl ketone, alkylester, arylester, amide, fluoroalkyl, fluoroaryl, and polyalkalene (e.g, mehtoxyethoxyethoxy, ethoxyethoxy, and —$(OCH_2CH_2)_nOH$, n=1-50), phenyl, alkyl-(alkoxy-, aryl-, fluoroalkyl-, fluoroaryl-)substituted phenyl, pyridyl, alkyl-(alkoxy-, aryl-, fluoroalkyl-, fluoroaryl-)substituted pyridyl, bipyridyl, alkyl-(alkoxy-, aryl-, fluoroalkyl-, fluoroaryl-)substituted bipyridyl tripyridyl, alkyl-(alkoxy-, aryl-, fluoroalkyl-, fluoroaryl-)substituted tripyridyl, furyl, alkyl-(alkoxy-, aryl-, fluoroalkyl-, fluoroaryl-)substituted furyl, thienyl, alkyl-(alkoxy-, aryl-, fluoroalkyl-, fluoroaryl-)substituted thienyl, pyrrolyl, alkyl-(alkoxy-, aryl-, fluoroalkyl-, fluoroaryl-)substituted pyrrolyl, pyrazolyl, alkyl-(alkoxy-, aryl-, fluoroalkyl-, fluoroaryl-)substituted pyrazolyl, oxazolyl, alkyl-(alkoxy-, aryl-, fluoroalkyl-, fluoroaryl-)substituted oxazolyl, thiazolyl, alkyl-(alkoxy-, aryl-, fluoroalkyl-, fluoroaryl-)substituted thiazolyl, imidazolyl, alkyl-(alkoxy-, aryl-, fluoroalkyl-, fluoroaryl-)substituted imidazolyl, pyrazinyl, alkyl-(alkoxy-, aryl-, fluoroalkyl-, fluoroaryl-)substituted pyrazinyl, benzooxadizolyl, alkyl-(alkoxy-, aryl-, fluoroalkyl-, fluoroaryl-)substituted benzooxadizolyl, benzothiadizolyl, alkyl-(alkoxy-, aryl-, fluoroalkyl-, fluoroaryl-)substituted benzothiadizolyl, fluorenyl, alkyl-(alkoxy-, aryl-, fluoroalkyl-, fluoroaryl-)substituted fluorenyl, triphenylaminyl-substituted fluorenyl, diphenylaminyl-substituted fluorenyl, alkyl-substituted carbazolyl, alkyl-substituted triphenylaminyl and alkyl-substituted thiophenyl. As exemplary embodiments, alkyl substituted phenyl can include 2-alkylphenyl, 3-alkylphenyl, 4-alkylphenyl, 2,4-dialkylphenyl, 3,5-dialkylphenyl, 3,4-dialkylphenyl; alkyl-substituted fluorenyl can include 9, 9-dialkyl-substituted fluorenyl, 7-alkyl-9,9-dialkyl-substituted fluorenyl, 6-alkyl-9,9-dialkyl-substituted fluorenyl, 7-triphenylaminyl-9,9-dialkyl-substituted fluorenyl and 7-diphenylaminyl-9,9-dialkyl-substituted fluorenyl; alkyl-substituted carbazolyl can include N-alkyl-substituted carbazolyl, 6-alkyl-substituted carbazolyl and 7-alkyl-substituted carbazolyl; alkyl-substituted triphenylaminyl can include 4'-alkyl-substituted triphenylaminyl, 3'-alkyl-substituted triphenylaminyl, 3',4'-dialkyl-substituted triphenylaminyl and 4',4"-alkyl-substituted triphenylaminyl;

alkyl-substituted thiophenyl can include 2-alkylthiophenyl, 3-alkylthiophenyl, and 4-alkylthiophenyl. The alkyl substituents can include $C_nH_{2n+1}$, or $C_nF_{2n+1}$ or —$CH_2CH_2[OCH_2CH_2]_n$—$OCH_3$, wherein n is 1 to 20. In some embodiments, n can be between 1 to 50 or higher.

Figure 10F:
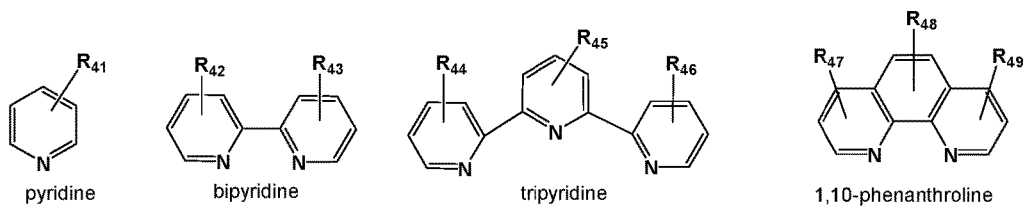
Figure 10F:
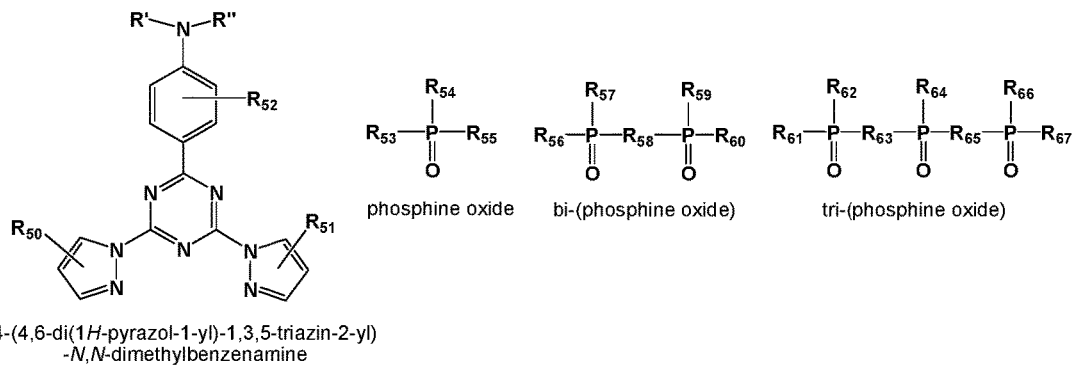

FIG. 10F shows non-limiting examples of neutral ligands $L_2$. In some embodiments, $L_2$ can include substituted or unsubstituted pyridine, substituted or unsubstituted bipyridine, substituted or unsubstituted tripyridine, substituted or unsubstituted 1,10-phenanthroline, substituted or unsubstituted phosphine oxide, substituted or unsubstituted bi-(phosphine oxide), substituted or unsubstituted tri-(phosphine oxide), substituted or unsubstituted 4-(4,6-di(1H-pyrazol-1-yl)-1,3,5-triazin-2-yl)-N,N'-dimethylbenzenamine, where substituted groups $R_{41}$-$R_{67}$ are independently selected from, but not limited to, hydrogen (H), deuterium (D), halogen, direct or branched alkyl, alkoxy, aryl, alkyl ketone, alkylester, arylester, amide, fluoroalkyl, fluoroaryl, and polyalkalene (e.g, mehtoxyethoxyethoxy, ethoxyethoxy, and —$(OCH_2CH_2)_nOH$, n=1-50), phenyl, alkyl-(alkoxy-, aryl-, fluoroalkyl-, fluoroaryl-)substituted phenyl, pyridyl, alkyl-(alkoxy-, aryl-, fluoroalkyl-, fluoroaryl-)substituted pyridyl, bipyridyl, alkyl-(alkoxy-, aryl-, fluoroalkyl-, fluoroaryl-)substituted bipyridyl tripyridyl, alkyl-(alkoxy-, aryl-, fluoroalkyl-, fluoroaryl-)substituted tripyridyl, furyl, alkyl-(alkoxy-, aryl-, fluoroalkyl-, fluoroaryl-)substituted furyl, thienyl, alkyl-(alkoxy-, aryl-, fluoroalkyl-, fluoroaryl-)substituted thienyl, pyrrolyl, alkyl-(alkoxy-, aryl-, fluoroalkyl-, fluoroaryl-)substituted pyrrolyl, pyrazolyl, alkyl-(alkoxy-, aryl-, fluoroalkyl-, fluoroaryl-)substituted pyrazolyl, oxazolyl, alkyl-(alkoxy-, aryl-, fluoroalkyl-, fluoroaryl-)substituted oxazolyl, thiazolyl, alkyl-(alkoxy-, aryl-, fluoroalkyl-, fluoroaryl-)substituted thiazolyl, imidazolyl, alkyl-(alkoxy-, aryl-, fluoroalkyl-, fluoroaryl-)substituted imidazolyl, pyrazinyl, alkyl-(alkoxy-, aryl-, fluoroalkyl-, fluoroaryl-) substituted pyrazinyl, benzooxadizolyl, alkyl-(alkoxy-, aryl-, fluoroalkyl-, fluoroaryl-)substituted benzooxadizolyl, benzothiadizolyl, alkyl-(alkoxy-, aryl-, fluoroalkyl-, fluoroaryl-)substituted benzothiadizolyl, fluorenyl, alkyl-(alkoxy-, aryl-, fluoroalkyl-, fluoroaryl-)substituted fluorenyl, triphenylaminyl-substituted fluorenyl, diphenylaminyl-substituted fluorenyl, alkyl-substituted carbazolyl, alkyl-substituted triphenylaminyl and alkyl-substituted thiophenyl. As exemplary embodiments, alkyl substituted phenyl can include 2-alkylphenyl, 3-alkylphenyl, 4-alkylphenyl, 2,4-dialkylphenyl, 3,5-dialkylphenyl, 3,4-dialkylphenyl; alkyl-substituted fluorenyl can include 9, 9-dialkyl-substituted fluorenyl, 7-alkyl-9,9-dialkyl-substituted fluorenyl, 6-alkyl-9,9-dialkyl-substituted fluorenyl, 7-triphenylaminyl-9,9-dialkyl-substituted fluorenyl and 7-diphenylaminyl-9,9-dialkyl-substituted fluorenyl; alkyl-substituted carbazolyl can include N-alkyl-substituted carbazolyl, 6-alkyl-substituted carbazolyl and 7-alkyl-substituted carbazolyl; alkyl-substituted triphenylaminyl can include 4'-alkyl-substituted triphenylaminyl, 3'-alkyl-substituted triphenylaminyl, 3',4'-dialkyl-substituted triphenylaminyl and 4',4"-alkyl-substituted triphenylaminyl; alkyl-substituted thiophenyl can include 2-alkylthiophenyl, 3-alkylthiophenyl, and 4-alkylthiophenyl, Each R' and R" groups are independently selected from H, substituted or unsubstituted alkyl, substituted or unsubstituted heteroalkyl, substituted or unsubstituted heteroaryl, halogen, substituted or unsubstituted aryl, substituted or unsubstituted fluoroalkyl, substituted or unsubstituted fluoroaryl, substituted or unsubstituted alkoxy, substituted or unsubstituted heteroaryl. The alkyl substituents can include $C_nH_{2n+1}$, or $C_nF_{2n+1}$ or —$CH_2CH_2[OCH_2CH_2]_n$—$OCH_3$, wherein n is 1 to 20. In some embodiments, n can be 1-50 or higher. $L_2$ can be bridged by alkyl, aryl, amine and other groups from $R_1$-$R_{41+n}$ and to form cryptands which can be coordinated to Ln to synthesize lanthanide cryptate.

Figure 10G:
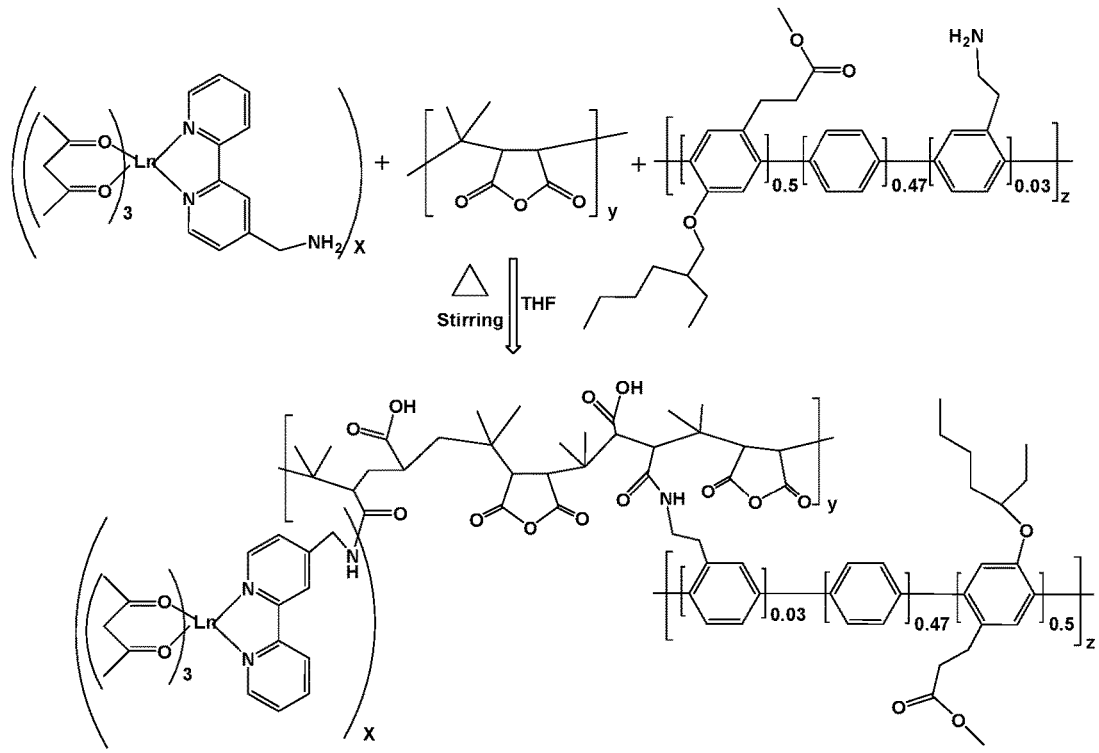
Figure 10H:
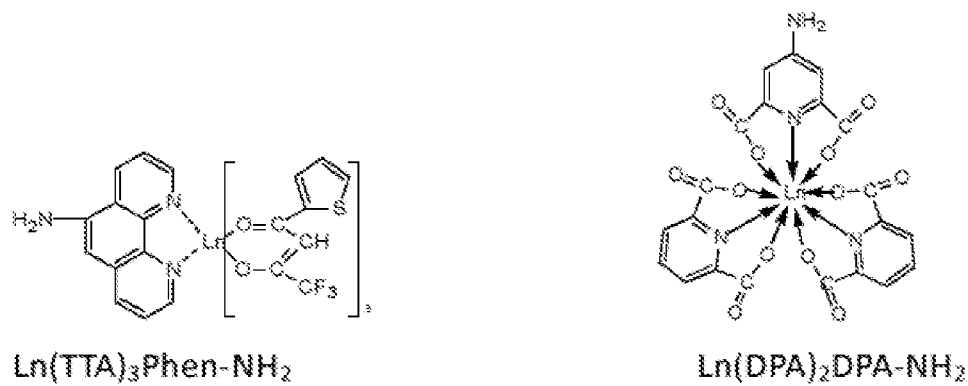
Figure 10H:
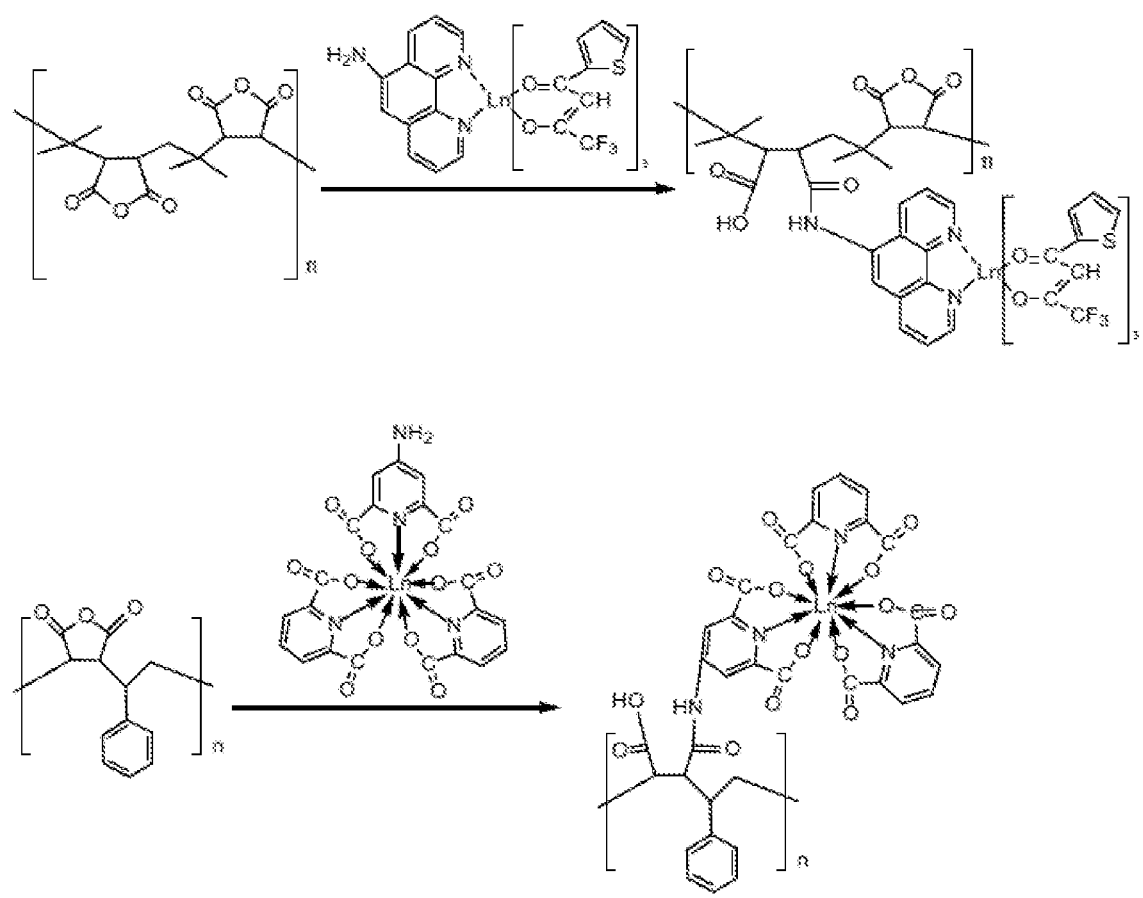

The methods of making the polymers and lanthanide complexes are generally well known in the art. FIG. 10G provides an example scheme for making narrow-band emissive polymers that can include, e.g., general monomers as donors and the lanthanide complexes for emission. In the method shown in FIG. 10G, both the general monomers and the lanthanide complexes include amino groups that can be covalently crosslinked with an amine reactive polymer to form lanthanide-complex grafted polymers for preparing narrow-band emissive polymer dots. As shown, a variety of lanthanide ions can be complexed with the ligands to form the lanthanide complex, e.g., Ln can be Ce (III), Pr(III), Nd(III), Sm(III), Eu(III), Tb(III), Dy(III), Ho(III), Er(III), Tm(III), or Yb(III). In some embodiments, the lanthanide ion can be Eu(III) or Tb(III). FIG. 10H shows another example method of making polymers having lanthanide complexes. For example, $Ln(TTA)_3Phen-NH_2$ and $Ln(DPA)_2DPA-NH_2$ can be attached to a side chain of a polymer by reaction with the $NH_2$ groups on either complex.

In some embodiments, the narrow-band emissive polymers for making Pdots include perylene and its derivatives as monomers. Perylene derivatives include but are not limited to their alkyl derivatives, aryl derivatives, alkyne derivatives, aromatic derivatives, alkoxide derivatives, aza derivatives, their extended systems and analogues. The narrow-band emissive polymers can also include any other monomers. The perylene derivatives can be energy acceptors so that the final Pdots can exhibit narrow-band emissions. The narrow-band emissive chromophoric polymers in good solvents may exhibit broad emissions or narrow emissions. However, their nanoparticle form gives narrow-band emissions. The emission FWHM of the above Pdots is less than 70 nm. In certain embodiments, the FWHM is less than 60 nm, less than 50 nm, less than 40 nm, less than 30 nm, or less than 20 nm.

Figure 11A:
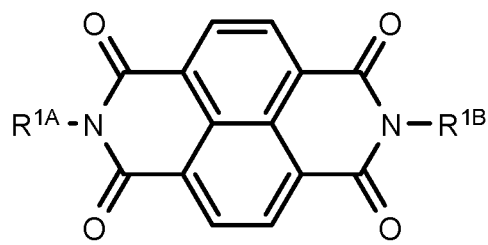
FIG. 11A shows a non-limiting list of perylene and its derivatives as narrow-band monomer. Each of the perylene derivatives can be used to synthesize a narrow-band emissive homopolymer. Each of the perylene derivatives can also be copolymerized with any of the general polymers to synthesize a narrow-band emissive copolymer. Each of the perylene derivatives can be used as a narrow-band emissive unit to cross-link with the side-chains of conventional semiconducting polymers to form narrow-band emissive polymers.
Figure 11A:
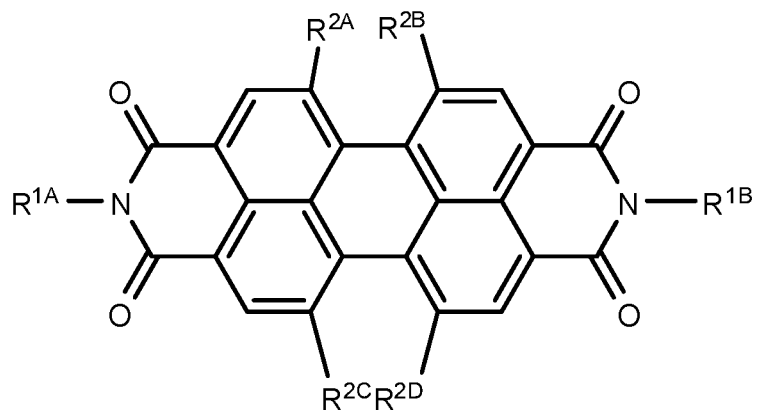
Figure 11A:
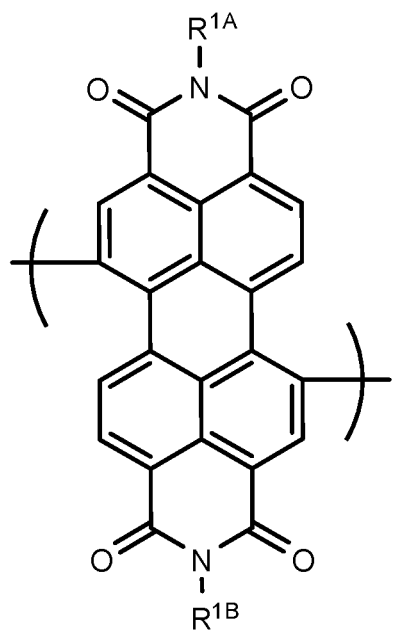

FIG. 11A shows example perylene derivatives that can be used as a narrow band monomer in the present invention. The narrow-band monomer can be integrated into a backbone of the polymer (e.g., by copolymerizing in the polymer) and/or attached by covalent attachment to the backbone, a terminus, or a sidechain of the polymer through at least one attachment to $R^{1A}$, $R^{1B}$, $R^{2A}$, $R^{2B}$, $R^{2C}$, $R^{2D}$ or a combination thereof. As shown by the parentheses in one example, the monomer can be integrated into the polymer and/or attached by covalent attachment to the backbone, a terminus, or a sidechain of the polymer by attachment to $R^{2B}$ and $R^{2C}$ groups. In certain embodiments, each of $R^{1A}$, $R^{1B}$, $R^{2A}$, $R^{2B}$, $R^{2C}$ and $R^{2D}$ can be independently selected from the group consisting of, but not limited to, phenyl, alkyl-substituted phenyl, alkyl-substituted fluorenyl, alkyl-substituted carbazolyl, alkyl-substituted triphenylaminyl, alkyl-substituted thiophenyl, fluorine (F), cyano (CN) and trifluoro ($CF_3$). Alkyl substituted phenyl can include 2-alkylphenyl, 3-alkylphenyl, 4-alkylphenyl, 2,4-dialkylphenyl, 3,5-dialkylphenyl, and 3,4-dialkylphenyl. Alkyl-substituted fluorenyl can include 9,9-dialkyl-substituted fluorenyl, 7-alkyl-9,9-dialkyl-substituted fluorenyl and 6-alkyl-9,9-dialkyl-substituted fluorenyl. Alkyl-substituted carbazolyl can include N-alkyl-substituted carbazolyl, 6-alkyl-substituted carbazolyl and 7-alkyl-substituted carbazolyl. Alkyl-substituted thiophenyl can include 2-alkylthiophenyl, 3-alkylthiophenyl, and 4-alkylthiophenyl. The alkyl substituents can include $C_nH_{2n+1}$ or $C_nF_{2n+1}$ or —$CH_2CH_2[OCH_2CH_2]_n$—$OCH_3$, wherein n is 1 to 20. In some embodiments, n can be between 1 to 50 or higher.

In some embodiments, the narrow-band emissive polymers for making Pdots include cyanine and its derivatives as monomers. Cyanine derivatives include but are not limited to their alkyl derivatives, aryl derivatives, alkyne derivatives, aromatic derivatives, alkoxide derivatives, aza derivatives, their extended systems and analogues. The narrow-band emissive polymers can also include any other monomers. The cyanine derivatives can be energy acceptors so that the final Pdots can exhibit narrow-band emissions. The narrow-band emissive chromophoric polymers in good solvents may exhibit broad emissions or narrow emissions. However, their nanoparticle form gives narrow-band emissions. The emission FWHM of the above Pdots is less than 70 nm. In certain embodiments, the FWHM is less than 60 nm, less than 50 nm, less than 40 nm, less than 30 nm, or less than 20 nm.

Figure 11B:
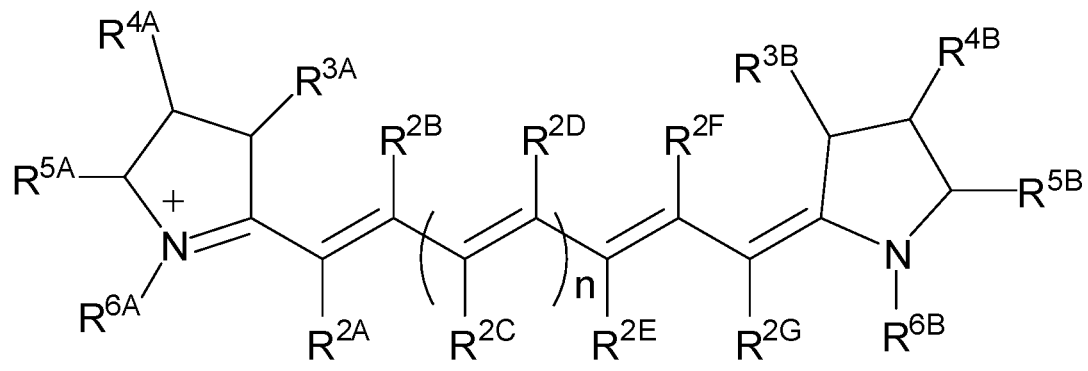
FIGS. 11B-11D show a non-limiting list of cyanine and its derivatives as narrow-band monomer. Each of the cyanine derivatives can be used to synthesize a narrow-band emissive homopolymer. Each of the cyanine derivatives can also be copolymerized with any of the general polymers to synthesize a narrow-band emissive copolymer. Each of the cyanine derivatives can be used as a narrow-band emissive unit to cross-link with the side-chains of conventional semiconducting polymers to form narrow-band emissive polymers.
Figure 11B:
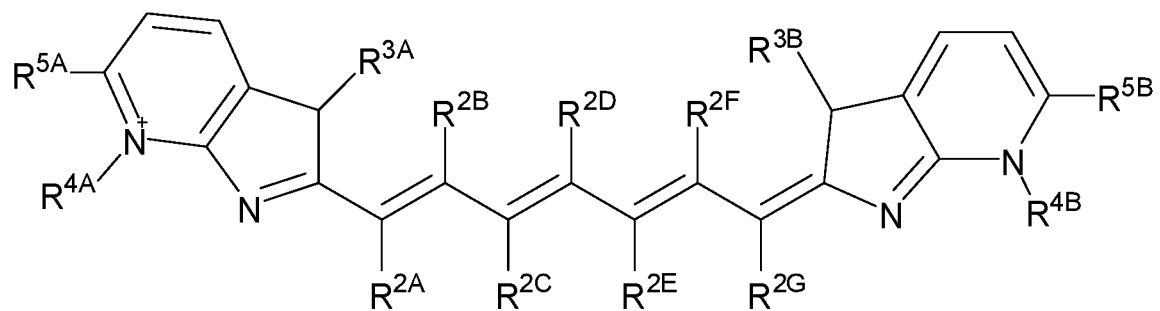

FIG. 11B shows one set of example cyanine derivatives that can be used as a narrow band monomer in the present invention. The narrow-band monomer can be integrated into a backbone of the polymer (e.g., by copolymerizing in the polymer) and/or attached by covalent attachment to the backbone, a terminus, or a sidechain of the polymer through at least one attachment to $R^{2A}$, $R^{2B}$, $R^{2C}$, $R^{2D}$, $R^{2E}$, $R^{2F}$, $R^{2G}$, $R^{3A}$, $R^{3B}$, $R^{4A}$, $R^{4B}$, $R^{5A}$, $R^5$, $R^{6A}$, $R^{6B}$ or a combination thereof. In certain embodiments, each of $R^{2A}$, $R^{2B}$, $R^{2C}$, $R^{2D}$, $R^{2E}$, $R^{2F}$, $R^{2G}$, $R^{3A}$ and $R^{3B}$ can be independently selected from the group consisting of, but not limited to, hydrogen, deuterium, alkyl, aryl, cyano, amino, sulfide, aldehyde, ester, ether, acid, hydroxyl, and halide. $R^{4A}$ and $R^{4B}$ can be independently selected from the group consisting of, but not limited to, hydrogen, deuterium, alkyl, aryl, acetyl, hydroxyl and phenyl. In certain embodiments, each of $R^{5A}$ and $R^{5B}$ can be independently selected from the group consisting of, but not limited to, phenyl, alkyl-substituted phenyl, alkyl-substituted fluorenyl, alkyl-substituted carbazolyl, alkyl-substituted triphenylaminyl, and alkyl-substituted thiophenyl. Alkyl substituted phenyl can include 2-alkylphenyl, 3-alkylphenyl, 4-alkylphenyl, 2,4-dialkylphenyl, 3,5-dialkylphenyl, and 3,4-dialkylphenyl. Alkyl-substituted fluorenyl can include 9,9-dialkyl-substituted fluorenyl, 7-alkyl-9,9-dialkyl-substituted fluorenyl and 6-alkyl-9,9-dialkyl-substituted fluorenyl. Alkyl-substituted carbazolyl can include N-alkyl-substituted carbazolyl, 6-alkyl-substituted carbazolyl and 7-alkyl-substituted carbazolyl. Alkyl-substituted thiophenyl can include 2-alkylthiophenyl, 3-alkylthiophenyl, and 4-alkylthiophenyl. The alkyl substituents can include $C_nH_{2n+1}$ or $C_nF_{2n+1}$ or —$CH_2CH_2[OCH_2CH_2]_n$—$OCH_3$, wherein n is 1 to 20. In some embodiments, n can be between 1 to 50 or higher. In certain embodiments, each of $R^{6A}$ and $R^{6B}$ can be independently selected from the group consisting of, but not limited to, alkyl, phenyl, and alkyl-substituted phenyl. Alkyl substituted phenyl can include 2-alkylphenyl, 3-alkylphenyl, 4-alkylphenyl, 2,4-dialkylphenyl, 3,5-dialkylphenyl, and 3,4-dialkylphenyl. The alkyl substituents can include $C_nH_{2n+1}$, or $C_nF_{2n+1}$ or —$CH_2CH_2[OCH_2CH_2]_n$—$OCH_3$, wherein n is 1 to 20. In some embodiments, n can be between 1 to 50 or higher.

Figure 11C:
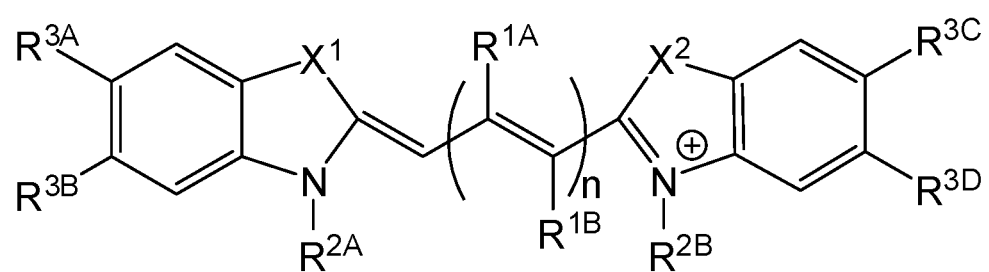
Figure 11C:
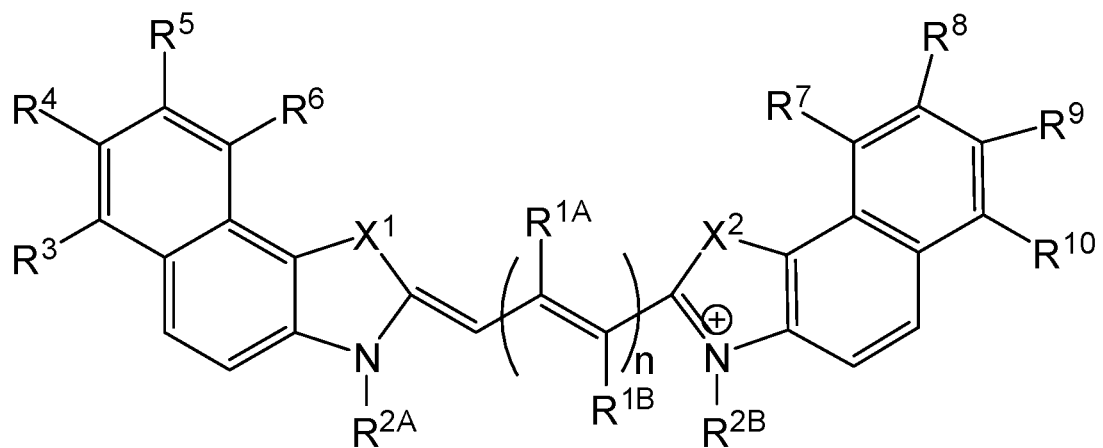

FIG. 11C shows another set of example cyanine derivatives that can be used as a narrow band monomer in the present invention. The narrow-band monomer can be integrated into a backbone of the polymer (e.g., by copolymerizing in the polymer) and/or attached by covalent attachment to the backbone, a terminus, or a sidechain of the polymer through at least one attachment to $R^{1A}$, $R^{1B}$, $R^{2A}$, $R^{2B}$, $R^{3A}$, $R^{3B}$ or a combination thereof. Each of $X^1$ and $X^2$ can include, but is not limited to, oxygen, sulfur, selenium, and —$C(CH_3)_2$. In certain embodiments, each of $R^{1A}$, $R^{1B}$, $R^{2A}$, $R^{2B}$, $R^3$, $R^{3A}$, $R^{3B}$, $R^4$, $R^5$, $R^6$, $R^7$, $R^8$, $R^9$ and $R^{10}$ can be independently selected from the group consisting of, but not limited to, hydrogen, deuterium, alkyl, aryl, cyano, amino, sulfide, aldehyde, ester, ether, acid, hydroxyl, and halide. The alkyl substituents can include $C_nH_{2n+1}$ or $C_nF_{2n+1}$ or —$CH_2CH_2[OCH_2CH_2]_n$—$OCH_3$, wherein n is 1 to 20. In some embodiments, n can be between 1 to 50 or higher.

Figure 11D:
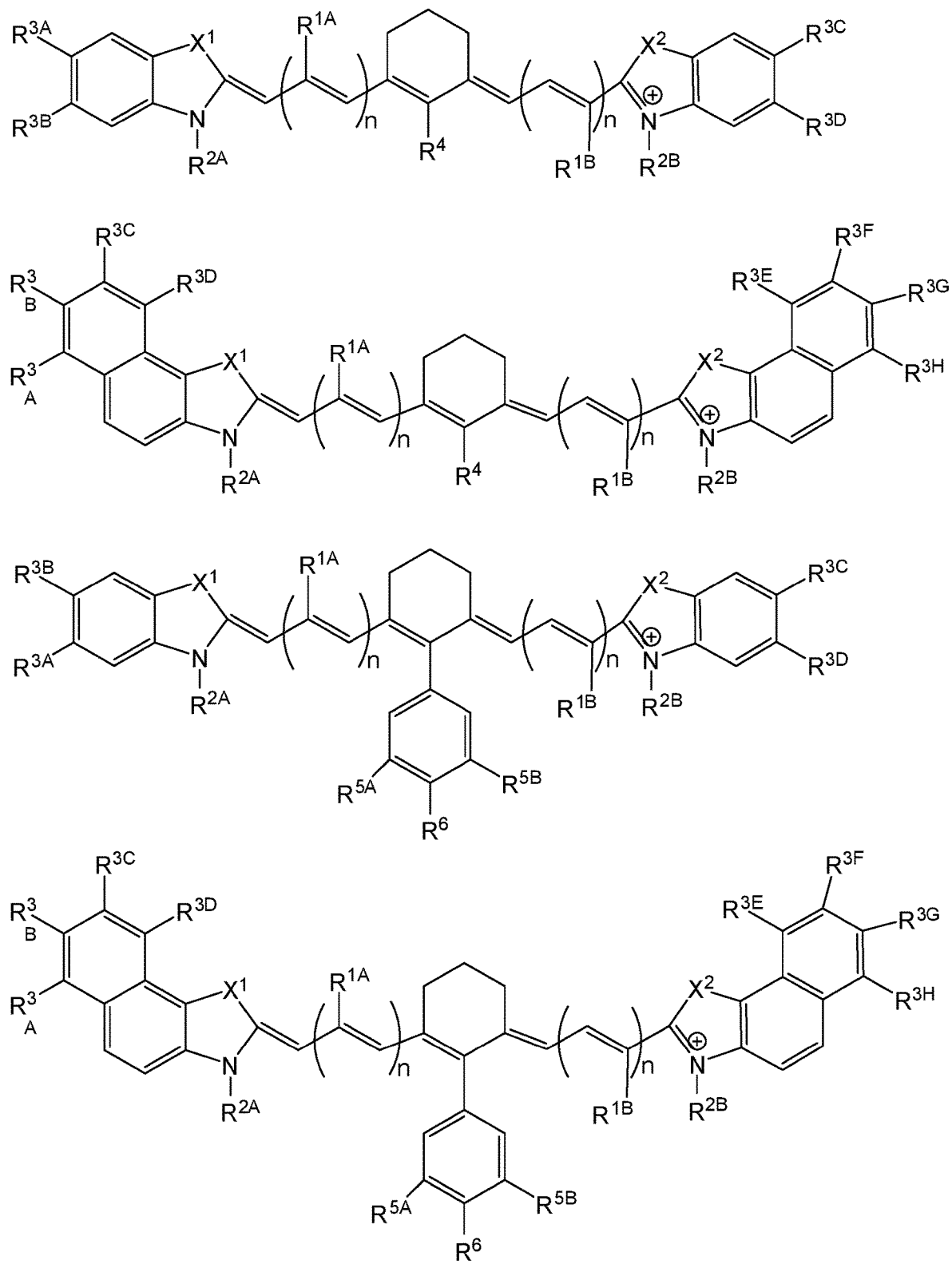

FIG. 11D shows another set of example cyanine derivatives that can be used as a narrow band monomer in the present invention. The narrow-band monomer can be integrated into a backbone of the polymer (e.g., by copolymerizing in the polymer) and/or attached by covalent attachment to the backbone, a terminus, or a sidechain of the polymer through at least one attachment to $R^{1A}$, $R^{1B}$, $R^{2A}$, $R^{2B}$, $R^{3A}$, $R^{3B}$, $R^{3C}$, $R^{3D}$, $R^4$, $R^{5A}$, $R^{5B}$, $R^6$, or a combination thereof. Each of $X^1$ and $X^2$ can include, but is not limited to, oxygen, sulfur, selenium, and —$C(CH_3)_2$. In certain embodiments, each of $R^{1A}$, $R^{1B}$, $R^{2A}$, $R^{2B}$, $R^{3A}$, $R^{3B}$, $R^{3C}$ and $R^{3D}$ can be independently selected from the group consisting of, but not limited to, hydrogen, deuterium, alkyl, aryl, cyano, amino, sulfide, aldehyde, ester, ether, acid, hydroxyl, and halide. In certain embodiments, $R^4$ can be independently selected from the group consisting of, but not limited to, hydrogen, deuterium, alkyl, aryl, cyano, amino, sulfide, aldehyde, ester, ether, acid, hydroxyl, and halide. In certain embodiments, each of $R^{5A}$ and $R^{5B}$ can be independently selected from the group consisting of, but not limited to, hydrogen, deuterium, alkyl, cyano, amino, sulfide, aldehyde, ester, ether, acid, hydroxyl, halide, phenyl, alkyl-substituted phenyl, alkyl-substituted fluorenyl, alkyl-substituted carbazolyl, alkyl-substituted triphenylaminyl, and alkyl-substituted thiophenyl. Alkyl substituted phenyl can include 2-alkylphenyl, 3-alkylphenyl, 4-alkylphenyl, 2,4-dialkylphenyl, 3,5-dialkylphenyl, and 3,4-dialkylphenyl. Alkyl-substituted fluorenyl can include 9,9-dialkyl-substituted fluorenyl, 7-alkyl-9,9-dialkyl-substituted fluorenyl and 6-alkyl-9,9-dialkyl-substituted fluorenyl. Alkyl-substituted carbazolyl can include N-alkyl-substituted carbazolyl, 6-alkyl-substituted carbazolyl and 7-alkyl-substituted carbazolyl. Alkyl-substituted thiophenyl can include 2-alkylthiophenyl, 3-alkylthiophenyl, and 4-alkylthiophenyl. The alkyl substituents can include $C_nH_{2n+1}$, or $C_nF_{2n+1}$ or —$CH_2CH_2[OCH_2CH_2]_n$—$OCH_3$, wherein n is 1 to 20. In some embodiments, n can be between 1 to 50 or higher. In certain embodiments, $R^6$ can be selected from the group consisting of, but not limited to, hydrogen, deuterium, alkyl, cyano, amino, sulfide, aldehyde, ester, ether, acid, hydroxyl, halide, phenyl, alkyl-substituted phenyl, alkyl-substituted fluorenyl, alkyl-substituted carbazolyl, alkyl-substituted triphenylaminyl, and alkyl-substituted thiophenyl. Alkyl substituted phenyl can include 2-alkylphenyl, 3-alkylphenyl, 4-alkylphenyl, 2,4-dialkylphenyl, 3,5-dialkylphenyl, and 3,4-dialkylphenyl. Alkyl-substituted fluorenyl can include 9,9-dialkyl-substituted fluorenyl, 7-alkyl-9,9-dialkyl-substituted fluorenyl and 6-alkyl-9,9-dialkyl-substituted fluorenyl. Alkyl-substituted carbazolyl can include N-alkyl-substituted carbazolyl, 6-alkyl-substituted carbazolyl and 7-alkyl-substituted carbazolyl. Alkyl-substituted thiophenyl can include 2-alkylthiophenyl, 3-alkylthiophenyl, and 4-alkylthiophenyl. The alkyl substituents can include $C_nH_{2n+1}$, or $C_nF_{2n+1}$ or —$CH_2CH_2[OCH_2CH_2]_n$—$OCH_3$, wherein n is 1 to 20. In some embodiments, n can be between 1 to 50 or higher.

In some embodiments, the narrow-band emissive polymers for making Pdots can include rhodamine based monomers and their derivatives as narrow-band monomers. Rhodamine based monomers and their derivatives include but are not limited to their alkyl derivatives, aryl derivatives, alkyne derivatives, aromatic derivatives, alkoxide derivatives, aza derivatives, rhodamine extended systems and rhodamine analogues. The narrow-band emissive polymers can also include any other monomers. The rhodamine based monomers can be energy acceptors so that the final Pdots can exhibit narrow-band emissions. The narrow-band emissive chromophoric polymers in good solvents may exhibit broad emissions or narrow emissions. However, their nanoparticle form gives narrow-band emissions. The emission FWHM of the Pdots including rhodamine based monomers and their derivatives as narrow-band monomers is less than 70 nm. In certain embodiments, the FWHM can be less than 60 nm, less than 50 nm, less than 40 nm, less than 30 nm, or less than 20 nm. A variety of other rhodamine derivatives can be used for the present invention. In some embodiments, the chromophoric polymer dots of the present invention can include a polymer that includes a narrow-band monomer having the formula:

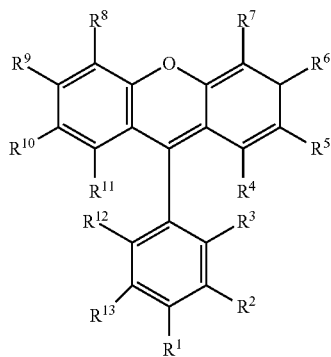

wherein each of $R^1$, $R^2$, $R^3$, $R^4$, $R^5$, $R^6$, $R^7$, $R^8$, $R^9$, $R^{10}$, $R^{11}$, $R^{12}$ and $R^{13}$ can be independently selected from the group consisting of, but not limited to, hydrogen, deuterium, halogen, cyano, nitro, thiocyanate, isothiocyanate, sulfite, carboxyl, amino, sulfide, aldehyde, ester, ether, acid, linear or branched alkyl, hydroxyl alkyl, aralkyl, alkylene, alkenylene, arylene, heteroarylene, phenylene, azulene, cycloalkylene, alkoxy, aryl, alkyl ketone, alkylester, arylester, amide, fluoroalkyl, fluoroaryl, and polyalkalene (e.g, mehtoxyethoxyethoxy, ethoxyethoxy, and —(OCH$_2$CH$_2$)$_n$OH, n=1-50), phenyl, alkyl-(alkoxy-, aryl-, fluoroalkyl-, fluoroaryl-)substituted phenyl, pyridyl, alkyl-(alkoxy-, aryl-, fluoroalkyl-, fluoroaryl-)substituted pyridyl, bipyridyl, alkyl-(alkoxy-, aryl-, fluoroalkyl-, fluoroaryl-)substituted bipyridyl tripyridyl, alkyl-(alkoxy-, aryl-, fluoroalkyl-, fluoroaryl-)substituted tripyridyl, furyl, alkyl-(alkoxy-, aryl-, fluoroalkyl-, fluoroaryl-)substituted furyl, thienyl, alkyl-(alkoxy-, aryl-, fluoroalkyl-, fluoroaryl-)substituted thienyl, pyrrolyl, alkyl-(alkoxy-, aryl-, fluoroalkyl-, fluoroaryl-)substituted pyrrolyl, pyrazolyl, alkyl-(alkoxy-, aryl-, fluoroalkyl-, fluoroaryl-)substituted pyrazolyl, oxazolyl, alkyl-(alkoxy-, aryl-, fluoroalkyl-, fluoroaryl-)substituted oxazolyl, thiazolyl, alkyl-(alkoxy-, aryl-, fluoroalkyl-, fluoroaryl-)substituted thiazolyl, imidazolyl, alkyl-(alkoxy-, aryl-, fluoroalkyl-, fluoroaryl-)substituted imidazolyl, pyrazinyl, alkyl-(alkoxy-, aryl-, fluoroalkyl-, fluoroaryl-) substituted pyrazinyl, benzooxadizolyl, alkyl-(alkoxy-, aryl-, fluoroalkyl-, fluoroaryl-)substituted benzooxadizolyl, benzothiadizolyl, alkyl-(alkoxy-, aryl-, fluoroalkyl-, fluoro-aryl-)substituted benzothiadizolyl, fluorenyl, alkyl-(alkoxy-, aryl-, fluoroalkyl-, fluoroaryl-)substituted fluorenyl, triphenylaminyl-substituted fluorenyl, diphenylaminyl-substituted fluorenyl, alkyl-substituted carbazolyl, alkyl-substituted triphenylaminyl and alkyl-substituted thiophenyl. As exemplary embodiments, alkyl substituted phenyl can include 2-alkylphenyl, 3-alkylphenyl, 4-alkylphenyl, 2,4-dialkylphenyl, 3,5-dialkylphenyl, 3,4-dialkylphenyl; alkyl-substituted fluorenyl can include 9, 9-dialkyl-substituted fluorenyl, 7-alkyl-9,9-dialkyl-substituted fluorenyl, 6-alkyl-9,9-dialkyl-substituted fluorenyl, 7-triphenylaminyl-9,9-dialkyl-substituted fluorenyl and 7-diphenylaminyl-9,9-dialkyl-substituted fluorenyl; alkyl-substituted carbazolyl can include N-alkyl-substituted carbazolyl, 6-alkyl-substituted carbazolyl and 7-alkyl-substituted carbazolyl; alkyl-substituted triphenylaminyl can include 4'-alkyl-substituted triphenylaminyl, 3'-alkyl-substituted triphenylaminyl, 3',4'-dialkyl-substituted triphenylaminyl and 4',4"-alkyl-substituted triphenylaminyl; alkyl-substituted thiophenyl can include 2-alkylthiophenyl, 3-alkylthiophenyl, and 4-alkylthiophenyl. The alkyl substituents can include $C_nH_{2n+1}$ or $C_nF_{2n+1}$ or —CH$_2$CH$_2$[OCH$_2$CH$_2$]$_n$—OCH$_3$, wherein n is 1 to 20. In some embodiments, n can be between 1 to 50 or higher. The narrow-band monomer can be integrated into a backbone of the polymer (e.g., by copolymerizing in the polymer) and/or attached by covalent attachment to the backbone, a terminus, or a sidechain of the polymer through at least one attachment to $R^1$, $R^2$, $R^3$, $R^4$, $R^5$, $R^6$, $R^7$, $R^8$, $R^9$, $R^{10}$, $R^{11}$, $R^{12}$ and $R^{13}$ or a combination thereof.

In some embodiments, the narrow-band emissive polymers for making Pdots include coumarin based monomers and their derivatives as narrow-band monomers. Coumarin based monomers and their derivatives include but are not limited to their alkyl derivatives, aryl derivatives, alkyne derivatives, aromatic derivatives, alkoxide derivatives, aza derivatives, coumarin extended systems and coumarin analogues. The narrow-band emissive polymers can also include any other monomers. The coumarin based monomers can be energy acceptors so that the final Pdots can exhibit narrow-band emissions. The narrow-band emissive chromophoric polymers in good solvents may exhibit broad emissions or narrow emissions. However, their nanoparticle form gives narrow-band emissions. The emission FWHM of the Pdots including coumarin based monomers and their derivatives is less than 70 nm. In certain embodiments, the FWHM is less than 60 nm, less than 50 nm, less than 40 nm, less than 30 nm, or less than 20 nm. A variety of other coumarin derivatives can be used for the present invention. In some embodiments, the chromophoric polymer dots of the present invention can include a polymer that includes a narrow-band monomer having the formula:

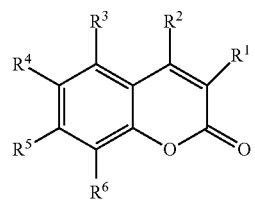

wherein each of $R^1$, $R^2$, $R^3$, $R^4$, $R^5$, $R^6$, and $R^7$ is independently selected from the group consisting of, but not limited to, hydrogen, deuterium, halogen, cyano, nitro, thiocyanate, isothiocyanate, sulfite, carboxyl, amino, sulfide, aldehyde, ester, ether, acid, direct or branched alkyl, hydroxyl alkyl, aralkyl, alkylene, alkenylene, arylene, heteroarylene, phenylene, azulene, cycloalkylene, alkoxy, aryl, alkyl ketone, alkylester, arylester, amide, fluoroalkyl, fluoroaryl, and polyalkalene (e.g, mehtoxyethoxyethoxy, ethoxyethoxy, and —(OCH$_2$CH$_2$)$_n$OH, n=1-50), phenyl, alkyl-(alkoxy-, aryl-, fluoroalkyl-, fluoroaryl-)substituted phenyl, pyridyl, alkyl-(alkoxy-, aryl-, fluoroalkyl-, fluoroaryl-)substituted pyridyl, bipyridyl, alkyl-(alkoxy-, aryl-, fluoroalkyl-, fluoroaryl-)substituted bipyridyl tripyridyl, alkyl-(alkoxy-, aryl-, fluoroalkyl-, fluoroaryl-)substituted tripyridyl, furyl, alkyl-(alkoxy-, aryl-, fluoroalkyl-, fluoroaryl-)substituted furyl, thienyl, alkyl-(alkoxy-, aryl-, fluoroalkyl-, fluoroaryl-)substituted thienyl, pyrrolyl, alkyl-(alkoxy-, aryl-, fluoroalkyl-, fluoroaryl-)substituted pyrrolyl, pyrazolyl, alkyl-(alkoxy-, aryl-, fluoroalkyl-, fluoroaryl-)substituted pyrazolyl, oxazolyl, alkyl-(alkoxy-, aryl-, fluoroalkyl-, fluoroaryl-)substituted oxazolyl, thiazolyl, alkyl-(alkoxy-, aryl-, fluoroalkyl-, fluoroaryl-)substituted thiazolyl, imidazolyl, alkyl-(alkoxy-, aryl-, fluoroalkyl-, fluoroaryl-)substituted imidazolyl, pyrazinyl, alkyl-(alkoxy-, aryl-, fluoroalkyl-, fluoroaryl-)substituted pyrazinyl, benzooxadizolyl, alkyl-(alkoxy-, aryl-, fluoroalkyl-, fluoroaryl-)substituted benzooxadizolyl, benzothiadizolyl, alkyl-(alkoxy-, aryl-, fluoroalkyl-, fluoroaryl-)substituted benzothiadizolyl, fluorenyl, alkyl-(alkoxy-, aryl-, fluoroalkyl-, fluoroaryl-)substituted fluorenyl, triphenylaminyl-substituted fluorenyl, diphenylaminyl-substituted fluorenyl, alkyl-substituted carbazolyl, alkyl-substituted triphenylaminyl and alkyl-substituted thiophenyl. As exemplary embodiments, alkyl substituted phenyl can include 2-alkylphenyl, 3-alkylphenyl, 4-alkylphenyl, 2,4-dialkylphenyl, 3,5-dialkylphenyl, 3,4-dialkylphenyl; alkyl-substituted fluorenyl can include 9, 9-dialkyl-substituted fluorenyl, 7-alkyl-9,9-dialkyl-substituted fluorenyl, 6-alkyl-9,9-dialkyl-substituted fluorenyl, 7-triphenylaminyl-9,9-dialkyl-substituted fluorenyl and 7-diphenylaminyl-9,9-dialkyl-substituted fluorenyl; alkyl-substituted carbazolyl can include N-alkyl-substituted carbazolyl, 6-alkyl-substituted carbazolyl and 7-alkyl-substituted carbazolyl; alkyl-substituted triphenylaminyl can include 4'-alkyl-substituted triphenylaminyl, 3'-alkyl-substituted triphenylaminyl, 3',4'-dialkyl-substituted triphenylaminyl and 4',4"-alkyl-substituted triphenylaminyl; alkyl-substituted thiophenyl can include 2-alkylthiophenyl, 3-alkylthiophenyl, and 4-alkylthiophenyl. The alkyl substituents can include C$_n$H$_{2n+1}$ or C$_n$F$_{2n+1}$ or —CH$_2$CH$_2$[OCH$_2$CH$_2$]$_n$—OCH$_3$, wherein n is 1 to 20. In some embodiments, n can be between 1 to 50 or higher. The narrow-band monomer can be integrated into a backbone of the polymer (e.g., by copolymerizing in the polymer) and/or attached by covalent attachment to the backbone, a terminus, or a sidechain of the polymer through at least one attachment R$^1$, R$^2$, R$^3$, R$^4$, R$^5$, and R$^6$, or a combination thereof.

In some embodiments, the narrow-band emissive polymers for making Pdots include xanthene based monomers and their derivatives as narrow-band monomers. Xanthene based monomers and their derivatives include but are not limited to their alkyl derivatives, aryl derivatives, alkyne derivatives, aromatic derivatives, alkoxide derivatives, aza derivatives, xanthene extended systems and xanthene analogues. The narrow-band emissive polymers can also include any other monomers. The xanthene based monomers can be energy acceptors so that the final Pdots can exhibit narrow-band emissions. The narrow-band emissive chromophoric polymers in good solvents may exhibit broad emissions or narrow emissions. However, their nanoparticle form gives narrow-band emissions. The emission FWHM of the Pdots including xanthene based monomers and their derivatives is less than 70 nm. In certain embodiments, the FWHM is less than 60 nm, less than 50 nm, less than 40 nm, less than 30 nm, or less than 20 nm. A variety of other xanthene derivatives can be used for the present invention. In some embodiments, the chromophoric polymer dots of the present invention can include a polymer that includes a narrow-band monomer having the formula:

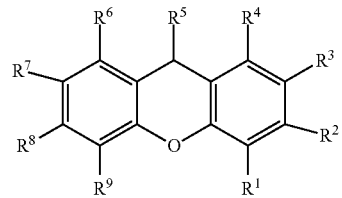

wherein each of R$^1$, R$^2$, R$^3$, R$^4$, R$^5$, R$^6$, R$^7$, R$^8$, and R$^9$ is independently selected from the group consisting of, but not limited to, hydrogen, deuterium, halogen, cyano, nitro, thiocyanate, isothiocyanate, sulfite, carboxyl, amino, sulfide, aldehyde, ester, ether, acid, direct or branched alkyl, hydroxyl alkyl, aralkyl, alkylene, alkenylene, arylene, heteroarylene, phenylene, azulene, cycloalkylene, alkoxy, aryl, alkyl ketone, alkylester, arylester, amide, fluoroalkyl, fluoroaryl, and polyalkalene (e.g., mehtoxyethoxyethoxy, ethoxyethoxy, and —(OCH$_2$CH$_2$)$_n$OH, n=1-50), phenyl, alkyl-(alkoxy-, aryl-, fluoroalkyl-, fluoroaryl-)substituted phenyl, pyridyl, alkyl-(alkoxy-, aryl-, fluoroalkyl-, fluoroaryl-)substituted pyridyl, bipyridyl, alkyl-(alkoxy-, aryl-, fluoroalkyl-, fluoroaryl-)substituted bipyridyl tripyridyl, alkyl-(alkoxy-, aryl-, fluoroalkyl-, fluoroaryl-)substituted tripyridyl, furyl, alkyl-(alkoxy-, aryl-, fluoroalkyl-, fluoroaryl-)substituted furyl, thienyl, alkyl-(alkoxy-, aryl-, fluoroalkyl-, fluoroaryl-)substituted thienyl, pyrrolyl, alkyl-(alkoxy-, aryl-, fluoroalkyl-, fluoroaryl-)substituted pyrrolyl, pyrazolyl, alkyl-(alkoxy-, aryl-, fluoroalkyl-, fluoroaryl-)substituted pyrazolyl, oxazolyl, alkyl-(alkoxy-, aryl-, fluoroalkyl-, fluoroaryl-)substituted oxazolyl, thiazolyl, alkyl-(alkoxy-, aryl-, fluoroalkyl-, fluoroaryl-)substituted thiazolyl, imidazolyl, alkyl-(alkoxy-, aryl-, fluoroalkyl-, fluoroaryl-)substituted imidazolyl, pyrazinyl, alkyl-(alkoxy-, aryl-, fluoroalkyl-, fluoroaryl-)substituted pyrazinyl, benzooxadizolyl, alkyl-(alkoxy-, aryl-, fluoroalkyl-, fluoroaryl-)substituted benzooxadizolyl, benzothiadizolyl, alkyl-(alkoxy-, aryl-, fluoroalkyl-, fluoroaryl-)substituted benzothiadizolyl, fluorenyl, alkyl-(alkoxy-, aryl-, fluoroalkyl-, fluoroaryl-)substituted fluorenyl, triphenylaminyl-substituted fluorenyl, diphenylaminyl-substituted fluorenyl, alkyl-substituted carbazolyl, alkyl-substituted triphenylaminyl and alkyl-substituted thiophenyl. As exemplary embodiments, alkyl substituted phenyl can include 2-alkylphenyl, 3-alkylphenyl, 4-alkylphenyl, 2,4-dialkylphenyl, 3,5-dialkylphenyl, 3,4-dialkylphenyl; alkyl-substituted fluorenyl can include 9, 9-dialkyl-substituted fluorenyl, 7-alkyl-9,9-dialkyl-substituted fluorenyl, 6-alkyl-9,9-dialkyl-substituted fluorenyl, 7-triphenylaminyl-9,9-dialkyl-substituted fluorenyl and 7-diphenylaminyl-9,9-dialkyl-substituted fluorenyl; alkyl-substituted carbazolyl can include N-alkyl-substituted carbazolyl, 6-alkyl-substituted carbazolyl and 7-alkyl-substituted carbazolyl; alkyl-substituted triphenylaminyl can include 4'-alkyl-substituted triphenylaminyl, 3'-alkyl-substituted triphenylaminyl, 3',4'-dialkyl-substituted triphenylaminyl and 4',4"-alkyl-substituted triphenylaminyl; alkyl-substituted thiophenyl can include 2-alkylthiophenyl, 3-alkylthiophenyl, and 4-alkylthiophenyl. The alkyl substituents can include C$_n$H$_{2n+1}$ or C$_n$F$_{2n+1}$ or —CH$_2$CH$_2$

[OCH$_2$CH$_2$]$_n$—OCH$_3$, wherein n is 1 to 20. In some embodiments, n can be between 1 to 50 or higher. The narrow-band monomer can be integrated into a backbone of the polymer (e.g., by copolymerizing in the polymer) and/or attached by covalent attachment to the backbone, a terminus, or a sidechain of the polymer through at least one attachment to R$^1$, R$^2$, R$^3$, R$^4$, R$^5$, R$^6$, R$^7$, R$^8$, and R$^9$ or a combination thereof.

In some embodiments, these narrow-band emissive monomers can be incorporated into the backbone of the conventional semiconducting polymer to obtain narrow-band emissive polymers. In this embodiment, the narrow-band emissive monomers can be copolymerized with other monomers such as fluorene monomer, phenylene vinylene monomer, phenylene monomer, benzothiadiazole monomer, thiophene monomer, carbazole monomer, and any other monomers to form narrow-band emissive polymers. In some embodiments, the narrow-band emissive units can be chemically linked to the side chains of the conventional semiconducting polymer to obtain narrow-band emissive polymers. In this embodiment, conventional luminescent semiconducting polymers include, but are not limited to fluorene polymers, phenylene vinylene polymers, phenylene polymers, benzothiadiazole polymers, thiophene polymers, carbazole fluorene polymers and their copolymers, and any other conventional semiconducting polymers.

In some embodiments, the ratio of the narrow-band monomers in the backbone (or the narrow-band emissive units in the side-chains) relative to other monomers in the polymer can be adjusted to obtain narrow-band emissive Pdots. As provided further herein, the ratios can be described a variety of ways that will be understood by one of ordinary skill in the art. For example, monomers in a polymer of the present invention can be identified as x and 1−x or x, y and z in which x+y+z=1. Alternatively, the ratios can be described as X and Y, in which the ratio can be X/(X+Y). In another way, the ratio can be identified with respect to the number of monomers (n) in a polymer (e.g., one monomer can be 0.02n, a second monomer can be 0.45n, a third monomer can be 0.03n, and a fourth monomer can be 0.5n). In some embodiments, the ratio of the narrow-band emissive monomer to other monomer is 1:1000. In some embodiments, the ratio of the narrow-band emissive monomer to other monomer is 1:500. In some embodiments, the ratio of the narrow-band emissive monomer to other monomer is 1:100. In some embodiments, the ratio of the narrow-band emissive monomer to other monomer is 1:90. In some embodiments, the ratio of the narrow-band emissive monomer to other monomer is 1:80. In some embodiments, the ratio of the narrow-band emissive monomer to other monomer is 1:70. In some embodiments, the ratio of the narrow-band emissive monomer to other monomer is 1:60. In some embodiments, the ratio of the narrow-band emissive monomer to other monomer is 1:50. In some embodiments, the ratio of the narrow-band emissive monomer to other monomer is 1:45. In some embodiments, the ratio of the narrow-band emissive monomer to other monomer is 1:40. In some embodiments, the ratio of the narrow-band emissive monomer to other monomer is 1:35. In some embodiments, the ratio of the narrow-band emissive monomer to other monomer is 1:30. In some embodiments, the ratio of the narrow-band emissive monomer to other monomer is 1:25. In some embodiments, the ratio of the narrow-band emissive monomer to other monomer is 1:20. In some embodiments, the ratio of the narrow-band emissive monomer to other monomer is 1:15. In some embodiments, the ratio of the narrow-band emissive monomer to other monomer is 1:10, 1:9, 1:8, 1:7, 1:6, 1:5, 1:4, 1:3, 1:2, 1:1, 1:0.5, 1:0.1, or higher. A variety of ratios can be optimized to obtain narrow-band emission depending on the monomers used. In certain embodiments, the ratio of the narrow-band monomer to the general monomer is less than about 1:1, less than about 0.8:1, less than about 0.6:1, less than about 0.5:1, less than about 0.4:1, less than about 0.3:1, less than about 0.2:1, less than about 0.1:1, less than about 0.08:1, less than about 0.06:1, less than about 0.04:1, or less than about 0.02:1. Example 1 and FIG. 13 describe an example approach to obtain narrow-band emission by adjusting the concentration of narrow-band monomers.

In some embodiments, the narrow-band emissive polymers (i.e. polymers comprising narrow-band monomers) may have narrow-band emissions in a good solvent, such as some hydrophobic polymer in tetrahydrofuran solution. After forming these polymers into Pdot nanoparticles in water, the Pdot also exhibit narrow-band emission. In this embodiment, the nanoparticle formation does not cause obvious change of the emission bandwidth. In some embodiments, the FWHM of the Pdot emission in water is less than about 70 nm. In some embodiments, the FWHM of the Pdot emission in water is less than about 60 nm. In some embodiments, the FWHM of the Pdot emission in water is less than about 50 nm. In some embodiments, the FWHM of the Pdot emission in water is less than about 45 nm. In some embodiments, the FWHM of the Pdot emission in water is less than about 40 nm. In some embodiments, the FWHM is less than about 35 nm, 30 nm, 25 nm, 24 nm, 23 nm, 22 nm, 21 nm, 20 nm, 19 nm, 18 nm, 17 nm, 16 nm, 15 nm, 14 nm, 13 nm, 12 nm, 11 nm, 10 nm, or less.

In some embodiments, the narrow-band emissive polymers (i.e. polymers comprising narrow-band monomers) may exhibit broad-band emissions in a good solvent, such as some hydrophobic polymer in tetrahydrofuran solution. However, after forming these polymers into Pdot nanoparticles in water, the Pdots exhibit narrow-band emissions. In a good solvent, hydrophobic semiconducting polymers typically adopt an extended rod-like conformation, and the inter-chain energy transfer is not efficient. When the polymers are densely packed into a compact nanoparticle, because intra-particle energy transfer and inter-chain energy transfer are much more efficient in the nanoparticle form, therefore the resulting Pdots have narrow-band emissions. Example 3 and 4, FIGS. 15 and 16 describe examples of synthesis and design of such polymers and Pdots. In some embodiments, the FWHM of the Pdot emission in water is less than about 70 nm. In some embodiments, the FWHM of the Pdot emission in water is less than about 60 nm. In some embodiments, the FWHM of the Pdot emission in water is less than about 50 nm. In some embodiments, the FWHM of the Pdot emission in water is less than about 45 nm. In some embodiments, the FWHM of the Pdot emission in water is less than about 40 nm. In some embodiments, the FWHM of the Pdot emission is less than about 35 nm, 30 nm, 25 nm, 24 nm, 23 nm, 22 nm, 21 nm, 20 nm, 19 nm, 18 nm, 17 nm, 16 nm, 15 nm, 14 nm, 13 nm, 12 nm, 11 nm, 10 nm, or less.

In some embodiments, the narrow-band emissive polymers (i.e. polymers comprising narrow-band monomers) may have narrow-band emissions in a good solvent, such as some hydrophobic polymer in toluene solution. After forming these polymers into Pdot nanoparticles in water using nanoprecipitation, however, the Pdots exhibit broad-band emissions because of the complex backbone folding behaviors, disordered morphologies and chain aggregation. In this embodiment, the narrow-band Pdots may be prepared using the miniemulsion method that may maintain the narrow emission from the polymer. In some embodiments, the emission FWHM of the Pdot formed by miniemulsion is less than about 70 nm. In some embodiments, the emission FWHM in water is less than about 60 nm. In some embodiments, the emission FWHM in water is less than about 50 nm. In some embodiments, the emission FWHM in water is less than about 45 nm. In some embodiments, the emission FWHM in water is less than about 40 nm. In some embodiments, the emission FWHM in water is less than about 35 nm, 30 nm, 25 nm, 24 nm, 23 nm, 22 nm, 21 nm, 20 nm, 19 nm, 18 nm, 17 nm, 16 nm, 15 nm, 14 nm, 13 nm, 12 nm, 11 nm, 10 nm, or less.

In some embodiments, the narrow-band emissive chromophoric polymer dots can include narrow-band emissive polymers physically blended or chemically cross-linked with conventional broad-band semiconducting polymers. In some embodiments, the conventional semiconducting polymer may have energy transfer to the narrow-band emissive polymers so that the final Pdots have narrow-band emissions. In some embodiments, the narrow-band emissive polymers can be chemically cross-linked with two or more broad-band polymers (FIG. 31A). The broad-band polymers can be energy donors and the narrow-band emissive polymer can be energy acceptors. Multi-step energy transfer occurs from the broad-band polymer to the narrow-band emissive polymer so that the polymer dots give narrow-band emissions. The chemical cross-linking between polymers can use the functional reactive groups such as haloformyl, hydroxyl, aldehyde, alkenyl, alkynyl, anhydride, carboxamide, amines, azo compound, carbonate, carboxylate, carboxyl, cyanates, ester, haloalkane, imine, isocyanates, nitrile, nitro, phosphino, phosphate, phosphate, pyridyl, sulfonyl, sulfonic acid, sulfoxide, thiol groups. These functional groups can be attached to the side chains and/or the terminus of each polymer chain.

The concentration of the narrow-band emissive polymers relative to broad-band semiconducting polymers can be adjusted to maximize the fluorescence performance of the narrow-band emissive Pdots, such as narrow emission FWHM, high fluorescence quantum yield, desirable fluorescence lifetime etc. In some embodiments, the FWHM of the Pdot emission is less than about 70 nm. In some embodiments, the FWHM of the Pdot emission is less than about 60 nm. In some embodiments, the FWHM of the Pdot emission is less than about 50 nm. In some embodiments, the FWHM of the Pdot emission is less than about 45 nm. In some embodiments, the FWHM of the Pdot emission is less than about 40 nm. In some embodiments, the FWHM of the Pdot emission is less than about 35 nm, 30 nm, 25 nm, 24 nm, 23 nm, 22 nm, 21 nm, 20 nm, 19 nm, 18 nm, 17 nm, 16 nm, 15 nm, 14 nm, 13 nm, 12 nm, 11 nm, 10 nm, or less.

In some embodiments, the narrow-band emissive chromophoric polymer dots can include conventional broad-band semiconducting polymers chemically cross-linked with other narrow-band emissive species. The narrow-band emissive species include but are not limited to small organic dye molecules, metal complexes, metal clusters, lanthanide complexes. In some embodiments, the semiconducting polymer may have energy transfer to the narrow-band emissive species so that the final Pdots have narrow-band emissions. The concentration of the narrow-band emissive species relative to semiconducting polymers can be adjusted to maximize the fluorescence performance of the narrow-band emissive Pdots, such as narrow emission FWHM, high fluorescence quantum yield, desirable fluorescence lifetime etc. In some embodiments, the FWHM of the Pdot emission is less than about 70 nm. In some embodiments, the FWHM of the Pdot emission is less than about 60 nm. In some embodiments, the FWHM of the Pdot emission is less than about 50 nm. In some embodiments, the FWHM of the Pdot emission is less than about 45 nm. In some embodiments, the FWHM of the Pdot emission is less than about 40 nm. In some embodiments, the FWHM of the Pdot emission is less than about 35 nm, 30 nm, 25 nm, 24 nm, 23 nm, 22 nm, 21 nm, 20 nm, 19 nm, 18 nm, 17 nm, 16 nm, 15 nm, 14 nm, 13 nm, 12 nm, 11 nm, 10 nm, or less.

Figure 26:
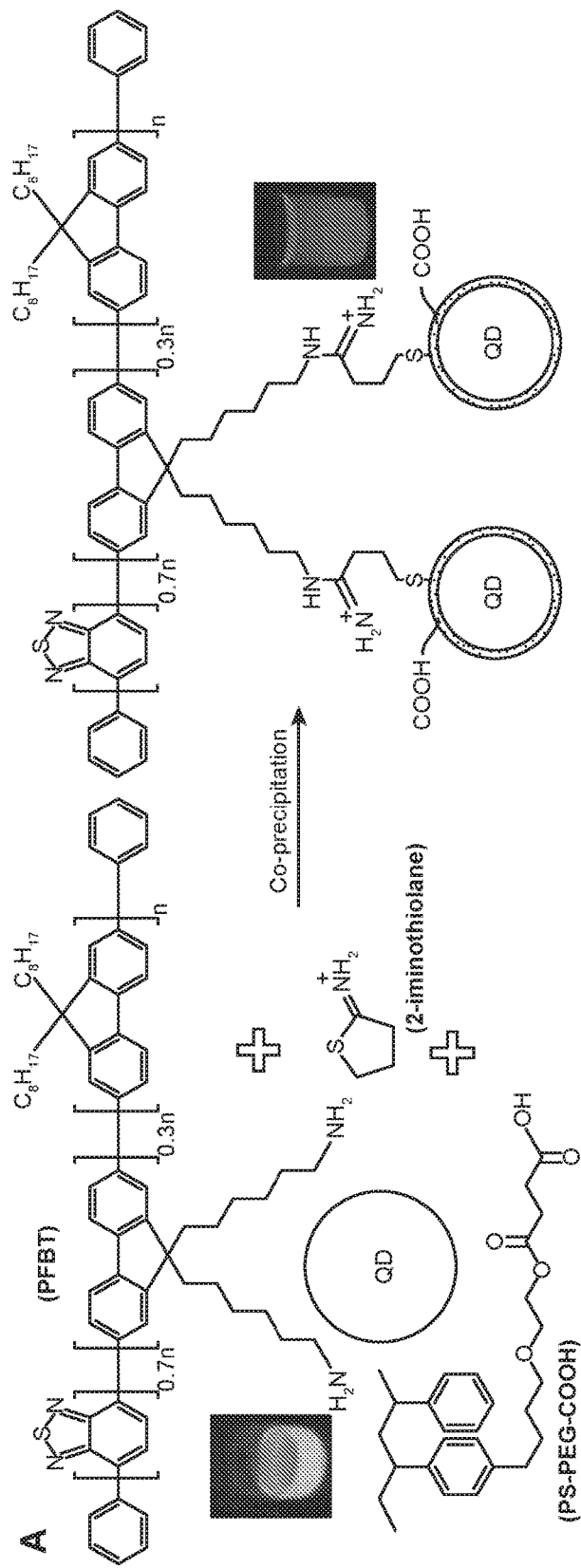
FIG. 26A shows the scheme for the preparation of Pdot-Qdot hybrid NPs. PFBT with amino terminal groups was converted to thiols first in order to covalently bind to the surfaces of QD. Then Pdot-Qdot mixtures were mixed well with PS-PEG-COOH in THF following the nanoprecipitation in water under vigorous sonication to make QD-embedded Pdots.
FIG. 26B shows TEM images of Pdot-Qdot nanocomposites. The inset in the upper-left corner shows the enlarged view of single Pdot-Qdot nanocomposites. The blue and white scale bars represent 20 nm and 2 nm, respectively.
FIG. 26C shows DLS measurements of the hydrodynamic diameters of Pdot-Qdot NPs.
Figure 26:
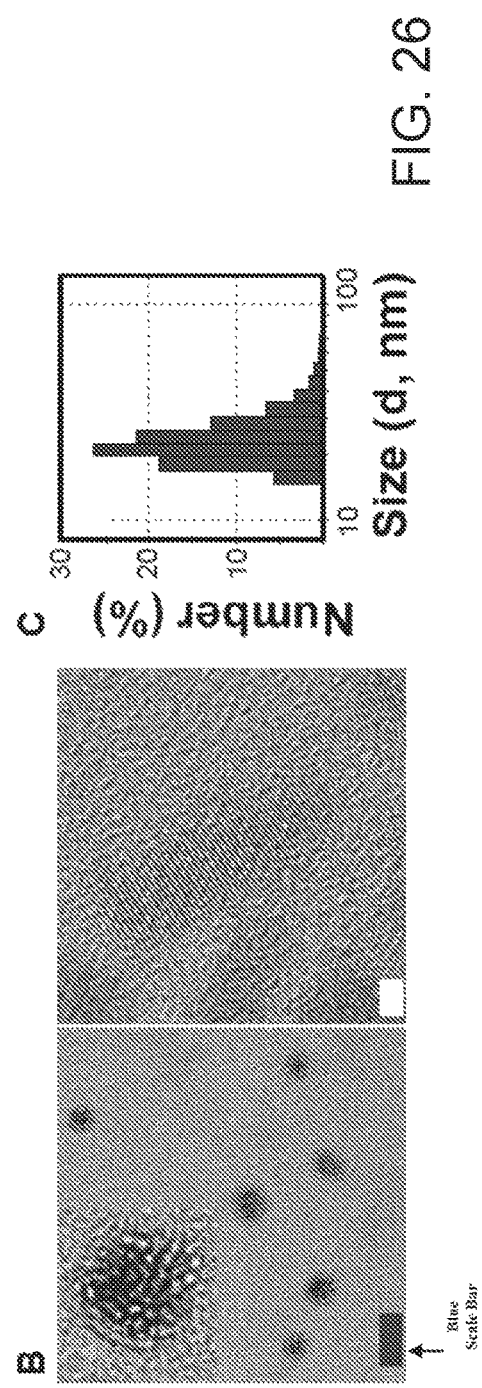
Figure 27:
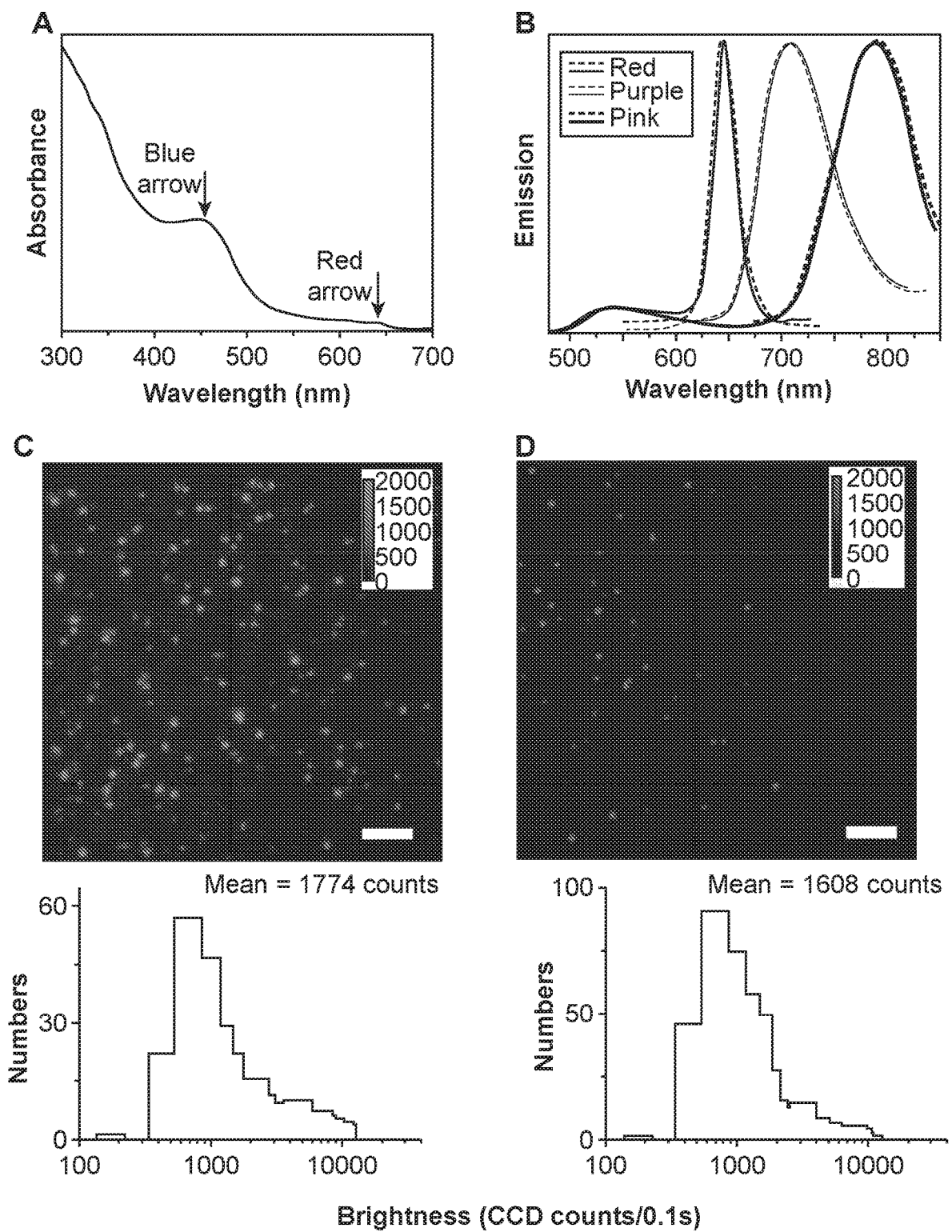
FIG. 27A shows UV-visible spectrum of Pdot-Qdot NPs in water.
FIG. 27B shows emission spectra of the Pdot-Qdot nanocomposites (solid lines). Dashed spectra show emission from QD655 (red), QD705 (purple), and QD800 (pink) in decane.
FIG. 27C shows single-particle fluorescence images of PFBT-DBT Pdots (upper graph) and the corresponding intensity distribution histograms (bottom graph).
FIG. 27D shows single-particle fluorescence images of PFBT-QD655 Pdots (upper graph) and the corresponding intensity distribution histograms (bottom graph). The scale bars are 4 μm.

In a particular embodiment, the narrow-band emissive chromophoric polymer dots can include polymer dots embedded with inorganic quantum dots. In some embodiments, the semiconducting polymer may have energy transfer to the quantum dots so that the final composite Pdots have narrow-band emissions. Example 9 and FIGS. 26-28 describe the Pdots embedded with inorganic quantum dots to obtain narrow-band emission. The concentration of the quantum dots relative to semiconducting polymers can be adjusted to maximize the fluorescence performance of the narrow-band emissive Pdots, such as narrow emission FWHM, high fluorescence quantum yield, etc. In some embodiments, the FWHM of the composite Pdot emission is less than about 70 nm. In some embodiments, the FWHM of the composite Pdot emission is less than about 60 nm. In some embodiments, the FWHM of the composite Pdot emission is less than about 50 nm. In some embodiments, the FWHM of the composite Pdot emission is less than about 45 nm. In some embodiments, the FWHM of the composite Pdot emission is less than about 40 nm. In some embodiments, the FWHM of the composite Pdot emission is less than about 35 nm, 30 nm, 25 nm, 24 nm, 23 nm, 22 nm, 21 nm, 20 nm, 19 nm, 18 nm, 17 nm, 16 nm, 15 nm, 14 nm, 13 nm, 12 nm, 11 nm, 10 nm, or less.

In some embodiments, the narrow-band emissive chromophoric polymer dot includes narrow-band emissive chromophoric polymer chemically cross-linked with small organic dye molecules, metal complexes, and any combinations thereof. These dyes or metal complexes may have sensing functions, such as oxygen sensing capability, ion sensing capability, glucose sensing capability, neurotransmitter sensing capability, drug sensing capability, metabolite sensing capability, protein sensing capability, signaling molecule sensing capability, toxin sensing capability, DNA and RNA sensing capability, and the like.

In some embodiments, the narrow-band emissive chromophoric polymer dot may also include narrow-band emissive semiconducting polymer, physically mixed or chemically cross-linked with other components including, e.g. inorganic luminescent materials, to tune emission color, improve quantum yield and photostability, and the like.

Functionalization and Bioconjugates of Chromophoric Polymers Dots with Narrow-Band Emissions In some embodiments, this invention provides narrow-band emissive Pdots functionalized with a functional group. As used herein the term "functional group" refers to any chemical unit that can be attached, such as by any stable physical or chemical association, to the chromophoric polymer dot, thereby rendering the surface of the chromophoric polymer dot available for conjugation or bioconjugation. In some embodiments, functional groups can be hydrophobic functional groups. Examples of hydrophobic functional groups include but not limited to alkyne, strained alkyne, azide, diene, alkene, cyclooctyne, and phosphine groups (for click chemistry). In some embodiments, functional groups can be hydrophilic functional groups. Examples of hydrophilic functional groups include but not limited to carboxylic acid or salts thereof, amino, mercapto, azido, diazo, aldehyde, ester, hydroxyl, carbonyl, sulfate, sulfonate, phosphate, cyanate, succinimidyl ester, substituted derivatives thereof. Such functional groups can be found by one of ordinary skill in the art, for example in Bioconjugate Techniques (Academic Press, New York, 1996 or later versions) the content of which is herein incorporated by reference in its entirety for all purposes.

In some embodiments, a functional group can be created with covalent bonding to the backbone, side chain, or terminating unit of the narrow-band emissive chromophoric polymer. Therefore, the resulting polymer dots exhibit narrow-band emission and simultaneously have functional groups for bioconjugation. Such functional groups could be found by one of ordinary skill in the art, for example in Bioconjugate Techniques (Academic Press, New York, 1996 or later versions) the content of which is herein incorporated by reference in its entirety for all purposes. In some embodiments, each narrow-band emissive polymer dot may have only one functional group. In some embodiments, each narrow-band emissive polymer dot may have only two functional groups. The two functional groups can be the same or different. In some embodiments, each narrow-band emissive polymer dot may have only three or more functional groups. The three or more functional groups can be the same or different.

In some embodiments, the present invention provides a bioconjugate comprising a narrow-band emissive chromophoric polymer dot as described above and a biomolecule, wherein the biomolecule is attached to the polymer dot either directly or indirectly by the functional group. The bioconjugates also include narrow-band emissive chromophoric polymer dot as described above, associated with biological particle such as virus, bacteria, cells, biological or synthetic vesicles such as liposomes. The term "biomolecule" is used to describe a synthetic or naturally occurring protein, glycoprotein, peptide, amino acid, metabolite, drug, toxin, nuclear acid, nucleotide, carbohydrate, sugar, lipid, fatty acid and the like. Desirably, the biomolecule is attached to the functional group of narrow-band emissive chromophoric polymer dot via a covalent bond. For example, if the functional group of the polymer dot is a carboxyl group, a protein biomolecule can be directly attached to the polymer dot by cross-linking the carboxyl group with an amine group of the protein molecule. In some embodiments, each narrow-band emissive polymer dot may have only one biomolecule attached. In some embodiments, each narrow-band emissive polymer dot may have only two biomolecule attached. The two biomolecules can be the same or different. In some embodiments, each narrow-band emissive polymer dot may have only three or more biomolecules attached. The three or more biomolecules can be the same or different. In some embodiments, the biomolecular conjugation does not change substantively the emissive properties of the narrow-band emissive Pdots. For example, the bioconjugation does not broaden the emission spectra, does not reduce fluorescence quantum yield, does not change the photostability etc.

Methods for Preparing Chromophoric Polymers Dots with Narrow-Band Emissions

A variety of polymerization reactions can be used for synthesis of the polymers described herein. For example, semiconducting polymers including homo-polymer and multi-component copolymer or heteropolymer can be synthesized by using a variety of different reactions. Non-limiting examples of reactions for synthesizing semiconducting polymers include the Heck, Mcmurray and Knoevenagel, Wittig, Horner, Suzuki-Miyaura, Sonogashira, Yamamoto and Stille coupling reaction and so on.

Other polymerization strategies such as electropolymerization, oxidative polymerization can also be employed to make semiconducting polymers. Furthermore, microwave-assisted polymerization takes less time and often can give higher molecular weight and yield.

Several of the above mentioned polymerization reactions are shown below, e.g., by using synthesis of polyfluorene and its derivatives as examples. The examples below show homo-polymer, but the reactions for the synthesis of heteropolymer or copolymer is similar except that the starting monomers are different. Using these reactions, we can form various polymers from the individual units or monomers described in this invention. The monomers and any of the substituents on the monomers (such as the substituents described herein) can also be made using standard synthesis methods generally well known in the art.

1) Stille polycondensation for synthesis of conjugated polymers

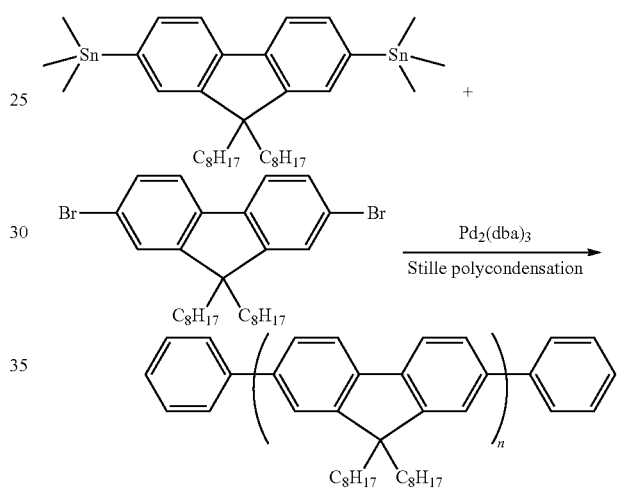

2) Suzuki polycondensation for synthesis of conjugated polymers.

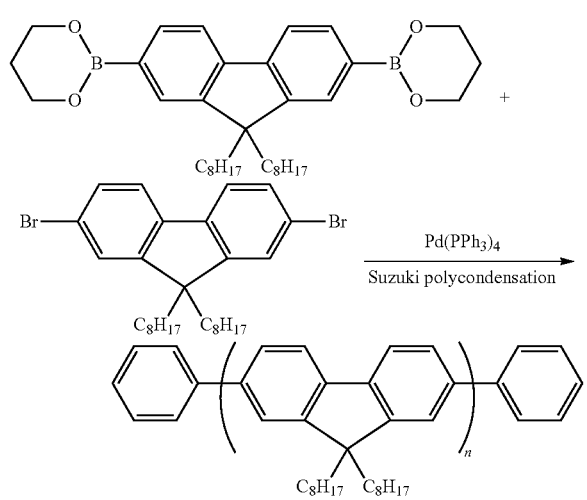

3) Yamamoto polycondensation for synthesis of conjugated polymers.

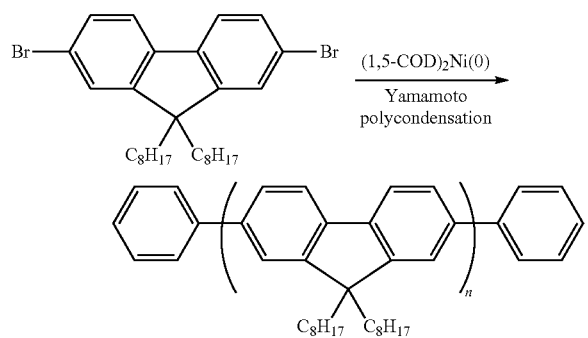
4) Sonogashira polycondensation for synthesis of conjugated polymers.
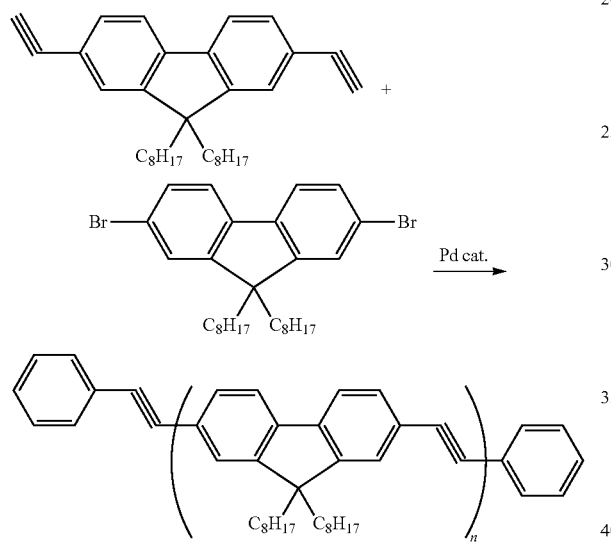
5) Heck reaction for synthesis of conjugated polymers.
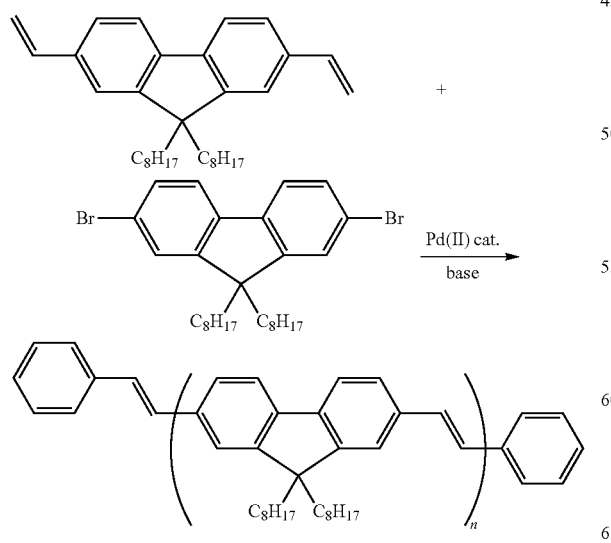
6) Mcmurray and Knoevenagel reaction for synthesis of conjugated polymers.
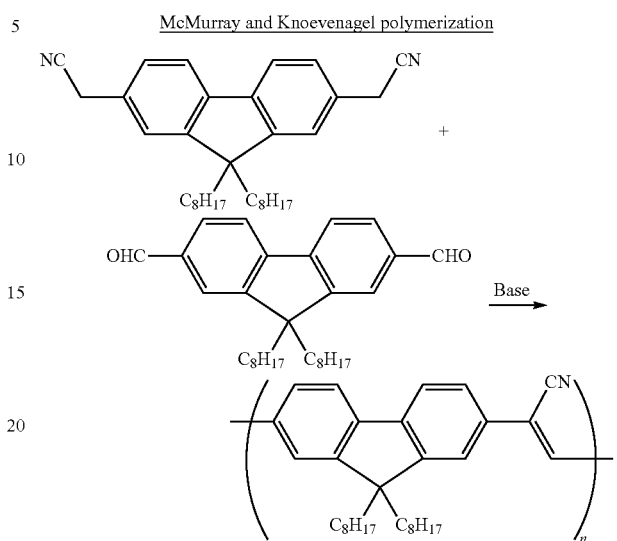
7) Mcmurray and Knoevenagel reaction for synthesis of conjugated polymers.
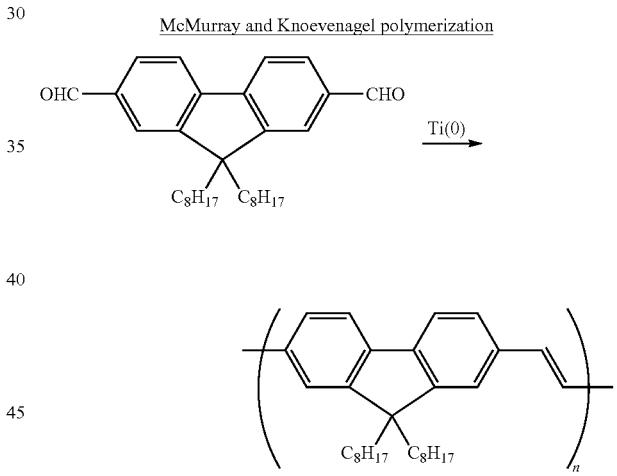
8) Electropolymerization for synthesis of conjugated polymers.
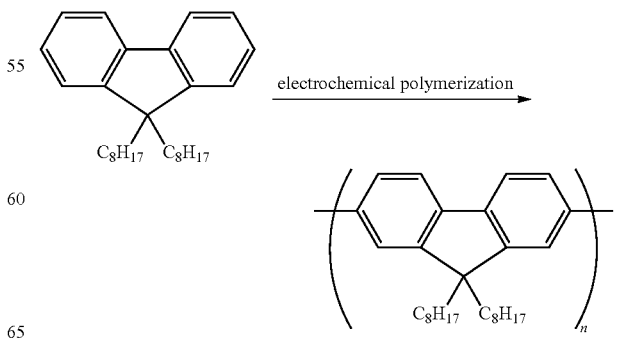

9) Wittig reaction for Synthesis of conjugated polymers.

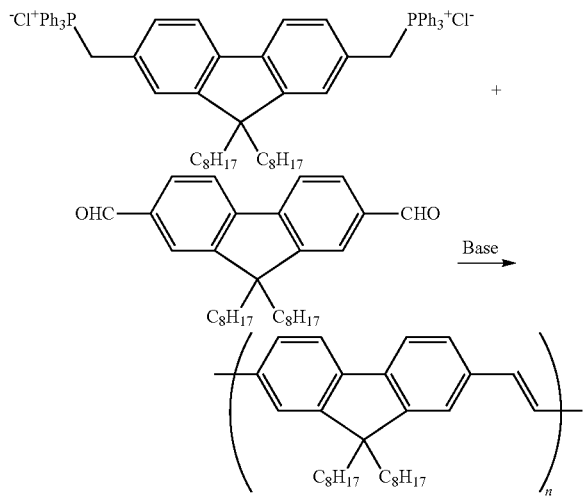

10) Horner-Wadsworth-Emmons reaction for synthesis of conjugated polymers.

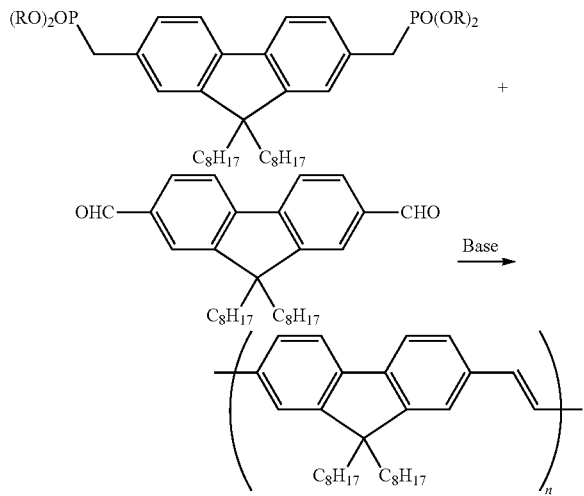

11) Oxidative polymerization for synthesis of conjugated polymers.

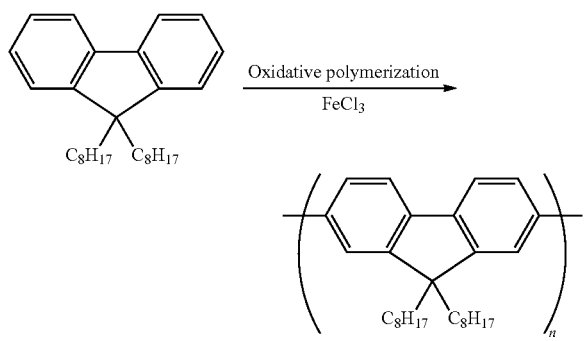

In some embodiments, narrow-band emissive chromophoric polymer dot can be prepared by using the solvent mixing method. The solvent mixing method involves quick mixing a solution of the chromophoric polymer in a good solvent (such as tetrahydrofuran) with a miscible solvent (such as water) to fold the polymer into a nanoparticle form, and Pdots can be obtained after removal of the good solvent. In some embodiments, the narrow-band emissive polymer dots can also be prepared by an emulsion or miniemulsion method, based on shearing a mixture comprising two immiscible liquid phases (such as water and another immiscible organic solvent) with the presence of a surfactant.

In one aspect, the present invention can include methods of making a polymer dot. The methods can include providing a solvent solution comprising a chromophoric polymer, the chromophoric polymer being in an elongated coil form and comprising a narrow-band monomer, and wherein the chromophoric polymer includes an emission spectrum with a full width half maximum (FWHM) of less than about 70 nm; and mixing the solvent solution comprising the chromophoric polymer with a miscible solvent to form a condensed chromophoric polymer, wherein the condensed chromophoric polymer includes an emission spectrum with a FWHM less than about 70 nm. In another aspect, the present invention can include a method of making a polymer dot that includes providing a solvent solution comprising a chromophoric polymer, the chromophoric polymer being in an elongated coil form and comprising a narrow-band monomer, and wherein the chromophoric polymer includes an emission spectrum with a full width half maximum (FWHM) of greater than about 70 nm; and mixing the solvent solution comprising the chromophoric polymer with a miscible solvent to form a condensed chromophoric polymer, wherein the condensed chromophoric polymer includes an emission spectrum with a FWHM less than about 70 nm.

In some embodiments, polymer dots can be made as condensed polymer nanoparticles that have intrachain energy transfer between, e.g., a narrow-band monomer and one or more general monomers on the same polymer chain. The present invention can further include methods of making polymer dots by physically blending and/or chemically crosslinking two or more polymer chains together. For example, the polymer dots can have interchain energy transfer in which a condensed polymer nanoparticle can include two or more polymer chains physically blended and/or chemically crosslinked together. For interchain energy transfer, one of the chains may include a narrow-band monomer and another chain may include one or more general monomers that can act as an energy donor to the narrow band monomer, which is an energy acceptor. As provided in the methods of making described above, broad-band polymer chains in good solvent (e.g., polymers that have a FWHM of greater than 70 nm) can be condensed and also physically blended and/or crosslinked so as to produce a narrow band emitting polymer dot (e.g., a polymer dot that has a FWHM of less than 70 nm). Some of the polymer dots can be made to have both intrachain and interchain energy transfer. In some instances, the combination of intrachain and interchain energy transfer can increase the quantum yield of the polymer dots. In certain embodiments, the final Pdots can exhibit narrow-band emissions because of energy transfer to the narrow-band monomers.

Methods of Using Chromophoric Polymer Dots with Narrow-Band Emissions

The present invention further provides methods of using the narrow-band emissive polymer dots described herein. For example, the present invention provides methods of fluorescence-based detection using the narrow-band emissive polymer dots as a novel class of fluorescent probe and their bioconjugates for a variety of applications, including but not limited to flow cytometry, fluorescence activated sorting, immunofluorescence, immunohistochemistry, fluorescence multiplexing, single molecule imaging, single particle tracking, protein folding, protein rotational dynamics, DNA and gene analysis, protein analysis, metabolite analysis, lipid analysis, FRET based sensors, high throughput screening, cell detection, bacteria detection, virus detection, biomarker detection, cellular imaging, in vivo imaging, bioorthogonal labeling, click reactions, fluorescence-based biological assays such as immunoassays and enzyme-based assays, and a variety of fluorescence techniques in biological assays and measurements. In certain aspects, the polymer dots disclosed herein can be used for methods of detection that involve multiplexing over a variety of wavelength ranges.

In one aspect, the present invention provides methods for imaging polymer dots that include administering a population of polymer dots described herein to a subject and exciting at least one polymer dot in the population of polymer dots, e.g., with an imaging system. The method can further include detecting a signal from at least one excited polymer dot in the population of polymer dots. As described further herein, the polymer dots can be administered in a composition.

In another aspect, the present invention includes a method of multiplex detection with a polymer dot. The method can include detecting the polymer dot with a detector system comprising a filter configured to pass a spectrum of light having a full width half maximum (FWHM) of less than about 70 nm, wherein the polymer dot includes a condensed chromophoric polymer comprising a narrow-band monomer, the condensed chromophoric polymer having an emission spectrum that is substantially passed through the filter. In certain embodiments, the FWHM is less than about 60 nm, less than about 50 nm, less than about 40 nm, less than about 30 nm, or less than about 20 nm. As described further herein, the polymer dots of the present invention can include, e.g., a homopolymer or heteropolymer including a narrow band monomer, such as BODIPY and/or BODIPY derivative monomer, a squaraine and/or squaraine derivative, a metal complex and/or metal complex derivative monomer, a porphyrin and/or porphyrin derivative monomer, a phthalocyanine and/or phthalocyanine derivative monomer, a lanthanide complex and/or lanthanide complex derivative monomer, a perylene and/or perylene derivative monomer, a cyanine and/or cyanine derivative monomer, a rhodamine and/or rhodamine derivative monomer, a coumarin and/or coumarin derivative monomer, and/or a xanthene and/or xanthene derivative monomer. A narrow band unit can be, e.g., a narrow band monomer or a fluorescent nanoparticle embedded in or attached to the polymer dot. The fluorescent nanoparticle can be, e.g., a quantum dot. A narrow band unit can also include a polymer or fluorescent dye molecule that gives a narrow emission in a polymer dot of the present invention.

The present invention also provides methods and compositions for administering the polymer dots described herein to a subject to facilitate diagnostic and/or therapeutic applications. In one aspect, the present invention provides a method for administering a polymer dot composition. The method can include administering a polymer dot composition described herein to a subject. A subject can include, but is not limited to, a mouse, a rat, a rabbit, a human, or other animal. In certain embodiments, the compositions can include a population of polymer dots and a pharmaceutically acceptable excipient. Pharmaceutical excipients useful in the present invention include, but are not limited to, binders, fillers, disintegrants, lubricants, coatings, sweeteners, flavors and colors. One of skill in the art will recognize that other pharmaceutical excipients are useful in the present invention.

The polymer dots of the present invention can be administered as frequently as necessary, including hourly, daily, weekly or monthly. The compounds utilized in the methods of the invention can be, e.g., administered at dosages ranging from, for example, about 1 mg to about 510 mg, or about 0.0125 mg/kg body weight to about 6.375 mg/kg body weight (assuming an average adult weighs 80 kg). The dosages, however, may be varied depending upon the requirements of the subject the severity of the condition being treated and/or imaged, and/or the polymer dot being employed. For example, dosages can be empirically determined considering the type and stage of disease diagnosed in a particular patient and/or the type of imaging modality being used in conjunction with the polymer dots. The dose administered to a subject, in the context of the present invention should be sufficient to effect a beneficial diagnostic or therapeutic response in the subject. The size of the dose also can be determined by the existence, nature, and extent of any adverse side-effects that accompany the administration of a particular polymer dot in a particular subject. Determination of the proper dosage for a particular situation is within the skill of the practitioner.

The compositions described herein can be administered to the patient in a variety of ways, including parenterally, intravenously, intradermally, intramuscularly, colonically, rectally or intraperitoneally. In some embodiments, the pharmaceutical compositions can be administered parenterally, intravenously, intramuscularly or orally. The oral agents comprising a population of the polymer dots of the invention can be in any suitable form for oral administration, such as liquid, tablets, capsules, or the like. The oral formulations can be further coated or treated to prevent or reduce dissolution in stomach.

The polymer dot compositions of the present invention can be administered to a subject using any suitable methods known in the art. Suitable formulations for use in the present invention and methods of delivery are generally well known in the art. For example, a population of polymer dots described herein can be formulated as pharmaceutical compositions with a pharmaceutically acceptable diluent, carrier or excipient. A population of polymer dots of the present invention can be administered in any pharmaceutically acceptable composition.

Furthermore, a population of polymer dots can be formulated for parenteral, topical, nasal, sublingual, gavage, or local administration. For example, the pharmaceutical compositions are administered parenterally, e.g., intravenously, subcutaneously, intradermally, or intramuscularly, or intranasally. Thus, the invention provides compositions for parenteral administration that include a solution of a single or mixture of a population of polymer dots described herein, dissolved or suspended in an acceptable carrier, e.g., an aqueous carrier. The compositions may contain pharmaceutically acceptable auxiliary substances as required to approximate physiological conditions including pH adjusting and buffering agents, tonicity adjusting agents, wetting agents and the like, such as, for example, sodium acetate, sodium lactate, sodium chloride, potassium chloride, calcium chloride, sorbitan monolaurate, triethanolamine oleate, etc.

The present invention also provides kits for administering the polymer dots to a subject for treating and/or diagnosing a disease state. Such kits typically include two or more components useful for administration. Components can include polymer dots of the present invention, reagents, containers and/or equipment.

In certain embodiments, the kits of the present invention can include packaging assemblies that can include one or more components. For example, a packaging assembly may include a container that houses at least one of the polymer dot compositions as described herein. A separate container may include other excipients or agents that can be mixed with the polymer dot compositions prior to administration to a patient. In some embodiments, a physician may select and match certain components and/or packaging assemblies depending on the particular diagnostic and/or therapeutic application.

The specific dimensions of any of the apparatuses, devices, systems, and components thereof, of the present invention can be readily varied depending upon the intended application, as will be apparent to those of skill in the art in view of the disclosure herein. Moreover, it is understood that the examples and embodiments described herein are for illustrative purposes only and that various modifications or changes in light thereof may be suggested to persons skilled in the art and are included within the spirit and purview of this application and scope of the appended claims. Numerous different combinations of embodiments described herein are possible, and such combinations are considered part of the present invention. In addition, all features discussed in connection with any one embodiment herein can be readily adapted for use in other embodiments herein. The use of different terms or reference numerals for similar features in different embodiments does not necessarily imply differences other than those expressly set forth. Accordingly, the present invention is intended to be described solely by reference to the appended claims, and not limited to the preferred embodiments disclosed herein.

EXAMPLES

The following examples are included to further describe some aspects of the present invention, and should not be used to limit the scope of the invention.

Example 1: Synthesis of BODIPY Monomer2a (FIG. 12) and a Series of Fluorene-BODIPY Copolymers at Different BODIPY Concentrations The present example provides a method for obtaining narrow-band BODIPY monomer2a and a series of fluorene-BODIPY copolymers at different BODIPY concentrations.

Instrumentation and Characterizations for Synthesis. $^1$H (500 MHz), $^{13}$C (125 MHz) NMR spectra were recorded on Bruker AV500 spectrometers. $^1$H NMR and $^{13}$C NMR spectra used tetramethylsilane (TMS) as an internal standard in CDCl$_3$. Mn and molecular weight distribution [weight-average molecular weight/number-average molecular weight (Mw/Mn)] values of all polymers were estimated by size exclusion chromatography (SEC) with a TOSOH G3000HXI system equipped with three consecutive polystyrene gel columns [TOSOH gels: ¦A-4000, ¦A-3000, and ¦A-2500] and refractive-index and ultraviolet detector at 40° C. The system was operated at a flow rate of 1.0 mL/min with a tetrahydrofuran as an eluent. Polystyrene standards were employed for calibration. All the chemicals were purchased from Sigma-Aldrich and TCI America.

Synthesis of BODIPY Monomer 2a (8-Mesityl-1,3,5,7-tetramethyl-4,4-difluoro-4-bora-3a,4a-diaza-s-indacene).

110 μl of trifluoroacetic acid in dry CH$_2$Cl$_2$ (10 ml) was added slowly to a solution of 2,4,6-trimethylbenzaldehyde (1.482 g, 10 mmol) and 2,4-dimethyl-1H-pyrrole (2.38 g, 25 mmol) in dry CH$_2$Cl$_2$ (250 ml) at room temperature. 2,3-Dichloro-5,6-dicyano-1,4-benzoquinone (2.27 g, 10 mmol) is added after 3 h stirring under ice bath cooling and stirred for 20 min. The solution is stirred for an additional 1 h at room temperature. NEt$_3$ (20 mL, 144 mmol) is added, followed by slow addition of BF$_3$·Et$_2$O (23 ml, 170 mmol). The reaction mixture is washed after 12 h of stirring at room temperature with saturated aqueous Na$_2$CO$_3$ solution (2×150 ml), dried over Na$_2$SO$_4$, and concentrated on a rotary evaporator. The brown, oily residue is purified by column chromatography on silica with hexane/CH$_2$Cl$_2$=3:1. The product fraction with greenish fluorescence is dried to yield a red-brown solid. Yield: 2.3 g, 62.8%. $^1$H NMR (500 MHz, CDCl$_3$): δ=6.979 (s, 2H), 5.993 (s, 2H), 2.592 (s, 6H), 2.368 (s, 3H), 2.128 (s, 6H), 1.417 (s, 6H). $^{13}$C NMR (125 MHz, CDCl$_3$): δ=155.09, 142.31, 141.68, 138.57, 134.92, 131.13, 130.62, 129.0, 120.79, 21.22, 19.51, 14.64, 13.41.

Synthesis of Fluorene-BODIPY Copolymer Series. BODIPY fluorene copolymer series with different BODIPY monomer molar ratio (2%, 5%, 10%, 25%, 50%) are synthesized by palladium-catalyzed Suzuki coupling reaction from 9,9-dioctylfluorene and BODIPY monomer. 9,9-Dioctyl-2,7-dibromofluorene, 9,9-Dioctylfluorene-2,7-diboronic acid bis(1,3-propanediol) ester, BODIPY monomer 1a, 2 drops of aliquot 336, 10 ml of 2M Na$_2$CO$_3$ aqueous solution, 15 ml of toluene were placed in a 50 ml flask. The flask was evacuated and refilled with N$_2$ four times by using the freeze/thaw method and Pd(PPh$_3$)$_4$ (1-1.5 mol %) was added. The flask was further degassed four times, then reaction was heated to 80° C. and stirred under N$_2$. After 70 h 0.2 ml of bromobenzene and 15 mg of phenylboronic acid were added to end-cap the polymer chain and the reaction was stirred for an additional 2 h at 80° C. respectively. The whole mixture was poured into 200 ml of MeOH, filtered, and washed with 0.2M of HCl. The precipitate was stirred in 50 ml of acetone at room temperature for 24 h and dried in vacuum oven to obtain dark pink to dark red solid. Yield: 73-81%. NMR results: for PFO-BODIPY10 $^1$H NMR (500 MHz, CDCl$_3$): δ=7.89-7.61 (m), 7.53 (m), 7.42 (m, 6H), 7.25 (m, 5H), 7.05 (m, 2H), 2.69 (s, 6H), 2.39 (s, 3H), 2.32 (s, 6H), 2.09-2.17 (s, 4H), 1.31 (s, 6H). 1.19 (s, 24), 0.87 (s, 6H). $^{13}$C NMR (125 MHz, CDCl$_3$): δ=154.07, 151.85, 151.74, 151.08, 141.94, 140.55, 140.08, 138.16, 135.05, 133.96, 132.24, 132.17130.63, 129.15, 128.96, 128.83, 128.57, 128.47, 127.25, 126.82, 126.19, 124.86, 121.53, 120.01, 119.55, 55.39, 55.29, 40.44, 30.08, 29.76, 29.26, 29.19, 23.95, 22.64, 21.31, 19.91, 14.11, 13.65, 11.74. Mn: 23048, Mw: 43610, PDI: 1.89.

Example 2: Synthesis of BODIPY Monomer1a (FIG. 12) and a Narrow-Band Emissive Fluorene-BODIPY Copolymer Polymer510

The present example provides a method for obtaining narrow-band BODIPY monomer2a and a narrow-band emissive fluorene-BODIPY copolymer polymer510.

Synthesis of 4-Methyl-3,5-Diiodobenzaldehyde for BODOPY Monomer1a. Powdered I$_2$ (3.04 g, 12 mmol) and then NaIO$_4$ (0.86 g, 4 mmol) were added slowly to stirred 98% H$_2$SO$_4$ (50 ml). Stirring was continued for 30 min at room temperature to give a dark brown iodinating solution. p-Tolualdehyde (1.5 g, 14 mmol) was added in one portion to the iodinating solution and the resulting solution was stirred overnight at room temperature. Then the reaction mixture was slowly poured into stirred ice water. The crude solid products were collected by filtration, washed with water until the filtrates were neutral, vacuum dried in the dark to get light brown powder, and re-crystallized from ethyl acetate to give light yellow solid. Yield: 2.13 g, 40.9%. $^1$H NMR (CDCl$_3$, 500 MHz): δ=9.823 (s, 1H), 8.306 (d, 2H), 2.842 (s, 3H). $^{13}$C NMR (CDCl$_3$, 125 MHz): δ=189.19, 162.98, 150.32, 140.83, 99.97, 35.98.

Synthesis of BODOPY Monomer1a. To a solution of 4-methyl-3,5-diiodobenzaldehyde (1.5 g, 4.2 mmol) and 2,4-dimethyl-1H-pyrrole (1 g, 10.5 mmol) in dry CH$_2$Cl$_2$ (120 ml) is added a solution of 110 μl trifluoroacetic acid in dry CH$_2$Cl$_2$ (5 ml) slowly at room temperature. 2,3-Dichloro-5,6-dicyano-1,4-benzoquinone (0.95 g, 4.2 mmol) is added after 3 h stirring under ice bath cooling and stirred for 10 min. The solution is stirred for an additional 1 h at room temperature. NEt$_3$ (10 ml, 72 mmol) is added, followed by slow addition of BF$_3$. Et$_2$O (12 mL, 81 mmol). The reaction mixture is washed after 10 h of stirring at room temperature with saturated aqueous Na$_2$CO$_3$ solution (2×100 ml), dried over Na$_2$SO$_4$, and concentrated on a rotary evaporator. The brown, oily residue is purified by column chromatography on silica with hexane/CH$_2$Cl$_2$=3:1. The product fraction with greenish fluorescence is dried to yield an orange solid. Yield: 0.48 g, 19.5%. $^1$H NMR (CDCl$_3$, 500 MHz): δ=7.831 (s, 2H), 6.042 (s, 2H), 2.874 (s, 3H), 2.581 (s, 6H), 1.544 (s, 6H). $^{13}$C NMR (CDCl$_3$, 125 MHz): δ=156.25, 144.12, 142.83, 138.94, 135.89, 131.11, 121.67, 99.09, 34.93, 15.14, 14.61.

Figure 21:
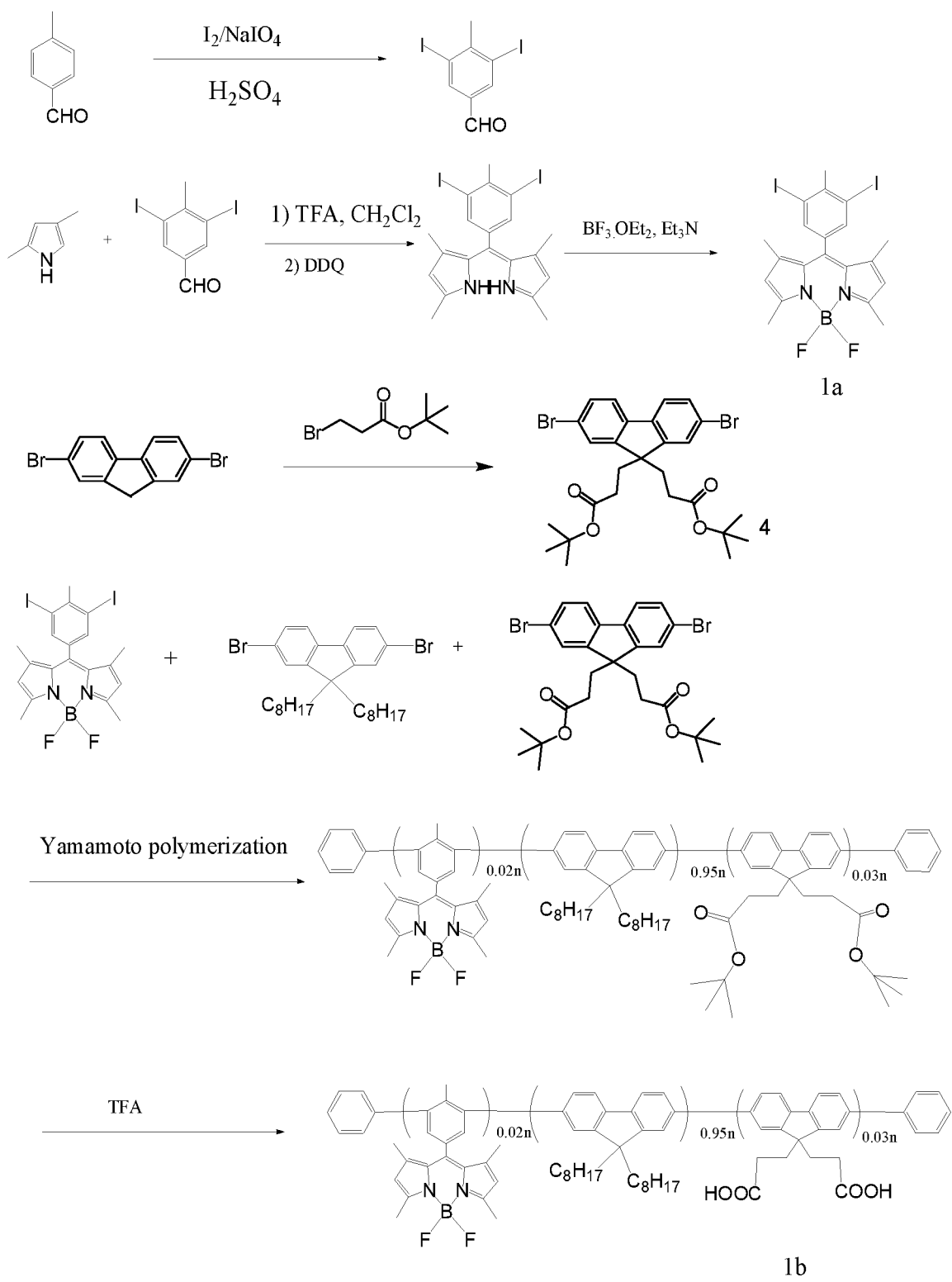
FIG. 21 shows multi-step synthesis of the BODIPY monomer 1a in FIG. 12 and the narrow-band emissive polymer Polymer510.
Figure 22:
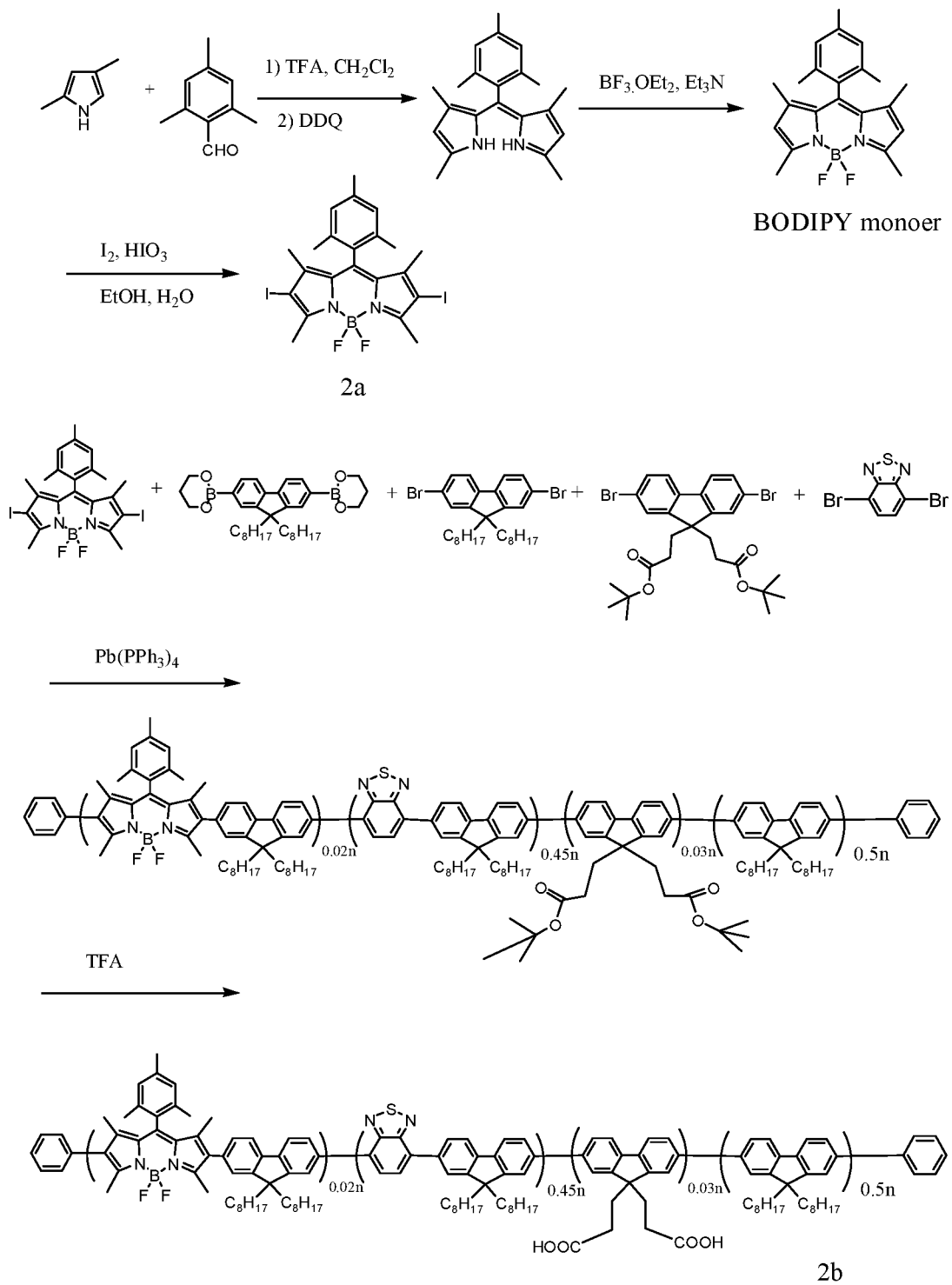
FIG. 22 shows multi-step synthesis of the BODIPY monomer 2a in FIG. 12 and the narrow-band emissive polymer Polymer590.
Figure 23:
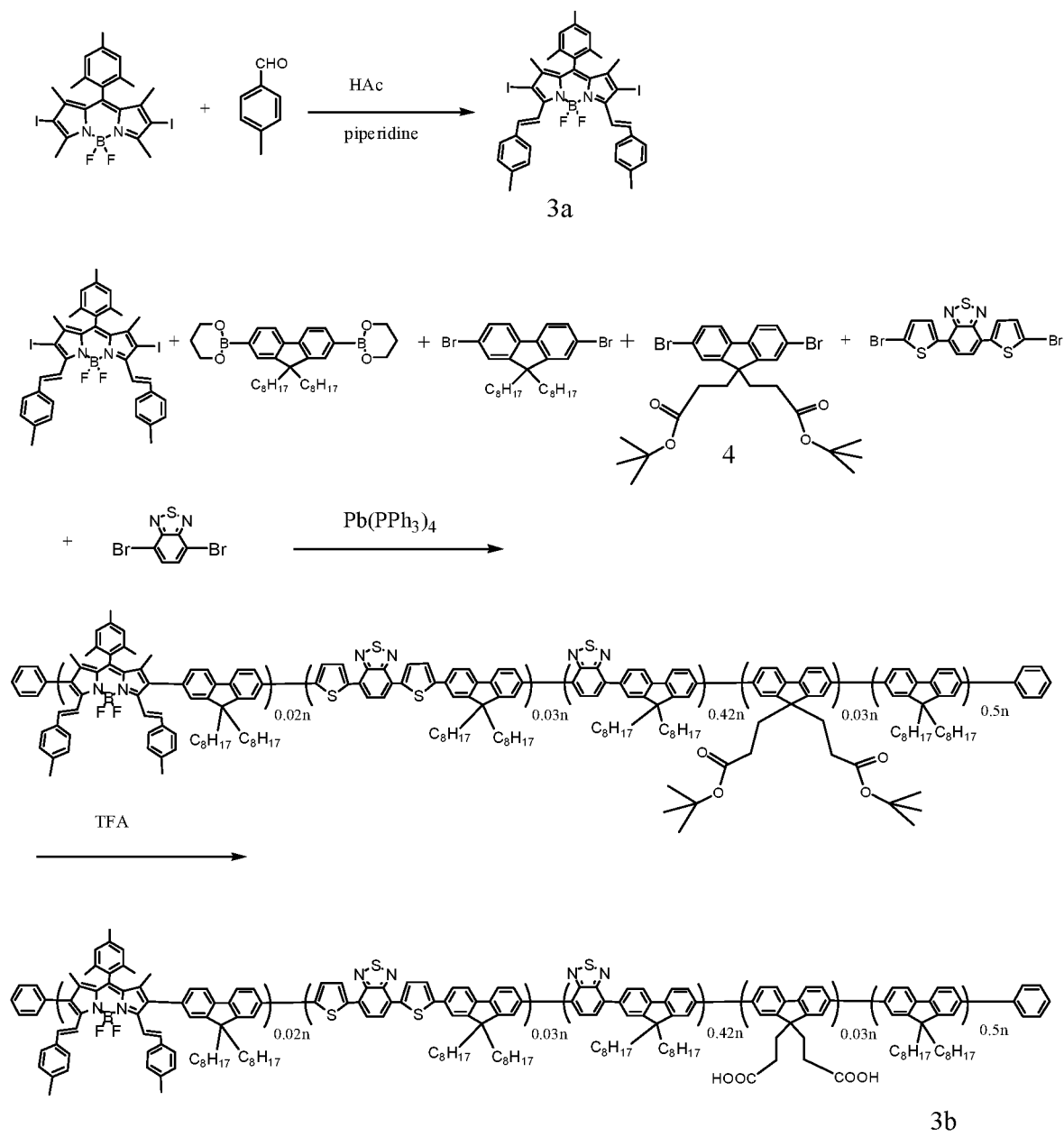
FIG. 23 shows multi-step synthesis of the BODIPY monomer 3a in FIG. 12 and the narrow-band emissive polymer Polymer680.

Synthesis of Monomer4 (FIG. 21) for Polymer510. A mixture of 2,7-dibromofluorene (15 mmol, 4.86 g), tert-butyl 3-bromopropanoate (33 mmol, 6.86 g), sodium hydroxide solution (40%, 35 mL), Bu$_4$NBr (1.5 mmol, 0.48 g), toluene (70 mL) was stirred at 85° C. overnight. The organic phase was separated, washed with water and dried over MgSO$_4$. After evaporation of the solvent, the residue was purified by column chromatography (DCM). The product was obtained as a white solid. Yield: 4.81 g, 83%. $^1$HNMR (500 MHz, CDCl$_3$): δ=7.47-7.54 (m, 6H), 2.30 (t, 4H), 1.47 (t, 4H), 1.33 (s, 18H). $^{13}$CNMR (125 MHz, CDCl$_3$): 172.71, 150.47, 139.60, 131.56, 126.99, 122.57, 121.93, 80.97, 54.58, 34.92, 30.36, 28.52.

Synthesis of Polymer510. In the glovebox under nitrogen atmosphere, a dry three neck 50 mL round-bottom flask with stir bar was charged with 248 mg (0.9 mmol) of bis(1,5-cyclooctadiene) nickel(0), 97.1 mg (0.9 mmol) of cyclooctadiene, and 140.6 mg (0.9 mmol) of bypyridine in 9.0 mL of a 1:1 mixture of toluene and dimethylformamide (DMF). A dark purple color then developed. The solution was heated to 60° C. In the glovebox, a dry 20 mL flask was charged with 7.04 mg (0.008 mmol) of BODIPY monomer 1a, 241.5 mg (0.376 mmol) of 9,9-Dioctyl-2,7-dibromofluorene and 9.7 mg (0.016 mmol) of monomer 4 in 4.0 mL of a 1:1 mixture of toluene and DMF, then they were added dropwise into the above catalyst mixture. The flask containing this solution was covered with foil to protect it from light and the reaction mixture was refluxed for 4 days. 4 drops of iodobenzene was added to end-cap the polymer chain and the reaction was stirred for an additional 6 h at 60° C. The product was precipitated in 30 mL of a 1:1 mixture of methanol and concentrated hydrochloric acid. The polymer was dissolved in dichloromethane and washed with aqueous 15 wt % of sodium thiosulfate solution (3×30 mL) followed by washing with Milli-Q water and drying over MgSO$_4$, for the removal of residual iodine from polymer. The concentrated polymer solution in dichloromethane was poured into 100 ml of MeOH, filtered. The precipitate was stirred in 50 ml of acetone at room temperature for 24 h. The polymer was obtained as a yellow powder. Deprotection of the tert-butyl esters was then followed by adding 1 ml of trifluoroacetic acid into a solution of polymer (70 mg) in DCM (40 ml) and stirred overnight. The organic layer was washed with water (100 ml×4) and concentrated to 10 ml and precipitated in methanol (100 ml). The final powder was collected by filtration, washed with acetone, and dried in vacuum oven to obtain green solid. yield: 101 mg, 64.5%. 1H NMR (CDCl$_3$, 500 MHz): δ=7.89-7.61 (m), 7.53 (m), 7.42 (m, 6H), 2.09-2.16 (s, 4H), 1.18 (s, 24H), 0.85 (s, 6H). $^{13}$C NMR (CDCl$_3$, 125 MHz): δ=151.86, 140.56, 140.06, 126.20, 121.55, 120.00, 55.38, 40.43, 31.84, 30.08, 29.27, 23.97, 22.64, 14.11.

Example 3: Synthesis of BODIPY Monomer2a (FIG. 12) and a Narrow-Band Emissive Fluorene-BODIPY Copolymer Polymer590

The present example provides a method for obtaining narrow-band BODIPY monomer2a and a narrow-band emissive fluorene-BODIPY copolymer polymer590.

Synthesis of BODOPY Monomer 2a. A 250 ml round-bottom flask was first charged with 2.2 g (6 mmol) of BODIPY monomer dissolved in 80 ml of ethanol. To this solution 4.57 g (18 mmol) of powdered I$_2$ was added and allowed to dissolve. 2.15 g (12.2 mmol) of HIO$_3$ was dissolved in a 0.7 g of water, and this solution was added dropwise by a syringe over a 20 min. After the addition was complete, the solution was heated to 60° C. and refluxed for 5 h. Ethanol was removed on a rotary evaporator. The residue was purified by column chromatography with a silica with hexane/CH$_2$Cl$_2$=3:1. The product 2a was dried to obtain a metallic dark red solid. Yield: 2.5 g, 68%. $^1$H NMR (500 MHz, CDCl$_3$): δ=7.008 (d, 2H), 2.682 (s, 6H), 2.391 (s, 3H), 2.096 (s, 6H), 1.437 (s, 6H). $^{13}$C NMR (125 MHz, CDCl$_3$): δ=156.42, 144.57, 141.72, 139.29, 134.81, 130.86, 130.52, 129.31, 85.30, 21.28, 19.55, 16.06, 15.80.

Synthesis of Polymer590. Fluorene-BODIPY copolymer Polymer590 are synthesized by palladium-catalyzed Suzuki coupling reaction from 9,9-dioctylfluorene, benzo[c]-1,2,5-thiadiazole and BODIPY monomer. 4,7-Dibromobenzo[c]-1,2,5-thiadiazole (52.9 mg, 0.18 mmol), 9,9-Dioctylfluorene-2,7-diboronic acid bis(1,3-propanediol) ester (111.68 mg, 0.20 mmol), BODIPY monomer 2a (5.03 mg, 0.008 mmol), monomer 4 (7.3 mg, 0.012 mmol), 2 drops of aliquat 336, 10 ml of 2M Na$_2$CO$_3$ aqueous solution, 15 ml of toluene were placed in a 50 ml round bottom flask. The flask was evacuated and refilled with N$_2$ four times by using the freeze/thaw method and Pd(PPh$_3$)$_4$ (10 mg, 0.0086 mmol) was added. The flask was further degassed four times, then reaction was heated to 80° C. and stirred under N$_2$. After 70 h 0.2 ml of bromobenzene and 15 mg of phenylboronic acid were added to end-cap the polymer chain and the reaction was stirred for an additional 2 h at 80° C. respectively. The whole mixture was poured into 200 ml of MeOH, filtered, and washed with 0.2M of HCl. The dried polymer was stirred in 50 ml of acetone at room temperature for 24 h. Polymer was obtained as a brown powder. Deprotection of the tert-butyl esters was then followed by adding 1 ml of trifluoroacetic acid into a solution of polymer in DCM (40 ml) and stirred overnight. The organic layer was washed with water (150 ml×5) and concentrated to 10 ml and precipitated in methanol (100 ml). The final powder was collected by filtration, washed with acetone, and dried in vacuum oven to get a brown solid. Yield: 112 mg, 73.2%. $^1$H NMR (500 MHz, CDCl$_3$): δ=8.14-8.08 (m, 2H), 8.01-7.72

(m), 7.83-7.73 (m), 7.40-7.43 (m, 6H), 7.24 (m, 5H), 7.09 (m, 2H), 6.97 (m, 2H), 3.95 (s, 4H), 2.53 (s, 6H), 2.40 (s, 6H), 2.19 (s, 8H), 1.51 (m, 6H), 1.20 (s, 24H), 0.85 (m, 6H). $^{13}$C NMR (125 MHz, CDCl$_3$): δ=154.43, 151.84, 140.95, 136.52, 133.67, 128.39, 128.03, 124.06, 120.12, 55.5, 55.27, 40.3, 31.89, 31.79, 30.17, 29.33, 29.31, 24.11, 22.67, 14.13. Mn: 14480, Mw: 28396, PDI: 1.96.

Example 4: Synthesis of BODIPY Monomer3a (FIG. 12) and a Narrow-Band Emissive Fluorene-BODIPY Copolymer Polymer680

The present example provides a method for obtaining narrow-band BODIPY monomer2a and a narrow-band emissive fluorene-BODIPY copolymer polymer590.

Synthesis of BODOPY Monomer 3a. p-tolualdehyde (392 mg, 4.24 mmol), monomer 2a (500 mg, 0.81 mmol), p-toluene sulfonic acid (90 mg), piperidine (3 ml) were dissolved in 100 ml of benzene reflux for 12 h by using Dean-Stark. The mixture was cooled to room temperature, the solvents were removed under vacuum, and the crude product was purified by column chromatography on silica gel eluted with ethyl acetate/hexane 1:7. The crude was recrystallized from chloroform/methanol to give the product as a metallic shiny solid. Yield: 420 mg, 62.3%. $^1$H NMR (500 MHz, CDCl$_3$): δ=8.157-8.191 (s, 2H), 7.689-7.722 (s, 2H), 7.589-7.605 (s, 4H), 7.258-7.274 (s, 4H), 7.029 (s, 2H), 2.435 (s, 6H), 2.409 (s, 3H), 2.127 (s, 6H), 1.512 (s 6H). $^{13}$C NMR (125 MHz, CDCl$_3$): δ=150.41, 145.17, 139.50, 139.48, 139.35, 139.32, 135.27, 134.05, 132.11, 131.32, 129.57, 129.33, 127.71, 117.98, 82.62, 21.53, 21.31, 19.73, 16.28.

Synthesis of Polymer680. 4,7-Bis(2-bromo-5-thienyl)-2,1,3-benzothiadiazole (5.5 mg, 0.012 mmol), 4,7-Dibromobenzo[c]-1,2,5-thiadiazole (49.4 mg, 0.168 mmol), 9,9-Dioctylfluorene-2,7-diboronic acid bis(1,3-propanediol) ester (111.68 mg, 0.20 mmol), BODIPY monomer 3a (6.58 mg, 0.008 mmol), monomer 4 (7.3 mg, 0.012 mmol), 2 drops of aliquat 336, 10 ml of 2M Na$_2$CO$_3$ aqueous solution, 15 ml of toluene were placed in a 50 ml round bottom flask. The flask was evacuated and refilled with N$_2$ four times by using the freeze/thaw method and Pd(PPh$_3$)$_4$ (10 mg, 0.0086 mmol) was added. The flask was further degassed four times, then reaction was heated to 80° C. and stirred under N$_2$. After 70 h 0.2 ml of bromobenzene and 15 mg of phenylboronic acid were added to end-cap the polymer chain and the reaction was stirred for an additional 2 h at 80° C. respectively. The whole mixture was poured into 300 ml of MeOH, filtered, and washed with 0.2M of HCl. The dried precipitate was stirred in 50 ml of acetone at room temperature for 24 h. Polymer 1b was obtained as a dark brown powder. Deprotection of the tert-butyl esters was then followed by adding 1 ml of trifluoroacetic acid into a solution of polymer in DCM (40 ml) and stirred overnight. The organic layer was washed with water (150 ml×5) and concentrated to 10 ml and precipitated in methanol (100 ml). The final powder was collected by filtration, washed with acetone, and dried in vacuum oven to obtain a dark brown solid. Yield: 70 mg, 62.1%. $^1$H NMR (500 MHz, CDCl$_3$): δ=8.23 (m, 2H), 8.08-8.14 (m, 2H), 8.02-7.98 (m, 2H), 7.85-7.83 (m, 2H), 7.78 (m, 2H), 7.58 (m, 4H), 7.44-7.38 (m, 4H), 7.21 (m, 4H), 7.08 (m, 2H), 6.97 (m, 2H), 2.38 (s, 3H), 2.33 (s, 6H), 1.48 (s, 6H), 1.20 (s, 24H), 0.85 (m, 6H). $^{13}$C NMR (125 MHz, CDCl$_3$): δ=154.42, 151.82, 140.95, 136.53, 133.66, 128.37, 128.03, 124.08, 120.11, 55.49, 55.26, 40.28, 31.88, 30.17, 30.12, 29.33, 29.30, 24.11, 22.66, 14.11.

Example 5: Preparation and Characterizations of Narrow-Band Emissive Pdots by Using Fluorene-BODIPY Copolymers The present example provides the preparation and characterizations of narrow-band emissive Pdots by using fluorene-BODIPY copolymers.

Fluorene-BODIPY Pdots were Prepared by Nanoprecipitaiton. A solution of polymer precursor in THF (2 mL, 100 ppm) was quickly injected into water (10 mL) under ultrasonication. THF was evaporated by N$_2$ flow at 70° C. and the solution was concentrated to 4-5 mL, followed by filtration through a 0.2 micron filter. The particle size and zeta-potentials of Pdots in bulk solution was characterized by dynamic light scattering (Malvern Zetasizer NanoS). TEM measurements were recorded on a transmission electron microscope (FEI Tecnai F20). UV-Vis absorption spectra were recorded with a DU 720 scanning spectrophotometer (Beckman Coulter, Inc., CA USA) using 1 cm quartz cuvettes. Fluorescence spectra were obtained using a commercial Fluorolog-3 fluorometer (HORIBA Jobin Yvon, NJ USA). Fluorescence quantum yields were measured using a Hamamatsu photonic multichannel analyzer C10027 equipped with CCD integrating sphere.

Figure 12A:
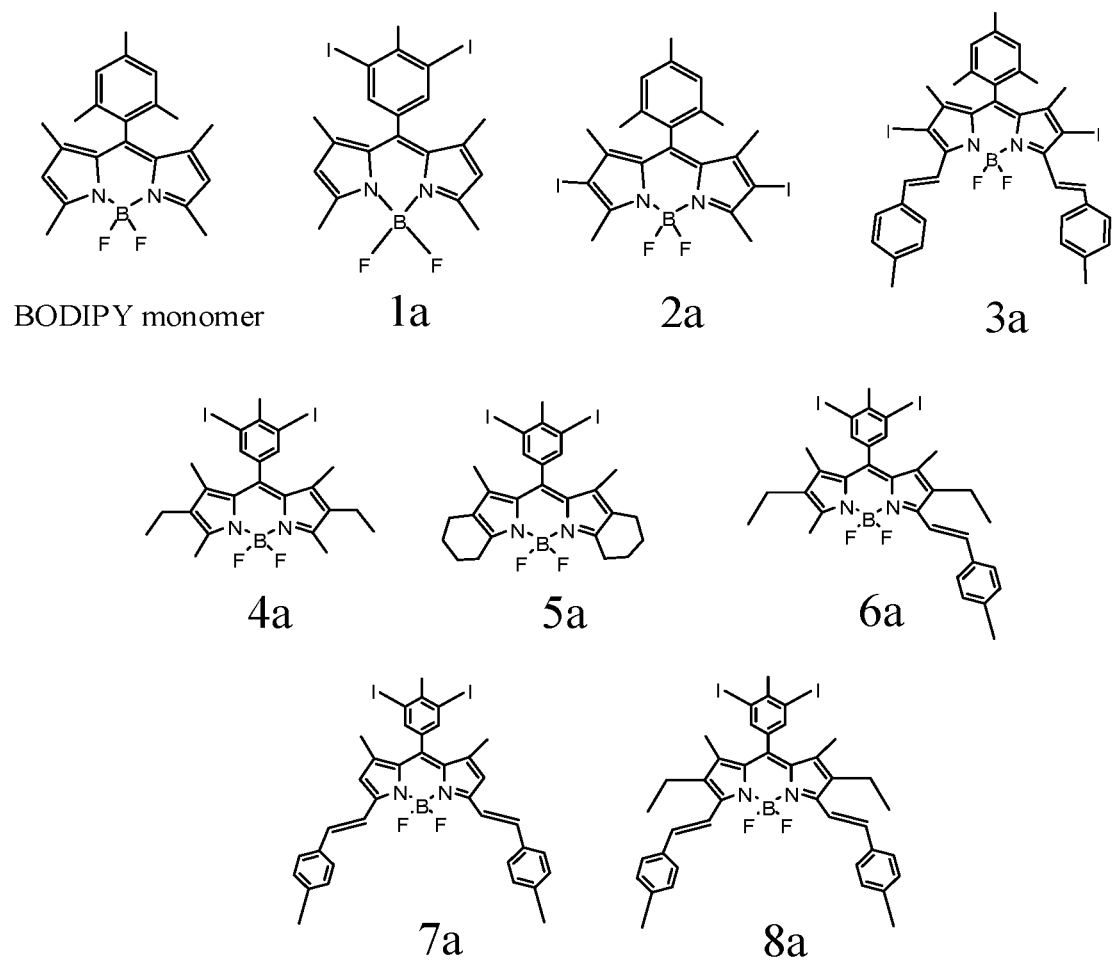
FIG. 12A shows chemical structures of examples of BODIPY monomers synthesized.
Figure 12B:
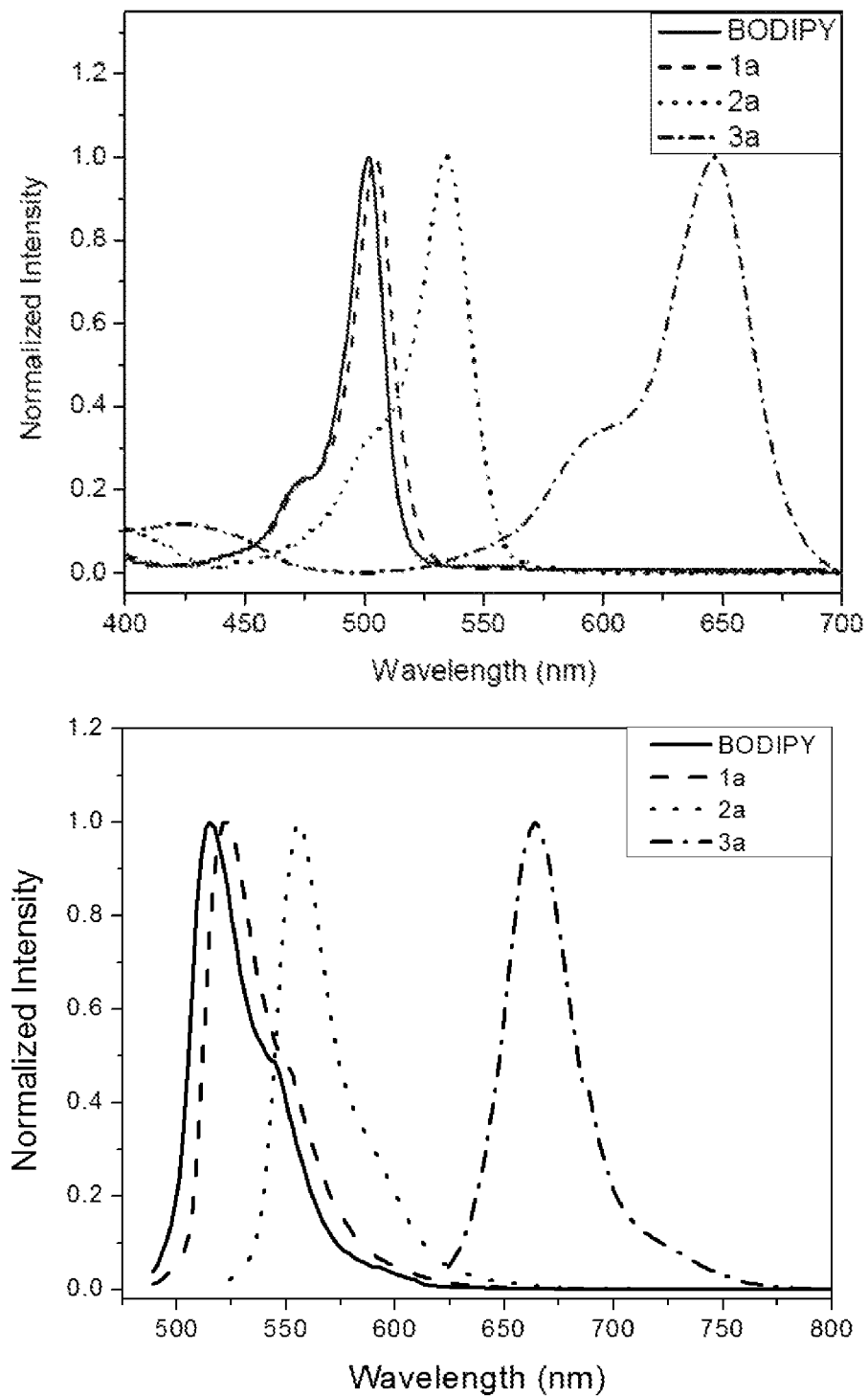
FIG. 12B shows their absorption spectra, fluorescence spectra, and fluorescence quantum yield.
Figure 13A:
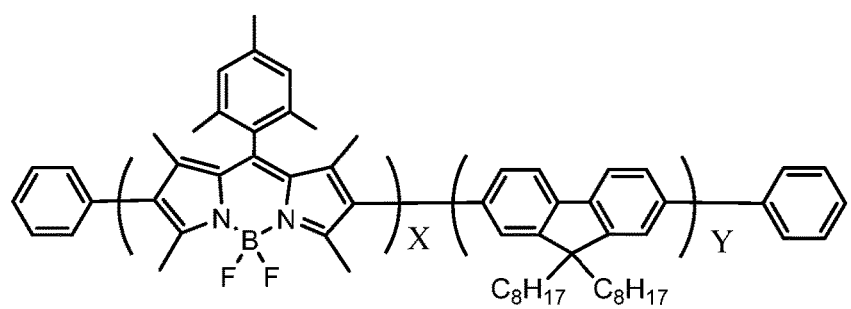
FIG. 13A shows a series of copolymers that include a general monomer fluorene and a narrow-band monomer (BODIPY Monomer 2a in FIG. 12) at different molar ratios.
Figure 13B:
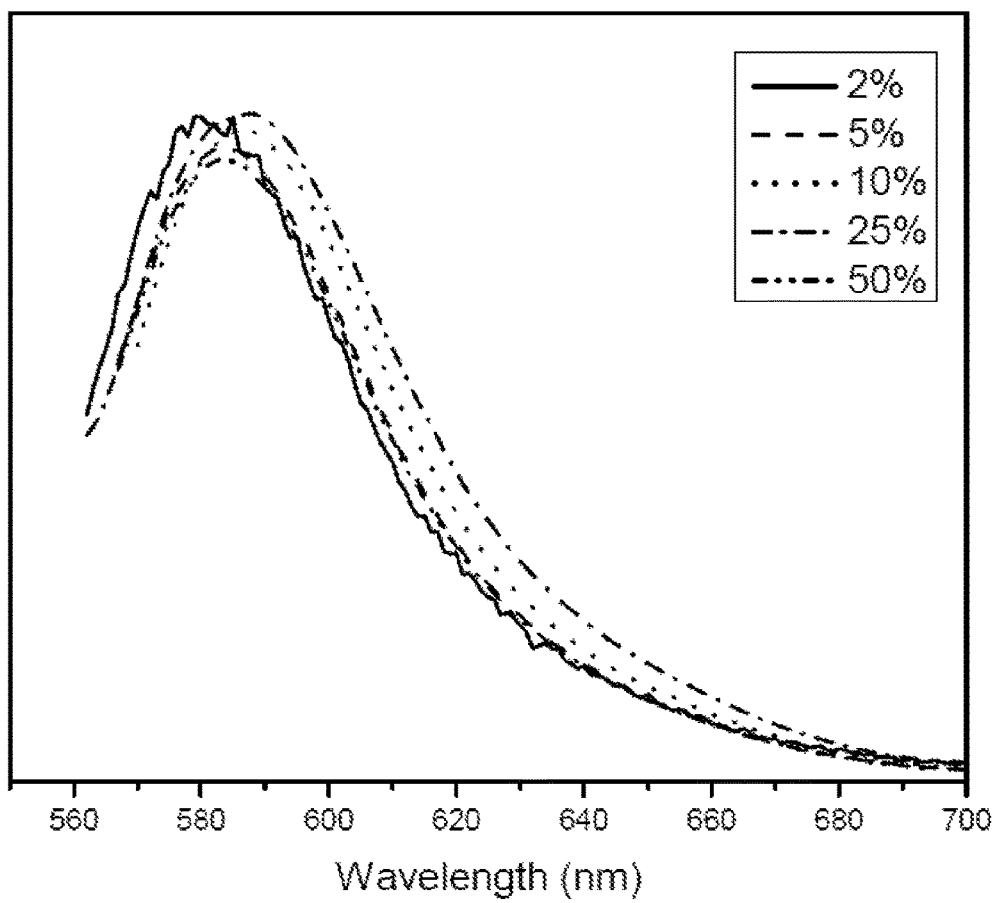
FIG. 13B shows the fluorescence spectra of the polymers in a good solvent tetrahydrofuran (THF).
Figure 13C:
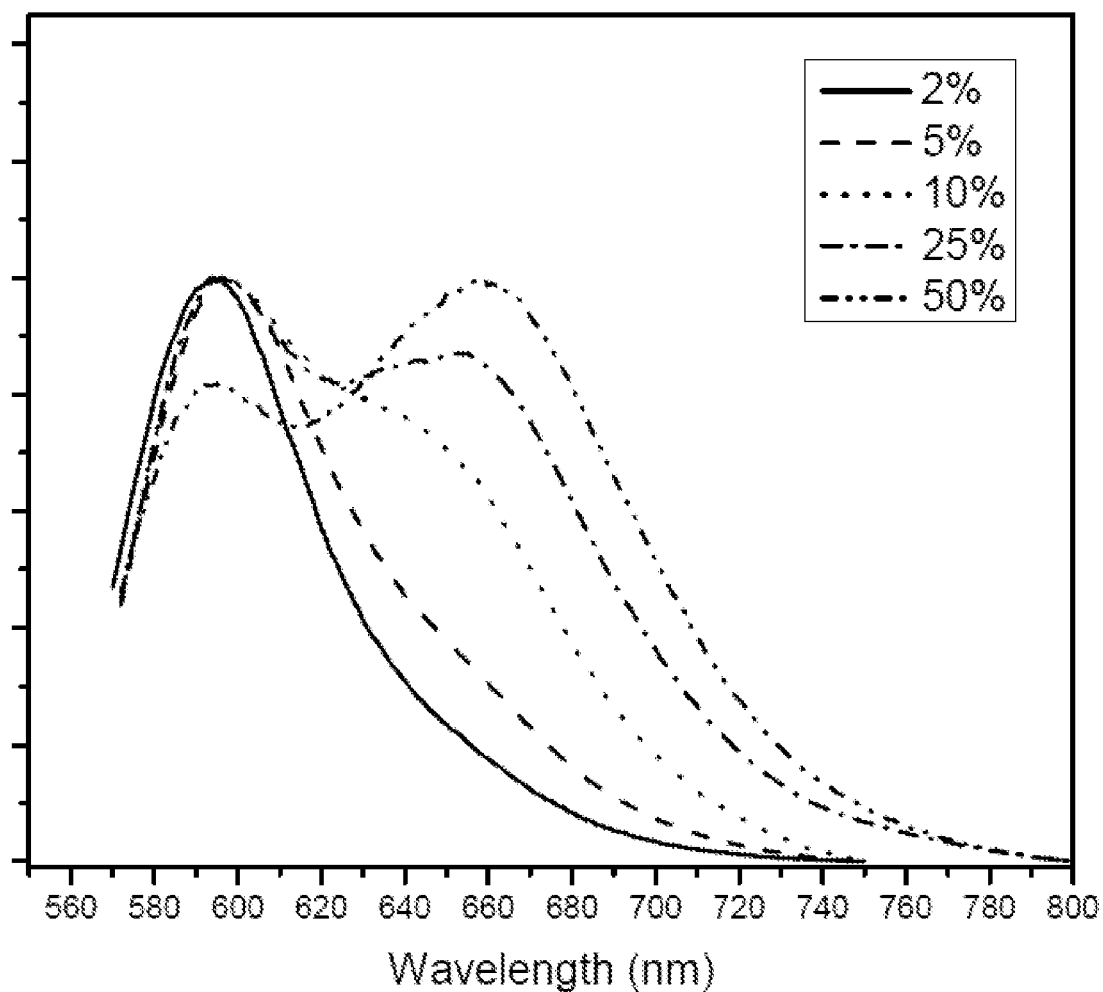
FIG. 13C shows the fluorescence spectra of the Pdots in water. As can be seen, the emission spectra of the polymers in THF exhibit similar FWHM for all the polymers. However, the Pdots shows quite different FWHM because of the chromophore packing in the nanoparticles. Narrow-band emissions can be obtained by adjusting the BODIPY ratio relative to the general fluorene monomer.
Figure 14A:
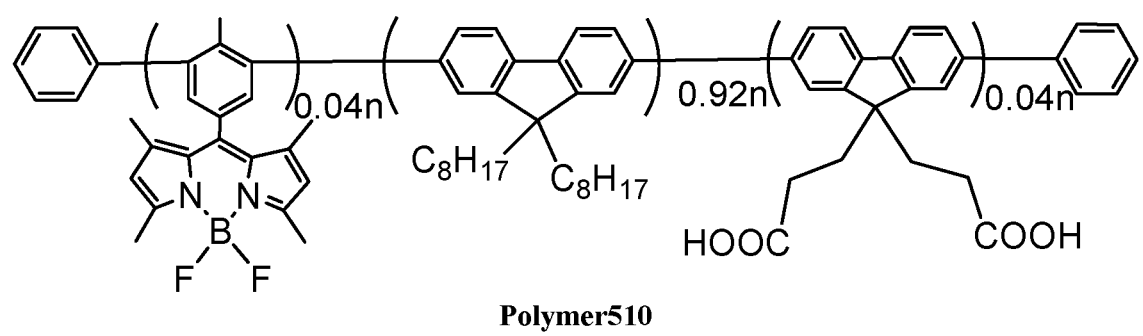
FIG. 14A shows the chemical structure of a narrow-band emissive polymer (Polymer510) synthesized by using the BODIPY monomer 1a in FIG. 12 as narrow-band monomer and several general monomers.
Figure 14B:
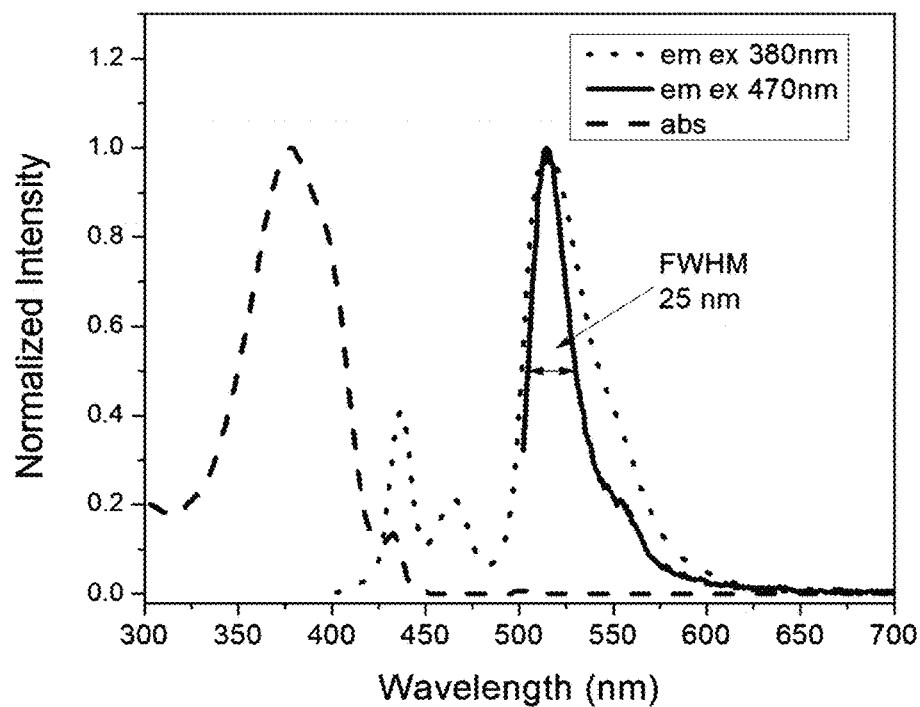
FIG. 14B shows the absorption spectrum and emission spectra of the Polymer510 Pdots in water. When excited at 380 nm, the Pdot emission exhibits a FWHM of 41 nm. When excited at 470 nm, the Pdot emission exhibits a FWHM of 25 nm. The fluorescence quantum yield was measured to be 64%.

FIG. 13A shows a series of fluorene-BODIPY copolymers that include a general monomer fluorene and a narrow-band monomer (BODIPY Monomer 2a in FIG. 12) at different molar ratios. FIG. 13B shows the fluorescence spectra of the polymers in a good solvent tetrahydrofuran (THF). FIG. 13C shows the fluorescence spectra of the Pdots in water (THF). As can be seen, the emission spectra of the polymers in THF exhibit similar FWHM for all the polymers. However, the Pdots shows quite different FWHM because of the densely packing of polymer chromophores in the nanoparticles. Narrow-band emissions can be obtained by adjusting the BODIPY ratio relative to the general fluorene monomer. FIG. 14A shows the chemical structure of a narrow-band emissive polymer (Polymer510) synthesized by using the BODIPY monomer1a as narrow-band monomer and several general monomers. FIG. 14B shows the absorption spectrum and emission spectra of the Polymer510 Pdots in water. When excited at 380 nm, the Pdot emission exhibits a FWHM of 41 nm. When excited at 470 nm, the Pdot emission exhibits a FWHM of 25 nm. The fluorescence quantum yield was measured to be 64%. These properties indicate that narrow-band emission can be obtained in the Pdots.

Figure 15A:
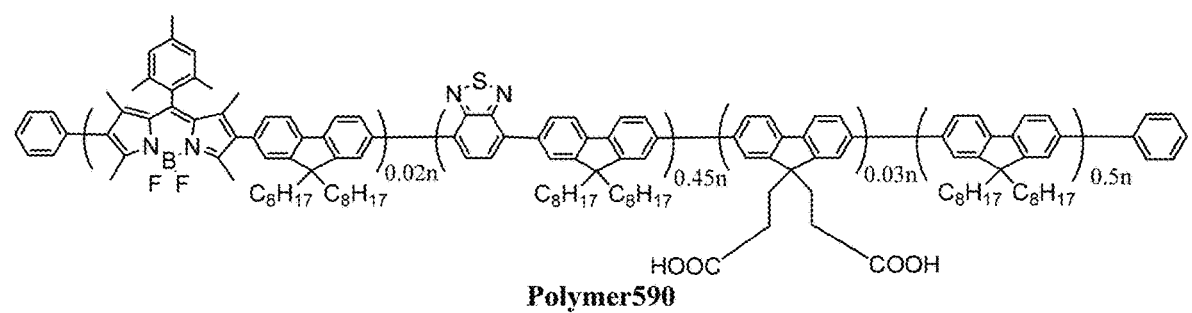
FIG. 15A shows the chemical structure of a narrow-band emissive polymer (Polymer 590) synthesized by using the BODIPY monomer 2a in FIG. 12 as narrow-band monomer and several general monomers.
Figure 15B:
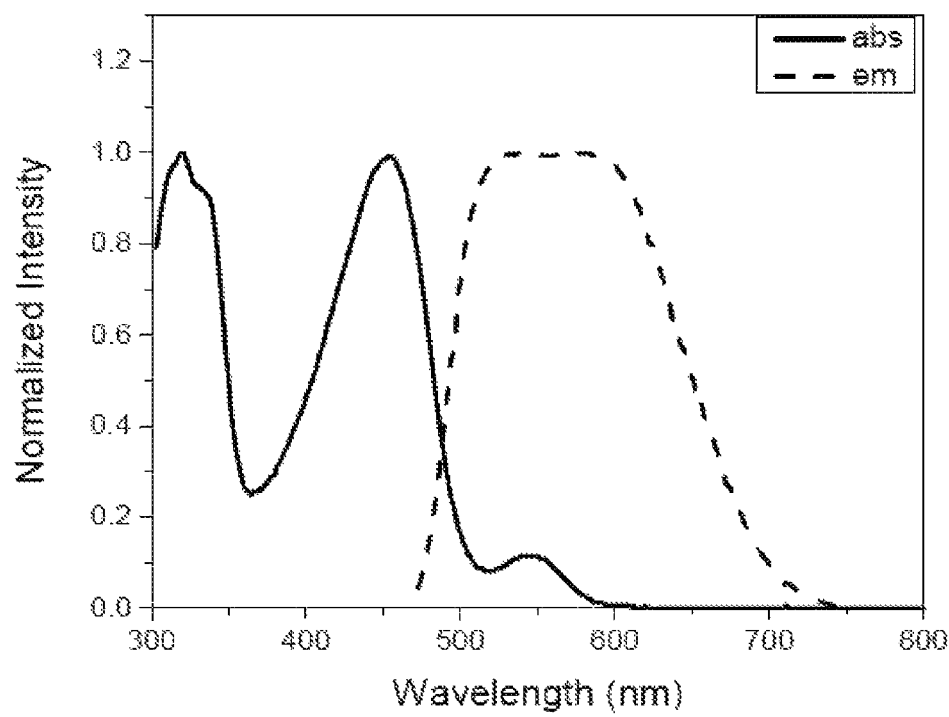
FIG. 15B shows the absorption and emission spectra of the Polymer590 in THF.
Figure 15C:
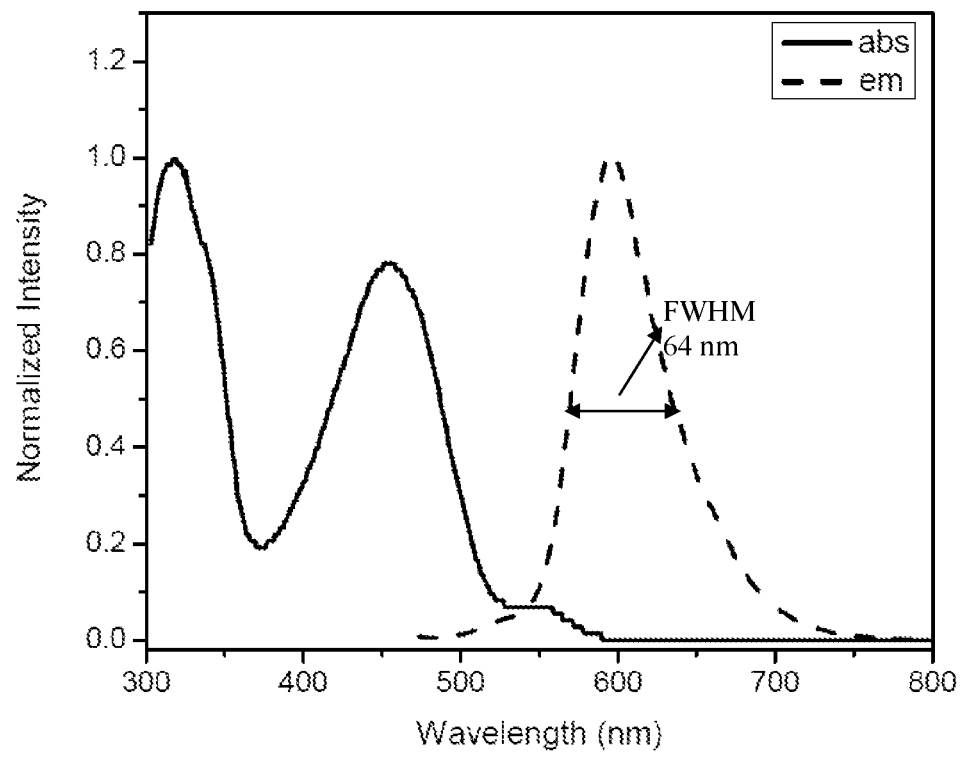
FIG. 15C shows the absorption and emission spectra of the Polymer590 Pdots in water. The Pdot emission exhibits a FWHM of 64 nm and fluorescence quantum yield is 0.13. As indicated by the spectra, the polymer shows broad emission in a good solvent such as THF. However, the Pdots show narrow-band emission.
Figure 16A:
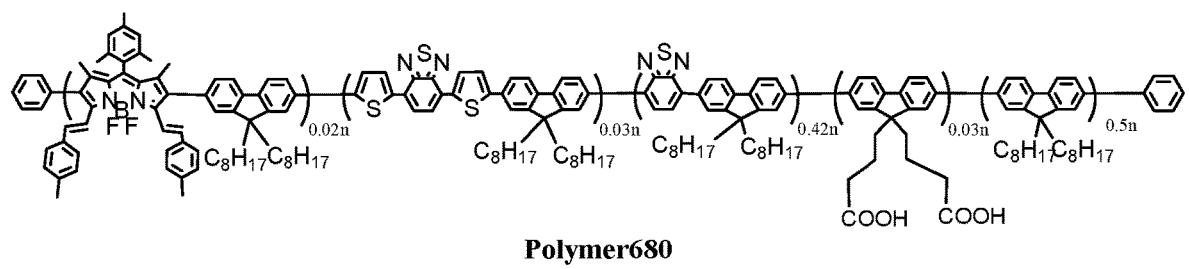
FIG. 16A shows the chemical structure of a narrow-band emissive polymer (Polymer 680) synthesized by using the BODIPY monomer 3a in FIG. 12 as narrow-band monomer and several general monomers.
Figure 16B:
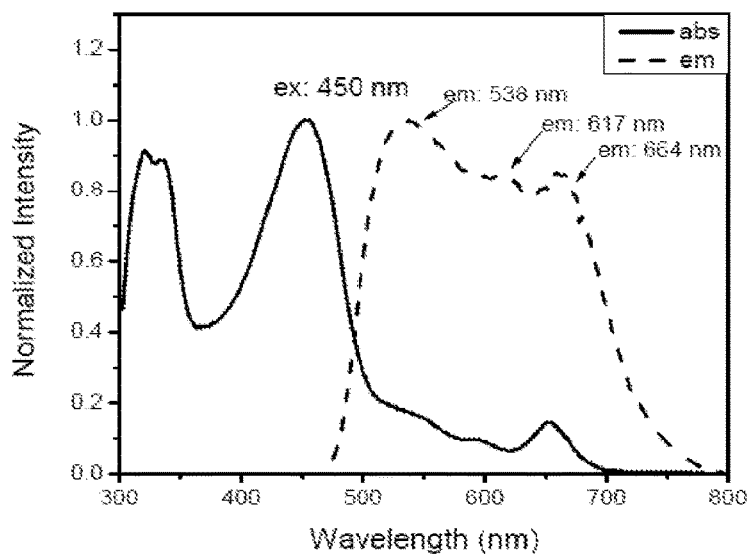
FIG. 16B shows the absorption and emission spectra of the Polymer680 in THF.
Figure 16C:
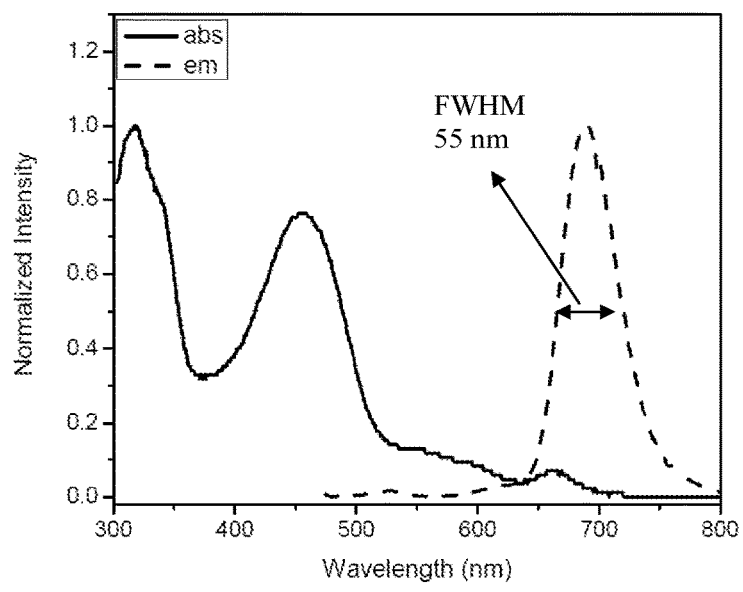
FIG. 16C shows the absorption and emission spectra of the Polymer680 Pdots in water. The Pdot emission exhibits a FWHM of 55 nm and fluorescence quantum yield is 0.19. As indicated by the spectra, the polymer shows broad emission in a good solvent such as THF. However, the Pdots show narrow-band emission.
Figure 17:
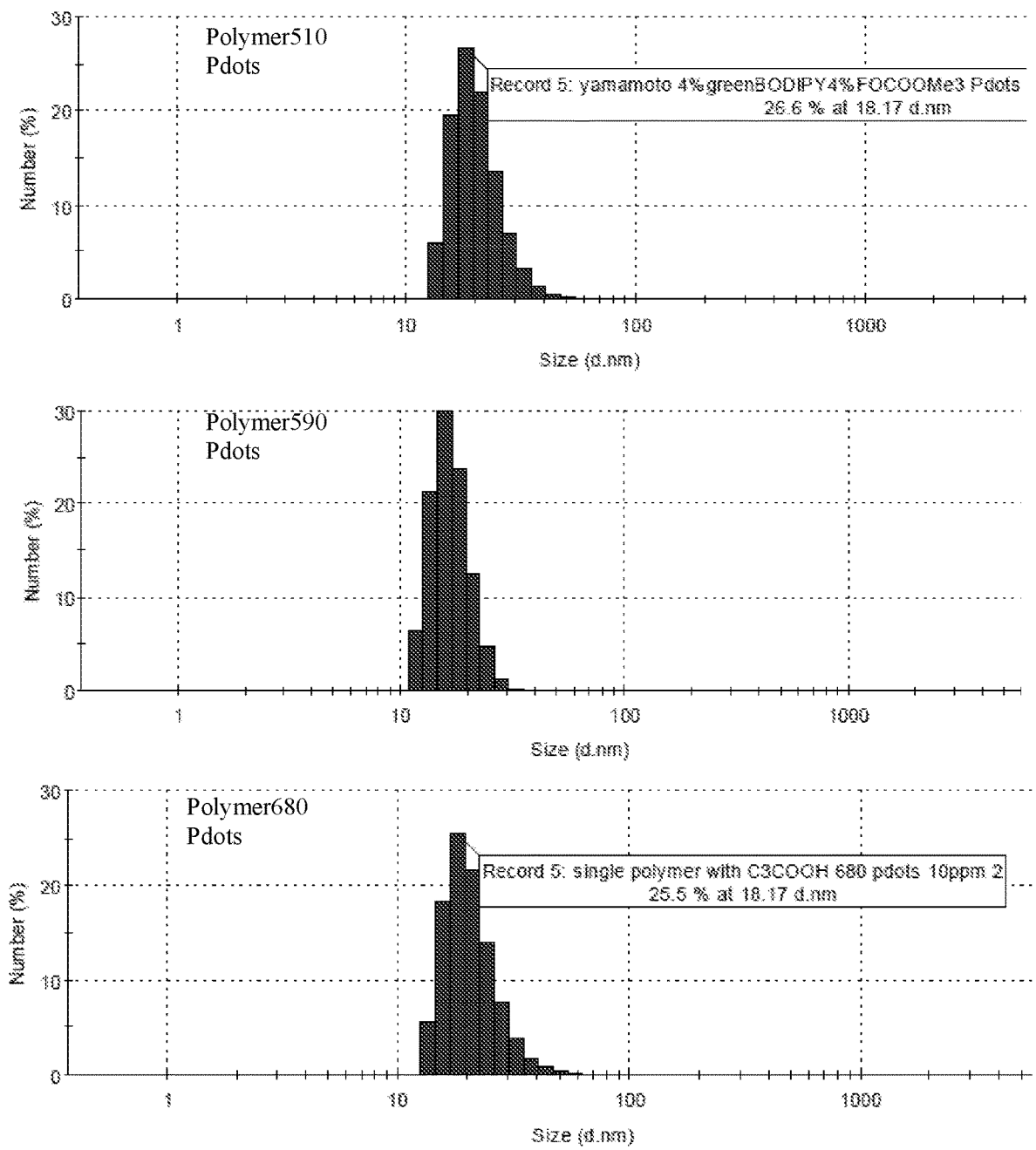
FIG. 17 shows particle size distributions of narrow-band emissive Polymer510 Pdots, Polymer590 Pdots, and Polymer680 Pdots, respectively. The data were measured by dynamic light scattering.

FIG. 15A shows the chemical structure of a narrow-band emissive polymer (Polymer2 590) synthesized by using the BODIPY monomer 2a as narrow-band monomer and several general monomers. FIG. 15B shows the absorption and emission spectra of the Polymer590 in THF. FIG. 15C shows the absorption and emission spectra of the Polymer590 Pdots in water. The Pdot emission exhibits a FWHM of 64 nm and fluorescence quantum yield is 0.13. As indicated by the spectra, the polymer shows broad emission in a good solvent such as THF. However, the Pdots show narrow-band emission. FIG. 16A shows the chemical structure of a narrow-band emissive polymer (Polymer3 680) synthesized by using the BODIPY monomer 3a as narrow-band monomer and several general monomers. FIG. 16B shows the absorption and emission spectra of the Polymer680 in THF. FIG. 16C shows the absorption and emission spectra of the Polymer680 Pdots in water. The Pdot emission exhibits a FWHM of 55 nm and fluorescence quantum yield is 0.19. As indicated by the spectra, the polymer shows broad emission in a good solvent such as THF. However, the Pdots show narrow-band emission. FIG. 17 show the particle size distributions of narrow-band emissive Polymer510 Pdots, Polymer590 Pdots, and Polymer680 Pdots, respectively. The data were measured by dynamic light scattering. All the Pdots show small particle size in the range of 10~20 nm.

Example 6: Bioconjugation of Narrow-Band Emissive Fluorene-BODIPY Pdots

The present example provides a method for bioconjugation to the narrow-band emissive fluorene-BODIPY Pdots.

Bioconjugation was performed by utilizing the EDC-catalyzed reaction between carboxyl groups on fluorene-BODIPY Pdots surface and amine groups on biomolecules. In a typical bioconjugation reaction, 80 µL of polyethylene glycol (5% w/v PEG, MW 3350) and 80 µL of concentrated HEPES buffer (1 M) were added to 4 mL of functionalized Pdot solution (50 µg/mL in MilliQ water), resulting in a Pdot solution in 20 mM HEPES buffer with a pH of 7.3. Then, 240 µL of streptavidin (purchased from Invitrogen (Eugene, Oreg., USA)) was added to the solution and mixed well on a vortex. 80 µL of freshly-prepared EDC solution (10 mg/mL in MilliQ water) was added to the solution, and the above mixture was left on a rotary shaker. After 4 hours at room temperature, Triton-X 100 (0.25% (w/v), 80 µL) and BSA (2% (w/v), 80 µL) were added. The mixture was then left on rotary shaker for one hour. Finally, the resulting Pdot bioconjugates were separated from free biomolecules by gel filtration using Sephacryl HR-300 gel media.

Example 7: Flow Cytometry and Confocal Imaging of MCF-7 Cells Labeled with Narrow-Band Emissive Fluorene-BODIPY Pdots The present example provides a method for using the narrow-band emissive fluorene-BODIPY Pdots for cellular labeling.

Cell Culture. The breast cancer cell line MCF-7 was ordered from American Type Culture Collection (ATCC, Manassas, Va., USA). Cells were cultured at 37° C., 5% $CO_2$ in Eagles minimum essential medium supplemented with 10% Fetal Bovine Serum (FBS), 50 U/mL penicillin, and 50 µg/mL streptomycin. The cells were cultured prior to experiments until confluence was reached. The cells were harvested from the culture flask by briefly rinsing with culture media followed by incubation with 5 mL of Trypsin-EDTA solution (0.25 w/v % Trypsin, 0.53 mM EDTA) at 37° C. for 5-15 minutes. After complete detachment, the cells were rinsed, centrifuged, and resuspended in 1×PBS buffer. The cell concentration was determined by microscopy using a hemocytometer.

Figure 18:
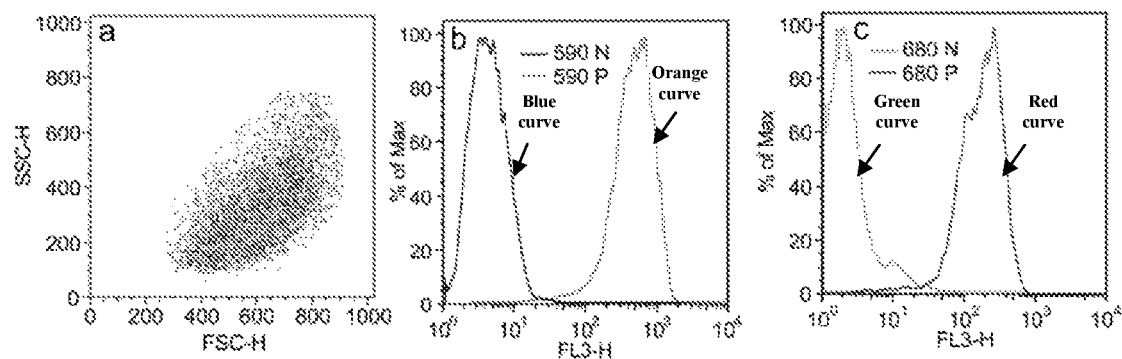
FIGS. 18A-C show flow cytometry results of Polymer590 Pdots and Polymer680 Pdots labeled MCF-7 cells, respectively.

Specific Labeling for Flow Cytometry. For specific cell labeling with the narrow-band emissive Pdot-streptavidin (Pdot-SA), a million cells were blocked with BlockAid blocking buffer (Invitrogen, Eugene, Oreg., USA) and then were incubated sequentially with biotinylated primary anti-EpCAM antibody (used to label the cell-surface EpCAM receptors on MCF-7 cells) and 20 µg/mL (based on Pdots) Pdot-SA for 30 minutes each, followed by two washing steps using labeling buffer. Finally, the specifically labeled cells were fixed in 0.6 mL 4% (v/v) paraformaldehyde solution. For the control labeling, no biotinylated primary anti-EpCAM antibody was added. Flow cytometry was operated on a BD FACS Canto flow cytometer (BD Biosciences, San Jose, Calif., USA). A 488 nm laser was used for excitation and emission was collected through FITC channel equipped with a 500 nm long-pass filter and a 530/30 nm bandpass filter. Data was analyzed using the FACSDival software. FIG. 18 shows flow cytometry results of Polymer590 Pdots and Polymer680 Pdots labeled MCF-7 cells, respectively. Panel A shows the side scattering (SSC) versus forward scattering (FSC). Panel B shows the fluorescence intensity distributions of the MCF-7 cells labeled with Polymer590 Pdots. Blue curve is the negative control, and Orange curve is the positive labeling. Panel C shows the fluorescence intensity distributions of the MCF-7 cells labeled with Polymer680 Pdots. Green curve is the negative control, and Red curve is the positive labeling. As can be seen, both the Polymer590 and Polymer680 Pdots are specific for labeling the cellular targets without nonspecific labeling.

Figure 19A:
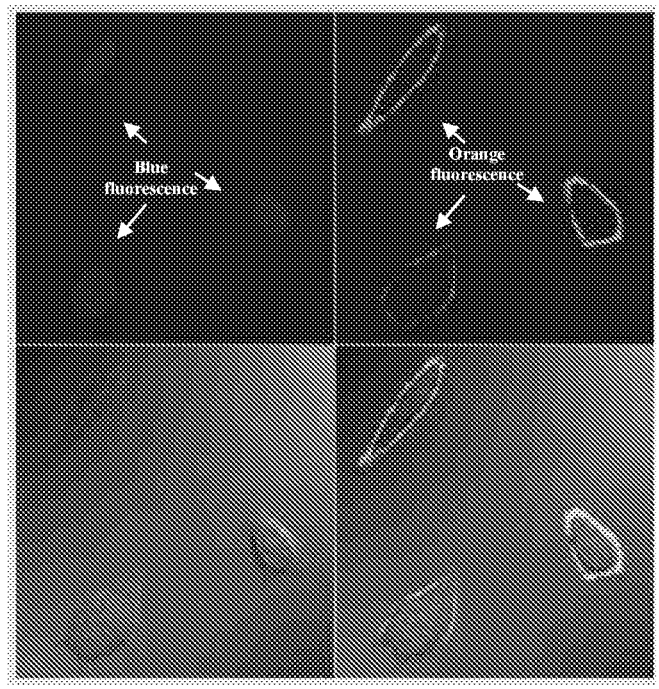
FIG. 19A shows fluorescence images of MCF-7 breast-cancer cells labeled with Polymer590 Pdot-streptavidin. Negative labeling performed under the same condition but in the absence of the biotinylated primary antibody does not show fluorescence signal. Images of blue fluorescence from the nuclear stain Hoechst 34580; orange fluorescence images from Pdot; Nomarski (DIC) images; combined fluorescence images.
Figure 19B:
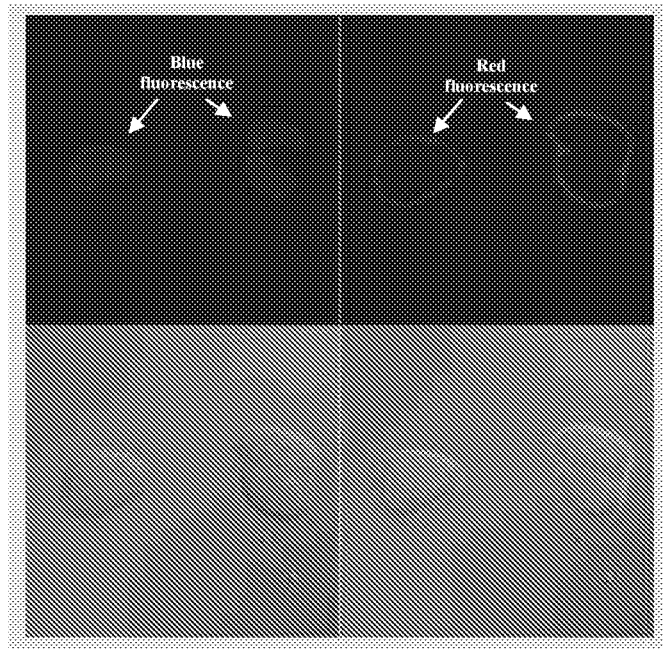
FIG. 19B shows fluorescence images of MCF-7 breast-cancer cells labeled with Polymer680 Pdot-streptavidin. Negative labeling performed under the same condition but in the absence of the biotinylated primary antibody does not show fluorescence signal. Images of blue fluorescence from the nuclear stain Hoechst 34580; red fluorescence images from Pdot; Nomarski (DIC) images; combined fluorescence images.
Figure 20:
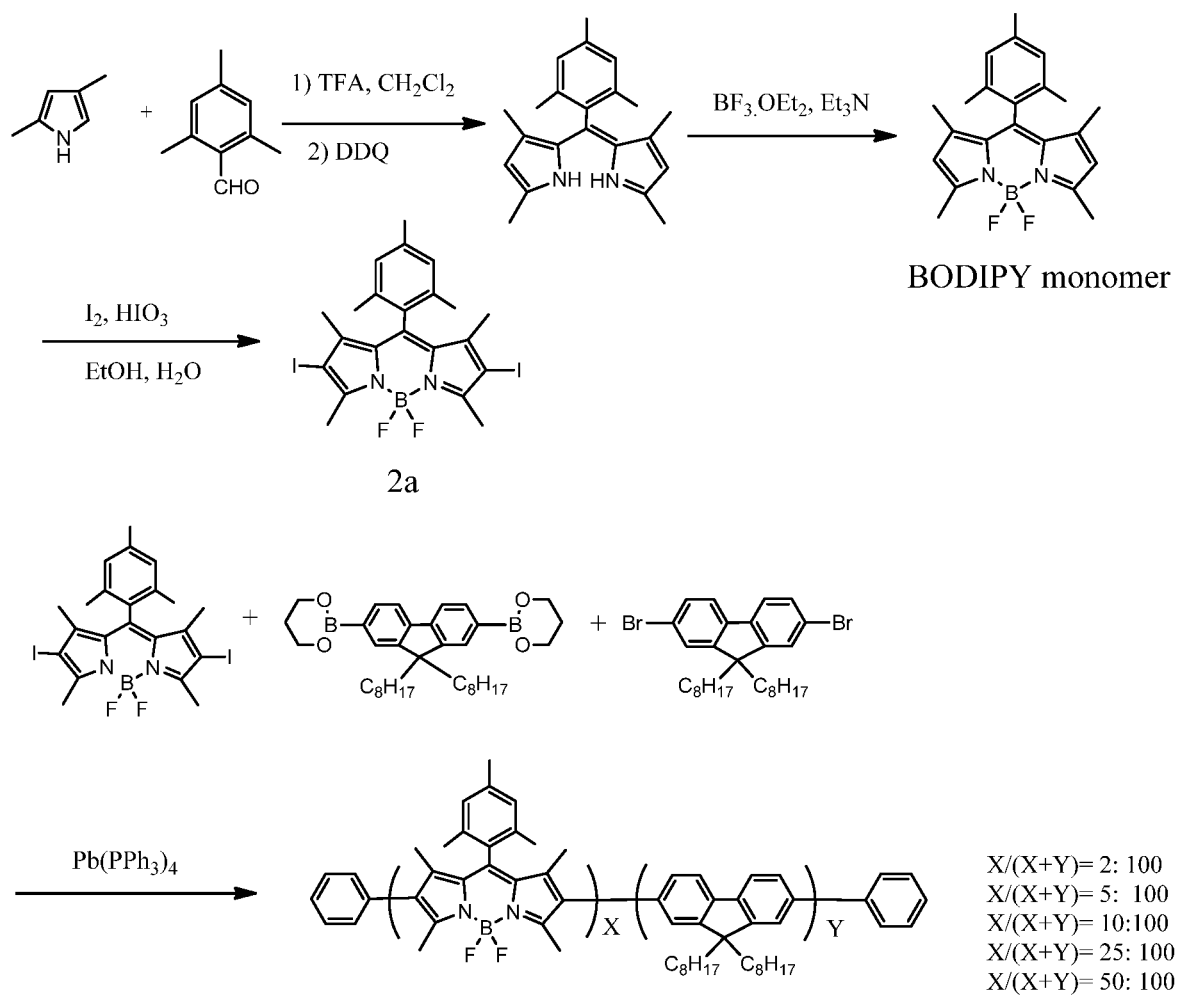
FIG. 20 shows multi-step synthesis of a series of copolymers that include a general monomer fluorene and a narrow-band monomer (BODIPY Monomer 2a in FIG. 12) at different molar ratios.

Specific Labeling for Cellular Surface Imaging. For labeling cellular surface with the narrow-band emissive Pdot-SA conjugates, live MCF-7 cells in the glass-bottomed culture dish were blocked with BlockAid blocking buffer (Invitrogen, Eugene, Oreg., USA). Then the MCF-7 cells were incubated sequentially with biotinylated primary anti-EpCAM antibody (were used to label the cell-surface EpCAM receptors on MCF-7 cells) and 5 nM Pdot-SA for 30 minutes each, followed by two washing steps after each incubation. For the control, no biotinylated primary anti-EpCAM antibody was added. The Pdot-tagged cells were then counterstained with Hoechst 34580 and imaged immediately on a fluorescence confocal microscope (Zeiss LSM 510). FIGS. 19A and 19B shows fluorescence images of MCF-7 breast-cancer cells labeled with Polymer590 Pdot-streptavidin and Polymer590 Pdot-streptavidin, respectively. Negative labeling performed under the same condition but in the absence of the biotinylated primary antibody does not show fluorescence signal, again indicating the narrow-band emissive Pdot probes are specific for cellular labeling.

Example 8: Synthesis of Narrow-Band Emissive Polymers (e.g., PFS and PFS5.5) Using Squaraine Derivatives as Narrow-Band Monomers and the Optical Characterizations The present example provides example methods for obtaining a narrow-band emissive fluorene-squaraine copolymers, such as PFS (polymer690) (shown in FIG. 24A) and PFS5.5 (shown in FIG. 24B).

Synthesis of Fluorene-Squaraine Copolymer PFS (Polymer690). Toluene (8 ml) and $Na_2CO_3$ (2M, 5 ml) were in the flask and degassed for half hour. A mixture of 9,9-dioctyl-2,7-dibromofluorene (105 mg, 0.192 mmol), 9,9-dioctyl-2,7-dibromofluorene (112 mg, 0.2 mmol), 2,5-bis[(5-bromo-1-hexadecyl-3,3-dimethyl-2,3-dihydroindole-2-ylidene)methyl]cyclobutendiylium-1,3-diolate (8 mg, 0.008 mmol), $Bu_4NBr$ (3 mg, 0.008 mmol) were added. The mixture was degassed and refilled with $N_2$ (repeated 4 times) before addition of $Pd(PPh_3)_4$ (8 mg. 0.007 mmol), the resulting mixture was stirred at 90° C. for 40 hours and phenylboronic acid (20 mg) dissolved in THF (0.2 ml) was added. After 2 hour, bromobenzene (0.2 ml) was added and then stirred for more 3 hours. The mixture was poured into MeOH (40 ml), then was filtered the precipitate. The precipitate were washed by MeOH, $H_2O$ and Acetone to remove monomers, small oligomer and salts, The solid was dissolved in DCM (5 ml), filtered through 0.2 um membrane and re-precipitated in MeOH (30 ml), the solid was stirred in acetone (40 ml) for 4 Hours and filtered off and dried in high vacuum.

Figure 24A:
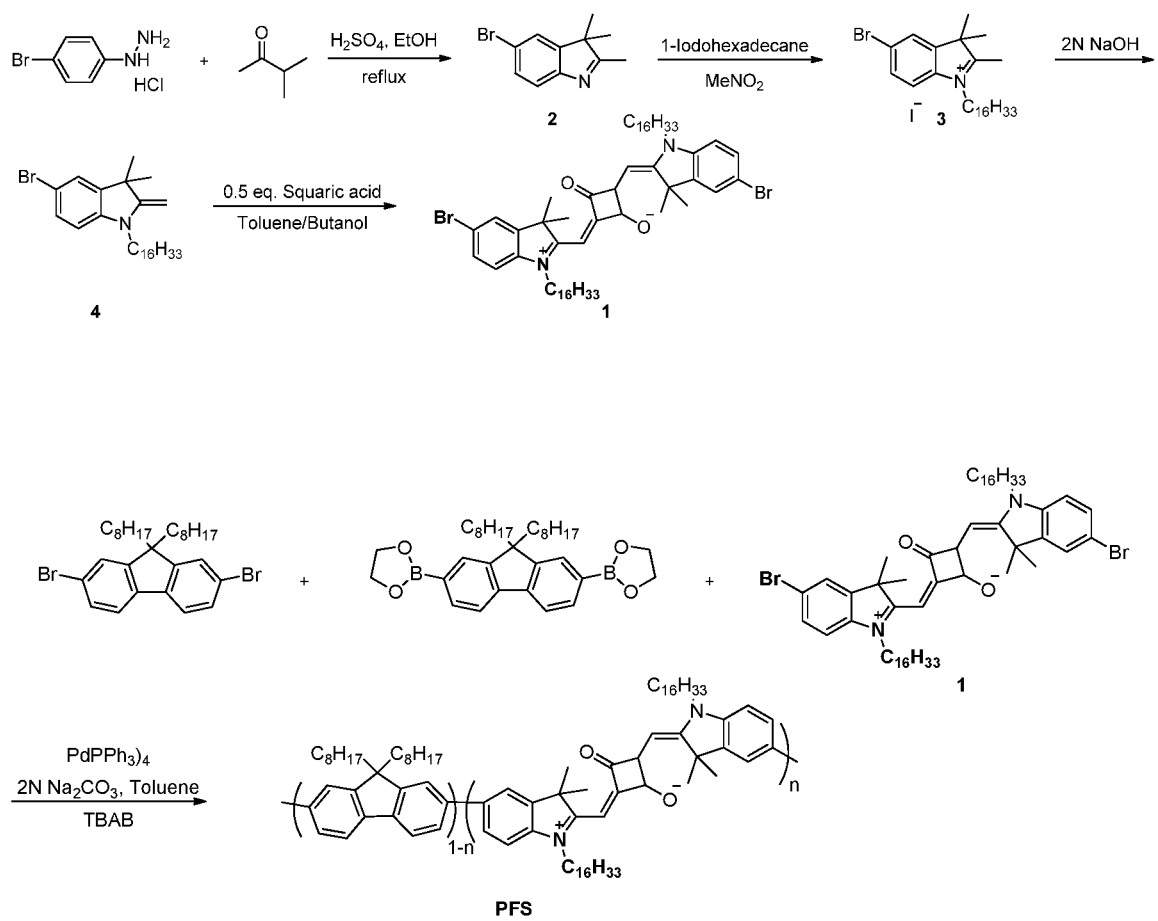
FIG. 24A shows multi-step synthesis of a squaraine derivative 1 and a narrow-band emissive polymer PFS (Polymer690) using a squaraine derivative as a narrow-band monomer and fluorene as general monomer.
Figure 24B:
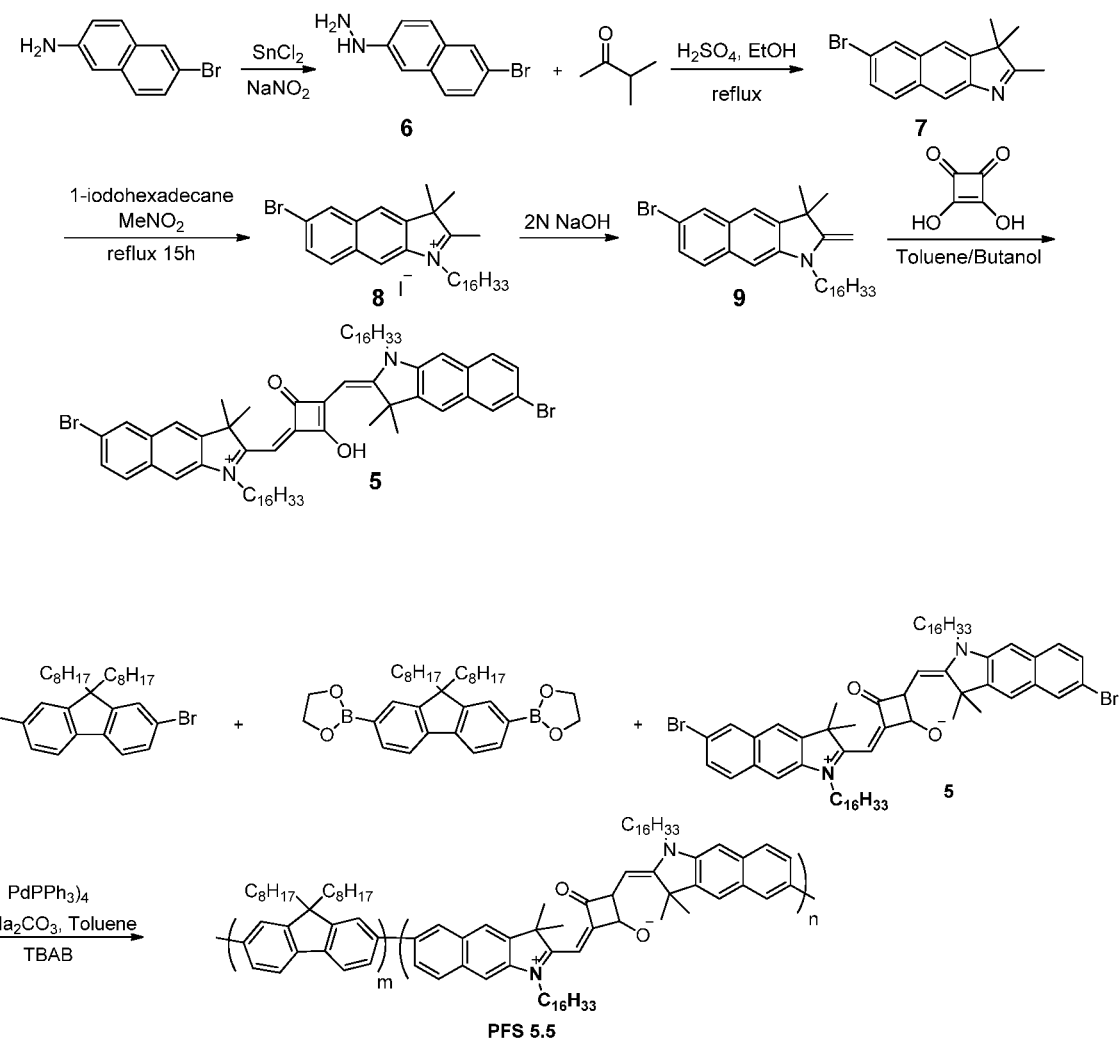
FIG. 24B shows multi-step synthesis of a squaraine derivative 5 and the narrow-band emissive polymer PFS5.5 using the squaraine as narrow-band monomer and fluorene as general monomer.
Figure 24C:
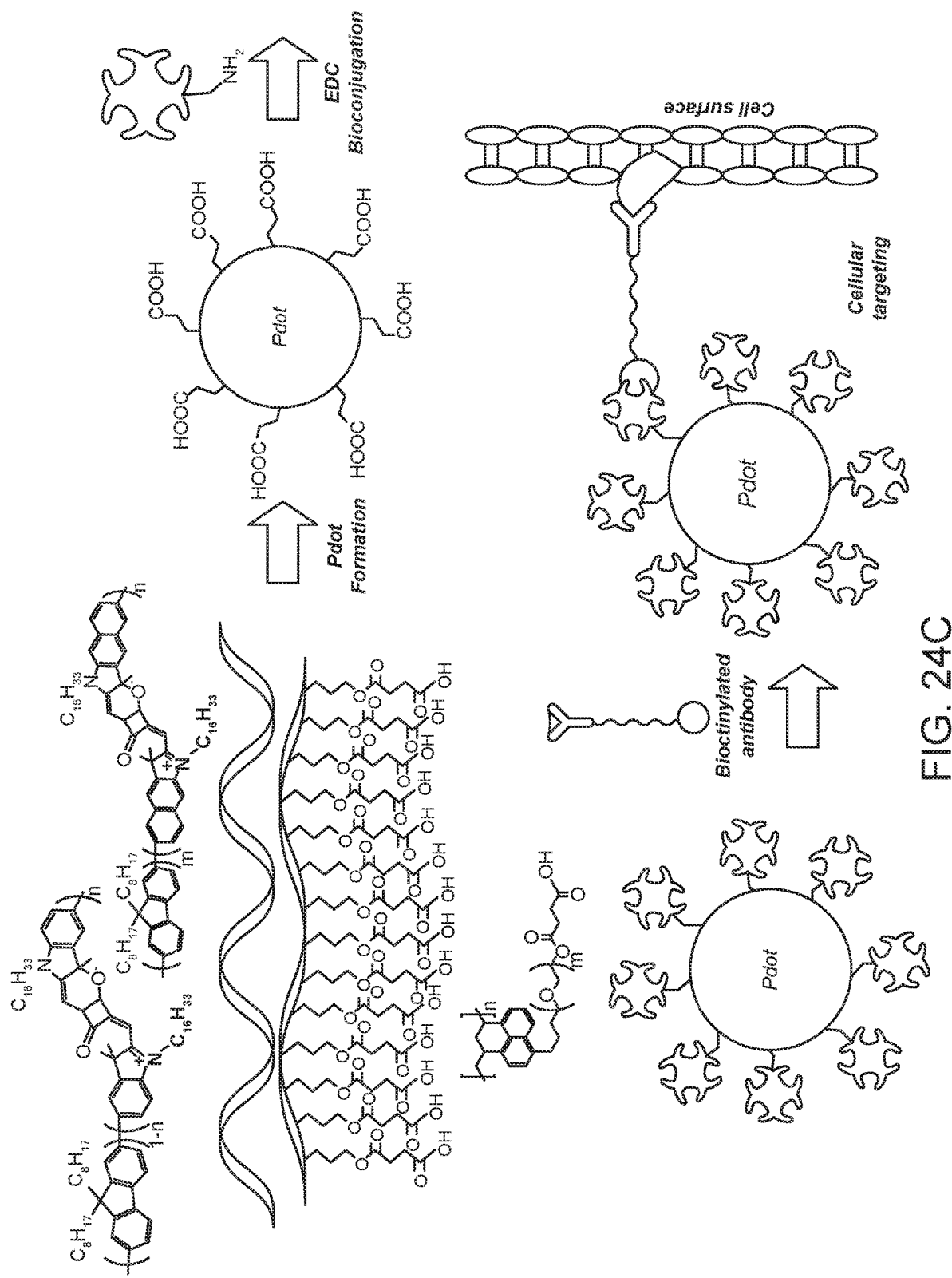
FIG. 24C shows a schematic illustration of the squaraine based narrow emissive polymer dots and Pdot-bioconjugates for specific cellular targeting.
Figures 25A, 25B:
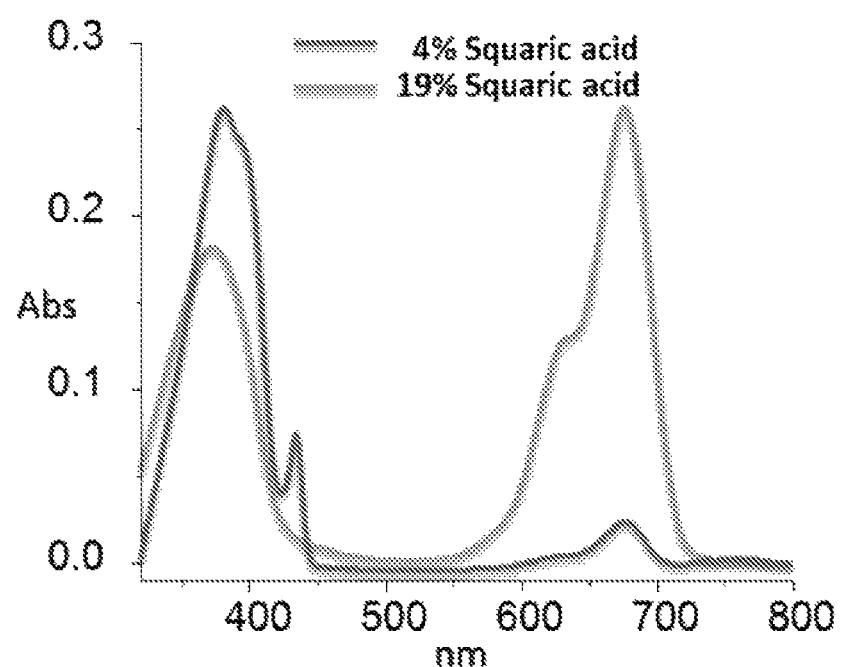
FIG. 25A shows photophysical data of the narrow-band emissive fluorene-4% squaraine copolymer and fluorene-19% squaraine copolymer.
FIG. 25B shows absorption spectra data of the fluorene-4% squaraine copolymer and fluorene-19% squaraine copolymer.
Figure 25C:
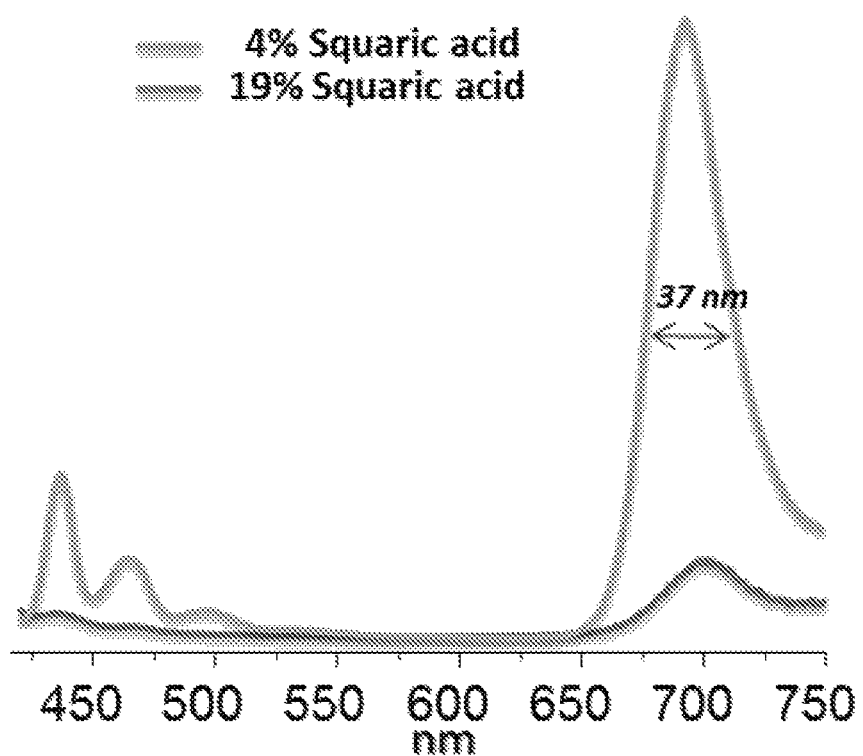
FIG. 25C shows emission spectra of the fluorene-4% squaraine copolymer and fluorene-19% squaraine copolymer excited at 405 nm. The fluorene-4% squaraine copolymer Pdots shows emission FWHM of 37 nm at 690 nm and fluorescence quantum yield is 0.23.
Figure 25D:
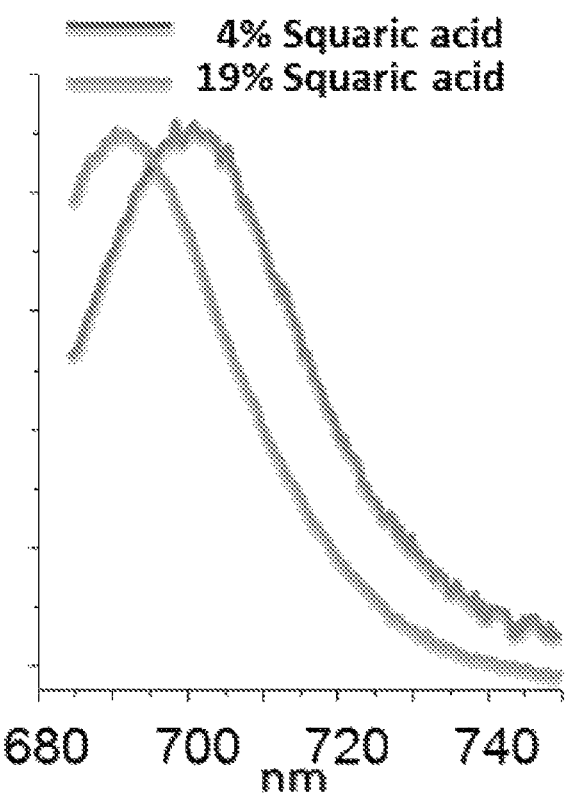
FIG. 25D shows emission spectra of the fluorene-4% squaraine copolymer and fluorene-19% squaraine copolymer excited at 675 nm.

FIG. 24A shows multi-step synthesis of narrow-band emissive polymer PFS (Polymer690) using a squaraine derivative as narrow-band monomer and fluorene as general monomer. FIG. 25A shows photophysical data of the narrow-band emissive fluorene-4% squaraine copolymer and fluorene-19% squaraine copolymer. FIG. 25B shows absorption spectra data of the fluorene-4% squaraine copolymer and fluorene-19% squaraine copolymer. FIG. 25C shows emission spectra of the fluorene-4% squaraine copolymer and fluorene-19% squaraine copolymer excited at 405 nm. The fluorene-4% squaraine copolymer Pdots shows emission FWHM of 37 nm at 690 nm and fluorescence quantum yield is 0.23. FIG. 25D shows emission spectra of the fluorene-4% squaraine copolymer and fluorene-19% squaraine copolymer excited at 675 nm. These data shows that both narrow-band emission and high fluorescence quantum yield can be obtained in the fluorene-squaraine copolymer based Pdots.

Synthesis of 5-Bromo-2,3,3-trimethylindolenine (Compound 2). A mixture of 4-bromophenylhydrazine (4.46 g, 20 mmol), isopropylmethylketone (3.44 g, 40 mmol), EtOH (80 mL) and concentrated $H_2SO_4$ (1.86 g, 40 mmol) in a 125 mL round bottom flask was heated under reflux for overnight. After cooling, the mixture was diluted with $CH_2Cl_2$ (100 mL) and was washed with 10% $NaHCO_3$ (100 ml) twice and water (100 mL) twice, then dried over Magnesium sulfate and filtered. The solution was then passed through a short column quickly, and evaporated under reduced pressure to get 4.25 g as a reddish oil. (Yield: 90%). $^1$H NMR (500 MHz, $CDCl_3$)=7.40~7.38 (m, 3H), 2.25 (s, 3H), 1.28 (s, 6H). $^{13}$C NMR ($CDCl_3$)=187.8, 152.2, 147.38, 130.1, 124.3, 120.8, 118.3, 53.5, 22.4, 14.9. HRMS (ESI): ($M^+$, $C_{11}H_{12}BrN$) calcd 237.0153; found 237.0150.

Synthesis of 5-Bromo-1-hexadecyl-2,3,3-trimethyl-3H-indolium Iodide (Compound 3). A mixture of 5-Bromo-2,3,3-trimethylindolenine 2 (900 mg, 3.78 mmol), 1-iodohexadecane (1.6 g, 4.45 mmol) and nitromethane (5 mL) was refluxed for overnight. After cooling and concentrating the mixture under reduced pressure, diethyl ether (25 mL) was added. The solution was cooled to 4° C. for 1 h, and the precipitate was collected, then washed with diethyl ether (50 mL) and dried. The yellow solid, 1.5 g, was obtained (Yield: 70%). $^1$H NMR (500 MHz, $CDCl_3$)=7.70~7.62 (m, 3H), 4.63 (t, J=7.6 Hz, 2H), 3.08 (s, 3H), 1.91-1.87 (m, 2H), 1.66 (s, 6H), 1.43~1.21 (m, 26H), 0.85 (t, J=7.0, 3H). $^{13}$C NMR ($CDCl_3$)=195.6, 143.4, 139.9, 132.6, 126.6, 124.3, 117.0, 54.7, 50.4, 31.7, 29.5, 29.4, 29.3, 29.1, 28.9, 27.7, 26.6, 23.0, 22.5, 17.2, 13.9. HRMS (ESI): ($M^+$, $C_{27}H_{45}BrIN$) calcd 589.1780; found 589.1782.

Synthesis of 5-bromo-1-hexadecyl-3,3-dimethyl-2-methyleneindoline (Compound 4). 5-Bromo-1-hexadecyl-2,3,3-trimethyl-3H-indolium Iodide 3 (2.92 g, 3.26 mmol) was suspended in 2N NaOH aqueous solution (50 mL) and diethyl ether (50 mL), stirred for 30 minutes, extracted with diethyl ether and water, then dried and evaporated under vacuum. The product was a yellowish oil, 1.84 g (Yield: 98%). $^1$H NMR (500 MHz, $CDCl_3$)=7.26 (s, 1H), 7.20 (d, J=2.0 Hz, 1H), 7.13 (s, 1H), 3.85 (d, J=2.0 Hz, 2H), 2.43 (t, J=7.3 Hz, 2H), 1.61 (m, 2H), 1.30~1.22 (m, 26H), 0.88 (t, J=7.0 Hz, 3H). HRMS (ESI): ($M^+$, $C_{27}H_{44}BrN$) calcd 461.2657; found 461.2661.

Synthesis of 2,5-Bis [(5-bromo-1-hexadecyl-3,3-dimethyl-2,3-dihydroindole-2-ylidene) methyl] cyclobutendiylium (Compound 1). A mixture of 3,4-dihydroxy-3-cyclobutene-1,2-dione 4 (105 mg, 0.9 mmol) and 5-Bromo-1-hexadecyl-3,3-dimethyl-2-methylene-2,3-dihydroindole (840 mg, 1.84 mmol) in toluene/butanol (1:1, 15 mL) was refluxed overnight with a Dean-Stark trap. After cooling to room temperature, the solvent was removed under vacuum. The residue was purified by silica gel with chromatography (PE/EA), and the product was obtained as a dark green solid, 500 mg (Yield: 50%). $^1$H NMR (500 MHz, $CDCl_3$)=7.45~7.41 (m, 4H), 6.87 (d, J=8.2 Hz, 2H), 6.61 (s, 2H), 3.98 (s, 4H), 1.81-1.75 (m, 16H), 1.44~1.28 (m, 52H), 0.86 (t, J=6.5 Hz, 6H). $^{13}$C NMR ($CDCl_3$)=182.2, 180.1, 169.4, 141.5, 130.6, 125.6, 116.5, 110.6, 49.3, 43.8, 31.9, 29.7, 29.67, 29.65, 29.57, 9.50, 29.44, 29.33, 27.02, 26.95, 22.67, 14.1.

General Procedure for the Synthesis of Squaraine Polymer PFS. Polymer PFS was synthesized using different feeding ratios of monomer by Suzuki Coupling. For example, in the synthesis of 1.5% PFS, 9, 9-Doctylfluorene-2, 7-diboronic acid bis(1, 3-propanediol)ether (11.68 mg, 0.2 mmol), 9, 9-Dioctyl-2, 7-dibromofluorene (105.3 mg, 0.193 mmol), 2,5-Bis[(5-bromo-1-hexadecyl-3,3-dimethyl-2,3-dihydroindole-2-ylidene)methyl]cyclobutendiylium 1 (8 mg, 0.008 mmol), TBAB (2.5 mg, 0.008 mmol), and $Pd(PPh_3)_4$ (8 mg, 3.5 mol %) was added in Toluene/2N $Na_2CO_3$ 1:1 (10 mL). The mixture was degassed and refilled with $N_2$, then refluxed for 2 days. Phenylboronic acid (20 mg), dissolved in THF (0.5 mL), was added, and after 2 h, bromobenzene (0.5 mL) was added and further stirred for 3 h. The mixture was poured into Methanol (100 mL), and the precipitate was filtered, washed with methanol, water and acetone to remove monomer, small oligomers, and inorganic salts. The crude product was dissolved in DCM (7 mL), filtered with 0.2 μm membrane and re-precipitated in methanol (75 mL). The powder was stirred in acetone (100 mL) for 4 h and collected by filtration and dried in vacuum.

Synthesis of 6-bromo-2,3,3-trimethyl-3H-benzo[f]indole (Compound 7). 6-bromonaphthalen-2-amine (2.5 g, 11.25 mmol) was used to synthesize compound 6,[3] (2.1 g, yield 80%). Without purification and following the procedure for making compound 2, compound 6 was used to synthesize compound 7 to obtain 2 g of product as a reddish oil (Yield: 80%). $^1$H NMR (500 MHz, $CDCl_3$)=8.09 (s, 1H), 7.88 (d, J=8.9 Hz, 2H), 7.79~7.74 (m, 2H), 7.61-7.59 (m, 1H), 2.37 (s, 3H), 1.52 (s, 6H). $^{13}$C NMR ($CDCl_3$)=151.2, 149.2, 133.3, 132.3, 131.9, 131.6, 131.3, 131.1, 129.6, 128.6, 127.9, 127.0, 124.1, 124.0, 121.0, 118.1, 23.1, 22.2, 15.7. HRMS (ESI): ($M^+$, $C_{15}H_{14}BrN$) calculated 287.0310; found 287.0308.

Synthesis of 6-bromo-1-hexadecyl-2,3,3-trimethyl-3H-benzo[f]indol-1-ium iodide (Compound 8). Following the procedure to make compound 3, we obtained compound 9 as a yellow oil, 1.5 g (Yield: 70%). $^1$H NMR (500 MHz, $CDCl_3$)=8.17 (s, 1H), 8.00~7.95 (m, 2H), 7.83-7.77 (m, 2H), 4.76 (t, J=7.6 Hz, 2H), 3.17 (s, 3H), 1.95~1.86 (m, 2H), 1.45~1.17 (m, 32H), 0.85 (t, J=7.0, 3H). HRMS (ESI): ($M^+$, $C_{31}H_{47}BrIN$) calcd 639.1937; found 639.1940.

Synthesis of 6-bromo-1-hexadecyl-3,3-dimethyl-2-methylene-2,3-dihydro-1H-benzo[f]indole (Compound 9). Following the procedure to make compound 4, we obtained compound 9 as a yellowish oil, 1.88 g (Yield: 90%). $^1$H NMR (500 MHz, $CDCl_3$)=7.87 (s, 1H), 7.80 (d, J=9.1 Hz, 1H), 7.57 (d, J=8.7 Hz, 1H), 7.42~7.39 (m, 1H), 6.95 (d, J=8.7 Hz, 1H), 3.94~3.92 (m, 2H), 3.56~3.54 (m, 2H), 1.65 (m, 2H), 1.33~1.20 (m, 26H), 0.87 (t, J=7.0 Hz, 3H). HRMS (ESI): ($M^+$, C31H46BrN) calcd 511.2814; found 511.2816.

Synthesis of 6-bromo-2-((Z)-(3-((E)-(6-bromo-1-hexadecyl-3,3-dimethyl-1H-benzo[f]indol-2(3H)-ylidene)methyl)-2-hydroxy-4-oxocyclobut-2-en-1-ylidene)methyl)-1-hexadecyl-3,3-dimethyl-3H-benzo[f]indol-1-iumn (Compound 5). Following procedure to make compound 4, we obtained compound 5 as a dark green solid, 350 mg (Yield: 45%). $^1$H NMR (500 MHz, $CDCl_3$)=8.06~8.04 (m, 4H), 7.77 (d, J=8.7 Hz, 2H), 7.64~7.62 (m, 2H), 7.30~7.29 (m, 2H), 6.02 (s, 2H), 4.08 (s, 4H), 1.86~1.61 (m, 16H), 1.45~1.21 (m, 52H), 0.87 (t, J=6.6 Hz, 6H). $^{13}$C NMR (CDCl$_3$)=182.7, 178.1, 170.9, 139.8, 134.4, 133.1, 132.8, 132.1, 131.5, 131.2, 131.1, 130.9, 130.4, 130.0, 129.5, 129.2, 128.6, 127.9, 126.9, 125.7, 124.7, 124.1, 123.8, 123.2, 117.7, 111.4, 110.7, 87.1, 86.0, 77.3, 77.0, 76.7, 50.9, 44.6, 43.7, 42.7, 32.6, 31.7, 30.8, 30.3, 29.5, 29.4, 29.2, 28.5, 28.2, 27.7, 27.2, 26.9, 26.6, 26.2, 25.3, 23.5, 22.5, 21.8, 21.6, 14.4, 14.2, 13.6.

General Procedure for the Synthesis of Squaraine Polymer PFS 5.5. Polymer PFS5.5 was synthesized using different feeding ratios of monomer by Suzuki Coupling following the same procedure as for the synthesis of the PFS polymer.

Preparation of Pdots. A solution of polymer PFS or PFS 5.5 with 20 wt % of PS-PEG-COOH or PSMA in THF (4 mL, 50 ppm) was injected into water (10 mL) under ultrasonication, respectively. THF was evaporated by N$_2$ flow at 70° C. and the solution was concentrated to 4-5 mL, followed by filtration through a 0.2 micron filter. Bioconjugation was performed by utilizing the EDC-catalyzed reaction between carboxyl groups on Pdots' surface and amine groups on biomolecules. In an example bioconjugation reaction, 80 µL of polyethylene glycol (5% w/v PEG, MW 3350) and 80 µL of concentrated HEPES buffer (1 M) were added to 4 mL of functionalized Pdot solution (50 mg/mL in MilliQ water), resulting in a Pdot solution in 20 mM HEPES buffer with a pH of 7.3. Then, 240 µL of streptavidin (from Invitrogen (Eugene, Oreg., USA)) was added to the solution and mixed well on a vortex. 80 µL of freshly-prepared EDC solution (10 mg/mL in MilliQ water) was added to the solution, and the above mixture was left on a rotary shaker. After 4 hours at room temperature, Triton-X 100 (0.25% (w/v), 80 µL) and BSA (2% (w/v), 80 µL) were added. The mixture was then left on rotary shaker for one hour. Finally, the resulting Pdot bioconjugates were separated from free biomolecules by gel filtration using Sephacryl HR-300 gel media.

Single-Particle Brightness Measurement. For the measurement of single-particle fluorescence brightness, samples were diluted in Milli-Q water, dried on cleaned glass coverslips (previously functionalized with (3-aminopropyl) trimethoxysilane (APTMS)), and imaged on a customized home-built wide-field epifluorescence microscope. Fluorescence intensity emitted per frame for a given particle was estimated by integrating the CCD signal over the fluorescent spot. The wide-field microscope was constructed by directing the 488-nm laser beam from a Sapphire laser (Coherent, Santa Clara, Calif. USA) or 405 nm laser beam from a diode laser (World Star Technologies, Toronto, Canada) into an inverted microscope (Nikon TE2000U, Melville, N.Y., USA) using home-built steering optics. Laser excitation power was measured at the nosepiece before the objective. The objective used for illumination and light collection was a Nikon CFI Plan Fluor 100×S Oil (with iris) objective with 100× magnification and 0.5-1.3 N.A (Nikon, Melville, N.Y., USA). Fluorescence signal was filtered by a 500 nm long pass filter (HQ500LP; Chroma, Rockingham, Vt., USA) and imaged onto an EMCCD camera (Photometrics Cascade: 512B, Tucson, Ariz. USA).

Figure 25F:
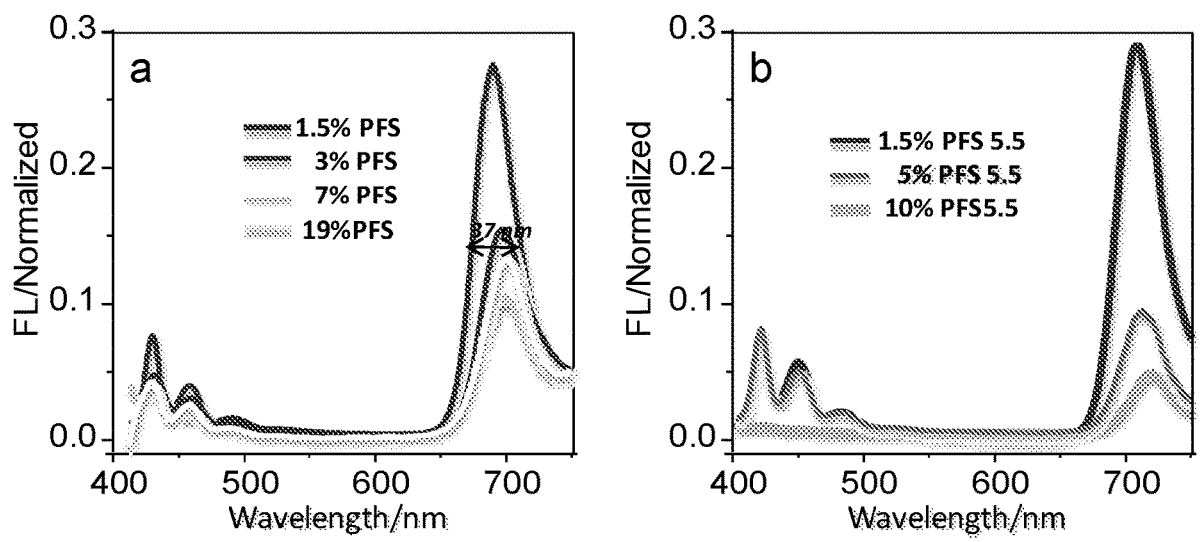
FIG. 25F shows the fluorescence emission spectra of the narrow-band emissive PFS Pdots and PFS 5.5 Pdots with varying squaraine ratio. The PFS-1.5% squaraine copolymer Pdots shows emission FWHM of 37 nm at 690 nm and fluorescence quantum yield is 0.30.
Figure 25G:
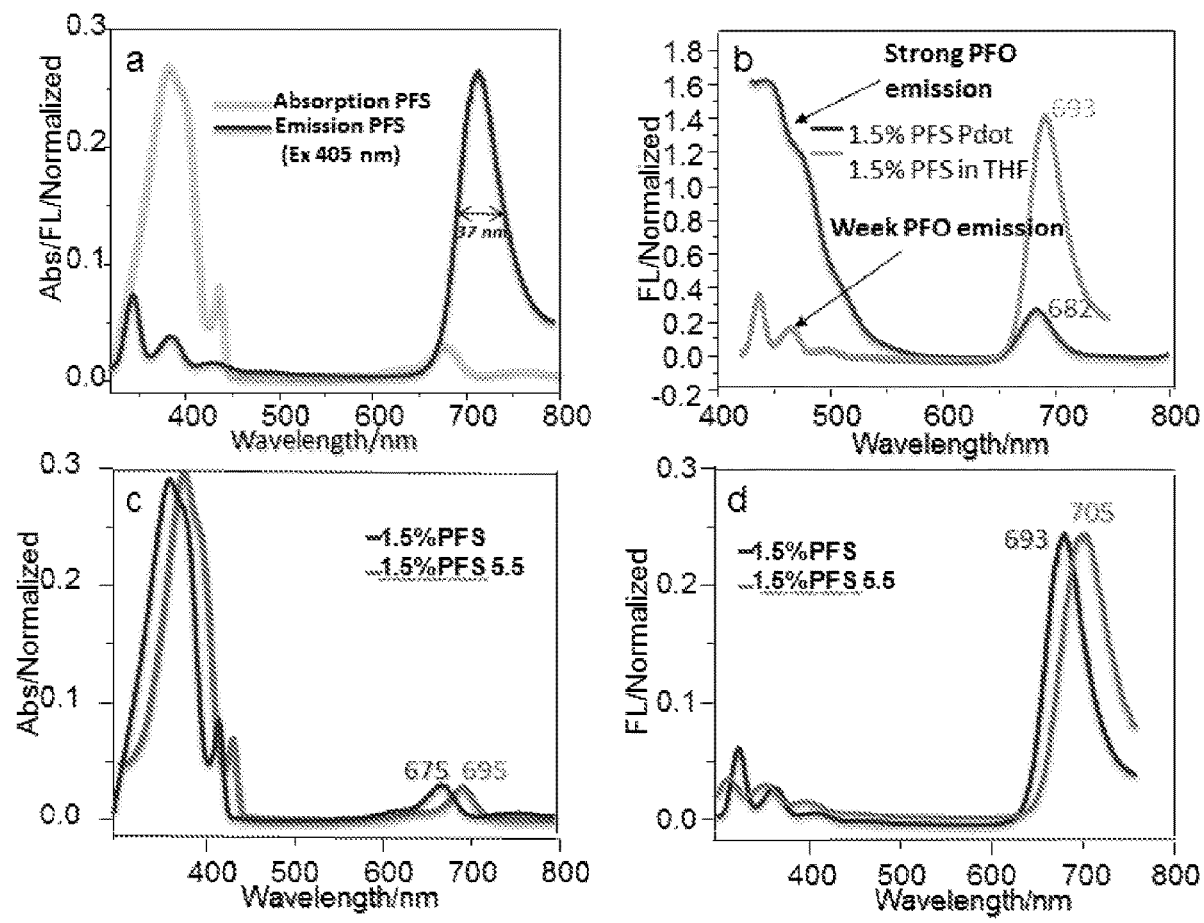
FIG. 25G shows absorption and fluorescence spectra of PFS and PFS5.5 Pdots with 1.5% squaraine molar ratio. Top-left panel a shows the absorption and fluorescence spectra of PFS Pdot with 1.5% squaraine molar ratio. Top-right panel b shows the fluorescence spectra of PFS Pdot at 1.5% molar ratio of squaraine dye in THF and the Pdots formed in water. Bottom-left panel c shows the absorption spectra of PFS and PFS 5.5 Pdots (with 1.5% squaraine molar ratio) in water. Bottom-right panel d shows the fluorescence spectra of PFS and PFS 5.5 Pdots (with 1.5% squaraine molar ratio) in water.
Figure 25H:
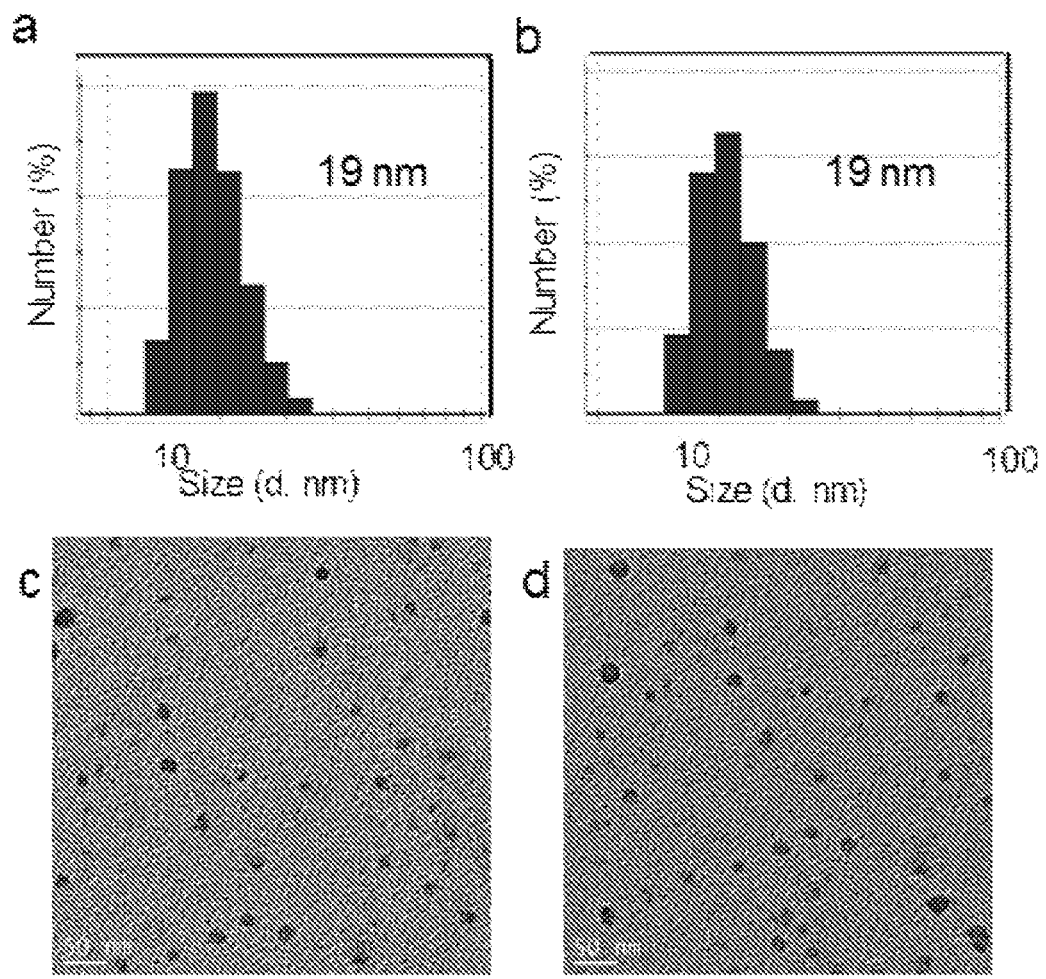
FIG. 25H shows the particle size distributions of PFS Pdots (average size of 19 nm) and PFS 5.5 Pdots (average size of 19 nm). Bottom panels show the TEM images of PFS Pdots (c) and PFS 5.5 Pdots (d).
Figure 25I:
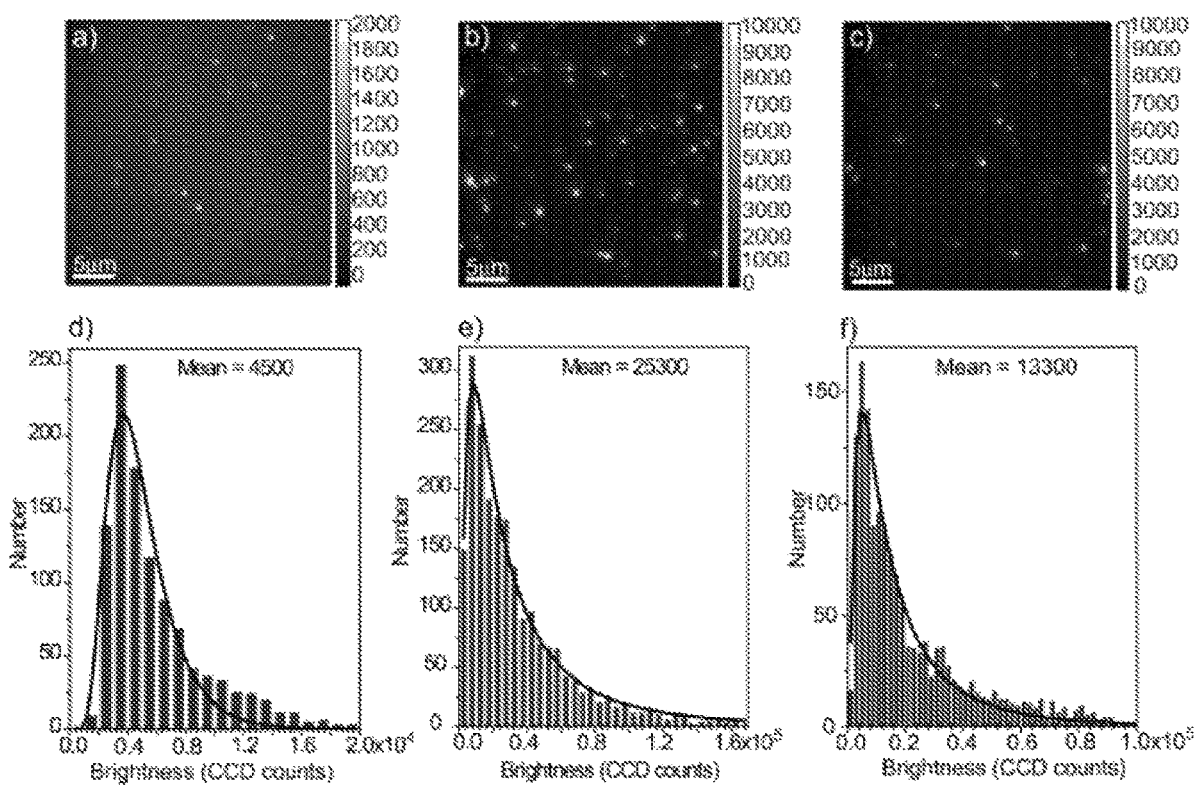
FIG. 25I shows single-particle brightness images with 405 nm excitation for three samples: (a) Qdots 705; (b) 1.5% PFS Pdots; (c) 1.5% PFS 5.5 Pdots. The images in the top panel were obtained under identical excitation and detection conditions. All scale bars represent 5 m. The bottom panels show the histograms of the brightness distributions.
Figure 25J:
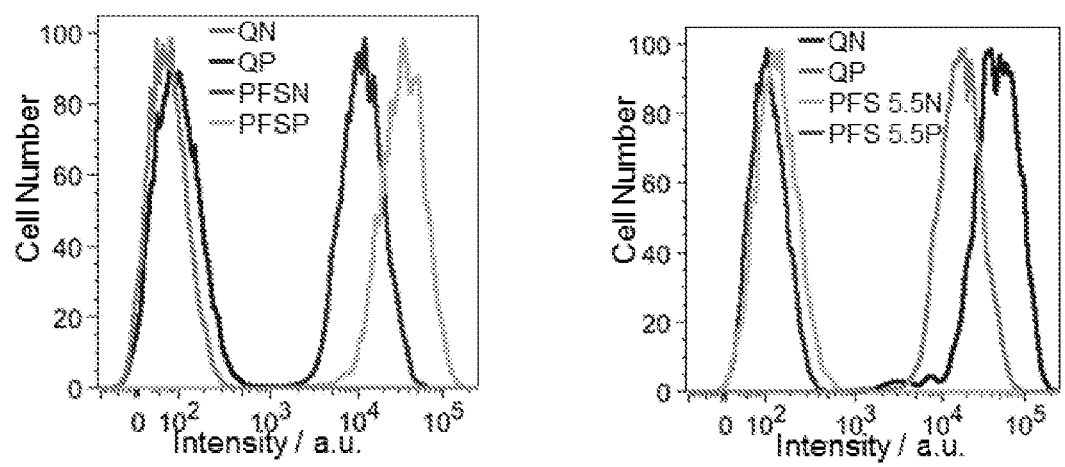
FIG. 25J shows flow cytometry intensity distributions of MCF-7 breast cancer cells labeled with Qdot 705-streptavidin, PFS Pdot-streptavidin, and PFS5.5 Pdot-streptavidin.
Figure 25K:
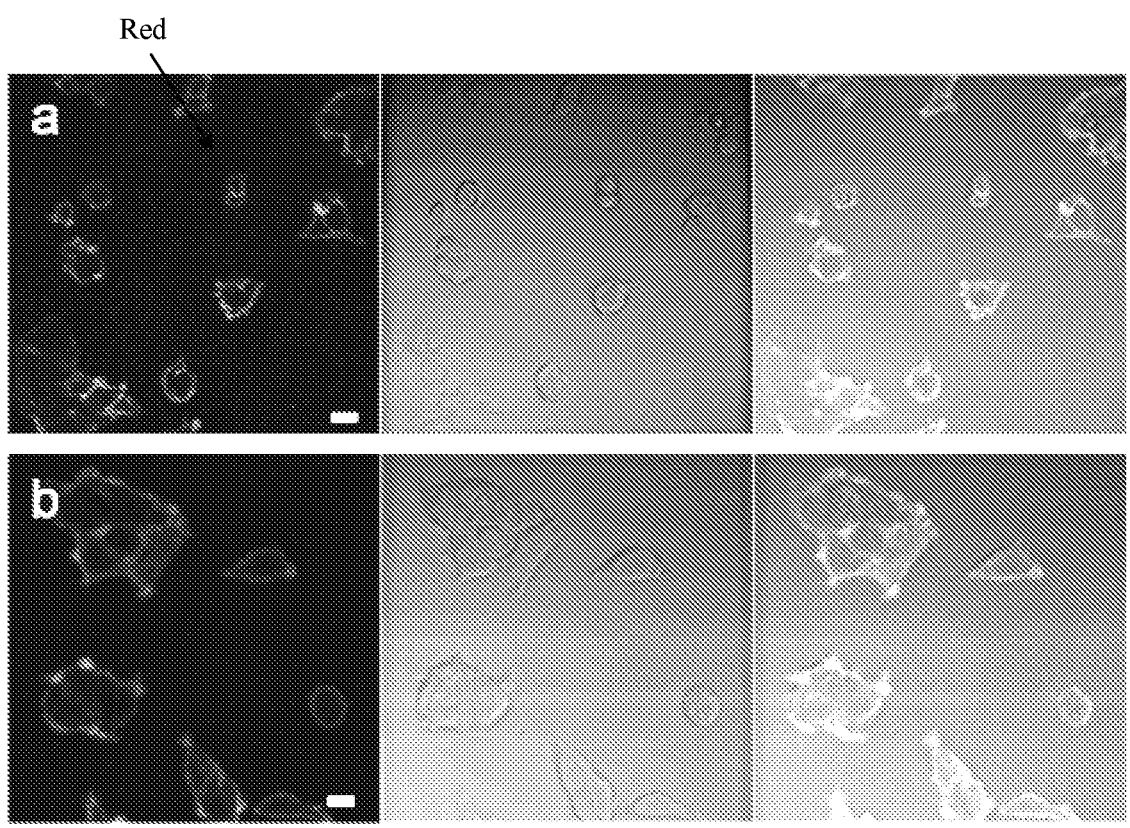
FIG. 25K shows confocal fluorescence images of MCF-7 cells labeled with PFS Pdot-streptavidin and PFS 5.5 Pdot-streptavidin probes.

Spectroscopic Characterizations and Biological Applications. Squaraine based monomers were synthesized and narrow-band emissive polymer dots based on fluorene and squaraine monomers were developed. These Pdots that emit in the NIR region and can be used, e.g., for biological applications. FIG. 24D, for example, shows a schematic illustration of a squaraine based narrow emissive polymer dots and Pdot-bioconjugates for specific cellular targeting. With their nanometer-scale particle sizes, high quantum yields in water, and small FWHM (<40 nm), these Pdots can, e.g., be used for multiplexing the simultaneous targeting of several molecules on the surfaces of cells. FIG. 25E shows photophysical data and particle size of the narrow-band emissive PFS Pdots and PFS 5.5 Pdots with varying squaraine ratio. FIG. 25F shows the fluorescence emission spectra of the narrow-band emissive PFS Pdots and PFS 5.5 Pdots with varying squaraine ratio. The PFS-1.5% squaraine copolymer Pdots shows emission FWHM of 37 nm at 690 nm and fluorescence quantum yield is 0.30. FIG. 25G shows absorption and fluorescence spectra of PFS and PFS5.5 Pdots with 1.5% squaraine molar ratio. Top-left panel a shows the absorption and fluorescence spectra of PFS Pdot with 1.5% squaraine molar ratio. Top-right panel b shows the fluorescence spectra of PFS Pdot at 1.5% molar ratio of squaraine dye in THF and the Pdots formed in water. Bottom-left panel c shows the absorption spectra of PFS and PFS 5.5 Pdots (with 1.5% squaraine molar ratio) in water. Bottom-right panel d shows the fluorescence spectra of PFS and PFS 5.5 Pdots (with 1.5% squaraine molar ratio) in water. FIG. 25H shows the particle size distributions of PFS Pdots (average size of 19 nm) and PFS 5.5 Pdots (average size of 19 nm). Bottom panels show the TEM images of PFS Pdots (c) and PFS 5.5 Pdots (d). FIG. 25I shows single-particle brightness images with 405 nm excitation for three samples: (a) Qdots 705; (b) 1.5% PFS Pdots; (c) 1.5% PFS 5.5 Pdots. The images in the top panel were obtained under identical excitation and detection conditions. All scale bars represent 5 am. The bottom panels show the histograms of the brightness distributions. FIG. 25J shows flow cytometry intensity distributions of MCF-7 breast cancer cells labeled with Qdot 705-streptavidin, PFS Pdot-streptavidin, and PFS5.5 Pdot-streptavidin. FIG. 25K shows confocal fluorescence images of MCF-7 cells labeled with PFS Pdot-streptavidin and PFS 5.5 Pdot-streptavidin probes.

Example 9: Narrow-Band Emissive Pdots Embedded with Quantum Dot (QD)

The present example provides a method for obtaining a narrow-band emissive Pdots embedded with inorganic quantum dots (QDs).

As shown in FIG. 26A, we synthesized a general semiconducting polymer PFBT functionalized with amino groups and then converted these amino groups to thiols by 2-iminothiolane (Traut's reagent) under THF in an effort to have an efficient ligand-exchange process with original amino capping ligands on QD surfaces. After the exchange reaction, we blended a copolymer, PS-PEG-COOH that consists of carboxyl groups for further biological applications, and then co-precipitated polymer-QD mixtures in water under sonication to from Pdot-QD NPs. From transmission electron microscopy (TEM) images (FIG. 1B), we can clearly see that a cluster of QDs was encapsulated by polymers in which there are ~30 QDs embedded inside each individual Pdot-Qdot nanoparticle. We found that the crystalline structure of QDs was preserved intact during the preparation processes (FIG. 26B) and remains optically stable and biologically active even after two months of storage at 4° C. in physiological pH buffers. Dynamic light scattering (DLS) measurements also showed that the average diameter of Pdot-Qdot NPs was 25 nm (FIG. 26C). We noticed that the color of emission changed drastically from bright yellow fluorescence before nanoprecipitation to deep red emission after nanoprecipitation. The yellow fluorescence is characteristic of PFBT, while the red fluorescence is from QDs under UV light irradiation. This phenomenon is indicative of a highly efficient energy from PFBT to QDs only when they are in close proximity.

FIG. 27A shows the absorption spectrum of Pdot-Qdot NPs. The absorption peak at ~450 nm (blue arrow) is evidence of PFBT and the small absorption at ~640 nm (red arrow) is from CdSe QDs, while the high absorption below 400 nm is attributed to both PFBT and QDs. In the present work, we employed three different sizes of QDs that emit at 655 nm (QD655), 705 nm (QD705), and 800 nm (QD800), respectively. We carefully optimized the quantitative ratio of PFBT to QD in order to have an efficient energy transfer from PFBT to QDs while keeping their compact size (i.e. minimal number of QDs inside a Pdot). As shown in FIG. 27B, the fluorescence signal of PFBT was almost completely quenched, indicating an efficient energy/electron transfer from PFBT to QDs. More importantly, the emission bandwidth of Pdot-Qdot NPs remained unaltered, allowing us to create Pdot-based NPs with narrow emission. Taking QD655 for example, the full width at half maximum of Pdot-QD655 in water is ~25 nm (solid red line in FIG. 27B), which is almost the same as the original QD655 in decane (dashed red line). Moreover, we have demonstrated this technique can be applied to NIR QDs such as QD705 and QD800 (purple and pink lines in FIG. 27B). The quantum yields of Pdot-QD655, Pdot-QD705, and Pdot-QD800 in buffer solutions were determined to be 23%, 38%, and 29%, respectively. This implies that we should be able to take the advantage of the unique optical properties of QDs such as narrow-band and NIR emission, while implanting the merits of Pdots on them, including the large absorption cross-sections and facile surface functionalization. To prove our concept, we first performed the experiments of single particle fluorescence brightness. We have shown that PFBT-DBT Pdots emitting at ~650 nm are 15 times brighter than single QD655. Here, we directly compared the single-particle brightness of PFBT-DBT Pdots with PFBT-QD655 NPs. We found the particle brightness of PFBT-QD655 is comparable to that of PFBT-DBT (FIG. 27C, 27D). Because the particle brightness is given by the product of absorption cross section and quantum yield and in this case the quantum yield was only slightly altered, we can then attribute the brightness enhancement to the vast increase in optical absorption cross section originated from polymer coating or/and QD multiples. To evaluate the bioconjugation activity of this hybrid material, we performed the subcellular microtubule labelling in HeLa cells. We first bioconjugate streptavidin onto Pdot-Qdot NP surfaces via 1-ethyl-3-[3-dimethylaminopropyl] carbodiimide hydrochloride-(EDC)-catalyzed coupling).

Figures 28A, 28B, 28C:
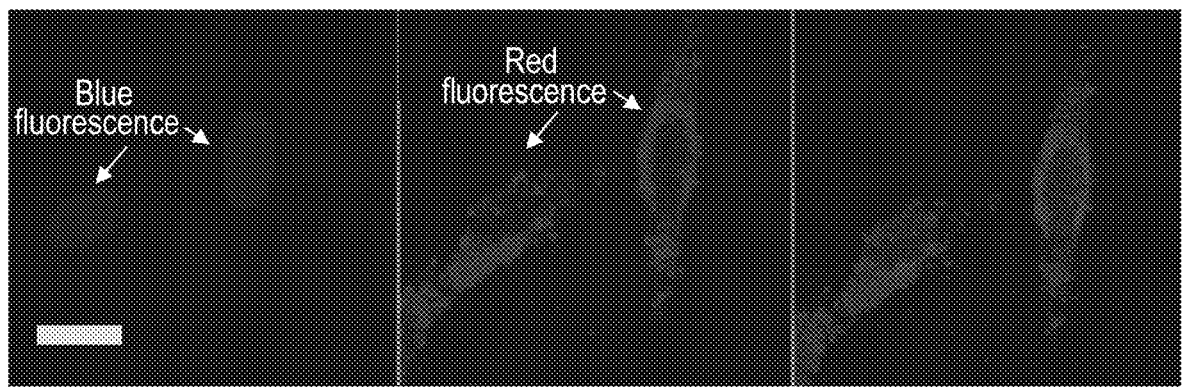
FIGS. 28A-28C show the two-color confocal microscopy images of microtubules in HeLa cells labeled with Pdot-QD705-streptavidin. The blue fluorescence is from nuclear counter-stain Hoechst 34580 (A), the red fluorescence (B) is from Pdot-QD705-streptavidin, and (C) is the overlay of panels (A) and (B).
Figures 28D, 28E, 28F:
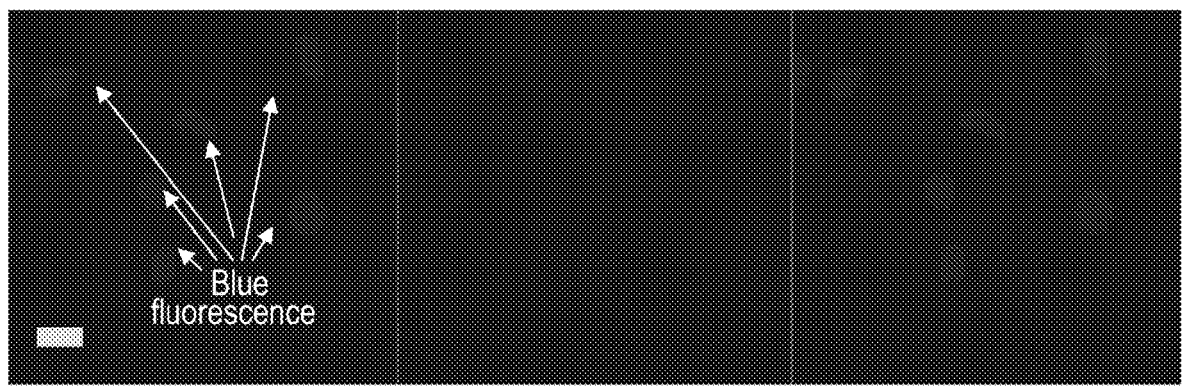
FIGS. 28D-28F are images of the control sample where cells were incubated with Pdot-QD705-streptavidin but in the absence of biotinylated primary antibody. The scale bars are 20 μm.
Figures 28G, 28H:
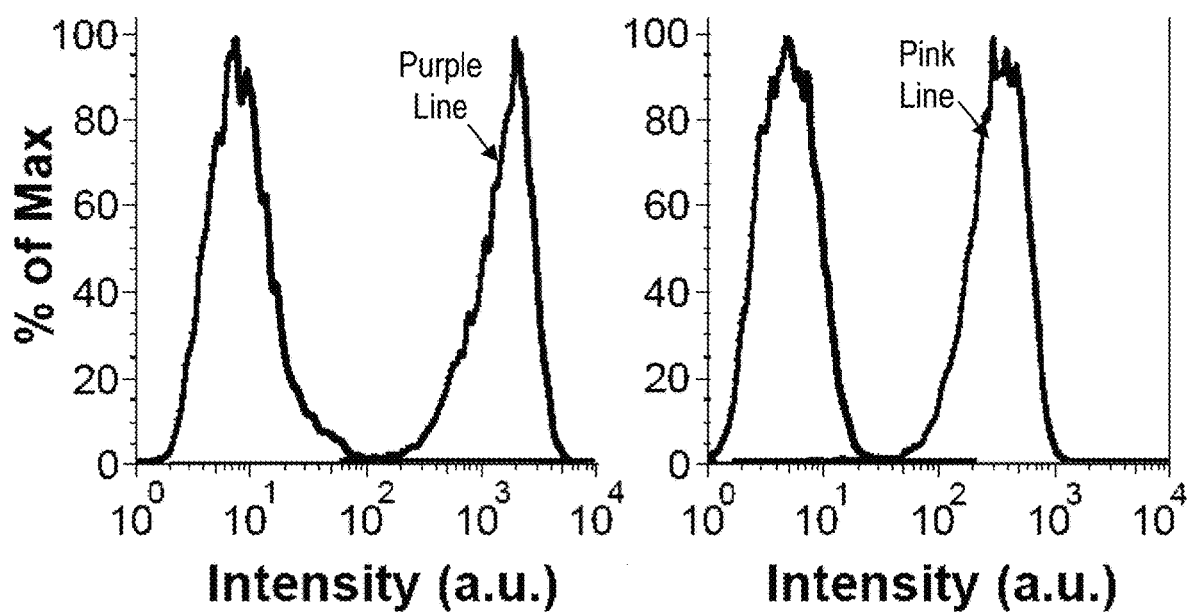
FIGS. 28G-28H show flow cytometry results of Pdot-Qdot labeled MCF-7 cells. The purple and pink lines show the fluorescence intensity distributions of Pdot-QD705-streptavidin and Pdot-QD800-streptavidin labeled cells, respectively. The black lines represent the results of control samples (no primary Biotin anti-human CD326 EpCAM antibody).

FIG. 28 shows the two-color confocal microscopy images of microtubules in HeLa cells labeled with Pdot-QD705-streptavidin. The blue fluorescence is from nuclear counterstain Hoechst 34580 (A), the red fluorescence (B) is from Pdot-QD705-streptavidin, and (C) is the overlay of panels (A) and (B). (D-F) are images of the control sample where cells were incubated with Pdot-QD705-streptavidin but in the absence of biotinylated primary antibody. As indicated by the fluorescence images, the Pdot-QD-streptavidin conjugates can specifically label the cellular targets. FIG. 28 G-H show the flow cytometry results of Pdot-Qdot labeled MCF-7 cells. The purple and pink lines show the fluorescence intensity distributions of Pdot-QD705-streptavidin and Pdot-QD800-streptavidin labeled cells, respectively. The black lines represent the results of control samples (no primary Biotin anti-human CD326 EpCAM antibody). Again, these results show specific labeling of the Pdot-QD probes without nonspecific labeling.

Example 10: Narrow-Band Emission from Blended Pdots Comprising a Narrow-Band Emissive Fluorene-BODIPY Copolymer The present example provides a method for obtaining narrow-band emission by using blended Pdots comprising a narrow-band emissive fluorene-BODIPY copolymer.

Figure 29A:
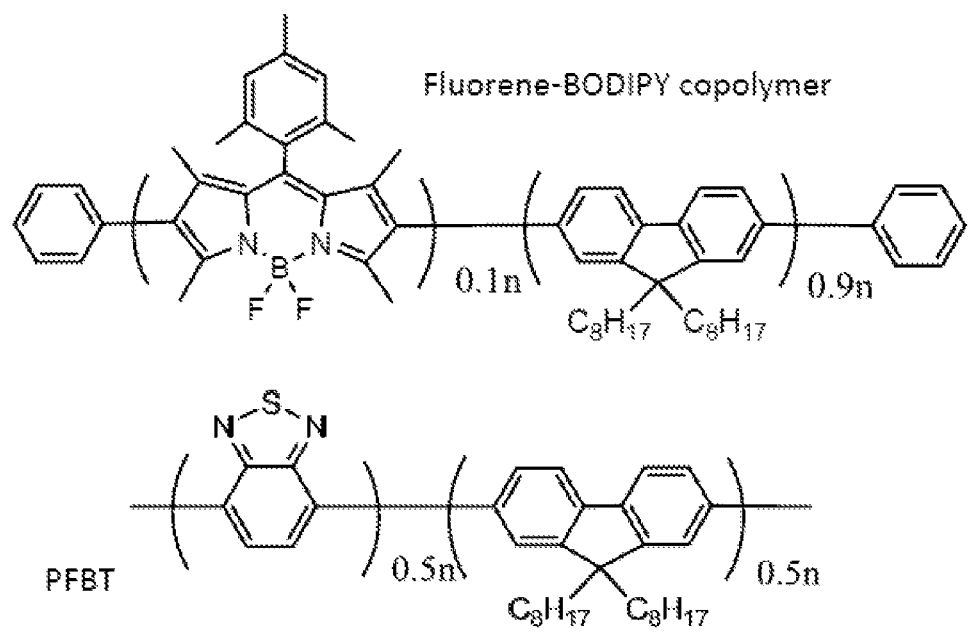
FIG. 29A shows the chemical structure of a conventional broad-band emission semiconducting polymer PFBT and a narrow-band emissive Fluorene-BODIPY copolymer synthesized by using the BODIPY monomer 2a in FIG. 12 as narrow-band monomer and fluorene as a general monomer.
Figure 29B:
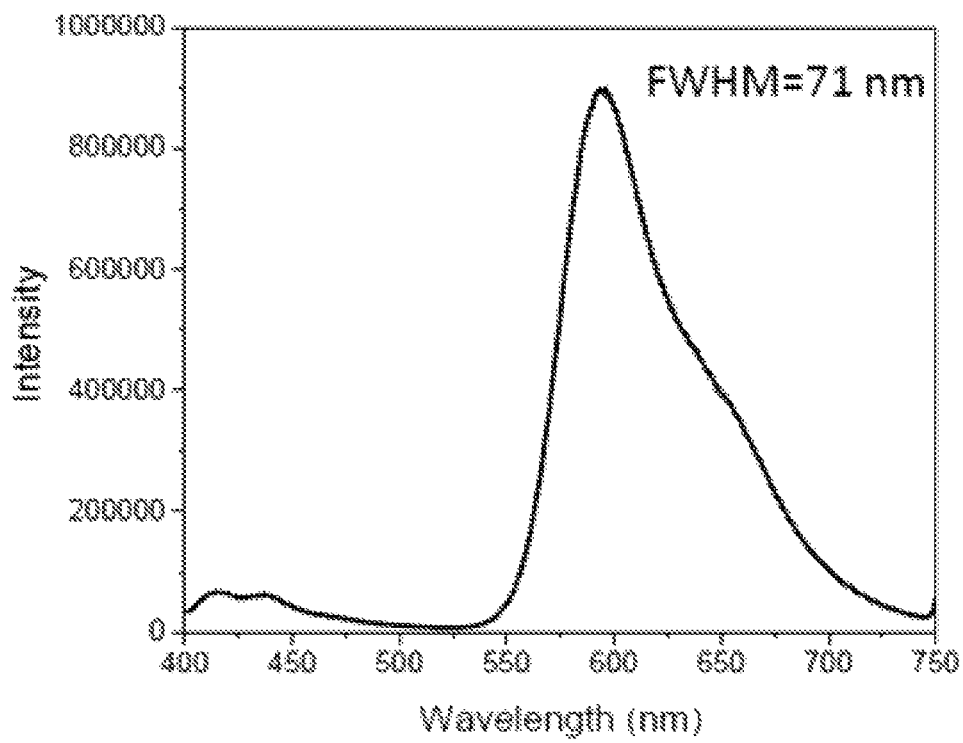
FIG. 29B shows the emission spectra of the Fluorene-BODIPY Pdots in water. As indicated by the spectra, these pure Fluorene-BODIPY Pdots show broad-band emission.
Figure 29C:
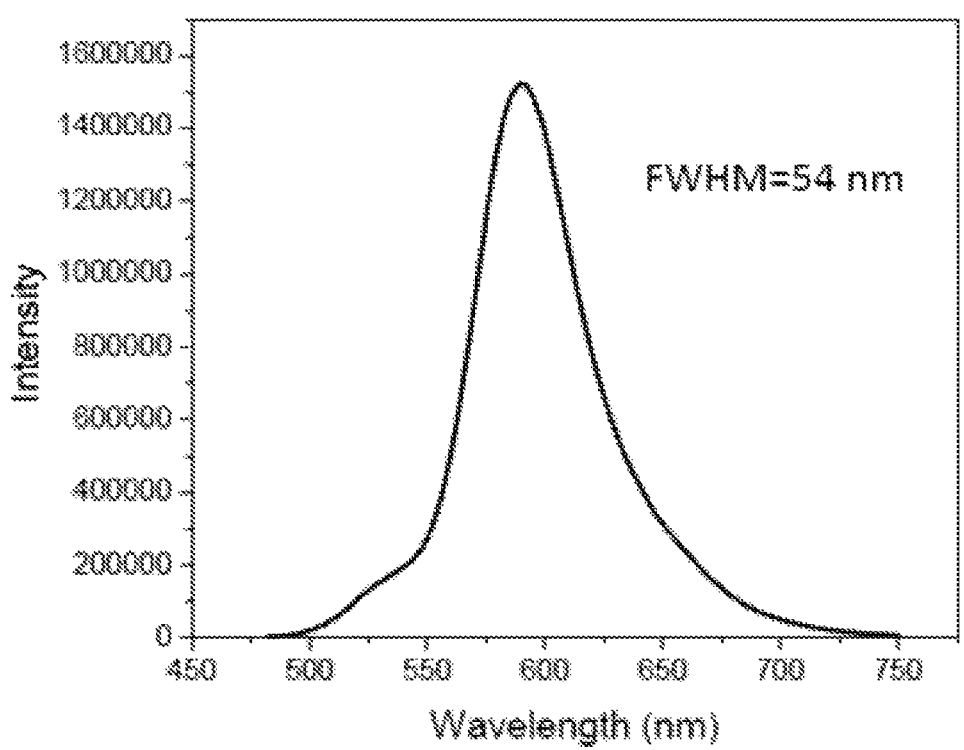
FIG. 29C shows emission spectra of the blended Pdots prepared from PFBT and Fluorene-BODIPY. The blended Pdot emission exhibits a FWHM of 54 nm, which is narrower as compared with the pure Pdots.

A narrow-band emissive copolymer was first synthesized by using the BODIPY monomer 2a in FIG. 12 as narrow-band monomer and fluorene as a general monomer. This copolymer in a good solvent such as THE exhibit narrow-band emission. However, the Pdots prepared by this polymer exhibit broad-band emission (FIG. 29B) because the fluorophores were densely packed and aggregation states were formed. We used a blending strategy to obtain narrow-band emission. The narrow-band emissive Fluorene-BODIPY polymer was mixed with a conventional broad-band emission semiconducting polymer PFBT in THF, and blended Pdots were prepared by injecting a THE solution of the polymer mixture into water. As indicated by the emission spectrum (FIG. 29C), the blended Pdots exhibit narrow-band emission as compared to the pure Fluoene-BODIPY Pdots. The narrow-band emissive Fluoene-BODIPY polymer was dispersed in the PFBT host, therefore preventing the formation of aggregation. There is also efficient intra-particle energy transfer from PFBT to the BODIPY units. As a result, the PFBT emission was completely quenched, and the blended Pdots gave narrow-band emission.

Figure 29D:
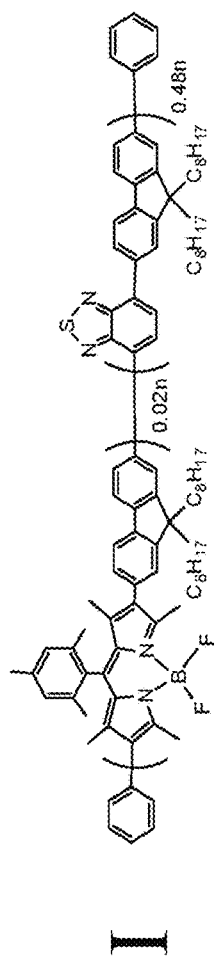
FIG. 29D shows other copolymers and blends of polymers and copolymers for forming chromophoric polymer dots.
Figure 29D:
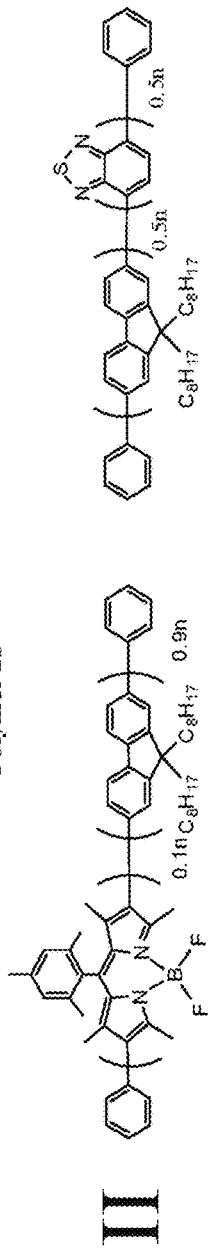
Figure 29D:

Figure 29D:
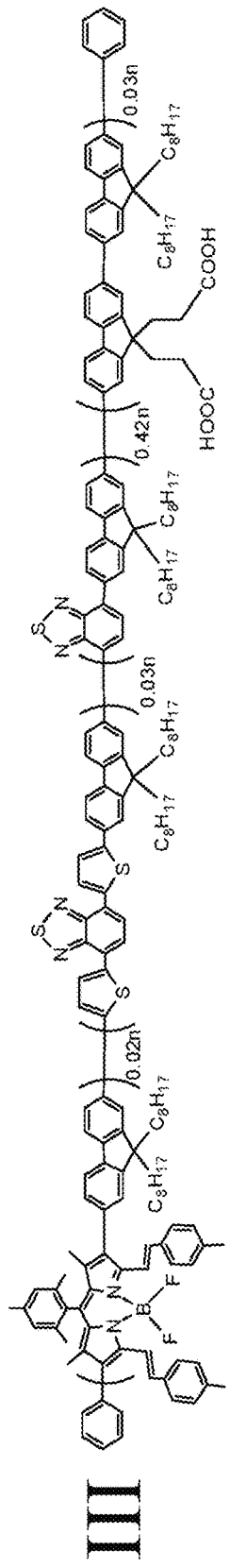
Figure 29D:
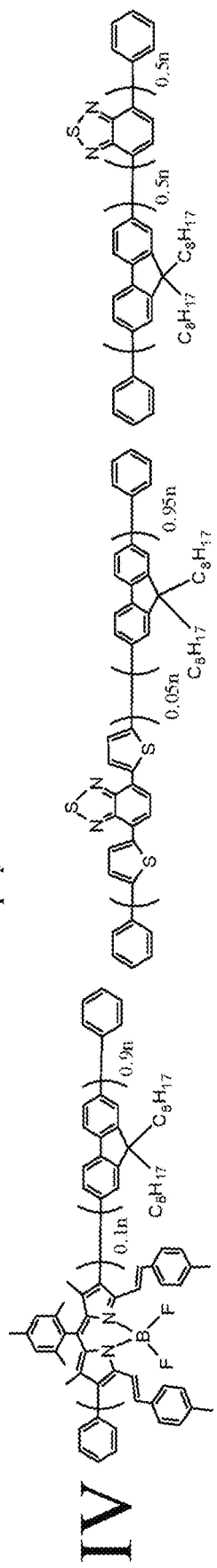
Figure 29D:
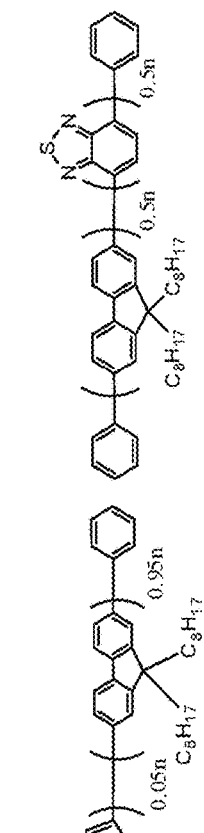
Figure 29E:
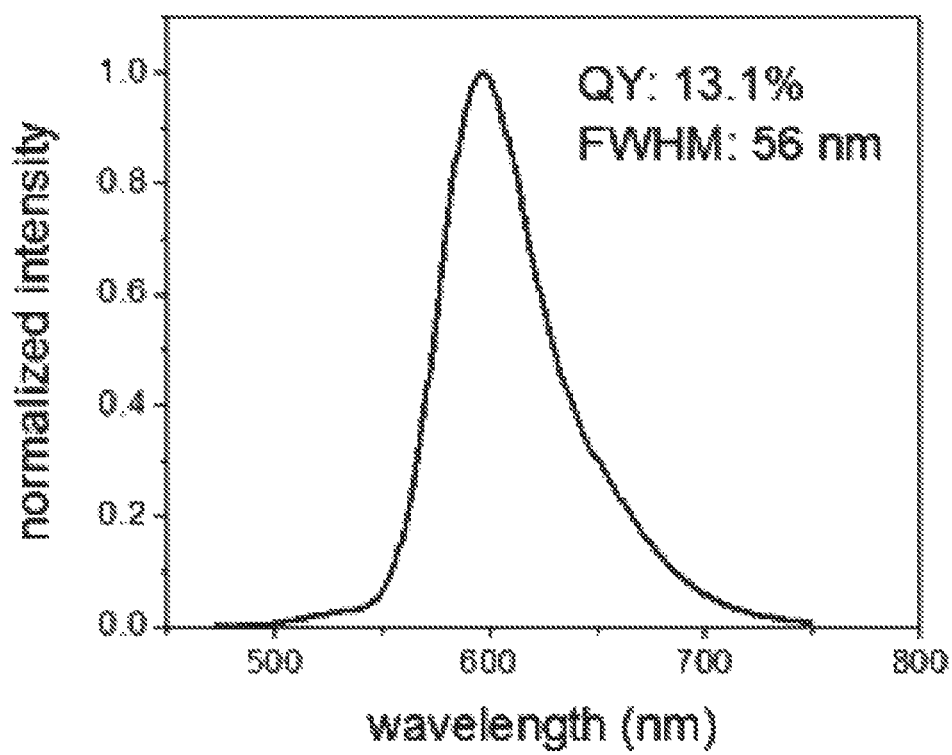
FIGS. 29E-29H show the corresponding optical properties and fluorescence emission spectra for the different chromophoric polymer dots formed using the copolymers or blends of polymers and copolymers shown in FIG. 29D.
Figure 29F:
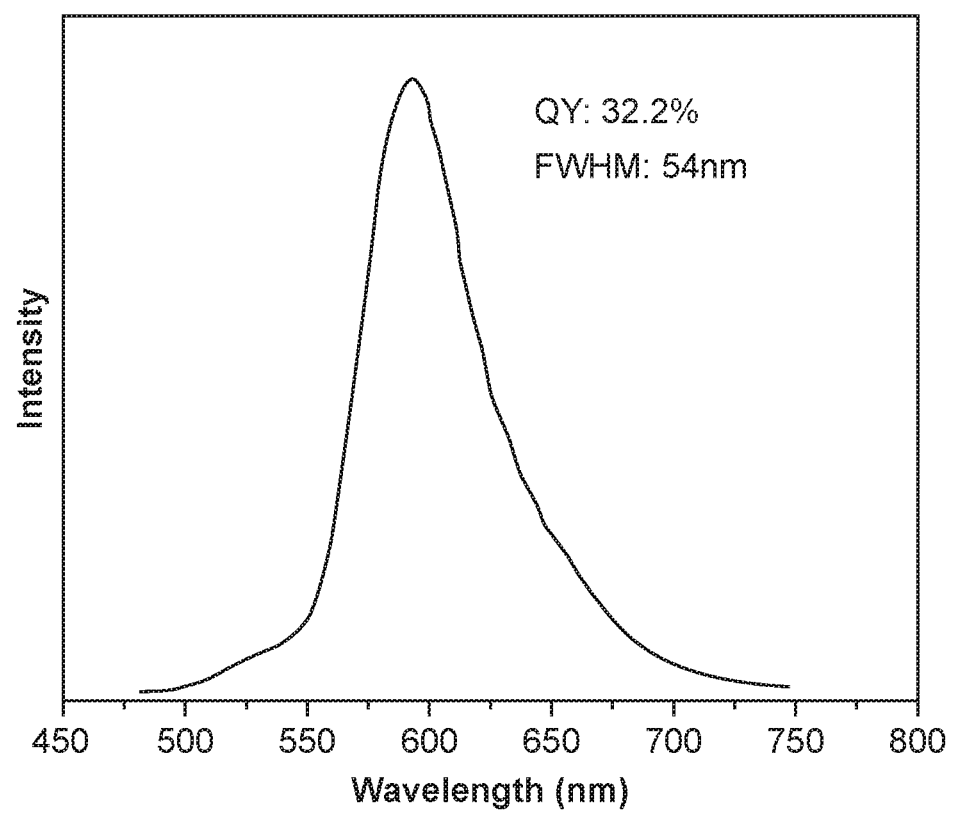
Figure 29G:
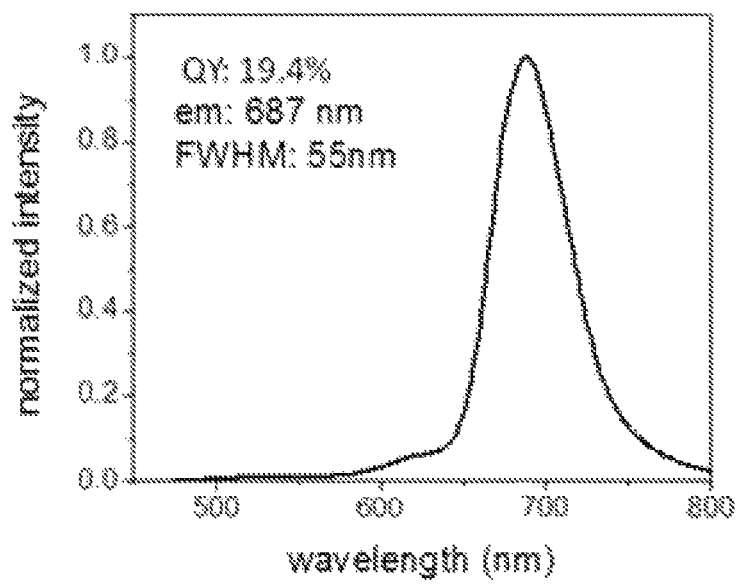
Figure 29H:
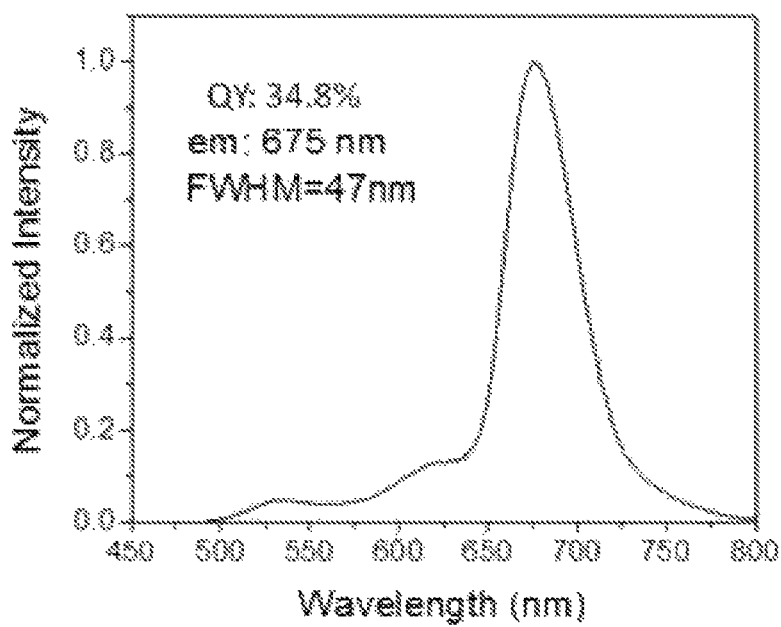

It is also possible to use other fluorescent polymers, copolymers, and in particular other BODIPY fluorescent copolymers such as the ones shown in FIG. 29D. FIG. 29F-29H corresponds to the fluorescence spectra of chromophoric polymer dots formed using the different copolymers and polymer blends shown in FIG. 29D (I-IV). It is evident from this example that different types of copolymers and blends of polymers and copolymers can be used, and also that blending can significantly improve the quantum yield of the resultant chromophoric polymer dots. These chromophoric polymer dots were formed from the polymers shown in FIG. 29D, where a solution of polymer precursor mixture in THF (for example, 1.2 mL, 100 ppm of PFBT solution, 0.6 mL, 100 pm of PF-5TBT solution, 0.2 mL, 100 ppm of 10% mol deep red BODIPY fluorene copolymer solution, 0.5 mL, 100 ppm of PSMA1800) was quickly injected into water (10 mL) under ultrasonication. THE was evaporated by $N_2$ flow at 60° C. and the solution was concentrated to 8-9 mL.

Example 11: Narrow-Band Emission Chromophoric Polymer Dots Formed from PFPPyBPh

Figure 30A:
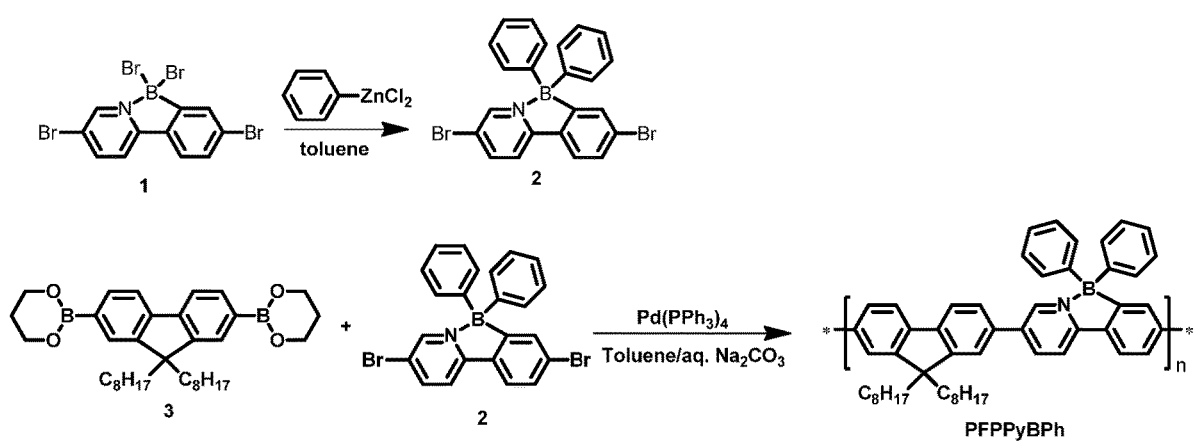
FIG. 30A provides an example scheme showing the synthetic procedure for synthesizing PFPPyBPh.

FIG. 30A shows the synthetic scheme of Poly[(9,9-dioctylfluoren-2,7-yl)-alt-(diphenyl-2-(2-pyridinyl-κN)phenyl-κC]-(T-4)-boron-5,5-yl)] (PFPPyBPh). Briefly, Compound 2: To a solution of phenyl lithium (1.7 mL, 1.8 M in dibutyl ether) was added $ZnCl_2$ (3.3 mL, 1 M in diethyl ether) at 0° C. The solution was stirred for 30 min at 0° C., and for 1 hour at room temperature. The compound 1 (0.6 g) and toluene (30 mL) were added in one portion. Then, the resultant solution was stirred at 80° C. overnight. After cooling to room temperature, the solution was poured into water. The organic phase was separated and the aqueous phase was extracted with dichloromethane twice. The combined organic phases were dried over anhydrous $Na_2SO_4$. After removing the solvent, the crude product was purified by silica column to give a white solid (0.3 g, 50%). $^1$H NMR (CDCl$_3$, ppm): 8.57 (dd, 1H), 8.20 (dd, 1H), 7.93 (dd, 1H), 7.82 (d, 1H), 7.74 (d, 1H), 7.50 (dd, 1H), 7.26-7.18 (m, 10H).

Polymer PFPPyBPh: In a 50-mL single-neck flask, the compounds 3 and 2 were charged. Toluene (3.5 mL), aqueous Na$_2$CO$_3$ (2 mL, 2M) and A336 (2 drops) were added consequently. The solution was degassed twice before adding Pd(PPh$_3$)$_4$ (7.5 mg). Then, the solution was heated to 120° C. for 48 hours. After cooling to room temperature, the solution was poured into methanol. The resultant solid was dissolved into chloroform and passed through a short column. The concentrated solution was then poured into methanol. The solid was collected by filtration and dried under vacuum overnight (120 mg, 68%).

Figure 30B:
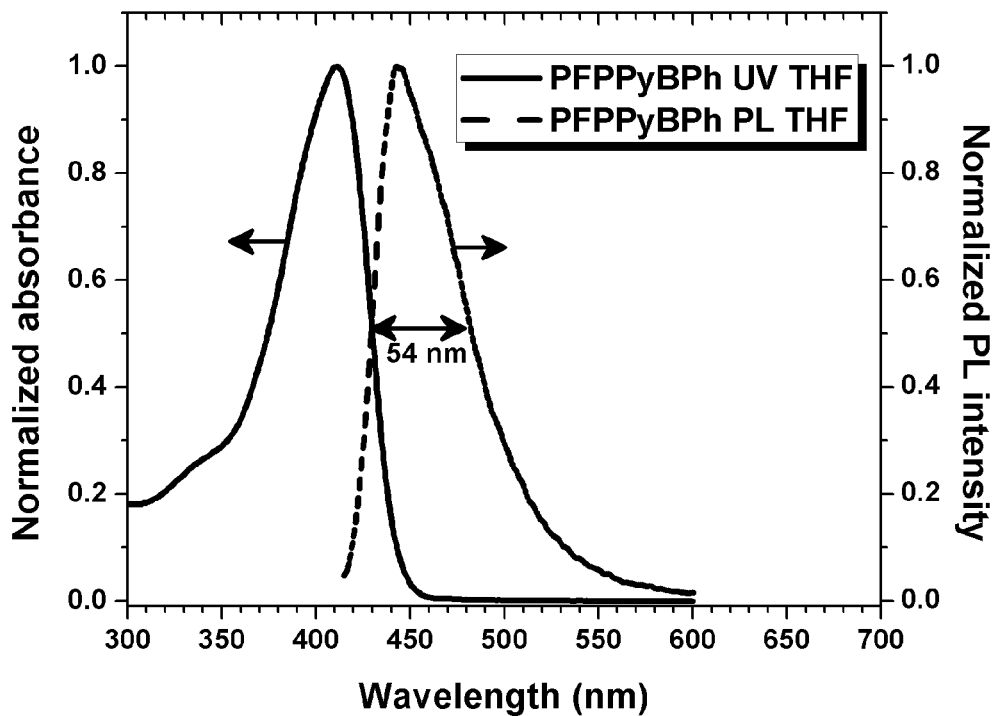
FIG. 30B shows the UV-Vis and fluorescence spectra of PFPPyBPh in THF.
Figure 30C:
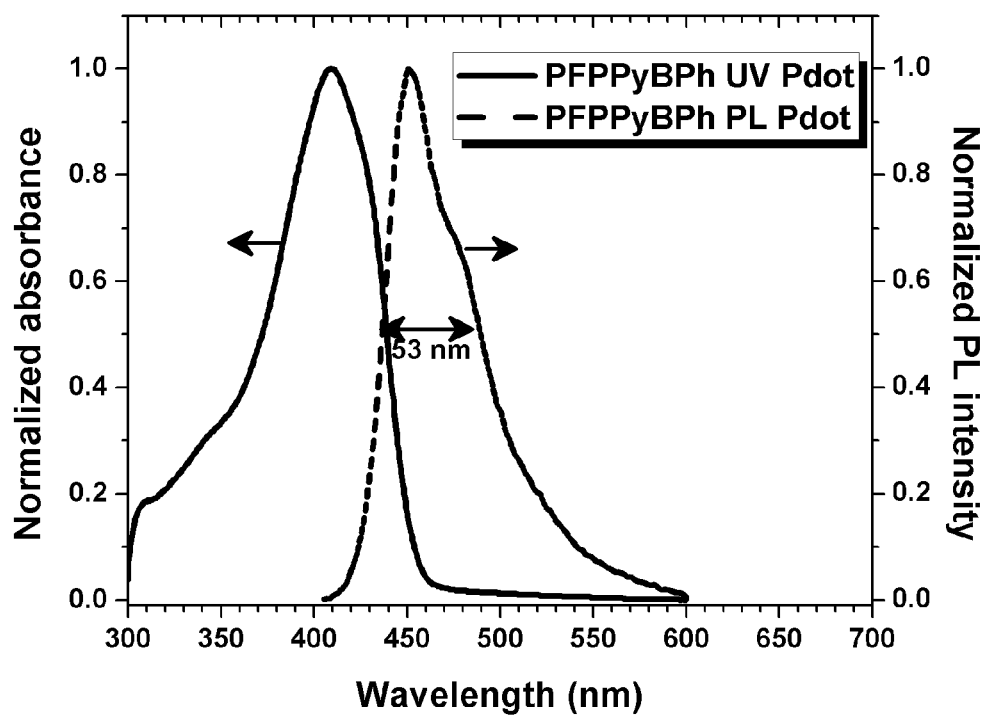
FIG. 30C shows the UV-Vis and fluorescence spectra of PFPPyBPh chromophoric polymer dot.

FIG. 30B shows the absorption and fluorescence spectra of the synthesized PFPPyBPh polymer in THF (tetrahydrofuran). FIG. 30C shows the absorption and fluorescence spectra of the chromophoric polymer dots formed using the synthesized PFPPyBPh polymer. The formed chromophoric polymer dots, which also contained some PSMA, were measured by dynamic light scattering to be around 15 nm in diameter.

Example 12: Synthesis of BODIPY Monomer 4a (Shown in FIG. 12) and Related Narrow-Band Emissive Polymer with Side-Chain Amine Groups The present example provides a method for obtaining narrow-band BODIPY monomer4a and a narrow-band emissive fluorene-BODIPY copolymer polymer540 with side-chain amine groups.

Synthesis of BODOPY Monomer 4a. To a solution of 4-methyl-3,5-diiodobenzaldehyde (1.5 g, 4.2 mmol) and 2,4-dimethyl-3-ethyl-1H-pyrrole (1 g, 10.5 mmol) in dry CH$_2$Cl$_2$ (120 ml) was added a solution of 110 μl trifluoroacetic acid in dry CH$_2$Cl$_2$ (5 ml) slowly at room temperature. 2,3-Dichloro-5,6-dicyano-1,4-benzoquinone (0.95 g, 4.2 mmol) was added after 3 h stirring under ice bath cooling and stirred for 10 min. The solution was stirred for an additional 1 h at room temperature. NEt$_3$ (10 ml, 72 mmol) was added, followed by slow addition of BF$_3$·Et$_2$O (12 ml, 81 mmol). The reaction mixture was washed after 10 h of stirring at room temperature with saturated aqueous Na$_2$CO$_3$ solution (2×100 ml), dried over Na$_2$SO$_4$, and concentrated on a rotary evaporator. The brown, oily residue was purified by column chromatography on silica with hexane/CH$_2$Cl$_2$=3:1. The product fraction with greenish fluorescence was dried to yield an orange solid. Yield: 0.48 g, 19.5%. $^1$H NMR (CDCl$_3$, 500 MHz): δ=7.831 (s, 2H), 6.042 (s, 2H), 2.874 (s, 3H), 2.581 (s, 6H), 1.544 (s, 6H). $^{13}$C NMR (CDCl$_3$, 125 MHz): δ=156.25, 144.12, 142.83, 138.94, 135.89, 131.11, 121.67, 99.09, 34.93, 15.14, 14.61. HRMS (ESI) (M$^+$, C$_{24}$H$_{27}$BF$_2$I$_2$N$_2$): calcd, 647.0442; found, 647.0432.

Synthesis of Fluorene-BODIPY Polymer540 with Side-Chain Amine Groups (PF5%540BODIPY4NH$_2$). In a glovebox under nitrogen atmosphere, a dry three neck 50 mL round-bottom flask with stir bar was charged with 372 mg (1.35 mmol) of bis(1,5-cyclooctadiene) nickel(0), 150 mg (1.35 mmol) of cyclooctadiene, and 210 mg (1.35 mmol) of bypyridine in 5.0 mL of a 1:1 mixture of toluene and dimethylformamide (DMF). A dark purple color then developed. The solution was heated to 60° C. In the glovebox, a dry 20 mL flask was charged with 19.4 mg (0.03 mmol) of BODIPY monomer 1a, 299.4 mg (0.546 mmol) of 9,9-Dioctyl-2,7-dibromofluorene and 15.3 mg (0.024 mmol) of monomer 4a in 4.0 mL of a 1:1 mixture of toluene and DMF, then they were added dropwise into the above catalyst mixture. The flask containing this solution was covered with foil to protect it from light and the reaction mixture was refluxed for 4 days. Then 4 drops of iodobenzene was added to end-cap the polymer chain and the reaction was stirred for an additional 12 h at 60° C. The product was diluted with 50 ml of toluene and washed with aqueous 15 wt % of sodium thiosulfate solution (3×50 mL) followed by washing with Milli-Q water and drying over MgSO$_4$, for the removal of residual iodine from polymer. The polymer solution was evaporated and dissolved in dichloromethane. After polymer solution was filtered, the concentrated polymer solution in dichloromethane was poured into 100 ml of MeOH, and filtered. The precipitate was stirred in 50 ml of acetone at room temperature for 24 h, and filtered. Polymer was obtained as orange solid (120 mg). De-protection of amine group from the polymer was finished as the following procedure, polymer was dissolved in DCM (50 mL) and TFA (1.5 mL) was added to remove protecting groups and generate amine groups. The mixture was stirred at room temperature overnight (in dark) and then washed with 10% NaOH water solution three times. DCM phase was separated, concentrated to ca. 5 mL, and then added into methanol (80 mL) to precipitate the final polymer. Yield: 130 mg, 54.2%. $^1$H NMR (CDCl$_3$, 500 MHz): δ=7.90-7.75 (m), 7.53 (m), 7.42-7.43 (m, 6H), 6.08 (m, 2H), 2.64 (s, 6H), 2.18 (s, 4H), 1.63 (s, 6H), 1.21 (s, 24H), 0.88 (s, 6H). $^{13}$C NMR (CDCl$_3$, 125 MHz): δ=151.87, 140.57, 140.07, 126.21, 121, 53, 120.02, 55.40, 40.46, 31.86, 30.1, 29.78, 29.3, 23.99, 22.66, 14.15. Mn: 57512, Mw: 90491, PDI: 1.573.

Example 13: Synthesis of Two General Fluorescent Polymers with Side-Chain Amine Groups for Chemically Cross-Linking with Narrow-Band Emissive Polymer The present example provides a method for obtaining general fluorescent polymer with side-chain amine groups that can chemically cross-link with narrow-band emissive polymers.

Synthesis of PF10BT with Amine Group (PF10BT4NH$_2$). Polymer is synthesized by palladium-catalyzed Suzuki coupling reaction from 9,9-dioctylfluorene and 4,7-Dibromobenzo[c]-1,2,5-thiadiazole. 197.4 mg (0.36 mmol) of 9,9-Dioctyl-2,7-dibromofluorene, 279.2 mg (0.5 mmol) of 9,9-dioctylfluorene-2,7-diboronic acid bis(1,3-propanediol) ester, 29.4 mg (0.1 mmol) of 4,7-dibromobenzo[c]-1,2,5-thiadiazole, 25.5 mg (0.04 mmol) of 2,7-dibromo-9,9-bis(3-(tert-butyl hexylcarbamate)fluorine, 2 drops of aliquot 336, 10 ml of 2M Na$_2$CO$_3$ aqueous solution, 15 ml of toluene were placed in a 50 ml flask. The flask was evacuated and refilled with N$_2$ four times by using the freeze/thaw method and Pd(PPh$_3$)$_4$ (1-1.5 mol %) was added. The flask was further degassed four times, then reaction was heated to 100° C. and stirred under N$_2$. After 70 h 0.2 ml of bromobenzene and 15 mg of phenylboronic acid in toluene were added to end-cap the polymer chain and the reaction was stirred for an additional 2 h at 100° C. respectively. The whole mixture was poured into 100 ml of MeOH, filtered, and washed with 0.2M of HCl. The precipitate was stirred in 50 ml of acetone at room temperature for 24 h and dried in vacuum oven to obtain dark yellow solid. De-protection of amine group from the polymer was finished as the following procedure, polymer was dissolved in DCM (50 mL) and TFA (1.5 mL) was added to remove protecting groups and generate amine groups. The mixture was stirred at room temperature overnight (in dark) and then washed with 10% NaOH water solution three times. DCM phase was separated, concentrated to ca. 10 mL, and then added into methanol (80 mL) to precipitate the final polymer. Yield: 320 mg, 79%.

Synthesis of PF5TBT with Amine Group (PF5TBT4NH$_2$). Polymer is synthesized by palladium-catalyzed Suzuki coupling reaction from 9,9-dioctylfluorene and 4,7-Bis(2-bromo-5-thienyl)-2,1,3-benzothiadiazole. 224.8 mg (0.41 mmol) of 9,9-Dioctyl-2,7-dibromofluorene, 279.2 mg (0.5 mmol) of 9,9-dioctylfluorene-2,7-diboronic acid bis(1,3-propanediol) ester, 22.9 mg (0.05 mmol) of 4,7-bis(2-bromo-5-thienyl)-2,1,3-benzothiadiazole, 25.5 mg (0.04 mmol) of 2,7-dibromo-9,9-bis(3-(tert-butyl hexylcarbamate)fluorine, 2 drops of aliquot 336, 10 ml of 2M Na$_2$CO$_3$ aqueous solution, 15 ml of toluene were placed in a 50 ml flask. The flask was evacuated and refilled with N$_2$ four times by using the freeze/thaw method and Pd(PPh$_3$)$_4$ (1-1.5 mol %) was added. The flask was further degassed four times, then reaction was heated to 100° C. and stirred under N$_2$. After 70 h 0.2 ml of bromobenzene and 15 mg of phenylboronic acid in toluene were added to end-cap the polymer chain and the reaction was stirred for an additional 2 h at 100° C. respectively. The whole mixture was poured into 100 ml of MeOH, filtered, and washed with 0.2M of HCl. The precipitate was stirred in 50 ml of acetone at room temperature for 24 h and dried in vacuum oven to obtain dark yellow solid. De-protection of amine group from the polymer was finished as the following procedure, polymer was dissolved in DCM (50 mL) and TFA (1.5 mL) was added to remove protecting groups and generate amine groups. The mixture was stirred at room temperature overnight (in dark) and then washed with 10% NaOH water solution three times. DCM phase was separated, concentrated to ca. 10 mL, and then added into methanol (80 mL) to precipitate the final polymer. Yield: 297 mg, 71%.

Example 14: Synthesis of BODIPY Monomer 5a (Shown in FIG. 12) and Related Narrow-Band Emissive Polymer with Side-Chain Amine Groups The present example provides a method for obtaining narrow-band BODIPY monomer5a and a narrow-band emissive fluorene-BODIPY copolymer polymer570 with side-chain amine groups.

Synthesis of BODOPY Monomer 5a. To a solution of 4-methyl-3,5-diiodobenzaldehyde (0.69 g, 1.9 mmol) and 2,3-Tetramethylenepyrrole (0.5 g, 4.1 mmol) in dry CH$_2$Cl$_2$ (100 ml) was added a solution of 90 µl trifluoroacetic acid in dry CH$_2$Cl$_2$ (5 ml) slowly at room temperature. 2,3-Dichloro-5,6-dicyano-1,4-benzoquinone (0.42 g, 2.0 mmol) was added after 3 h stirring under ice bath cooling and stirred for 10 min. The solution was stirred for an additional 1 h at room temperature. NEt$_3$ (5 ml, 36 mmol) was added, followed by slow addition of BF$_3$·Et$_2$O (6 ml, 40 mmol). The reaction mixture was washed after 10 h of stirring at room temperature with saturated aqueous Na$_2$CO$_3$ solution (2×50 ml), dried over Na$_2$SO$_4$, and concentrated on a rotary evaporator. The brown, oily residue was purified by column chromatography on silica with hexane/CH$_2$Cl$_2$=3:1. The product fraction with greenish fluorescence was dried to yield a red solid. Yield: 146 mg, 12%.

Synthesis of Fluorene-BODIPY Polymer570 with an Amine Group (PF5%570BODIPY4NH$_2$). In a glovebox under nitrogen atmosphere, a dry three neck 50 mL round-bottom flask with stir bar was charged with 316 mg (1.15 mmol) of bis(1,5-cyclooctadiene) nickel(0), 128 mg (1.15 mmol) of cyclooctadiene, and 178 mg (1.15 mmol) of bypyridine in 5.0 mL of a 1:1 mixture of toluene and dimethylformamide (DMF). A dark purple color then developed. The solution was heated to 60° C. In the glovebox, a dry 20 mL flask was charged with 32.2 mg (0.025 mmol) of BODIPY monomer 5a, 250 mg (0.455 mmol) of 9,9-Dioctyl-2,7-dibromofluorene and 12.8 mg (0.02 mmol) of 2,7-dibromo-9,9-bis(3-(tert-butyl hexylcarbamate)fluorine in 4.0 mL of a 1:1 mixture of toluene and DMF, then they were added dropwise into the above catalyst mixture. The flask containing this solution was covered with foil to protect it from light and the reaction mixture was refluxed for 4 days. Then 4 drops of iodobenzene was added to end-cap the polymer chain and the reaction was stirred for an additional 12 h at 60° C. The product was diluted with 50 ml of toluene and washed with aqueous 15 wt % of sodium thiosulfate solution (3×50 mL) followed by washing with Milli-Q water and drying over MgSO$_4$, for the removal of residual iodine from polymer. The polymer solution was evaporated and dissolved in dichloromethane. After polymer solution was filtered, the concentrated polymer solution in dichloromethane was poured into 100 ml of MeOH, and filtered. The precipitate was stirred in 50 ml of acetone at room temperature for 24 h, and filtered. Polymer was obtained as red solid. De-protection of amine group from the polymer was finished as the following procedure, polymer was dissolved in DCM (50 mL) and TFA (1.5 mL) was added to remove protecting groups and generate amine groups. The mixture was stirred at room temperature overnight (in dark) and then washed with 10% NaOH water solution three times. DCM phase was separated, concentrated to ca. 5 mL, and then added into methanol (80 mL) to precipitate the final polymer. Yield: 116 mg, 58%.

Example 15: Synthesis of BODIPY Monomer 6a (Shown in FIG. 12) and Related Narrow-Band Emissive Polymer with Side-Chain Amine Groups The present example provides a method for obtaining narrow-band BODIPY monomer5a and a narrow-band emissive fluorene-BODIPY copolymer polymer600 with side-chain amine groups.

Synthesis of BODOPY Monomer 6a. p-tolualdehyde (120 mg, 0.96 mmol), BODIPY monomer 4a (400 mg, 0.62 mmol), p-toluene sulfonic acid (60 mg), 2 ml of acetic acid, and piperidine (3 ml) were dissolved in 30 ml of benzene refluxed for 10 h by using a Dean-Stark apparatus. The mixture was cooled to room temperature, the solvents were removed under vacuum, and the crude product was purified by column chromatography on silica gel eluted with ethyl acetate/hexane 1:7. The crude was recrystallized from chloroform/methanol to give the product as a metallic shiny solid. Yield: 70 mg, 15%.

Synthesis of Fluorene-BODIPY Polymer600 with Amine Group (PF5%600BODIPY4NH$_2$). In a glovebox under nitrogen atmosphere, a dry three neck 50 mL round-bottom flask with stir bar was charged with 248 mg (0.9 mmol) of bis(1,5-cyclooctadiene) nickel(0), 97 mg (0.9 mmol) of cyclooctadiene, and 140 mg (0.9 mmol) of bypyridine in 4.0 mL of a 1:1 mixture of toluene and dimethylformamide (DMF). A dark purple color then developed. The solution was heated to 60° C. In the glovebox, a dry 20 mL flask was charged with 15.2 mg (0.02 mmol) of BODIPY monomer 6a, 199.6 mg (0.364 mmol) of 9,9-Dioctyl-2,7-dibromofluorene and 10.2 mg (0.016 mmol) of 2,7-dibromo-9,9-bis(3-(tert-butyl hexylcarbamate)fluorine in 4.0 mL of a 1:1 mixture of toluene and DMF, then they were added dropwise into the above catalyst mixture. The flask containing this solution was covered with foil to protect it from light and the reaction mixture was refluxed for 4 days. Then 4 drops of iodobenzene was added to end-cap the polymer chain and the reaction was stirred for an additional 12 h at 60° C. The product was diluted with 50 ml of toluene and washed with aqueous 15 wt % of sodium thiosulfate solution (3×50 mL) followed by washing with Milli-Q water and drying over $MgSO_4$, for the removal of residual iodine from polymer. The polymer solution was evaporated and dissolved in dichloromethane. After polymer solution was filtered, the concentrated polymer solution in dichloromethane was poured into 100 ml of MeOH, and filtered. The precipitate was stirred in 50 ml of acetone at room temperature for 24 h, and filtered. Polymer was obtained as red solid. De-protection of amine group from the polymer was finished as the following procedure, polymer was dissolved in DCM (50 mL) and TFA (1.0 mL) was added to remove protecting groups and generate amine groups. The mixture was stirred at room temperature overnight (in dark) and then washed with 10% NaOH water solution three times. DCM phase was separated, concentrated to ca. 5 mL, and then added into methanol (80 mL) to precipitate the final polymer. Yield: 105 mg, 65.6%.

Example 16: Synthesis of a Fluorescent Polymers with Side-Chain Amine Groups for Chemically Cross-Linking with Narrow-Band Emissive Polymer The present example provides a method for obtaining a fluorescent polymer with side-chain amine groups that can chemically cross-link with narrow-band emissive polymers.

Synthesis of PF47BSeD with Amine Group ($PF47BSeD3NH_2$). Polymer is synthesized by palladium-catalyzed Suzuki coupling reaction from 9,9-dioctylfluorene and 4,7-dibromobenzo[c]-1,2,5-selenadiazole. 224.8 mg (0.41 mmol) of 9,9-dioctyl-2,7-dibromofluorene, 139.6 mg (0.25 mmol) of 9,9-dioctylfluorene-2,7-diboronic acid bis (1,3-propanediol) ester, 80.1 mg (0.235 mmol) of 4,7-dibromobenzo[c]-1,2,5-selenadiazole, 9.57 mg (0.015 mmol) of 2,7-dibromo-9,9-bis(3-(tert-butyl hexylcarbamate)fluorene, 2 drops of aliquot 336, 10 ml of 2M $Na_2CO_3$ aqueous solution, 15 ml of toluene were placed in a 50 ml flask. The flask was evacuated and refilled with $N_2$ four times by using the freeze/thaw method and $Pd(PPh_3)_4$ (1-1.5 mol %) was added. The flask was further degassed four times, then reaction was heated to 100° C. and stirred under $N_2$. After 70 h 0.2 ml of bromobenzene and 15 mg of phenylboronic acid in toluene were added to end-cap the polymer chain and the reaction was stirred for an additional 2 h at 100° C. respectively. The whole mixture was poured into 100 ml of MeOH, filtered, and washed with 0.2M of HCl. The precipitate was stirred in 50 ml of acetone at room temperature for 24 h and dried in vacuum oven to obtain dark yellow solid. De-protection of amine group from the polymer was finished as the following procedure, polymer was dissolved in DCM (50 mL) and TFA (1.0 mL) was added to remove protecting groups and generate amine groups. The mixture was stirred at room temperature overnight (in dark) and then washed with 10% NaOH water solution three times. DCM phase was separated, concentrated to ca. 10 mL, and then added into methanol (80 mL) to precipitate the final polymer. Yield: 114 mg, 76%.

Example 17: Synthesis of BODIPY Monomer 7a (Shown in FIG. 12) and Related Narrow-Band Emissive Polymer with Side-Chain Amine Groups The present example provides a method for obtaining narrow-band BODIPY monomer7a and a narrow-band emissive fluorene-BODIPY copolymer polymer655 with side-chain amine groups.

Synthesis of BODOPY Monomer 5a. p-tolualdehyde (168 mg, 1.4 mmol), BODIPY monomer 1a (200 mg, 0.34 mmol), p-toluene sulfonic acid (50 mg), 3 ml of acetic acid, and piperidine (3 ml) were dissolved in 30 ml of benzene refluxed for 10 h by using a Dean-Stark apparatus. The mixture was cooled to room temperature, the solvents were removed under vacuum, and the crude product was purified by column chromatography on silica gel eluted with ethyl acetate/hexane 1:7. The crude was recrystallized from chloroform/methanol to give the product as a metallic shiny solid. Yield: 99 mg, 37%.

Synthesis of Fluorene-BODIPY Polymer655 with Amine Group ($PF5%655BODIPY4NH_2$). In a glovebox under nitrogen atmosphere, a dry three neck 50 mL round-bottom flask with stir bar was charged with 248 mg (0.9 mmol) of bis(1,5-cyclooctadiene) nickel(0), 97 mg (0.9 mmol) of cyclooctadiene, and 140 mg (0.9 mmol) of bypyridine in 4.0 mL of a 1:1 mixture of toluene and dimethylformamide (DMF). A dark purple color then developed. The solution was heated to 60° C. In the glovebox, a dry 20 mL flask was charged with 15.9 mg (0.02 mmol) of BODIPY monomer 7a, 199.6 mg (0.364 mmol) of 9,9-dioctyl-2,7-dibromofluorene and 10.2 mg (0.016 mmol) of 2,7-dibromo-9,9-bis(3-(tert-butyl hexylcarbamate)fluorine in 4.0 mL of a 1:1 mixture of toluene and DMF, then they were added dropwise into the above catalyst mixture. The flask containing this solution was covered with foil to protect it from light and the reaction mixture was refluxed for 4 days. Then 4 drops of iodobenzene was added to end-cap the polymer chain and the reaction was stirred for an additional 12 h at 60° C. The product was diluted with 50 ml of toluene and washed with aqueous 15 wt % of sodium thiosulfate solution (3×50 mL) followed by washing with Milli-Q water and drying over $MgSO_4$, for the removal of residual iodine from polymer. The polymer solution was evaporated and dissolved in dichloromethane. After polymer solution was filtered, the concentrated polymer solution in dichloromethane was poured into 100 ml of MeOH, and filtered. The precipitate was stirred in 50 ml of acetone at room temperature for 24 h, and filtered. Polymer was obtained as red solid. De-protection of amine group from the polymer was finished as the following procedure, polymer was dissolved in DCM (50 mL) and TFA (1.0 mL) was added to remove protecting groups and generate amine groups. The mixture was stirred at room temperature overnight (in dark) and then washed with 10% NaOH water solution three times. DCM phase was separated, concentrated to ca. 5 mL, and then added into methanol (80 mL) to precipitate the final polymer. Yield: 97 mg, 60.6%.

Example 18: Synthesis of BODIPY Monomer 8a (Shown in FIG. 12) and Related Narrow-Band Emissive Polymer with Side-Chain Amine Groups The present example provides a method for obtaining narrow-band BODIPY monomer8a and a narrow-band emissive fluorene-BODIPY copolymer polymers with side-chain amine groups.

Synthesis of BODIPY Monomer 8a. p-Tolualdehyde (300 mg, 2.5 mmol), BODIPY monomer 4a (400 mg, 0.62 mmol), p-toluene sulfonic acid (80 mg), 2 ml of acetic acid, and piperidine (3 ml) were dissolved in 35 ml of benzene refluxed for 10 h by using a Dean-Stark apparatus. The mixture was cooled to room temperature, the solvents were removed under vacuum, and the crude product was purified by column chromatography on silica gel eluted with ethyl acetate/hexane 1:7. The crude was recrystallized from chloroform/methanol to give the product as a metallic shiny solid. Yield: 180 mg, 33%.

Synthesis of Fluorene-BODIPY Polymer670 with Amine Group (PF5%670BODIPY4NH$_2$). In a glovebox under nitrogen atmosphere, a dry three neck 50 mL round-bottom flask with stir bar was charged with 248 mg (0.9 mmol) of bis(1,5-cyclooctadiene) nickel(0), 97 mg (0.9 mmol) of cyclooctadiene, and 140 mg (0.9 mmol) of bypyridine in 4.0 mL of a 1:1 mixture of toluene and dimethylformamide (DMF). A dark purple color then developed. The solution was heated to 60° C. In the glovebox, a dry 20 mL flask was charged with 17.6 mg (0.02 mmol) of BODIPY monomer 8a, 199.6 mg (0.364 mmol) of 9,9-Dioctyl-2,7-dibromofluorene and 10.2 mg (0.016 mmol) of 2,7-dibromo-9,9-bis(3-(tert-butyl hexylcarbamate)fluorine in 4.0 mL of a 1:1 mixture of toluene and DMF, then they were added dropwise into the above catalyst mixture. The flask containing this solution was covered with foil to protect it from light and the reaction mixture was refluxed for 4 days. Then 4 drops of iodobenzene was added to end-cap the polymer chain and the reaction was stirred for an additional 12 h at 60° C. The product was diluted with 50 ml of toluene and washed with aqueous 15 wt % of sodium thiosulfate solution (3×50 mL) followed by washing with Milli-Q water and drying over MgSO$_4$, for the removal of residual iodine from polymer. The polymer solution was evaporated and dissolved in dichloromethane. After polymer solution was filtered, the concentrated polymer solution in dichloromethane was poured into 100 ml of MeOH, and filtered. The precipitate was stirred in 50 ml of acetone at room temperature for 24 h, and filtered. Polymer was obtained as red solid. Deprotection of amine group from the polymer was finished as the following procedure, polymer was dissolved in DCM (50 mL) and TFA (1.0 mL) was added to remove protecting groups and generate amine groups. The mixture was stirred at room temperature overnight (in dark) and then washed with 10% NaOH water solution three times. DCM phase was separated, concentrated to ca. 5 mL, and then added into methanol (80 mL) to precipitate the final polymer. Yield: 109 mg, 68.1%.

Synthesis of Fluorene-BODIPY Polymer680 with Amine Group (PF5%680BODIPY4NH$_2$). In a glovebox under nitrogen atmosphere, a dry three neck 50 mL round-bottom flask with stir bar was charged with 248 mg (0.9 mmol) of bis(1,5-cyclooctadiene) nickel(0), 97 mg (0.9 mmol) of cyclooctadiene, and 140 mg (0.9 mmol) of bypyridine in 4.0 mL of a 1:1 mixture of toluene and dimethylformamide (DMF). A dark purple color then developed. The solution was heated to 60° C. In the glovebox, a dry 20 mL flask was charged with 16.5 mg (0.02 mmol) of BODIPY monomer 3a, 199.6 mg (0.364 mmol) of 9,9-Dioctyl-2,7-dibromofluorene and 10.2 mg (0.016 mmol) of 2,7-dibromo-9,9-bis(3-(tert-butyl hexylcarbamate)fluorine in 4.0 mL of a 1:1 mixture of toluene and DMF, then they were added dropwise into the above catalyst mixture. The flask containing this solution was covered with foil to protect it from light and the reaction mixture was refluxed for 4 days. Then 4 drops of iodobenzene was added to end-cap the polymer chain and the reaction was stirred for an additional 12 h at 60° C. The product was diluted with 50 ml of toluene and washed with aqueous 15 wt % of sodium thiosulfate solution (3×50 mL) followed by washing with Milli-Q water and drying over MgSO$_4$, for the removal of residual iodine from polymer. The polymer solution was evaporated and dissolved in dichloromethane. After polymer solution was filtered, the concentrated polymer solution in dichloromethane was poured into 100 ml of MeOH, and filtered. The precipitate was stirred in 50 ml of acetone at room temperature for 24 h, and filtered. Polymer was obtained as red solid. Deprotection of amine group from the polymer was finished as the following procedure, polymer was dissolved in DCM (50 mL) and TFA (1.0 mL) was added to remove protecting groups and generate amine groups. The mixture was stirred at room temperature overnight (in dark) and then washed with 10% NaOH water solution three times. DCM phase was separated, concentrated to ca. 5 mL, and then added into methanol (80 mL) to precipitate the final polymer. Yield: 122 mg, 76.2%.

Figure 31B:
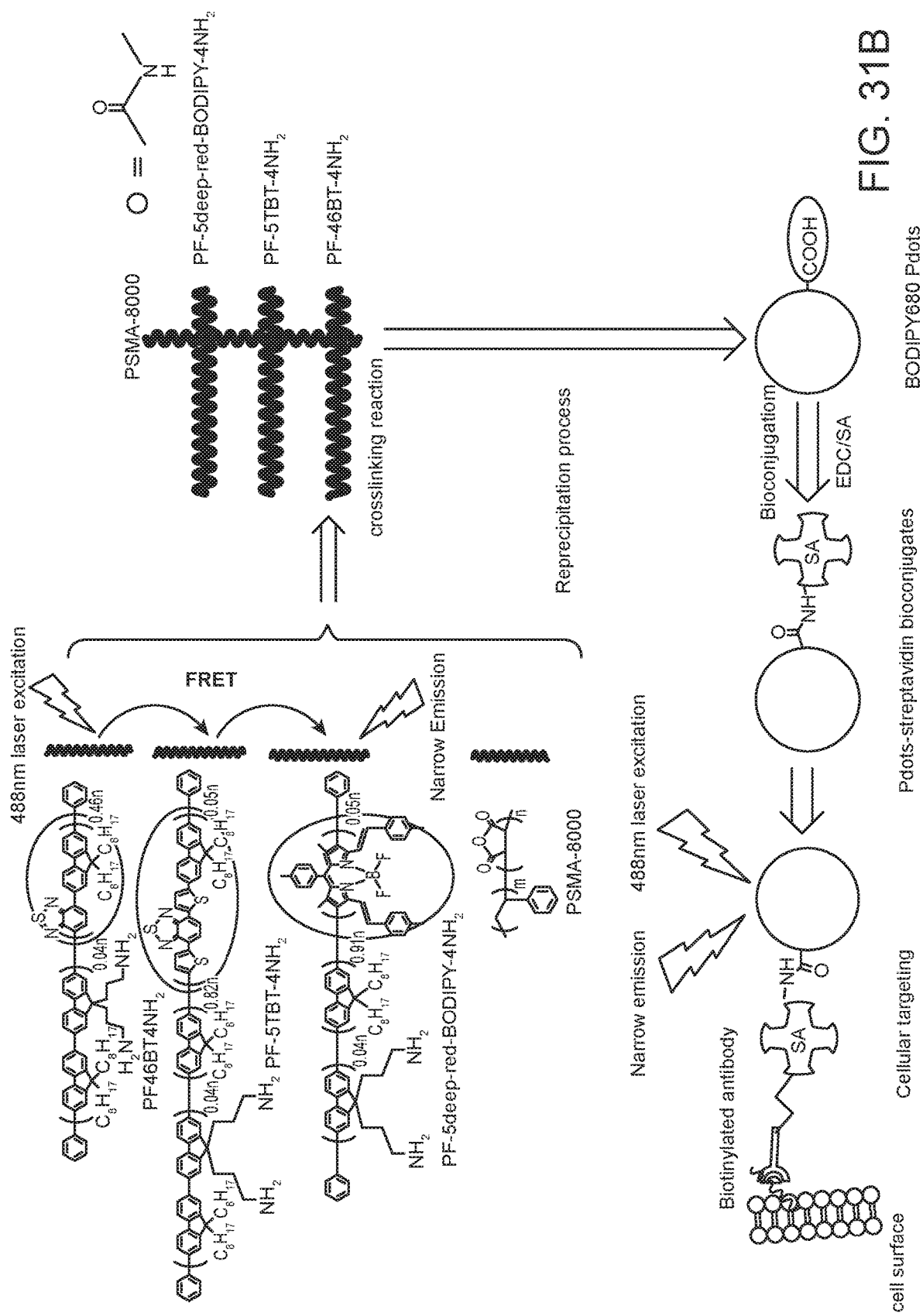
FIG. 31B show an example of a narrow emissive polymer chemically cross-linked with broad-band semiconducting polymer and the formation of Pdot-bioconjugates for specific cellular targeting. Two broad-band fluorescent polymers containing benzothiadiazole (BT) and 4,7-dithiophenyl-2,1,3-benzothiadiazole (TBT) are energy donors and the narrow-band emissive polymer containing BODIPY is energy acceptor. The three fluorescent polymers with amine group can react with amphiphilic polymer such as poly (styrene-co-maleic anhydride) (PSMA). After cross-linking reaction and Pdot formation, multi-step energy-transfer inside Pdots results in narrow-band emissions.
Figure 32:
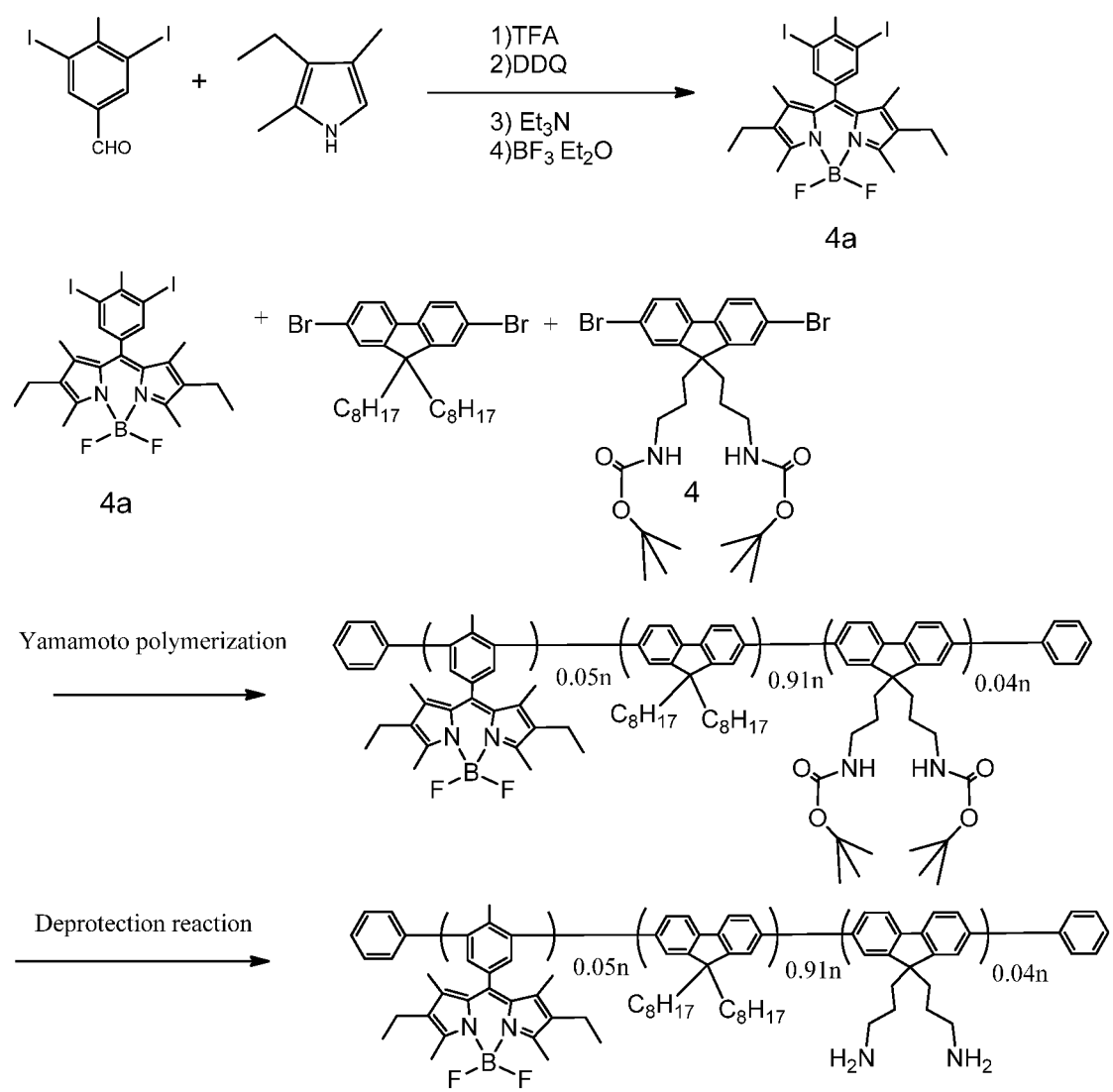
FIG. 32 shows an example multi-step synthesis of BODIPY monomer 4a in FIG. 12 and copolymer that include a general monomer fluorene and BODIPY monomer 4a with amine group via Yamamoto polymerization (PF5%540BODIPY4NH$_2$).
Figure 33:
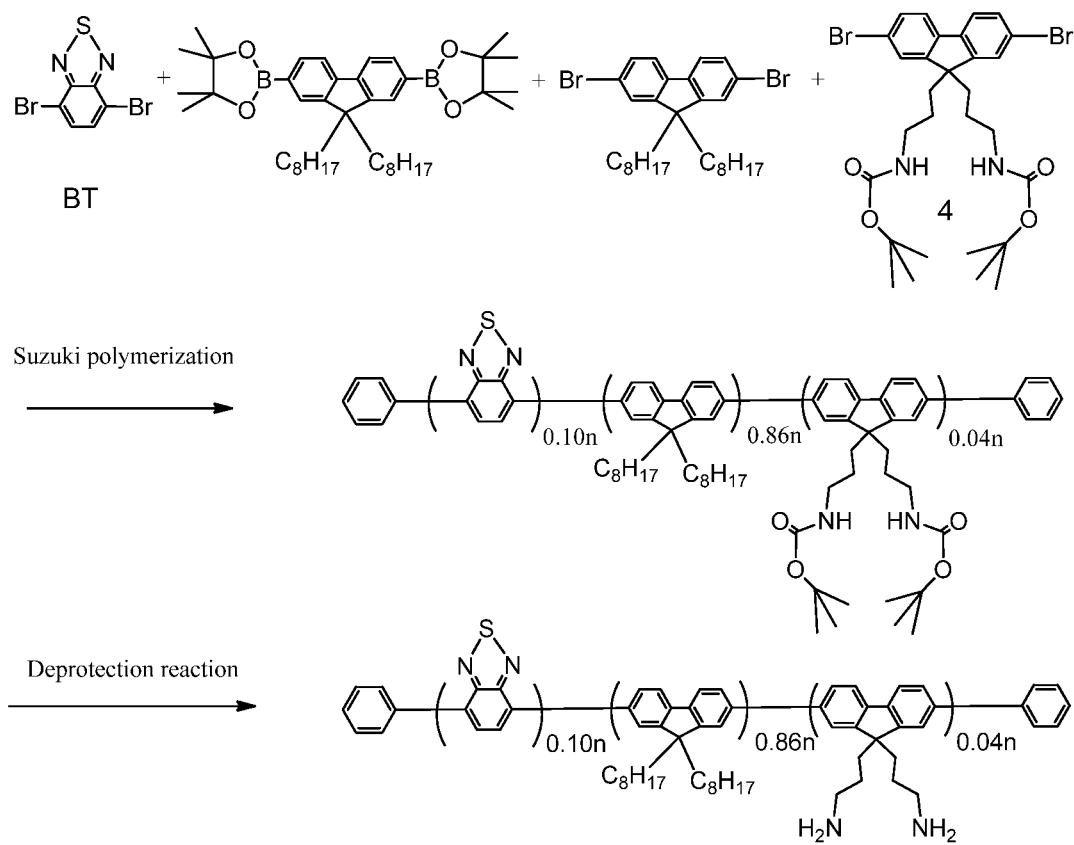
FIG. 33 shows an example synthesis of PF10BT polymer with an amine group via Suzuki coupling polymerization (PF10BT4NH$_2$).
Figure 34:
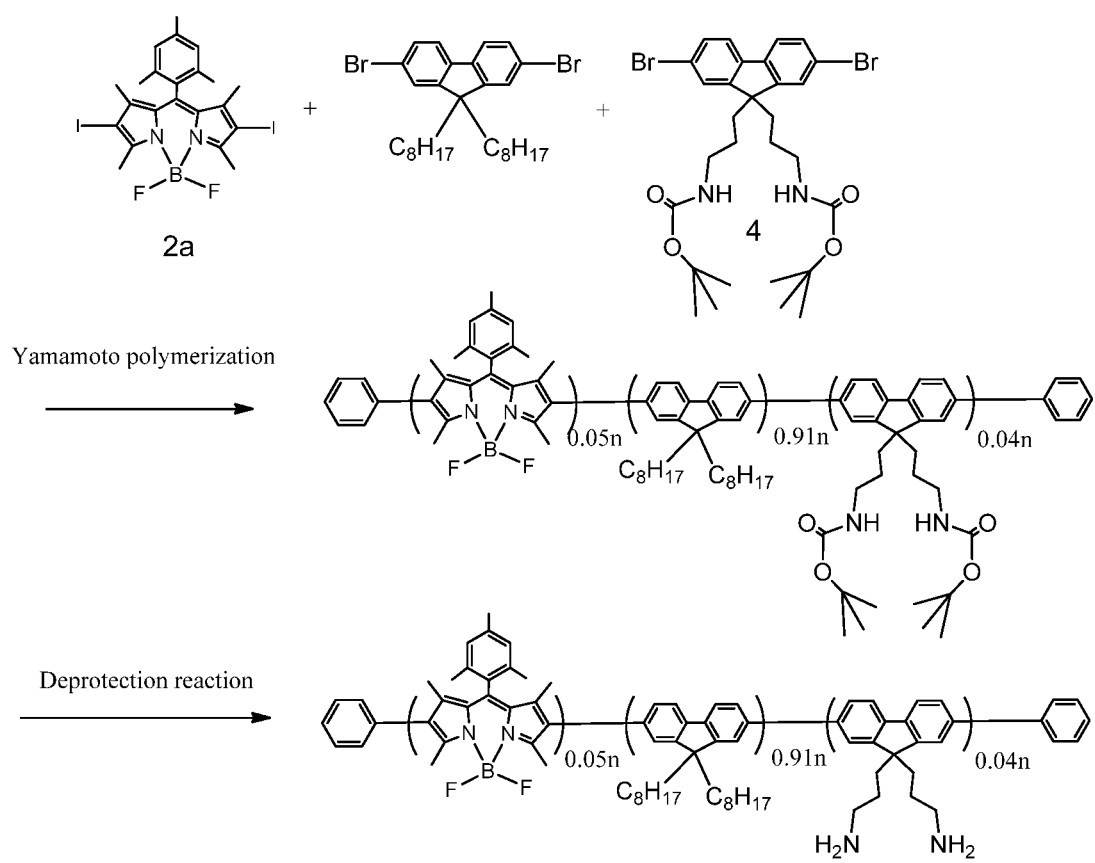
FIG. 34 shows an example synthesis of copolymer that comprises a general monomer fluorene and BODIPY monomer 2a in FIG. 12 with an amine group via Yamamoto polymerization (PF5%540BODIPY4NH$_2$).
Figure 35:
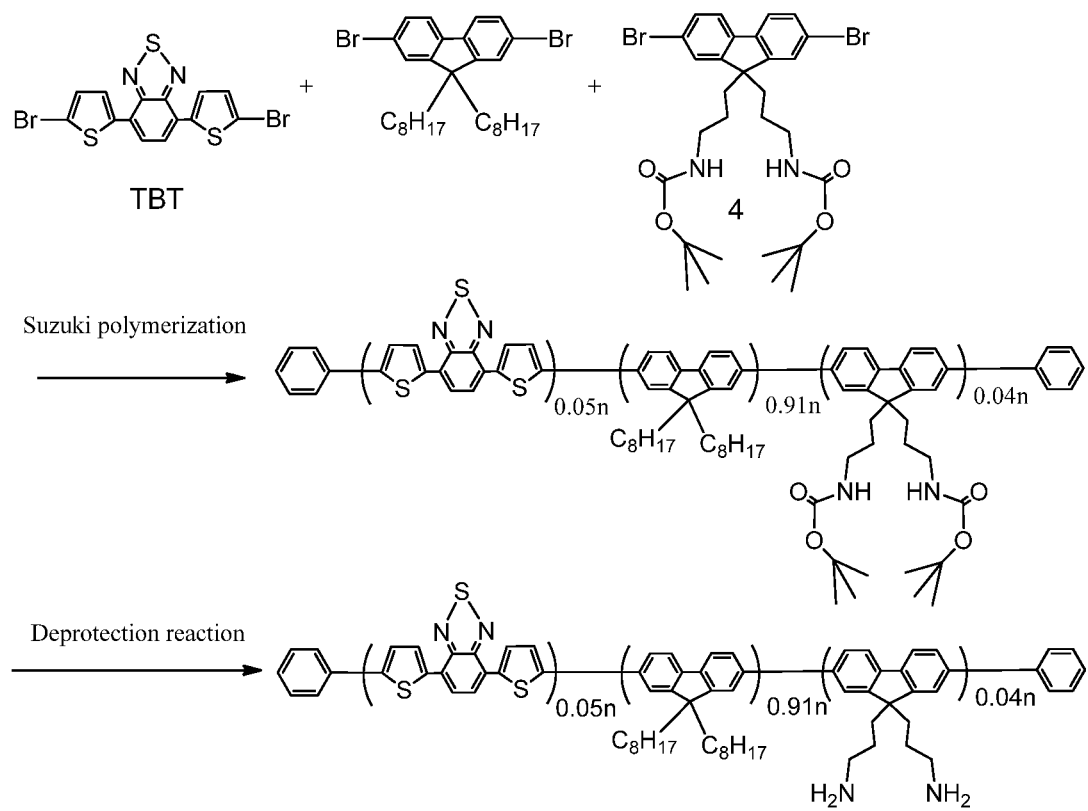
FIG. 35 shows an example synthesis of PFTBT copolymer with an amine group via Suzuki coupling polymerization (PF5TBT4NH$_2$).
Figure 36:
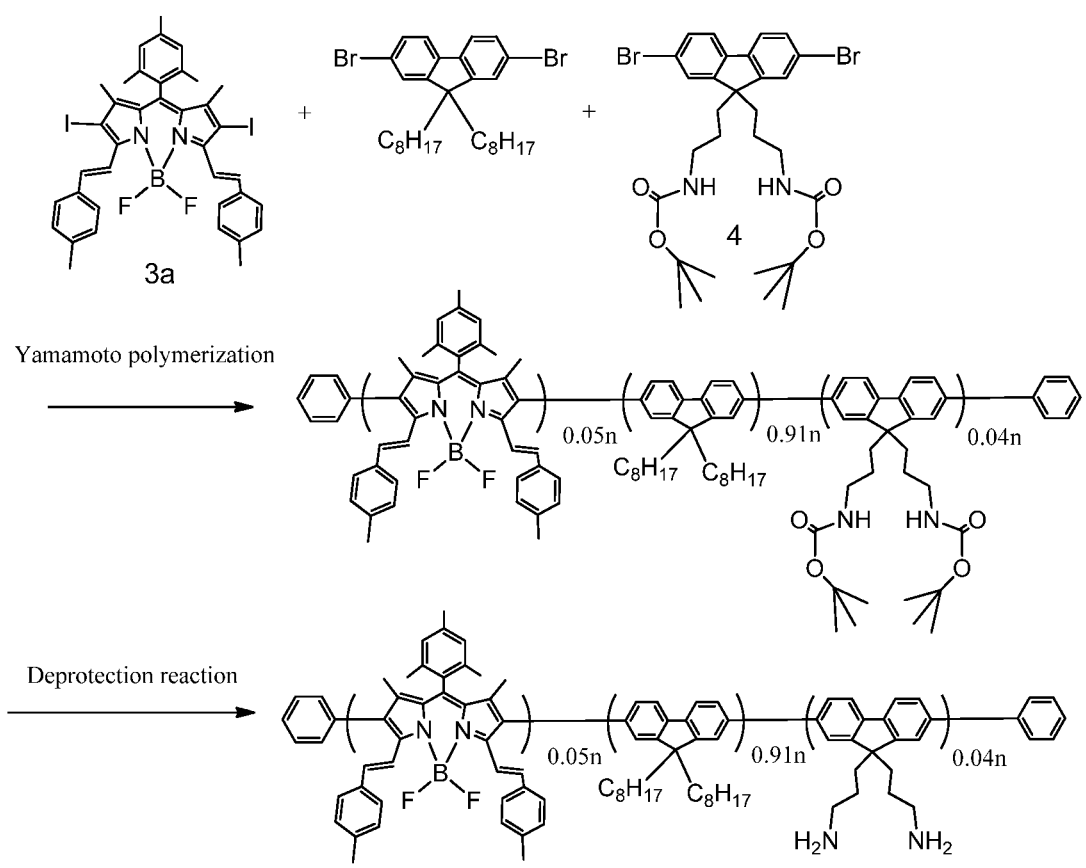
FIG. 36 shows an example synthesis of copolymer that comprises a general monomer fluorene and BODIPY Monomer 3a in FIG. 12 with amine group via Yamamoto polymerization (PF5%680BODIPY4NH$_2$).
Figure 37:
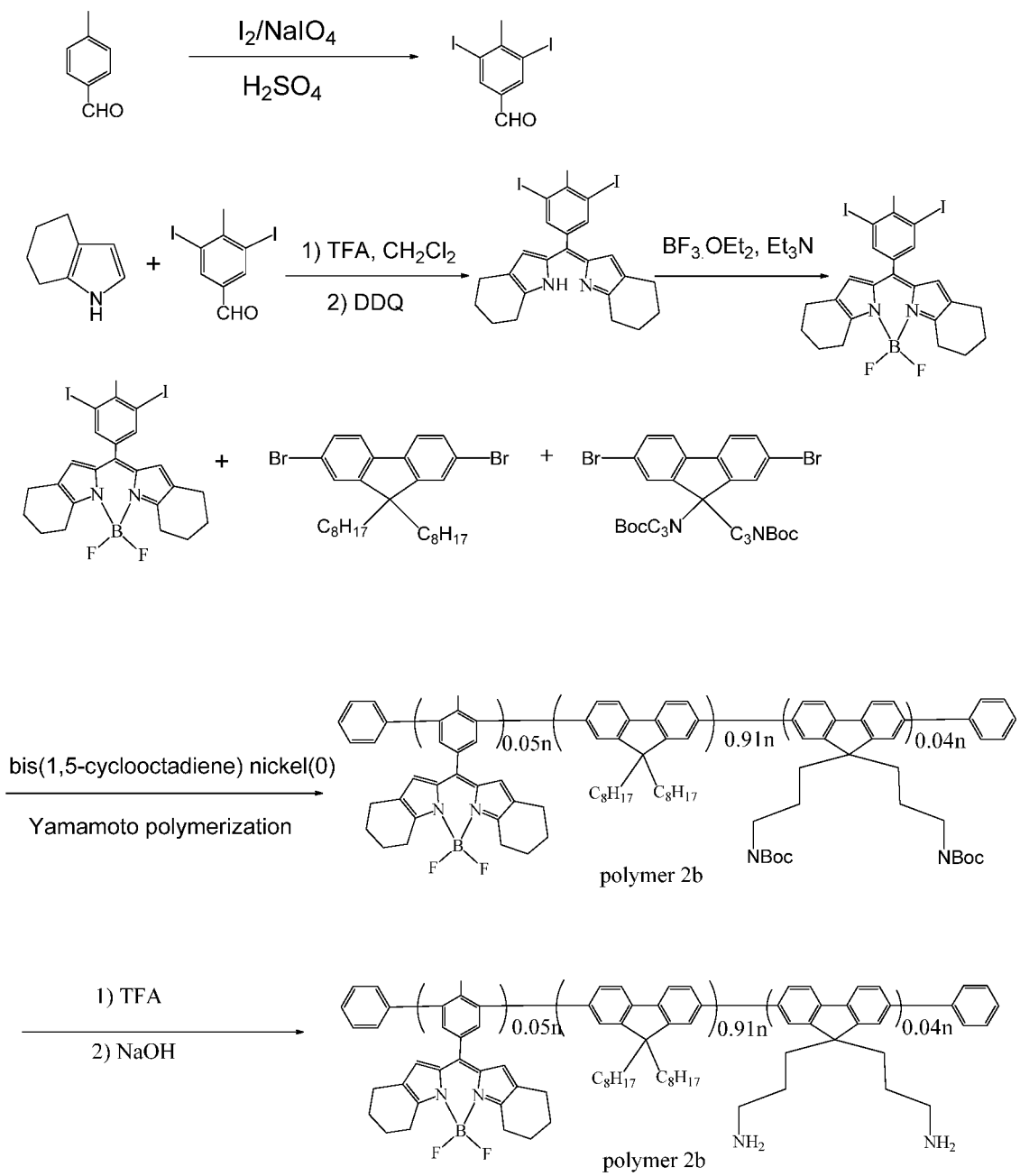
FIG. 37 shows an example multi-step synthesis of BODIPY monomer 5a in FIG. 12 and copolymer that includes a general monomer fluorene and BODIPY Monomer 5a with amine group via Yamamoto polymerization (PF5%570BODIPY4NH$_2$).
Figure 38:
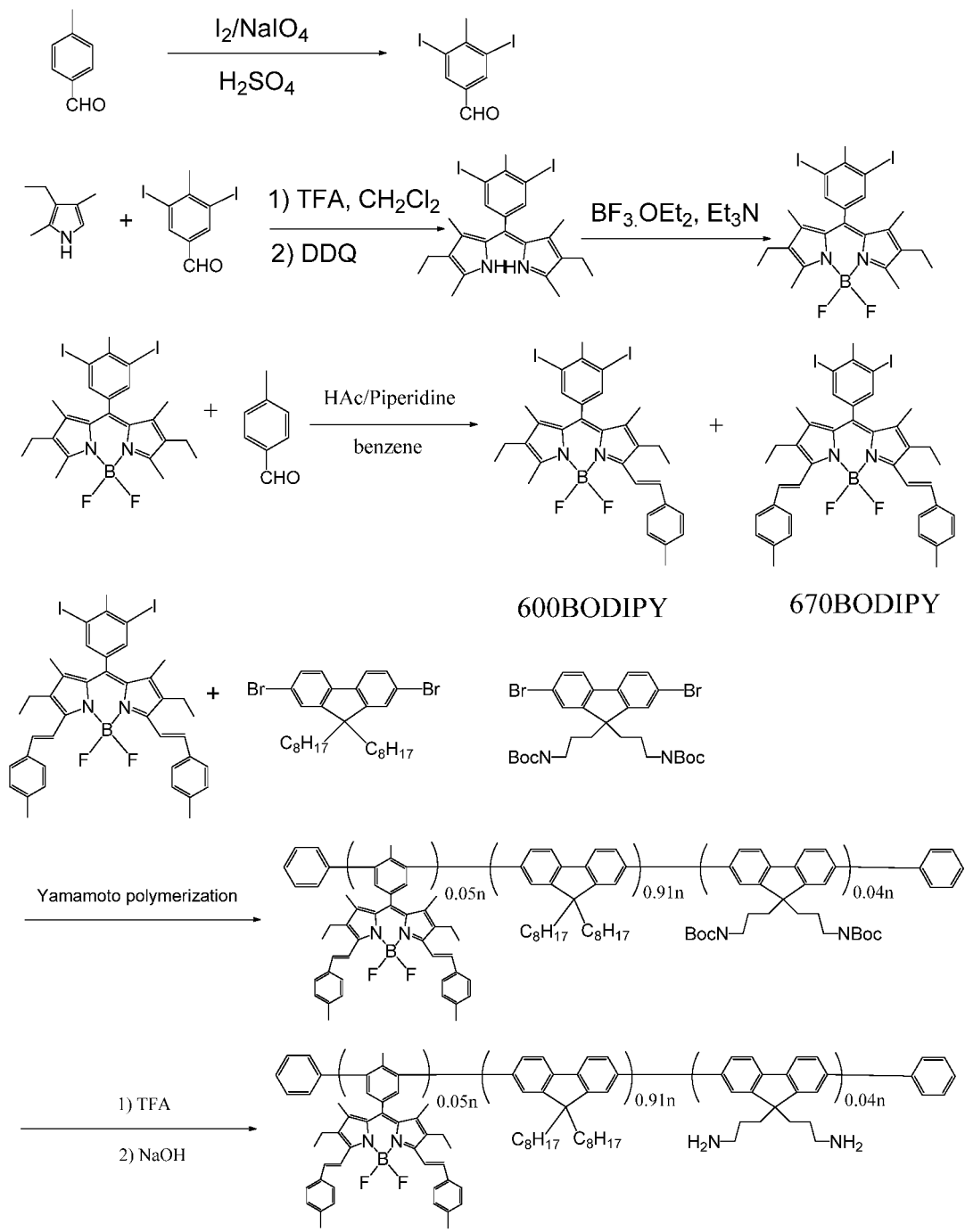
FIG. 38 shows an example multi-step synthesis of BODIPY monomer 8a in FIG. 12 and copolymer that comprises a general monomer fluorene and BODIPY Monomer 8a with amine group via Yamamoto polymerization (PF5%670BODIPY4NH$_2$).
Figure 39:
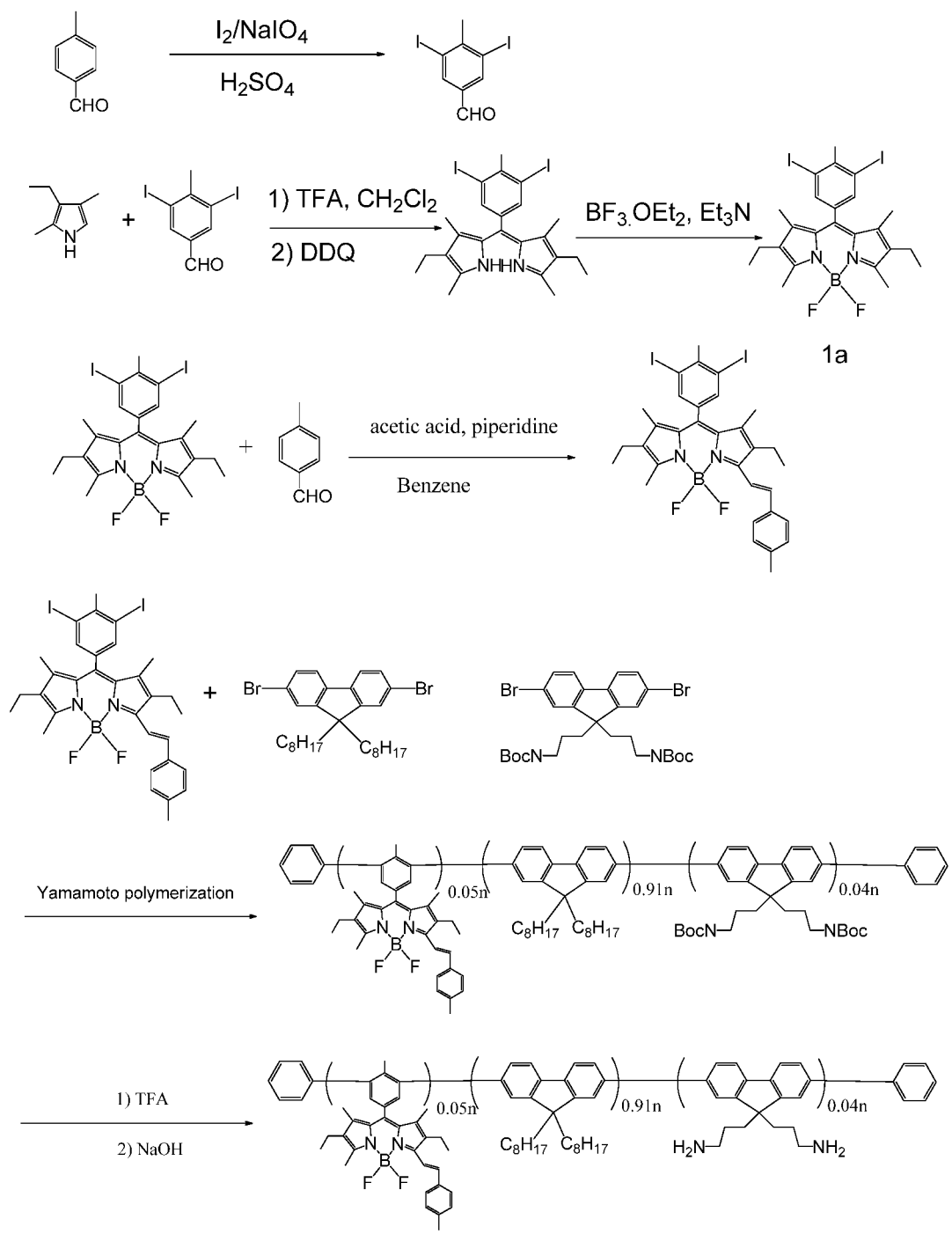
FIG. 39 shows an example multi-step synthesis of BODIPY monomer 6a in FIG. 12 and copolymer that comprise a general monomer fluorene and BODIPY monomer 6a with amine group via Yamamoto polymerization (PF5%600BODIPY4NH$_2$).
Figure 40:
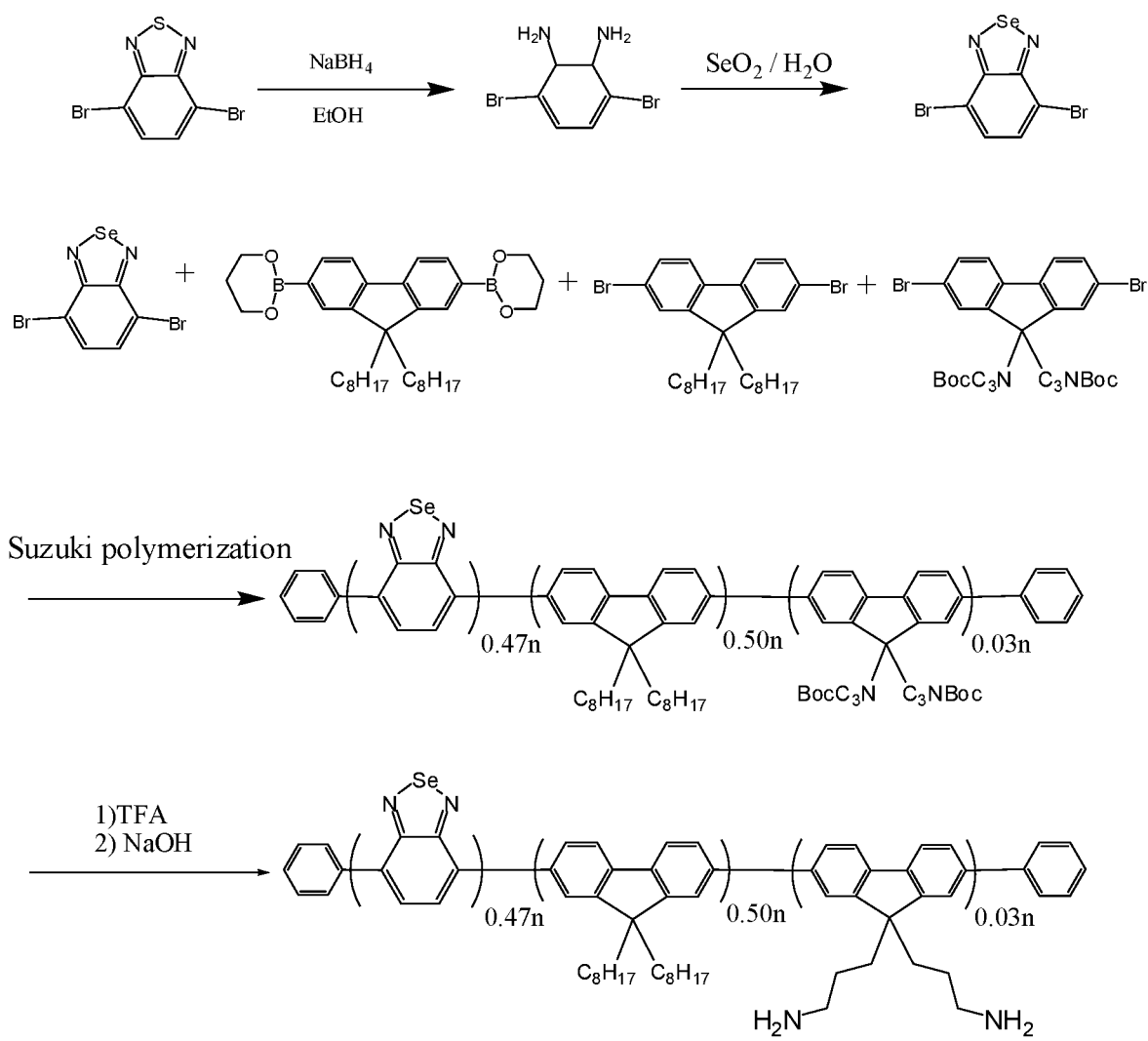
FIG. 40 shows an example synthesis of copolymer that comprises 2,1,3-benzoselenadiazole and a general monomer fluorene with amine group via Suzuki polymerization (PF47BSeD3NH$_2$).
Figure 41A:
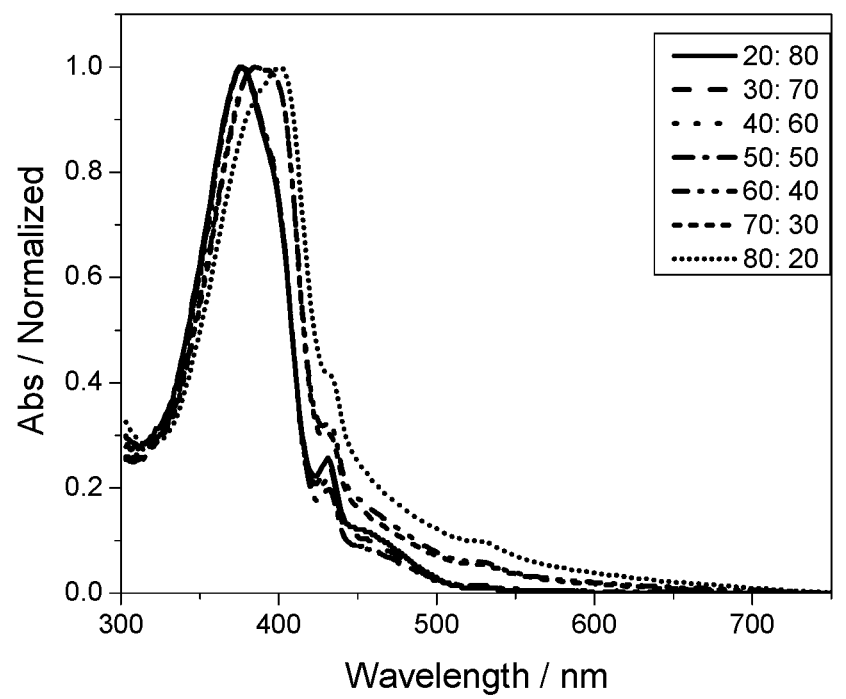
FIG. 41A shows absorption and emission spectra of example blended Pdots prepared from PF10BT4NH$_2$ and 540BODIPY fluorine copolymer with amine group and amphiphilic polymer PS-PEG-COOH. The blended Pdot emission exhibits a FWHM of 39 nm without fluorene's emission under the 405 laser excitation when blending ratio of 540BODIPY copolymer to PF10BT4NH$_2$ was greater than 30:70 and less than 70:30.
Figure 41A:
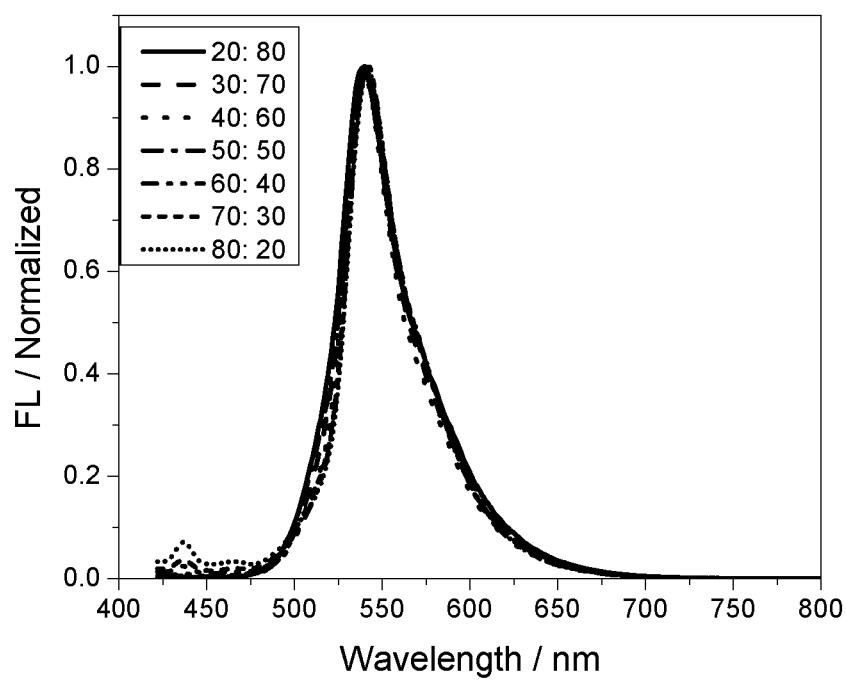
Figure 41B:
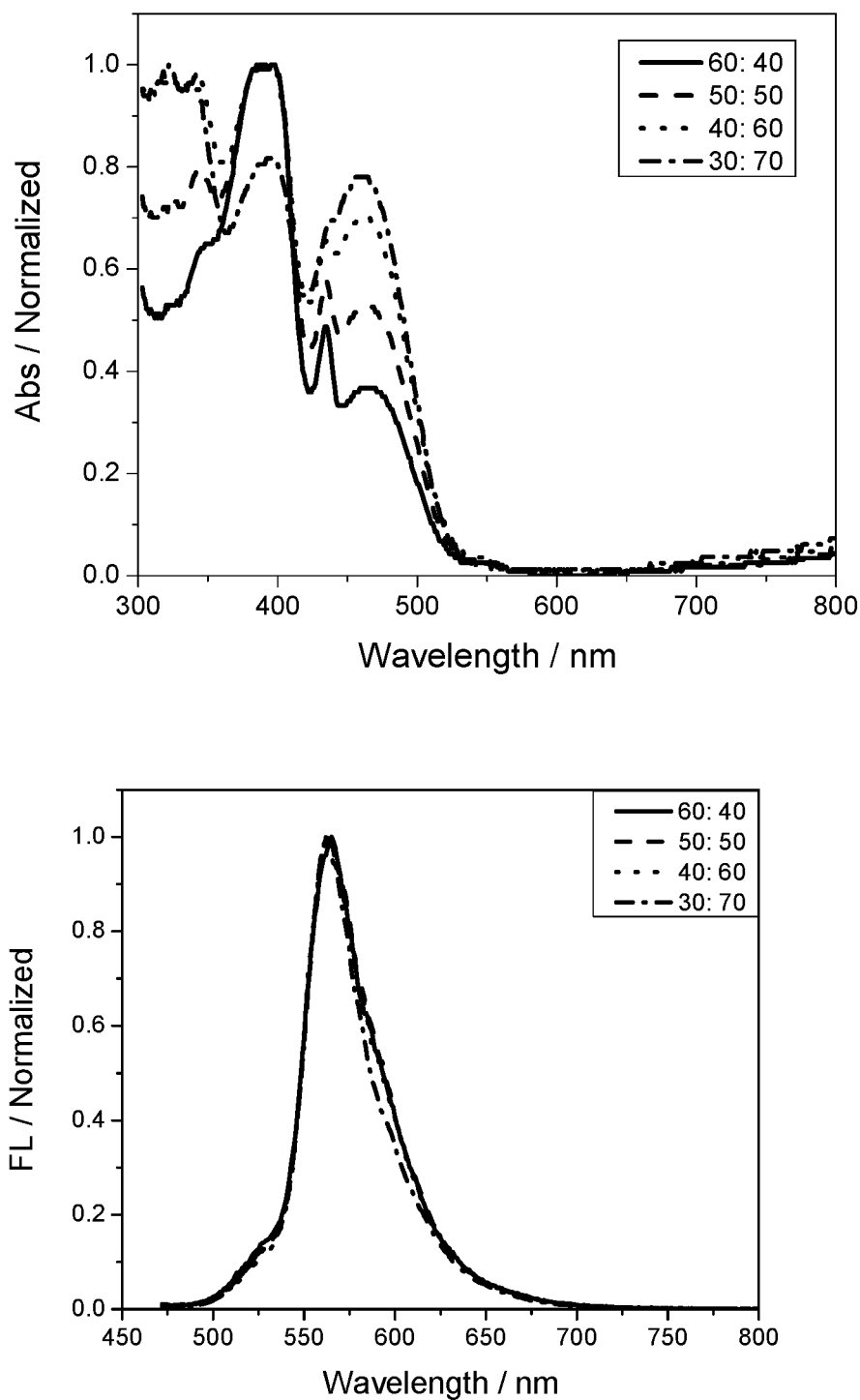
FIG. 41B shows absorption and emission spectra of the blended Pdots prepared from PF46BT4NH$_2$ and 570BODIPY fluorene copolymer with amine group and amphiphilic polymer PS-PEG-COOH. The blended Pdot emission exhibits a FWHM of 38 nm when a blending ratio of 570BODIPY copolymer to PF46BT4NH$_2$ was 30:70.
Figure 41C:
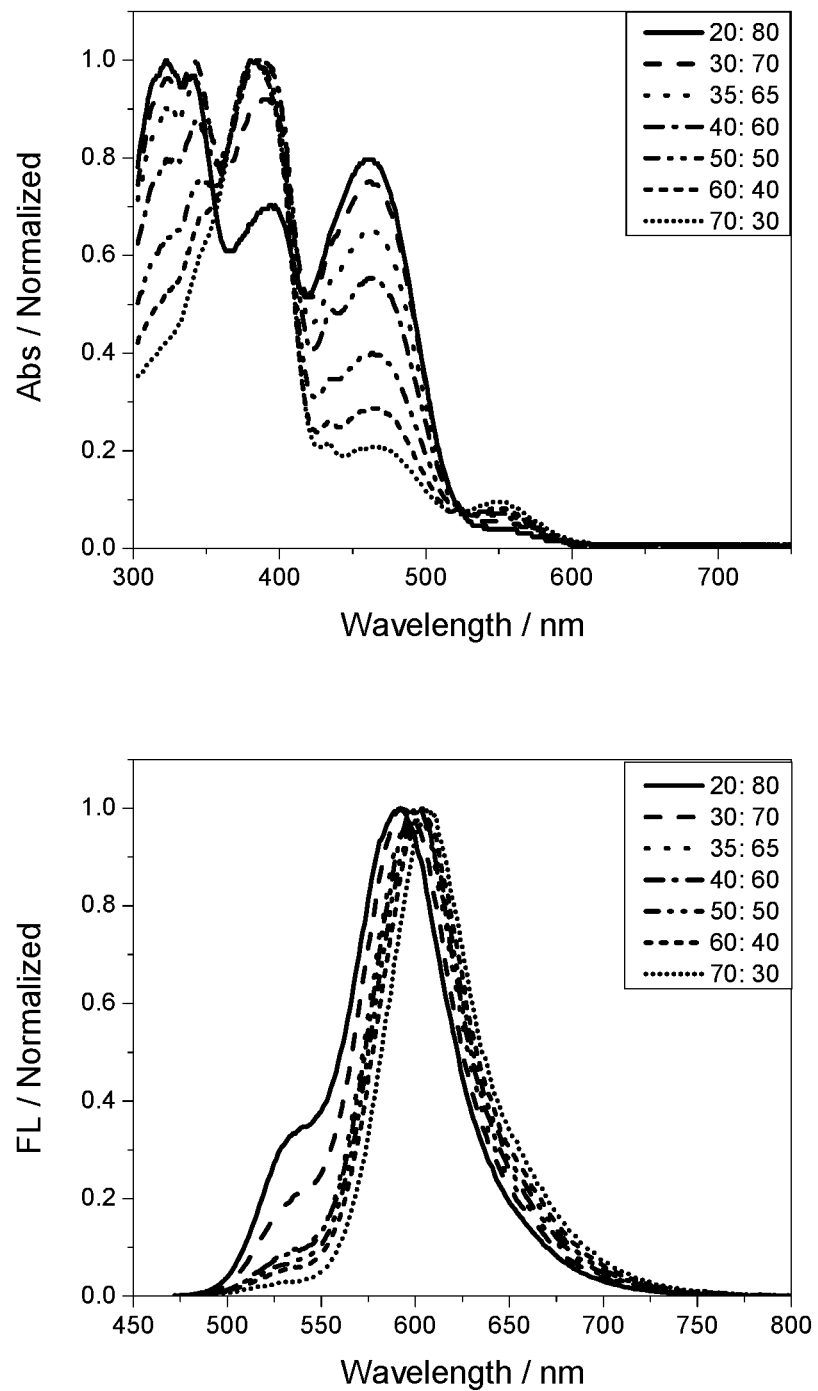
FIG. 41C shows absorption and emission spectra of the blended Pdots prepared from PF46BT4NH$_2$ and 590BODIPY fluorene copolymer with amine group and amphiphilic polymer PS-PEG-COOH. The blended Pdot emission exhibits a FWHM of 55 nm when blending ratio of 590BODIPY copolymer to PF10BT4NH$_2$ was greater than 35:65.
Figure 41D:
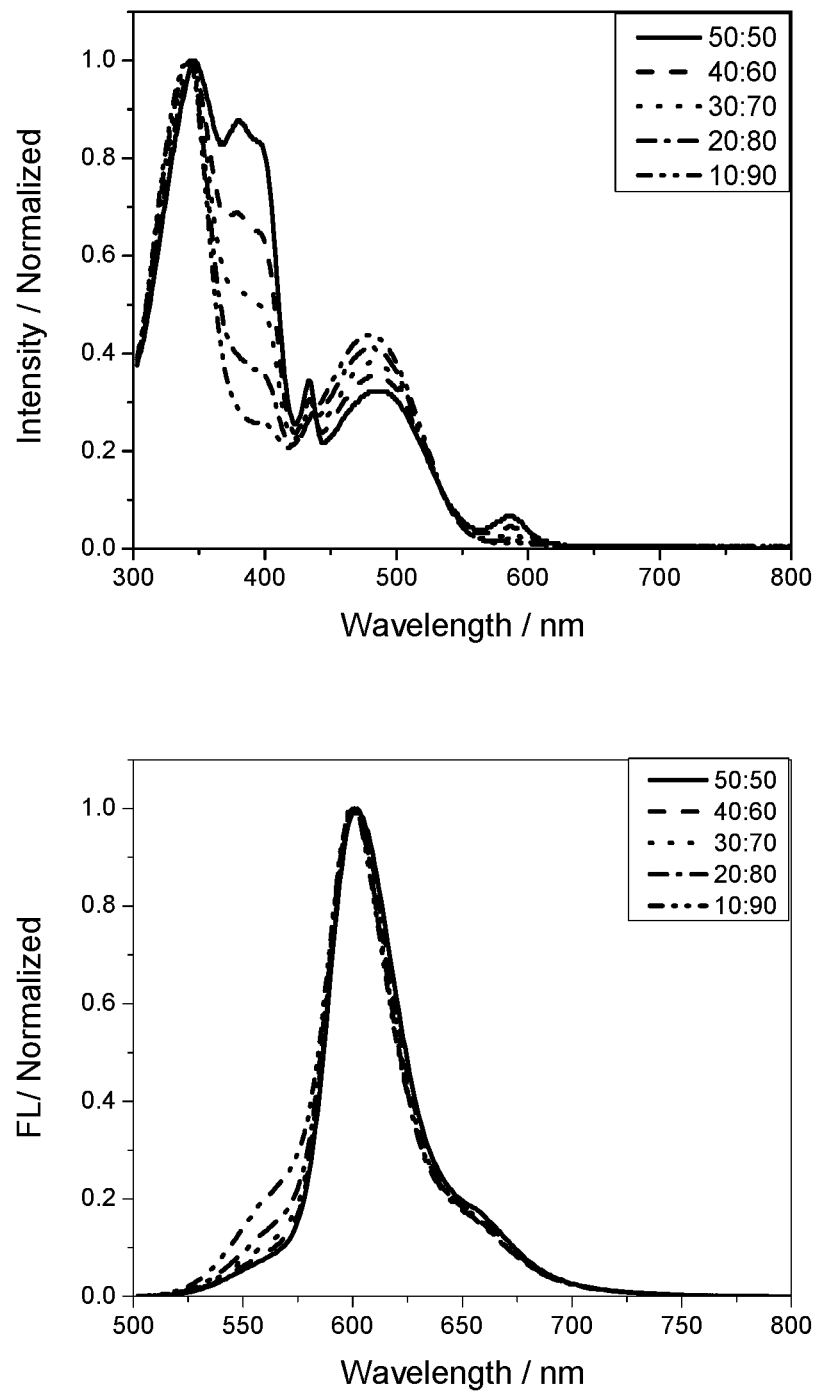
FIG. 41D shows absorption and emission spectra of the blended Pdots prepared from PF47BSeD3NH$_2$ and 600BODIPY fluorene copolymer with amine group and amphiphilic polymer PS-PEG-COOH. The blended Pdot emission exhibits a FWHM of 38 nm when blending ratio of 600BODIPY copolymer to PF47BSeD3NH$_2$ was greater than 30:70.
Figure 41E:
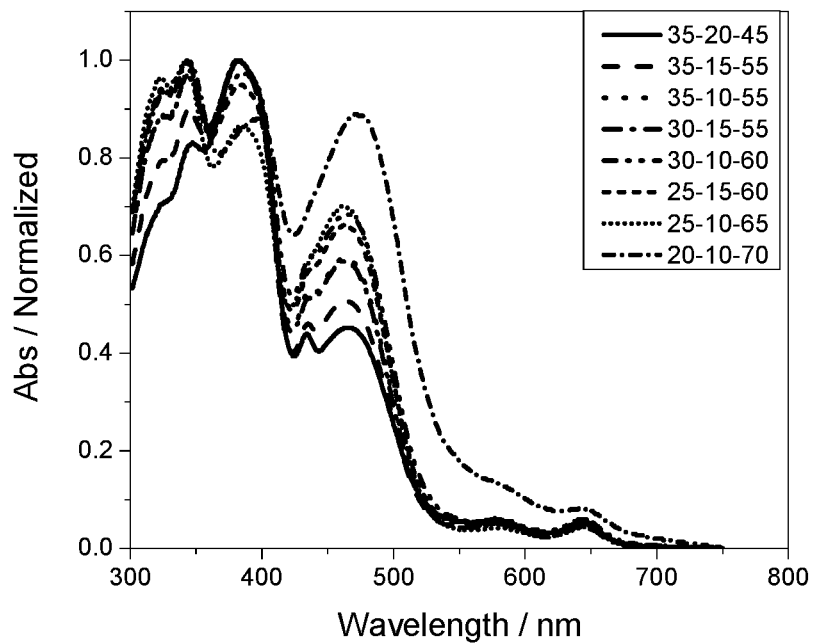
FIG. 41E shows absorption and emission spectra of the blended Pdots prepared from PF46BT4NH$_2$, PF5TBT4NH$_2$ and 655BODIPY fluorene copolymer with amine group and amphiphilic polymer PS-PEG-COOH. The blended Pdot emission exhibits a FWHM of 38 nm when blending ratio of 600BODIPY copolymer to PF5TBT4NH$_2$ and PF46BT4NH$_2$ was 20:10:70.
Figure 41E:
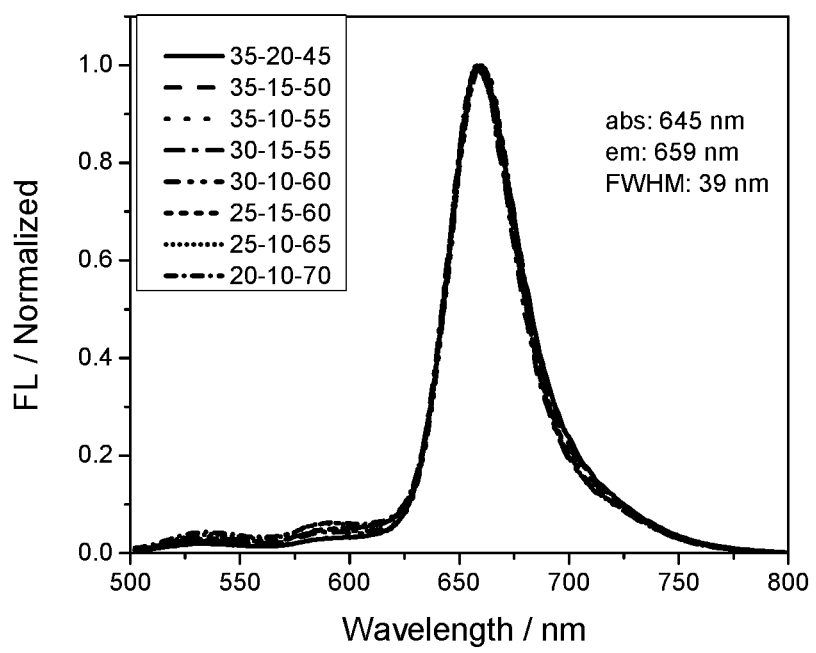
Figure 41F:
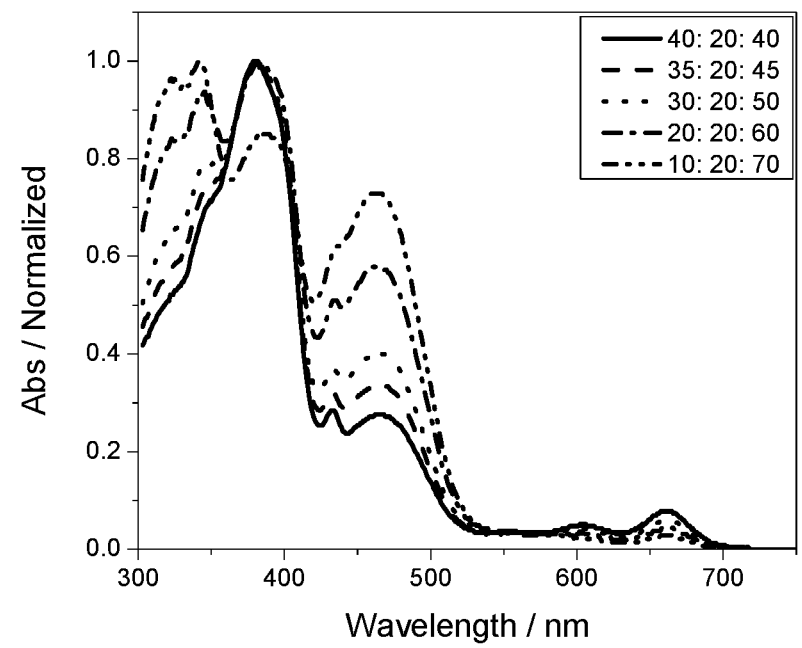
FIG. 41F shows absorption and emission spectra of the blended Pdots prepared from PF46BT4NH$_2$, PF5TBT4NH$_2$ and 680BODIPY fluorene copolymer with amine group and amphiphilic polymer PS-PEG-COOH. The blended Pdot emission exhibits a FWHM of 44 nm when blending ratio of 680BODIPY copolymer to PF5TBT4NH$_2$ and PF46BT4NH$_2$ was 35:20:45.
Figure 41F:
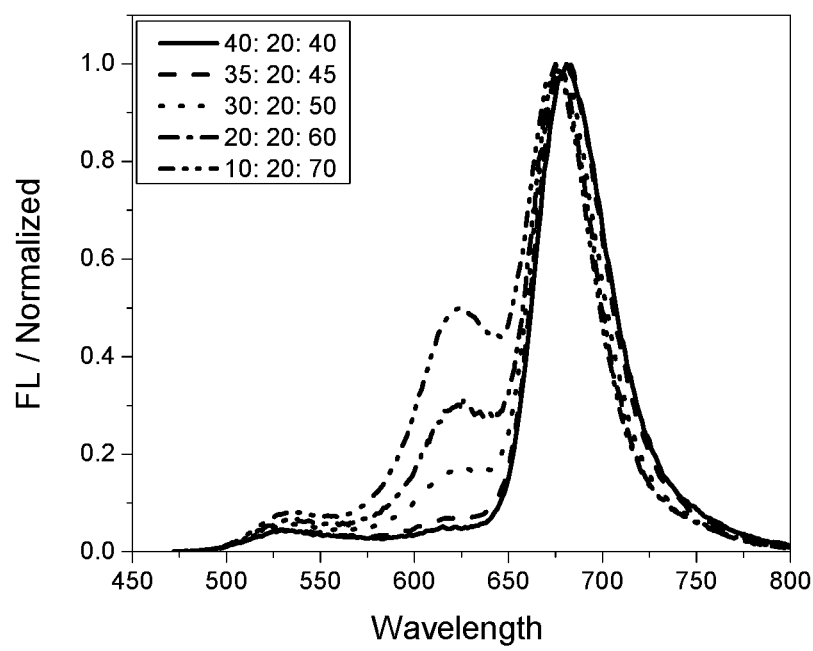

Example 19: Formation of Narrow-Band Emissive Polymer Dots by Chemically Cross-Linking General Fluorescent Polymer with Narrow-Band Emissive Polymer The present example provides a method for obtaining narrow-band emissive polymer dots by chemically cross-linking general fluorescent polymer with narrow-band fluorene-BODIPY polymers. The synthesis scheme is shown in FIG. 31.

Figure 42A:
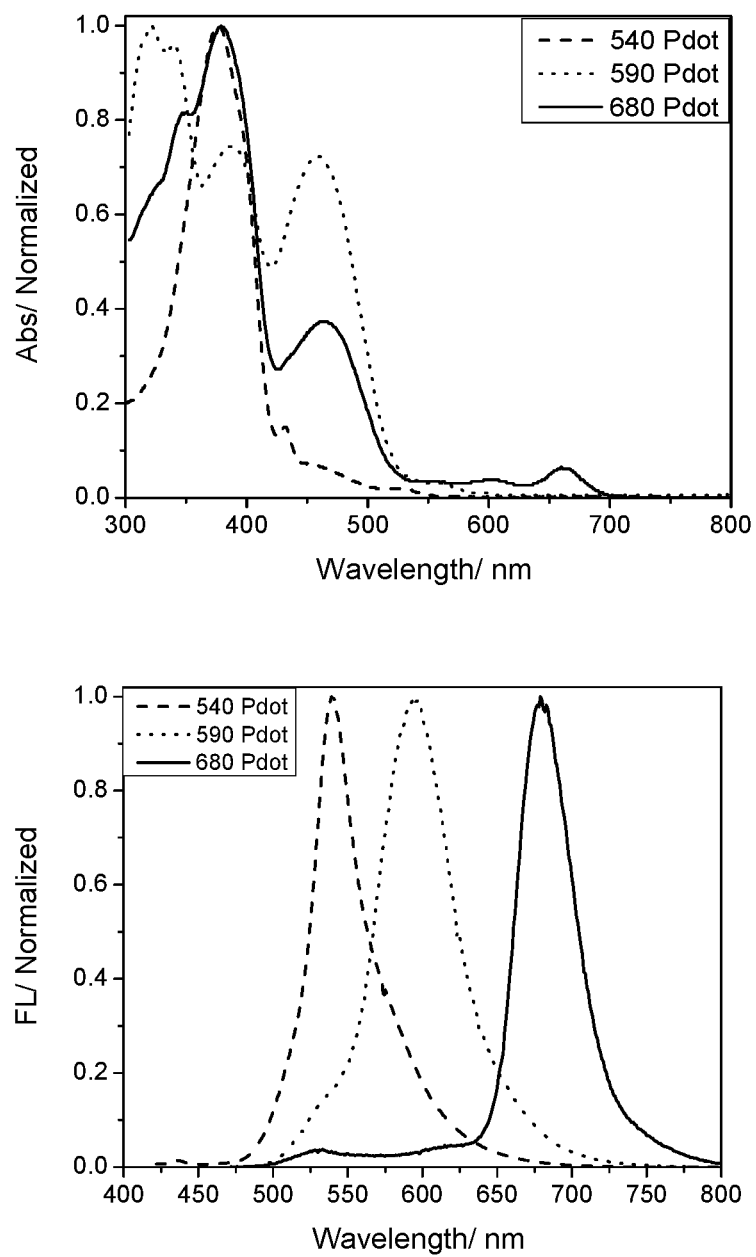
FIG. 42A shows absorption and emission spectra of example cross-linked 540Pdots prepared from PF10BT4NH$_2$ and 540BODIPY fluorene copolymer with amine group and reactive amphiphilic polymer PSMA; the cross-linked 590 Pdots prepared from PF46BT4NH$_2$ and 590BODIPY fluorene copolymer with amine group and reactive amphiphilic polymer PSMA; the cross-linked 680 Pdots prepared from PF46BT4NH$_2$, PF5TBT4NH$_2$ and 680BODIPY fluorene copolymer with amine group and reactive amphiphilic polymer PSMA, respectively. The cross-linked 540, 590 and 680 Pdots emission exhibit a FWHM of 39 nm, 55 nm, and 44 nm, respectively.

Cross-Linking Reaction of PF5%540BODIPY4NH$_2$ and PF10BT4NH$_2$ with PSMA. 1 mg of PF5%540BODIPY4NH$_2$ and 1 mg of PF10BT-4NH$_2$ were dissolved in 2 mL of THF, then 125 μL (4000 ppm) of 0.5 PSMA-8000 (33% MA, 67% PS, Mw: 8000) in THF was added into the above THF solution. The solution was covered with foil to protect it from light and stirred for 72 h at room temperature. 100-200 μL of above solution was diluted to 40-50 ppm with THF and was used for Pdots preparation. FIG. 42A shows the absorption and fluorescence spectra of resulting crosslinked Pdots. The crosslinked 540 Pdots emission exhibit a FWHM of 39 nm.

Figure 42B:
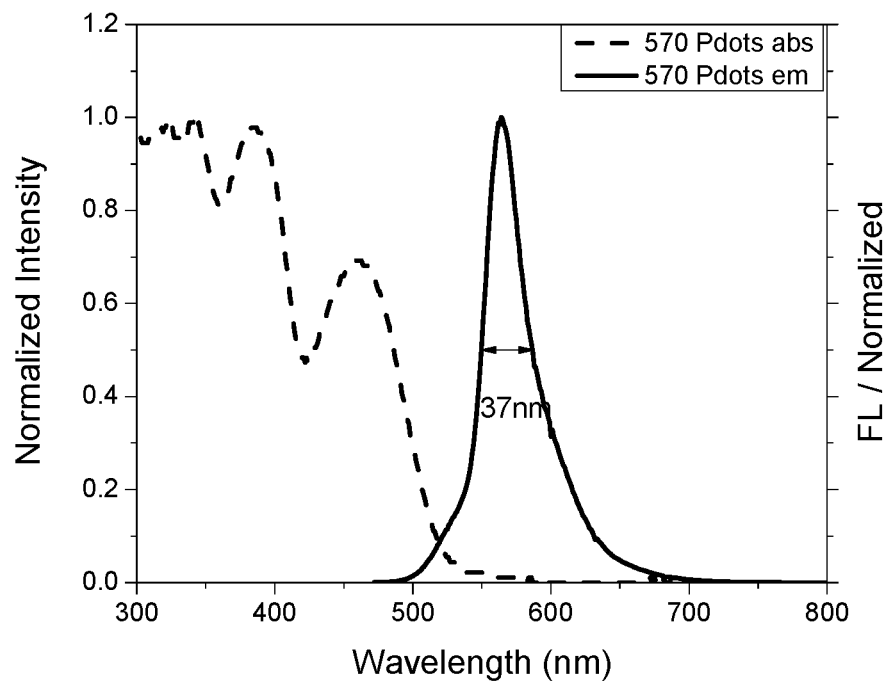
FIG. 42B shows absorption and emission spectra of the cross-linked 570 Pdots prepared from PF46BT4NH$_2$ and 570BODIPY fluorene copolymer with amine group and reactive amphiphilic polymer PSMA. The cross-linked Pdot emission exhibits a FWHM of 37 nm when reactant ratio of 570BODIPY copolymer to PF46BT4NH$_2$ was 35:65.

Crosslinking reaction of PF5%570BODIPY4NH$_2$ and PF46BT4NH$_2$ with PSMA. 0.7 mg of PF5%570BODIPY4NH$_2$ and 1.3 mg of PF10BT-4NH$_2$ were dissolved in 2 mL of THF, then 125 μL (4000 ppm) of 0.5 PSMA-8000 (33% MA, 67% PS, Mw: 8000) in THF was added into the above THF solution. The solution was covered with foil to protect it from light and stirred for 72 h at room temperature. 100-200 μL of above solution was diluted to 40-50 ppm with THF and was used for Pdots preparation. FIG. 42B shows the absorption and fluorescence spectra of resulting crosslinked Pdots. The crosslinked 570 Pdots emission exhibit a FWHM of 37 nm.

Cross-Linking Reaction of PF5%590BODIPY4NH$_2$ and PF46BT4NH$_2$ with PSMA. 0.8 mg of PF5%570BODIPY4NH$_2$ and 1.2 mg of PF46BT-4NH$_2$ were dissolved in 2 mL of THF, then 125 μL (4000 ppm) of 0.5 PSMA-8000 (33% MA, 67% PS, Mw: 8000) in THF was added into the above THF solution. The solution was covered with foil to protect it from light and stirred for 72 h at room temperature. 100-200 μL of above solution was diluted to 40-50 ppm with THF and was used for Pdots preparation. FIG. 42A shows the absorption and fluorescence spectra of resulting crosslinked Pdots. The crosslinked 590 Pdots emission exhibit a FWHM of 55 nm.

Figure 42C:
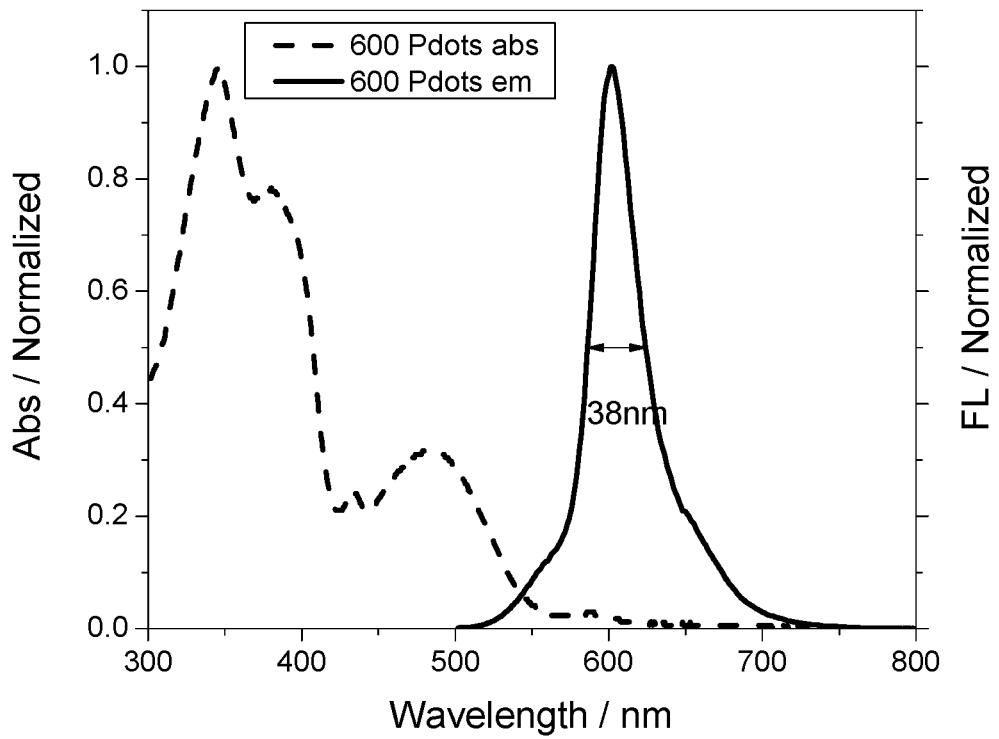
FIG. 42C shows absorption and emission spectra of the cross-linked 600 Pdots prepared from PF47BSeD3NH$_2$ and 600BODIPY fluorene copolymer with amine group and reactive amphiphilic polymer PSMA. The cross-linked Pdot emission exhibits a FWHM of 38 nm when reactant ratio of 600BODIPY copolymer to PF47BSeD3NH$_2$ was 40:60.

Cross-Linking Reaction of PF5%600BODIPY4NH$_2$ and PF47BSeD4NH$_2$ with PSMA. 0.8 mg of PF5%600BODIPY4NH$_2$ and 1.2 mg of PF46BT-4NH$_2$ were dissolved in 2 mL of THF, then 125 μL (4000 ppm) of 0.5 PSMA-8000 (33% MA, 67% PS, Mw: 8000) in THF was added into the above THF solution. The solution was covered with foil to protect it from light and stirred for 72 h at room temperature. 100-200 μL of above solution was diluted to 40-50 ppm with THF and was used for Pdots preparation. FIG. 42C shows the absorption and fluorescence spectra of resulting crosslinked Pdots. The crosslinked 600 Pdots emission exhibit a FWHM of 38 nm.

Figure 42D:
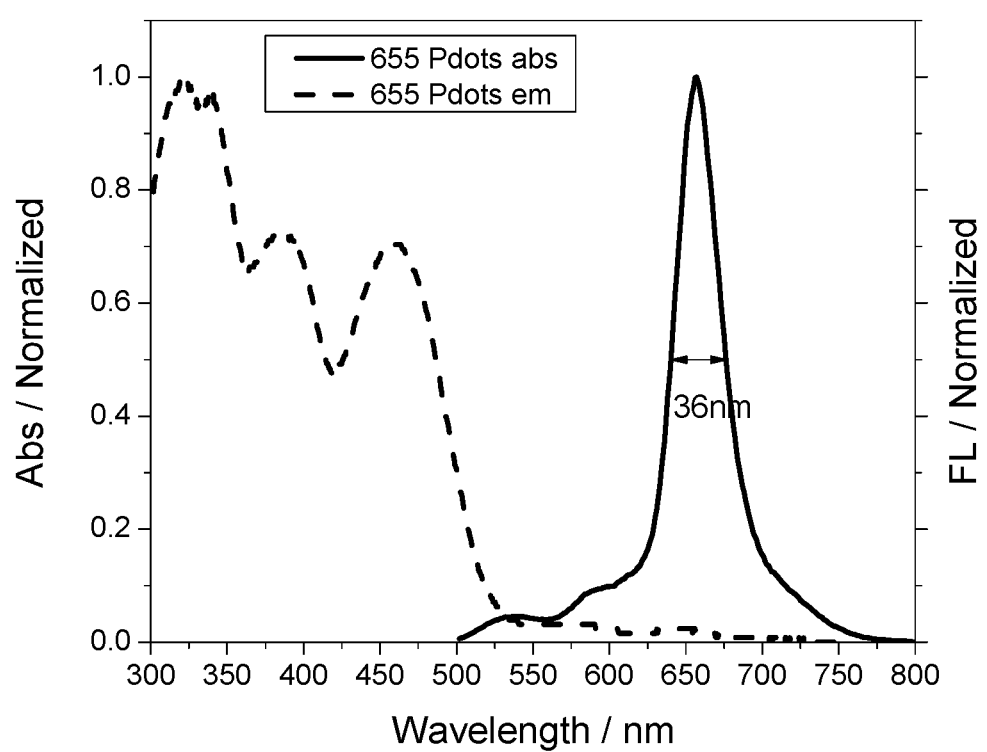
FIG. 42D shows absorption and emission spectra of the cross-linked 655 Pdots prepared from PF46BT4NH$_2$, PF5TBT4NH$_2$ and 655BODIPY fluorene copolymer with amine group and reactive amphiphilic polymer PSMA, The cross-linked Pdot emission exhibits a FWHM of 36 nm when reactant ratio of 655BODIPY copolymer to PF5TBT4NH$_2$ and PF46BT4NH$_2$ was 20:10:70.

Cross-Linking Reaction of PF5%655BODIPY4NH$_2$, PF46BT4NH$_2$ and PF5TBT4NH$_2$ with PSMA. 0.4 mg of PF5%600BODIPY4NH$_2$, 0.2 mg of PF5TBT4NH$_2$ and 1.4 mg of PF46BT-4NH$_2$ were dissolved in 2 mL of THF, then 125 µL (4000 ppm) of 0.5 PSMA-8000 (33% MA, 67% PS, Mw: 8000) in THF was added into the above THF solution. The solution was covered with foil to protect it from light and stirred for 72 h at room temperature. 100-200 µL of above solution was diluted to 40-50 ppm with THF and was used for Pdots preparation. FIG. 42D shows the absorption and fluorescence spectra of resulting crosslinked Pdots. The crosslinked 655 Pdots emission exhibit a FWHM of 36 nm.

Cross-Linking Reaction of PF5%680BODIPY4NH$_2$, PF46BT4NH$_2$ and PF5TBT4NH$_2$ with PSMA. 0.7 mg of PF5%680BODIPY4NH$_2$, 0.3 mg of PF5TBT4NH$_2$ and 1.0 mg of PF46BT-4NH$_2$ were dissolved in 2 mL of THF, then 125 µL (4000 ppm) of 0.5 PSMA-8000 (33% MA, 67% PS, Mw: 8000) in THF was added into the above THF solution. The solution was covered with foil to protect it from light and stirred for 72 h at room temperature. 100-200 µL of above solution was diluted to 40-50 ppm with THF and was used for Pdots preparation. FIG. 42A shows the absorption and fluorescence spectra of resulting crosslinked Pdots. The crosslinked 680 Pdots emission exhibit a FWHM of 44 nm.

Example 20: Synthesis of a Narrow-Band Emissive Pdots with Absorption Peak Near 488 nm The present example provides a method for obtaining narrow-band emissive polymer dots with absorption peak near 488 nm (FIGS. 43 and 44A-C).

Figure 43:
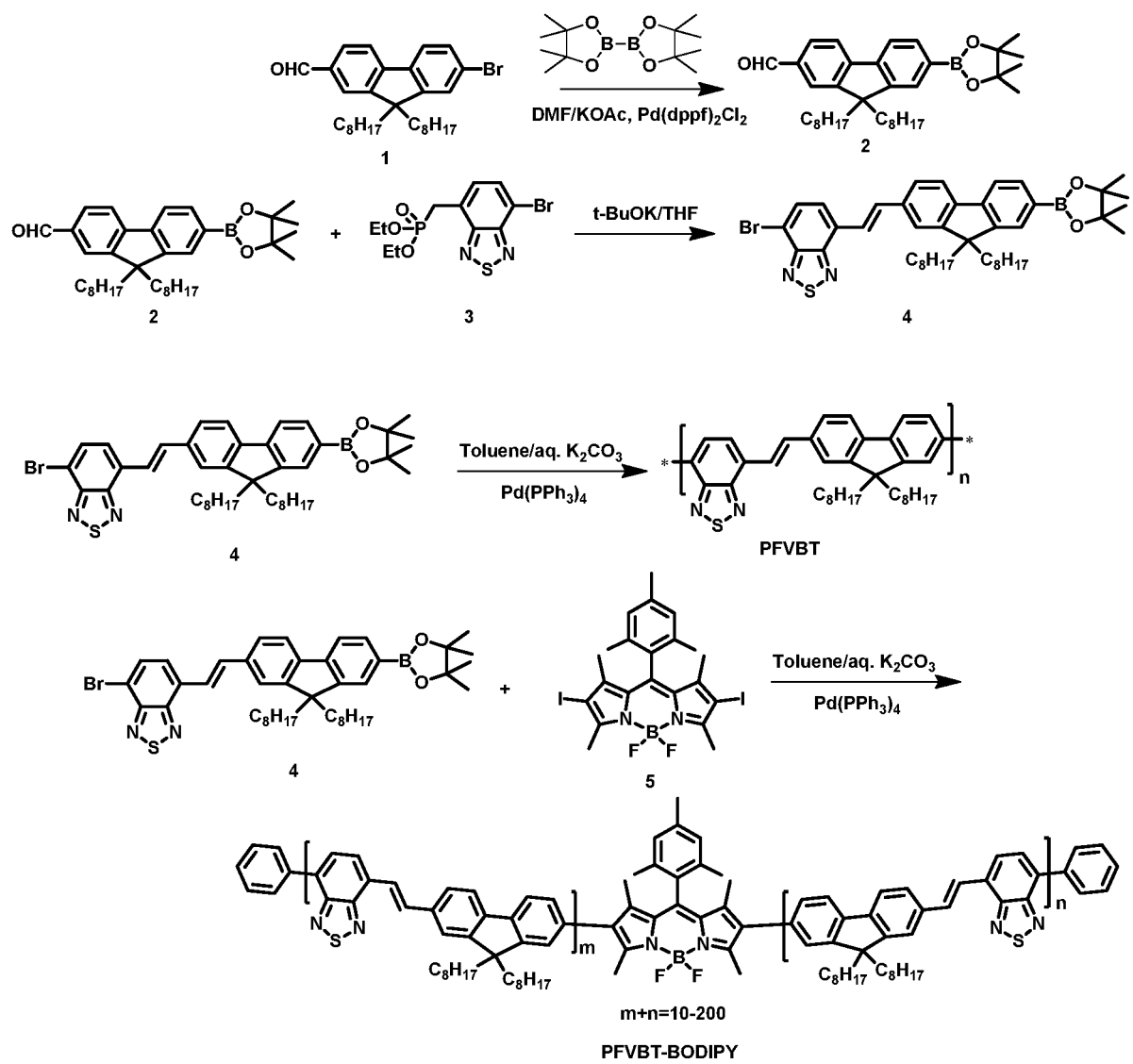
FIG. 43 shows the synthesis of a narrow-band BODIPY monomer, a general fluorene-vinyl-benzothiadiazol monomer FVBT, and the copolymer PFVBT-BODIPY. The absorption peak of the polymer is tuned to 492 nm to match the 488 nm laser generally used in biological applications.

Synthesis of Compound 2 (FIG. 43). In a 100-mL flask, compound 1 (4 g, 8 mmol), KOAc (4 g) and DMF (60 mL) were added. After the mixture was degassed twice, Pd(dppf)$_2$Cl$_2$ (300 mg) was added. Then, the mixture was heated to 90° C. overnight. The resulted dark solution was poured into water after cooling to room temperature, and extracted with dichloromethane three times. The organic phase was washed with water and dried over anhydrous Na$_2$SO$_4$. After removing the solvent, the crude product was purified by silica column to give a colorless liquid (2.7 g, 62%). $^1$H NMR (CDCl$_3$, δ): 10.06 (s, 1H), 7.86-7.83 (d, 4H), 7.79-7.76 (d, 2H), 2.06 (t, 4H), 1.40 (s, 12H), 1.20-1.15 (m, 24H), 1.01 (t, 6H). Synthesis of compound 3. 4-Bromo-7-(bromomethyl)-[2,1,3]-benzothiadiazole (2.2 g, 7.1 mmol) was added into a 50-mL flask. After adding triethyl phosphate (15 mL), the solution was refluxed for 4 hours. Then, the excessed triethyl phosphate was removed under vacuum to give the crude compound 3, which was used without further purification. $^1$H NMR (CDCl$_3$, δ): 7.84 (d, 1H), 7.53 (m, 1H), 4.10 (q, 4H), 3.75 (s, 1H), 3.68 (s, 1H), 1.25-1.20 (t, 7H).

Synthesis of Compound 4 (FIG. 43). Compound 2 (1.2 g, 2.2 mmol) and 3 (1 g, 2.7 mmol) in THE (10 mL) were charged into a 50-mL single-neck flask under nitrogen flow. The mixture was stirred at room temperature overnight after t-BuOK in methanol (3 mL) was added dropwisely at 0° C. Then, the solution was poured into water and extracted with dichloromethane twice. The combined organic phase was dried over anhydrous Na$_2$SO$_4$. After removing solvent, the crude product was purified by silica column to give a yellow solid (0.6 g, 38%). $^1$H NMR (CDCl$_3$, δ): 8.09 (d, 1H), 7.90-7.83 (m, 2H), 7.78-7.72 (m, 3H), 7.68-7.61 (m, 4H), 2.05 (t, 4H), 1.42 (s, 12H), 1.06 (m, 24H), 0.81 (t, 6H).

Synthesis of PFVBT (FIG. 43). In a 25-mL flask, compound 4 (150 mg, 0.20 mmol) was added under nitrogen. Toluene (3 mL), aqueous Na$_2$CO$_3$ (2 mL, 2M) and A336 (2 drops) were added consequently. The solution was degassed twice before adding Pd(PPh$_3$)$_4$ (8 mg). Then, the solution was heated to 120° C. for 48 hours. After cooling to room temperature, the solution was poured into methanol. The resulted solid was dissolved into toluene and passed through a short column. The concentrated solution was then poured into methanol. The solid was collected by filtration and dried under vacuum overnight (90 mg, 82%). $^1$H NMR (CDCl$_3$, δ): 8.23-7.62 (m, 10H), 2.14 (br, 4H), 1.15 (br, 24H), 0.82 (t, 6H).

Synthesis of polymer PFVBT-BODIPY (FIG. 43). Here is an example of PFVBT polymer with 2% BODIPY, named as PFVBT-BODIPY2. In a 25-mL flask, compound 4 (203 mg, 0.27 mmol) and compound 5 (3.4 mg, 0.0055 mol) were added under nitrogen. Toluene (4 mL), aqueous Na$_2$CO$_3$ (2 mL, 2M) and A336 (2 drops) were added consequently. The solution was degassed twice before adding Pd(PPh$_3$)$_4$ (10 mg). Then, the solution was heated to 120° C. for 48 hours, and phenyl boronic acid (50 mg) was added and stirred for 12 hours, and bromobenzene (0.2 mL) was added and stirred for 12 hours. After cooling to room temperature, the solution was poured into methanol. The resulted solid was dissolved into toluene and passed through a short column. The concentrated solution was then poured into methanol. The solid was collected by filtration and dried under vacuum overnight (110 mg, 74%). $^1$H NMR (CDCl$_3$, δ): 8.18-7.72 (m, 10H), 2.15 (br, 4H), 1.15 (br, 24H), 0.82 (br, 6H).

Figure 44A:
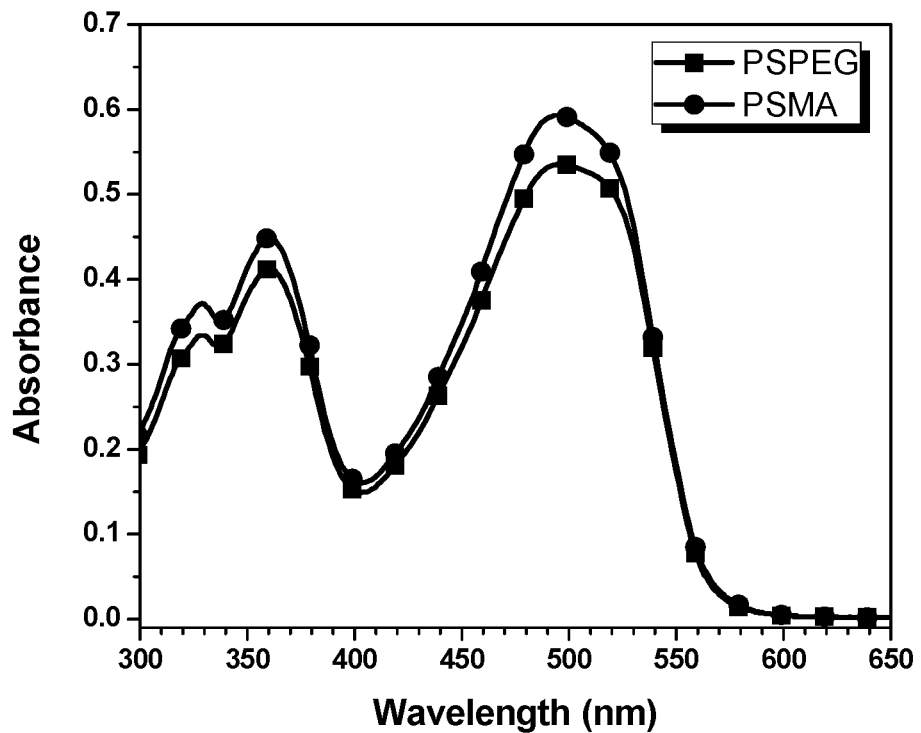
FIG. 44A shows the UV-Vis absorption and fluorescence spectra of PFVBT-BODIPY Pdots functionalized with PS-PEG-COOH and PSMA polymers.
Figure 44B:
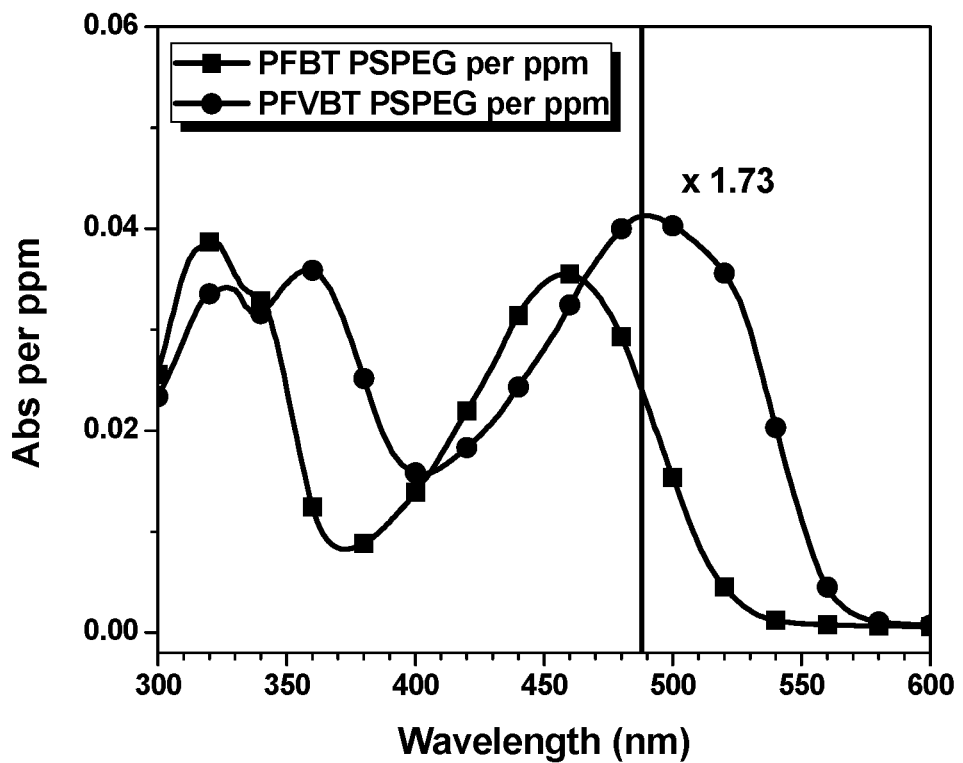
FIG. 44B show the comparison on the absorption profile between PFBT and PFVBT Pdots.
Figure 45A:
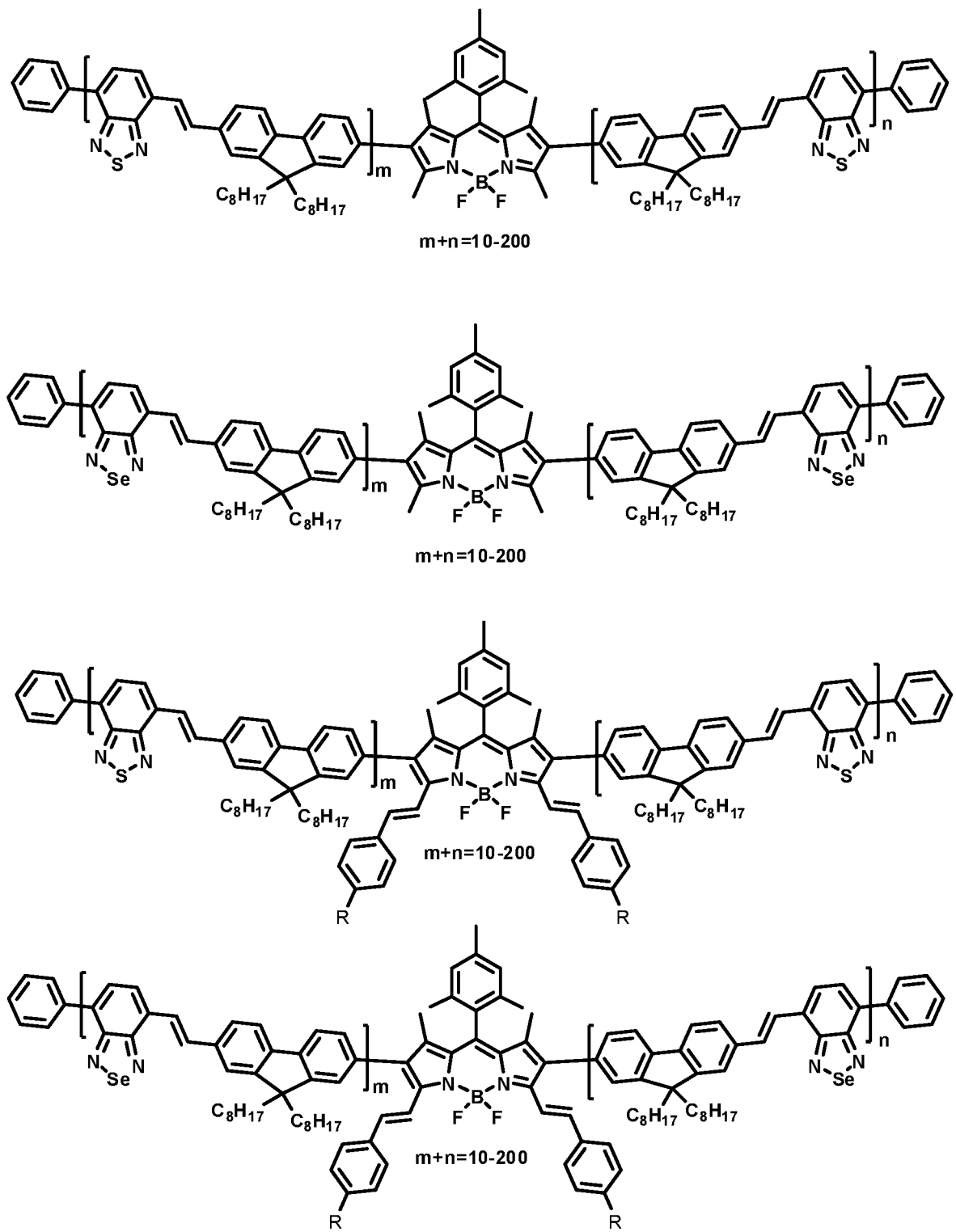
FIGS. 45A-45C shows a non-limiting list of examples of BODIPY based narrow-band emissive poymers. Their absorption peak can be tuned from the visible to near infra-red region.
Figure 45A:
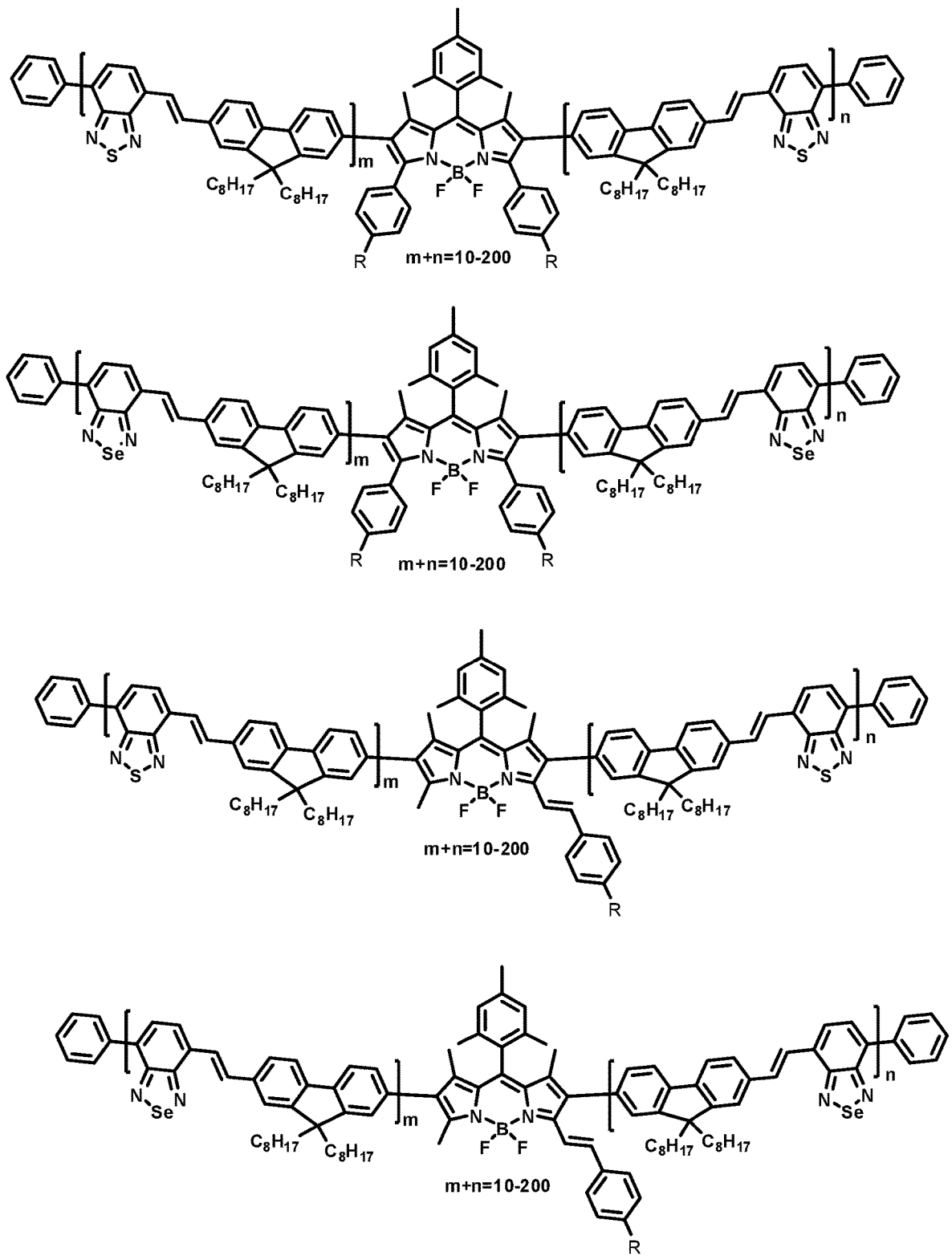
Figure 45B:
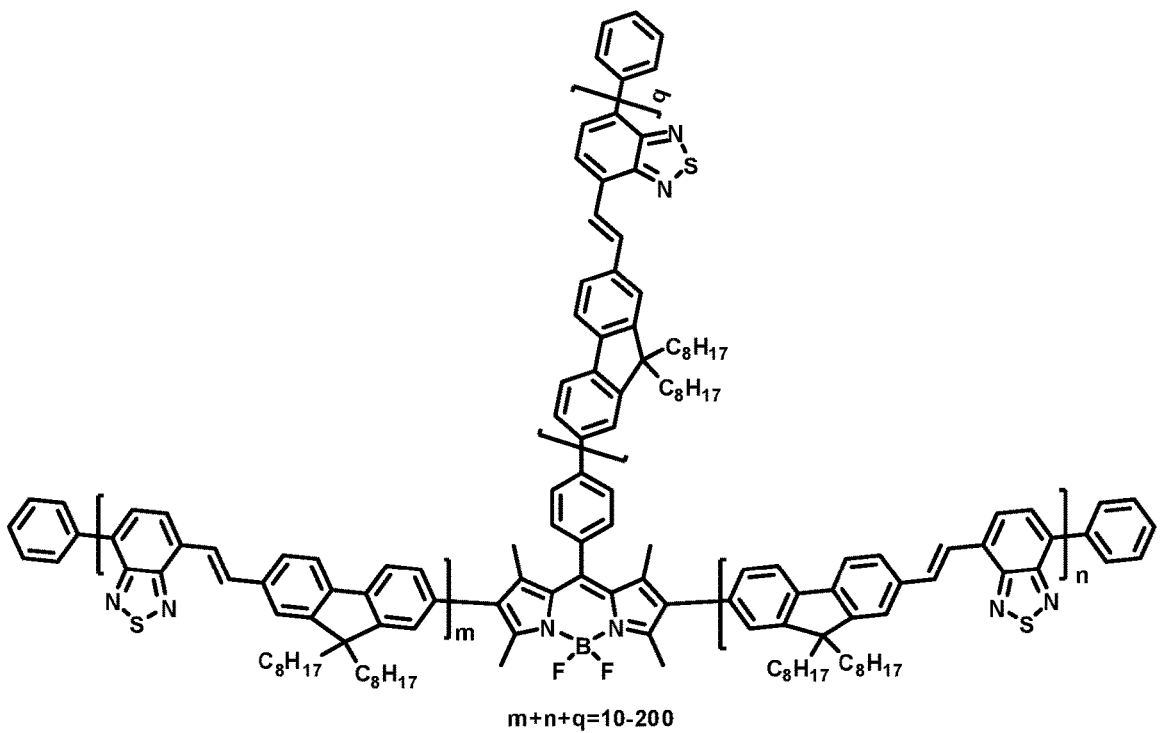
Figure 45B:
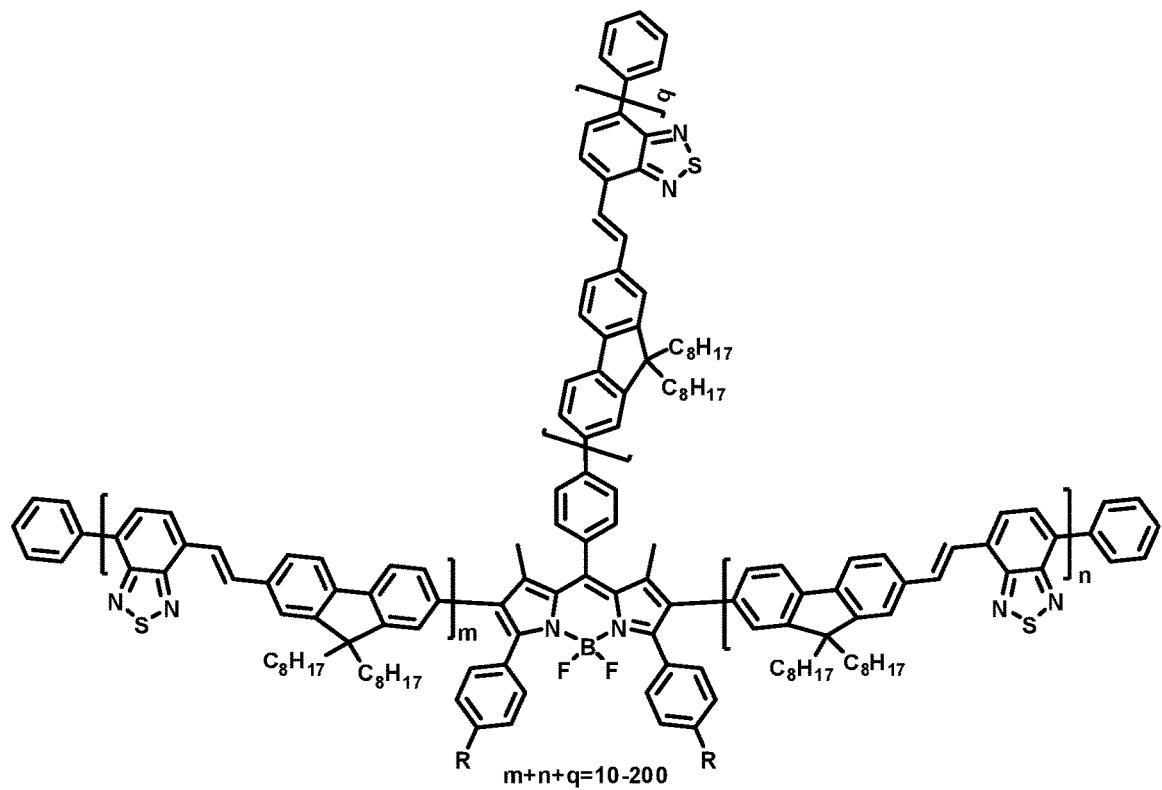
Figure 45B:
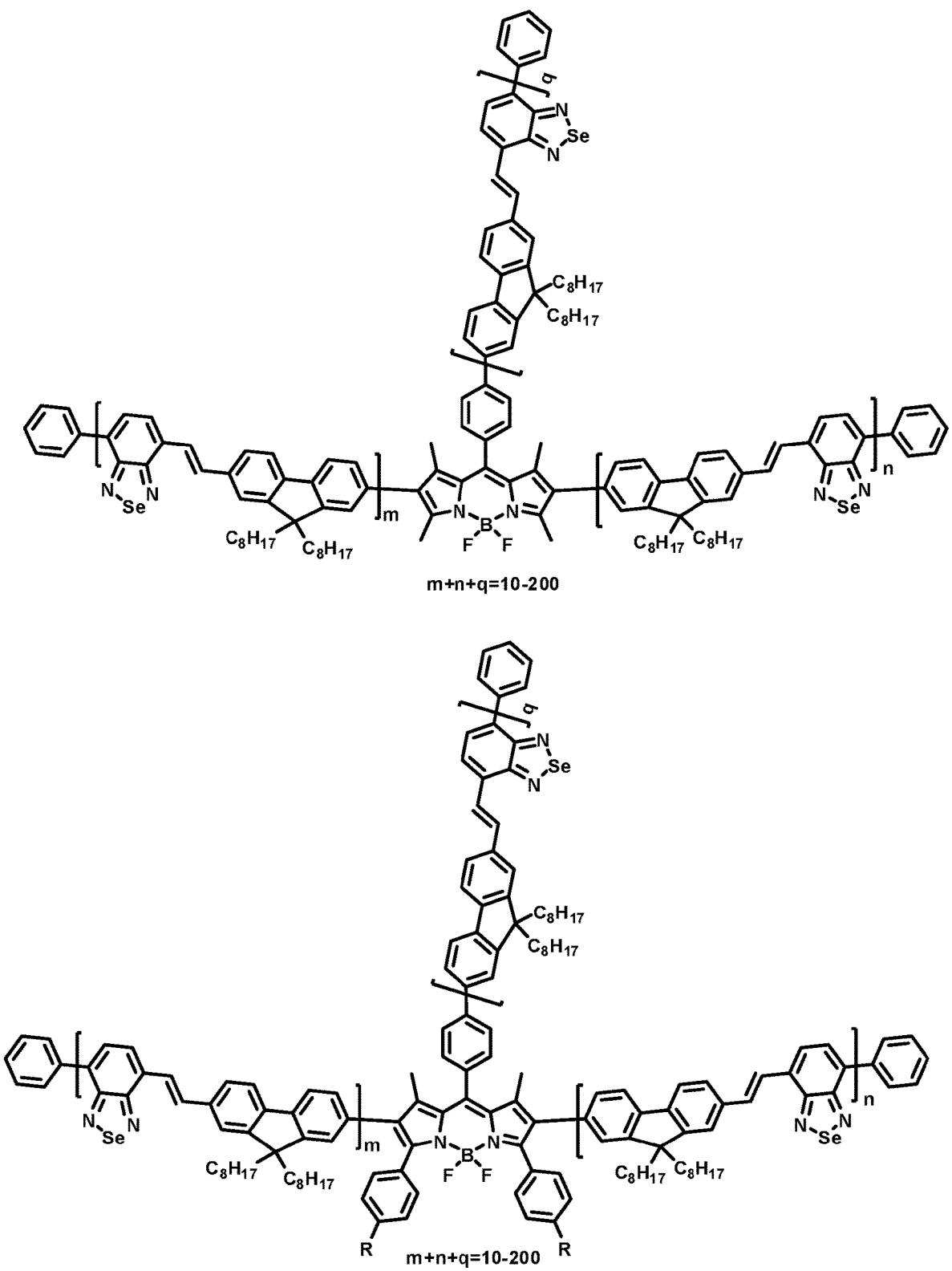
Figure 45C:
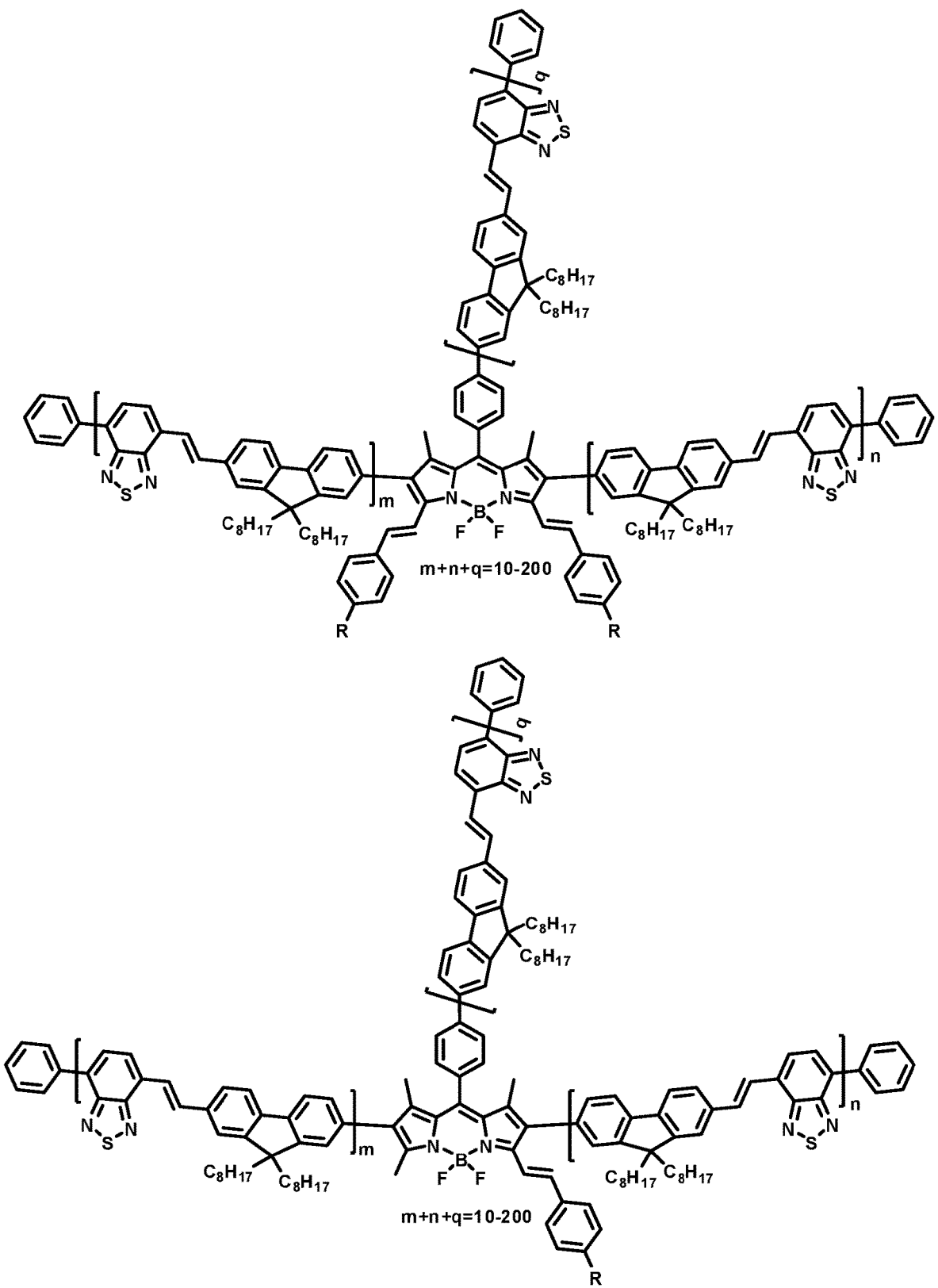
Figure 45C:
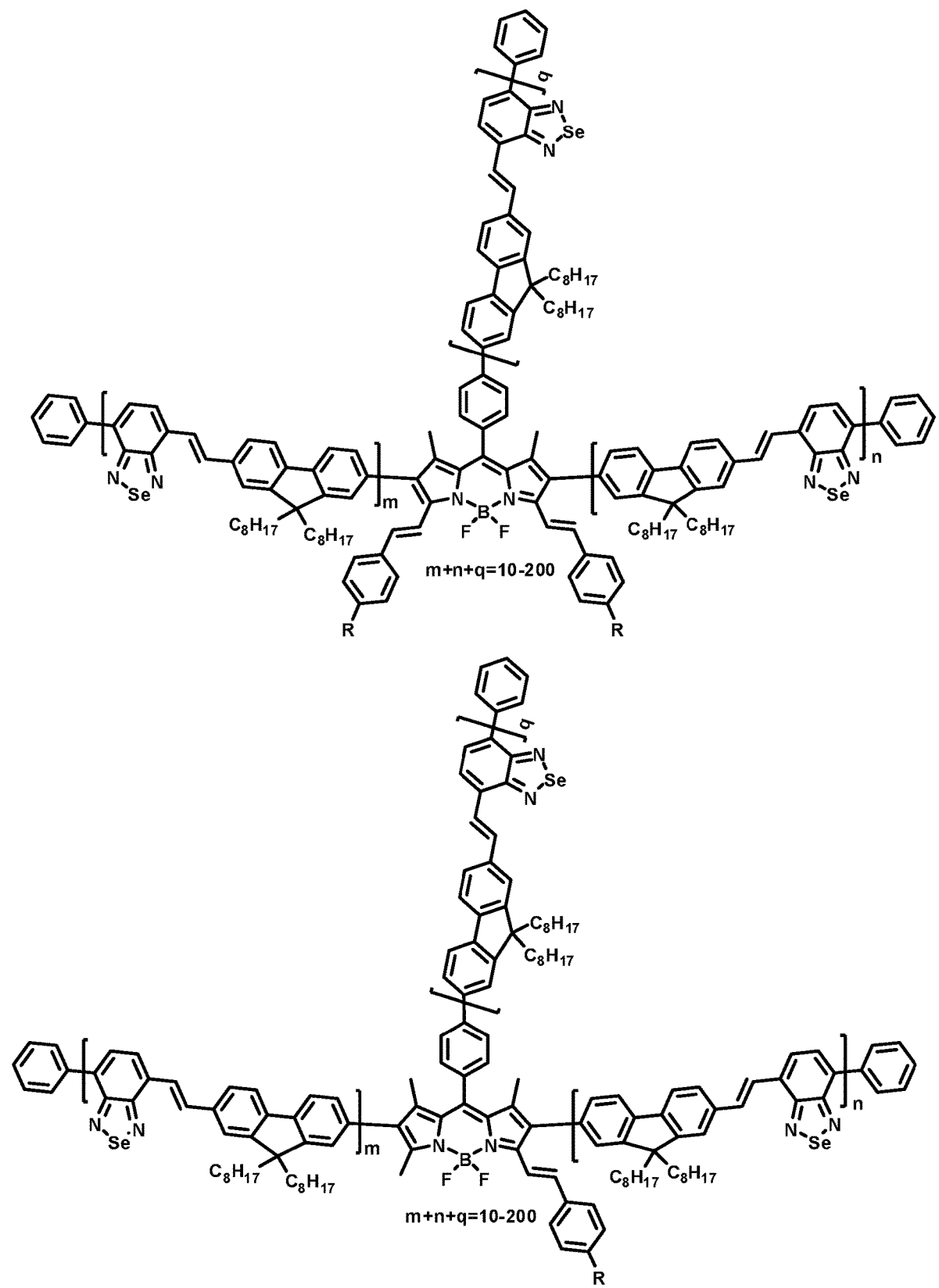

Preparation and Characterization of PFVBT-BODIPY Pdots (FIGS. 44A-C). PFVBT-BODIPY2 Pdots were prepared by nano-coprecipitaiton method. A solution of polymer blend PFVBT-BODIPY (200 ppm) and PSPEG or PSMA (100 ppm)) in THF (4 mL) was quickly injected into water (10 mL) under ultrasonication. THF was evaporated by N$_2$ flow at 95° C. and the solution was concentrated to ~8 mL, followed by filtration through a 0.2 micron filter. The prepared Pdots aqueous solutions were kept in refrigerator for further use. The particle size and zeta-potentials of Pdots in bulk solution was characterized by dynamic light scattering (DLS) (Malvern Zetasizer NanoS). UV-Vis absorption spectra were recorded with a DU 720 scanning spectrophotometer (Beckman Coulter, Inc., CA, USA) using 1 cm quartz cuvettes. Fluorescence spectra were obtained using a commercial Perkin-Elmer fluorometer. Fluorescence quantum yields were measured using a Hamamatsu photonic multichannel analyzer C10027 equipped with CCD integrating sphere.

Figure 46:
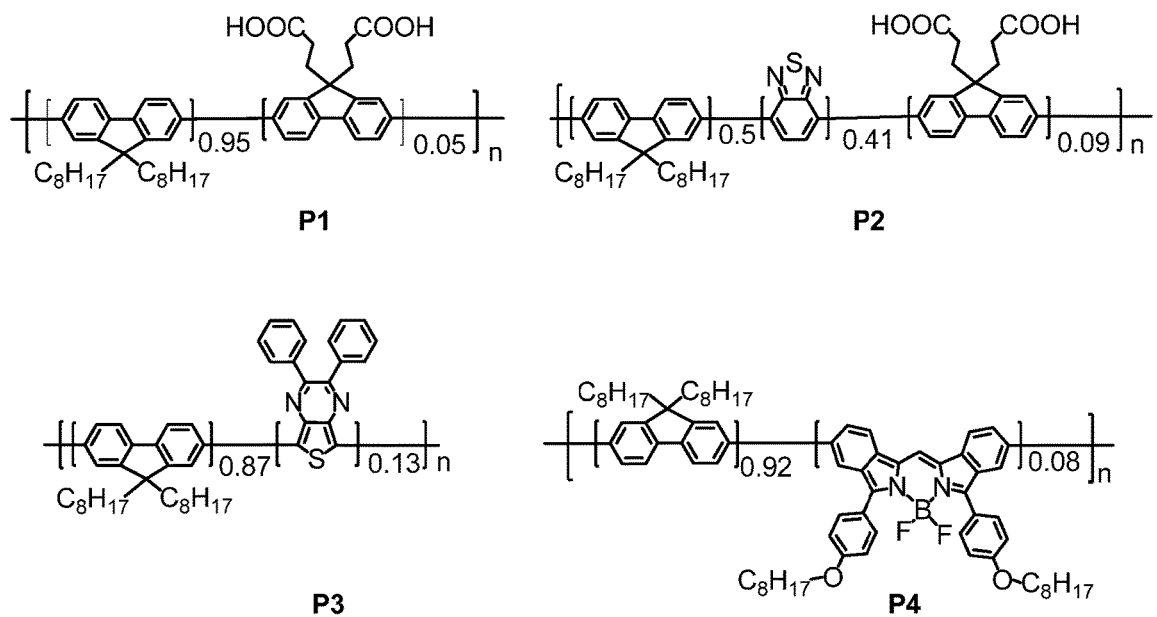
FIG. 46 shows chemical structures of three general broadband polymers P1, P2, P3, and one narrow-band emissive polymer P4. The blended polymer dots made from the four polymers exhibit narrow-band emissions in the near infrared region.

Example 21: Synthesis of BODIPY Based Narrow-Band Emissive Polymer (Shown in FIG. 46) and Blended Narrow-Band Emissive Polymer Dots Emitting in the Near Infrared Region The present example provides a method for obtaining BODIPY based narrow-band emissive polymer (FIG. 46) and narrow-band emissive polymer dots emitting in the near infrared region by blending several types of semiconducting polymers.

Figure 47A:
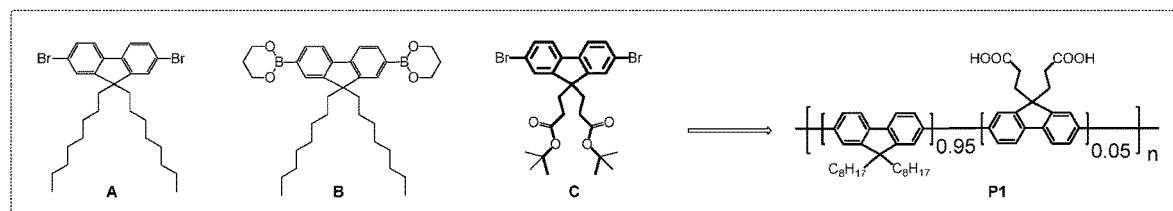
FIGS. 47A-47D show the synthetic procedure of the four polymers shown in FIG. 46.

Synthesis of Monomer C (FIG. 47A). A mixture of 2,7-dibromofluorene (15 mmol, 4.86 g), tert-butyl 3-bromopropanoate (33 mmol, 6.86 g), sodium hydroxide solution (40%, 35 mL) and Bu$_4$NBr (1.5 mmol, 0.48 g), toluene (70 mL) was stirred at 85° C. overnight. The organic phase was separated, washed with water and dried over MgSO$_4$. After evaporation of the solvent, the residue was purified by column chromatography (DCM). The product was obtained as a white solid. Yield: 4.81 g, 83%. $^1$HNMR (500 MHz, CDCl$_3$): δ=7.47-7.54 (m, 6H), 2.30 (t, 4H), 1.47 (t, 4H), 1.33 (s, 18H). $^{13}$CNMR (500 MHz, CDCl$_3$): 172.71, 150.47, 139.60, 131.56, 126.99, 122.57, 121.93, 80.97, 54.58, 34.92, 30.36, 28.52.

Synthesis of Polymer P1 (FIG. 47A). To a 100 mL flask was added monomer A (0.9 mmol, 493 mg), monomer B (1.02 mmol, 569 mg), monomer C (0.1 mmol, 58 mg), Bu$_4$NBr (15 mg), toluene (20 mL), Na$_2$CO$_3$ (2M, 10 mL). The mixture was stirred at room temperature and the flask was degassed and recharged with N$_2$, which was repeated four times before and after addition of Pd(PPh$_3$)$_4$ (0.02 mmol, 23 mg). The reactants were stirred at 90° C. for 48 hours and then phenylboronic acid (100 mg) dissolved in THF (1 mL) was added. After two hours, bromobenzene (1 mL) was added and further stirred for 3 hours. The mixture was poured into methanol (200 mL). The precipitate was filtered, washed with methanol, water, and acetone to remove monomers, small oligomers, and inorganic salts. The crude product was dissolved in DCM (15 mL), filtered through a 0.2 μm membrane and re-precipitated in methanol (150 mL). The powder was then stirred in acetone (200 mL) overnight and collected by filtration, and dried in vacuum. Yield: 580 mg (74%). $^1$HNMR (500 MHz, CDCl$_3$): δ=7.84 (d, J=7.8 Hz, 2H), 7.63-7.73 (m, 4H), 2.12 (broad, 4H), 1.32 (s, 1H), 1.10-1.25 (m, 20H), 0.68-0.92 (m, 10H). The t-Butyl protected polymer (200 mg) was dissolved in DCM (20 mL) and TFA (3 mL) was added and the mixture was stirred at room temperature in dark overnignt and then poured into methanol (150 mL). The precipitate was collected by filtration, washed with methanol, water, and acetone thoroughly, and then dried in vacuum. ($^1$HNMR and $^{13}$CNMR).

Figure 47B:
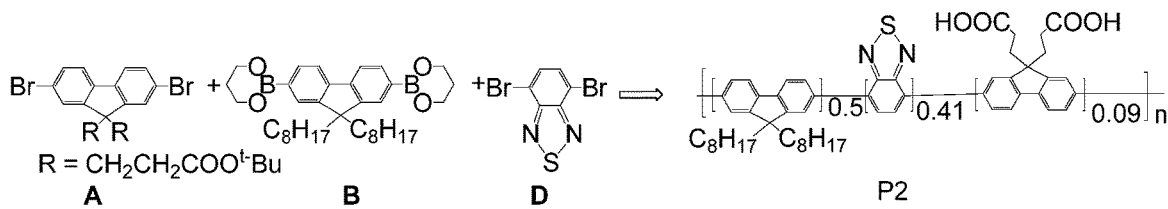

Synthesis of Polymer P2 (FIG. 47B). P2 was synthesized by copolymerization of monomers 2,7-dibromo-9,9-bis(3-(tert-butyl propanoate))fluorene (A), 9,9-dioctylfluorene-2,7-diboronic acid bis(1,3-propanediol) ester (B), 4,7-dibromobenzo[c][1,2,5]thiadiazole (D) by Suzuki Coupling with different monomer feed ratios. We use PFBT-C2 as an example here: In a 100 mL flask, monomer A (0.18 mmol, 104.8 mg), B (0.82 mmol, 235.9 mg), C (1 mmol, 558.4 mg), was dissolved in toluene (30 mL), Bu$_4$NBr (0.04 mmol, 12.5 mg) and Na$_2$CO$_3$ (2M, 12 mL) was added. The mixture was degassed and refilled with N$_2$ (repeated 4 times) before and after addition of Pd(PPh$_3$)$_4$ (0.035 mmol, 40 mg). The reactants were stirred at 90° C. for 40 hours and phenylboronic acid (100 mg) dissolved in THF (1 mL) was added. After two hours, bromobenzene (1 mL) was added and further stirred for 3 hours. The mixture was poured into methanol (200 mL). The precipitate was filtered, washed with methanol, water, and acetone to remove monomers, small oligomers, and inorganic salts. The crude product was dissolved in DCM (15 mL), filtered through a 0.2 μm membrane and re-precipitated in methanol (150 mL). The powder was then stirred in acetone (200 mL) overnight and collected by filtration, and dried in vacuum. Yield: 412 mg (70%). $^1$HNMR (500 MHz, CDCl$_3$): δ=7.90-8.20 (m, 8H), 2.00-2.30 (broad, 4H), 1.32 (s, 0.86H), 1.08-1.26 (m, 20H), 0.96 (broad, 4H), 0.81 (t, d=6 Hz, 6H). The protecting tert-butyl esters group was removed by TFA at room temperature. Trifluoroacetic acid (3 mL) was added into a solution of polymer (200 mg) in DCM (60 mL) and stirred overnight. The organic layer was washed with water (100×3) and then stirred with NaOH solution (10%, 30 mL) for 10 minutes. The mixture was then acidified with acetic acid. The DCM phase was washed with water and concentrated to 10 mL and precipitated in methanol (100 mL). The final powder was collected by filtration, washed with acetone, and dried in vacuum.

Figure 47C:
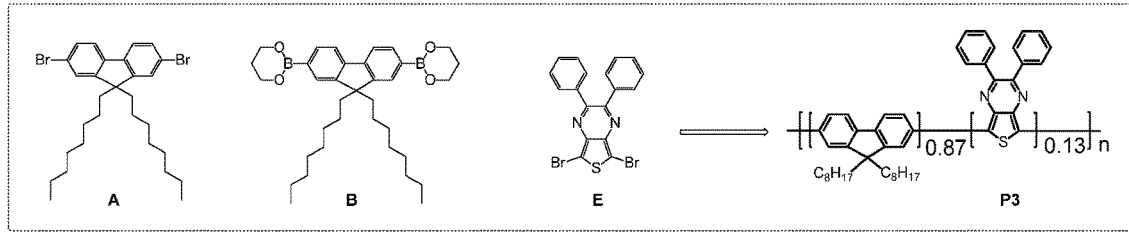

Synthesis of Polymer P3 (FIG. 47C). To a 100 mL flask was added monomer A (0.7 mmol, 384 mg), monomer B (1.02 mmol, 569 mg), monomer E (0.3 mmol, 134 mg), Bu$_4$NBr (15 mg), toluene (20 mL), Na$_2$CO$_3$ (2M, 10 mL). The mixture was stirred at room temperature and the flask was degassed and recharged with N$_2$, which was repeated four times before and after addition of Pd(PPh$_3$)$_4$ (0.02 mmol, 23 mg), respectively. The reactants were stirred at 90° C. for 48 hours and then phenylboronic acid (100 mg) dissolved in THF (1 mL) was added. After two hours, bromobenzene (1 mL) was added and further stirred for 3 hours. The mixture was poured into methanol (200 mL). The precipitate was filtered, washed with methanol, water, and acetone to remove monomers, small oligomers, and inorganic salts. The crude product was dissolved in DCM (15 mL), filtered through a 0.2 μm membrane and re-precipitated in methanol (150 mL). The powder was then stirred in acetone (200 mL) overnight and collected by filtration, and dried in vacuum. Yield: 532 mg (71%). $^1$HNMR (300 MHz, CDCl$_3$): δ=7.84 (d, J=8.1 Hz, 2H), 7.53-7.62 (broad, 4H), 7.48 (t, J=7.2 Hz, 0.28H), 7.36-7.43 (broad, 1.07H), 2.12 (broad, 4H), 1.10-1.22 (m, 20H), 0.76-0.89 (m, 10H).

Figure 47D:
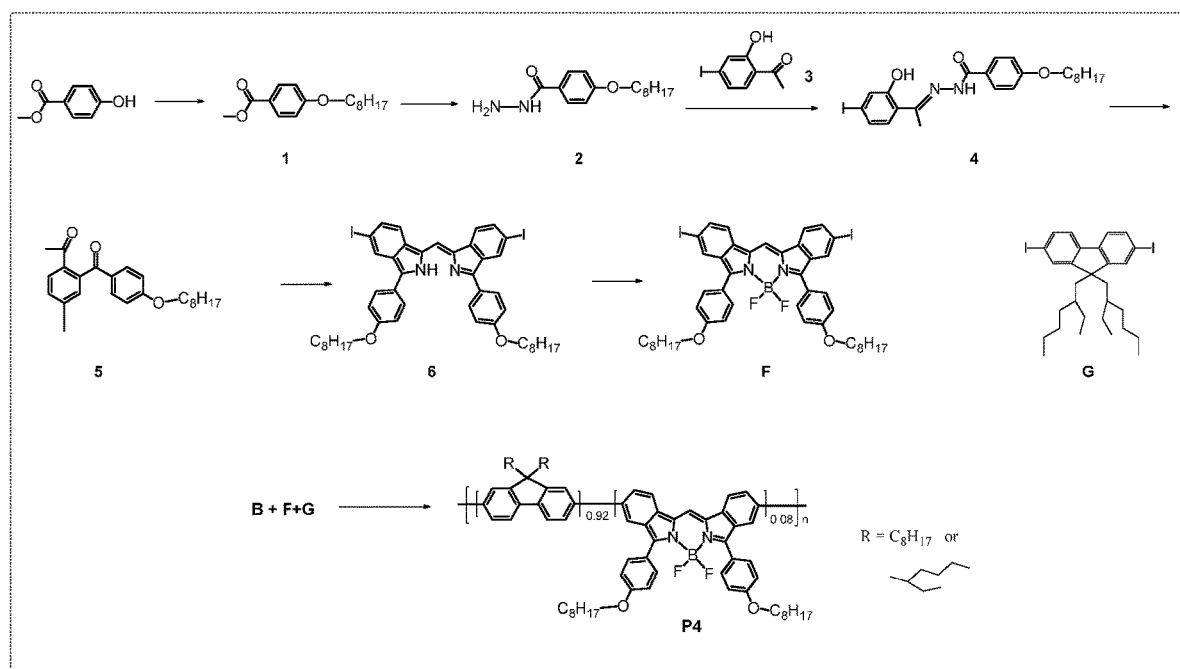
Figure 48:
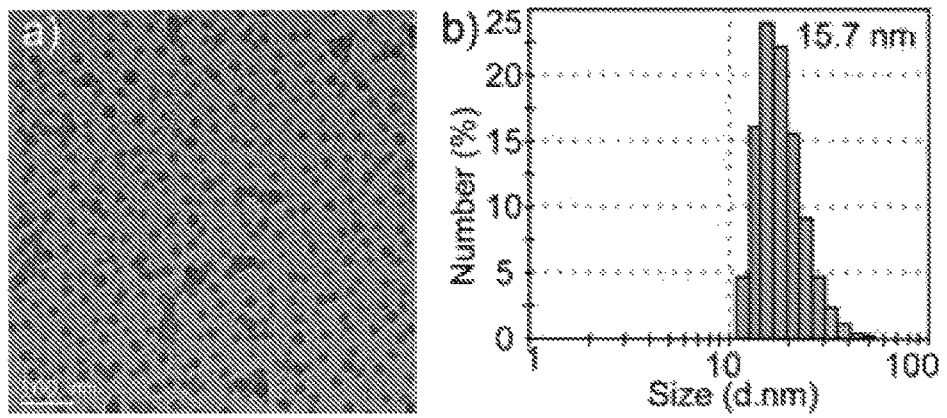
FIG. 48 top panel shows the TEM images and size distribution histogram measured by DLS of the four-component Pdots (4-NIR Pdots) made from P1, P2, P3, P4 polymers. The bottom panel shows the TEM images and size distribution histogram measured by DLS of the three-component Pdots (3-NIR Pdots) made from P2, P3, and P4 polymers.
Figure 48:
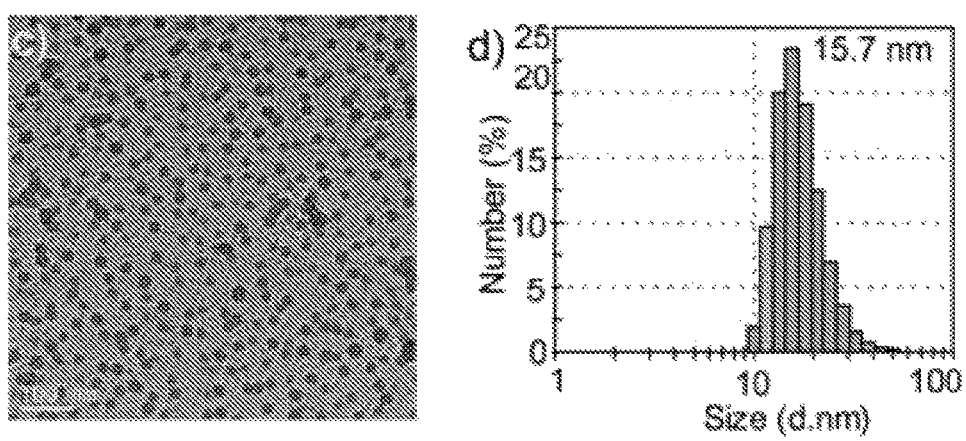

Synthesis of Polymer P4 (FIG. 47D). To a 100 mL flask was added monomer B (0.122 mmol, 71.7 mg), monomer F (0.022 mmol, 21 mg), monomer G (0.1 mmol, 64.2 mg), toluene (4 mL), Na$_2$CO$_3$ (2M, 3 mL), ethanol (0.7 mL). The mixture was stirred at room temperature and the flask was degassed and recharged with N$_2$, which was repeated four times before and after addition of Pd(PPh$_3$)$_4$ (0.004 mmol, 4.6 mg), respectively. The reactants were stirred at 83° C. for 30 hours and then phenylboronic acid (20 mg) dissolved in THF (0.5 mL) was added. After two hours, bromobenzene (0.5 mL) was added and further stirred for 2 hours. The mixture was poured into methanol (100 mL). The precipitate was filtered, washed with methanol, water, and acetone to remove monomers, small oligomers, and inorganic salts. The crude product was dissolved in DCM (5 mL), filtered through a 0.2 μm membrane and re-precipitated in methanol (60 mL). The powder was collected by filtration, and dried in vacuum. Yield: 252 mg (77%). $^1$HNMR (300 MHz, CDCl$_3$): 7.55-7.95 (m, 6.66H), 4.06 (t, J=6.9 Hz, 0.31H), 2.09 (broad, 3.65H), 1.85 (m, 0.32H), 1.4-0.6 (m, 30H).

Figure 49:
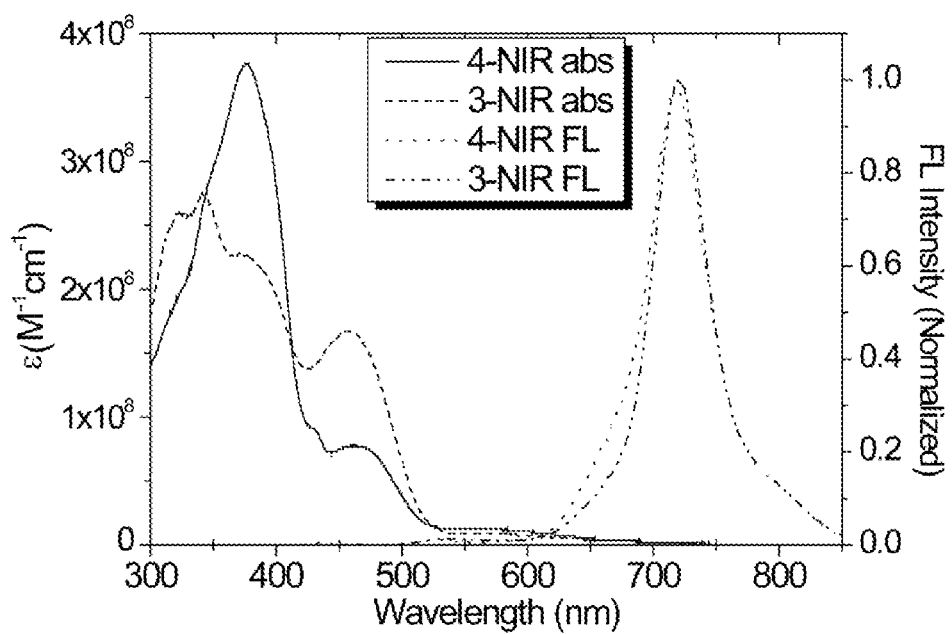
FIG. 49 shows the absorption spectra of 4-NIR Pdots (solid line), 3-NIR Pdots (dashed line) and fluorescence spectra of 4-NIR Pdots (dot line, $\lambda_{ex}$=380 nm) and 3-NIR Pdots (dashed-dot-dot line, $\lambda_{ex}$=450 nm).
Figure 50:
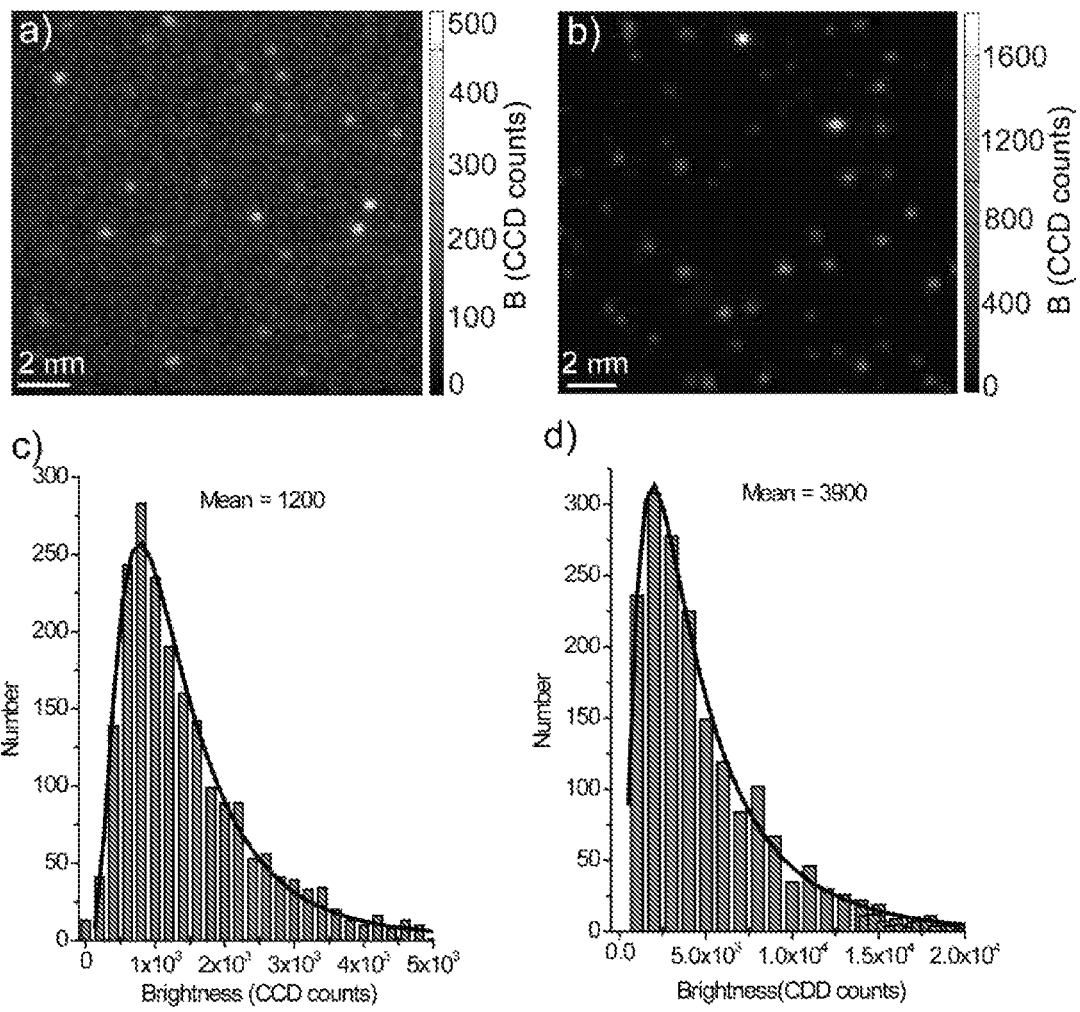
FIGS. 50A and B show single-particle fluorescence images of Qdot705 (a) and 3-NIR Pdots (b) obtained under identical excitation and detection conditions.
FIGS. 50C-D show the histograms of intensity distribution of single-particle fluorescence for Qdot705 (mean=1200 CCD counts) and 3-NIR Pdots (mean=3900 CCD counts).
Figure 51:
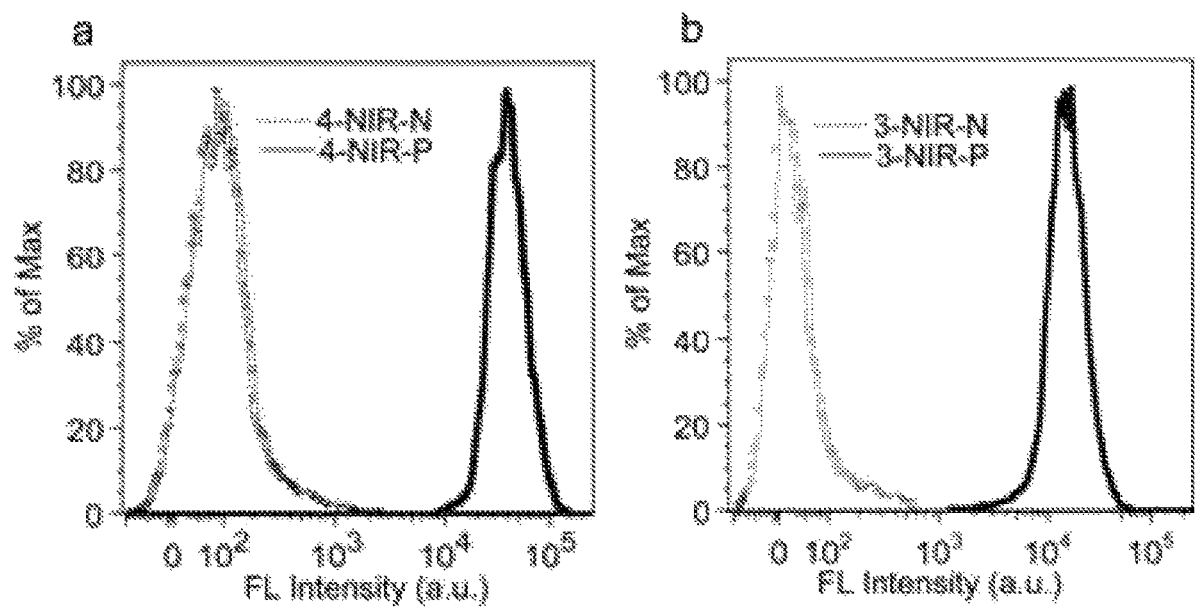
FIGS. 51A and B show flow cytometry measurements of the intensity distributions of MCF-7 cells labeled with 4-NIR Pdot-streptavidin (a, negative labeling, dot line; positive labeling, solid line) and 3-NIR Pdot-streptiavidin. (b, negative labeling, dot line; positive labeling, solid line). All the negative and positive labelings were completed and measured under identical experimental conditions, only in the negative labeling primary biotinylated antibody was absent.
Figure 52:
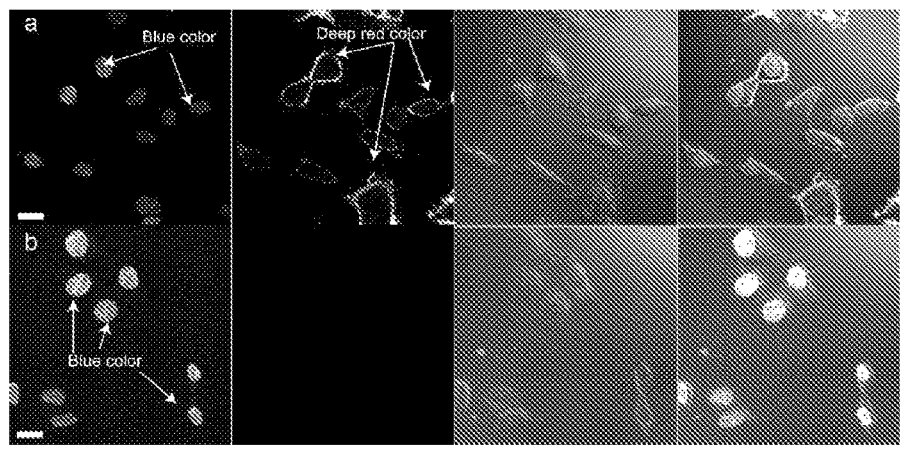
FIGS. 52A and B show fluorescence images of MCF-7 cells labeled with 3-NIR-SA probes. (a) Positive labeling using 3-NIR-Pdot-SA probe. (b) Negative labeling carried out under the same condition as (a) but in the absence of biotinylated antibody on the surface of the MCF-7 cells. From left to right: blue fluorescence from the nuclear stain Hoechst 34580; red fluorescence images from 3-NIR-SA probes; Nomarski (DIC) images; and combined fluorescence images. Scale bars: 20 μm.

Preparation, Characterizations and Bioapplications of the Pdots (FIG. 48-52). The semiconducting polymer dots were prepared by co-precipitation method. All polymers were dissolved into anhydrous THF, respectively, to form a 1 mg/mL THF solution, then as the weight ratio of 50:50:70:8 to mix polymers P1, P2, P3, P4 (for 4-NIR Pdots) THF solution, and the weight ratio of 100:50:6 to mix polymers P2, P3, P4 (for 3-NIR Pdots) THF solution. Then 0.2 mL mixed solution was added into 1.8 mL anhydrous THF, which was further injected directly into 10 mL DI H$_2$O under ultrasonication. THF was removed by N$_2$ flow at room temperature. The sizes of these two kinds of Pdots (4-NIR Pdots and 3-NIR Pdots) three polymers were characterized as 15.7 nm by dynamic light scattering. FIG. 48A shows a TEM image of 4-NIR Pdots (P1/P2/P3/P4). FIG. 48B shows particle size distributions of narrow-band emissive 4-NIR Pdots (P1/P2/P3/P4). FIG. 48C shows TEM image of 3-NIR (P2/P3/P4) Pdots. FIG. 48D shows particle size distributions of narrow-band emissive 3-NIR (P2/P3/P4) Pdots. The data were measured by dynamic light scattering. FIG. 49 shows the absorption spectra of 4-NIR Pdots (solid line), 3-NIR Pdots (dashed line) and fluorescence spectra of 4-NIR Pdots (dot line, $\lambda_{ex}$=380 nm) and 3-NIR Pdots (dashed-dot-dot line, $\lambda_{ex}$=450 nm) with narrow emission bands (FWHM=55 nm). FIG. 50A shows the single-particle fluorescence image of Qdot705. FIG. 50B shows the single-particle fluorescence image of —NIR Pdots. FIG. 50C shows the corresponding intensity distribution histograms of Qdot705. FIG. 50D shows the corresponding intensity distribution histograms of 3-NIR Pdots. From the distribute curves of single-particle brightness of several thousand particles of Qdot705 and 3-NIR Pdots, respectively, we can know that 3-NIR Pdots were 3 times brighter than Qdot 705. FIG. 51A shows the flow cytometry measurements of the intensity distributions of MCF-7 cells labeled with 4-NIR Pdot-streptavidin (negative labeling, dot line; positive labeling, solid line). FIG. 51B shows the flow cytometry measurements of the intensity distributions of MCF-7 cells labeled with 3-NIR Pdot-streptavidin. (negative labeling, dot line; positive labeling, solid line). All the negative and positive labelings were completed and measured under identical experimental conditions, only in the negative labeling primary biotinylated antibody was absent. FIG. 52 shows fluorescence images of MCF-7 breast-cancer cells labeled with 3-NIR Pdot-streptavidin. Negative labeling performed under the same condition but in the absence of the biotinylated primary antibody does not show fluorescence signal. From left to right: blue fluorescence from the nuclear stain Hoechst 34580; red fluorescence images from 3-NIR-SA probes; Nomarski (DIC) images; and combined fluorescence images. Scale bars: 20 µm.

Example 22: Narrow-Band Emissive Lanthanide Polymer Dots with a <10 nm FWHM Bandwidth Emission This example describes polymer dots that include a violet-emissive polymer as a donor and red emissive europium complexes as acceptors along with the application of time-gated fluorescence bioimaging based on the Eu complexes/PVK Pdots. As described further below, the europium complexes were integrated with polymers and condensed to form polymer dots that exhibited a less than about 10 nm FWHM emission.

Figure 53:
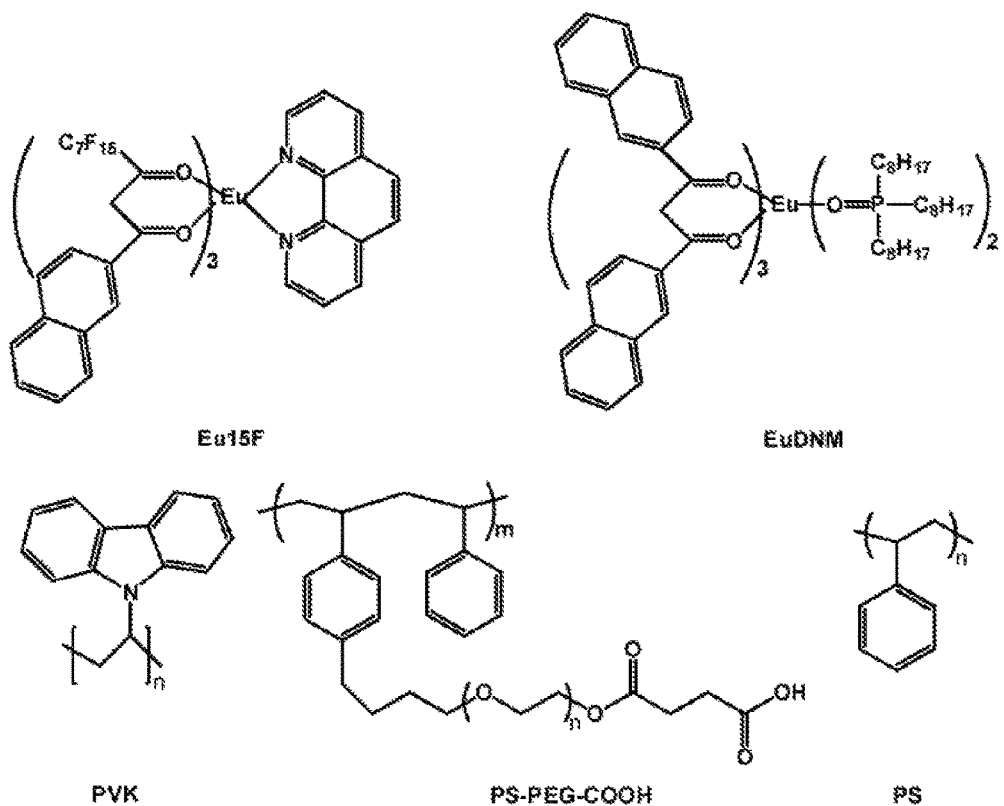
FIG. 53 shows chemical structures of a general emissive polymer PVK, europium complexes (Eu15F and EuDNM), a general non-emissive polymer PS, and a functional polymer PS-PEG-COOH.

FIG. 53 shows example polymers and lanthanide complexes that were used to produce example polymer dots of the present invention. Example Europium complexes included Eu15F and EuDNM. The polymers included, e.g., polyvinyl-N-carbazole (PVK), polystyrene polymer conjugated with polyethylene glycol having a COOH terminus (PS-PEG-COOH), and polystyrene (PS). The length of the various polymers can be denominated by m and n as shown in FIG. 53. The number of repeating units, m and n, can be any desired length. For example, in PVK, n can range from 5 to 10,000; in PS-PEG-COOH, m can range from 10-1000, and n can range from 1-100; and in PS, n can range from 5 to 10,000). In this example, PVK has an average Mw=75,000, polydispersity=2. PS-PEG-COOH has a main chain Mw=8,500, graft chain Mw=1,200, and total chain Mw=21,700, polydispersity=1.25). PS has an average Mw=41,000.

Figure 54:
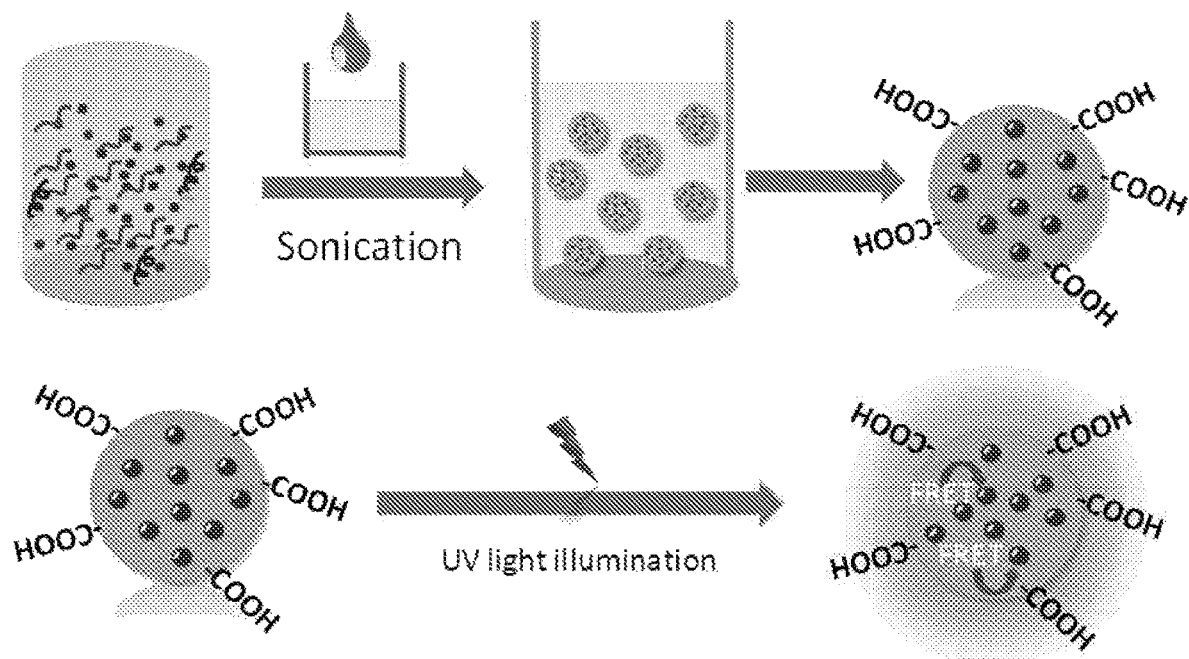
FIG. 54 shows schematic illustration of a non-limiting example for forming Pdots using a general emissive PVK polymer and Eu complexes.

FIG. 54 shows an example preparation method of making polymer dots containing PVK and Eu complex.

Figure 55:
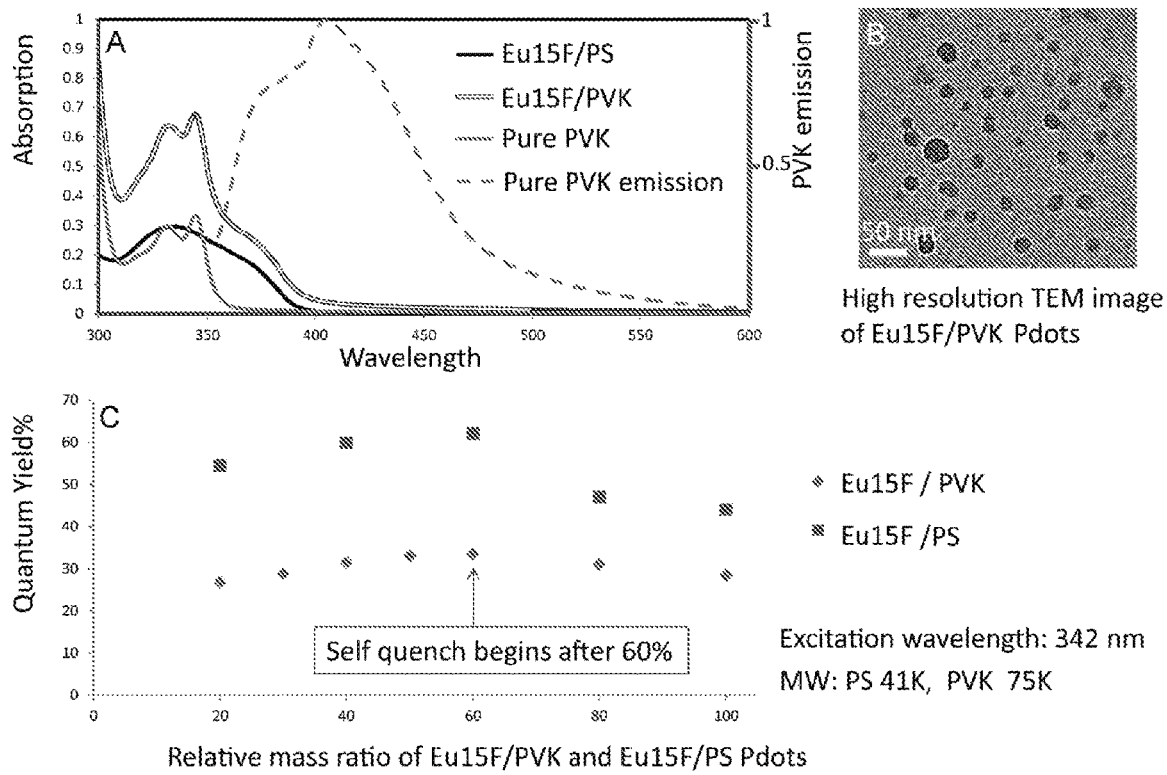
FIG. 55 shows spectroscopic and TEM characterizations of Eu15F/Polymer Pdots. (a) Absorption spectra of Eu15F/PS nanoparticles, Eu15F/PVK Pdots and pure PVK Pdots, and the emission spectra of PVK Pdots. (b) TEM image of Eu15F/PVK Pdots. (c) Quantum yields of Eu15F/PS Pdots and Eu15F/PVK Pdots versus the ratios of Eu15F.

Spectroscopic and TEM characterizations of Eu15F/Polymer Pdots were performed. FIG. 55A shows that the emission spectrum of PVK overlapped with the absorption spectrum of Eu15F. This spectral overlap makes it possible for the fluorescence energy transfer from PVK donor to the acceptor Eu15F. The average particle diameter of the Eu15F (60 wt %)/PVK Pdots was about 16 nm as measured by high resolution TEM (FIG. 55B). The quantum yields of Eu15F (at different ratios)/PVK Pdots were measured and compared to those of Eu15F in non-fluorescent polymer polystyrene, Eu15F (at different ratios)/PS nanoparticles. As shown in the quantum yield curves (FIG. 55C), self-quenching for these particles occurred when the ratio of Eu15F was higher than 60%.

Figure 56:
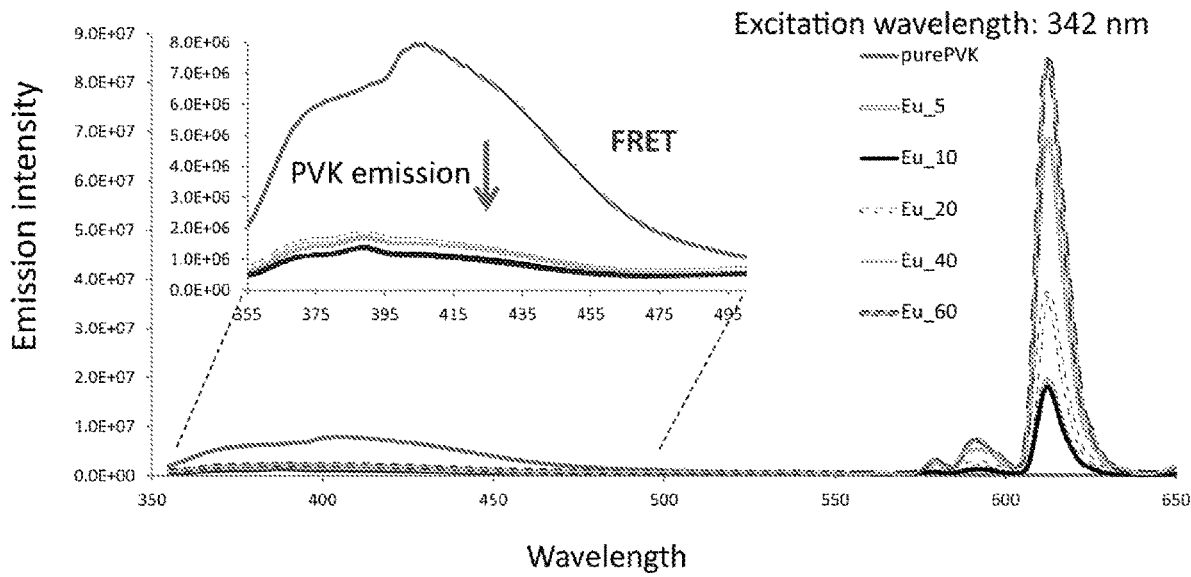
FIG. 56 shows emission spectra of Eu15F/PVK Pdots with varying ratios of Eu15 F.

FIG. 56 shows that fluorescence resonance energy transfer (FRET) existed between conjugated polymer PVK and Eu15F complex. As shown in the emission spectra (FIG. 57), the intensity of the narrow emission peak of Eu15F complex at 612 nm (characteristic emission of Eu) was increased when the ratio of Eu15F was increased. As shown, the emission intensity (355 nm-500 nm) of PVK dropped when the ratio of Eu15F increased from 0% to 60%. The emission intensity (575 nm-625 nm) of Eu15F increased. While not being limited by any particular theory, the change was likely due to the energy transfer from PVK to Eu15F. The emission spectra indicates that the FWHM of the emission spectra of Eu15F(60 wt %)/PVK Pdots is lower than ~10 nm.

Figure 57:
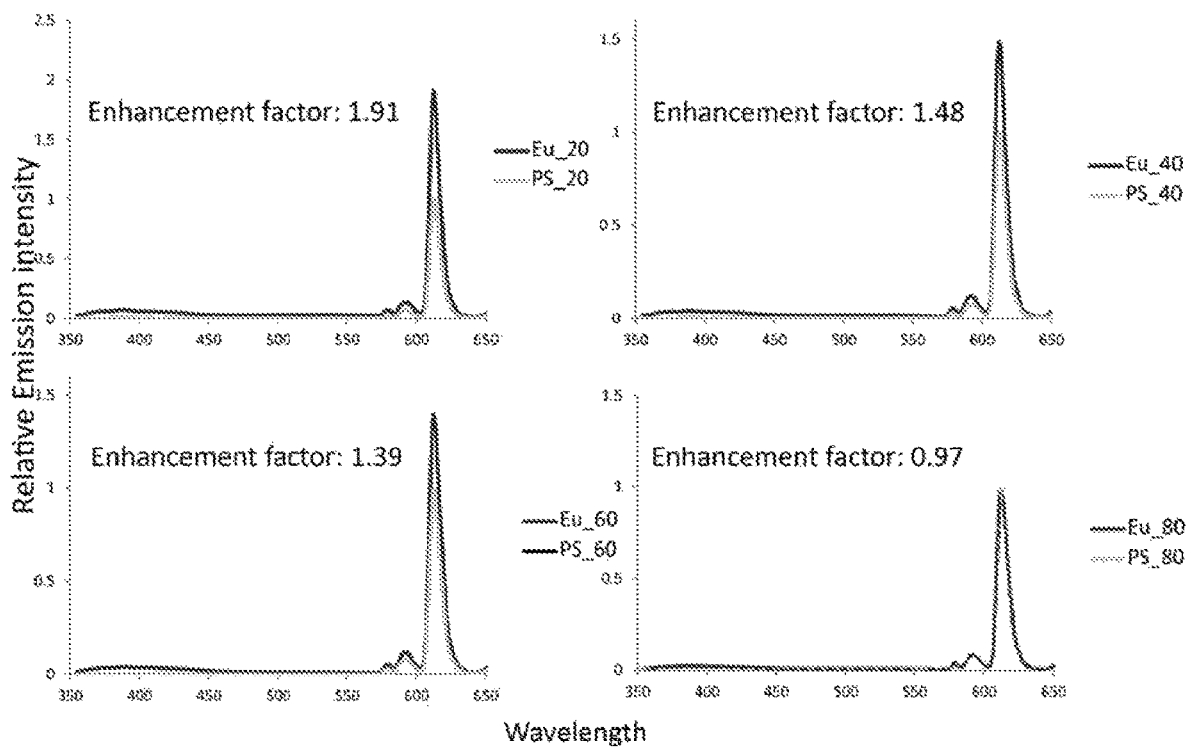
FIG. 57 shows emission intensity comparison between Eu15F/PS nanoparticles and Eu15F/PVK Pdots with varying Eu15F ratios.

Fluorescence emission intensity from Eu was enhanced at least in part by the large absorption cross-section of the conjugated polymer PVK, as compared to PS. FIG. 57 shows emission intensity comparisons between Eu15F/PS nanoparticles and Eu15F/PVK Pdots with varying Eu15F ratios (e.g., from 20% to 80% Eu15F) upon excitation at 342 nm. As shown in FIG. 57, the emission intensities of Eu15F/PVK Pdots were larger than that of Eu15F/PS nanoparticles before the ratio of Eu15F reached 60 wt %. Considering that quantum yields of Eu15F/PS nanoparticles were larger than that of Eu15F/PVK Pdots when the ratio of Eu15F was in the range from 20%-90% (FIG. 55), the emission intensity enhancement results demonstrated that the absorption cross-sections of Eu15F/PVK Pdots were larger than that of Eu15F-PS nanoparticles. When the ratio of Eu15F increased, self-quenching also began to happen. The self-quenching effect became more and more dominant when the ratio of Eu15F was increased. For example, when the ratio reached 80%, the emission brightness enhancement of Eu15F/PVK Pdots over that of Eu15F/PS nanoparticles decreased to 1.

Figure 58:
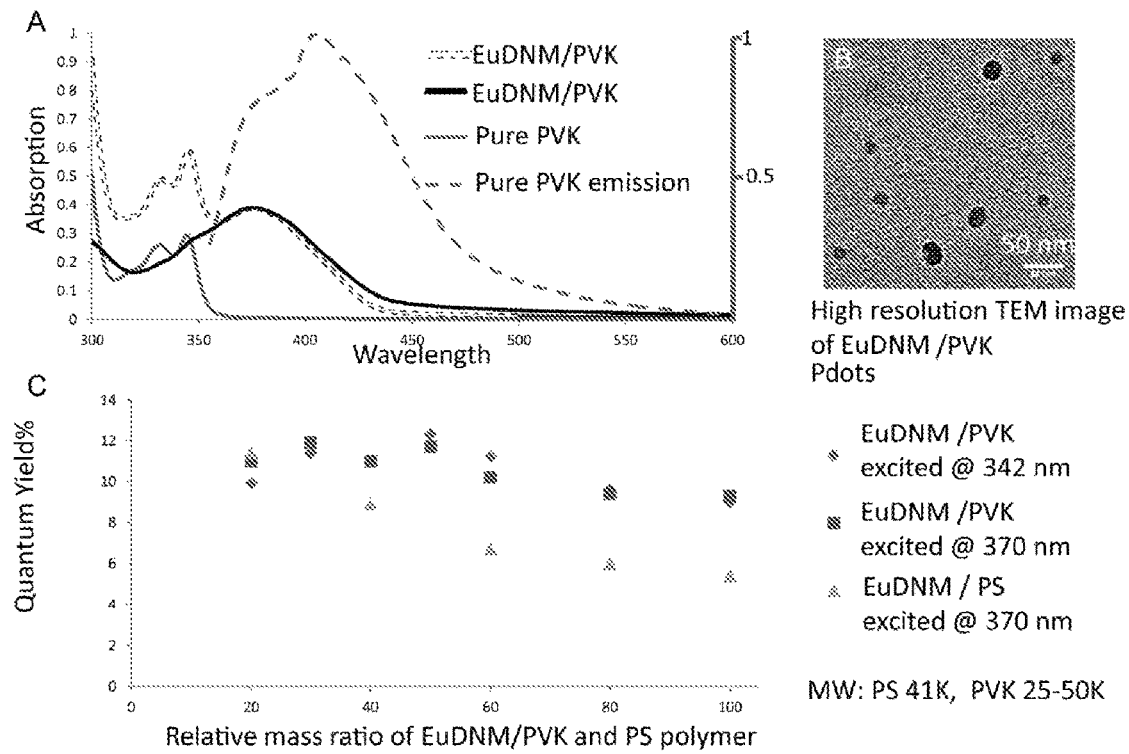
FIGS. 58A-C show spectroscopic and TEM characterizations of EuDNM/Polymer Pdots. (a) Absorption spectra of EuDNM/PS nanoparticles, EuDNM/PVK Pdots and pure PVK Pdots, and the emission spectra of PVK Pdots. (b) TEM image of EuDNM/PVK Pdots. (c) The quantum yields of EuDNM/PS Pdots and Eu15F/PVK Pdots versus the ratios of EuDNM.

Spectroscopic and TEM characterizations of EuDNM/Polymer Pdots were also performed. FIG. 58A shows absorption spectra of EuDNM/PS nanoparticles, EuDNM/PVK Pdots and pure PVK Pdots, and the emission spectra of PVK Pdots. FIG. 58B shows TEM image of EuDNM/PVK Pdots. FIG. 58C shows the quantum yields of EuDNM/PS nanoparticles and Eu15F/PVK Pdots versus the ratios of EuDNM complexes. In this example, the emission spectrum of PVK shows a better overlap with the absorption spectrum of EuDNM than that of Eu15F. So there can be more efficient energy transfer from PVK to EuDNM complex. The average particle size (diameter) of prepared Pdots was around 17 nm as measured by high resolution TEM. The quantum yields of EuDNM/PVK were measured and compared to that of EuDNM in non-fluorescent polystyrene nanoparticles. As shown in the quantum yield curve, decrease of quantum yield due to self-quenching happened when the ratio of EuDNM was beyond 50%. The molecular weight of PS was chosen to be close to that of conjugated polymer PVK.

Figure 59:
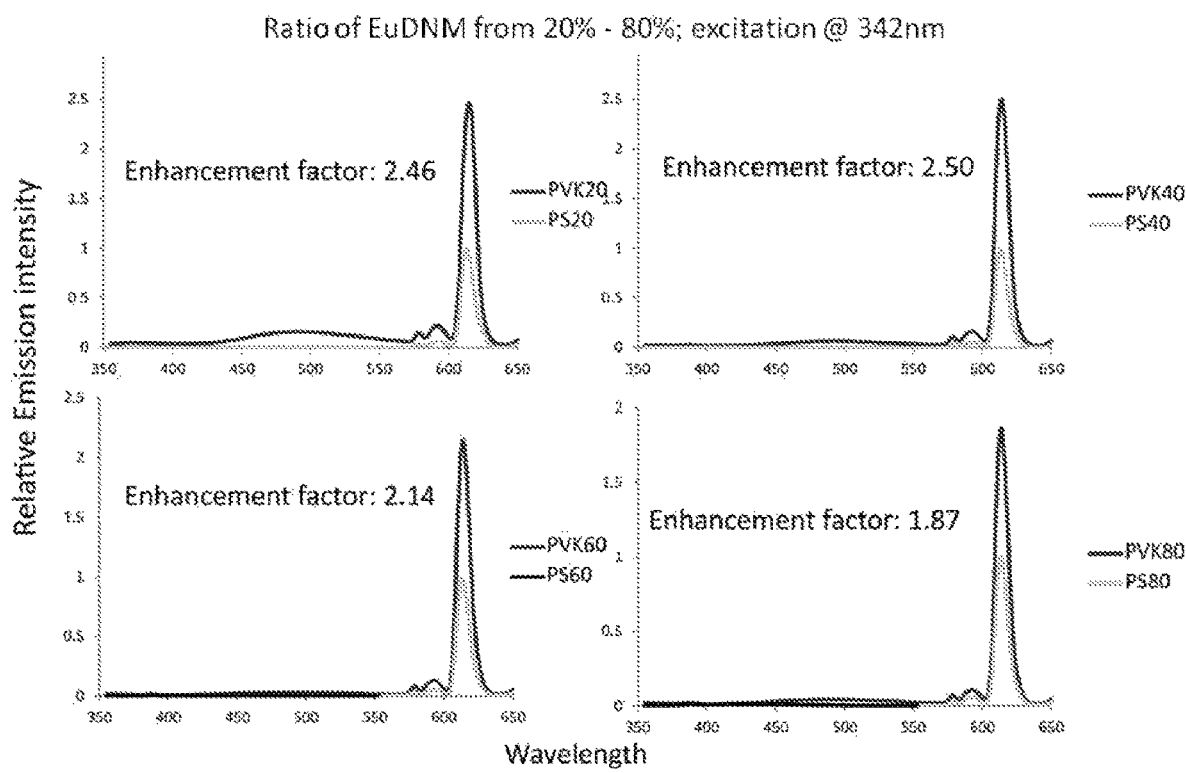
FIG. 59 shows emission intensity comparison between EuDNM/PS nanoparticles and EuDNM/PVK Pdots with varying ratios of EuDNM.

FIG. 59 depicts emission intensity comparisons between EuDNM/PS nanoparticles and EuDNM/PVK Pdots with varying ratios of EuDNM complex. As shown in FIG. 59, the emission intensities of EuDNM/PVK Pdots were larger than that of EuDNM/PS nanoparticles when the ratio of EuDNM was from 20% to 80%. In this example, the brightness enhancement of EuDNM/PVK over EuDNM/PS nanoparticles was much larger than their quantum yield enhancements. The results demonstrated that the absorption cross-sections of EuDNM/PVK Pdots were larger than that of EuDNM/PS nanoparticles.

Figure 60:
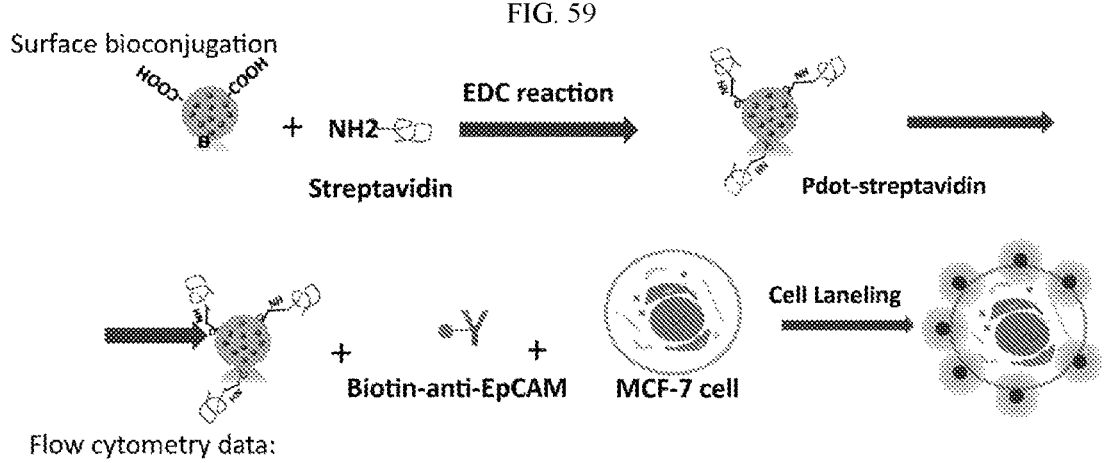
FIG. 60 shows bioconjugation scheme and the flow cytometry results of the two types of Eu/PVK Pdots.
Figure 60:
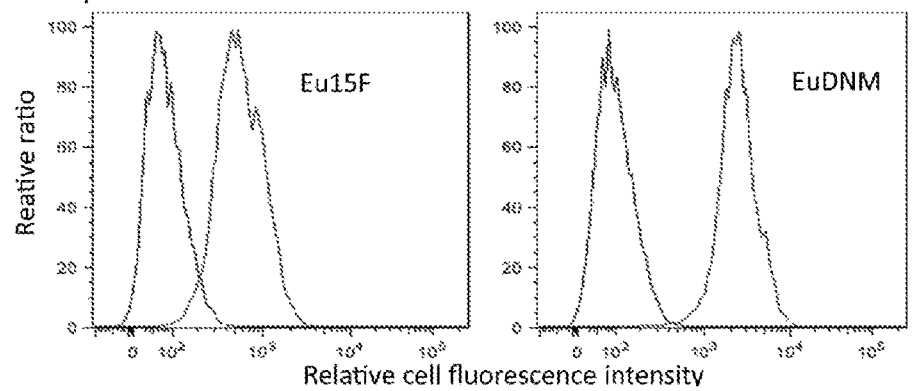
Figure 61:
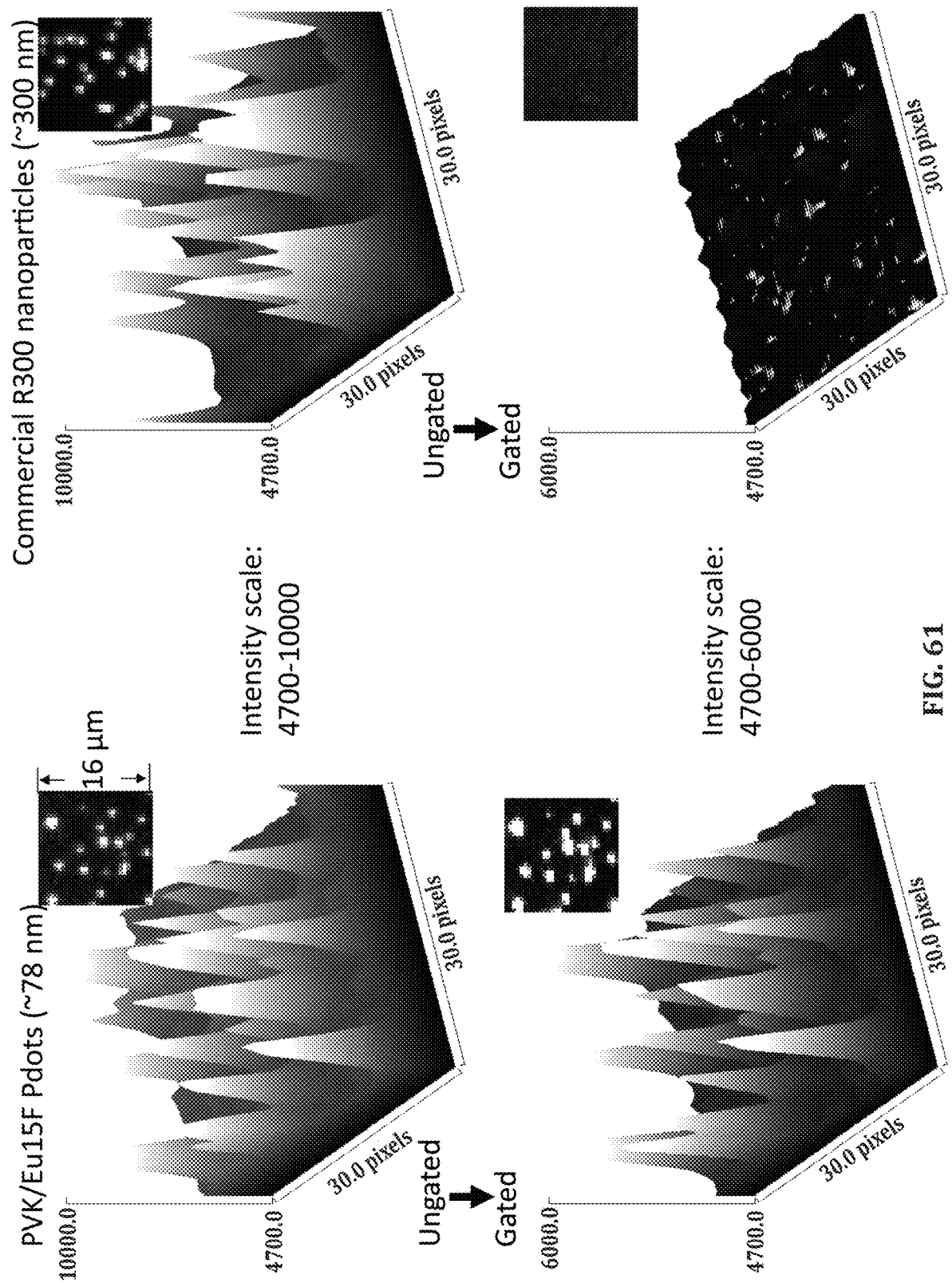
FIG. 61 shows time-gated and un-gated fluorescence images of Eu15F/PVK Pdots (left panel) and commercial R300 red fluorescence emitting nanoparticles (right panel).

This example also includes application of Eu/PVK Pdots for flow cytometry and time-gated fluorescence imaging. The scheme in FIG. 60 shows the bioconjugation and cellular surface labeling procedures for Eu/PVK Pdots. The bottom curves show the flow cytometry measurements of the intensity distributions of MCF-7 cells labeled with Eu/PVK Pdots (negative labeling, left line; positive labeling, right line). All the negative and positive labeling experiments were completed and measured under identical conditions, except that biotinylated antibody was absent in the negative labeling. It is notable, given the long lifetime of the Lanthanide Pdots, that they produce excellent signal to noise in the flow cytometry application where signal integration time is so short. To collect time-gated fluorescence images, a high speed optical chopper was placed in the intermediate image plane of an inverted Nikon T-2000 microscope. One focusing lens was placed in the middle of the optical chopper and the EMCCD camera. The distance between optical chopper and EMCCD was 4 times of the focusing length of the focusing lens. A UV LED (365 nm) was used as the illumination light source. The optical chopper and the UV LED were synchronized through a home-built synchronizer. Time-gated-fluorescence image of Eu15F/PVK Pdots and commercial red fluorescence emitting nanoparticles R300 are shown in FIG. 61. The fluorescence lifetime of Eu15F/PVK Pdots was measured to be around 500 as; while that of the commercial R300 nanoparticles was around 1 ns. As shown in images, the Eu15F/PVK Pdots still emitted many photons after 200 s delay (the time between excitation and signal collection). But the commercial R300 nanoparticles did not emit photons any more after 200 µs delay. The experimental conditions are as below: time delay, around 200 µs; excitation LED wavelength, 365 nm; emission collection filter, 545-625 nm; objective, 20×; N.A., 0.65; EMCCD: photonmax; exposure time, 200 ms; image size, 16 m×16 m.

Figure 62:
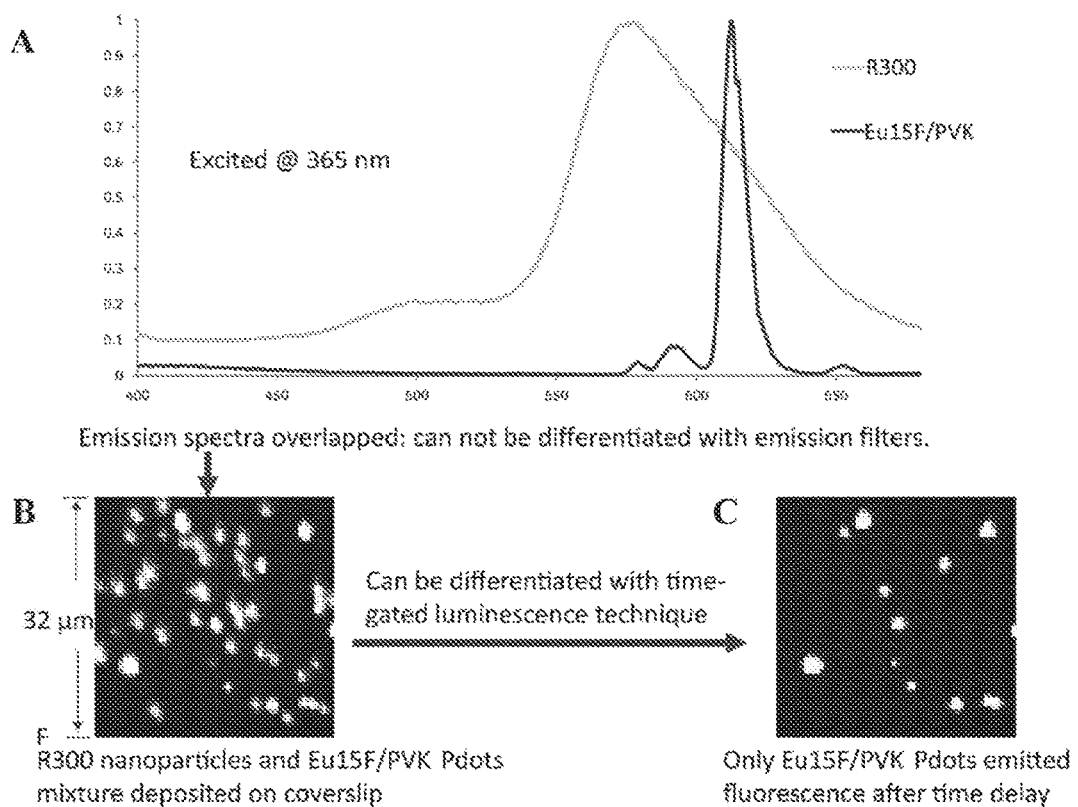
FIG. 62 shows the distinguishing of Eu15F/PVK Pdots and commercial 300 red fluorescence emitting nanoparticles based on their fluorescence lifetime difference. A shows the emission spectra of the Eu15F/PVK Pdots and commercial R300 red fluorescence emitting nanoparticles. The un-gated normal fluorescence image (left bottom; B) and time-gated-fluorescence image (C) of Eu15F/PVK Pdots and commercial R300 red fluorescence emitting nanoparticle mixture deposited on the coverslip.

The long lifetime of Eu15F/PVK Pdots can be differentiated from commercial R300 nanoparticles by utilizing their fluorescence lifetime difference. As shown in the fluorescence emission spectra (FIG. 62A), both particles emit red fluorescence. Due to the spectral overlap, the two types of particles were not differentiated by simply using bandpass filters (FIG. 62B). However, the two types of particles could be easily differentiated by utilizing their lifetime difference. As shown in the normal fluorescence image (FIG. 62B), both particles emitted photons. When there was time delay between excitation and signal collection, only some of the particles emitted photons (FIG. 62C). And these particles were Eu15F/PVK Pdots. Therefore the two different types of particles with overlapping emission spectra were easily differentiated by using their difference in lifetime.

Figure 63:
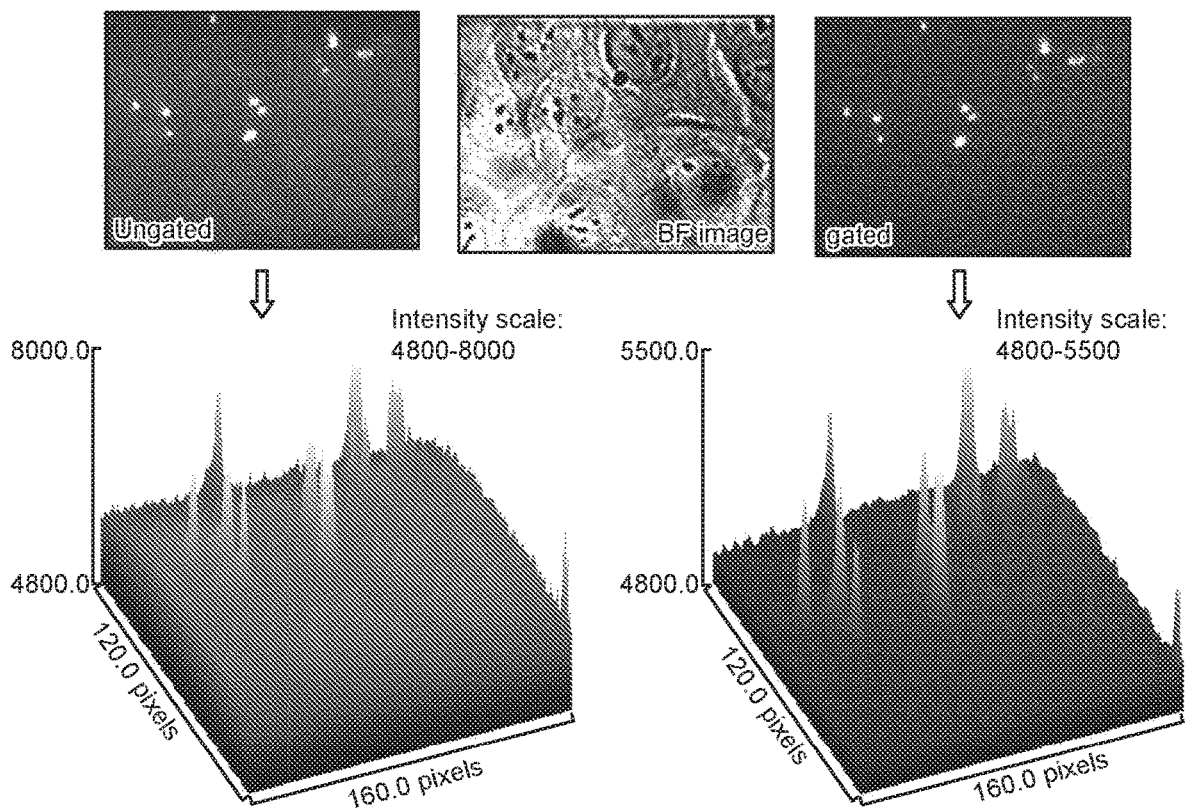
FIG. 63 shows time-gated fluorescence images of Eu15F/PVK Pdots endocytosed by MCF-7 cells.

Eu15F/PVK Pdots were applied for live cell imaging, as shown in FIG. 63. Eu15F/PVK Pdots were incubated with MCF-7 cells overnight. Before being placed on a microscope stage for imaging, the cells were fixed with paraformaldehyde for 10 mins, and then washed with 1×PBS buffer solution three times. The experimental conditions were as below: Time delay: 200 µs; excitation LED wavelength: 365 nm; emission collection filter: 500 nm longpass filter; Objective: 20×; N.A.: 0.65; Exposure time: 200 ms (EMCCD from photonmax); Image size: 85 m×64 m. In a normal fluorescence image, the background intensity level is usually high due to the auto-fluorescence of cells (top left image), while the background intensity level decreased significantly in a time-gated fluorescence image (top right image). As a result, the signal/noise ratio could be improved.

What is claimed is:

1. A polymer dot comprising:
   A condensed chromophoric polymer comprising a narrow-band monomer and one or more general monomers wherein the narrow-band monomer is integrated into the chromophoric polymer, the condensed chromophoric polymer having an emission spectrum with a full width half maximum (FWHM) of 5 nm to 70 nm,
   wherein a ratio of a number of the narrow-band monomer to the general monomers is 1:20 to 1:1000; and wherein the general monomers comprise energy donors and the narrow-band monomer is an energy acceptor configured to receive energy from one or more of the general monomers,
   wherein the polymer dot is a sub-micron sized particle,
   wherein the condensed chromophoric polymer is collapsed or packed in the sub-micron sized particle,
   wherein the chromophoric polymer is a semiconducting polymer,
   wherein the narrow-band monomer is selected from the group consisting of a BODIPY monomer, a BODIPY derivative monomer, a squaraine monomer, a squaraine derivative monomer, a metal complex monomer, a metal complex derivative monomer, a porphyrin monomer, and a porphyrin derivative monomer, and
   wherein the general monomers are selected from the group consisting of: fluorene, a fluorene derivative, phenylene vinylene, a phenylene vinylene derivative, phenylene, a phenylene derivative, benzothiadiazole, a benzothiadiazole derivative, thiophene, a thiophene derivative, carbazole fluorene, and a carbazole fluorene derivative.

2. The polymer dot of claim 1, wherein the ratio of the narrow-band monomer to a total of the general monomer is 0.1:1.

3. The polymer dot of claim 1, wherein the general monomers comprise a first general monomer, a second general monomer, or a combination thereof, and wherein the first and second general monomer have an emission spectrum with a FWHM of greater than 70 nm.

4. The polymer dot of claim 3, wherein the narrow-band monomer, the first general monomer, the second general monomer, or a combination thereof are integrated into a backbone of the chromophoric polymer.

5. The polymer dot of claim 1, wherein the BODIPY derivative has the formula:

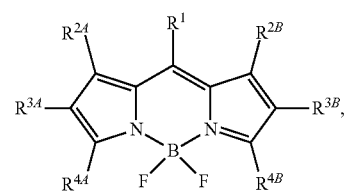

wherein each of $R^1$, $R^{2A}$, $R^{2B}$, $R^{3A}$, $R^{3B}$, $R^{4A}$ and $R^{4B}$ is independently selected from the group consisting of hydrogen, alkyl, aralkyl, aryl, and alkoxy-aryl, and wherein the BODIPY derivative is integrated into a backbone, a terminus or a sidechain of the chromophoric polymer by attachment to $R^1$, $R^{2A}$, $R^{2B}$, $R^{3A}$, $R^{3B}$, $R^{4A}$, $R^{4B}$ or any combination thereof.

6. The polymer dot of claim 1, further comprising a functional monomer that provides a reactive functional group suitable for bioconjugation, wherein the reactive functional group is conjugated to a biomolecule.

7. The polymer dot of claim 6, wherein the biomolecule is selected from the group consisting of: a protein, a glycoprotein, a peptide, an amino acid, a metabolite, a drug, a toxin, a nucleic acid, a carbohydrate, a sugar, a lipid, and a fatty acid.

8. The polymer dot of claim 1, further comprising a polymer physically blended or chemically cross-linked with the chromophoric polymer.

9. The polymer dot of claim 1, wherein the narrow-band monomer is covalently attached to a backbone or sidechain of the chromophoric polymer.

10. The polymer dot of claim 1, wherein the condensed chromophoric polymer is stable over a period of greater than about 1 month.

11. The polymer dot of claim 1, wherein the FWHM is less than about 50 nm.

12. A polymer dot comprising:
a condensed chromophoric polymer comprising a narrow-band unit and one or more general monomers wherein the narrow band unit is attached to a backbone or a sidechain of the chromophoric polymer, wherein the condensed chromophoric polymer having an emission spectrum with a full width half maximum (FWHM) of 5 mm to 70 nm,
wherein a ratio of a number of the narrow-band unit to the general monomer is 1:20 to 1:1000 and wherein general monomers comprise energy donors and the narrow-band unit is an energy acceptor configured to receive energy from one or more of the general monomers,
wherein the polymer dot is a sub-micron sized particle,
wherein the condensed chromophoric polymer is collapsed or packed in the sub-micron sized particle,
wherein the chromophoric polymer is a semiconducting polymer,
wherein the narrow-band unit is selected from the group consisting of a fluorescent nanoparticle embedded in or attached to the polymer dot, a BODIPY monomer, a BODIPY derivative monomer, a squaraine monomer, a squaraine derivative monomer, a metal complex monomer, a metal complex derivative monomer, a porphyrin monomer, and a porphyrin derivative monomer, and
wherein the general monomers comprise a first general monomer and a second general monomer, wherein the first general monomer and the second general monomer are each independently selected from the group consisting of: fluorene, a fluorene derivative, phenylene vinylene, a phenylene vinylene derivative, phenylene, a phenylene derivative, benzothiadiazole, a benzothiadiazole derivative, thiophene, a thiophene derivative, carbazole fluorene, and a carbazole fluorene derivative.

13. The polymer dot of claim 12, wherein the narrow-band unit is covalently attached to the backbone or the sidechain of the chromophoric polymer.

14. The polymer dot of claim 12, wherein the BODIPY derivative has the formula:

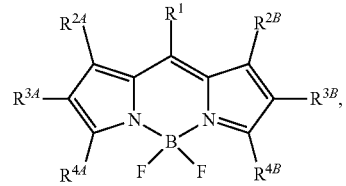

wherein each of $R^1$, $R^{2A}$, $R^{2B}$, $R^{3A}$, $R^{3B}$, $R^{4A}$ and $R^{4B}$ is independently selected from the group consisting of hydrogen, alkyl, aralkyl, aryl, and alkoxy-aryl, and wherein the BODIPY derivative is integrated into the backbone, a terminus or a sidechain of the chromophoric polymer by attachment to $R^1$, $R^{2A}$, $R^{2B}$, $R^{3A}$, $R^{3B}$, $R^{4A}$, $R^{4B}$ or any combination thereof.

15. The polymer dot of claim 12, wherein the FWHM is less than about 50 nm.

16. The polymer dot of claim 12, wherein the condensed chromophoric polymer comprises a quantum yield greater than about 30%.

17. The polymer dot of claim 12, wherein the condensed chromophoric polymer is stable over a period of greater than about 1 month.

18. The polymer dot of claim 12, wherein the ratio of a number of the narrow-band monomer to the first general monomer is 0.1:1.

19. The polymer dot of claim 1, wherein the squaraine derivative has the formula:

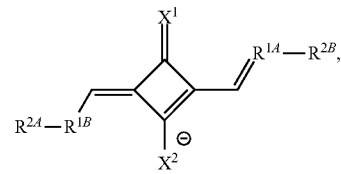

wherein
each of X1 and X2 is independently selected from the group consisting of oxygen, sulfur and nitrogen;
each of R1A and R1B is independently selected from the group consisting of alkylene, alkenylene, arylene, heteroarylene, phenylene, azulene, cycloalkylene, and heterocycloalkylene;
each of R2A and R2B is a reactive group independently selected from the group consisting of a halide, hydroxyl, and amino, and
the squaraine derivative is integrated into the chromophoric polymer by attachment to R1A, R1B, R2A, R2B or a combination thereof.

20. The polymer dot of claim 1, wherein the squaraine derivative has the formula:

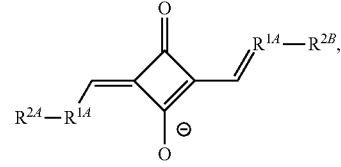

wherein
each of $R^{1A}$ and $R^{1B}$ is independently selected from the group consisting of alkylene, alkenylene, arylene, heteroarylene, phenylene, azulene, cycloalkylene, and heterocycloalkylene; and each of $R^{2A}$ and $R^{2B}$ is a reactive group independently selected from the group consisting of a halide, hydroxyl, and amino.

21. The polymer dot of claim 1, wherein the squaraine derivative has the formula:

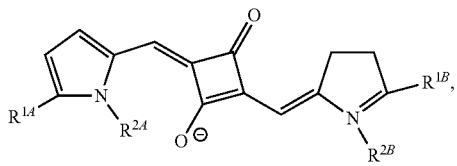

wherein
each of $R^{1A}$ and $R^{1B}$ is a reactive group independently selected from the group consisting of chloro, bromo, iodo, and hydroxyl; and
each of $R^{2A}$ and $R^{2B}$ is selected from the group consisting of hydrogen, methyl, alkyl, phenyl, araalkyl, and alkoxy-phenyl.

22. The polymer dot of claim 1, wherein the squaraine derivative has the formula:

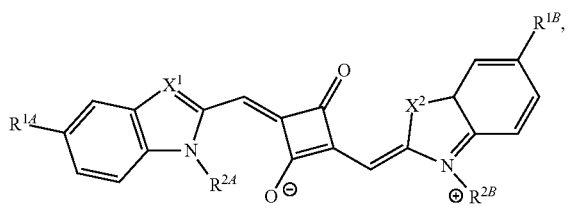

wherein
each of $X^1$ and $X^2$ is independently selected from the group consisting of carbon, sulphur, and selenium;
each of $R^{1A}$ and $R^{1B}$ is a reactive group independently selected from the group consisting of chloro, bromo, iodo, and hydroxyl; and
each of $R^{2A}$ and $R^{2B}$ is independently selected from the group consisting of hydrogen, methyl, alkyl, phenyl, araalkyl, alkoxy-phenyl, N-dialkyl-4-phenyl, N-diphenyl-4-phenyl, and N-dialkoxylphenyl-4-phenyl.

23. The polymer dot of claim 1, wherein the squaraine derivative has the formula:

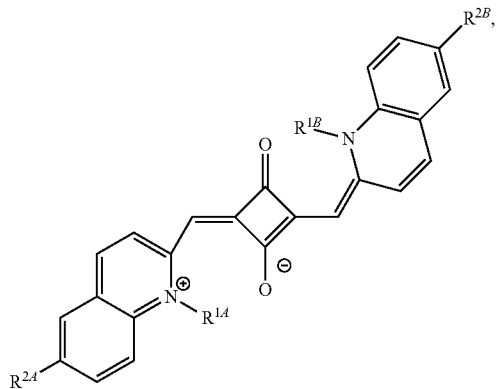

wherein
each of $R^{2A}$ and $R^{2B}$ is a reactive group independently selected from the group consisting of chloro, bromo, iodo, and hydroxyl; and
each of $R^{1A}$ and $R^{1B}$ is selected from the group consisting of hydrogen, methyl, alkyl, phenyl, araalkyl, alkoxy-phenyl, N-dialkyl-4-phenyl, N-diphenyl-4-phenyl, and N-dialkoxylphenyl-4-phenyl.

24. The polymer dot of claim 12, wherein the backbone comprises a functional monomer that provides a reactive functional group suitable for bioconjugation, wherein the reactive functional group is conjugated to a biomolecule.

25. The polymer dot of claim 24, wherein the biomolecule is selected from the group consisting of: a protein, a glycoprotein, a peptide, an amino acid, a metabolite, a drug, a toxin, a nucleic acid, a carbohydrate, a sugar, a lipid, and a fatty acid.

26. The polymer dot of claim 6, wherein the biomolecule is an antibody.

* * * * *